US 8,987,314 B2

(12) United States Patent
Finlay et al.

(10) Patent No.: US 8,987,314 B2
(45) Date of Patent: Mar. 24, 2015

(54) AMIDE, UREA OR SULFONE AMIDE LINKED BENZOTHIAZOLE INHIBITORS OF ENDOTHELIAL LIPASE

(71) Applicant: Bristol-Myers Squibb Company, Princeton, NJ (US)

(72) Inventors: Heather Finlay, Skillman, NJ (US); Ji Jiang, West Windsor, NJ (US); Soong-Hoon Kim, Titusville, NJ (US); Brandon Parkhurst, Holland, MI (US); Jennifer X. Qiao, Princeton, NJ (US); Tammy C. Wang, Lawrenceville, NJ (US); Zulan Pi, Pennington, NJ (US); George O. Tora, Langhorne, NJ (US); John Lloyd, Yardley, PA (US); James A. Johnson, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 28 days.

(21) Appl. No.: 13/944,921

(22) Filed: Jul. 18, 2013

(65) Prior Publication Data
US 2014/0045811 A1 Feb. 13, 2014

Related U.S. Application Data

(60) Provisional application No. 61/673,488, filed on Jul. 19, 2012, provisional application No. 61/770,523, filed on Feb. 28, 2013.

(51) Int. Cl.
| C07D 277/64 | (2006.01) |
| C07D 417/04 | (2006.01) |
| C07D 417/10 | (2006.01) |
| C07D 417/12 | (2006.01) |
| C07D 417/14 | (2006.01) |
| A61K 31/428 | (2006.01) |
| A61P 9/10 | (2006.01) |

(52) U.S. Cl.
CPC ............ *C07D 277/64* (2013.01); *C07D 417/04* (2013.01); *C07D 417/14* (2013.01); *C07D 417/12* (2013.01); *C07D 417/10* (2013.01)
USPC ........... 514/367; 548/152; 548/159; 548/179; 548/180; 544/135

(58) Field of Classification Search
CPC .. C07D 277/64; C07D 417/04; C07D 417/10; C07D 417/12; C07D 417/14; A61K 31/428
USPC .................. 514/367; 548/152, 159, 179, 180; 544/135
See application file for complete search history.

(56) References Cited

U.S. PATENT DOCUMENTS

| 7,217,727 | B2 | 5/2007 | Eacho et al. |
| 7,595,403 | B2 | 9/2009 | Eacho et al. |
| 2006/0211755 | A1 | 9/2006 | Eacho et al. |
| 2008/0287448 | A1 | 11/2008 | Zoller et al. |
| 2009/0054478 | A1 | 2/2009 | Zoller et al. |
| 2009/0076068 | A1 | 3/2009 | Zoller et al. |
| 2011/0251386 | A1 | 10/2011 | Masuda et al. |
| 2012/0253040 | A1 | 10/2012 | Masuda et al. |

FOREIGN PATENT DOCUMENTS

| WO | WO99/32611 | 7/1999 |
| WO | WO2004/093872 | 11/2004 |
| WO | WO2004/094393 | 11/2004 |
| WO | WO2004/094394 | 11/2004 |
| WO | WO2007/042178 | 4/2007 |
| WO | WO2007/110215 | 10/2007 |
| WO | WO2007/110216 | 10/2007 |
| WO | WO2009/123164 | 10/2009 |
| WO | WO2009/133834 | 11/2009 |
| WO | WO2012/081563 | 6/2012 |
| WO | WO2012/173099 | 12/2012 |

OTHER PUBLICATIONS

U.S. Appl. No. 13/936,311, filed Jul. 8, 2013, Johnson et al.
Bevilacqua, M.P. et al., "Selectins, Perspectives", J. Clinical Invest., vol. 91(2), pp. 379-387 (1993).
Bundgaard, H. et al., "Glycolamide Esters as Biolabile Prodrugs of Carboxylic Acid Agents: Synthesis, Stability, Bioconversion, and Physicochemical Properties", J. of Pharmaceutical Sciences, vol. 77(4), pp. 285-298 (1988).
Bundgaard, H., "(C) Means to Enhance Penetration (1) Prodrugs as a means to improve the delivery of peptide drugs", Advanced Drug Delivery Reviews, vol. 8, pp. 1-38 (1992).

(Continued)

*Primary Examiner* — Sreeni Padmanabhan
*Assistant Examiner* — Irina Neagu
(74) *Attorney, Agent, or Firm* — Jing G. Sun

(57) ABSTRACT

The present invention provides compounds of Formula (I):

as defined in the specification and compositions comprising any of such novel compounds. These compounds are endothelial lipase inhibitors which may be used as medicaments.

16 Claims, No Drawings

(56) References Cited

OTHER PUBLICATIONS deLemos, A.S. et al., "Identification of Genetic Variants in Endothelial Lipase in Persons With Elevated High-Density Lipoprotein Cholesterol", Circulation, vol. 106(11), pp. 1321-1326 (2002).
Group Writing Members, et al., Heart Disease and Stroke Statistics—2012 Update: A Report From the American Heart Association, Circulation, vol. 125, pp. e2-e220, (2011).
Folkman, J. et al., "Angiogenesis, Minireview" The J. of Biological Chemistry, vol. 267(16), pp. 10931-10934, (1992).
Folkman, J. et al., "Angiogenic Factors", Science, vol. 235, pp. 442-447 (1987).
Gordon, D.J. et al., "High-Density Lipoprotein Cholesterol and Cardiovascular Disease" Circulation, vol. 79(1), pp. 8-15, (1989).
Gordon, D.J. et al., "High-Density Lipoprotein—The Clinical Implications of Recent Studies", New England J. Med., vol. 321(19), pp. 1311-1316 (1989).
Hirata, Ken-ichi, et al., "Cloning of a Unique Lipase from Endothelial Cells Extends the Lipase Gene Family", The J. of Biological Chemistry, vol. 274(20), pp. 14170-14175 (1999).
Janssens, S.P. et al., "Cloning and Expression of a cDNA Encoding Human Endothelium-deriving Relaxing Factor/Nitric Oxide Synthase", The J. of Biological Chemistry, Vo. 267(21), pp. 14519-14522 (1992).
Jaye, M. et al., "A novel endothelial-derived lipase that modulates HDL metabolism", Nature Genetics, vol. 21, pp. 424-428 (1999).
Jin, W. et al., "Lipases and HDL metabolism", *Trends* in Endocrinology & Metabolism, vol. 13(4), pp. 174-178 (2002).
Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxlyic Acid", Chem. Pharm. Bulletin, vol. 32(2), pp. 692-698 (1984).
Lamas, S. et al., "Endothelial nitric oxide synthase: Molecular cloning and characterization of a distinct constitutive enzyme isoform", PNAS, vol. 89(14), pp. 6348-6352, (1992).
Lüscher, T.F. et al., "Endothelium-Derived Contracting Factors", Hypertension, vol. 19(2), pp. 117-130 (1992).
McCoy, M.G. et al., "Characterization of the lipolytic activity of endothelial lipase", Journal of Lipid Research, vol. 43, pp. 921-929 (2002).
Ross, R., "The pathogenesis of atherosclerosis: a perspective for the 1990s" Nature, vol. 362, pp. 801-809 (1993).
Strauss, Juliane G. et al., "Endothelial cell-derived lipase mediates uptake and binding of high-density lipoprotein (HDL) particles and the selective uptake of HDL-associated cholesterol esters independent of its enzymic activity", Biochem. J., vol. 368, pp. 69-79 (2002).
Williams, T.J. et al., "Adhesion Molecules Involved in the Microvascular Inflammatory Response", Am Rev Respir Dis., vol. 146, pp. S45-S50 (1992).
Winum, J. et al., "*N*-(*tert*-Butoxycarbonyl)-*N*-[4-(dimethylazaniumylidene)-1,4-dihydropyridina-1-ylsulfonyl]azanide: A New Sulfamoylating Agent. Structure and Reactivity toward Amines", Organic Letters, vol. 3(14), pp. 2241-2243 (2001).
Wong, H. et al., "The lipase gene family" thematic review. J. of Lipid Research, vol. 43, pp. 993-999 (2002).
Yanagisawa, M. et al., "A novel potent vasoconstrictor peptide produced by vascular endothelial cells", Nature, vol. 332(6163), pp. 411-415 (1988).
International Search Report and the Written Opinion, PCT Application No. PCT/US2013/05972, dated Nov. 4, 2013.

AMIDE, UREA OR SULFONE AMIDE LINKED BENZOTHIAZOLE INHIBITORS OF ENDOTHELIAL LIPASE

This application claims the benefit of U.S. Provisional Patent Application 61/770,523, filed on 28 Feb. 2013 and of U.S. Provisional Patent Application 61/673,488, filed 19 Jul. 2012.

FIELD OF THE INVENTION

The present invention provides novel amide, urea or sulfone amide linked benzothiazole compounds and analogues, which are endothelial lipase (EL) inhibitors, compositions containing them, and methods of using them, for example, for the treatment and/or prophylaxis of dyslipidemias and the sequelae thereof.

BACKGROUND OF THE INVENTION

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors (for a detailed review, see Ross, R., *Nature*, 362(6423):801-809 (1993)). Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis (Gordon, D. J. et al., *N. Engl. J. Med.*, 321(19):1311-1316 (1989)).

The metabolism of HDL is influenced by several members of the phospholipase and triacylglycerol (TG) lipase family of proteins, which hydrolyze triglycerides, phospholipids (PL), and cholesteryl esters (CE), generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol (Jin, W. et al., *Trends Endocrinol. Metab.*, 13(4):174-178 (2002); Wong, H. et al., *J. Lipid Res.*, 43:993-999 (2002)). Endothelial lipase (also known as EDL, EL, LIPG, endothelial-derived lipase, and endothelial cell-derived lipase) is synthesized in endothelial cells, a characteristic that distinguishes it from the other members of the family.

Recombinant endothelial lipase protein has substantial phospholipase activity but has been reported to have less hydrolytic activity toward triglyceride lipids (Hirata, K. et al., *J. Biol. Chem.*, 274(20):14170-14175 (1999); Jaye, M. et al., *Nat. Genet.*, 21:424-428 (1999)). However, endothelial lipase does exhibit triglyceride lipase activity ex vivo in addition to its HDL phospholipase activity, and endothelial lipase was found to hydrolyze HDL more efficiently than other lipoproteins (McCoy, M. G. et al., *J. Lipid Res.*, 43:921-929 (2002)). Overexpression of the human endothelial lipase gene in the livers of mice markedly reduces plasma concentrations of HDL cholesterol and its major protein, apolipoprotein A-I (apoA-I) (Jaye, M. et al., *Nat. Genet.*, 21:424-428 (1999)).

Various types of compounds have been reported to modulate the expression of endothelial lipase, for example, 3-oxo-1,3-dihydro-indazole-2-carboxamides (WO 2004/093872, US 2006/0211755A1), 3-oxo-3-H-benzo[d]isoxazole-2-carboxamides (WO 2004/094393, U.S. Pat. No. 7,217,727), and benzisothiazol-3-one-2-carboxamides (WO 2004/094394, U.S. Pat. No. 7,595,403) by Eli Lilly & Co.; diacylindazole derivatives (WO 2007/042178, US 2008/0287448A1) and imidazopyridin-2-one derivatives (WO 2007/110215, US 2009/0076068A1), and azolopyridin-3-one derivatives (WO 2007/110216, US 2009/0054478A1) by Sanofi-Aventis; heterocyclic derivatives (WO 2009/123164), keto-amide derivatives (WO 2009/133834), acetic acid amide derivatives (WO20/10/44441, US 2011/0251386A1), oxadiazole derivatives (WO 2011074560, US2012253040 A1), benzothiazole and azabenzothiazole derivatives (WO 2012081563) and amino derivatives (WO2012173099) by Shionogi & Co., Ltd. However, because endothelial lipase is a relatively new member in the lipase gene family, a full understanding of the potential of endothelial lipase inhibitors to human health, as well as the inhibitors of other lipases in general, requires more studies.

Thus, there is a clear need for new types of compounds capable of inhibiting the activity of lipases, particularly endothelial lipase, that would constitute effective treatments to the diseases or disorders associated with the activity of such lipases.

SUMMARY OF THE INVENTION

The present disclosure provides amide, urea or sulfone amide linked benzothiazole compounds and their analogues, including stereoisomers, tautomers, pharmaceutically acceptable salts, or solvates thereof, which are useful as EL inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of dyslipidemias and the sequelae thereof.

The compounds of the invention may be used in therapy.

The compounds of the invention may be used for the manufacture of a medicament for the treatment and/or prophylaxis of dyslipidemias and the sequelae thereof.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

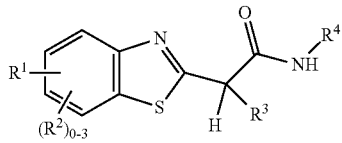
(I)

or a stereoisomer, a tautomer, a pharmaceutically acceptable salt, or a solvate thereof, wherein:

$R^1$ is independently selected from: halogen, CN, $CO_2(C_{1-4}$ alkyl), —CO—$R^j$, —CONH—$(CH_2)_m$—$R^j$,

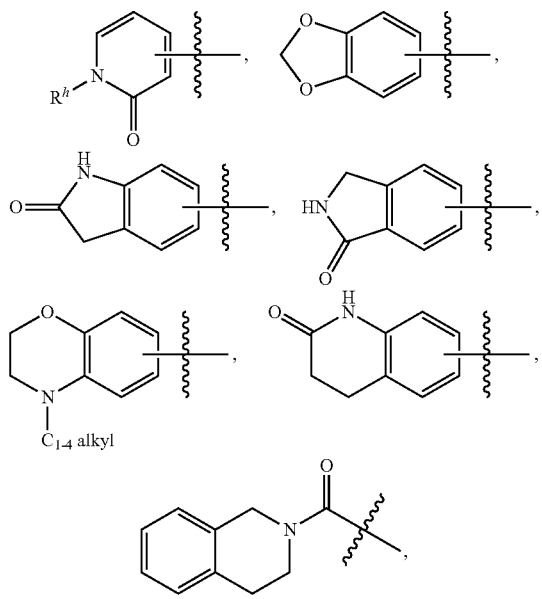

(phenyl substituted with 0-3 $R^a$), and (a 5- to 6-membered heteroaryl comprising: carbon atoms and 1-4 heteroatoms selected from N, $NR^c$, O, and $S(O)_p$; wherein said heteroaryl is substituted with 0-3 $R^a$);

$R^2$ is, independently at each occurrence, selected from: halogen, OH, $C_{1-4}$ alkyl, $C_{1-4}$ alkoxy, $C_{1-4}$ haloalkyl, $C_{1-4}$ haloalkoxy, CN, $NH_2$, $NO_2$, $NH(C_{1-4}$ alkyl), $N(C_{1-4}$ alkyl)$_2$, $CO_2H$, $CO_2(C_{1-4}$ alkyl), and $CONH_2$;

$R^3$ is independently selected from: —$SO_2R^5$ and —NH-$COR^6$;

$R^4$ independently selected from:

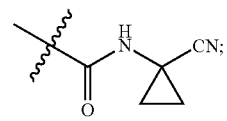

$R^5$ is independently selected from: $C_{1-6}$ alkyl substituted with 0-1 $R^g$, $C_{2-6}$ alkenyl, $C_{1-6}$ haloalkyl, $C_{1-6}$ alkoxy, —$(CH_2)_m$—$(O)_p$—$(C_{3-6}$ carbocycle substituted with 0-3 $R^b$), and —$(CH_2)_m$—$(O)_p$-(5- to 6-membered heterocycle comprising: carbon atoms and 1-4 heteroatoms selected from N, $NR^c$, O, and $S(O)_p$; wherein said heterocycle is substituted with 0-2 $R^b$);

$R^6$ is independently selected from: $C_{1-6}$ alkyl, $C_{2-6}$ alkenyl, $C_{1-6}$ alkoxy, $C_{1-4}$ haloalkyl, —$(CH_2)_m$—$(C_{3-6}$ carbocycle substituted with 0-3 $R^b$), —$(CH_2)_m$-(pyridyl substituted with 0-2 $R^b$), —NH($C_{1-4}$ alkyl), —NHCH$_2$CO$_2$($C_{1-4}$ alkyl), —NH (4-halo-Ph), and —NHBn, and

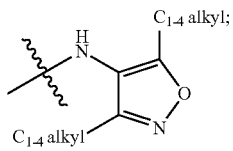

$R^7$ is independently selected from: $CONH_2$, $CONH(C_{1-4}$ alkyl), $CON(C_{1-4}$ alkyl)$_2$, $SO_2NHSO_2(C_{1-4}$ alkyl), $SO_2NH$ $(CH_2)_{2-4}CO_2(C_{1-4}$ alkyl), $NHSO_2NH_2$, $NHSO_2(C_{1-4}$ alkyl), $N(C_{1-4}$ alkyl)$SO_2NH_2$, $N(CO_2C_{1-4}$ alkyl)$SO_2(C_{1-4}$ alkyl), $SO_2R^{10}$, and

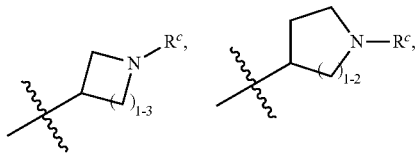

$R^8$ is independently selected from

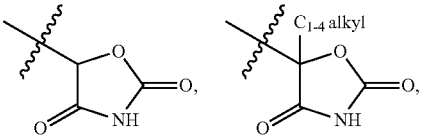

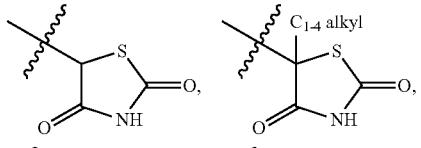

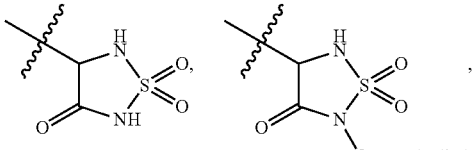

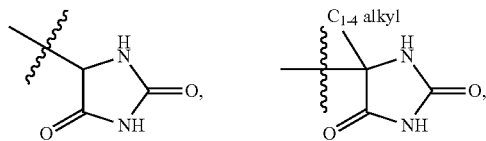

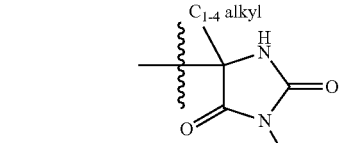

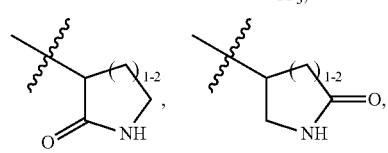

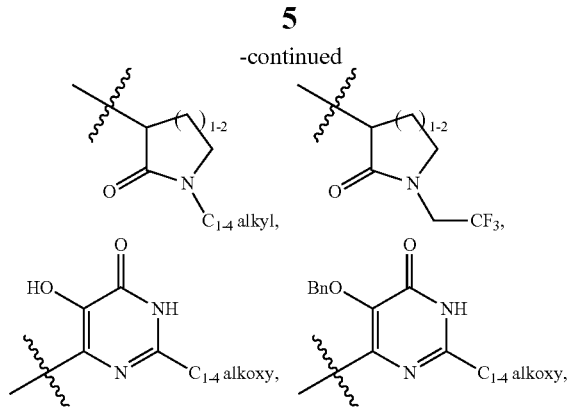

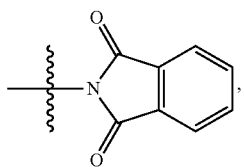 [SMILES: *N1C(=O)c2ccccc2C1=O ; ","]

phenyl and a 5- to 6-membered heteroaryl comprising: carbon atoms and 1-4 heteroatoms selected from N, $NR^c$, O, and $S(O)_p$; wherein said phenyl and heteroaryl are is substituted with 0-2 $R^{11}$;

$R^9$ is independently selected from: halogen, $C_{1-4}$ alkoxy, $C_{1-4}$ haloalkyl, $C_{1-4}$ haloalkoxy, $NH_2$, $CO_2H$, $CO_2(C_{1-4}$ alkyl), $SO_3H$, $CONHR^d$, $NHCONHR^d$, $NHCO_2R^d$,

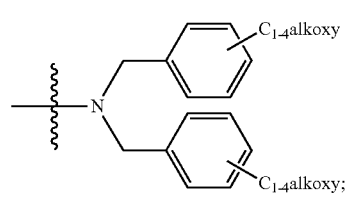

and 5- to 6-membered heterocycle comprising: carbon atoms and 1-4 heteroatoms selected from N, $NR^g$, O, and $S(O)_p$;

$R^{10}$ is independently selected from: OH, $C_{1-6}$ alkyl, $C_{2-6}$ alkenyl, $NH_2$, $NH(C_{1-6}$ alkyl substituted with 0-1 $CO_2(C_{1-4}$ alkyl)), $NH(C_{2-6}$ alkyl), $NH(C_{1-4}$ haloalkyl), NHPh, phenyl substituted with 0-2 halogens, and

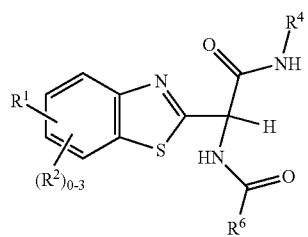

$R^{11}$ is, independently at each occurrence, selected from: halogen, $C_{1-4}$ alkyl, $C_{1-4}$ haloalkyl, $NH_2$, and phenyl;

$R^a$ is, independently at each occurrence, selected from: halogen, $C_{1-6}$ alkyl substituted with 0-1 $R^f$, $C_{1-4}$ alkoxy substituted with 0-1 $R^f$, $C_{1-6}$ haloalkyl, $C_{1-6}$ haloalkoxy, OH, CN, $NO_2$, $CO_2H$, $CO_2(C_{1-4}$ alkyl), $NR^gR^h$, $CONR^gR^h$, $CONR^gR^j$, $NHCOR^i$, $NHCO_2R^i$, $SO_2NR^gR^h$, $—(O)_n—(CH_2)_t—R^j$, and $—CO—R^j$;

$R^b$ is, independently at each occurrence, selected from: halogen, $C_{1-4}$ alkyl, $C_{1-4}$ alkoxy, $C_{1-4}$ haloalkyl, $C_{1-4}$ haloalkoxy, OH, CN, $NH_2$, $NO_2$, $NH(C_{1-4}$ alkyl), $N(C_{1-4}$ alkyl)$_2$, $CO_2H$, $CO_2(C_{1-4}$ alkyl), $SO_2(C_{1-4}$ alkyl), $CONH_2$, and $CONH(C_{1-4}$ alkyl);

$R^c$ is, independently at each occurrence, selected from: H, $C_{1-6}$ alkyl substituted with 0-1 $R^e$, $CO(C_{1-4}$ alkyl), $CO_2(C_{1-4}$ alkyl), $COBn$, $CO_2Bn$, $—(CH_2)_t$-piperidinyl, $—(CH_2)_t$-morpholinyl, $—(CH_2)_t$-piperazinyl, pyrimidinyl, $—(CH_2)_t—$($C_{3-6}$ carbocycle substituted with 0-2 $R^e$), and

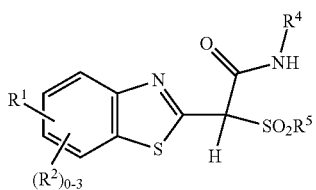

$R^d$ is, independently at each occurrence, selected from: $C_{1-6}$ alkyl and $—(CH_2)_t$-(phenyl substituted with 0-2 $R^e$);

$R^e$ is, independently at each occurrence, selected from: halogen, $C_{1-4}$ alkyl, $C_{1-4}$ alkoxy, $C_{1-4}$ haloalkyl, and $C_{1-4}$ haloalkoxy;

$R^f$ is, independently at each occurrence, selected from: OH, halogen, $C_{1-4}$ alkyl, $C_{1-4}$ alkoxy, $C_{1-4}$ haloalkyl, and $C_{1-4}$ haloalkoxy;

$R^g$ is, independently at each occurrence, selected from: H and $C_{1-4}$ alkyl;

$R^h$ is, independently at each occurrence, selected from: H, $C_{1-6}$ haloalkyl and $C_{1-6}$ alkyl substituted with 0-1 $R^f$;

$R^i$ is, independently at each occurrence, selected from: $C_{1-4}$ haloalkyl and $C_{1-4}$ alkyl substituted with 0-1 $R^f$;

$R^j$ is, independently at each occurrence: $C_{3-6}$ carbocycle or a 4- to 6-membered heterocycle comprising: carbon atoms and 1-4 heteroatoms selected from N, $NR^g$, O, and $S(O)_p$; wherein said carbocycle and heterocycle are substituted with 0-2 $R^f$;

m and t are, independently at each occurrence, selected from 0, 1, 2, and 3;

n is, independently at each occurrence, selected from 0 and 1;

p is, independently at each occurrence, selected from 0, 1, and 2; and s is, independently at each occurrence, selected from 1, 2, and 3.

In a second aspect, the present invention includes a compound of Formula (Ia) or (Ib):

or a stereoisomer, a tautomer, a pharmaceutically acceptable salt, or a solvate thereof, within the scope of the first aspect, wherein:

m and t are, independently at each occurrence, selected from 0, 1, and 2; and s is, independently at each occurrence, selected from 1 and 2.

In a third aspect, the present invention includes a compound of Formula (IIa) or (IIb):

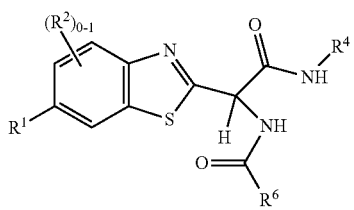
(IIa)

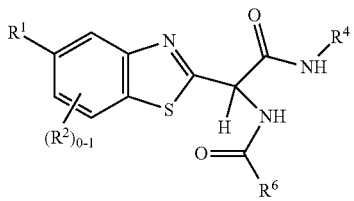
(IIb)

or a stereoisomer, a tautomer, a pharmaceutically acceptable salt, or a solvate thereof, within the scope of any of the first and second aspects; wherein:

R² is independently selected from: halogen and $C_{1-4}$ alkyl.

In a fourth aspect, the present invention includes a compound of Formula (Ia) (IIa) or (IIb), or a stereoisomer, a tautomer, a pharmaceutically acceptable salt, or a solvate thereof, within the scope of the first, second and third aspects, wherein:

R¹ is independently selected from: 4-halo-Ph, 6-halo-pyrid-3-yl, and

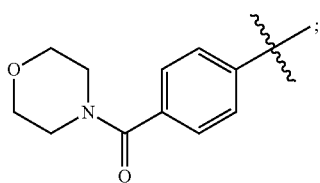 [SMILES: ";" ; *c1ccc(C(=O)N2CCOCC2)cc1];

R⁴ is

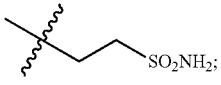;

and

R⁶ is independently selected from: $C_{1-4}$ alkyl, —CHF₂, NHBn, 4-CF₃-Ph, and pyrid-3-yl.

In a fifth aspect, the present invention includes a compound of Formula (IIIa) or (IIIb):

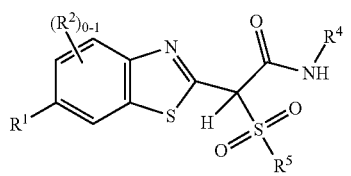
(IIIa)

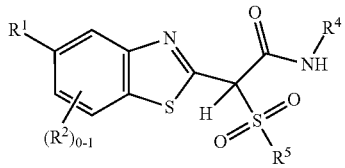
(IIIb)

or a stereoisomer, a tautomer, a pharmaceutically acceptable salt, or a solvate thereof, within the scope of any of the first and second aspects; wherein:

R² is independently selected from: halogen, $C_{1-4}$ alkyl and $C_{1-4}$ haloalkyl.

In a sixth aspect, the present invention includes a compound of Formula (I), (Ib), (IIIa) or (IIIb), or a stereoisomer, a tautomer, a pharmaceutically acceptable salt, or a solvate thereof, within the scope of the first, second and fifth aspects, wherein:

R¹ is independently selected from:

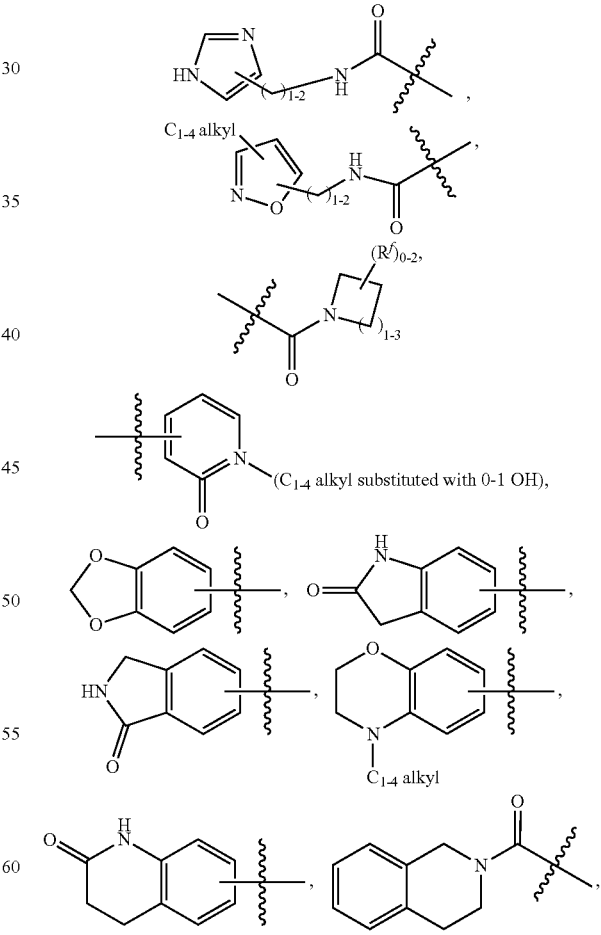

(phenyl substituted with 0-2 $R^a$), and (a heteroaryl substituted with 0-2 $R^a$ and selected from: isoxazolyl, pyrazolyl, 1-$R^c$-pyrazolyl, pyridyl, and pyrimidinyl);

$R^4$ is independently selected from:

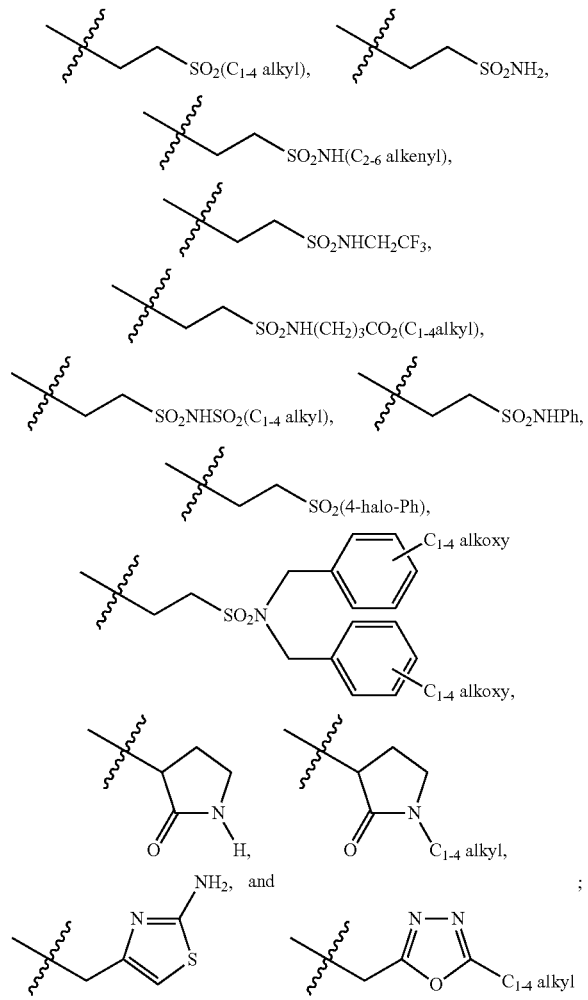

$R^5$ is independently selected from: $C_{1-4}$ alkyl substituted with 0-1 $R^9$, $C_{2-4}$ alkenyl, —$(CH_2)_{0-1}$—$C_{3-6}$ cycloalkyl, —$(CH_2)_{0-1}$-(phenyl substituted with 0-1 $R^b$) and

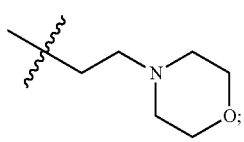 [SMILES: *CCN1CCOCC1]

$R^9$ is independently selected from: $C_{1-4}$ alkoxy, $C_{1-4}$ haloalkyl, $NH_2$, and $NHCO_2Bn$;

$R^a$ is, independently at each occurrence, selected from: OH, halogen, CN, $C_{1-4}$ alkyl substituted with 0-1 OH, $C_{1-4}$ alkoxy, —$O(CH_2)_{1-2}O(C_{1-4}$ alkyl), $C_{1-4}$ haloalkyl, $C_{1-4}$ haloalkoxy, $NH_2$, $CO_2H$, $CO_2$ $(C_{1-4}$ alkyl), $CONH_2$, $CONH$ $(C_{1-4}$ alkyl), $CONH(CH_2)_{2-3}OH$, $CONH(CH_2)_{1-3}O(C_{1-4}$ alkyl), $CON(C_{1-4}$ alkyl)$(CH_2)_{1-3}O(C_{1-4}$ alkyl), $CONH(C_{1-4}$ haloalkyl), $NHCO(C_{1-4}$ alkyl), $NHCO(C_{1-4}$ haloalkyl), $NHCO_2(C_{1-4}$ alkyl), $SO_2N(C_{1-4}$ alkyl)$_2$, $SO_2NH(CH_2)_{2-3}$ OH, pyrazolyl, —$(CH_2)_{0-2}$-morpholinyl, —CO-morpholinyl, piperazinyl,

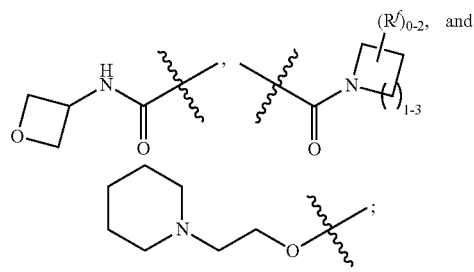

$R^b$ is independently selected from: halogen and $C_{1-4}$ haloalkyl;

$R^c$ is, independently at each occurrence, selected from: H, $C_{1-4}$ alkyl, —$(CH_2)_2(C_{1-4}$ alkoxy), —$(CH_2)_{0-2}$-(phenyl substituted with 0-1 halo), —$(CH_2)_{0-2}$-piperidinyl, —$(CH_2)_{0-2}$-morpholinyl, and

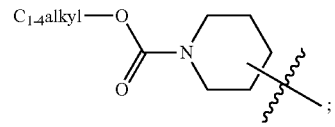

and $R^f$ is, independently at each occurrence, selected from: OH, halogen, $C_{1-4}$ alkyl, $C_{1-4}$ haloalkyl, $C_{1-4}$ alkoxy, and $C_{1-4}$ haloalkoxy.

In a seventh aspect, the present invention includes a compound of Formula (I), (Ib), (IIIa) or (IIIb), or a stereoisomer, a tautomer, a pharmaceutically acceptable salt, or a solvate thereof, within the scope of any of the first, second, fifth and sixth aspects, wherein:

$R^1$ is independently selected from: Ph, 3-halo-Ph, 4-halo-Ph, 3-$C_{1-4}$ alkoxy-Ph, 4-$CH_2OH$-Ph, 3-CN-Ph, 4-CN-Ph, 4-$CO_2H$-Ph, 4-$CO_2(C_{1-4}$ alkyl)-Ph, 3-NHCO($C_{1-4}$ alkyl)-Ph, 4-NHCO($C_{1-4}$ alkyl)-Ph, 4-(pyrazol-1-yl)-Ph, 2-$C_{1-4}$ alkoxy-pyridyl, pyrimidinyl and

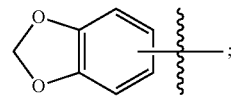

$R^4$ is independently selected from:

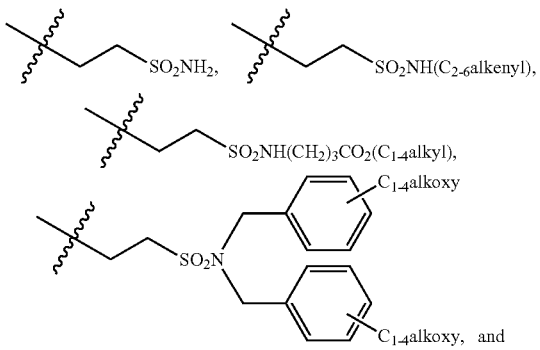

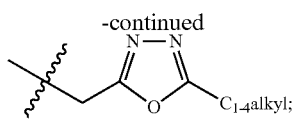

$R^5$ is independently selected from: $C_{1-4}$ alkyl substituted with 0-1 $R^9$, and $C_{2-4}$ alkenyl, Bn, and 4-halo-Bn; and $R^9$ is independently selected from: $C_{1-4}$ alkoxy, $C_{1-4}$ haloalkyl, $NH_2$, and $NHCO_2Bn$.

In an eighth aspect, the present invention includes a compound of Formula (I), (Ib), (IIIa) or (IIIb), or a stereoisomer, a tautomer, a pharmaceutically acceptable salt, or a solvate thereof, within the scope of any of the first, second, fifth, sixth and seventh aspects, wherein:

$R^1$ is independently selected from: Ph, 3-halo-Ph, 4-halo-Ph, 3-$C_{1-4}$ alkoxy-Ph, 4-$CH_2OH$-Ph, 3-CN-Ph, 4-CN-Ph, 4-$CO_2H$-Ph, 4-$CO_2(C_{1-4}$ alkyl)-Ph, 3-NHCO($C_{1-4}$ alkyl)-Ph, 4-NHCO($C_{1-4}$ alkyl)-Ph, 4-(pyrazol-1-yl)-Ph, pyrimidinyl and $R^4$ is

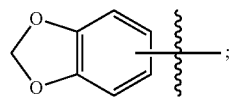

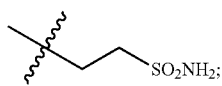

$R^5$ is independently selected from: $C_{1-4}$ alkyl substituted with 0-1 $R^9$, and $C_{2-4}$ alkenyl, Bn, and 4-halo-Bn; and $R^9$ is independently selected from: $C_{1-4}$ alkoxy, $C_{1-4}$ haloalkyl, $NH_2$, and $NHCO_2Bn$.

In a ninth aspect, the present invention includes a compound of Formula (I), (Ib), (IIIa) or (IIIb), or a stereoisomer, a tautomer, a pharmaceutically acceptable salt, or a solvate thereof, within the scope of any of the first, second, fifth, sixth, seventh and eighth aspects, wherein:

$R^1$ is independently selected from: Ph, 3-F-Ph, 4-F-Ph, 3-OMe-Ph, 4-$CH_2OH$-Ph, 3-CN-Ph, 4-CN-Ph, 4-$CO_2H$-Ph, 4-$CO_2Me$-Ph, 3-NHCOMe-Ph, 4-NHCOMe-Ph, 4-(pyrazol-1-yl)-Ph, pyrimidin-5-yl, and

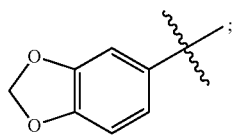 [SMILES: ";" ; *c1ccc2c(c1)OCO2]

and $R^5$ is independently selected from: Me, Et, Pr, i-Bu,

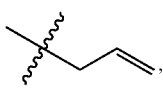

Bn, 4-F-Bn, —$(CH_2)_2OMe$, —$(CH_2)_2CF_3$, —$(CH_2)_2NH_2$, and —$(CH_2)_2NHCO_2Bn$.

In a tenth aspect, the present invention includes a compound of Formula (I), (Ib), (IIIa) or (IIIb), or a stereoisomer, a tautomer, a pharmaceutically acceptable salt, or a solvate thereof, within the scope of any of the first, second, fifth, sixth and seventh aspects, wherein:

$R^1$ is Ph;

$R^4$ is independently selected from:

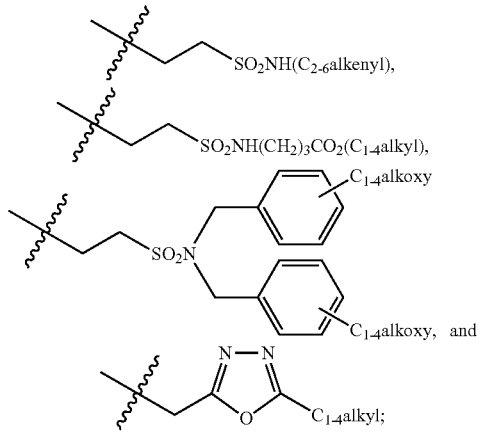

$R^5$ is independently selected from: $C_{1-4}$ alkyl, $C_{2-4}$ alkenyl, —$(CH_2)_2O(C_{1-4}$ alkyl), and —$(CH_2)_2NHCO_2Bn$.

In an eleventh aspect, the present invention includes a compound of Formula (Ib), (IIIa) or (IIIb), or a stereoisomer, a tautomer, a pharmaceutically acceptable salt, or a solvate thereof, within the scope of any of the first, second, fifth, sixth, seventh and tenth aspects, wherein:

$R^4$ is independently selected from:

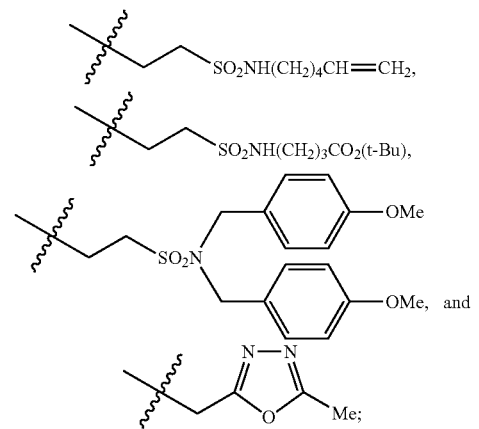

$R^5$ is independently selected from: Me,

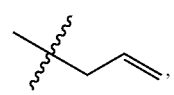

—$(CH_2)_2OMe$, and —$(CH_2)_2NHCO_2Bn$.

In a twelfth aspect, the present invention includes a compound of Formula (I), (Ib), (IIIa) or (IIIb), or a stereoisomer, a tautomer, a pharmaceutically acceptable salt, or a solvate thereof, within the scope of any of the first, second, fifth and sixth aspects, wherein:

$R^1$ is independently selected from:

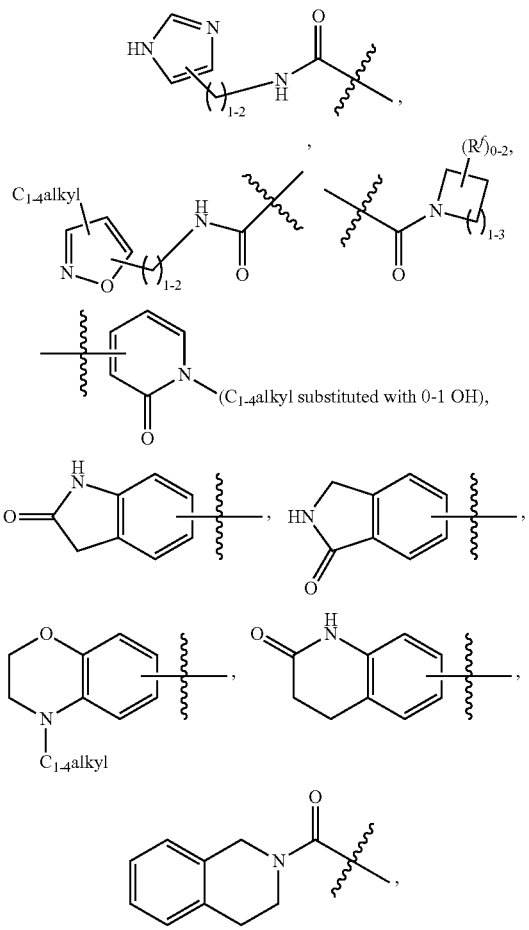

(phenyl substituted with 0-2 $R^a$), and (a heteroaryl substituted with 0-2 Ra and selected from: isoxazolyl, pyrazolyl, 1-$R^c$-pyrazolyl, pyridyl, and pyrimidinyl);

$R^4$ is independently selected from:

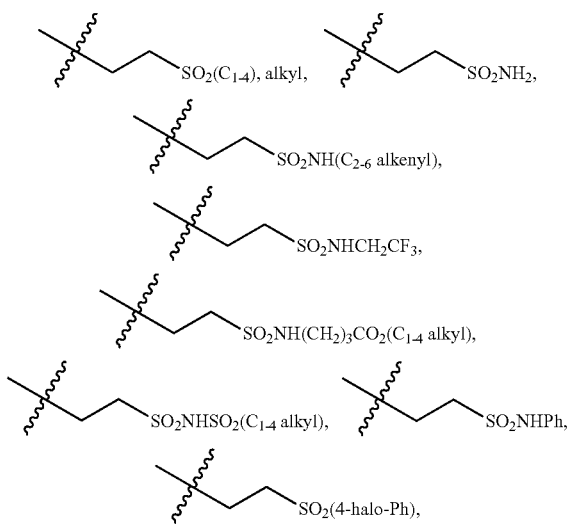

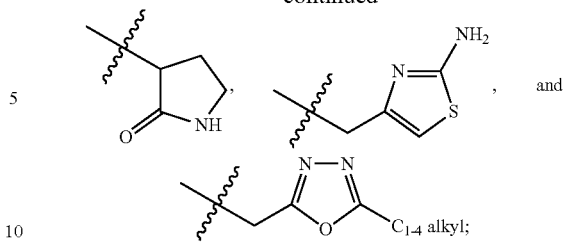

$R^5$ is independently selected from: $C_{1-4}$ alkyl substituted with 0-1 $R^9$, —$(CH_2)_{0-1}$—$C_{3-6}$ cycloalkyl, benzyl substituted with 0-1 Rb, and

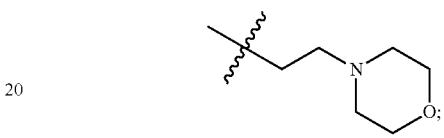

$R^9$ is independently selected from: $C_{1-4}$ alkoxy, $C_{1-4}$ haloalkyl, $NH_2$, and $NHCO_2Bn$;

$R^a$ is, independently at each occurrence, selected from: OH, halogen, $C_{1-4}$ alkyl substituted with 0-1 OH, $C_{1-4}$ alkoxy, —$O(CH_2)_2O(C_{1-4}$ alkyl), $C_{1-4}$ haloalkyl, $C_{1-4}$ haloalkoxy, $NH_2$, $CONH_2$, $CONH(C_{1-4}$ alkyl), $CONH(CH_2)_{2-3}OH$, $CONH(CH_2)_{1-3}O(C_{1-4}$ alkyl), $CON(C_{1-4}$ alkyl)$(CH_2)_{1-3}O$ ($C_{1-4}$ alkyl), $CONH(C_{1-4}$ haloalkyl), $NHCO_2(C_{1-4}$ alkyl), $SO_2N(C_{1-4}$ alkyl)$_2$, $SO_2NH(CH_2)_{2-3}OH$, —$(CH_2)_{0-2}$-morpholinyl, —CO-morpholinyl, piperazinyl,

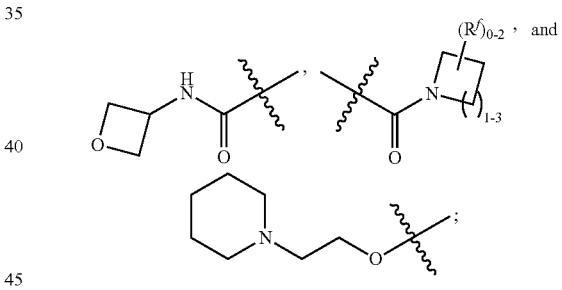

$R^b$ is independently selected from: CN, halogen and $C_{1-4}$ haloalkyl;

$R^c$ is, independently at each occurrence, selected from: H, $C_{1-4}$ alkyl substituted with 0-1 $C_{1-4}$ alkoxy, —$(CH_2)_{0-2}$-(phenyl substituted with 0-1 halo), —$(CH_2)_{0-2}$-piperidinyl, —$(CH_2)_{0-2}$-morpholinyl, and

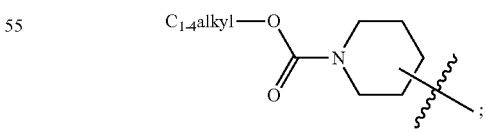

$R^f$ is, independently at each occurrence, selected from: OH, CN, halogen, $C_{1-4}$ alkyl, and $C_{1-4}$ alkoxy.

In a thirteenth aspect, the present invention includes a compound of Formula (I), (Ib), (IIIa) or (IIIb), or a stereoisomer, a tautomer, a pharmaceutically acceptable salt, or a solvate thereof, within the scope of any of the first, second, fifth, sixth and twelfth aspects, wherein:

$R^1$ is independently selected from: 3-$(CH_2)_2$OH-Ph, 4-$(CH_2)_2$OH-Ph, 4-O$(CH_2)_2$O($C_{1-4}$ alkyl)-Ph, 4-$C_{1-4}$ haloalkoxy-Ph, 4-$NH_2$-Ph, 4-$CONH_2$-Ph, 4-CONH($C_{1-4}$ alkyl)-Ph, 4-CONH$(CH_2)_2$OH-Ph, 3-CONH$(CH_2)_2$O($C_{1-4}$ alkyl)-Ph, 4-CONH$(CH_2)_2$O($C_{1-4}$ alkyl)-Ph, 4-CONH($C_{1-4}$ haloalkyl)-Ph, 3-CON($C_{1-4}$ alkyl)$(CH_2)_2$O($C_{1-4}$ alkyl)-Ph, 4-NHCO$_2$($C_{1-4}$ alkyl)-Ph, 4-SO$_2$N($C_{1-4}$ alkyl)-2-Ph, 4-SO$_2$NH$(CH_2)_2$OH-Ph, 1H-3-$C_{1-4}$ haloalkyl-pyrazol-4-yl, 1-$C_{1-4}$ alkyl-pyrazol-4-yl, 1-Bn-pyrazol-4-yl, 3-$C_{1-4}$ alkyl-pyrid-4-yl, 6-OH-pyrid-2-yl, 6-OH-pyrid-3-yl, 2-OH-pyrid-4-yl, 6-$C_{1-4}$ alkoxy-pyrid-2-yl, 2-$C_{1-4}$ alkoxy-pyrid-3-yl, 6-$C_{1-4}$ alkoxy-pyrid-3-yl, 2-$C_{1-4}$ alkoxy-pyrid-4-yl, 6-halo-pyrid-3-yl, 2-halo-pyrid-4-yl, 6-$C_{1-4}$ haloalkyl-pyrid-3-yl, 5-$C_{1-4}$ alkyl-6-halo-pyrid-3-yl, 3-halo-6-$C_{1-4}$ alkoxy-pyrid-4-yl, pyrimidin-5-yl,

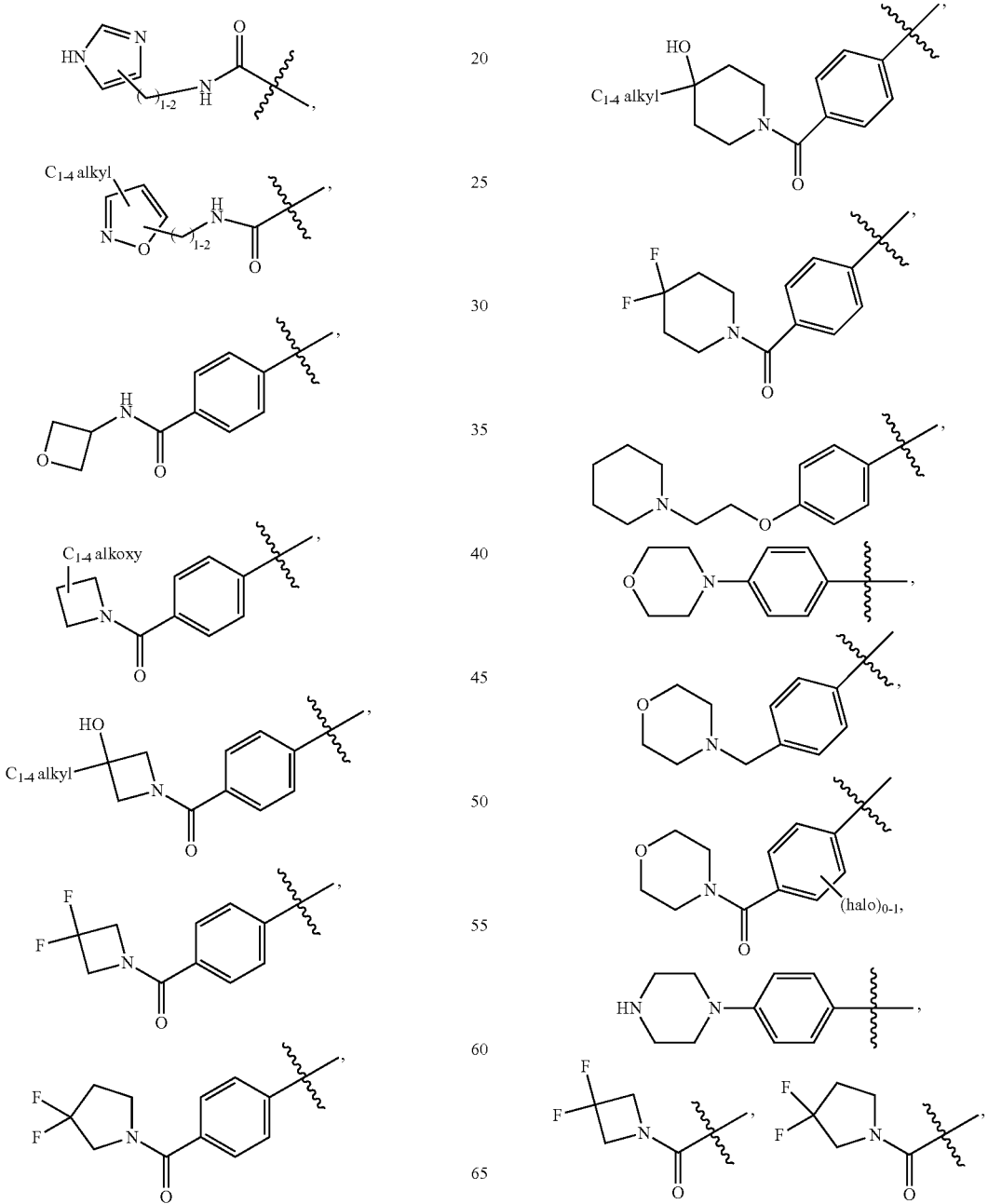

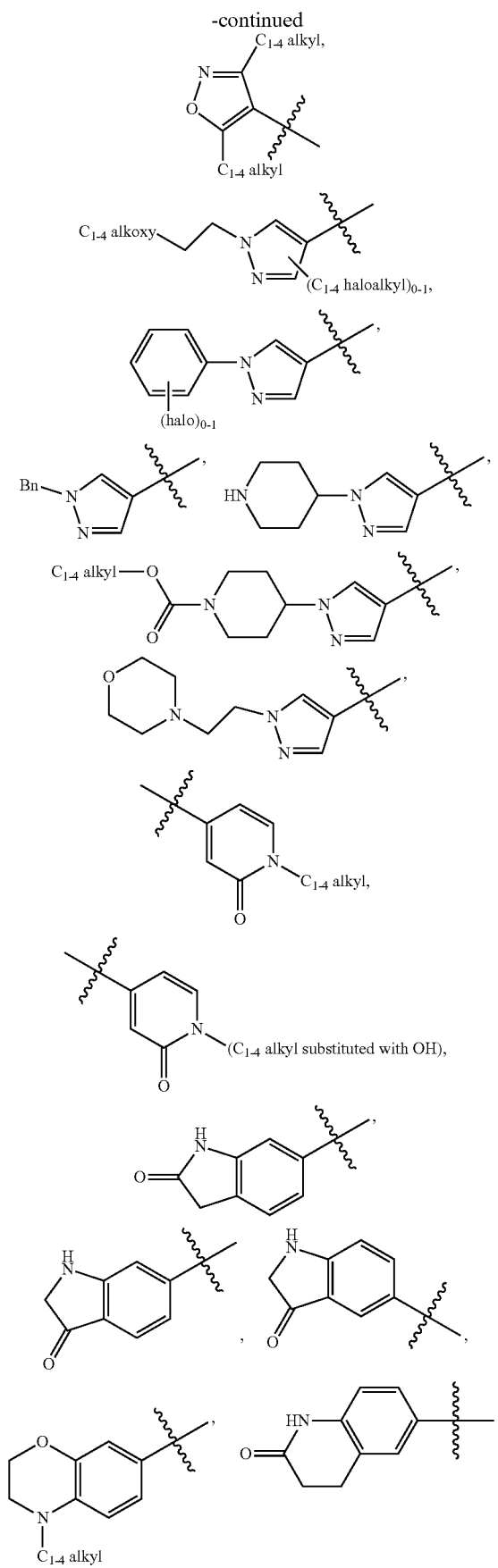

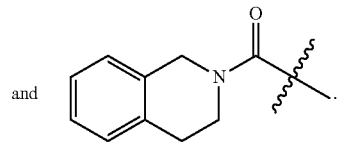

and

In a fourteenth aspect, the present invention includes a compound of Formula (I), (Ib), (IIIa) or (IIIb), or a stereoisomer, a tautomer, a pharmaceutically acceptable salt, or a solvate thereof, within the scope of any of the first, second, fifth, sixth, twelfth and thirteenth aspects, wherein:

$R^1$ is independently selected from: 3-$(CH_2)_2$OH-Ph, 4-$(CH_2)_2$OH-Ph, 4-O$(CH_2)_2$OMe-Ph, 4-OCF$_3$-Ph, 4-NH$_2$-Ph, 4-CONH$_2$-Ph, 4-CONH(t-Bu)-Ph, 4-CONH$(CH_2)_2$OH-Ph, 3-CONH$(CH_2)_2$OMe-Ph, 4-CONH$(CH_2)_2$OMe-Ph, 4-CON(Me)$(CH_2)_2$OMe-Ph, 4-CONHCH$_2$CF$_3$-Ph, 4-NHCO$_2$Me-Ph, 4-NHCO$_2$(t-Bu)-Ph, 4-SO$_2$N(Me)$_2$-Ph, 4-SO$_2$NH$(CH_2)_2$OH-Ph, 1H-3-CF$_3$-pyrazol-4-yl, 1-Me-pyrazol-4-yl, 1-(i-Bu)-pyrazol-4-yl, 1-Bn-pyrazol-4-yl, 3-Me-pyrid-4-yl, 6-OH-pyrid-2-yl, 6-OH-pyrid-3-yl, 2-OH-pyrid-4-yl, 6-OMe-pyrid-2-yl, 2-OMe-pyrid-3-yl, 6-OMe-pyrid-3-yl, 2-OMe-pyrid-4-yl, 6-F-pyrid-3-yl, 2-F-pyrid-4-yl, 2-Cl-pyrid-4-yl, 6-CF$_3$-pyrid-3-yl, 5-Me-6-F-pyrid-3-yl, 3-F-6-OMe-pyrid-4-yl, pyrimidin-5-yl,

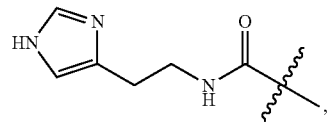

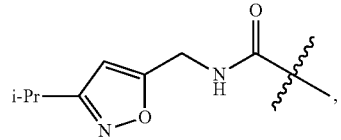

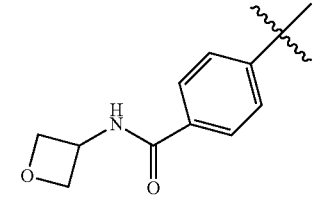

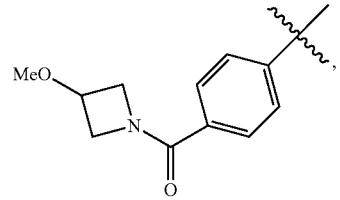

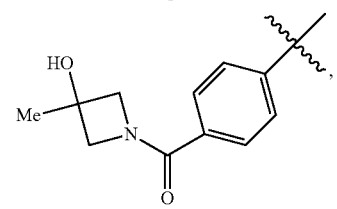

-continued
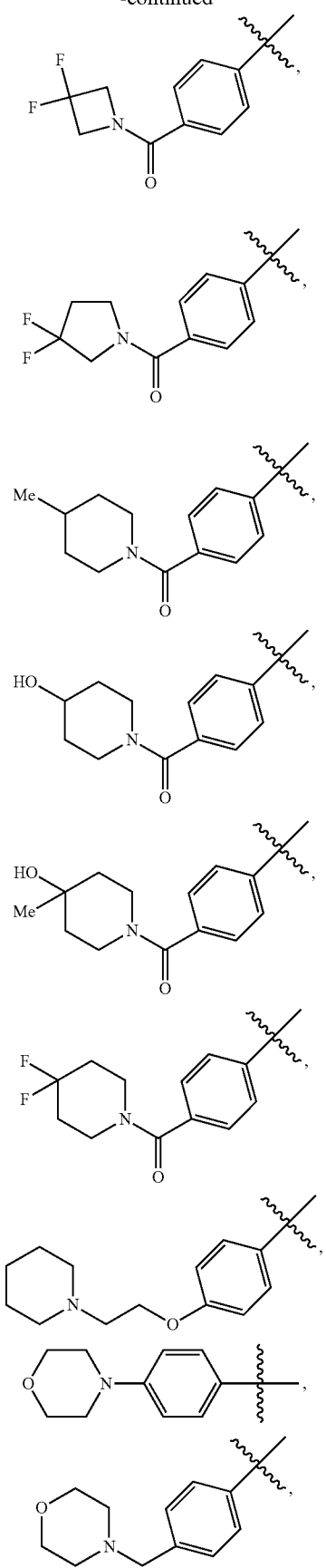
-continued
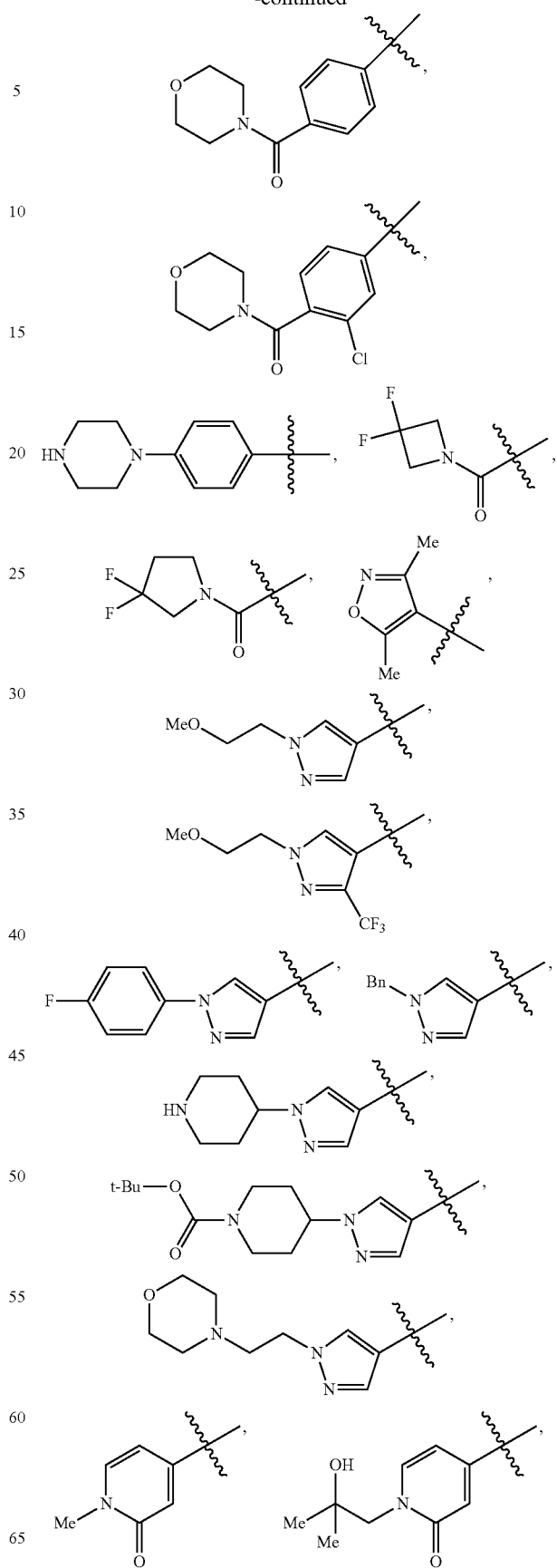

-continued

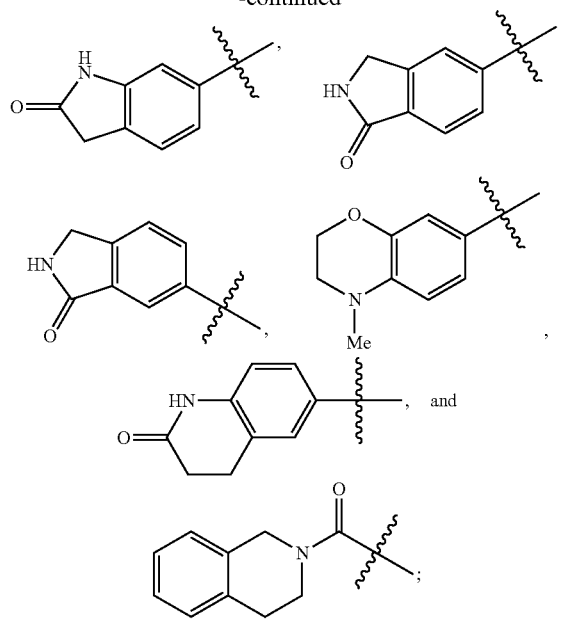

R⁴ is independently selected from:

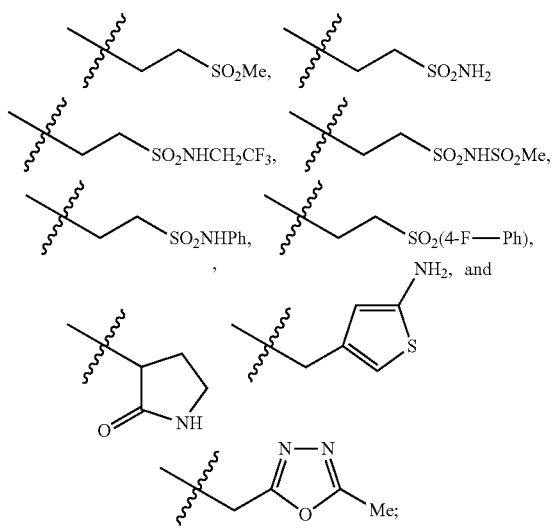

and
R⁵ is independently selected from: Me, Pr, i-Pr, i-Bu, —(CH$_2$)$_2$OMe, —(CH$_2$)$_2$CF$_3$, —(CH$_2$)$_3$CF$_3$, —(CH$_2$)$_2$NH$_2$, cyclopropylmethyl, Bn, 4-F-Bn, 4-CF$_3$-Bn, —(CH$_2$)$_2$NHCO$_2$Bn, and

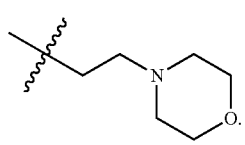 [SMILES: *CCN1CCOCC1]

In another aspect, the present invention provides a compound of Formula (I), or a stereoisomer, a tautomer, a pharmaceutically acceptable salt, or a solvate thereof, within the scope of the first aspect, wherein:

R¹ is independently selected from: phenyl and a 5- to 6-membered heteroaryl comprising: carbon atoms and 1-4 heteroatoms selected from N, NR$^c$, O, and S(O)$_p$; wherein each phenyl and heteroaryl are substituted with 0-3 R$^a$;

R² is, independently at each occurrence, selected from: halogen, OH, C$_{1-4}$ alkyl, C$_{1-4}$ alkoxy, C$_{1-4}$ haloalkyl, C$_{1-4}$ haloalkoxy, CN, NH$_2$, NO$_2$, NH(C$_{1-4}$ alkyl), N(C$_{1-4}$ alkyl)$_2$, CO$_2$H, CO$_2$(C$_{1-4}$ alkyl), and CONH$_2$;

R³ is independently selected from: —SO$_2$R⁵ and —NH-COR⁶;

R⁴ independently selected from:

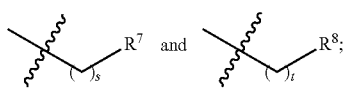

R⁵ is independently selected from: C$_{1-6}$ alkyl, C$_{2-6}$ alkenyl, —(CH$_2$)$_m$CHF$_2$, —(CH$_2$)$_m$CF$_3$, —(CH$_2$)$_m$—(O)$_m$—(C$_{3-6}$ carbocycle substituted with 0-3 R$^b$), —(CH$_2$)$_m$—(O)$_m$-(pyridyl substituted with 0-2 R$^b$), —(CH$_2$)$_s$NHCONHR$^d$, —(CH$_2$)$_s$NHCO$_2$R$^d$,

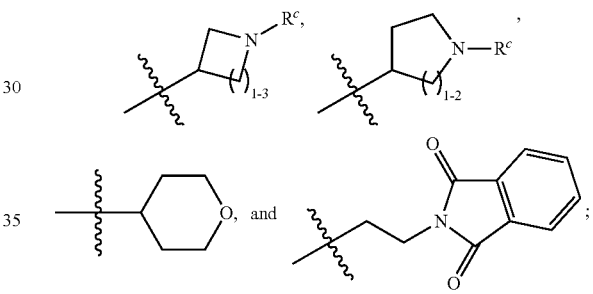

R⁶ is independently selected from: C$_{1-6}$ alkyl, C$_{2-6}$ alkenyl, C$_{1-6}$ alkoxy, —(CH$_2$)$_m$CHF$_2$, —(CH$_2$)$_m$CF$_3$, —(CH$_2$)$_m$—(C$_{3-6}$ carbocycle substituted with 0-3 R$^b$), —(CH$_2$)$_m$-(pyridyl substituted with 0-2 R$^b$), —NH(C$_{1-4}$ alkyl), —NHCH$_2$CO$_2$(C$_{1-4}$ alkyl), —NH(4-halo-Ph), —NHBn, and

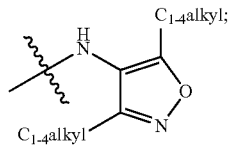

R⁷ is independently selected from: CONH$_2$, CONH(C$_{1-4}$ alkyl), CON(C$_{1-4}$ alkyl)$_2$, SO$_2$OH, SO$_2$(4-halo-Ph), SO$_2$NH$_2$, SO$_2$NHCH$_2$CF$_3$, SO$_2$NHPh, NHSO$_2$NH$_2$, NHSO$_2$(C$_{1-4}$ alkyl), N(C$_{1-4}$ alkyl)SO$_2$NH$_2$, N(CO$_2$C$_{1-4}$ alkyl)SO$_2$(C$_{1-4}$ alkyl), and

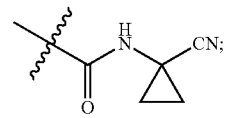 [SMILES: *C(=O)NC1(C#N)CC1]

$R^8$ is independently selected from:

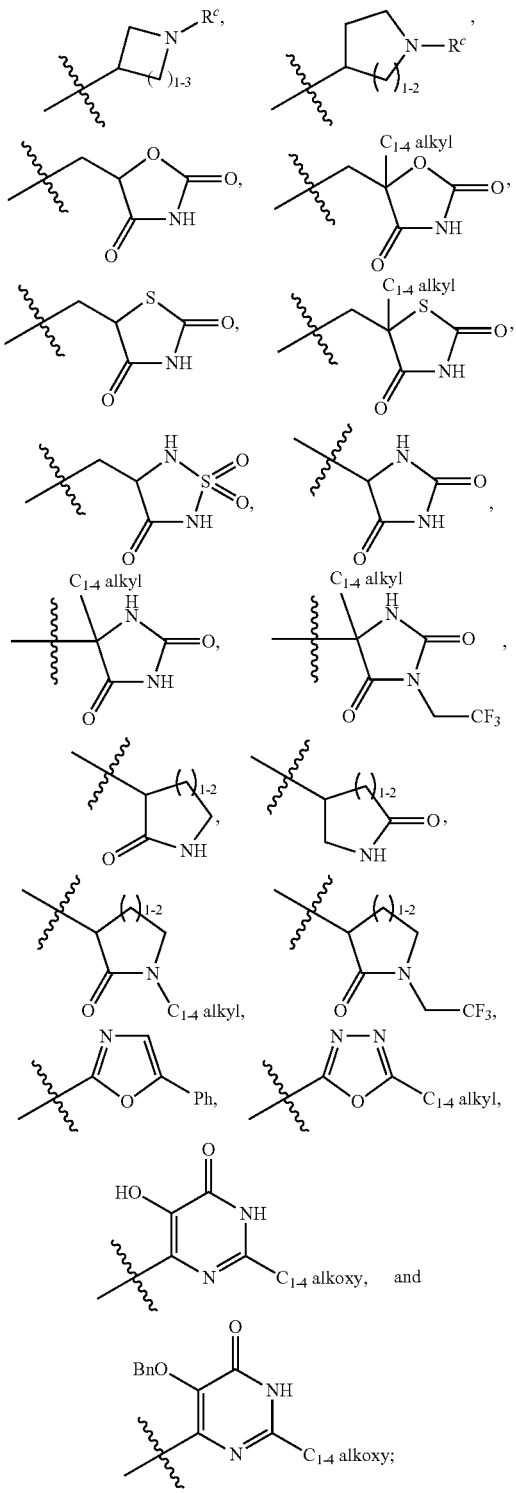

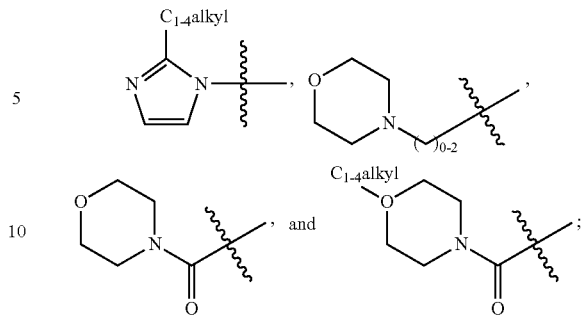

$R^b$ is, independently at each occurrence, selected from: halogen, $C_{1-4}$ alkyl, $C_{1-4}$ alkoxy, $C_{1-4}$ haloalkyl, $C_{1-4}$ haloalkoxy, OH, CN, $NH_2$, $NO_2$, $NH(C_{1-4}$ alkyl), $N(C_{1-4}$ alkyl)$_2$, $CO_2H$, $CO_2(C_{1-4}$ alkyl), $SO_2(C_{1-4}$ alkyl), $CONH_2$, and $CONH(C_{1-4}$ alkyl);

$R^c$ is, independently at each occurrence, selected from: H, $C_{1-6}$ alkyl, $CO(C_{1-4}$ alkyl), $CO_2(C_{1-4}$ alkyl), COBn, $CO_2Bn$,

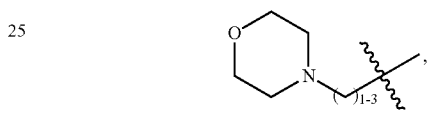

pyrimidinyl and —$(CH_2)_t$—($C_{3-6}$ carbocycle substituted with 0-2 $R^e$);

$R^d$ is, independently at each occurrence, selected from: $C_{1-6}$ alkyl and —$(CH_2)_t$-(phenyl substituted with 0-2 $R^e$);

$R^e$ is, independently at each occurrence, selected from: halogen, $C_{1-4}$ alkyl, $C_{1-4}$ alkoxy, $C_{1-4}$ haloalkyl, and $C_{1-4}$ haloalkoxy;

m and t are, independently at each occurrence, selected from 0, 1, 2, and 3;

n is, independently at each occurrence, selected from 0 and 1;

p is, independently at each occurrence, selected from 0, 1, and 2; and s is, independently at each occurrence, selected from 1, 2, and 3.

In another aspect, the present invention includes a compound of Formula (I), (Ia) or (Ib), or a stereoisomer, a tautomer, a pharmaceutically acceptable salt, or a solvate thereof, within the scope of the first or second aspect, wherein:

$R^4$ is independently selected from:

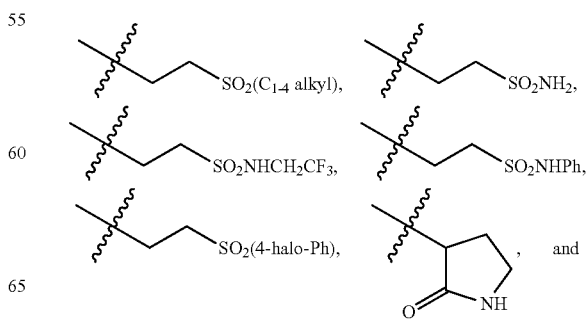

$R^a$ is, independently at each occurrence, selected from: halogen, $C_{1-6}$ alkyl substituted with 0-1 OH, $C_{1-4}$ alkoxy, $C_{1-6}$ haloalkyl, $C_{1-6}$ haloalkoxy, OH, CN, $NO_2$, $NH_2$, $NH(C_{1-4}$ alkyl), $N(C_{1-4}$ alkyl)$_2$, $CO_2H$, $CO_2(C_{1-4}$ alkyl), $CONH_2$, $CONH(C_{1-4}$ alkyl), $SO_2NH_2$, $SO_2N(C_{1-4}$ alkyl)$_2$, $CONH(CH_2)_{1-3}CF_3$, pyrazolyl, -continued

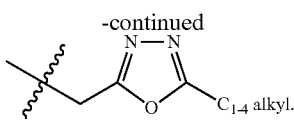

In another aspect, the present invention includes a compound of Formula (I), (Ib) or (IIIa), or a stereoisomer, a tautomer, a pharmaceutically acceptable salt, or a solvate thereof, wherein:

R[1] is independently selected from: Ph, 4-CO$_2$(C$_{1-4}$ alkyl)-Ph, 4-NH$_2$-Ph, 4-CONH$_2$-Ph, 4-SO$_2$N(C$_{1-4}$ alkyl)-2-Ph, 4-NHCO$_2$(C$_{1-4}$ alkyl)-Ph, 4-(pyrazol-1-yl)-Ph, 3-C$_{1-4}$ alkyl-pyrid-4-yl, 6-C$_{1-4}$ alkoxy-pyrid-3-yl, 6-halo-pyrid-3-yl, 3-halo-pyrid-4-yl, 6-CF$_3$-pyrid-3-yl,

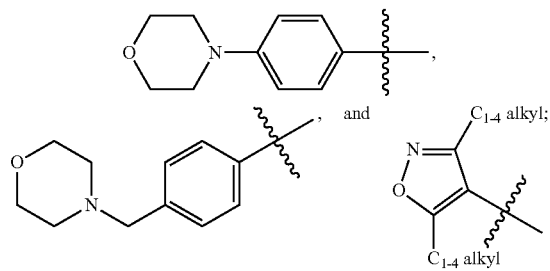

R[4] is independently selected from:

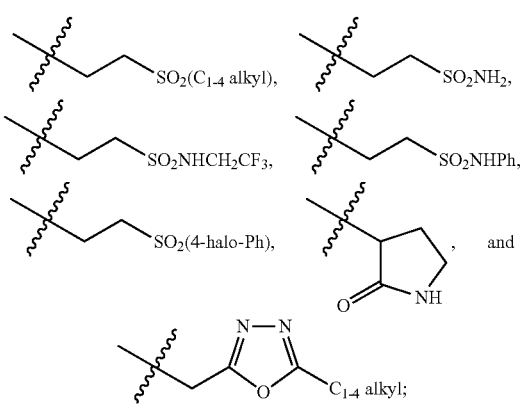

and

R[5] is independently selected from: C$_{1-4}$ alkyl, C$_{2-4}$ alkenyl, Bn, 4-CF$_3$-Bn, and —(CH$_2$)$_{1-3}$CF$_3$.

In another aspect, the present invention includes a compound of Formula (I), (Ib) or (IIIa), or a stereoisomer, a tautomer, a pharmaceutically acceptable salt, or a solvate thereof, wherein:

R[1] is independently selected from: Ph, 4-CO$_2$(C$_{1-4}$ alkyl)-Ph and 4-(pyrazol-1-yl)-Ph;

R[4] is

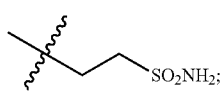

and

R[5] is independently selected from: C$_{1-4}$ alkyl and C$_{2-4}$ alkenyl.

In another aspect, the present invention includes a compound of Formula (I), (Ib) or (IIIa), or a stereoisomer, a tautomer, a pharmaceutically acceptable salt, or a solvate thereof, wherein:

R[1] is independently selected from: Ph, 4-CO$_2$Me-Ph and 4-(pyrazol-1-yl)-Ph; and R[5] is independently selected from: Me and

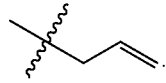

In another aspect, the present invention includes a compound of Formula (I), (Ib) or (IIIa), or a stereoisomer, a tautomer, a pharmaceutically acceptable salt, or a solvate thereof, within the scope of any of the first, second, third, sixth and seventh aspects, wherein:

R[1] is independently selected from: 4-NH$_2$-Ph, 4-CONH$_2$-Ph, 4-SO$_2$N(C$_{1-4}$ alkyl)-2-Ph, 4-NHCO$_2$(C$_{1-4}$ alkyl)-Ph, 3-C$_{1-4}$ alkyl-pyrid-4-yl, 6-C$_{1-4}$ alkoxy-pyrid-3-yl, 6-halo-pyrid-3-yl, 3-halo-pyrid-4-yl, 6-CF$_3$-pyrid-3-yl,

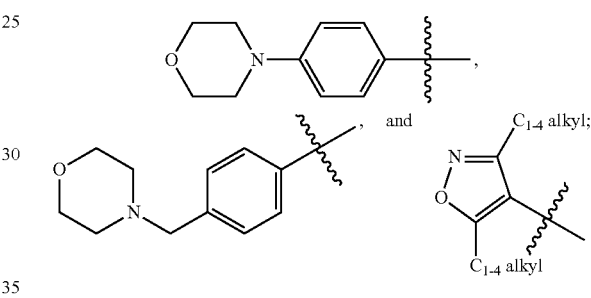

R[4] is independently selected from:

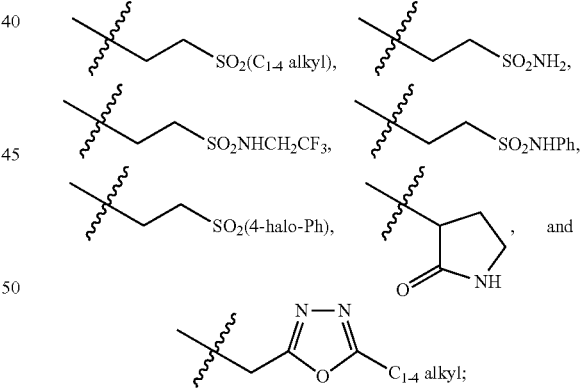

and

R[5] is independently selected from: C$_{1-4}$ alkyl, Bn, 4-CF$_3$-Bn, and —(CH$_2$)$_{1-3}$CF$_3$.

In another aspect, the present invention includes a compound of Formula (I), (Ib) or (IIIa), or a stereoisomer, a tautomer, a pharmaceutically acceptable salt, or a solvate thereof, within the scope of any of the first, second, third, sixth and tenth aspects, wherein:

R[1] is independently selected from: 4-NH$_2$-Ph, 4-CONH$_2$-Ph, 4-SO$_2$N(Me)$_2$-Ph, 4-NHCO$_2$Me-Ph, 3-Me-pyrid-4-yl, 6-OMe-pyrid-3-yl, 6-F-pyrid-3-yl, 3-F-pyrid-4-yl, 3-Cl-pyrid-4-yl, 6-CF$_3$-pyrid-3-yl,

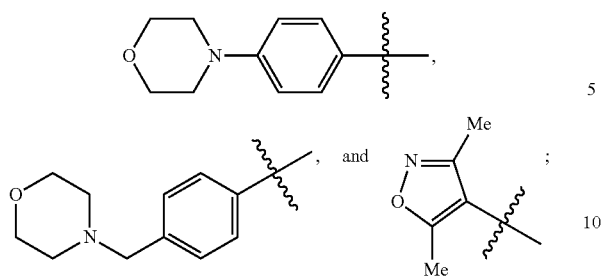

R⁴ is independently selected from:

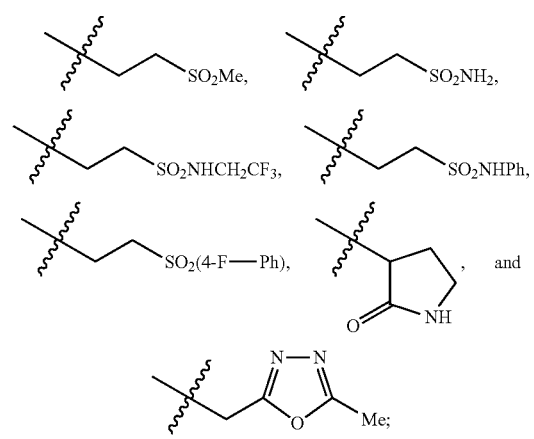

and

R⁵ is independently selected from: Me, Pr, i-Pr, Bn, 4-CF$_3$-Bn, and —(CH$_2$)$_2$CF$_3$.

In another aspect, the present invention includes a compound of Formula (I), (Ib), (IIIa) or (IIIb), or a stereoisomer, a tautomer, a pharmaceutically acceptable salt, or a solvate thereof, wherein:

R$^1$ is independently selected from: 4-CO$_2$H-Ph, 4-NHCO(C$_{1-4}$ alkyl)-Ph, 4-CONH$_2$-Ph, 4-CONH(CH$_2$)$_{2-3}$OH-Ph, 4-CONH(CH$_2$)$_2$O(C$_{1-4}$ alkyl)-Ph, 4-CONH(CH$_2$)C(C$_{1-4}$ alkyl)$_2$OH-Ph, 4-CONH(C$_{3-6}$ cycloalkyl)-Ph, 3-halo-4-CON(C$_{1-4}$ alkyl)-2-Ph, 6-halo-pyrid-3-yl, 6-OH-pyrid-2-yl, 6-OH-pyrid-3-yl, 2-OH-pyrid-4-yl, 2-OH-3-halo-pyrid-4-yl, 2-OH-5-halo-pyrid-4-yl, pyrimidin-5-yl,

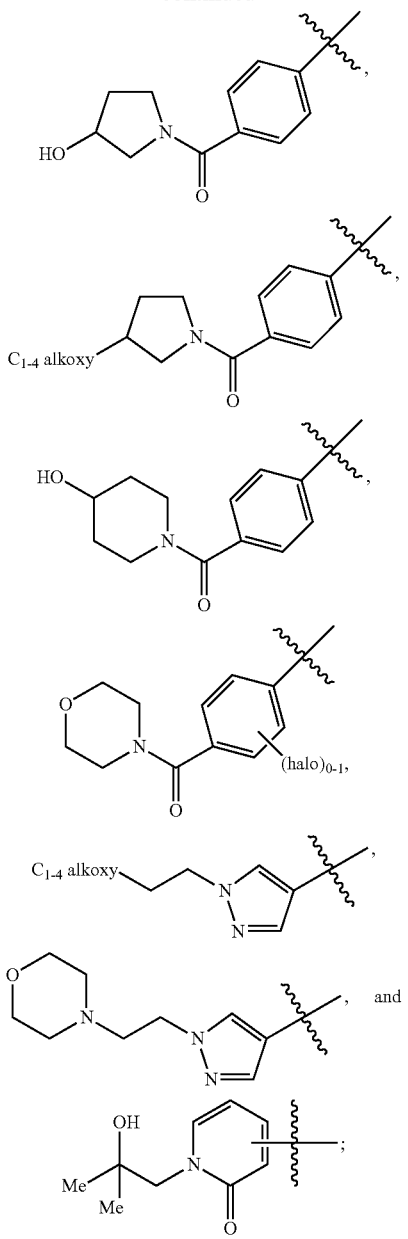

R$^4$ is independently selected from:

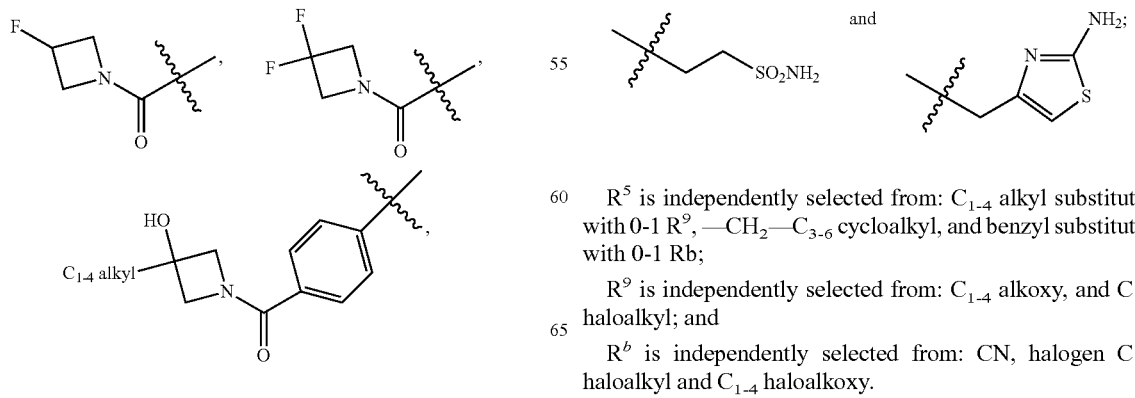

R$^5$ is independently selected from: C$_{1-4}$ alkyl substituted with 0-1 R$^9$, —CH$_2$—C$_{3-6}$ cycloalkyl, and benzyl substituted with 0-1 Rb;

R$^9$ is independently selected from: C$_{1-4}$ alkoxy, and C$_{1-4}$ haloalkyl; and R$^b$ is independently selected from: CN, halogen C$_{1-4}$ haloalkyl and C$_{1-4}$ haloalkoxy.

In another aspect, the present invention includes a compound of Formula (I), (Ib), (IIIa) or (IIIb), or a stereoisomer, a tautomer, a pharmaceutically acceptable salt, or a solvate thereof, wherein:

$R^1$ is independently selected from: 4-CO$_2$H-Ph, 4-NH-COMe-Ph, 4-CONH$_2$-Ph, 4-CONH(CH$_2$)$_{2-3}$OH-Ph, 4-CONH(CH$_2$)$_2$OMe-Ph, 4-CONH(CH$_2$)C(Me)$_2$OH-Ph, 4-CONH(cyclopropyl)-Ph, 3-F-4-CON(Me)$_2$-Ph, 6-F-pyrid-3-yl, 6-OH-pyrid-2-yl, 6-OH-pyrid-3-yl, 2-OH-pyrid-4-yl, 2-OH-3-F-pyrid-4-yl, 2-OH-5-F-pyrid-4-yl, pyrimidin-5-yl,

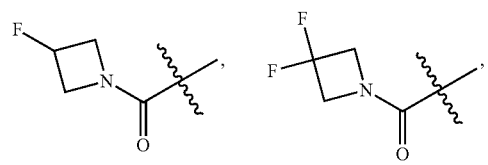

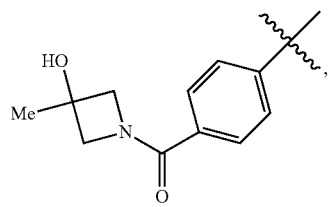

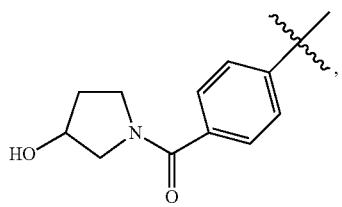

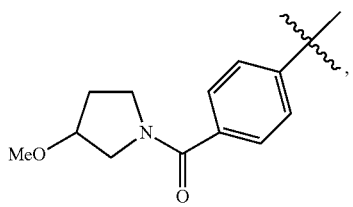

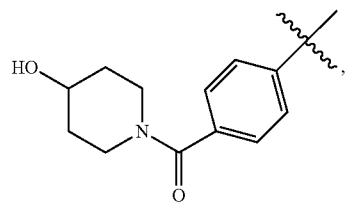

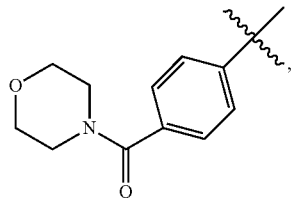

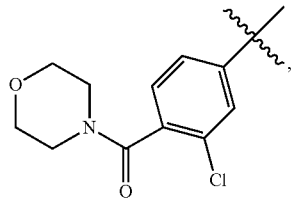

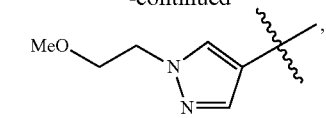

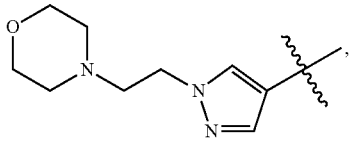

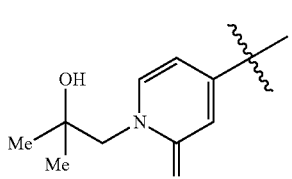

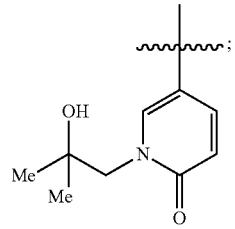

$R^4$ is independently selected from:

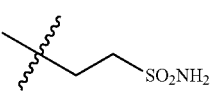 and 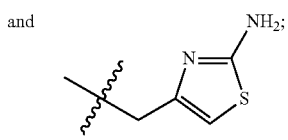

and $R^5$ is independently selected from: Me, i-Pr, —(CH$_2$)$_2$OMe, —(CH$_2$)$_2$CF$_3$, cyclopropylmethyl, Bn, 3-CN-Bn, 3-F-Bn, 4-F-Bn, 4-CF$_3$-Bn, and 4-OCF$_3$-Bn.

In a fifteenth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the twelfth aspect.

In another embodiment, the compounds of the present invention have EL IC$_{50}$ values ≤500 nM.

In another embodiment, the compounds of the present invention have EL IC$_{50}$ values ≤100 nM.

In another embodiment, the compounds of the present invention have EL IC$_{50}$ values ≤50 nM.

In another embodiment, the compounds of the present invention have EL IC$_{50}$ values ≤25 nM.

In another embodiment, the compounds of the present invention have EL IC$_{50}$ values ≤10 nM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the treatment and/or prophylaxis of dyslipidemias and the sequelae thereof comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of endothelial lipase that can be prevented, modulated, or treated according to the present invention include, but are not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

In one embodiment, the present invention provides a method for the treatment and/or prophylaxis of atherosclerosis, coronary heart disease, cerebrovascular disorders and dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of dyslipidemias and the sequelae thereof.

In another embodiment, the present invention also provides the use of a compound of the present invention for the manufacture of a medicament for the treatment and/or prophylaxis of dyslipidemias and the sequelae thereof.

In another embodiment, the present invention provides a method for the treatment and/or prophylaxis of dyslipidemias and the sequelae thereof, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of dyslipidemias and the sequelae thereof.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, antioxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle," "carbocyclyl," or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0] bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl," "$C_{6-10}$ aryl," or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As a person of ordinary skill in the art would be able to understand that imine and carbonyl groups in a molecule may tautomerize to their enamine and enol forms, and the double bond can exist as geometrical (E and Z) isomers as shown in the following equation, wherein $R^1$, $R^2$, $R^3$ and $R^4$ are as defined above:

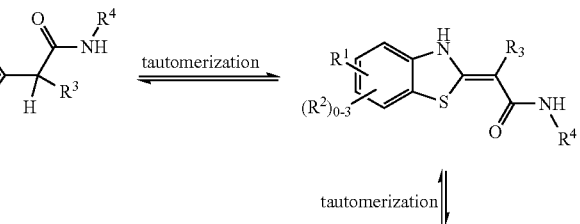
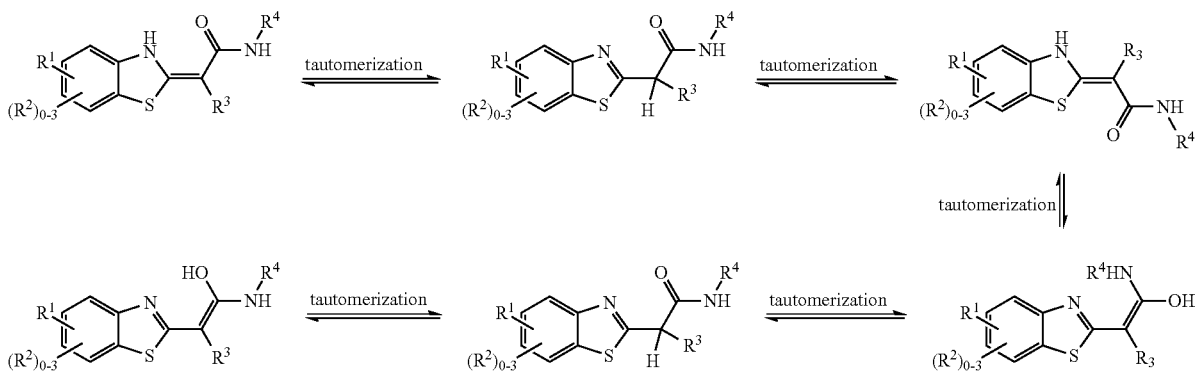

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of Formula (I), Formula (II), or Formula (III) may have prodrug forms. Any compound that will be converted in vivo to provide the bioactive agent (i.e., a compound of Formula (I), Formula (II) or Formula (III)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield Formula (I), (IIa), (IIb), (IIIa) or (IIIb) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl), glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

AcOH or HOAc acetic acid
$AlCl_3$ aluminum chloride
Alk alkyl

BBr₃ boron tribromide
BCl₃ boron trichloride
Bn benzyl
Boc tert-butyloxycarbonyl
BOP reagent benzotriazol-1-yloxytris(dimethylamino)phosphonium hexafluorophosphate
Bu butyl
i-Bu isobutyl
t-Bu tert-butyl
t-BuOH tert-butanol
Cbz carbobenzyloxy
CDCl₃ deutero-chloroform
CD₃OD deutero-methanol
CH₂Cl₂ dichloromethane
CH₃CN or ACN acetonitrile
CHCl₃ chloroform
CO₂ carbon dioxide
mCPBA or m-CPBA meta-chloroperbenzoic acid
Cs₂CO₃ cesium carbonate
Cu(OAc)₂ copper (II) acetate
DBU 1,8-diazabicyclo[5.4.0]undec-7-ene
DCE 1,2-dichloroethane
DCM dichloromethane
DEA diethylamine
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
EDC N-(3-dimthylaminopropyl)-N'-ethylcarbodiimide
EDTA ethylenediaminetetraacetic acid
Et ethyl
Et₃N or TEA triethylamine
Et₂O diethyl ether
EtOAc ethyl acetate
EtOH ethanol
HATU (2-(7-aza-1H-benzotriazole-1-yl)-1,1,3,3-tetramethyluronium hexafluorophosphate)
HCl hydrochloric acid
HOBt or HOBT 1-hydroxybenzotriazole
HPLC high-performance liquid chromatography
H₃PO₄ phosphoric acid
H₂SO₄ sulfuric acid
K₂CO₃ potassium carbonate
KOAc potassium acetate
K₃PO₄ potassium phosphate
LAH lithium aluminum hydride
LDA lithium diisopropylamide
LG leaving group
LiOH lithium hydroxide
Me methyl
MeOH methanol
MgSO₄ magnesium sulfate
MsOH or MSA methylsulfonic acid
NaCl sodium chloride
Na₂CO₃ sodium carbonate
NaH sodium hydride
NaHB(OAc)₃ sodium triacetoxyborohydride
NaHCO₃ sodium bicarbonate
NaHMDS sodium hexamethyldisilazane
NaOH sodium hydroxide
NaOMe sodium methoxide
Na₂SO₃ sodium sulfite
Na₂SO₄ sodium sulfate
NBS N-bromosuccinimide
NH₃ ammonia
NH₄Cl ammonium chloride
NH₄OAc ammonium acetate
NH₄OH ammonium hydroxide
OTf triflate or trifluoromethanesulfonate
Pd₂(dba)₃ tris(dibenzylideneacetone)dipalladium(0)
Pd(OAc)₂ palladium(II) acetate
Pd/C palladium on carbon
Pd(dppf)Cl₂ [1,1'-bis(diphenylphosphino)-ferrocene]dichloropalladium(II)
Ph₃PCl₂ triphenylphosphine dichloride
PG protecting group
Ph phenyl
PMB p-methoxybenzyl
POCl₃ phosphorus oxychloride
Pr propyl
i-Pr isopropyl
i-PrOH or IPA isopropanol
PS polystyrene
PS-Pd(Ph₃)₄ tetrakis(triphenylphosphine)palladium (0) on polystyrene support
PyBOP (benzotriazol-1-yloxy)tripyrrolidinophosphonium hexafluorophosphate
SiO₂ silica oxide
SnCl₂ tin(II) chloride
TBAF tetra-n-butylammonium fluoride
TBAI tetra-n-butylammonium iodide
TEA triethylamine
TFA trifluoroacetic acid
THF tetrahydrofuran
TMSCHN₂ trimethylsilyldiazomethane
T3P 1-propanephosphonic acid cyclic anhydride
Xantphos or X-Phos 4,5-bis(diphenylphosphino)-9,9-dimethylxanthene Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH Publishers, Inc., New York (1999). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts, P. G. M. and Greene, T. W (*Protective Groups in Organic Synthesis*, 4$^{th}$ Edition, Wiley (2007)).

Generic Schemes

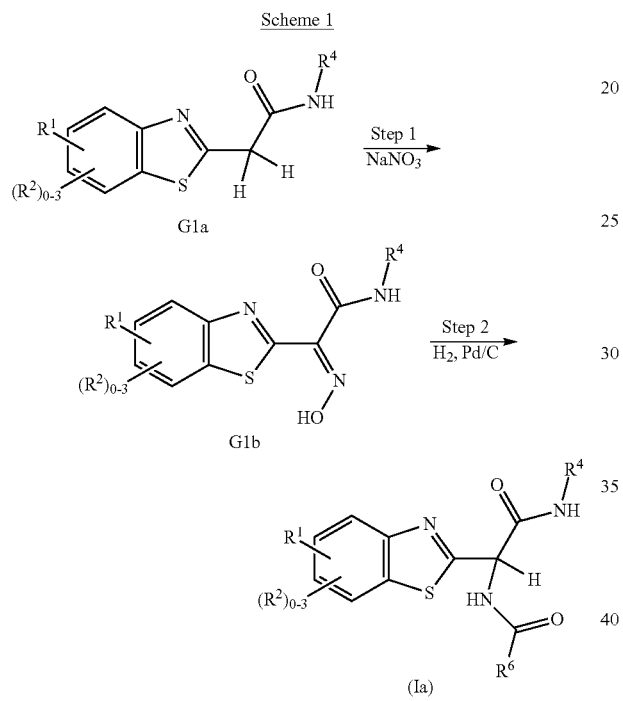

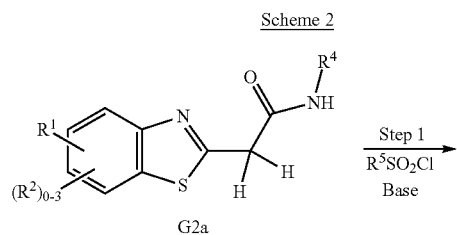

Step 1
Step 1 describes the preparation of compounds of Formula (G1b) by reacting amides of Formula (G1a) with a sodium nitrite. A preferred solvent is water, and a preferred acid is acetic acid.

Step 2
Step 2 describes the preparation of amides and ureas of Formula (I) by reacting compounds of the Formula (G1b) with an anhydride or isocyanate and Pd/C in a hydrogen atmosphere. Preferred solvents are polar protic solvents, such as MeOH and EtOH.

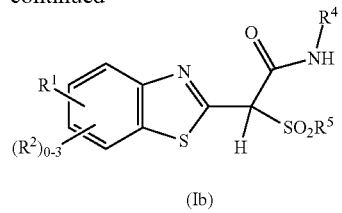

Step 1
Step 1 describes the preparation of compounds of Formula (I) by reacting a compound of Formula (G2a) with a sulfonylating reagent R$^5$—SO$_2$Cl. Preferred solvents are polar aprotic solvents (such as N,N-dimethylformamide) and ethers (such as tetrahydrofuran, dioxane and the like). Preferred bases include metal hydrides (such as sodium hydride and the like), metal amides (such as sodium bis(trimethylsilyl)amide and lithium diisopropylamide and the like) and organic amines (such as DBU, triethylamine and the like).

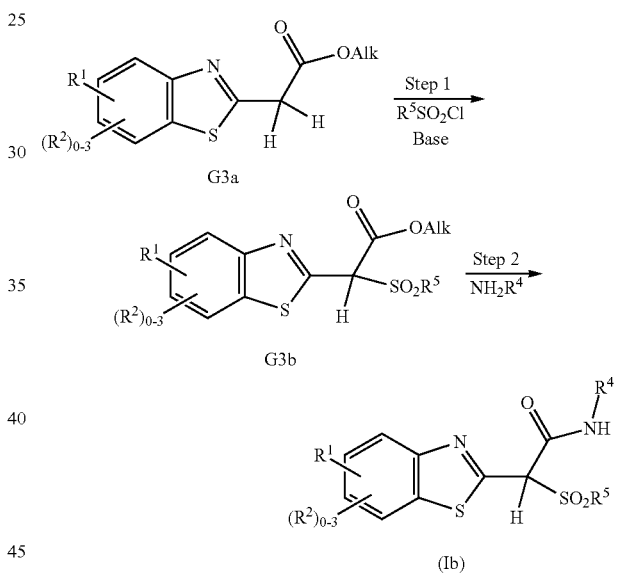

Step 1
Step 1 describes the preparation of a compound of Formula (G3b) from a compound of Formula (G3a) and is analogous to Step 1 in Scheme 1.

Step 2
Step 2 describes the preparation of a compound of Formula (I) from a compound of Formula (G3b) by direct exchange of an ester group with an amine of formula H$_2$NR$^4$. Preferred reaction solvents are polar aprotic solvents such as ethers (such as tetrahydrofuran, dioxane and the like), DMF and NMP. Bases such as an organic amine (such as triethylamine, diisopropylamine, DBU, 2,6-lutidine and the like) can be used.

General Methods
The following methods were used in the exemplified Examples, except where noted otherwise.
Products were analyzed by reverse phase analytical HPLC carried out on a Shimadzu Analytical HPLC system running Discovery VP software using Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B: 10% water, 89.9% methanol, 0.1% $NH_4OAc$, UV 220 nm).

Purification of intermediates and final products was carried out via either normal or reverse phase chromatography. Normal phase chromatography was carried out using prepacked $SiO_2$ cartridges eluted with gradients of hexanes and ethyl acetate or methylene chloride and methanol. Reverse phase preparative HPLC was carried out using a Shimadzu Preparative HPLC system running Discovery VP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Axia Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

Alternatively, reverse phase preparative HPLC was carried out using a Varian ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm).

LCMS chromatograms were obtained on a Shimadzu HPLC system running Discovery VP software, coupled with a Waters ZQ mass spectrometer running MassLynx version 3.5 software and using the following respective methods. Unless specified otherwise, for each method, the LC column was maintained at room temperature and UV detection was set to 220 nm.

Method A: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5 μm C18 (4.5×50 mm). Flow rate was 4 mL/min.

Method B: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 5 μm C18 (2.0×30 mm). Flow rate was 1 mL/min.

Method C: A linear gradient using solvent A (10% acetonitrile, 90% water, 10 mM $NH_4OAc$) and solvent B (90% acetonitrile, 10% water, 10 mM $NH_4OAc$); 0-100% of solvent B over 4 min and then 100% of solvent B over 1 min. Column: PHENOMENEX® Luna 5 μm C18 (4.5×50 mm). Flow rate was 4 mL/min.

Method D: A linear gradient using solvent A (10% acetonitrile, 90% water, 0.05% of TFA) and solvent B (90% acetonitrile, 10% water, 0.05% of TFA); 0-100% of solvent B over 2 min and then 100% of solvent B over 1 min. Column: PHENOMENEX® Luna 5 μm C18 (4.5×30 mm). Flow rate was 1 mL/min.

Method E: A linear gradient using solvent A (10% MeOH, 90% water, 10 mM $NH_4OAc$) and solvent B (90% MeOH, 10% water, 10 mM $NH_4OAc$); 0-100% of solvent B over 4 min and then 100% of solvent B over 1 min. Column: PHENOMENEX® Luna 5 μm C18 (4.5×50 mm). Flow rate was 4 mL/min.

Method F: A linear gradient using solvent A (10 mM $NH_4OAc$, 95% water, 5% ACN) and solvent B (10 mM $NH_4OAc$, 95% ACN, 5% water); 0-100% of solvent B over 4 min and then 100% of solvent B over 1 min. Column: MacMod Halo (C18, 4.6×50 mm). Flow rate was 4 mL/min.

Method G: A linear gradient using solvent A (10% acetonitrile, 90% water, 0.1% TFA) and solvent B (90% acetonitrile, 10% water, 0.1% TFA); 0-100% of solvent B over 4 min and then 100% of solvent B over 1 min. Column: PHENOMENEX® Luna 3 μm C18 (2.0×50 mm). Flow rate was 4 mL/min.

Method H: A linear gradient using solvent A (10% methanol, 90% water, 0.1% of formic acid) and solvent B (90% methanol, 10% water, 0.1% of formic acid); 0-100% of solvent B over 2 min and then 100% of solvent B over 1 min. Column: PHENOMENEX® Luna 3 μm C18 (2.0×30 mm). Flow rate was 1 mL/min.

Method I: A linear gradient using solvent A (10% MeOH, 90% water, 10 mM $NH_4OAc$) and solvent B (90% MeOH, 10% water, 10 mM $NH_4OAc$); 0-100% of solvent B over 2 min and then 100% of solvent B over 1 min. Column: PHENOMENEX® Luna 3 μm C18 (2.0×30 mm). Flow rate was 1 mL/min.

Method J: A linear gradient using solvent A (10% methanol, 90% water, 0.1% of formic acid) and solvent B (90% methanol, 10% water, 0.1% of TFA); 0-100% of solvent B over 4 min and then 100% of solvent B over 1 min. Column: PHENOMENEX® Luna 5 μm C18 (4.5×50 mm). Flow rate was 4 mL/min.

Method K: A linear gradient using solvent A (10 mM $NH_4OAc$, 95% water, 5% ACN) and solvent B (10 mM $NH_4OAc$, 95% ACN, 5% water); 0-100% of solvent B over 5.5 min and then 100% of solvent B over 1.5 min. Column: SUPELCO Ascentis 4.6×50 mm 2.7 μm C18. Flow rate was 4 mL/min.

Method L: A linear gradient using solvent A (5% methanol, 95% water, 0.05% of TFA) and solvent B (95% methanol, 5% water, 0.05% of TFA); 0-100% of solvent B over 4 min and then 100% of solvent B over 1 min. Column: WATERS® XBridge C18 (4.6×50 mm, 5 μm). Flow rate was 4 mL/min. The LC column was maintained at 35° C.

Method M: A linear gradient using of Solvent A (0.05% TFA, 100% water) and Solvent B (0.05% TFA, 100% ACN); 2 to 98% B over 1 min, with 0.5 min hold time at 98% B. Column: WATERS® BEH C18 (2.1×50 mm). Flow rate: 0.8 mL/min.

Method N: A linear gradient using solvent A (5% ACN, 95% water, 10 mM $NH_4OAc$) and solvent B (95% ACN, 5% water, 10 mM $NH_4OAc$); 0-100% of solvent B over 3 min and then 100% of solvent B over 1 min. Column: WATERS® BEH C18 (2.1×50 mm). Flow rate: 1.1 mL/min.

Method O: A linear gradient using solvent A (5% ACN, 95% water, 0.05% of TFA) and solvent B (95% ACN, 5% water, 0.05% of TFA); 0-100% of solvent B over 3 min and then 100% of solvent B over 1 min. Column: WATERS® BEH C18 (2.1×50 mm). Flow rate: 1.1 mL/min.

Method P: A linear gradient using solvent A (5% ACN, 95% water, 10 mM NH$_4$OAc) and solvent B (95% ACN, 5% water, 10 mM NH$_4$OAc); 0-100% of solvent B over 4 min and then 100% of solvent B over 1 min. Column: WATERS® XBridge C18 (4.6×50 mm, 5 µm). Flow rate was 4 mL/min.

Method Q: A linear gradient using solvent A (10% MeOH, 90% water, 0.1% TFA) and solvent B (90% MeOH, 10% water, 0.1% TFA); 0-100% of solvent B over 2 min and then 100% of solvent B over 1 min. Column: PHENOMENEX® Luna 3 µm C18 (2.0×50 mm). Flow rate was 1 mL/min.

Method R: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min.

Preparative HPLC methods employed in the purification of products:

Method A: Linear gradient of 0 to 100% B over 10 min, with 5 min hold time at 100% B; Shimadzu LC-8A binary pumps Waters ZQ mass spectrometer using Waters Masslynx 4.0 SP4 MS software UV visualization at 220 nm
Column: WATERS® XBridge 19×150 mm 5 µm C18
Flow rate: 20 mL/min
Peak collection triggered by mass spectrometry
Solvent A: 0.1% TFA, 10% ACN, 90% water
Solvent B: 0.1% TFA, 90% ACN, 10% water NMR Employed in Characterization of Examples $^1$H NMR spectra were obtained with Bruker or JEOL Fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for CD$_2$HSOCD$_3$, 3.30 ppm for CD$_2$HOD, and 7.24 ppm for CHCl$_3$, and which in $^{13}$C NMR spectra appear at 39.7 ppm for CD$_3$SOCD$_3$, 49.0 ppm for CD$_3$OD, and 77.0 ppm for CDCl$_3$. All $^{13}$C NMR spectra were proton decoupled.

IV. Biology

The endothelium occupies a pivotal position at the interface between the circulating humoral and cellular elements of the blood, and the solid tissues which constitute the various organs. In this unique position, endothelial cells regulate a large number of critical processes, including leukocyte adherence and transit through the blood vessel wall, local control of blood vessel tone, modulation of the immune response, the balance between thrombosis and thrombolysis, and new blood vessel development. Thus, endothelial cell dysfunction has been postulated as a central feature of vascular diseases such as hypertension and atherosclerosis. (WO 1999/032611 and references cited therein, e.g., Folkman, J. et al., *Science*, 235:442-447 (1987); Yanagisawa, M. et al., *Nature*, 332(6163):411-415 (1988); Folkman, J. et al., *J. Biol. Chem.*, 267(16):10931-10934 (1992); Janssens, S. P. et al., *J. Biol. Chem.*, 267(21):14519-14522 (1992); Lamas, S. et al., *Proc. Natl. Acad. Sci. U.S.A.*, 89(14):6348-6352 (1992); Luscher, T. F. et al., *Hypertension*, 19(2):117-130 (1992); Williams et al., *Am. Rev. Respir. Dis.*, 146:S45-S50 (1992); and Bevilacqua, M. P. et al., *J. Clin. Invest.*, 91(2):379-387 (1993)).

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S. In 2008, cardiovascular disease accounted for 33% of all deaths in the U.S., and ~1 of every 6 deaths were specifically caused by atherosclerotic coronary heart disease (*Circulation* 125:e2-e220 (2012)).

Risk for development of atherosclerosis has been shown to be strongly correlated with certain plasma lipid levels. While elevated low density lipoprotein-cholesterol (LDL-C) may be the most recognized form of dyslipidemia, it is by no means the only significant lipid associated contributor to CHD. A low level of high density lipoprotein-cholesterol (HDL-C) is also a known risk factor for CHD (Gordon, D. J. et al., *Circulation*, 79(1):8-15 (1989)).

High LDL-C and triglyceride levels are positively correlated, while high levels of HDL-C are negatively correlated with the risk for developing cardiovascular diseases. Thus, dyslipidemia is not a unitary risk profile for CHD but may be comprised of one or more, preferably one to three, lipid aberrations.

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects (deLemos, A. S. et al., *Circulation*, 106(11):1321-1326 (2002)). Notably, the endothelial lipase-mediated binding and uptake of HDL particles and the selective uptake of HDL-derived cholesterol esters have been reported to be independent of its enzymatic lipolytic activity (Strauss, J. G. et al., *Biochem. J.*, 368:69-79 (2002)).

Because of the beneficial effects widely associated with elevated HDL levels, an agent which inhibits EL activity in humans, by virtue of its HDL increasing ability, are expected to be useful for the treatment, prevention, the arrestment and/or regression of atherosclerosis, coronary heart disease, cerebrovascular disorders etc., especially those (but not restricted thereto) which are characterized by one or more of the following factors: (a) high plasma triglyceride concentrations, high postprandial plasma triglyceride concentrations; (b) low HDL cholesterol concentration; (c) low apoA1 lipoprotein concentrations; (d) high LDL cholesterol concentrations; (e) high levels of small dense LDL cholesterol particles; and (f) high apoB lipoprotein concentrations.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

Biological Activity

Endothelial lipase (EL) and hepatic lipase (HL) activities were measured using a fluorescent substrate, A10070, (Invitrogen, CA) doped into an artificial vesicle containing DMPG (Avanti Polar Lipids) as the excipient. Vesicles were prepared by combining 571 µL of 29 mM DMPG in a 1:1 mixture of MeOH and $CHCl_3$ with 2000 µL of 1 mM A10070 in a 1:1 mixture of MeOH and $CHCl_3$. The mixture was dried under nitrogen in multiple vials then resuspended in 20 mL total volume of 50 mM HEPES pH 8.0 buffer containing 50 mM NaCl and 0.2 mM EDTA. The sample was allowed to sit at room temperature for 15 min and then was sonicated 3×4 mins on ice with a Branson Sonicator using duty cycle 1. This preparation provides vesicles with a mole fraction of 0.11 for the FRET substrate.

The enzymatic assay was measured using 384-well white Optiplates. Each well contained 20 µL of assay buffer (50 mM HEPES pH 8.0, 50 mM NaCl and 1 mM $CaCl_2$) and 0.25 µL of a DMSO solution containing a compound of interest. EL or HL (10 µL) was added and allowed to incubate with the compound for 30 min at 37° C. The source of EL was conditioned media obtained from HT-1080 cells that were transformed using RAGE technology (Athersys) to overexpress endogenous EL, and HL was partially purified from conditioned media obtained from COS cells overexpressing HL. The reaction was started by the addition of 10 µL of a 1:10 dilution of vesicles. The final total reaction volume was 20.25 µL. The reaction rates were measured on a Gemini plate reader with an excitation wavelength of 490 nm and an emission wavelength of 530 nm. Readings were taken over a period of 60 minutes, and the slope between 300 and 900 secs of the readout was used to calculate the rate of the reaction.

Reference Compounds

The following reference compounds and their preparations are described below. The EL $IC_{50}$ values were measured using the EL assay described above.

| Compound No. | Structure | EL $IC_{50}$ (nM) |
|---|---|---|
| Reference 1 | 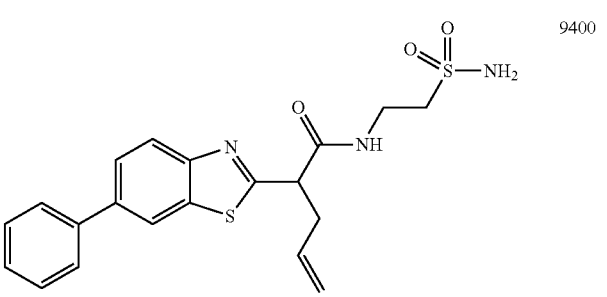 | 9400 |

| Compound No. | Structure | EL IC$_{50}$ (nM) |
|---|---|---|
| Reference 2 | (structure: 6-phenylbenzothiazole-2-yl-C(Me)(Me)-C(O)-NH-CH$_2$-isoxazole with i-Pr substituent) | i-Pr >62000 |
| Reference 3 | (structure: 6-phenylbenzothiazole-2-yl-C(Me)(Me)-C(O)-NH-CH$_2$-isoxazole with Me substituent) | Me >62000 |

The exemplified compounds, Example A1 to Example A9 and Example B1 to Example 205 and Example 207 to Example B397, disclosed in the present invention were tested in the EL assay described above. Surprisingly, Examples A1-A9 B1-B205, and B207-B397 were found having a range of EL IC$_{50}$ values of ≤0.3 µM (300 nM), as shown below.

Accordingly, the compounds of the present invention can be administered to mammals, preferably humans, for the treatment of a variety of conditions and disorders, including, but not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

VI. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors or other pharmaceutically active material.

The compounds of the present invention may be employed in combination with other EL inhibitors or one or more, preferably one to three, other suitable therapeutic agents useful in the treatment of the aforementioned disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, $DHEA-SO_4$); anti-glucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving endothelial lipase or HDL activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving endothelial lipase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

Example A1
N-(1-(6-(6-Fluoropyridin-3-yl)benzo[d]thiazol-2-yl)-2-oxo-2-((2-sulfamoylethyl)amino)ethyl)-4-(trifluoromethyl)benzamide
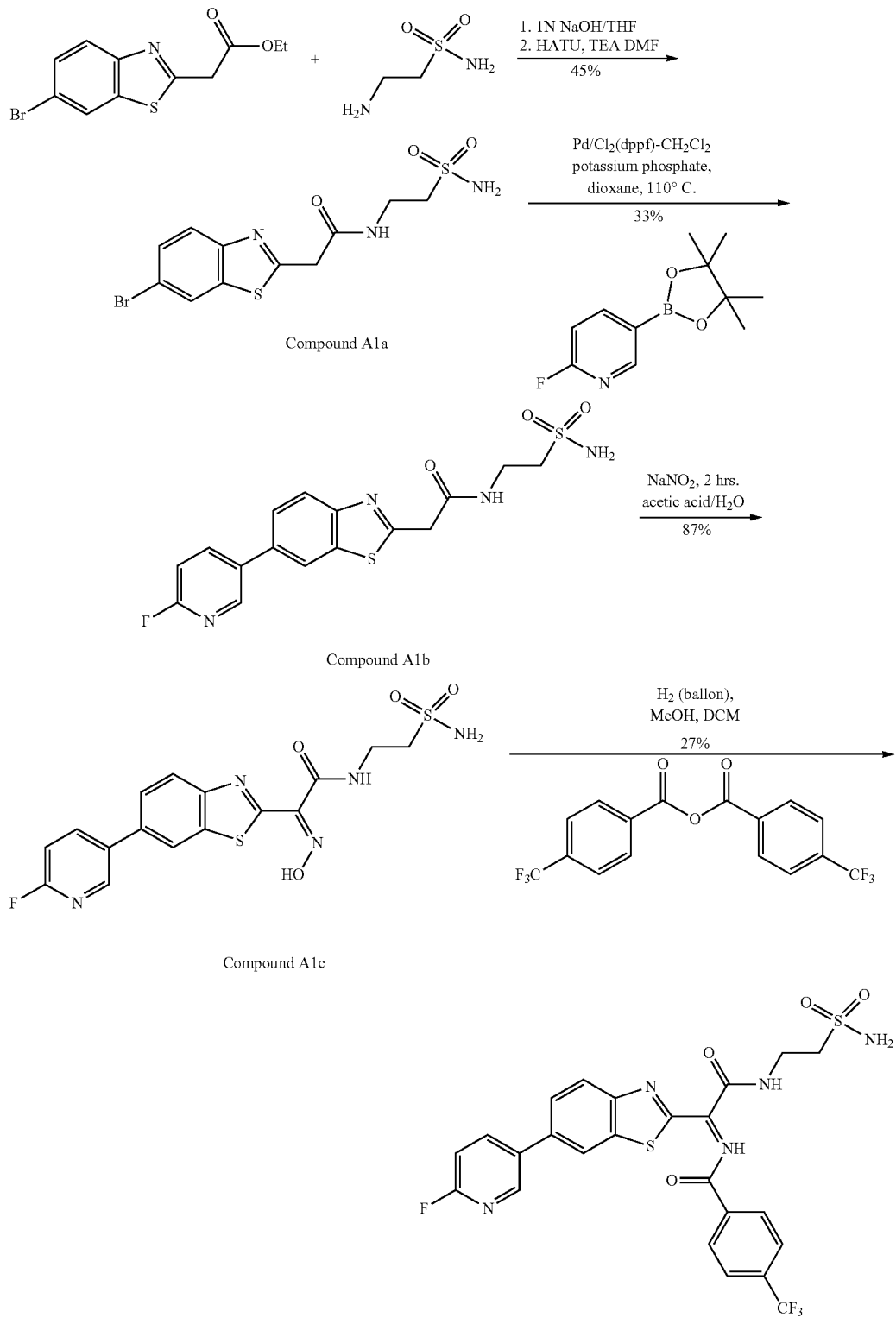
Compound A1a
Compound A1b
Compound A1c
Example A1

Compound A1a. 2-(6-Bromobenzo[d]thiazol-2-yl)-N-(2-sulfamoylethyl)acetamide

Ethyl 2-(6-bromobenzo[d]thiazol-2-yl)acetate (described in WO2011/074560, 250 mg, 0.83 mmol) in THF (4 mL) was treated with sodium hydroxide (1N NaOH, 0.92 mL, 0.92 mmol). After 2 hours, the reaction mixture was concentrated to dryness under reduced pressure, and the residue was co-evaporated with toluene (5 mL), re-dissolved in DMF (4 mL), and treated with 2-aminoethanesulfonamide hydrochloride (201 mg, 1.30 mmol), TEA (1.2 mL, 8.3 mmol) and HATU (475 mg, 1.30 mmol). After 16 hours, the reaction mixture was diluted with water (20 mL), extracted with DCM (3×10 mL), dried over $Na_2SO_4$, and concentrated under reduced pressure. The residue was dissolved in DMF/methanol and purified using reverse phase HPLC (Phenomemenx Luna AXIA 5 micron C18, 21.2×100 mm, 30 to 100% B over 15 minutes with 10 minute hold time, solvent A: 90% water/ACN/0.1% TFA, solvent B:90% ACN/water/0.1% TFA, Flow rate 20 mL/min; detector at 254). The pooled fractions were lyophilized to Compound A1a, (170 mg, 45% yield) as a white solid. HPLC: RT=0.75 (LCMS Method O). MS (ES): m/z=379.7 [M+H]$^+$. $^1$H NMR (400 MHz, DMF-d$_7$) δ 8.40 (d, J=2.0 Hz, 1H), 7.92 (d, J=8.8 Hz, 1H), 7.69 (dd, J=8.8, 2.0 Hz, 1H), 6.97 (s, 2H), 3.82-3.61 (m, 2H), 3.46 (s, 3H), 3.33 (dd, J=7.9, 6.4 Hz, 3H).

Compound A1b. 2-(6-(6-Fluoropyridin-3-yl)benzo[d]thiazol-2-yl)-N-(2-sulfamoylethyl)acetamide $PdCl_2$(dppf)-$CH_2Cl_2$ (21.6 mg, 0.026 mmol) was added to a solution of Compound A1a (100 mg, 0.26 mmol), potassium phosphate (84 mg, 0.40 mmol) and 2-fluoro-5-(4,4,5,5-tetramethyl-1,3,2-dioxaborolan-2-yl)pyridine (88 mg, 0.40 mmol) in dioxane (4 mL). The reaction mixture was purged with argon, and the reaction vessel was sealed and heated at 110° C. for 18 hrs. The reaction mixture was allowed to cool to room temperature, diluted with water (20 mL), extracted with DCM (3×15 mL), dried over $Na_2SO_4$, and concentrated under reduced pressure. The residue was purified using reverse phase HPLC (Waters Sunfire 5 micron 19×10 mm; 15 min. Gradient, Flow rate 20 mL/min.; wavelength at 220 nm; start % B=20 & final % B=100); Solvent A=10% MeOH-90% $H_2O$-0.1% NH4Oac:Solvent B=90% MeOH-10% $H_2O$-0.1% $NH_4$Oac). The fractions containing product were combined and concentrated under reduced pressure to give Compound A1b (34 mg, 33% yield) as a white solid. HPLC: RT=0.76 (LCMS Method O). MS (ES): m/z=395.1 [M+H]$^+$. $^1$H NMR (400 MHz, DMF-d$_7$) δ 8.76-8.68 (m, 1H), 8.54-8.49 (m, 1H), 8.48-8.36 (m, 1H), 8.12-8.07 (m, 2H), 7.96-7.85 (m, 1H), 7.41-7.30 (m, 1H), 7.05-6.94 (m, 1H), 5.83 (s, 1H), 4.22 (s, 2H), 3.80-3.67 (m, 2H), 3.38-3.32 (m, 2H).

Compound A1c. (E)-2-(6-(6-Fluoropyridin-3-yl)benzo[d]thiazol-2-yl)-2-(hydroxyimino)-N-(2-sulfamoylethyl)acetamide To a suspension of Compound A1b (100 mg, 0.25 mmol) in acetic acid (4 mL) and water (0.4 mL) was added sodium nitrite (21 mg, 0.30 mmol), and the reaction stirred at room temperature for 2 hours. A precipitate formed and the reaction mixture was filtered, the solids were washed successively with water, dichloromethane, ether and dried under reduced pressure to give Compound A1c (93 mg, 87% yield) as a yellow solid. HPLC: RT=0.77 (LCMS Method O). MS (ES): m/z=424.1 [M+H]$^+$. $^1$H NMR (400 MHz, DMF-d$_7$) δ 8.71 (d, J=2.5 Hz, 1H), 8.59-8.36 (m, 2H), 8.18 (d, J=8.5 Hz, 1H), 7.95 (dd, J=8.4, 1.6 Hz, 1H), 7.34 (dd, J=8.5, 3.0 Hz, 1H), 4.04 (br. s., 1H), 3.93-3.76 (m, 1H), 3.64-3.34 (m, 2H).

Example A1

To a suspension of Compound A1c (34 mg, 0.080 mmol) in MeOH (10 mL) was added 4-(trifluoromethyl)benzoic anhydride (116 mg, 0.320 mmol) and 10% Pd/C (3 mg, 0.05 mmol). The reaction mixture was degased with argon and stirred under hydrogen atmosphere (ballon) for 2 hours at room temperature. The reaction mixture was diluted with DMF (2 mL), filtered, concentrated under reduced pressure and purified by preparatory HPLC (Sunfire 5μ 19×100 mm; 25 min. gradient; inj. vol. 2 mL, Flow rate 20 mL/min.; wavelength 220 nm; start % B=20, final % B=100, Solvent A=10% MeOH–90% H2O–0.1% TFA, Solvent B=90% MeOH–10% $H_2O$–0.1% TFA) to give Example A1 (13 mg, 27% yield). HPLC: RT=0.9 (LCMS Method O). MS (ES): m/z=581.9 [M+H]$^+$. $^1$H NMR (400 MHz, DMSO-d$_6$) δ 9.78 (s, 1H), 8.64 (d, J=2.5 Hz, 1H), 8.49 (d, J=1.8 Hz, 1H), 8.37 (d, J=2.8 Hz, 1H), 8.17 (d, J=8.0 Hz, 2H), 8.09 (d, J=8.5 Hz, 1H), 7.95-7.80 (m, 3H), 7.32 (dd, J=8.7, 2.9 Hz, 1H), 6.93 (s, 2H), 6.14 (d, J=7.8 Hz, 1H), 3.57 (t, J=6.5 Hz, 2H), 3.26-3.09 (m, 2H). EL IC$_{50}$ 35 nM.

The following compounds, Example A2 to Example A8 were prepared by the general procedures described for Example A1.

| Ex # | Structure | Name | $^1$H NMR (400 MHz, DMSO-$d_6$, unless indicated otherwise) | LC/MS RT (min) Method M + H | EL IC$_{50}$ (nM) |
|---|---|---|---|---|---|
| A2 | 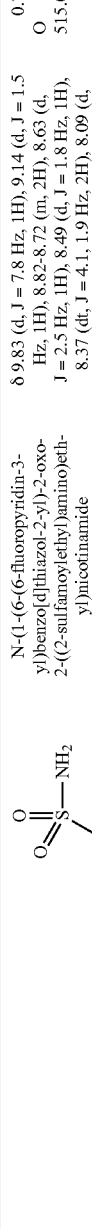 | N-(1-(6-(6-fluoropyridin-3-yl)benzo[d]thiazol-2-yl)-2-oxo-2-((2-sulfamoylethyl)amino)ethyl)nicotinamide | δ 9.83 (d, J = 7.8 Hz, 1H), 9.14 (d, J = 1.5 Hz, 1H), 8.82-8.72 (m, 2H), 8.63 (d, J = 2.5 Hz, 1H), 8.49 (d, J = 1.8 Hz, 1H), 8.37 (dt, J = 4.1, 1.9 Hz, 2H), 8.09 (d, J = 8.5 Hz, 1H), 7.87 (dd, J = 8.5, 1.8 Hz, 1H), 7.61 (s, 1H), 7.35-7.28 (m, 1H), 6.94 (br. s., 2H), 6.15 (d, J = 7.8 Hz, 1H), 3.64-3.53 (m, 2H), 3.20 (dd, J = 8.4, 6.4 Hz, 2H) | 0.7 O 515.0 | <10 |
| A3 | 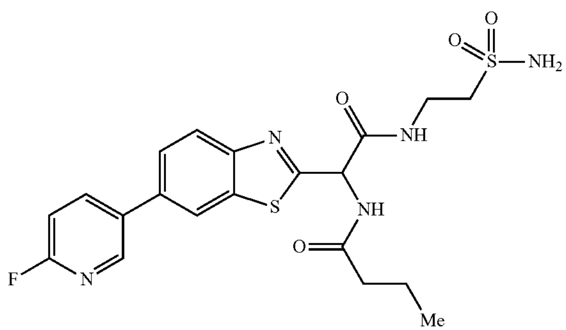 [SMILES: CCCC(=O)NC(C(=O)NCCS(N)(=O)=O)c1nc2ccc(-c3ccc(F)nc3)cc2s1] | N-(1-(6-(6-fluoropyridin-3-yl)benzo[d]thiazol-2-yl)-2-oxo-2-((2-sulfamoylethyl)amino)ethyl)butyramide | δ 9.00 (d, J = 7.8 Hz, 1H), 8.75 (s, 1H), 8.64 (d, J = 2.5 Hz, 1H), 8.49 (d, J = 1.5 Hz, 1H), 8.45-8.31 (m, 1H), 8.07 (d, J = 8.3 Hz, 1H), 7.88 (dd, J = 8.5, 1.8 Hz, 2H), 7.33 (dd, J = 8.5, 2.8 Hz, 1H), 6.93 (s, 2H), 5.92 (d, J = 7.8 Hz, 1H), 3.65-3.49 (m, 2H), 3.17 (t, J = 7.4 Hz, 2H), 2.37-2.19 (m, 2H), 1.57 (qd, J = 7.4, 1.8 Hz, 2H), 0.96-0.81 (m, 3H) | 0.79 O 480.0 | <10 |

-continued

| Ex # | Structure | Name | ¹H NMR (400 MHz, DMSO-d₆, unless indicated otherwise) | LC/MS RT (min) Method M + H | EL IC₅₀ (nM) |
|---|---|---|---|---|---|
| A4 | 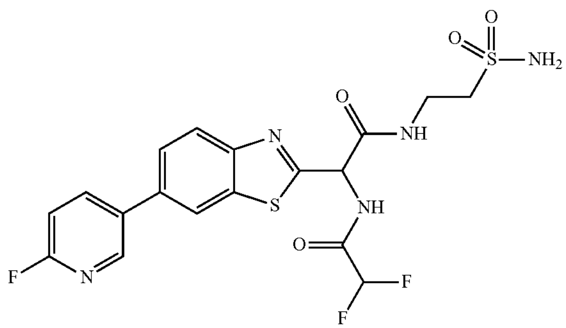 [SMILES: NS(=O)(=O)CCNC(=O)C(NC(=O)C(F)F)c1nc2ccc(-c3ccc(F)nc3)cc2s1] | 2-(2,2-difluoroacetamido)-2-(6-(6-fluoropyridin-3-yl)benzo[d]thiazol-2-yl)-N-(2-sulfamoylethyl)acetamide | δ 10.06-9.93 (m, 1H), 8.90-8.80 (m, 1H), 8.67-8.60 (m, 1H), 8.54-8.49 (m, 1H), 8.42-8.34 (m, 1H), 8.16-8.08 (m, 1H), 7.95-7.85 (m, 1H), 7.40-7.29 (m, 1H), 7.26-7.16 (m, 1H), 7.11-7.04 (m, 1H), 6.98-6.89 (m, 3H), 6.59-6.24 (m, 1H), 6.05-5.91 (m, 1H), 5.79-5.71 (m, 1H), 3.59-3.48 (m, 2H), 3.21-3.10 (m, 2H) | 0.8 O 488.0 | <10 |
| A5 | 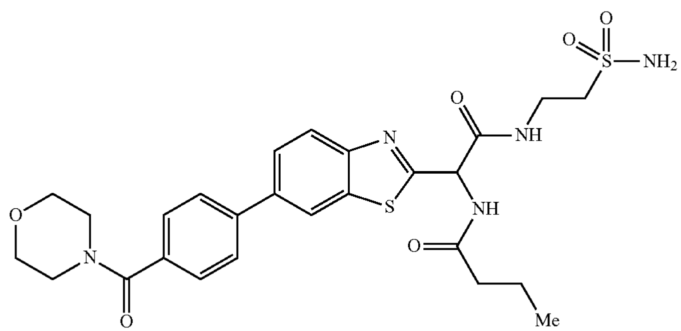 [SMILES: CCCC(=O)NC(C(=O)NCCS(N)(=O)=O)c1nc2ccc(-c3ccc(C(=O)N4CCOCC4)cc3)cc2s1] | N-(1-(6-(4-(morpholine-4-carbonyl)phenyl)benzo[d]thiazol-2-yl)-2-oxo-2-((2-sulfamoylethyl)amino)ethyl)butyramide | δ 8.99 (d, J = 7.7 Hz, 1H), 8.75 (s, 1H), 8.46 (d, J = 1.5 Hz, 1H), 8.04 (d, J = 8.6 Hz, 1H), 7.89-7.79 (m, 3H), 7.59-7.48 (m, 2H), 6.93 (d, J = 10.1 Hz, 2H), 5.91 (d, J = 7.9 Hz, 1H), 3.71-3.44 (m, 10H), 3.16 (t, J = 7.5 Hz, 2H), 2.36-2.15 (m, 2H), 1.56 (dd, J = 7.3, 1.5 Hz, 2H), 0.95-0.76 (m, 3H) | 0.7 O 574.0 | <10 |

| Ex # | Structure | Name | $^1$H NMR (400 MHz, DMSO-$d_6$, unless indicated otherwise) | LC/MS Method | RT (min) M + H | EL IC$_{50}$ (nM) |
|---|---|---|---|---|---|---|
| A6 | 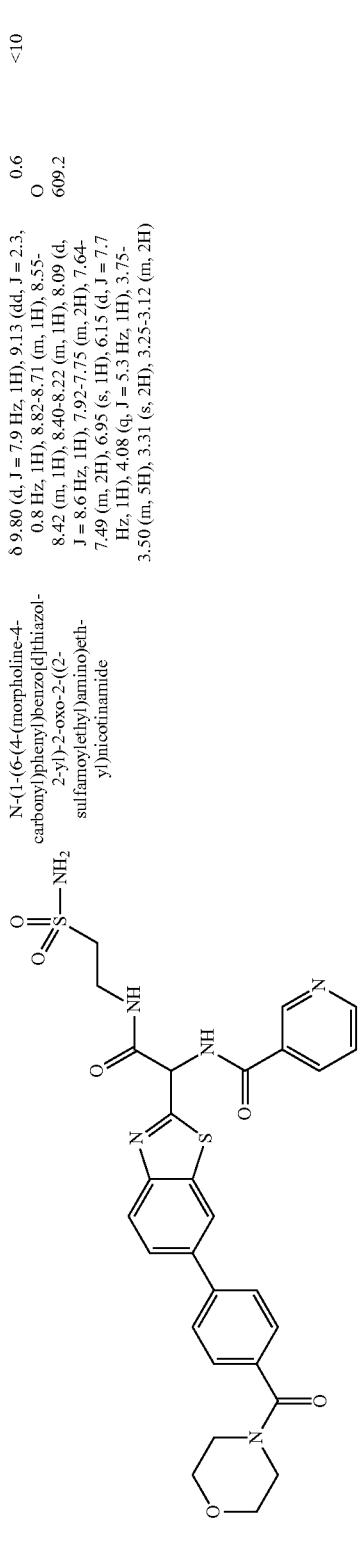 | N-(1-(6-(4-(morpholine-4-carbonyl)phenyl)benzo[d]thiazol-2-yl)-2-oxo-2-((2-sulfamoylethyl)amino)ethyl)nicotinamide | δ 9.80 (d, J = 7.9 Hz, 1H), 9.13 (dd, J = 2.3, 0.8 Hz, 1H), 8.82-8.71 (m, 1H), 8.55-8.42 (m, 1H), 8.40-8.22 (m, 1H), 8.09 (d, J = 8.6 Hz, 1H), 7.92-7.75 (m, 2H), 7.64-7.49 (m, 2H), 6.95 (s, 1H), 6.15 (d, J = 7.7 Hz, 1H), 4.08 (q, J = 5.3 Hz, 1H), 3.75-3.50 (m, 5H), 3.31 (s, 2H), 3.25-3.12 (m, 2H) | O | 0.6 609.2 | <10 |
| A7 | 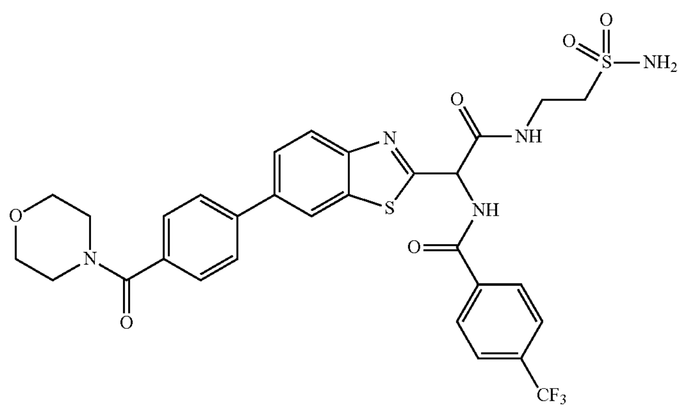 [SMILES: NS(=O)(=O)CCNC(=O)C(NC(=O)c1ccc(C(F)(F)F)cc1)c1nc2ccc(-c3ccc(C(=O)N4CCOCC4)cc3)cc2s1] | 4-carbonyl)phenyl)benzo[d]thiazol-2-yl)-2-oxo-2-((2-sulfamoylethyl)amino)-4-(trifluoromethyl)benzamide | δ 9.80 (d, J = 7.7 Hz, 1H), 8.86-8.72 (m, 1H), 8.48 (d, J = 1.5 Hz, 1H), 8.19 (d, J = 8.1 Hz, 1H), 8.09 (d, J = 8.6 Hz, 1H), 8.00-7.80 (m, 3H), 7.60-7.48 (m, 1H), 7.01-6.89 (m, 1H), 6.18-5.72 (m, 2H), 3.73-3.54 (m, 4H), 3.28-3.15 (m, 2H) | O | 0.9 676.2 | <10 |

| Ex # | Structure | Name | $^1$H NMR (400 MHz, DMSO-$d_6$, unless indicated otherwise) | LC/MS RT (min) Method M + H | EL IC$_{50}$ (nM) |
|---|---|---|---|---|---|
| A8 | 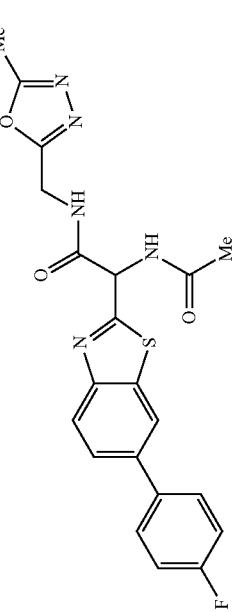 | 2-acetamido-2-(6-(4-fluorophenyl)benzo[d]thiazol-2-yl)-N-((5-methyl-1,3,4-oxadiazol-2-yl)methyl)acetamide | δ 9.32 (t, J = 5.8 Hz, 1H), 9.09 (d, J = 8.0 Hz, 1H), 8.41-8.38 (m, 1H), 8.02 (d, J = 8.5 Hz, 1H), 7.83-7.76 (m, 4H), 7.37-7.29 (m, 3H), 5.99 (d, J = 8.0 Hz, 1H), 4.65-4.48 (m, 2H), 2.44 (s, 3H), 2.01-1.99 (m, 3H) | 0.8 O 440.2 | <10 |

Example A9

2-(3-Benzylureido)-2-(6-(4-fluorophenyl)benzo[d]thiazol-2-yl)-N-((5-methyl-1,3,4-oxadiazol-2-yl)methyl)acetamide

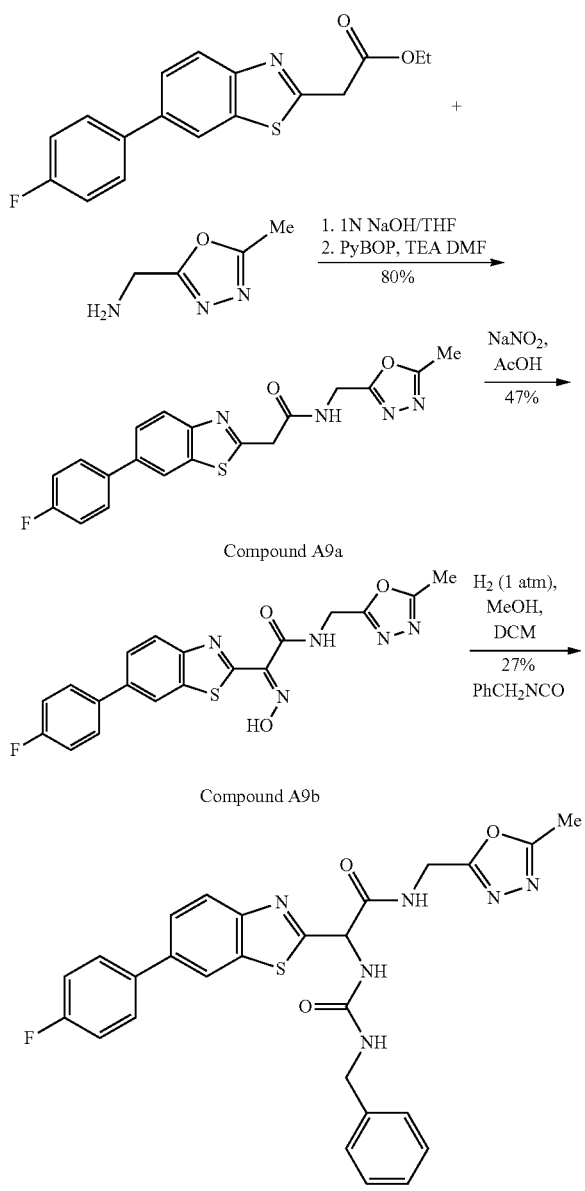

Example A9

Compound A9a. 2-(6-(4-Fluorophenyl)benzo[d]thiazol-2-yl)-N-((5-methyl-1,3,4-oxadiazol-2-yl)methyl)acetamide Ethyl 2-(6-(4-fluorophenyl)benzo[d]thiazol-2-yl)acetate (described in WO2011/074560, 500 mg, 1.59 mmol) in THF (4 mL) was treated with sodium hydroxide (1N NaOH, 1.9 mL, 1.9 mmol). After 2 hours, the reaction mixture was concentrated to dryness under reduced pressure. The residue was co-evaporated with toluene (5 mL), re-dissolved in DMF (4 mL), and treated with (5-methyl-1,3,4-oxadiazol-2-yl)methanamine hydrochloride (284 mg, 1.90 mmol), TEA (2.2 mL, 16 mmol) and PyBOP (990 mg, 1.9 mmol). After 16 hours, the reaction mixture was diluted with water (20 mL), extracted with DCM (3×10 mL), dried over $Na_2SO_4$ and concentrated under reduced pressure. The residue was purified by silica gel (eluting with 0-20% DCM/MeOH) to give Compound A9a (485 mg, 80.0% yield) as an oil.

HPLC: RT=0.88 (LCMS Method O). MS (ES): m/z=383.2 [M+H]$^+$. $^1$H NMR (400 MHz, DMF-$d_7$) δ 9.12 (br. s., 1H), 8.41 (d, J=1.8 Hz, 1H), 7.93-7.76 (m, 3H), 7.43-7.27 (m, 2H), 4.69 (d, J=5.8 Hz, 2H), 4.28 (s, 2H), 2.50 (s, 3H).

Compound A9b. (Z)-2-(6-(4-Fluorophenyl)benzo[d]thiazol-2-yl)-2-(hydroxyimino)-N-((5-methyl-1,3,4-oxadiazol-2-yl)methyl)acetamide Compound A9b) 50 mg, 47% yield) was prepared from Compound A9a as described in the general procedure given for Compound A1c. HPLC: RT=0.93 (LCMS Method O). MS (ES): m/z=412.2 [M+H]$^+$. $^1$H NMR (400 MHz, DMF-$d_7$) δ 8.34-8.27 (m, 1H), 7.98-7.93 (m, 1H), 7.89-7.84 (m, 2H), 7.82-7.78 (m, 1H), 7.41-7.28 (m, 2H), 5.04-4.95 (m, 2H), 2.54 (s, 3H).

Example A9

To a suspension of Compound A9b (50 mg, 0.12 mmol) in EtOH (10 mL) was added (isocyanatomethyl) benzene (16 mg, 0.12 mmol) and 10% Pd/C (3 mg, 0.05 mmol). The mixture was degased with argon and stirred under hydrogen atmosphere (balloon) at room temperature for 2 hours. The reaction mixture was diluted with DMF (2 mL), filtered, concentrated under reduced pressure and purified by preparatory HPLC (Phenomenex AXIA Luna 5μ 75×30 mm; 35 min. gradient; inj. vol. 2 mL, Flow rate 40 mL/min.; wavelength 220 nm; start % B=20, final % B=100) Solvent A=10% MeOH–90% $H_2O$–0.1% TFA:Solvent B=90% MeOH–10% $H_2O$–0.1% TFA) to give Example A9 (10 mg, 15% yield). HPLC: RT=0.95 (LCMS Method O). MS (ES): m/z=531.2 [M+H]$^+$. $^1$H NMR (400 MHz, DMSO-$d_6$) δ 8.41 (d, J=1.8 Hz, 1H), 8.02 (d, J=8.5 Hz, 1H), 7.86-7.74 (m, 3H), 7.40-7.23 (m, 9H), 6.98 (s, 1H), 5.87 (d, J=8.0 Hz, 1H), 4.65-4.48 (m, 2H), 4.27 (d, J=5.8 Hz, 2H), 2.42 (s, 3H). EL IC$_{50}$ 50 nM.

Example B1

2-(Methylsulfonyl)-2-(6-phenylbenzo[d]thiazol-2-yl)-N-(2-sulfamoylethyl)acetamide

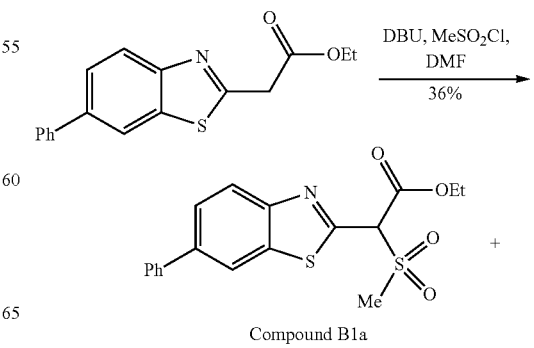

Compound B1a

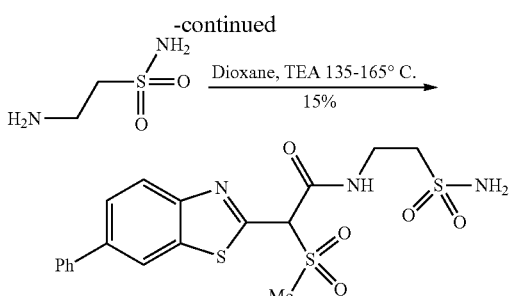

Example B1

Compound B1a. Ethyl 2-(methylsulfonyl)-2-(6-phenylbenzo[d]thiazol-2-yl)acetate Ethyl 2-(6-phenylbenzo[d]thiazol-2-yl)acetate (described in WO2011/074560, 550 mg, 1.9 mmol) was dissolved in DMF (10 mL) and cooled to 0° C. DBU (0.61 mL, 4.1 mmol) was added. After 10 minutes, methanesulfonyl chloride (0.2 mL, 3 mmol) was added dropwise. The reaction mixture was removed from the ice bath and stirred at room temperature. After 4 hours, the reaction mixture was cooled back to 0° C., and additional methane sulfonyl chloride (0.11 mL, 1.4 mmol) was added. Following addition, the reaction mixture was removed from ice bath and stirred at room temperature. After 3 days, the reaction mixture was quenched by the addition of water (20 mL), and the resulting solid was collected by filtration. The solids were dissolved in DCM, washed with aqueous 10% LiCl, 1N HCl, brine, dried over MgSO$_4$, concentrated under reduced pressure, and purified by silica gel chromatography (eluting with 0-20% DCM/MeOH) to give Compound B1a (250 mg, 36% yield) as a yellow oil. HPLC: RT=1.03 min (LCMS Method O). MS (ES): m/z=376.0 [M+H]$^+$. $^1$H NMR (400 MHz, pyridine-d$_5$) δ 8.07 (br. s., 1H), 7.79-7.64 (m, 4H), 7.51 (t, J=7.7 Hz, 2H), 7.40 (s, 1H), 4.39 (d, J=7.0 Hz, 2H), 3.49 (s, 3H), 1.29 (t, J=7.0 Hz, 3H).

Example B1

Compound B1a (110 mg, 0.29 mmol) was dissolved in dioxane (1 mL) and TEA (1 mL). 2-Aminoethanesulfonamide hydrochloride (94 mg, 0.59 mmol) was added, and the reaction mixture was sealed in a pressure vessel and heated at 135° C. for 18 hours. Additional 2-aminoethanesulfonamide hydrochloride (94 mg, 0.59 mmol) was added, and the reaction mixture was heated for an additional 3 hours at 165° C. The reaction mixture was allowed to cool to room temperature, concentrated under reduced pressure, and the residue dissolved in DMF and purified by reverse phase HPLC (Waters Sunfire 5μ 19×100 mm; 10 min. Gradient/5-75 mg; inj. vol. 2 mL, Flow rate 20 mL/min.; wavelength 220 nm; start % B=80 & final % B=100) Solvent A=10% MeOH–90% H$_2$O–0.1% NH$_4$OAc:Solvent B=90% MeOH–10% H$_2$O–0.1% NH$_4$Oac) to give Example B1 (20 mg, 15% yield) as a white solid. HPLC: RT=0.86 (LCMS Method O). MS (ES): m/z=453.9 [M+H]$^+$. $^1$H NMR (400 MHz, pyridine-d$_5$) δ 10.14 (s, 2H), 9.63 (br. s., 1H), 9.33-9.12 (m, 3H), 9.09 (s, 1H), 8.98 (t, J=7.7 Hz, 2H), 8.87 (d, J=7.3 Hz, 1H), 5.76 (d, J=6.0 Hz, 2H), 5.34 (t, J=6.3 Hz, 2H), 5.01 (br. s., 2H). EL IC$_{50}$<10 nM.

Example B2

2-(Allylsulfonyl)-2-(6-phenylbenzo[d]thiazol-2-yl)-N-(2-sulfamoylethyl)acetamide

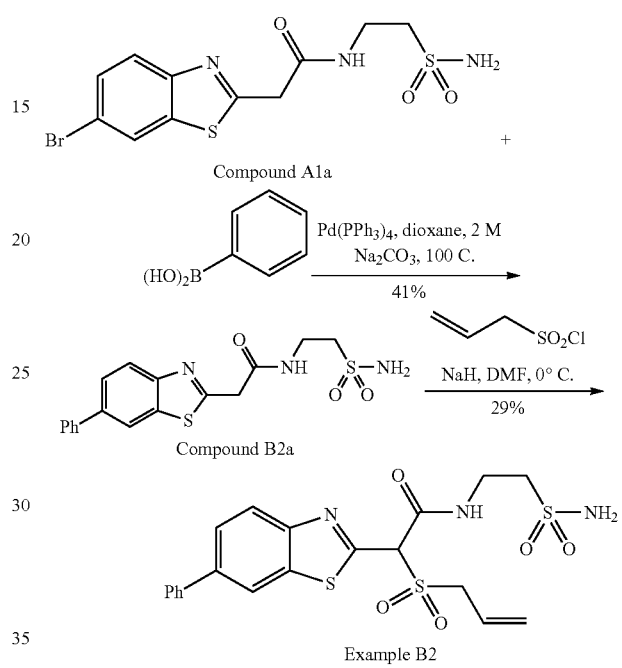

Compound B2a. 2-(6-Phenylbenzo[d]thiazol-2-yl)-N-(2-sulfamoylethyl)acetamide Pd(PPh$_3$)$_4$ (51 mg, 0.044 mmol) was added to dioxane (2 mL)/2M Na$_2$CO$_3$ (1 mL) solution of Compound A1a (73 mg, 0.15 mmol) and phenylboronic acid (27 mg, 0.22 mmol). The reaction mixture was purged with argon gas and heated at 100° C. After 90 minutes, the reaction mixture was diluted with water (20 mL), extracted with DCM (3×15 mL), and the combined organic portions dried over Na$_2$SO$_4$, filtered and concentrated under reduced pressure. The residue was dissolved in DMF/methanol and purified using reverse phase HPLC (Phenomemenx Luna AXIA 5 micron C18, 21.2×100 mm, 30 to 100% B over 15 minutes with 10 minute hold time, solvent A: 90% water/ACN/0.1% TFA, solvent B:90% ACN/water/0.1% TFA, Flow rate 20 mL/min; detector at 254). The pooled fractions were diluted with saturated NaHCO$_3$ (20 mL), extracted with DCM (3×15 mL), dried over Na$_2$SO$_4$, and concentrated under reduced pressure to give Compound B2a (23 mg, 41% yield) as a white solid. HPLC: RT=0.83 min (LCMS Method M). MS (ES): m/z=375.9 [M+H]$^+$. $^1$H NMR (500 MHz, DMSO-d$_6$) δ 8.44-8.68 (1H, m), 8.36 (1H, d, J=1.93 Hz), 7.88 (1H, d, J=8.80 Hz), 7.56-7.70 (1H, m), 6.90 (2H, s), 4.06 (2H, s), 3.43-3.62 (2H, m), 3.07-3.22, (2H, m).

Example B2

Compound B2a (22 mg, 0.059 mmol) was dissolved in DMF (1 mL) and treated with NaH (60% in nujol, 11.7 mg, 0.300 mmol) at 0° C. The reaction mixture was maintained at 0° C. for 2 minutes, allowed to reach room temperature for 3 minutes, and cooled back to 0° C. After 2 minutes, prop-2-ene-1-sulfonyl chloride (12.4 mg, 0.0900 mmol) was added. After 20 minutes, the reaction mixture was quenched by the addition of 0.1 mL acetic acid, diluted with DMF/methanol and purified using reverse phase HPLC (Phenomemenx Luna AXIA 5 micron C18, 21.2×100 mm, 30 to 100% B over 15 minutes with 10 minute hold time, solvent A: 90% water/ACN/0.1% TFA, solvent B: 90% ACN/water/0.1% TFA, Flow rate 20 mL/min; detector at 254). The fractions containing product were lyophilized to yield Example B2 (8.1 mg, 29% yield) as an off-white solid. HPLC: RT=0.93 min (LCMS Method M). MS (ES): m/z=479.8 [M+H]$^+$. $^1$H NMR (500 MHz, DMSO-d$_6$) δ 9.16-8.93 (m, 1H), 8.48 (d, J=1.4 Hz, 1H), 8.15 (d, J=8.5 Hz, 1H), 7.88 (d, J=1.7 Hz, 1H), 7.77 (dd, J=8.3, 1.1 Hz, 2H), 7.51 (d, J=8.0 Hz, 2H), 7.50-7.31 (m, 1H), 6.95 (s, 2H), 6.06 (s, 1H), 5.91-5.74 (m, 1H), 5.64-5.45 (m, 2H), 4.30-4.13 (m, 2H), 3.65-3.51 (m, 2H), 3.19 (d, J=1.4 Hz, 2H). EL IC$_{50}$<10 nM The following compounds, Example B3 to Example B22 were prepared as described in the general procedure given for Example B2.

| Ex # | Structure | Name | $^{1}$H NMR (500 MHz, DMSO-$d_6$, unless indicated otherwise) | LC/MS RT (min) Method M + H | EL IC$_{50}$ (nM) |
|---|---|---|---|---|---|
| B3 | 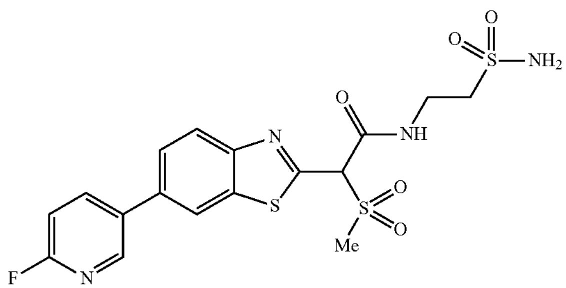 [SMILES: CS(=O)(=O)C(C(=O)NCCS(N)(=O)=O)c1nc2ccc(-c3ccc(F)nc3)cc2s1] | 2-(6-(6-fluoro-3-pyridinyl)-1,3-benzothiazol-2-yl)-2-(methylsulfonyl)-N-(2-sulfamoylethyl)acetamide | $^{1}$H NMR (400 MHz, DMSO-$d_6$) δ 8.97 (s, 1H), 8.65 (d, J = 1.8 Hz, 1H), 8.55 (d, J = 1.5 Hz, 1H), 8.38 (d, J = 2.5 Hz, 1H), 8.18 (d, J = 8.5 Hz, 1H), 7.92 (dd, J = 8.5, 1.8 Hz, 1H), 7.33 (dd, J = 8.5, 2.8 Hz, 1H), 6.93 (s, 2H), 6.04 (s, 1H), 3.60 (d, J = 6.3 Hz, 2H), 3.23 (s, 3H), 3.21-3.16 (m, 2H) | 0.75 O 473.0 | <10 |
| B4 | 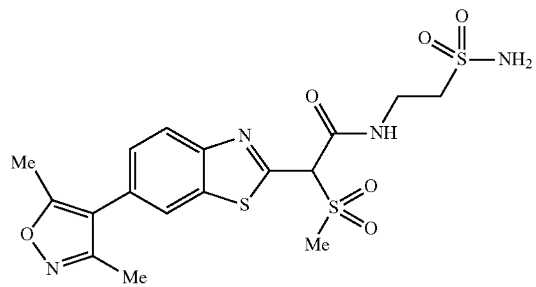 [SMILES: Cc1noc(C)c1-c1ccc2nc(C(C(=O)NCCS(N)(=O)=O)S(C)(=O)=O)sc2c1] | 2-(6-(3,5-dimethyl-4-isoxazolyl)-1,3-benzothiazol-2-yl)-2-(methylsulfonyl)-N-(2-sulfamoylethyl)acetamide | $^{1}$H NMR (400 MHz, DMSO-$d_6$) δ 8.98 (s, 1H), 8.21 (d, J = 1.3 Hz, 1H), 8.15 (d, J = 8.5 Hz, 1H), 7.56 (dd, J = 8.5, 1.8 Hz, 1H), 6.94 (s, 2H), 6.04 (s, 1H), 3.25-3.16 (m, 8H), 2.44 (s, 4H), 2.26 (s, 4H) | 0.74 O 472.9 | 13 |
| B5 | 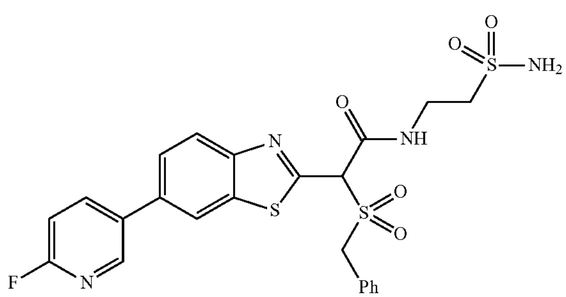 [SMILES: NS(=O)(=O)CCNC(=O)C(c1nc2ccc(-c3ccc(F)nc3)cc2s1)S(=O)(=O)Cc1ccccc1] | 2-(benzylsulfonyl)-2-(6-(6-fluoro-3-pyridinyl)-1,3-benzothiazol-2-yl)-N-(2-sulfamoylethyl)acetamide | $^{1}$H NMR (400 MHz, DMSO-$d_6$) δ 9.09-8.96 (m, 1H), 8.66 (d, J = 2.5 Hz, 1H), 8.56 (d, J = 1.8 Hz, 2H), 8.39 (td, J = 8.2, 2.6 Hz, 1H), 8.22 (d, J = 8.5 Hz, 1H), 8.13 (s, 1H), 7.93 (dd, J = 8.5, 2.0 Hz, 1H), 7.41-7.37 (m, 6H), 7.36-7.23 (m, 6H), 6.94 (s, 4H), 6.10 (s, 1H), 4.85-4.51 (m, 3H), 3.60 (q, J = 6.4 Hz, 2H), 3.29-3.10 (m, 2H) | 0.89 O 548.9 | <10 |

| Ex # | Structure | Name | ¹H NMR (500 MHz, DMSO-d₆, unless indicated otherwise) | LC/MS RT (min) Method M + H | EL IC$_{50}$ (nM) |
|---|---|---|---|---|---|
| B6 | 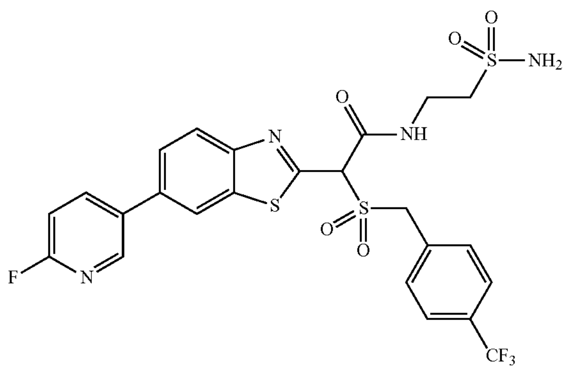 [SMILES: NS(=O)(=O)CCNC(=O)C(c1nc2ccc(-c3ccc(F)nc3)cc2s1)S(=O)(=O)Cc1ccc(C(F)(F)F)cc1] | 2-(6-(6-fluoro-3-pyridinyl)-1,3-benzothiazol-2-yl)-N-(2-sulfamoylethyl)-2-((4-(trifluoromethyl)benzyl)sulfonyl)acetamide | ¹H NMR (400 MHz, DMSO-d₆) δ 9.02 (s, 1H), 8.65 (d, J = 2.5 Hz, 1H), 8.54 (d, J = 1.5 Hz, 2H), 8.38 (d, J = 2.5 Hz, 1H), 8.20 (d, J = 8.5 Hz, 1H), 8.13 (d, J = 1.5 Hz, 1H), 7.93 (dd, J = 8.7, 1.9 Hz, 1H), 7.73 (d, J = 8.5 Hz, 2H), 7.68-7.51 (m, 5H), 7.34 (dd, J = 8.8, 2.8 Hz, 2H), 6.94 (s, 4H), 6.12 (s, 1H), 4.88 (d, J = 3.0 Hz, 2H), 3.60 (d, J = 6.3 Hz, 3H), 3.22-3.15 (m, 2H) | 0.95 O 616.9 | <10 |
| B7 | 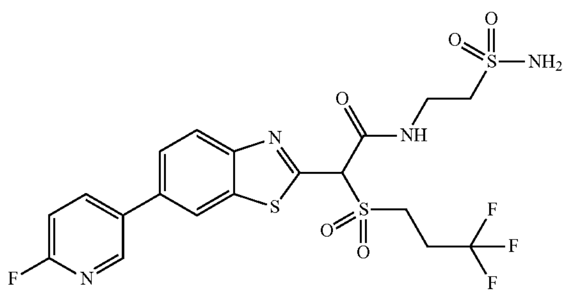 [SMILES: NS(=O)(=O)CCNC(=O)C(c1nc2ccc(-c3ccc(F)nc3)cc2s1)S(=O)(=O)CCC(F)(F)F] | 2-(6-(6-fluoropyridin-3-yl)benzo[d]thiazol-2-yl)-N-(2-sulfamoylethyl)-2-((3,3,3-trifluoropropyl)sulfonyl)acetamide | ¹H NMR (400 MHz, DMSO-d₆) δ 8.95 (d, J = 4.8 Hz, 1H), 8.65 (br. s., 1H), 8.57 (br. s., 2H), 8.39 (d, J = 3.3 Hz, 1H), 8.24-8.15 (m, 2H), 7.94 (d, J = 6.3 Hz, 1H), 7.76 (br. s., 1H), 7.33 (d, J = 6.0 Hz, 2H), 6.94 (br. s., 3H), 6.27 (d, J = 5.5 Hz, 1H), 3.88-3.50 (m, 4H), 3.27-2.66 (m, 5H) | 0.89 O 554.9 | <10 |
| B8 | 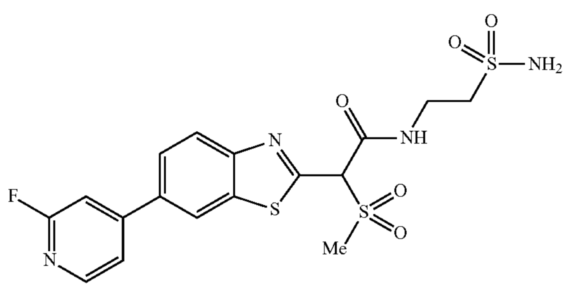 | 2-(6-(2-fluoro-4-pyridinyl)-1,3-benzothiazol-2-yl)-2-(methylsulfonyl)-N-(2-sulfamoylethyl)acetamide | δ 9.00 (s, 1H), 8.75 (d, J = 1.9 Hz, 1H), 8.37 (d, J = 5.2 Hz, 1H), 8.23 (d, J = 8.5 Hz, 1H), 8.07 (dd, J = 8.8, 1.9 Hz, 1H), 7.82 (d, J = 5.2 Hz, 1H), 7.65 (s, 1H), 6.96 (s, 2H), 6.07 (s, 1H), 3.69-3.55 (m, 3H), 3.28-3.23 (m, 3H), 3.23-3.09 (m, 2H) | 0.74 M 472.8 | <10 |

| Ex # | Structure | Name | $^1$H NMR (500 MHz, DMSO-$d_6$, unless indicated otherwise) | LC/MS RT (min) Method M + H | EL IC$_{50}$ (nM) |
|---|---|---|---|---|---|
| B9 | 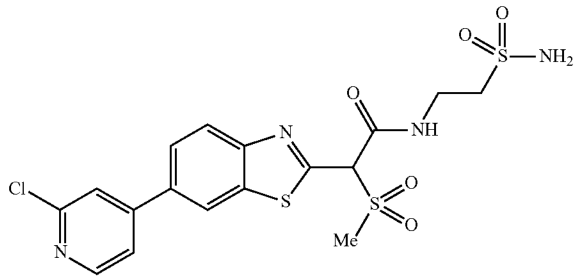 [SMILES: CS(=O)(=O)C(C(=O)NCCS(N)(=O)=O)c1nc2ccc(-c3ccnc(Cl)c3)cc2s1] | 2-(6-(2-chloro-4-pyridinyl)-1,3-benzothiazol-2-yl)-2-(methylsulfonyl)-N-(2-sulfamoylethyl)acetamide | δ 9.00 (s, 1H), 8.74 (d, J = 1.7 Hz, 1H), 8.53 (d, J = 5.2 Hz, 1H), 8.22 (d, J = 8.5 Hz, 1H), 8.06 (dd, J = 8.5, 1.9 Hz, 1H), 7.98 (d, J = 1.1 Hz, 1H), 7.87 (dd, J = 5.4, 1.5 Hz, 1H), 6.96 (s, 1H), 6.52 (s, 1H), 6.07 (s, 1H), 3.65-3.58 (m, 2H), 3.25 (s, 3H), 3.23-3.18 (m, 2H) | 0.77 M 488.7 | <10 |
| B10 | 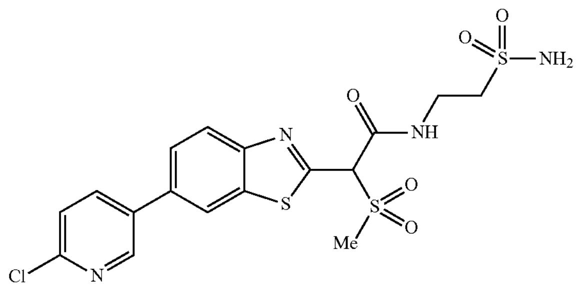 [SMILES: CS(=O)(=O)C(C(=O)NCCS(N)(=O)=O)c1nc2ccc(-c3ccc(Cl)nc3)cc2s1] | 2-(6-(6-chloro-3-pyridinyl)-1,3-benzothiazol-2-yl)-2-(methylsulfonyl)-N-(2-sulfamoylethyl)acetamide | δ 8.92 (s, 1H), 8.81-8.73 (m, 1H), 8.53 (d, J = 1.9 Hz, 1H), 8.20 (dd, J = 8.4, 2.6 Hz, 1H), 8.13 (d, J = 8.5 Hz, 1H), 7.88 (dd, J = 8.8, 1.9 Hz, 1H), 7.60 (d, J = 8.3 Hz, 1H), 6.88 (s, 2H), 5.98 (s, 1H), 3.58-3.50 (m, 2H), 3.17 (s, 3H), 3.15-3.08 (m, 2H) | 0.79 M 488.7 | <10 |
| B11 | 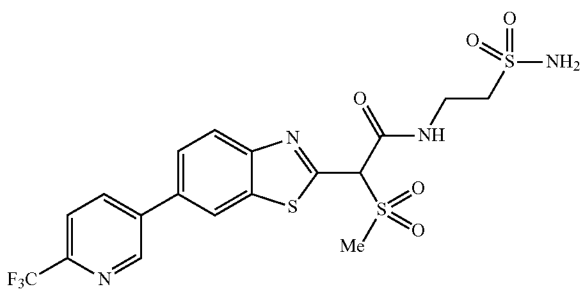 | 2-(methylsulfonyl)-N-(2-sulfamoylethyl)-2-(6-(6-(trifluoromethyl)-3-pyridinyl)-1,3-benzothiazol-2-yl)acetamide | δ 9.21 (d, J = 2.2 Hz, 1H), 9.00 (t, J = 5.8 Hz, 1H), 8.70 (d, J = 1.7 Hz, 1H), 8.48 (dd, J = 8.1, 2.1 Hz, 1H), 8.25 (d, J = 8.5 Hz, 1H), 8.09-8.00 (m, 2H), 6.96 (s, 2H), 6.07 (s, 1H), 3.65-3.58 (m, 2H), 3.27-3.24 (m, 3H), 3.24-3.17 (m, 2H) | 0.84 M 527.7 | <10 |

| Ex # | Structure | Name | ¹H NMR (500 MHz, DMSO-d₆, unless indicated otherwise) | LC/MS RT (min) Method M + H | EL IC$_{50}$ (nM) |
|---|---|---|---|---|---|
| B12 | 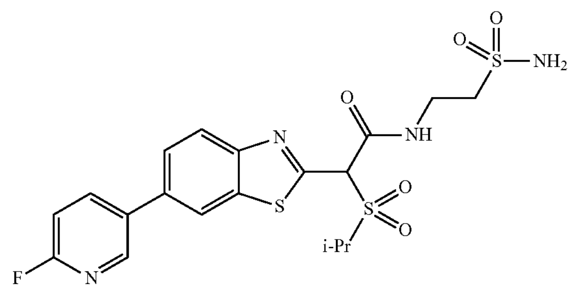 [SMILES: CC(C)S(=O)(=O)C(C(=O)NCCS(N)(=O)=O)c1nc2ccc(-c3ccc(F)nc3)cc2s1] | 2-(6-(6-fluoro-3-pyridinyl)-1,3-benzothiazol-2-yl)-2-(isopropylsulfonyl)-N-(2-sulfamoylethyl)acetamide | ¹H NMR (400 MHz, DMSO-d₆) δ 9.04 (t, J = 5.5 Hz, 1H), 8.64 (d, J = 2.3 Hz, 1H), 8.61-8.50 (m, 1H), 8.38 (td, J = 8.2, 2.5 Hz, 1H), 8.30 (br. s., 1H), 8.16 (d, J = 8.5 Hz, 1H), 8.05-7.82 (m, 1H), 7.72 (d, J = 7.3 Hz, 1H), 7.40-7.19 (m, 1H), 6.94 (br. s., 1H), 6.18 (s, 1H), 3.95-3.35 (m, 3H), 3.29-3.10 (m, 2H), 1.42-1.17 (m, 6H) | 0.83 M 500.9 | <10 |
| B13 | 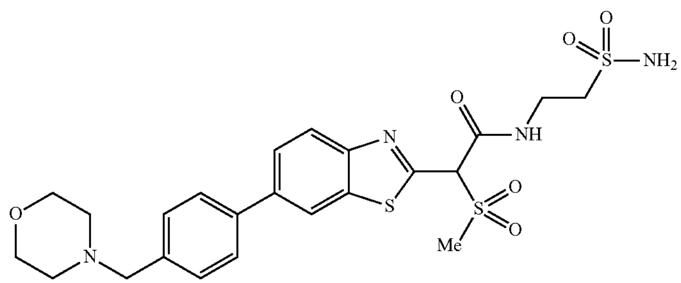 [SMILES: CS(=O)(=O)C(C(=O)NCCS(N)(=O)=O)c1nc2ccc(-c3ccc(CN4CCOCC4)cc3)cc2s1] | 2-(methylsulfonyl)-2-(6-(4-(4-morpholinylmethyl)phenyl)-1,3-benzothiazol-2-yl)-N-(2-sulfamoylethyl)acetamide | δ 9.14-8.95 (m, 1H), 8.23-8.09 (m, 1H), 7.66 (s, 1H), 7.30 (s, 1H), 7.03 (d, J = 1.9 Hz, 3H), 6.86-6.69 (m, 2H), 6.10 (s, 2H), 3.62-3.48 (m, 2H), 3.18-3.05 (m, 2H), 2.73 (d, J = 6.1 Hz, 5H), 2.37 (s, 3H), 2.35-2.20 (m, 6H) | 0.58 M 552.9 | <10 |
| B14 | 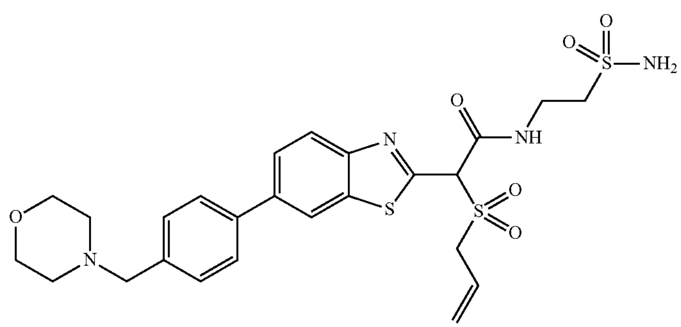 [SMILES: C=CCS(=O)(=O)C(C(=O)NCCS(N)(=O)=O)c1nc2ccc(-c3ccc(CN4CCOCC4)cc3)cc2s1] | 2-(allylsulfonyl)-2-(6-(4-(4-morpholinylmethyl)phenyl)-1,3-benzothiazol-2-yl)-N-(2-sulfamoylethyl)acetamide | δ 7.98-7.82 (m, 2H), 7.67-7.57 (m, 2H), 7.51-7.42 (m, 2H), 7.39-7.30 (m, 2H), 6.95-6.78 (m, 2H), 5.91-5.65 (m, 1H), 5.25-5.05 (m, 2H), 4.28-4.09 (m, 2H), 3.59 (d, J = 3.9 Hz, 6H), 3.24-3.09 (m, 2H), 2.45-2.30 (m, 6H) | 0.64 M 578.9 | <10 |

| Ex # | Structure | Name | ¹H NMR (500 MHz, DMSO-d₆, unless indicated otherwise) | LC/MS RT (min) Method M+H | EL IC$_{50}$ (nM) |
|---|---|---|---|---|---|
| B15 | 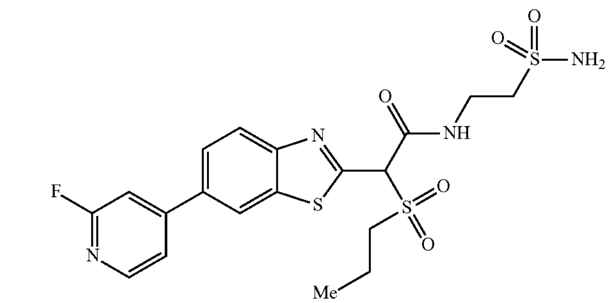 [SMILES: CCCS(=O)(=O)C(C(=O)NCCS(N)(=O)=O)c1nc2ccc(-c3ccnc(F)c3)cc2s1] | 2-(6-(2-fluoro-4-pyridinyl)-1,3-benzothiazol-2-yl)-2-(propylsulfonyl)-N-(2-sulfamoylethyl)acetamide | δ 9.05-8.98 (m, 1H), 8.74 (d, J = 1.7 Hz, 1H), 8.37 (d, J = 5.2 Hz, 1H), 8.22 (d, J = 8.5 Hz, 1H), 8.06 (dd, J = 8.5, 1.9 Hz, 1H), 7.82 (d, J = 5.2 Hz, 1H), 7.65 (s, 1H), 6.96 (s, 2H), 6.09 (s, 1H), 3.66-3.56 (m, 3H), 3.43-3.38 (m, 2H), 3.23-3.12 (m, 2H), 1.82-1.70 (m, 2H), 1.00 (t, J = 7.4 Hz, 3H) | 0.83 M 500.8 | <10 |
| B16 | 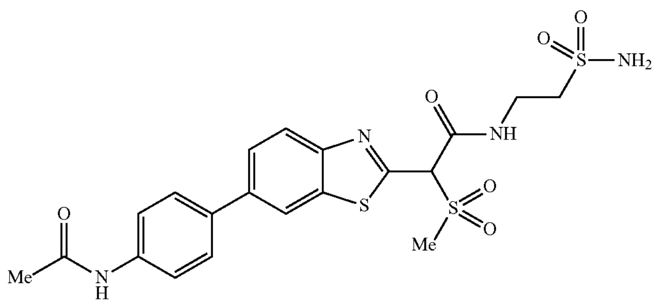 [SMILES: CC(=O)Nc1ccc(-c2ccc3nc(C(C(=O)NCCS(N)(=O)=O)S(C)(=O)=O)sc3c2)cc1] | 2-(6-(4-acetamidophenyl)-1,3-benzothiazol-2-yl)-2-(methylsulfonyl)-N-(2-sulfamoylethyl)acetamide | ¹H NMR (500 MHz, METHANOL-d₄) δ 8.28-8.13 (m, 1H), 8.08-7.95 (m, 1H), 7.81-7.69 (m, 1H), 7.59 (m, 4H), 3.86-3.61 (m, 2H), 3.32-3.23 (m, 2H), 3.12 (s, 3H), 2.06 (s, 3H) | 0.69 M 511.1 | 40 |
| B17 | 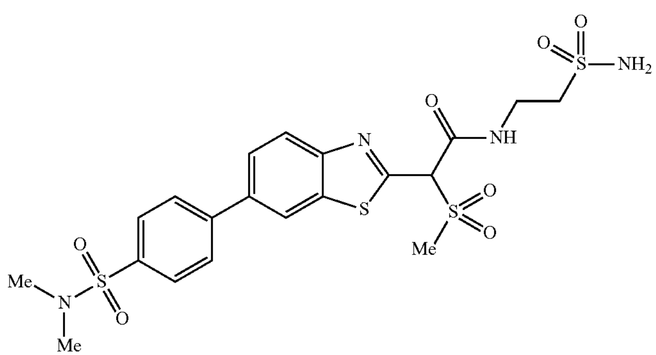 [SMILES: CN(C)S(=O)(=O)c1ccc(-c2ccc3nc(C(C(=O)NCCS(N)(=O)=O)S(C)(=O)=O)sc3c2)cc1] | 2-(6-(4-(dimethylsulfamoyl)phenyl)-1,3-benzothiazol-2-yl)-2-(methylsulfonyl)-N-(2-sulfamoylethyl)acetamide | δ 9.08-8.92 (m, 1H), 8.61 (d, J = 1.7 Hz, 1H), 8.20 (d, J = 8.5 Hz, 1H), 8.04 (d, J = 8.5 Hz, 1H), 7.97 (d, J = 1.9 Hz, 1H), 7.87 (d, J = 8.5 Hz, 2H), 6.95 (s, 2H), 3.60 (m, 2H), 3.24 (s, 3H), 3.19 (d, J = 2.2 Hz, 2H), 2.75-2.60 (s, 6H) | 0.78 M 561.1 | <10 |

| Ex # | Structure | Name | ¹H NMR (500 MHz, DMSO-d₆, unless indicated otherwise) | LC/MS RT (min) Method M + H | EL IC$_{50}$ (nM) |
|---|---|---|---|---|---|
| B18 | 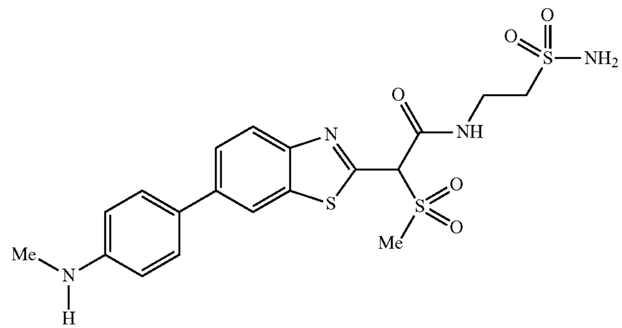 [SMILES: CNc1ccc(-c2ccc3nc(C(C(=O)NCCS(N)(=O)=O)S(C)(=O)=O)sc3c2)cc1] | 2-(6-(4-(methylamino)phenyl)-1,3-benzothiazol-2-yl)-2-(methylsulfonyl)-N-(2-sulfamoylethyl)acetamide | δ 9.06-8.91 (m, 1H), 8.39-8.28 (m, 1H), 8.11-8.04 (m, 1H), 7.83-7.75 (m, 1H), 7.65-7.50 (m, 2H), 7.46-7.36 (m, 1H), 6.95 (s, 2H), 6.78-6.64 (m, 2H), 3.22 (m, 7H), 2.74 (s, 3H) | 0.61 M 483.1 | 13 |
| B19 | 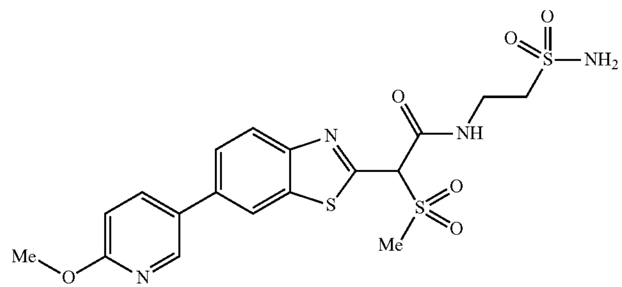 [SMILES: COc1ccc(-c2ccc3nc(C(C(=O)NCCS(N)(=O)=O)S(C)(=O)=O)sc3c2)cn1] | 2-(6-(6-methoxy-3-pyridinyl)-1,3-benzothiazol-2-yl)-N-(2-(methylsulfonyl)-N-(2-sulfamoylethyl)acetamide | δ 9.02-8.96 (m, 1H), 8.60 (d, J = 2.8 Hz, 1H), 8.49 (d, J = 1.9 Hz, 1H), 8.19-8.09 (m, 2H), 7.88 (dd, J = 8.7, 1.8 Hz, 1H), 7.00-6.90 (m, 3H), 6.03 (s, 1H), 3.95-3.89 (m, 3H), 3.64-3.58 (m, 2H), 3.24 (s, 3H), 3.22-3.15 (m, 3H) | 0.76 M 484.9 | <10 |
| B20 | 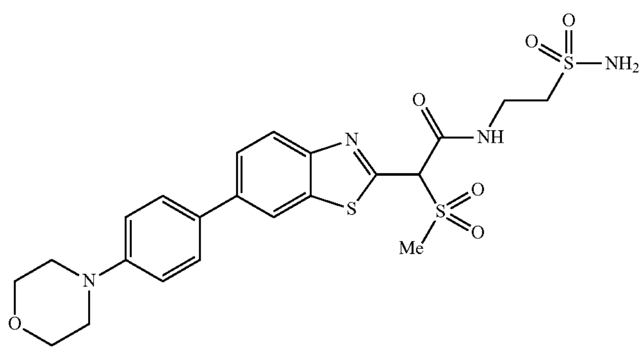 [SMILES: CS(=O)(=O)C(C(=O)NCCS(N)(=O)=O)c1nc2ccc(-c3ccc(N4CCOCC4)cc3)cc2s1] | 2-(methylsulfonyl)-2-(6-(4-(4-morpholinyl)phenyl)-1,3-benzothiazol-2-yl)-N-(2-sulfamoylethyl)acetamide | δ 8.98 (t, J = 5.6 Hz, 1H), 8.41 (d, J = 1.4 Hz, 1H), 8.10 (d, J = 8.5 Hz, 1H), 7.83 (dd, J = 8.8, 1.9 Hz, 1H), 7.67 (d, J = 8.8 Hz, 2H), 7.08 (d, J = 9.1 Hz, 2H), 6.96 (s, 2H), 6.01 (s, 1H), 3.81-3.75 (m, 4H), 3.65-3.57 (m, 3H), 3.24 (s, 3H), 3.19 (t, J = 5.0 Hz, 6H) | 0.76 M 538.9 | <10 |

-continued

| Ex # | Structure | Name | ¹H NMR (500 MHz, DMSO-d₆, unless indicated otherwise) | LC/MS RT (min) Method M + H | EL IC₅₀ (nM) |
|---|---|---|---|---|---|
| B21 | 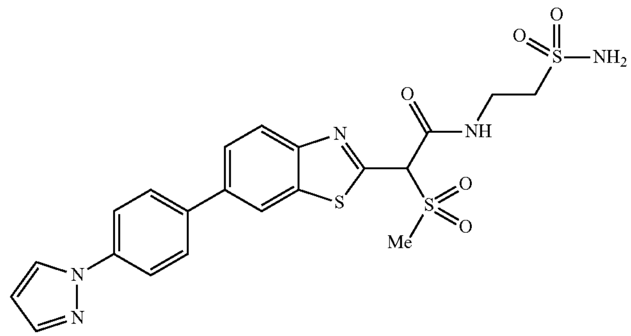 [SMILES: CS(=O)(=O)C(C(=O)NCCS(N)(=O)=O)c1nc2ccc(-c3ccc(-n4cccn4)cc3)cc2s1] | 2-(methylsulfonyl)-2-(6-(4-(1H-pyrazol-1-yl)phenyl)-1,3-benzothiazol-2-yl)-N-(2-sulfamoylethyl)acetamide | δ 8.97-8.86 (m, 1H), 8.54-8.44 (m, 1H), 8.10 (d, J = 8.5 Hz, 1H), 7.96-7.89 (m, 2H), 7.88-7.79 (m, 2H), 7.79-7.65 (m, 2H), 6.88 (s, 2H), 6.56-6.47 (m, 1H), 3.58-3.50 (m, 2H), 3.21-3.15 (m, 3H), 3.15-3.08 (m, 2H) | 0.84 M 519.9 | <10 |
| B22 | 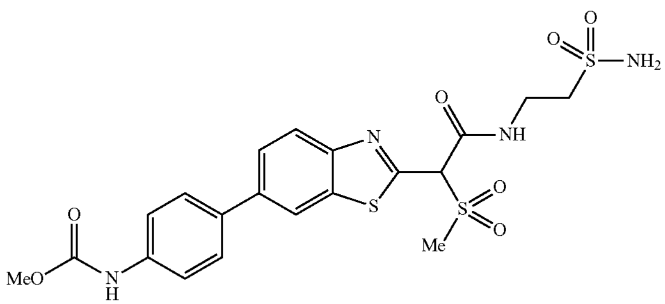 [SMILES: COC(=O)Nc1ccc(-c2ccc3nc(C(C(=O)NCCS(N)(=O)=O)S(C)(=O)=O)sc3c2)cc1] | methyl (4-(2-(1-(methylsulfonyl)-2-oxo-2-((2-sulfamoylethyl)amino)ethyl)-1,3-benzothiazol-6-yl)phenyl)carbamate | δ 9.72 (s, 1H), 8.95-8.87 (m, 1H), 8.36 (d, J = 1.7 Hz, 1H), 8.04 (d, J = 8.8 Hz, 1H), 7.77 (dd, J = 8.8, 1.9 Hz, 1H), 7.64 (d, J = 8.8 Hz, 2H), 7.52 (d, J = 8.5 Hz, 2H), 6.88 (s, 1H), 5.94 (s, 1H), 3.64-3.61 (m, 2H), 3.57-3.49 (m, 3H), 3.17-3.14 (m, 3H), 3.14-3.08 (m, 2H) | 0.76 M 526.9 | <10 |

Example B23

2-(6-(2-Fluoro-4-pyridinyl)-1,3-benzothiazol-2-yl)-2-(methylsulfonyl)-N-(2-(methylsulfonyl)ethyl)acetamide

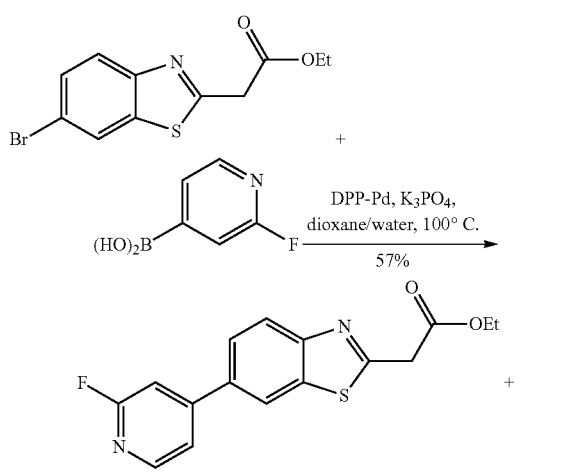
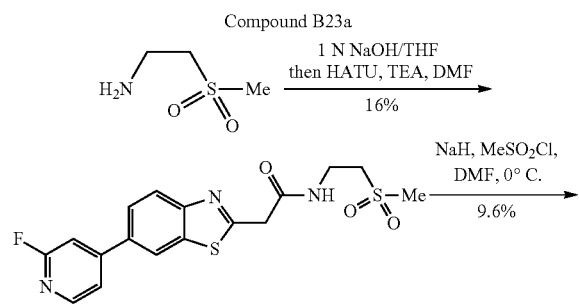
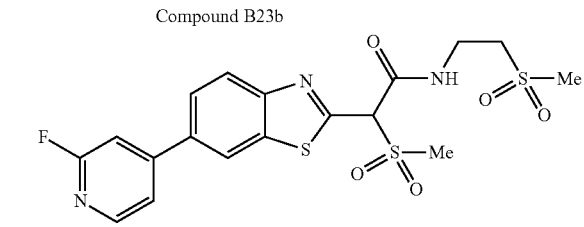

Compound B23a. Ethyl 2-(6-(2-fluoropyridin-4-yl)benzo[d]thiazol-2-yl)acetate SiliaCat DPP-Pd (0.26 mmol/g loading, from Silicycle, 100 mg, 0.67 mmol), ethyl 2-(6-bromobenzo[d]thiazol-2-yl)acetate (described in WO2011/074560, 200 mg, 0.67 mmol), potassium phosphate (348 mg, 2.00 mmol) and (2-fluoropyridin-4-yl)boronic acid (141 mg, 1.00 mmol) in dioxane (5 mL)/water (0.2 mL) were purged with argon for 5 minutes and then heated at 90° C. After 4 hours, the reaction mixture was diluted with water (50 mL), extracted with DCM (3×50 mL), dried over $MgSO_4$, and concentrated under reduced pressure. The residue was purified by silica gel chromatography (0 to 100% ethyl acetate/hexanes over 15 minutes) to give Compound B23a (120 mg, 57% yield) as a brown solid. HPLC: RT=0.95 min (LCMS Method M). MS (ES): m/z=316.9 $[M+H]^+$. $^1$H NMR (500 MHz, DMSO-$d_6$) δ 8.68 (d, J=1.7 Hz, 1H), 8.35 (d, J=5.2 Hz, 1H), 8.12 (d, J=8.5 Hz, 1H), 8.02 (dd, J=8.5, 1.9 Hz, 1H), 7.81 (d, J=5.2 Hz, 1H), 7.64 (s, 1H), 4.38 (s, 2H), 4.19 (q, J=7.1 Hz, 2H), 1.24 (t, J=7.0 Hz, 3H).

Compound B23b. 2-(6-(2-Fluoropyridin-4-yl)benzo[d]thiazol-2-yl)-N-(2-(methylsulfonyl)ethyl)acetamide Compound B23b (16 mg, 16% yield) was prepared from Compound B23a as described in the general procedure given for Compound A1a. HPLC: RT=0.73 min (LCMS Method M). MS (ES): m/z=393.8 $[M+H]^+$. $^1$H NMR (500 MHz, DMSO-$d_6$) δ 8.69-8.62 (m, 2H), 8.34 (d, J=5.5 Hz, 1H), 8.08 (d, J=8.5 Hz, 1H), 8.00 (dd, J=8.5, 1.9 Hz, 1H), 7.81 (d, J=5.2 Hz, 1H), 7.64 (s, 1H), 4.13 (s, 2H), 3.58-3.51 (m, 2H), 3.31 (t, J=6.9 Hz, 2H), 3.03 (s, 3H).

Example B23

Example B23 (2.3 mg, 9.6% yield) was prepared from Compound B23b as described in the general procedure given for Example B2. HPLC: RT=0.76 min (LCMS Method M). MS (ES): m/z=471.7 $[M+H]^+$. $^1$H NMR (500 MHz, DMSO-$d_6$) δ 9.08 (s, 1H), 8.75 (d, J=1.7 Hz, 1H), 8.37 (d, J=5.5 Hz, 1H), 8.23 (d, J=8.5 Hz, 1H), 8.07 (dd, J=8.7, 1.8 Hz, 1H), 7.86-7.79 (m, 1H), 7.65 (s, 1H), 6.09 (s, 1H), 3.65 (d, J=5.8 Hz, 2H), 3.37-3.32 (m, 2H), 3.26 (s, 3H), 3.04 (s, 3H). EL $IC_{50}$ 210 nM.

The following compounds, Example B24 and Example B25 were prepared as described in the general procedure given for Example B24.

| Ex # | Structure | Name | 1H NMR (500 MHz, DMSO-d6) | LC/MS RT (min) Method M + H | EL IC50 (nM) |
|---|---|---|---|---|---|
| B24 | 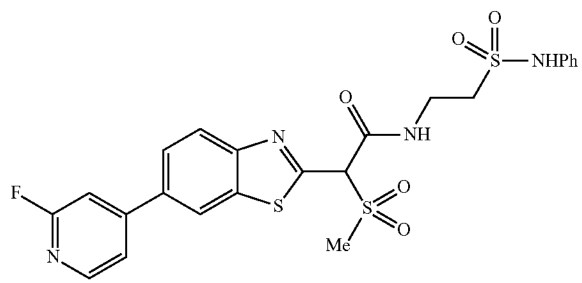 | 2-(6-(2-fluoro-4-pyridinyl)-1,3-benzothiazol-2-yl)-2-(methylsulfonyl)-N-(2-(phenylsulfamoyl)ethyl)acetamide | δ 8.75-8.68 (m, 1H), 8.66 (d, J = 1.4 Hz, 1H), 8.34 (d, J = 5.5 Hz, 1H), 8.08 (d, J = 8.5 Hz, 1H), 8.00 (dd, J = 8.5, 1.9 Hz, 1H), 7.81 (dd, J = 5.4, 1.8 Hz, 1H), 7.64 (s, 1H), 7.57-7.46 (m, 4H), 4.13 (s, 1H), 3.87 (t, J = 6.9 Hz, 2H), 3.64 (d, J = 5.8 Hz, 2H), 3.53 (s, 3H) | 0.89 M 548.7 | 35 |
| B25 | 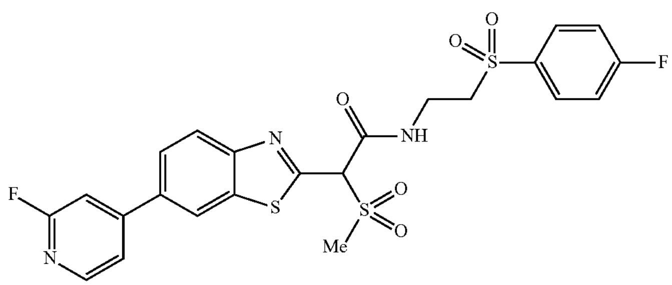 [SMILES: CS(=O)(=O)C(C(=O)NCCS(=O)(=O)c1ccc(F)cc1)c1nc2ccc(-c3ccnc(F)c3)cc2s1] | N-(2-((4-fluorophenyl)sulfonyl)ethyl)-2-(6-(2-fluoropyridin-4-yl)-1,3-benzothiazol-2-yl)-2-(methylsulfonyl)acetamide | δ 9.04-8.95 (m, 1H), 8.74 (d, J = 1.4 Hz, 1H), 8.37 (d, J = 5.5 Hz, 1H), 8.22 (d, J = 8.5 Hz, 1H), 8.07 (dd, J = 8.7, 1.8 Hz, 1H), 7.99-7.93 (m, 2H), 7.82 (d, J = 5.5 Hz, 1H), 7.66 (s, 1H), 7.44-7.36 (m, 2H), 5.96 (s, 1H), 3.62-3.47 (m, 4H), 3.22 (s, 2H) | 0.74 M 472.8 | 110 |

Example B26

2-(4-Fluoro-6-phenylbenzo[d]thiazol-2-yl)-N-(2-sulfamoylethyl)-2-((3,3,3-trifluoropropyl)sulfonyl)acetamide

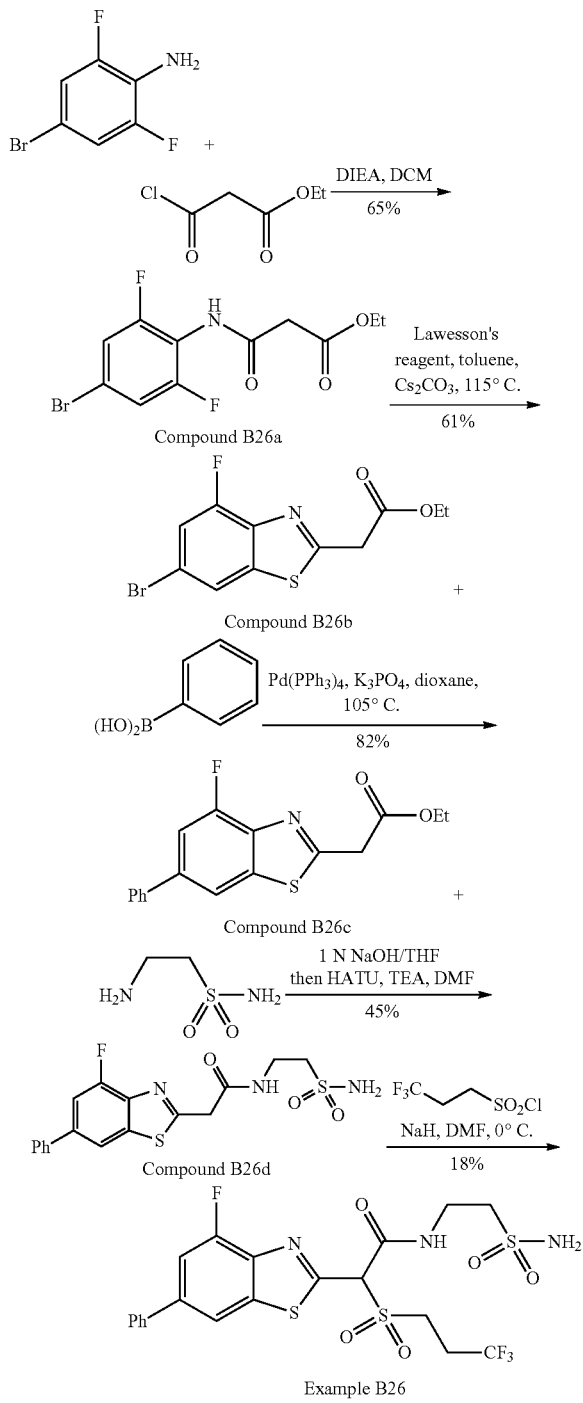

Compound B26a. Ethyl 3-((4-bromo-2,6-difluorophenyl)amino)-3-oxopropanoate

To a solution of 4-bromo-2,6-difluoroaniline (10 g, 48 mmol) in DCM (15 mL) was added ethyl 3-chloro-3-oxopropanoate (6.8 mL, 53 mmol) and DIEA (9.2 mL, 53 mmol) at room temperature. After 1 hour, the reaction mixture was partitioned between $H_2O$ and DCM. The organic phase was washed with saturated $NH_4Cl$, $H_2O$, dried over $Na_2SO_4$, and filtered. The filtrate was concentrated under reduced pressure to give Compound B26a (10 g, 65% yield). HPLC: RT=1.6 (LCMS Method Q). MS (ES): m/z=321.9 $[M+H]^+$. $^1H$ NMR (500 MHz, CHLOROFORM-d) δ 8.89 (br. s., 1H), 7.20-7.15 (m, 2H), 4.29 (q, J=7.2 Hz, 2H), 3.54 (s, 2H), 1.36-1.31 (m, 3H).

Compound B26b. Ethyl 2-(6-bromo-4-fluorobenzo[d]thiazol-2-yl)acetate

To a solution of Compound B26a (2.0 g, 6.2 mmol) in toluene (20 mL) was added Lawesson's reagent (1.5 g, 3.7 mmol), and the reaction mixture was heated at reflux. After 3 hours, $Cs_2CO_3$ (5.1 g, 16 mmol) was added, and the reaction mixture was heated at reflux. After 16 hours, the reaction mixture was filtered, concentrated under reduced pressure and purified using silica gel chromatography (eluting with 0 to 100% EtOAc in hexanes) to give Compound B26b (1.2 g, 61% yield). HPLC: RT=2.02 (LCMS Method Q). MS (ES): m/z=319.9 $[M+H]^+$. $^1H$ NMR (500 MHz, CHLOROFORM-d) δ ppm 7.93 (1H, d), 7.66 (1H, d, J=1.7 Hz), 4.28 (2H, q, J=7.2 Hz), 4.22-4.24 (2H, m), 1.33 (3H, t, J=7.2 Hz).

Compound B26c. Ethyl 2-(4-fluoro-6-phenylbenzo[d]thiazol-2-yl)acetate

To a solution of Compound B26b (1.0 g, 3.1 mmol) in dioxane (20 mL) was added phenylboronic acid (460 mg, 3.8 mmol), potassium phosphate, (1.7 g, 7.9 mmol), and $Pd(PPh_3)_4$ (730 mg, 0.63 mmol). The reaction mixture was purged with argon and heated at 105° C. for 16 hours. The reaction mixture was allowed to cooled to room temperature and filtered. The filtrate was concentrated under reduced pressure and purified by silica gel chromatography (30 minutes gradient from 0 to 100% EtOAc in DCM) to give Compound B26c (810 mg, 82% yield). HPLC: RT=2.2 min (LCMS Method Q). MS (ES): m/z=316 $[M+H]^+$. $^1H$ NMR (500 MHz, CHLOROFORM-d) δ ppm 7.88 (1H, d, J=1.4 Hz), 7.61-7.67 (2H, m), 7.47-7.54 (2H, m), 7.39-7.47 (2H, m), 4.30 (2H, q, J=7.2 Hz), 4.26 (2H, s), 1.33-1.38 (3H, m).

Compound B26d. 2-(4-Fluoro-6-phenylbenzo[d]thiazol-2-yl)-N-(2-sulfamoylethyl)acetamide Compound B26d (14.5 mg, 45% yield) was prepared from Compound B26c as described in the general procedure given for Compound A1a. HPLC: RT=1.81 min (LCMS Method Q). MS (ES): m/z=394.9 $[M+H]^+$. $^1H$ NMR (500 MHz, METHANOL-d4) δ 8.12 (d, J=1.4 Hz, 1H), 7.81-7.70 (m, 2H), 7.59 (dd, J=11.8, 1.7 Hz, 1H), 7.52 (t, J=7.7 Hz, 2H), 7.44 (d, J=7.4 Hz, 1H), 4.17 (s, 2H), 3.71 (t, J=6.7 Hz, 2H), 2.64 (dt, J=3.8, 1.8 Hz, 2H).

Example B26

Example B26 (2.6 mg, 18% yield) was prepared from Compound B26d as described in the general procedure given for Example B2. HPLC: RT=2.0 (LCMS Method Q). MS (ES): m/z=554.1 $[M+H]^+$. $^1H$ NMR (500 MHz, METHANOL-$d_4$) δ 8.18-8.15 (m, 1H), 7.77-7.72 (m, 2H), 7.70-7.66 (m, 1H), 7.63 (dd, J=11.8, 1.4 Hz, 1H), 7.54-7.48 (m, 2H), 7.46-7.39 (m, 1H), 3.82 (td, J=6.7, 4.4 Hz, 2H), 3.77 (dt, J=9.8, 5.9 Hz, 2H), 3.40-3.35 (m, 2H), 2.88-2.74 (m, 2H). EL $IC_{50}$<10 nM.

The following compounds, Example B27 to Example B29 were prepared as described in the general procedure given for Example B26.

| Ex # | Structure | Name | ¹H NMR (400 MHz, METHANOL-d₄) | LC/MS RT (min) Method M + H | EL IC$_{50}$ (nM) |
|---|---|---|---|---|---|
| B27 | 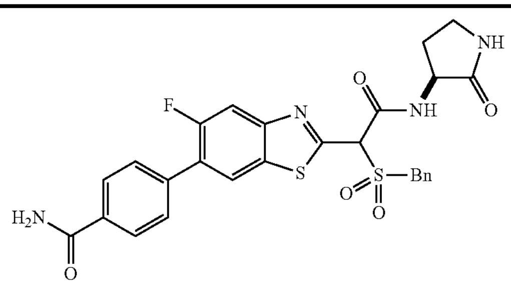 | 4-(2-(1-(benzylsulfonyl)-2-oxo-2-(((3R)-2-oxo-3-pyrrolidinyl)amino)ethyl)-5-fluoro-1,3-benzothiazol-6-yl)benzamide | δ 6.67-8.44 (m, 12H), 4.70-5.02 (m, 1H), 4.27-4.66 (m, 2H), 3.35-3.59 (m, 2H), 2.56 (br. s., 1H), 1.82-2.16 (m, 1H). | 1.75 Q 566.9 | 93 |
| B28 | 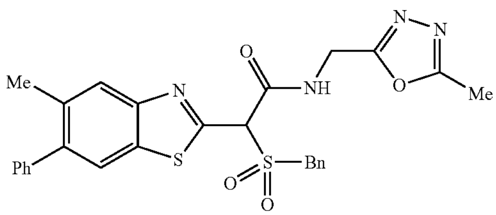 [SMILES: Cc1nnc(CNC(=O)C(c2nc3cc(C)c(-c4ccccc4)cc3s2)S(=O)(=O)Cc2ccccc2)o1] | 2-(benzylsulfonyl)-N-((5-methyl-1,3,4-oxadiazol-2-yl)methyl)-2-(5-methyl-6-phenyl-1,3-benzothiazol-2-yl)acetamide | δ 6.40-8.60 (m, 13H), 3.51-4.72 (m, 4H), 1.73-2.84 (m, 6H) | 2.18 Q 533.0 | 12 |
| B29 | 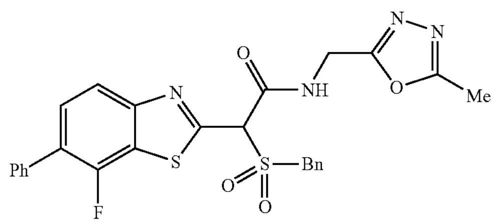 [SMILES: Cc1nnc(CNC(=O)C(c2nc3ccc(-c4ccccc4)c(F)c3s2)S(=O)(=O)Cc2ccccc2)o1] | 2-(6-(4-chlorophenyl)-1,3-benzothiazol-2-yl)-N-((5-methyl-1,3,4-oxadiazol-2-yl)methyl)acetamide | δ 6.52-8.81 (m, 13H), 3.48-4.77 (m, 4H), 2.17-2.94 (m, 3H). | 2.12 Q 536.0 | 131 |

Example B30

2-(6-(2-Fluoro-4-pyridinyl)-1,3-benzothiazol-2-yl)-2-(methylsulfonyl)-N-(2-((2,2,2-trifluoroethyl)sulfamoyl)ethyl)acetamide

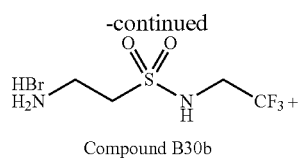
Compound B30b

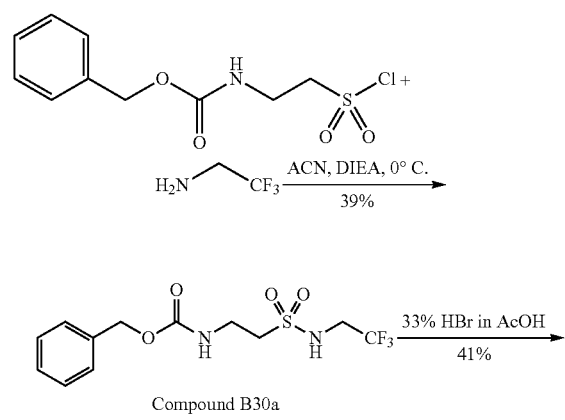
Compound B30a

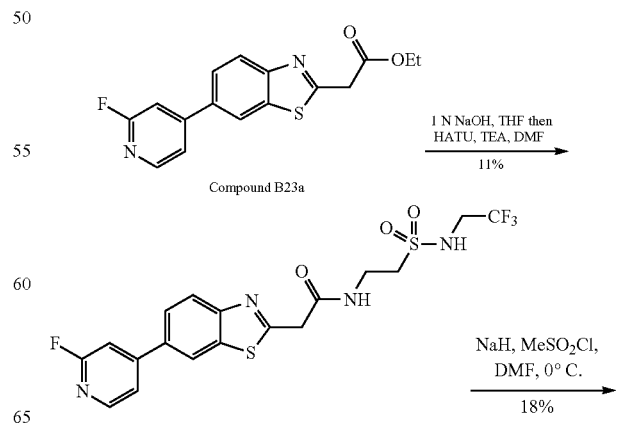
Compound B30c

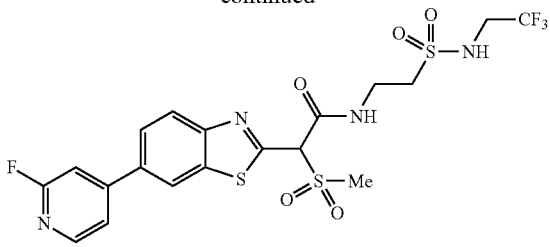

Example B30

Compound B30a. Benzyl (2-(N-(2,2,2-trifluoroethyl) sulfamoyl)ethyl)carbamate

To a dioxane (1 mL) solution of 2,2,2-trifluoroethanamine (80 mg, 0.81 mmol) and DIEA (0.28 mL, 1.6 mmol) at 0° C. was added benzyl (2-(chlorosulfonyl)ethyl)carbamate (150 mg, 0.54 mmol) in acetonitrile (1 mL). The reaction was allowed to reach room temperature over a period of 20 minutes. The reaction mixture was concentrated under reduced pressure, and the residue purified using reverse phase HPLC (YMC Sunfire 5u (C18) 30×100 mm, 0-100% ACN (90% in $H_2O$, 0.1% TFA) using gradient over 16 min with flow rate 40 mL/min and UV detection at 220 nm) to give Compound B30a (95 mg, 39% yield). HPLC: RT=3.84 (LCMS Method M). MS (ES): m/z=340.9 [M+H]$^+$. $^1$H NMR (500 MHz, CHLOROFORM-d) δ 7.43-7.34 (m, 5H), 5.28 (br. s., 2H), 5.15 (s, 2H), 3.86-3.68 (m, 4H), 3.35-3.24 (m, 2H).

Compound B30b. 2-Amino-N-(2,2,2-trifluoroethyl)ethanesulfonamide

HBr (1 mL, 33% solution in acetic acid) was added to Compound B30a (95 mg, 0.28 mmol) at room temperature. After 5 minutes, the reaction mixture was diluted with diethyl ether (5 mL), and the resulting solid, Compound B30b (42 mg, 41%) was isolated by filtration. HPLC: RT=0.39 (LCMS Method M). MS (ES): m/z=207.0 [M+H]$^+$. $^1$H NMR (500 MHz, DMSO-$d_6$) δ 8.46 (br. s, 1H), 7.87 (br. s., 2H), 3.87 (td, J=6.3, 3.0 Hz, 2H), 3.40 (t, J=7.4 Hz, 2H), 3.17 (br. s., 2H)

Compound B30c. 2-(6-(2-Fluoropyridin-4-yl)benzo[d]thiazol-2-yl)-N-(2-(N-(2,2,2-trifluoroethyl)sulfamoyl)ethyl)acetamide Compound B30c (10 mg, 11%) was prepared from Compound B30b and Compound B23a as described in the general procedure given for Compound A1a. HPLC: RT=0.83 (LCMS Method M). MS (ES): m/z=476.8 [M+H]$^+$. $^1$H NMR (500 MHz, DMSO-$d_6$) δ 8.66 (d, J=1.9 Hz, 1H), 8.58 (s, 1H), 8.34 (d, J=5.2 Hz, 1H), 8.17 (t, J=6.7 Hz, 1H), 8.08 (d, J=8.5 Hz, 1H), 8.03-7.98 (m, 1H), 7.83-7.78 (m, 1H), 7.64 (s, 1H), 4.13 (s, 2H), 3.82 (dd, J=9.6, 6.9 Hz, 2H), 3.54-3.47 (m, 2H), 3.30-3.26 (m, 2H).

Example B30

Example B31 (2.0 mg, 18% yield) was prepared from Compound B31c as described in the general procedure given for Example B2. HPLC: RT=0.83 (LCMS Method M). MS (ES): m/z=476.8 [M+H]$^+$. $^1$H NMR (500 MHz, DMSO-$d_6$) δ 8.66 (d, J=1.9 Hz, 1H), 8.58 (s, 1H), 8.34 (d, J=5.2 Hz, 1H), 8.17 (t, J=6.7 Hz, 1H), 8.08 (d, J=8.5 Hz, 1H), 8.03-7.98 (m, 1H), 7.83-7.78 (m, 1H), 7.64 (s, 1H), 4.13 (s, 2H), 3.82 (dd, J=9.6, 6.9 Hz, 2H), 3.54-3.47 (m, 2H), 3.30-3.26 (m, 2H). EL $IC_{50}$ 277 nM.

Example B31

N-tert-Butyl-4-(2-(1-(methylsulfonyl)-2-oxo-2-((2-sulfamoylethyl)amino)ethyl)-1,3-benzothiazol-6-yl)benzamide

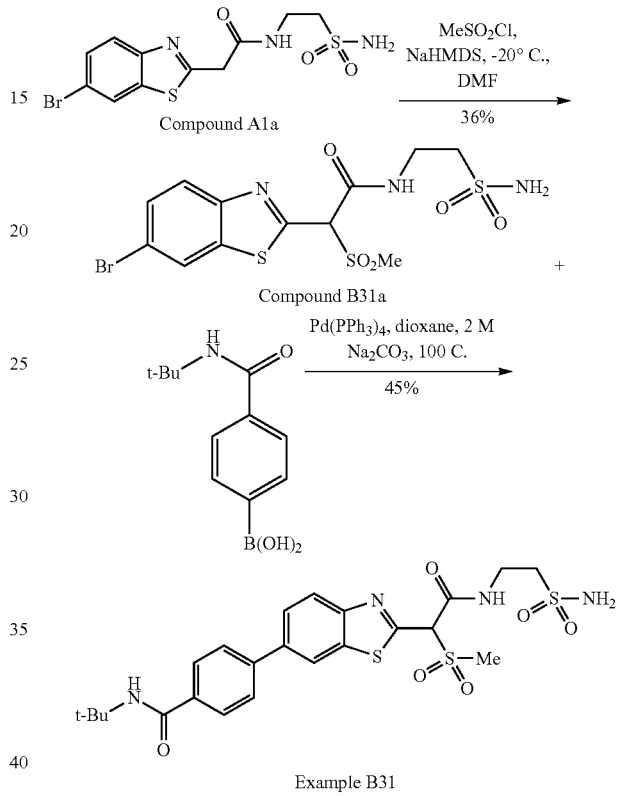

Example B31

Compound B31a. Ethyl 2-(6-bromobenzo[d]thiazol-2-yl)-2-(methylsulfonyl)acetate 1 M NaHMDS in THF (0.40 mL, 0.40 mmol) was added dropwise to a cooled (−20° C.) DMF (3 mL) solution of Compound A1a (100 mg, 0.26 mmol). After 3 minutes, methanesulfonyl chloride (0.03 mL, 0.40 mmol) was added. After 5 minutes, the reaction was quenched with acetic acid (0.2 mL), diluted with methanol (0.5 mL), and purified using reverse HPLC (Phenomemenx Luna AXIA 5 micron C18, 21.2×100, UV at 220 nm, 10 to 70% B over 15 minutes with 10 minute hold time, solvent A: 90% water/ACN1/0.1% TFA, solvent B:90% ACN/water/0.1% TFA, Flow rate 20 mL/min; detector at 254) to isolate Compound B31a (43 mg, 36% yield) as a white solid. HPLC: Rt=0.80 min (LCMS Method M). MS (ES): m/z=457.6 [M+H]$^+$. $^1$H NMR (500 MHz, DMSO-$d_6$) δ 8.97 (t, J=5.8 Hz, 1H), 8.47 (d, J=1.9 Hz, 1H), 8.02 (d, J=8.5 Hz, 1H), 7.72 (dd, J=8.8, 1.9 Hz, 1H), 6.94 (s, 2H), 6.01 (s, 1H), 3.78-3.48 (m, 2H), 3.21 (s, 3H), 3.20-3.13 (m, 2H).

Example B31

Example B31 (14 mg, 45% yield) was prepared from Compound B31a as described in the general procedure given for Compound B2a. EL IC$_{50}$<10 nM. HL IC$_{50}$ 257 nM. HPLC: RT=0.86 min (LCMS Method M). MS (ES): m/z=552.8 [M+H]$^+$. $^1$H NMR (500 MHz, DMSO-d$_6$) δ 8.98 (t, J=5.8 Hz, 1H), 8.55 (d, J=1.4 Hz, 1H), 8.17 (d, J=8.8 Hz, 1H), 8.00-7.90 (m, 3H), 7.88-7.77 (m, 3H), 6.95 (s, 2H), 6.03 (s, 1H), 3.61 (q, J=6.8 Hz, 2H), 3.24 (s, 3H), 3.22-3.15 (m, 2H), 1.47-1.33 (m, 9H).

Example B32 to Example B97 were prepared as described in the general procedure given for Example B31.

Example B98

2-(Methylsulfonyl)-2-(6-(1-(4-piperidinyl)-1H-pyrazol-4-yl)-1,3-benzothiazol-2-yl)-N-(2-sulfamoylethyl)acetamide

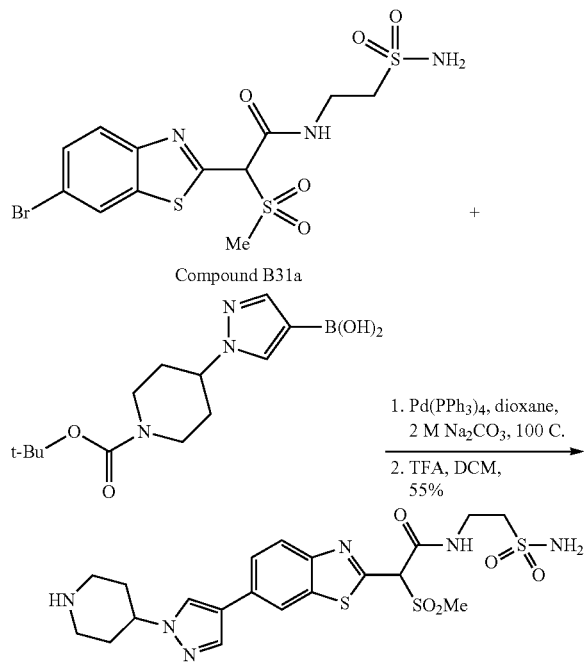

Example B98

A mixture of Compound B31a, (1-(1-(tert-butoxycarbonyl)piperidin-4-yl)-1H-pyrazol-4-yl)boronic acid (15.5 mg, 0.0530 mmol) and Pd(PPh$_3$)$_4$ (12.2 mg, 10.5 μmol) in dioxane (2 mL) and 2M Na$_2$CO$_3$ (1 mL) was purged with argon and heated at 90° C. for 2 hours. The reaction mixture was concentrated under reduced pressure, dissolved in DMF (2 mL) and filtered. The filtrate was concentrated under reduced pressure, dissolved in DCM (1 mL) and treated with TFA (1 mL). After 16 hours, the reaction mixture was concentrated under reduced pressure, dissolved in DMF/methanol and purified by reverse phase HPLC (Column: Waters X Bridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-25% B over 20 minutes, then a 5-minute hold at 100% B; Flow: 20 mL/min) to give Example B98 (12.4 mg, 54.0% yield). EL IC$_{50}$<10 nM. HL IC$_{50}$ 464 nM. HPLC: RT=1.0 min (LCMS Method N). MS (ES): m/z=527.2 [M+H]$^+$. $^1$H NMR (500 MHz, DMSO-d$_6$) δ 9.38-8.85 (m, 1H), 8.51-8.13 (m, 2H), 8.13-7.67 (m, 2H), 7.40 (br. s., 1H), 6.88 (br. s., 2H), 4.42 (br. s., 1H), 3.66-3.58 (m, 3H), 3.19 (br. s., 5H), 2.97 (br. s., 2H), 2.90 (br. s., 1H), 2.18 (d, J=12.1 Hz, 2H), 2.06 (d, J=10.5 Hz, 2H).

Example B99

4-(2-(1-(Benzylsulfonyl)-2-oxo-2-((2-sulfamoylethyl)amino)ethyl)-1,3-benzothiazol-6-yl)-N-(2-methoxyethyl)benzamide

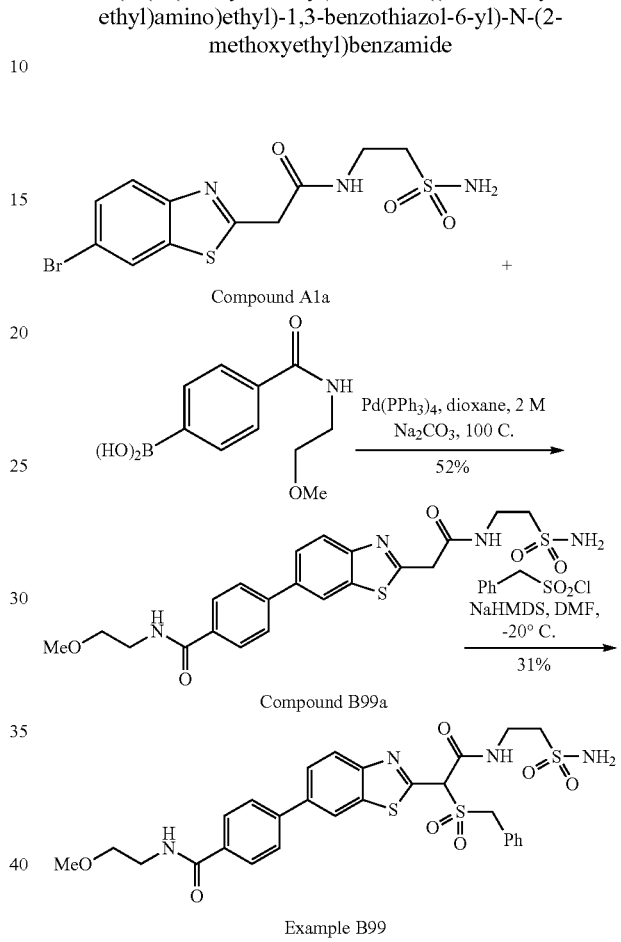

Compound B99a. N-(2-Methoxyethyl)-4-(2-(2-oxo-2-((2-sulfamoylethyl)amino)ethyl)benzo[d]thiazol-6-yl)benzamide Compound B99a (26 mg, 52% yield) was prepared from Compound A1a and (4-((2-methoxyethyl)carbamoyl)phenyl)boronic acid as described in the general procedure given for Compound B2a. HPLC: RT=0.83 min (LCMS Method M). MS (ES): m/z=375.9 [M+H]$^+$. $^1$H NMR (500 MHz, DMSO-d$_6$) δ 8.44-8.68 (1H, m), 8.36 (1H, d, J=1.93 Hz), 7.88 (1H, d, J=8.80 Hz), 7.56-7.70 (1H, m), 6.90 (2H, s), 4.06 (2H, s), 3.43-3.62 (2H, m), 3.07-3.22, (2H, m).

Example B100

Example B99 (10 mg, 31% yield) was prepared from Compound B99a and benzyl sulfonylchloride as described in the general procedure given for Compound B31a. EL IC$_{50}$<10 nM. HL IC$_{50}$ 55 nM. HPLC: RT=0.83 min (LCMS Method M). MS (ES): m/z=630.8 [M+H]$^+$. $^1$H NMR (500 MHz, DMSO-d$_6$) δ 9.02 (t, J=5.8 Hz, 1H), 8.65-8.50 (m, 1H), 8.25-8.13 (m, 1H), 7.99 (d, J=8.5 Hz, 1H), 7.95 (dt, J=8.5, 1.7

Hz, 1H), 7.88 (d, J=8.5 Hz, 1H), 7.78 (br. s., 1H), 7.40 (s, 2H), 7.37-7.14 (m, 2H), 7.00-6.90 (m, 2H), 6.10 (s, 1H), 4.74 (q, J=13.5 Hz, 1H), 4.68-4.51 (m, 1H), 3.71-3.56 (m, 2H), 3.52-3.42 (m, 4H), 3.29-3.27 (m, 3H), 3.24-3.08 (m, 2H).

Example B100 to Example B156 were prepared as described in the general procedure given for Example B99.

Example B157

2-{6-[4-(4-Morpholinylcarbonyl)phenyl]-1,3-benzothiazol-2-yl}-2-{[2-(4-morpholinyl)ethyl]sulfonyl}-N-(2-sulfamoylethyl)acetamide DMSO-$d_6$) δ 8.96 (s, 1H), 8.48 (d, J=2.0 Hz, 1H), 8.02 (d, J=8.6 Hz, 1H), 7.73 (dd, J=8.6, 2.0 Hz, 1H), 7.47 (br. s., 1H), 7.40-7.22 (m, 5H), 6.90 (s, 2H), 5.03 (s, 2H), 3.74-3.34 (m, 6H), 3.25-3.02 (m, 2H).

Compound B157b. 2-((2-Aminoethyl)sulfonyl)-2-(6-bromobenzo[d]thiazol-2-yl)-N-(2-sulfamoylethyl) acetamide hydrobromide To Compound B157a (253 mg, 0.41 mmol) was added 33% HBr in AcOH (4 mL). After 1 h, the reaction mixture was diluted with Et$_2$O (~50 mL) generating a white precipitate,

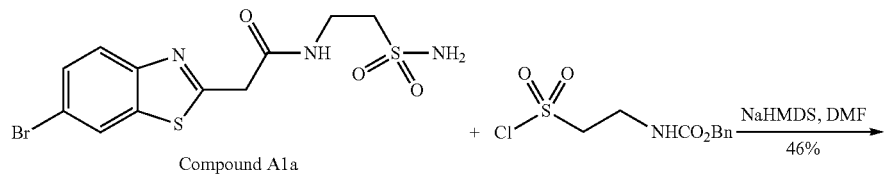

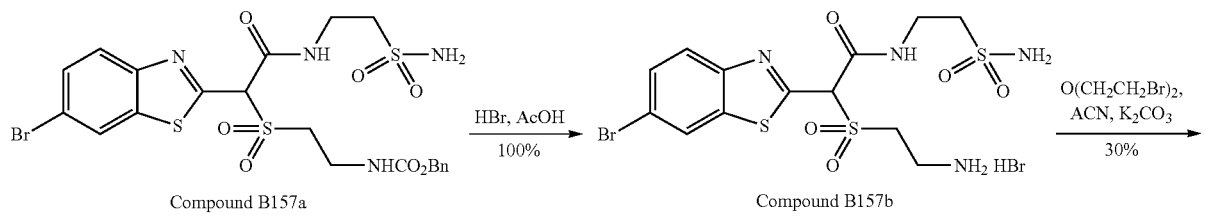

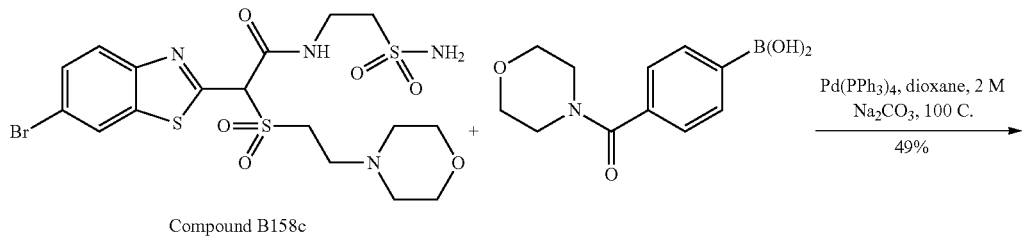

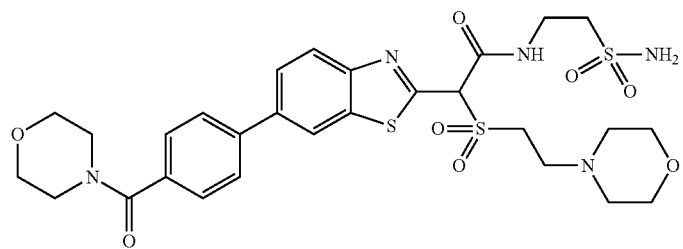

Example B157

Compound B157a. Benzyl (2-((1-(6-bromobenzo[d] thiazol-2-yl)-2-oxo-2-((2-sulfamoylethyl)amino) ethyl)sulfonyl)ethyl)carbamate Compound B157a (260 mg, 46% yield) was prepared from Compound A1a as described in the general procedure given for Compound B31a. HPLC: RT=1.12 min (LCMS Method M). MS (ES): m/z=619.1 [M+H]$^+$. $^1$H NMR (400 MHz, which was filtered and dried under reduced pressure to give Compound B157b (230 mg, 100% yield) as a brown solid. HPLC: RT=0.84 min (LCMS Method M). MS (ES): m/z=487.0 [M+H]$^+$. $^1$H NMR (400 MHz, DMF) δ 9.52 (t, J=5.6 Hz, 1H), 8.56 (d, J=2.0 Hz, 1H), 8.06-8.03 (m., 1H), 7.80 (dd, J=8.6, 2.0 Hz, 1H), 7.33 (s, 2H), 7.05 (s, 3H), 6.74 (s, 1H), 4.27-4.10 (m, 2H), 3.86-3.77 (m, 2H), 3.77-3.66 (m, 4H), 3.47-3.33 (m, 2H).

Compound B157c. 2-(6-Bromobenzo[d]thiazol-2-yl)-2-((2-morpholinoethyl)sulfonyl)-N-(2-sulfamoylethyl)acetamide To a solution of Compound B157b (105 mg, 0.190 mmol) in acetonitrile (7 mL) was added 2,2'-dibromodiethyl ether (0.027 mL, 0.20 mmol) followed by K$_2$CO$_3$ (130 mg, 0.93 mmol), and the reaction mixture heated at 65° C. for 2 days. The reaction mixture was concentrated under reduced pressure and purified by silica gel chromatography eluting with 0.5 to 10% MeOH/DCM to give Compound B157c (31 mg, 30% yield) as a white solid. HPLC: RT=1.39 min (LCMS Method B). MS (ES): m/z=557.0 [M+H]$^+$. $^1$H NMR (400 MHz, DMF) δ 8.80 (br. s., 1H), 8.43 (br. s., 1H), 8.00 (d, J=8.6 Hz, 1H), 7.72 (d, J=7.9 Hz, 1H), 7.03 (br. s., 2H), 3.82 (d, J=5.9 Hz, 2H), 3.66 (d, J=6.4 Hz, 2H), 3.65-3.44 (m, 4H), 3.44-3.31 (m, 2H), 2.89-2.81 (m, 2H), 2.48 (br. s., 4H).

Example B157

Example B157 (18 mg, 49% yield) was prepared from Compound B157c and 4-(morpholine-4-carbonyl)phenyl)boronic acid as described in the general procedure given for Compound B2a. EL IC$_{50}$<10 nM. HL IC$_{50}$ 147 nM HPLC: RT=1.36 min (LCMS Method B). MS (ES): m/z=666.1 [M+H]$^+$. $^1$H NMR (400 MHz, METHANOL-d$_4$) δ 8.00 (br. s., 1H), 7.76 (s, 6H), 7.55 (d, J=8.1 Hz, 1H), 4.09-3.47 (m, 25H).

Example B158 to Example B161 were prepared as described in the general procedure given for Example B157.

Example B162

2-(6-(1-(2-Methoxyethyl)-1H-pyrazol-4-yl)-1,3-benzothiazol-2-yl)-2-(methylsulfonyl)-N-(2-sulfamoylethyl)acetamide

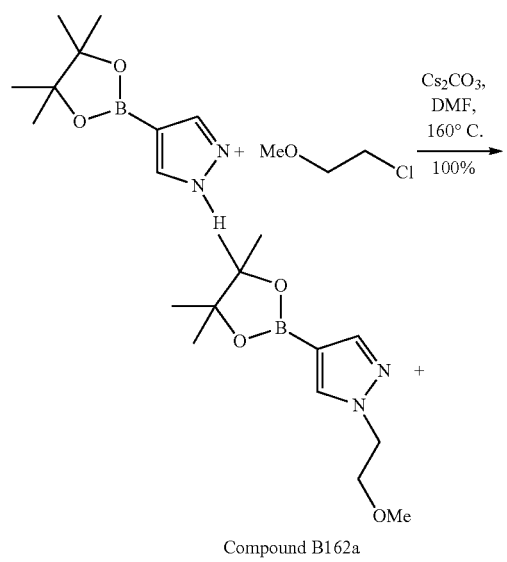

Compound B162a

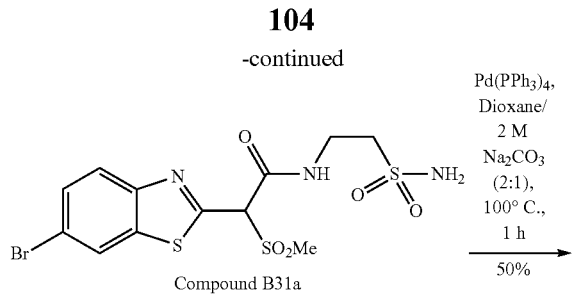

Compound B31a

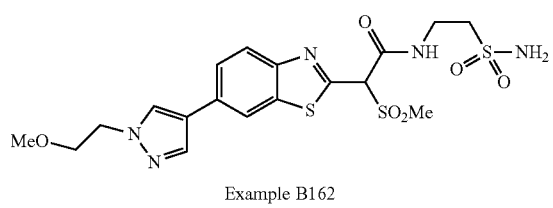

Example B162

Compound B162a. 1-(2-Methoxyethyl)-4-(4,4,5,5-tetramethyl-1,3,2-dioxaborolan-2-yl)-1H-pyrazole 4-(4,4,5,5-Tetramethyl-1,3,2-dioxaborolan-2-yl)-1H-pyrazole (100 mg, 0.52 mmol), 1-chloro-2-methoxyethane (0.056 mL, 0.62 mmol) and cesium carbonate (252 mg, 0.73 mmol) in DMF (1 mL) were heated in microwave reactor at 160° C. for 30 min. The reaction mixture was concentrated under reduced pressure and purified by silica gel chromatography (ISCO, hexanes/ethyl acetate 0-100% over 15 min) to isolate Compound B162a (130 mg, 100% yield). HPLC: RT=1.0 min (LCMS Method M). MS (ES): m/z=253.0 [M+H]$^+$. $^1$H NMR (500 MHz, CHLOROFORM-d) δ 8.04 (s, 1H), 7.83 (d, J=18.4 Hz, 1H), 4.37 (t, J=5.2 Hz, 1H), 3.78 (t, J=5.2 Hz, 1H), 3.38-3.31 (m, 2H), 2.98 (s, 3H), 2.90 (s, 3H), 1.34 (s, 6H), 1.26 (s, 3H).

Example B162

Example B162 (9 mg, 50% yield) was prepared from Compound B162a and Compound B31a as described in the general procedure given for Example B2a. EL IC$_{50}$<10 nM. HL IC$_{50}$ 995 nM. HPLC: RT=0.7 min (LCMS Method M). MS (ES): m/z=501.8 [M+H]$^+$. $^1$H NMR (500 MHz, DMSO-d$_6$) δ 8.97 (s, 1H), 8.36 (d, J=1.4 Hz, 1H), 8.27 (s, 1H), 8.05 (d, J=8.5 Hz, 1H), 8.00 (d, J=0.6 Hz, 1H), 7.79 (dd, J=8.5, 1.9 Hz, 1H), 6.95 (s, 2H), 5.99 (s, 1H), 4.30 (t, J=5.2 Hz, 3H), 3.74 (t, J=5.4 Hz, 3H), 3.65-3.56 (m, 6H), 3.28-3.24 (m, 4H), 3.21-3.15 (m, 3H).

Example B163 to Example B165 were prepared as described in the general procedure given for Example B162.

Example B166

2-(6-(4-(3,3-Difluoroazetidine-1-carbonyl)phenyl)benzo[d]thiazol-2-yl)-2-(methylsulfonyl)-N-(2-sulfamoylethyl)acetamide

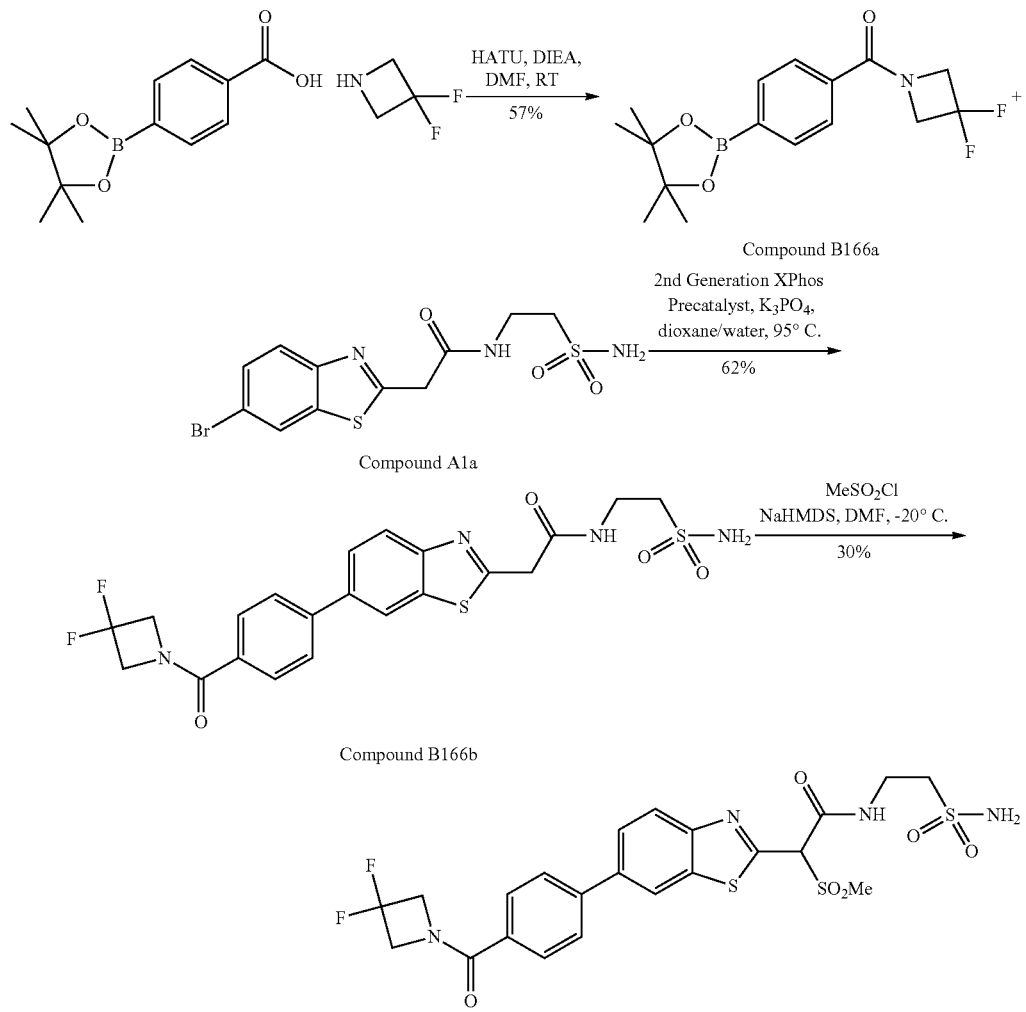

Compound B166a. (3,3-Difluoroazetidin-1-yl)(4-(4,4,5,5-tetramethyl-1,3,2-dioxaborolan-2-yl)phenyl)methanone A mixture of 4-(4,4,5,5-tetramethyl-1,3,2-dioxaborolan-2-yl)benzoic acid (490 mg, 2.0 mmol), 3,3-difluoroazetidine hydrochloride (260 mg, 2.00 mmol), DIPEA (0.686 mL, 3.93 mmol) and HATU (900 mg, 2.4 mmol) in DMF (4 mL) was stirred at room temperature for 3 days. The reaction mixture was diluted with EtOAc, the organic portion washed successively with water and brine, dried over sodium sulfate and filtered. The filtrate was concentrated under reduced pressure. The residue was purified by silica gel chromatography (eluting with 0-100% EtOAc/hexane) to give Compound B166a (360 mg, 57% yield) as a white solid. HPLC: RT=1.9 min (LCMS Method Q). MS (ES): m/z=324.0 [M+H]$^+$. $^1$H NMR (400 MHz, CHLOROFORM-d) δ 7.87 (s, 2H), 7.62 (d, J=8.1 Hz, 2H), 4.53 (t, J=12.0 Hz, 4H), 1.36 (s, 12H).

Compound B166b. 2-(6-(4-(3,3-difluoroazetidine-1-carbonyl)phenyl)benzo[d]thiazol-2-yl)-N-(2-sulfamoylethyl)acetamide A mixture of Compound B166a (140 mg, 0.37 mmol), Compound A1a (144 mg, 0.44 mmol), K$_3$PO$_4$ (196 mg, 0.93 mmol) and chloro(2-dicyclohexylphosphino-2',4',6'-triisopropyl-1,1'-biphenyl)[2-(2'-amino-1,1'-biphenyl)]palladium(II) (2nd generation X-Phos precatalyst, 29 mg, 0.037 mmol) in dioxane (3 mL) and water (1 mL) was purged with argon gas and heated at 95° C. for 1 hour. The reaction mixture was concentrated under reduced pressure. The residue was purified by silica gel chromatography (eluting with 0-10% MeOH/DCM) to give Compound B166b (116 mg, 62.0% yield) as a white solid. HPLC: RT=1.6 min (LCMS Method Q). MS (ES): m/z=495 [M+H]$^+$. $^1$H NMR (400 MHz, DMSO-d$_6$) δ 8.55 (t, J=5.4 Hz, 1H), 8.48 (d, J=1.5 Hz, 1H), 8.05 (d, J=8.6 Hz, 1H), 7.90-7.85 (m, 3H), 7.83 (s, 2H), 6.92 (s, 2H), 5.05-4.33 (m, 4H), 4.15-4.09 (m, 2H), 3.60-3.44 (m, 2H), 3.18 (d, J=5.3 Hz, 2H).

Example B166

Example B166 (16.4 mg, 30% yield) was prepared from Compound B166b as described in the general procedure given for Compound B31a. EL IC$_{50}$<10 nM. HL IC$_{50}$ 13 nM. HPLC: RT=1.4 min (LCMS Method O). MS (ES): m/z=573.0 [M+H]$^+$. $^1$H NMR (500 MHz, DMSO-d$_6$) δ 8.98 (t, J=5.6 Hz, 1H), 8.57 (s, 1H), 8.18 (d, J=8.5 Hz, 1H), 7.97-7.90 (m, 2H), 7.89-7.85 (m, 2H), 7.85-7.81 (m, 2H), 6.98-6.82 (m, 2H), 6.04 (s, 1H), 3.61 (q, J=6.9 Hz, 2H), 3.25-3.23 (m, 3H), 3.22-3.16 (m, 2H).

Example B167 to Example B171 were prepared as described in the general procedure given for Example B166.

Example B172

N-(2-Methoxyethyl)-N-methyl-4-(2-(1-(methylsulfonyl)-2-oxo-2-((2-sulfamoylethyl)amino)ethyl)-1,3-benzothiazol-6-yl)benzamide

Example B172

Example B172 (2.2 mg, 7% yield) was prepared from Compound B172a as described in the general procedure given for Compound B2a. EL IC$_{50}$<10 nM. HL IC$_{50}$ 77 nM. HPLC: RT=1.22 min (LCMS Method N). MS (ES): m/z=569.1 [M+H]$^+$. $^1$H NMR (500 MHz, DMSO-d$_6$) δ 9.02 (br. s., 1H), 8.54 (s, 1H), 8.17 (d, J=8.5 Hz, 1H), 7.99-7.88 (m, 1H), 7.83 (br. s., 2H), 7.52 (d, J=7.7 Hz, 2H), 6.97 (s, 2H), 6.04 (s, 1H), 3.67-3.55 (m, 4H), 3.44 (br. s., 5H), 3.31 (br. s., 2H), 3.22-3.14 (m, 3H), 3.00 (br. s., 3H)

and HOBT hydrate (247 mg, 1.60 mmol). After 3 days at room temperature, the reaction mixture was diluted in water (15 mL), extracted with DCM (3×10 mL), the combined organic portions dried over Na$_2$SO$_4$, filtered, concentrated under reduced pressure and purified by reverse phase HPLC (Phenomemenx Luna AXIA 5 micron C18, 21.2×100, UV at 220 nm, 10 to 70% B over 30 minutes with 10 minute hold time, solvent A: 90% water/ACNl/0.1% TFA, solvent B:90% ACN/water/0.1% TFA, Flow rate 20 mL/min; detector at 254) to isolate Compound B172a (47 mg, 18% yield) as a clear oil. HPLC: RT=0.96 min (LCMS Method M). MS (ES): m/z=319.7 [M+H]$^+$. $^1$H NMR (500 MHz, CHLOROFORM-d) δ 9.45-8.71 (m, 1H), 7.85 (d, J=7.2 Hz, 2H), 7.40 (d, J=8.0 Hz, 2H), 3.89-3.64 (m, 2H), 3.42 (d, J=12.1 Hz, 3H), 3.34-3.12 (m, 3H), 3.04 (s, 2H), 1.36 (s, 12H).

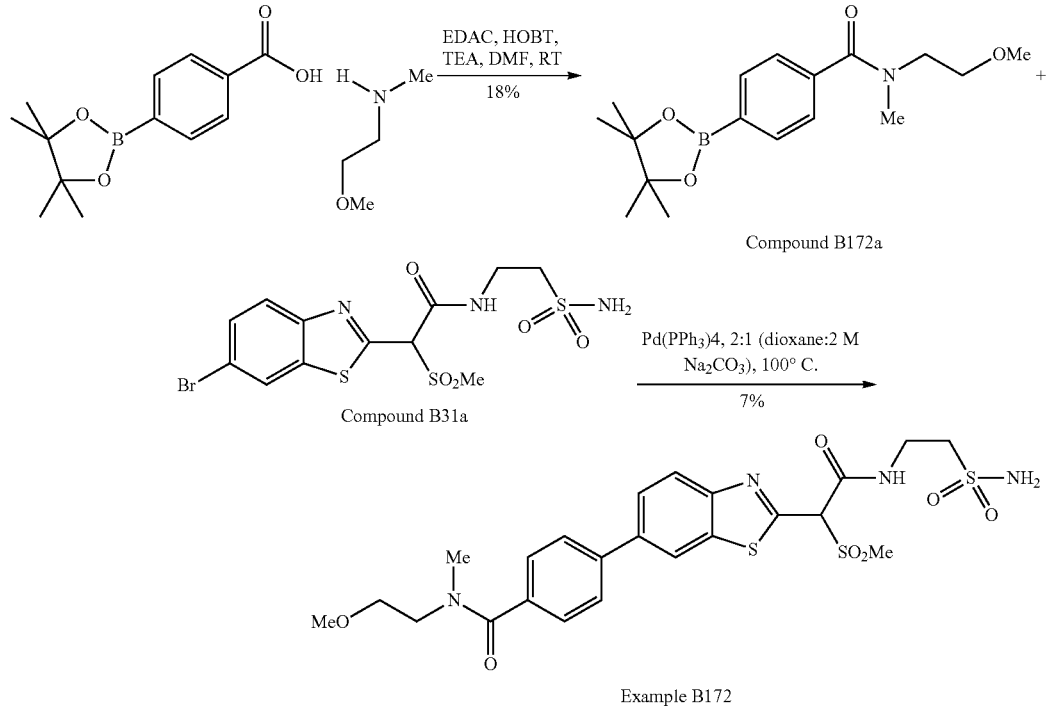

Compound B172a. N-(2-methoxyethyl)-N-methyl-4-(4,4,5,5-tetramethyl-1,3,2-dioxaborolan-2-yl)benzamide EDC (310 mg, 1.6 mmol) was added to DMF (4 mL) solution of 4-(4,4,5,5-tetramethyl-1,3,2-dioxaborolan-2-yl) benzoic acid (200 mg, 0.81 mmol), 2-methoxy-N-methylethanamine (144 mg, 1.6 mmol), TEA (0.23 mL, 1.6 mmol)

Example B173

4-(2-(1-(Methylsulfonyl)-2-oxo-2-(2-sulfamoylethylamino)ethyl)benzo[d]thiazol-6-yl)benzoic acid

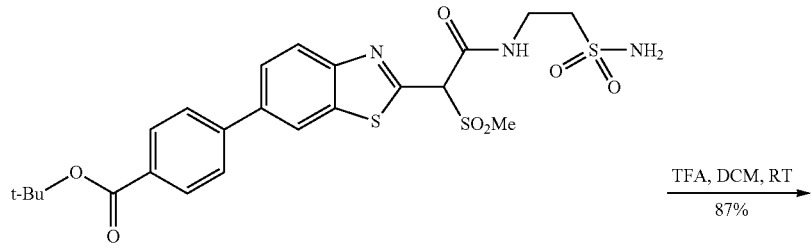

Example B157

TFA, DCM, RT
87%

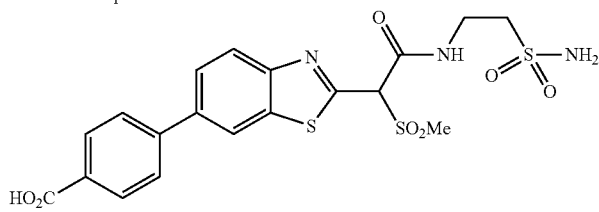

Example B173

To a solution of Example B157 (101 mg, 0.18 mmol) in DCM (2.0 mL) was added TFA (1.0 mL, 13 mmol). The mixture was stirred at room temperature for 3 hours. The mixture was concentrated under reduced pressure. The residue was dissolved in DMF (2 mL), filtered and purified by preparative HPLC (Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-30% B over 20 minutes, then a 5-minute hold at 100% B; Flow: 20 mL/min). Fractions containing the desired product were combined and dried via centrifugal evaporation to give Example B173 (79 mg, 87% yield). EL IC$_{50}$<10 nM. HL IC$_{50}$ 274 nM. HPLC: RT=1.1 min (LCMS Method O). MS (ES): m/z=498.0 [M+H]$^+$. $^1$H NMR (500 MHz, DMSO-d$_6$) δ 13.05 (br. s., 1H), 9.03 (br. s., 1H), 8.60 (br. s., 1H), 8.20 (d, J=7.7 Hz, 1H), 8.10-8.04 (m, 2H), 7.97-7.89 (m, 3H), 6.99 (br. s., 2H), 6.06 (br. s., 1H), 3.62 (br. s., 2H), 3.26 (br. s., 3H), 3.22-3.17 (m, 2H).

Example B174

2-(6-(4-(3-Hydroxy-3-methylazetidine-1-carbonyl)phenyl)benzo[d]thiazol-2-yl)-2-(methylsulfonyl)-N-(2-sulfamoylethyl)acetamide

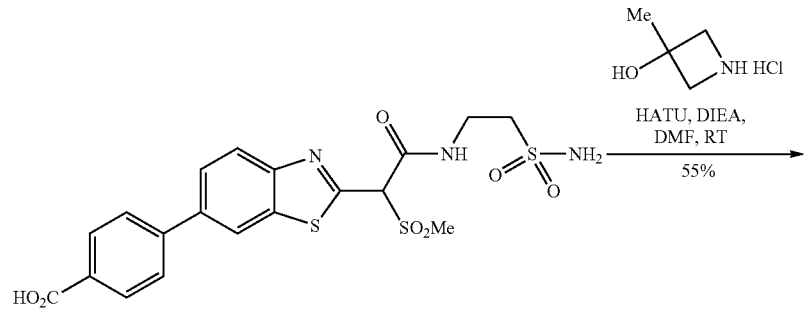

Compound B173

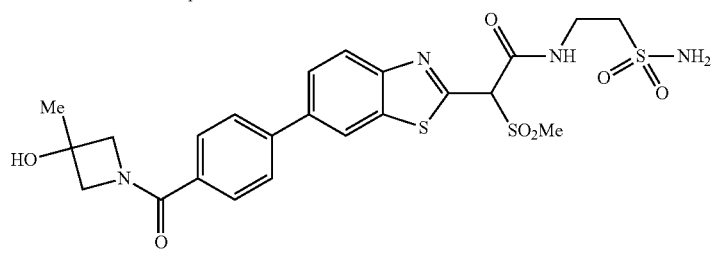

Example B174

Example B174 (15 mg, 55%) was prepared from Example B173 and 3-methylazetidin-3-ol hydrochloride as described in the general procedure given for Example B166. EL IC$_{50}$<10 nM. HL IC$_{50}$ 402 nM. HPLC: RT=1.0 min (LCMS Method O). MS (ES): m/z=567.0 [M+H]$^+$. $^1$H NMR (500 MHz, DMSO-d$_6$) δ 9.00 (br. s., 1H), 8.56 (br. s., 1H), 8.19 (d, J=8.5 Hz, 1H), 7.99-7.90 (m, 2H), 7.86 (d, J=7.2 Hz, 2H), 7.77 (d, J=6.6 Hz, 2H), 6.96 (br. s., 2H), 6.06 (br. s., 1H), 5.70 (br. s., 1H), 4.20 (d, J=16.5 Hz, 2H), 4.00-3.85 (m, 4H), 3.62 (br. s., 2H), 3.27-3.24 (m, 3H), 3.23-3.17 (m, 2H).

Example B175 to Example B179 were prepared as described in the general procedure given for Example B174.

Example B180

2-(Methylsulfonyl)-2-(6-(2-oxo-2,3-dihydro-1H-indol-5-yl)-1,3-benzothiazol-2-yl)-N-(2-sulfamoyl-ethyl)acetamide

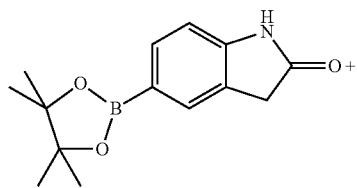

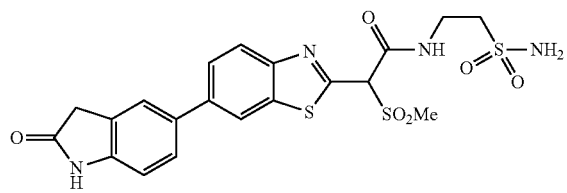

Example B180

Example B180 (3.8 mg, 14%) was prepared from Compound B31a and 5-(4,4,5,5-tetramethyl-1,3,2-dioxaborolan-2-yl)indolin-2-one as described in the general procedure given for Example 166. EL IC$_{50}$<10 nM. HL IC$_{50}$ 170 nM. HPLC: RT=1.1 min (LCMS Method Q). MS (ES): m/z=509.1 [M+H]$^+$. $^1$H NMR (500 MHz, DMSO-d$_6$) δ 10.54 (br. s., 1H), 9.02 (br. s., 1H), 8.41 (br. s., 1H), 8.12 (d, J=8.5 Hz, 1H), 7.82 (d, J=8.5 Hz, 1H), 7.69-7.56 (m, 2H), 7.03-6.97 (m, 2H), 6.03 (br. s., 1H), 3.92 (br. s., 1H), 3.64-3.54 (m, 4H), 3.30-3.10 (m, 5H).

Example B181 to Example B186 were prepared as described in the general procedure given for Example B180.

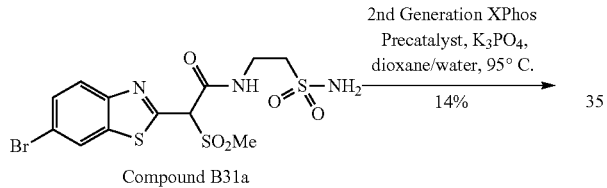

Compound B31a

2nd Generation XPhos Precatalyst, K$_3$PO$_4$, dioxane/water, 95° C.

14%

Example B187

2-(Methylsulfonyl)-2-(6-(6-oxo-1,6-dihydro-3-pyridinyl)-1,3-benzothiazol-2-yl)-N-(2-sulfamoylethyl)acetamide

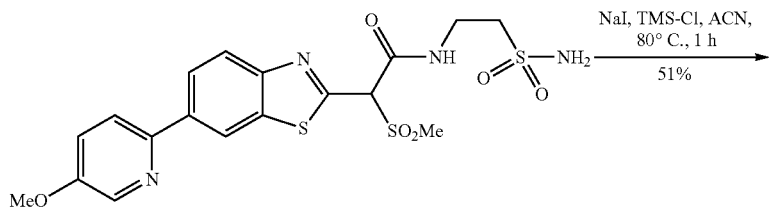

Example B19

NaI, TMS-Cl, ACN, 80° C., 1 h

51%

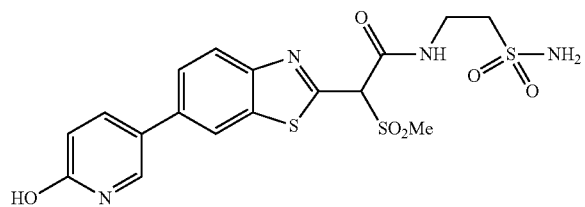

Example B187

A mixture of Example B19 (12 mg, 0.025 mmol), NaI (11 mg, 0.074 mmol) and TMS-Cl (0.016 mL, 0.12 mmol) in acetonitrile (1.5 mL) was stirred at 80° C. for 2 hours. The reaction mixture was quenched with water and purified by reverse phase preparative HPLC (method A) to give Example B187 (6 mg, 50% yield). EL IC$_{50}$ 16 nM. HL IC$_{50}$ 155 nM. HPLC: RT=1.2 min (LCMS Method Q). MS (ES): m/z=471.0 [M+H]$^+$. $^1$H NMR (400 MHz, DMSO-d$_6$) δ 11.97 (br. s., 1H), 9.01 (t, J=5.6 Hz, 1H), 8.39 (s, 1H), 8.18-8.06 (m, 1H), 7.98-7.92 (m, 1H), 7.88-7.82 (m, 1H), 7.79 (dd, J=8.6, 1.8 Hz, 1H), 6.99 (s, 2H), 6.02 (s, 1H), 3.66-3.56 (m, 2H), 3.23 (s, 3H), 3.21-3.13 (m, 2H).

Example B188 to Example B195 were prepared as described in the general procedure given for Example B187.

Example B196 tert-Butyl 2-(2-oxo-2-((2-sulfamoylethyl)amino)-1-((3,3-trifluoropropyl)sulfonyl)ethyl)benzo[d]thiazole-6-carboxylate

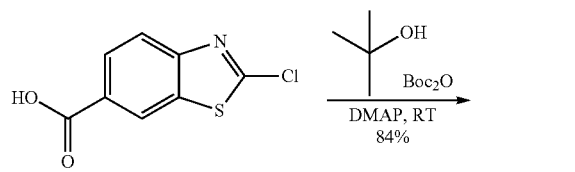

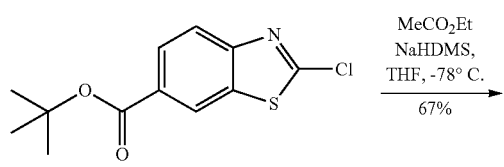

Compound B196a

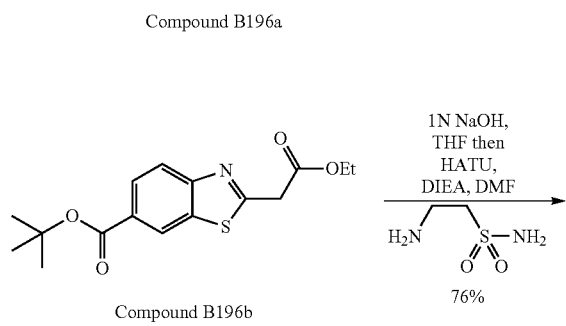

Compound B196b

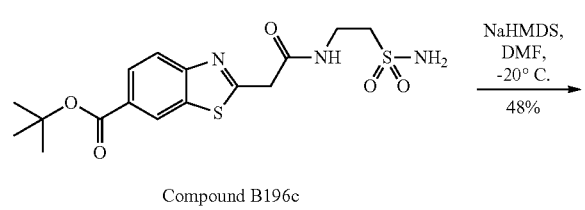

Compound B196c

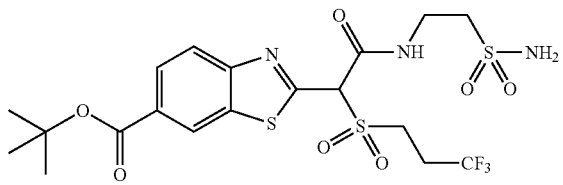

Example B196

Compound B196a. tert-Butyl 2-chlorobenzo[d]thiazole-6-carboxylate

To a solution of di-tert-butyl dicarbonate (1.2 mL, 5.0 mmol) and 2-chlorobenzo[d]thiazole-6-carboxylic acid (530 mg, 2.5 mmol) in anhydrous t-butanol (10 mL) was added dimethylaminopyridine (91 mg, 0.74 mmol) at room temperature. After 1 hour, the reaction mixture was concentrated under reduced pressure and purified by silica gel chromatography (ISCO: 0-50% EtOAc/Hexane) to afford Compound B196a (560 mg, 84% yield) as a clear oil. HPLC: RT=2.22 min (LCMS Method B). MS (ES): m/z=270.0 [M+H]$^+$. $^1$H NMR (400 MHz, CHLOROFORM-d) δ 8.45 (d, J=1.5 Hz, 1H), 8.12 (dd, J=8.6, 1.8 Hz, 1H), 7.97 (d, J=8.6 Hz, 1H), 1.55-1.42 (m, 9H).

Compound B196b. tert-Butyl 2-(2-ethoxy-2-oxoethyl)benzo[d]thiazole-6-carboxylate

Ethyl acetate (0.26 mL, 2.67 mmol) was added to cooled (−78° C.) solution of NaHMDS (1 M in THF, 4.9 mL, 4.9 mmol) in toluene (10 mL) over a period of 15 minutes. After one hour, Compound B196a (0.6 g, 2.2 mmol in toluene (5 mL) was added over a period of 15 minutes. After one hour, the reaction mixture was warmed to −5° C. over a period of 90 minutes. The reaction mixture was diluted with 1N HCl (50 mL) and extracted with ethyl acetate (3×50 mL). The organic phase was washed with brine (100 mL), dried over Na$_2$SO$_4$, filtered and concentrated under reduced pressure. The residue was purified by silica gel chromatography (0 to 50% ethyl acetate/hexanes) to isolate Compound B196b (480 mg, 67% yield) as a white solid. HPLC: RT=2.13 min (LCMS Method B). MS (ES): m/z=322.0 [M+H]$^+$. $^1$H NMR (400 MHz, CHLOROFORM-d) δ 8.57-8.52 (m, 1H), 8.11 (dd, J=8.6, 1.5 Hz, 1H), 8.04-7.98 (m, 1H), 4.32-4.25 (m, 2H), 4.20 (s, 2H), 1.63 (s, 9H), 1.32 (t, J=7.2 Hz, 3H).

Compound B196c. tert-Butyl 2-(2-oxo-2-((2-sulfamoylethyl)amino)ethyl)benzo[d]thiazole-6-carboxylate

Compound B196c (810 mg, 76% yield) was prepared from Compound B196b as described in the general procedure given for Compound A1a. HPLC: RT=1.88 min (LCMS Method B). MS (ES): m/z=399.9 [M+H]$^+$. $^1$H NMR (400 MHz, CHLOROFORM-d) d 8.51-8.47 (m, 1H), 8.07 (dd, J=8.6, 1.5 Hz, 1H), 7.97 (dd, J=8.6, 0.4 Hz, 1H), 4.11 (s, 2H), 3.83 (m, 2H), 3.39 (m, 2H), 1.62 (s, 9H).

Example B196

Example B196 (120 mg, 48% yield) was prepared from Compound B196c as described in the general procedure given for Compound B31a. EL IC$_{50}$ 65 nM. HL IC$_{50}$ 379 nM. HPLC: RT=2.16 min (LCMS Method B). MS (ES): m/z=560.0 [M+H]$^+$. $^1$H NMR (400 MHz, CHLOROFORM-d) δ 7.78-7.74 (m, 1H), 7.33 (dd, J=8.6, 1.5 Hz, 1H), 7.23 (dd, J=8.6, 0.4 Hz, 1H), 3.37 (s, 2H), 3.09 (m, 2H), 2.96 (m, 2H), 0.88 (s, 9H).

Example B197

2-(6-(3,3-Difluoropyrrolidine-1-carbonyl)benzo[d]thiazol-2-yl)-N-(2-sulfamoylethyl)-2-((3,3,3-trifluoropropyl)sulfonyl)acetamide

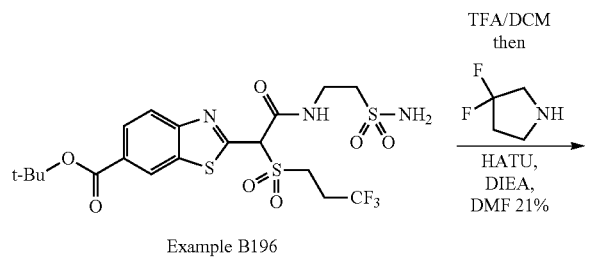

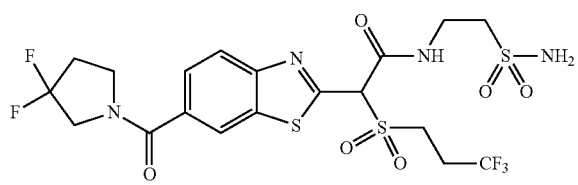

Example B197

Example B197 (6.2 mg, 21% yield) was prepared from Example B196 as described in the general procedure given for Example B174. EL IC$_{50}$<10 nM. HL IC$_{50}$ 10,100 nM. HPLC: RT=2.16 (LCMS Method O). MS (ES): m/z=593.05 [M+H]$^+$. $^1$H NMR (500 MHz, DMSO-d$_6$) δ 8.15 (d, J=8.5 Hz, 1H), 6.99 (m, 2H), 4.04-3.53 (m, 8H), 3.27-3.13 (m, 2H), 2.94-2.80 (m, 2H), 2.50-2.35 (m, 2H).

Example B198 to Example B201 were prepared as described in the general procedure given for Example B197.

Example B202

N-(2-methoxyethyl)-3-(2-(2-oxo-2-((2-sulfamoylethyl)amino)-1-((3,3,3-trifluoropropyl)sulfonyl)ethyl)benzo[d]thiazol-6-yl)benzamide

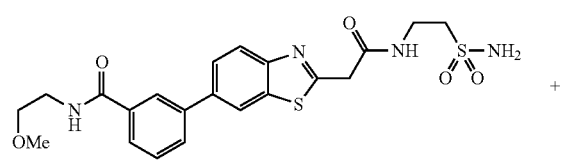

Compound B202a

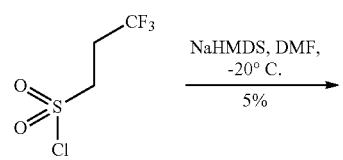

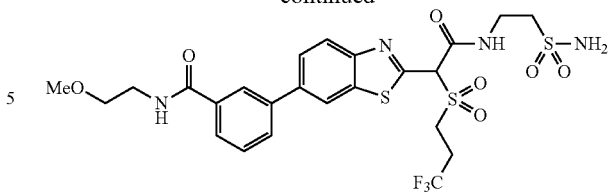

Example B202

Example B202 (1.7 mg, 5.0% yield) was prepared from Compound B202a as described in the general procedure given for Example B99. EL IC$_{50}$ 24 nM. HL IC$_{50}$ 170 nM. HPLC: RT=1.51 (LCMS Method O). MS (ES): m/z=637.1 [M+H]$^+$. $^1$H NMR (500 MHz, DMSO-d$_6$) δ 8.19-8.09 (m, 2H), 7.92-7.80 (m, 3H), 7.58-7.48 (m, 2H), 3.55 (m, 4H), 3.41 (m, 4H), 3.21 (s, 3H), 3.10-3.13 (m, 2H), 2.81-2.75 (m, 2H).

Example B203

2-(5-methyl-6-(1-methyl-1H-pyrazol-4-yl)-1,3-benzothiazol-2-yl)-2-(methylsulfonyl)-N-(2-sulfamoylethyl)acetamide

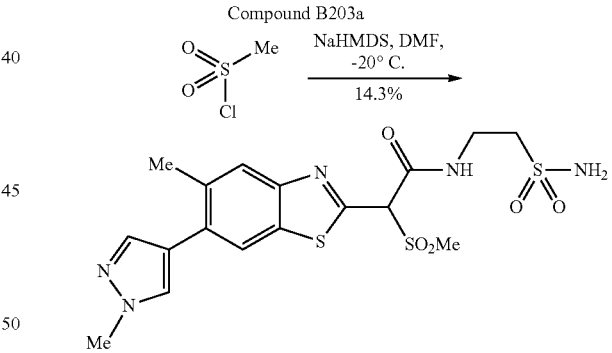

Example B203

Example B203 (4.1 mg, 14.3% yield) was prepared from Compound B203a as described in the general procedure given for Example B99. EL IC$_{50}$ 10 nM. HL IC$_{50}$ 141 nM. HPLC: RT=0.70 (LCMS Method M). MS (ES): m/z=472.8 [M+H]$^+$. $^1$H NMR (500 MHz, METHANOL-d$_4$) δ 7.98 (s, 1H), 7.95 (s, 1H), 7.90 (s, 1H), 7.76 (d, J=0.55 Hz, 1H), 5.49 (s, 1H), 3.97-4.00 (m, 3H), 3.80 (d, J=2.75 Hz, 1H), 3.59 (d, J=7.98 Hz, 1H), 3.19-3.22 (m, 2H), 3.17 (s, 3H), 2.44-2.55 (m, 3H).

Example B204 to Example B205 were prepared as described in the general procedure given for Example B2.

Example B207 to Example B281 were prepared as described in the general procedure given for Example B31.

Example B282 to Example B312 were prepared as described in the general procedure given for Example B99.

Example B313 to Example B316 were prepared as described in the general procedure given for Example B157.

Example B317 was prepared as described in the general procedure given for Example B162.

Example B318 to Example B324 were prepared as described in the general procedure given for Example B166.

Example B325 to Example B327 were prepared as described in the general procedure given for Example B173.

Example B328 to Example B351 were prepared as described in the general procedure given for Example B174.

Example B352 to Example B374 were prepared as described in the general procedure given for Example B180.

Example B375 to Example B385 were prepared as described in the general procedure given for Example B187.

Example B386 was prepared as described in the general procedure given for Example B31.

Example B387

2-{6-[1-(2-Hydroxy-2-methylpropyl)-2-oxo-1,2-dihydropyridin-4-yl]-1,3-benzothiazol-2-yl}-N-(2-sulfamoylethyl)-2-{[4-(trifluoromethyl)phenyl]methanesulfonyl}acetamide

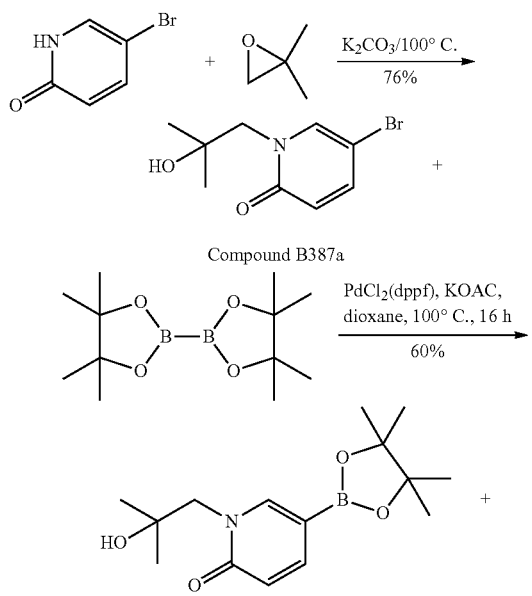

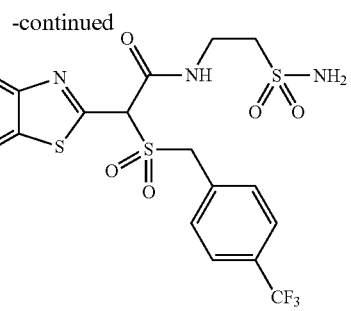

Example B387

Compound B387a. 5-bromo-1-(2-hydroxy-2-methylpropyl)pyridin-2(1H)-one

A mixture of 5-bromopyridin-2(1H)-one (600 mg, 3.5 mmol), 2,2-dimethyloxirane (750 mg, 10 mmol) and $K_2CO_3$ (960 mg, 6.9 mmol) in DMF (3 mL) was heated at 100° C. for 2 hours. The reaction mixture was allowed to cool to room temperature. The reaction mixture was diluted with ethyl acetate (80 mL), washed with water, brine, and dried over $MgSO_4$. The organic layer was filtered and concentrated under reduced pressure. The residue was purified by silica gel chromatography (eluting with 10 to 50% EtOAc/hexane) to give Compound B387a (650 mg, 76% yield). $^1$H NMR (400 MHz, CHLOROFORM-d) δ 7.50 (d, J=2.6 Hz, 1H), 7.40 (dd, J=9.6, 2.8 Hz, 1H), 6.54 (d, J=9.7 Hz, 1H), 3.99 (s, 2H), 3.57-3.39 (s, 1H), 1.27 (s, 6H).

Compound B387b. 1-(2-hydroxy-2-methylpropyl)-5-(4,4,5,5-tetramethyl-1,3,2-dioxaborolan-2-yl)pyridin-2(1H)-one To a solution of Compound B387a (500 mg, 2.0 mmol) was added bis(pinacolato)diboron (1.0 g, 4.1 mmol), $PdCl_2$(dppf)-$CH_2Cl_2$ adduct (166 mg, 0.200 mmol) and potassium acetate (995 mg, 10.1 mmol). The reaction mixture was heated at 100° C. for 16 hours. The reaction mixture was allowed to cool to room temperature and concentrated under reduced pressure. The residue was purified by silica gel chromatography (eluting with 0-10% MeOH) to give Compound B387b (360 mg, 1.2 mmol, 60% yield). $^1$H NMR (400 MHz, CHLOROFORM-d) δ 7.83-7.59 (m, 2H), 6.59 (d, J=9.0 Hz, 1H), 4.10-3.94 (m, 2H), 1.46-1.19 (m, 18H).

Example B387

Example B387 (2.2 mg, 9.0% yield) was prepared from Compound B387c (prepared as described in the general procedure given for Example B31) and Compound B387b as described in the general procedure given for Example B180. EL $IC_{50}$ 13.6 nM. HL $IC_{50}$ 6544 nM. HPLC: RT=1.4 min (LCMS Method Q). MS (ES): m/z=687.1 [M+H]$^+$. $^1$H NMR (500 MHz, DMSO-$d_6$) δ 14.04 and 11.46 and 6.15 (s, 1H), 9.12-9.02 and 8.61 (1H), 8.19 (br. s., 1H), 7.97 (s, 1H), 7.82-7.55 (m, 6H), 6.97 (br. s., 2H), 6.82 and 6.64-6.56 (1H), 6.77-6.66 (m, 1H), 6.53 (s, 1H), 6.15 (s, 1H), 4.93-4.71 (m, 2H), 4.03-3.91 (m, 2H), 3.68-3.57 (m, 2H), 3.25-3.14 (m, 2H), 1.13 (d, J=6.9 Hz, 6H).

Example B388 to Example B390 were prepared as described in the general procedure given for Example B388.

Example B391 tert-Butyl 2-(1-(methylsulfonyl)-2-oxo-2-((2-sulfa-moylethyl)amino)ethyl)-1,3-benzothiazole-5-carboxylate

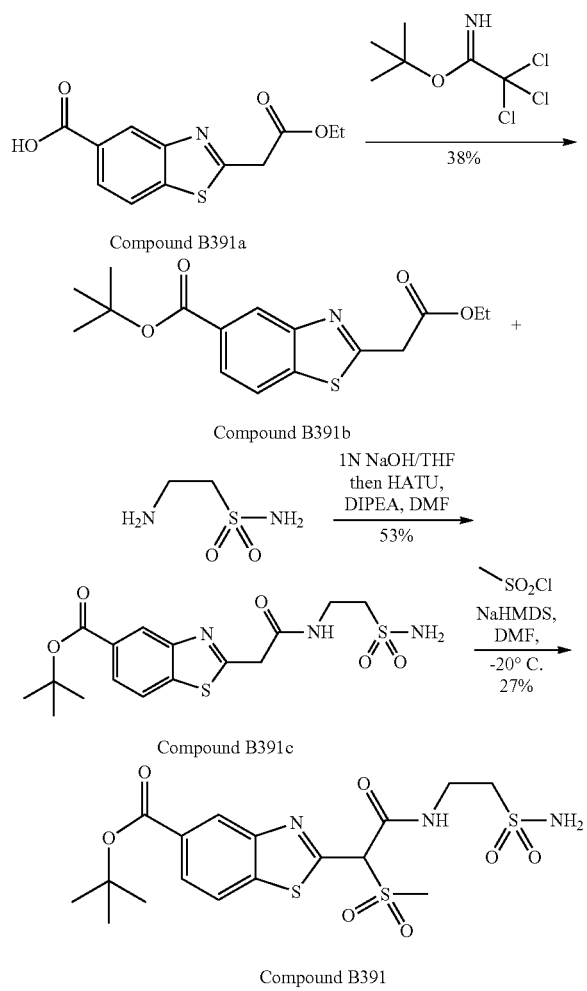

Compound B391b. tert-Butyl 2-(2-ethoxy-2-oxoethyl)benzo[d]thiazole-5-carboxylate To a solution of Compound B391a (1.49 mmol, 395 mg, prepared as described in the general procedure given for Example B26) in dichloromethane (20 mL) was added tert-butyl 2,2,2-trichloroacetamidate (1.6 g, 7.4 mmol). Boron trifluoride etherate (38 mL, 0.30 mmol) was added, and the mixture was stirred at room temperature. After 7 hours, the mixture was loaded onto Celite and purified by ISCO flash chromatography (120 g silica gel cartridge, 0-50% ethyl acetate-hexane gradient over 24 min., 85 mL/min.). The fractions containing the product were combined, and the solvent removed under reduced pressure to provide Compound B391b (184 mg, 38.0% yield). HPLC: RT=2.07 min (LCMS Method B). MS (ES): m/z=322 [M+H]$^+$. $^1$H NMR (400 MHz, CHLOROFORM-d) δ 8.64 (d, J=1.1 Hz, 1H), 8.03 (dd, J=8.4, 1.5 Hz, 1H), 7.90 (d, J=8.4 Hz, 1H), 4.27 (q, J=7.3 Hz, 2H), 4.19 (s, 2H), 1.63 (s, 9H), 1.31 (t, J=7.2 Hz, 3H).

Compound B391c. tert-Butyl 2-(2-oxo-2-((2-sulfamoylethyl)amino)ethyl)benzo[d]thiazole-5-carboxylate Compound B391b (184 mg, 0.570 mmol) was dissolved in THF (2 mL) and sodium hydroxide (0.57 mL, 0.57 mmol., 1.0 M) was added. After 1 hour, the solvent was removed under reduced pressure, and the residue dried in vacuo. The residue was dissolved in DMF (2 mL) and 2-aminoethanesulfonamide HCl salt was added. Diisopropylethyl amine (0.20 mL, 1.2 mmol) and HATU (240 mg, 0.63 mmol) were added, and the mixture was stirred at room temperature for 7 hours. DMF was removed in vacuo, and the residue was purified by ISCO flash chromatography (12 g silica gel cartridge, 0-100% acetonitrile-dichloromethane gradient over 11 min., 30 mL/min.). The fractions containing the product were combined, and the solvent removed to provide Compound B391c (131 mg, 53.0% yield). HPLC: RT=1.71 min (LCMS Method B). MS (ES): m/z=400 [M+H]$^+$. $^1$H NMR (400 MHz, CHLOROFORM-d) δ 8.61 (d, J=0.9 Hz, 1H), 8.05 (dd, J=8.4, 1.5 Hz, 1H), 7.90 (dd, J=8.4, 0.4 Hz, 1H), 7.68 (br. s., 1H), 5.05 (br. s., 2H), 4.10 (s, 2H), 3.87 (q, J=6.1 Hz, 2H), 3.40-3.31 (m, 2H), 1.64 (s, 9H).

Example B391

Compound B391c (28 mg, 0.070 mmol) was dissolved in DMF (2 mL), and the mixture was cooled to −25° C. Sodium bis(trimethylsilyl)amide (0.10 mL, 0.10 mmol, 1.0 M in THF) was added dropwise. After 10 min, methanesulfonyl chloride (8 μL, 0.1 mmol) was added. After 30 min., the reaction was quenched by the addition of acetic acid, and the solvent was removed in vacuo. The residue was purified by ISCO flash chromatography (4 g silica gel cartridge, 0-100% acetonitrile-dichloromethane gradient over 11 min., 18 mL/min.). The fractions containing the product were combined and the solvent removed to provide Example B391 (10 mg, 28% yield). EL IC$_{50}$ 25 nM. HL IC$_{50}$ 53.4 nM. HPLC: RT=1.72 min (LCMS Method B). MS (ES): m/z=478 [M+H]$^+$. $^1$H NMR (400 MHz, DMSO-d$_6$) δ 8.98 (t, J=5.7 Hz, 1H), 8.57-8.54 (m, 1H), 8.30 (d, J=8.4 Hz, 1H), 8.02 (dd, J=8.4, 1.5 Hz, 1H), 6.96 (s, 2H), 6.08 (s, 1H), 3.64-3.57 (m, 2H), 3.24 (s, 3H), 3.22-3.16 (m, 2H), 1.60 (s, 9H).

Example B392

2-(1-(Methylsulfonyl)-2-oxo-2-((2-sulfamoylethyl)amino)ethyl)benzo[d]thiazole-5-carboxylic acid

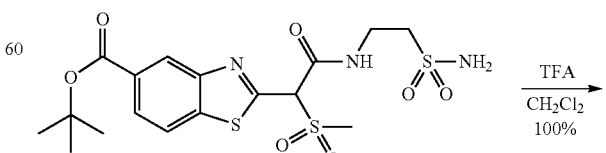

Example B391

-continued

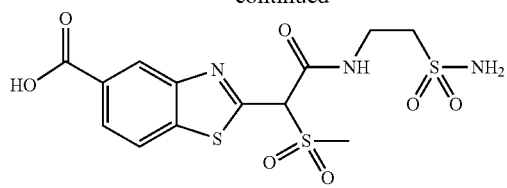

Compound B392a

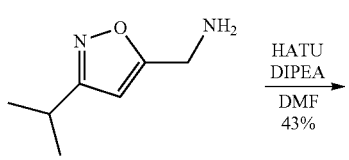

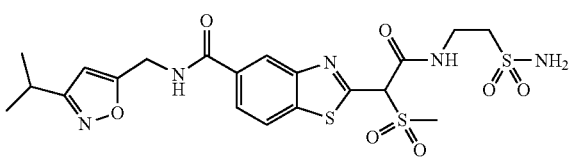

Example B392

Compound B392a. 2-(1-(Methylsulfonyl)-2-oxo-2-((2-sulfamoylethyl)amino)ethyl)benzo[d]thiazole-5-carboxylic acid Compound B392a was synthesized by cleaving the tert-butyl ester of Example B391 using the procedure described for Example B197. HPLC: RT=1.14 min (LCMS Method B). MS (ES): m/z=421.9 [M+H]$^+$. The product was used without further purification or characterization assuming 100% yield.

Example B392

Example B392 (5.9 mg, 43% yield) was prepared from Compound B392a and (3-isopropylisoxazol-5-yl)methanamine as described in the general procedure given for Example B197. EL IC$_{50}$ 3.1 nM. HL IC$_{50}$ 92.7 nM. HPLC: RT=1.24 min. (LCMS Method N). MS (ES): m/z=478 [M+H]$^+$. $^1$H NMR (500 MHz, DMSO-d$_6$) δ 9.35 (br. s., 1H), 8.99 (br. s., 1H), 8.63 (s, 1H), 8.29 (d, J=8.3 Hz, 1H), 8.03 (d, J=8.3 Hz, 1H), 7.97 (s, 1H), 6.96 (s, 2H), 6.37 (s, 1H), 6.09 (s, 1H), 4.63 (d, J=5.0 Hz, 2H), 3.62 (m, 2H), 3.25 (s, 3H), 3.21 (br. m., 2H), 3.03-2.93 (m, 1H), 1.22 (d, J=6.9 Hz, 6H).

Example B393 to Example B394 were prepared as described in the general procedure given for Example B392.

Example B395

2-(6-(5-(4-Fluorophenyl)-1,3,4-oxadiazol-2-yl)benzo[d]thiazol-2-yl)-2-(methylsulfonyl)-N-(2-sulfamoylethyl)acetamide

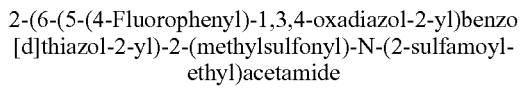

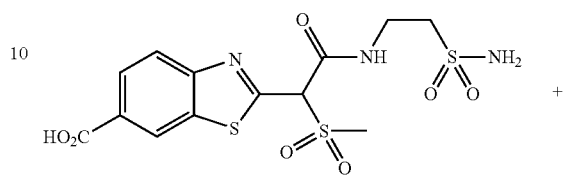

Compound B395a

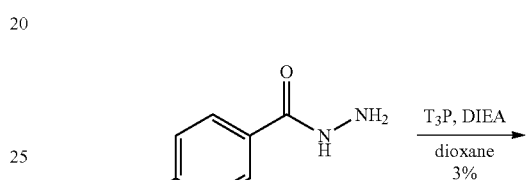

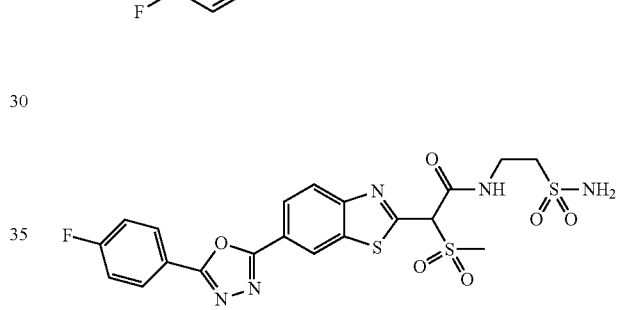

Example B395

Compound B395a (prepared following the general procedure given for Example B197) and 4-fluorobenzohydrazide (10 mg, 0.065 mmol) were dissolved in dioxane (1.0 mL) and treated with DIEA (0.036 mL, 0.21 mmol) and 1-propanephosphonic acid cyclic anhydride (0.12 mL, 0.21 mmol, 50% in ethyl acetate). The reaction mixture was heated at 70° C. for 1 hour, allowed to cool to room temperature and concentrated under reduced pressure. The material was purified via preparative HPLC (Column: Waters XBridge C18, 19×200 mm, 5-μm particles; Mobile Phase A: 5:95 acetonitrile:water with 0.1% TFA; Mobile Phase B: 95:5 acetonitrile:water with 0.1% TFA; Gradient: 10-55% B over 20 minutes, then a 5-minute hold at 100% B; Flow: 20 mL/min). Fractions containing the desired product were combined and dried via centrifugal evaporation to afford Example B395 (1 mg, 3% yield) as a clear oil. EL IC$_{50}$ 148 nM. HL IC$_{50}$ 275.5 nM. HPLC: RT=1.50 min (LCMS Method N). MS (ES): m/z=540.15 [M+H]$^+$. $^1$H NMR (500 MHz, DMSO-d6) δ 9.08-8.99 (m, 1H), 8.31 (s, 1H), 8.29-8.21 (m, 2H), 7.58-7.45 (m, 2H), 6.95 (m, 1H), 3.68-3.56 (m, 2H), 3.26 (s, 3H), 3.23-3.16 (m, 2H).

Example B396

2-[6-(6-fluoropyridin-3-yl)-1,3-benzothiazol-2-yl]-2-(2-methoxyethanesulfonyl)-N-[(methylcarbamoyl)methyl]acetamide

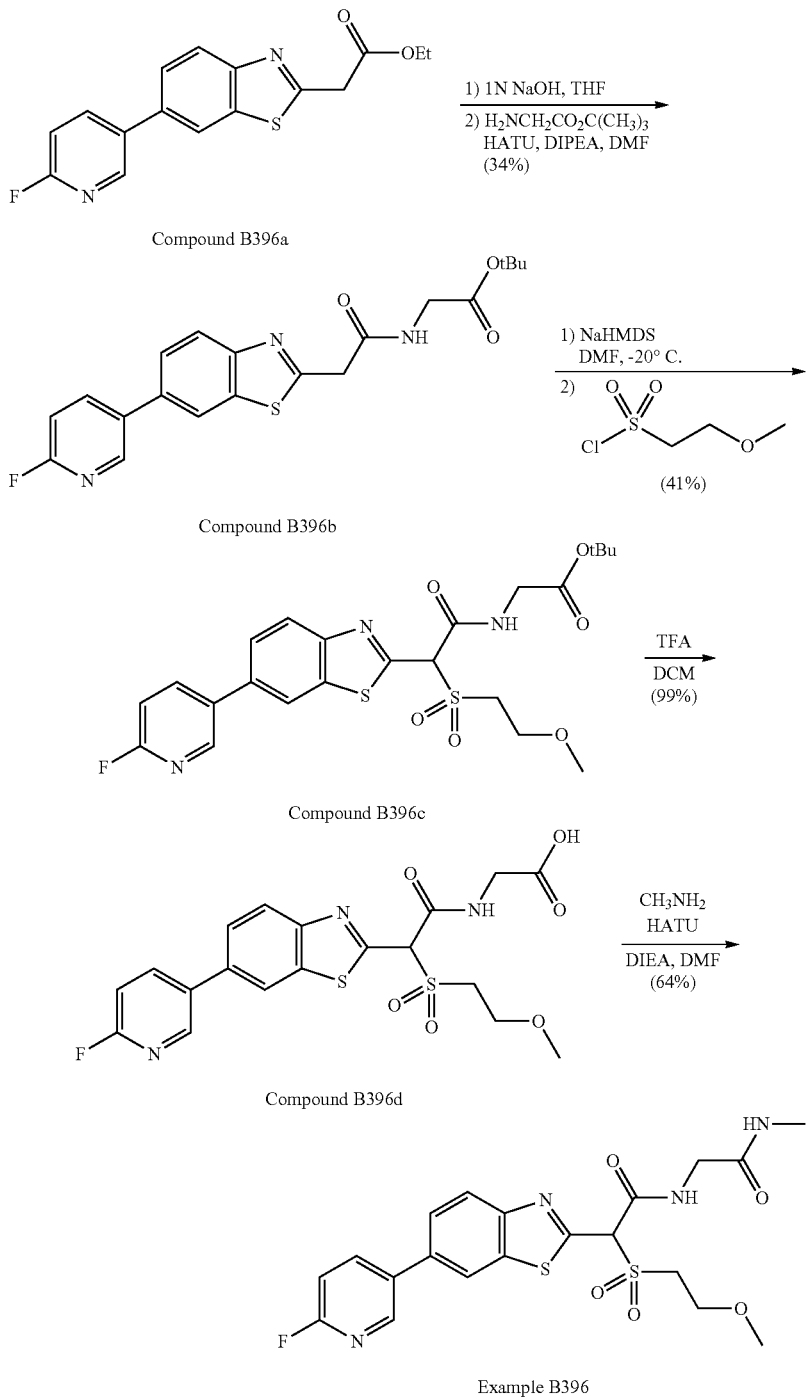

Compound B396b. tert-butyl 2-(2-(6-(6-fluoropyridin-3-yl)benzo[d]thiazol-2-yl)acetamido)acetate

To a solution of Compound B396a (440 mg, 1.4 mmol, prepared as described in the general procedure given for Compound B23a) in THF (10 mL) at 0° C. was added 1N NaOH (1.5 mL, 1.5 mmol). The ice bath was removed and the mixture stirred for 4 h. The mixture was evaporated under reduced pressure and the residue evaporated from toluene (2×) under reduced pressure. The residue was dissolved in DMF (7 mL) at 0° C. then DIPEA (0.73 mL, 4.2 mmol) added followed by glycine tert-butyl ester hydrochloride (280 mg, 1.7 mmol) and HATU (690 mg, 1.8 mmol). The mixture was stirred for 1 h then poured into saturated NH₄Cl and extracted with EtOAc (3×). The combined organic extracts were washed with brine, dried (Na$_2$SO$_4$) filtered and concentrated under reduced pressure. The residue was purified by silica gel chromatography eluting with 10 to 75% EtOAc/DCM to give Compound B396b (190 mg, 34% yield) as a yellow solid. RT=1.85 min (LCMS Method B). MS (ES): m/z=403.1 [M+H]$^+$. $^1$H NMR (400 MHz, CDCl$_3$) δ 8.48 (d, J=2.0 Hz, 1H), 8.12 (d, J=8.6 Hz, 1H), 8.07-7.97 (m, 2H), 7.65 (dd, J=8.5, 1.7 Hz, 1H), 7.45 (br. s., 1H), 7.05 (dd, J=8.5, 3.0 Hz, 1H), 4.14 (s, 2H), 4.01 (d, J=5.1 Hz, 2H), 1.47 (s, 9H).

Compound B396c. tert-butyl 2-(2-(6-(6-fluoropyridin-3-yl)benzo[d]thiazol-2-yl)-2-((2-methoxyethyl)sulfonyl)acetamido)acetate To a solution of Compound B396b (190 mg, 0.47 mmol) in DMF (5 mL) at brine/ice bath temperature was added 1N NaHMDS in THF (0.71 mL, 0.71 mmol) and the mixture stirred for 2 min. A solution of 2-methoxyethanesulfonyl chloride (113 mg, 0.710 mmol) in DMF (0.5 mL) was added dropwise and the reaction stirred for 5 min. The reaction was quenched by the addition of saturated NH$_4$Cl and extracted with 50% EtOAc/hexanes (3×). The combined organic extracts were washed with brine then dried (Na$_2$SO$_4$) filtered and concentrated. The residue was purified by silica gel chromatography eluting with 5 to 50% EtOAc/DCM to give Compound B396c (100 mg, 41% yield) as a brown solid. RT=1.93 min (LCMS Method B). MS (ES): m/z=524.1 [M+H]$^+$. $^1$H NMR (400 MHz, CDCl$_3$) δ 14.41 (s, 1H), 8.42 (d, J=2.6 Hz, 1H), 8.13 (t, J=5.3 Hz, 1H), 8.00-7.90 (m, 1H), 7.78-7.71 (m, 1H), 7.57-7.49 (m, 1H), 7.44-7.36 (m, 1H), 7.03 (dd, J=8.8, 2.9 Hz, 1H), 4.09-3.96 (m, 2H), 3.84 (t, J=6.2 Hz, 2H), 3.55-3.47 (m, 2H), 3.28 (s, 3H), 1.50 (s, 9H).

Compound B396d. 2-(2-(6-(6-fluoropyridin-3-yl)benzo[d]thiazol-2-yl)-2-((2-methoxyethyl)sulfonyl)acetamido)acetic acid To a flask charged with Compound B396c (95 mg, 0.18 mmol) was added 50% TFA in DCM (1 mL) and the mixture stirred for 1 h. The mixture was evaporated under reduced pressure and the residue evaporated from toluene (2×) under reduced pressure to give Compound B396d (84 mg, 99% yield) as a brown solid. RT=1.60 min (LCMS Method B). MS (ES): m/z=468.0 [M+H]$^+$. $^1$H NMR (400 MHz, DMSO-d$_6$) δ 9.09 (t, J=5.6 Hz, 1H), 8.66 (d, J=2.4 Hz, 1H), 8.56 (d, J=1.8 Hz, 1H), 8.39 (td, J=8.2, 2.5 Hz, 1H), 8.20 (d, J=8.6 Hz, 1H), 7.95-7.90 (m, 1H), 7.35 (dd, J=8.4, 2.9 Hz, 1H), 6.19 (s, 1H), 3.98 (dd, J=10.8, 5.7 Hz, 2H), 3.80-3.70 (m, 4H), 3.28 (s, 3H).

Example B396

To a solution of Compound B396d (15 mg, 0.032 mmol) in DMF (0.5 mL) was added methylamine hydrochloride (3.3 mg, 0.048 mmol) followed by DIEA (0.017 mL, 0.10 mmol) and HATU (16 mg, 0.042 mmol) and the mixture stirred for 1.5 h. Reaction mixture was diluted with DMF and filtered. The material was purified via prepative HPLC (Column:Phenomex Axia Luna C18, 30×100 mm, 5-μm particles; Mobile Phase A: 10:90 acetonitrile:water with 0.1% TFA; Mobile Phase B: 90:10 acetonitrile:water with 0.1% TFA; Gradient: 20-100% B over 20 minutes, then a 5-minute hold at 100% B; Flow: 20 mL/min). The fractions containing product were combined and concentrated under reduced pressure to give Example 396 (10 mg, 64% yield) as a yellow solid. RT=1.56 min (LCMS Method B). MS (ES): m/z=481.0 [M+H]$^+$. $^1$H NMR (400 MHz, DMSO-d$_6$) δ 9.03 (t, J=5.4 Hz, 1H), 8.66 (d, J=2.2 Hz, 1H), 8.57 (d, J=1.5 Hz, 1H), 8.40 (td, J=8.1, 2.6 Hz, 1H), 8.20 (d, J=8.6 Hz, 1H), 7.95-7.91 (m, 2H), 7.35 (dd, J=8.6, 2.6 Hz, 1H), 6.21 (s, 1H), 3.87 (dd, J=15.5, 5.6 Hz, 2H), 3.82-3.75 (m, 2H), 3.75-3.69 (m, 2H), 3.28 (s, 3H), 2.62 (d, J=4.6 Hz, 3H).

Example B397

N-[(ethylcarbamoyl)methyl]-2-[6-(6-fluoropyridin-3-yl)-1,3-benzothiazol-2-yl]-2-(2-methoxyethanesulfonyl)acetamide

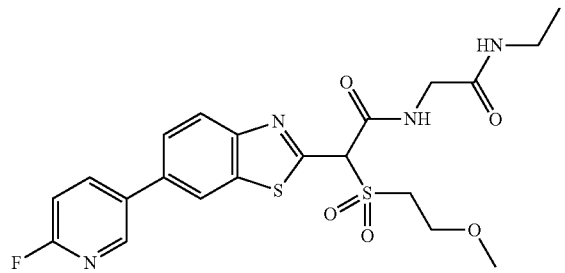 [SMILES: CCNC(=O)CNC(=O)C(c1nc2ccc(-c3ccc(F)nc3)cc2s1)S(=O)(=O)CCOC]

Example B397 was prepared from Compound B396d as described in the general procedure given for Example B396 (8 mg, 49%). EL IC$_{50}$ 109 nM. HL IC$_{50}$ 460 nM. RT=1.63 min (LCMS Method B). MS (ES): m/z=495.1 [M+H]$^+$. $^1$H NMR (400 MHz, DMSO-d$_6$) δ 9.02 (t, J=5.6 Hz, 1H), 8.66 (d, J=2.4 Hz, 1H), 8.57 (d, J=1.8 Hz, 1H), 8.40 (td, J=8.1, 2.6 Hz, 1H), 8.20 (d, J=8.6 Hz, 1H), 7.95-7.91 (m, 2H), 7.35 (dd, J=8.7, 2.8 Hz, 1H), 6.22 (s, 1H), 3.89-3.84 (m, 2H), 3.78 (dt, J=5.0, 2.7 Hz, 2H), 3.75-3.69 (m, 2H), 3.28 (s, 3H), 3.16-3.05 (m, 2H), 1.03 (t, J=7.3 Hz, 3H).

| Ex # | Structure | Name | ¹H NMR (500 MHz, DMSO-d₆ unless indicated otherwise) | LC/MS RT (min) Method M + H | EL IC$_{50}$ (nM) | HL IC$_{50}$ (nM) |
|---|---|---|---|---|---|---|
| B32 | 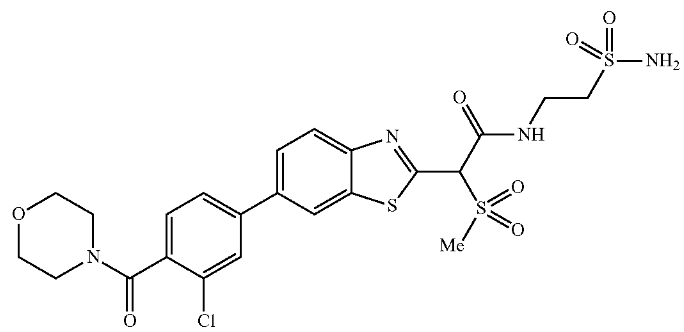 [SMILES: CS(=O)(=O)C(C(=O)NCCS(N)(=O)=O)c1nc2ccc(-c3ccc(C(=O)N4CCOCC4)c(Cl)c3)cc2s1] | 2-(6-(3-chloro-4-(4-morpholinylcarbonyl)phenyl)-1,3-benzothiazol-2-yl)-2-(methylsulfonyl)-N-(2-sulfamoylethyl)acetamide | δ 8.99 (t, J = 5.8 Hz, 1H), 8.58 (d, J = 1.7 Hz, 1H), 8.17 (d, J = 8.8 Hz, 1H), 8.01-7.91 (m, 2H), 7.83 (dd, J = 8.0, 0.8 Hz, 1H), 7.53 (d, J = 8.0 Hz, 1H), 6.95 (s, 2H), 6.05 (s, 1H), 3.76-3.51 (m, 8H), 3.25 (s, 3H), 3.22-3.09 (m, 4H) | 0.75 M 600.8 | <10 | 923 |
| B33 | 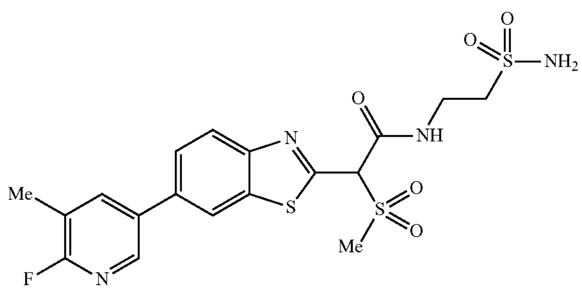 [SMILES: Cc1cc(-c2ccc3nc(C(C(=O)NCCS(N)(=O)=O)S(C)(=O)=O)sc3c2)cnc1F] | 2-(6-(6-fluoro-5-methyl-3-pyridinyl)-1,3-benzothiazol-2-yl)-2-(methylsulfonyl)-N-(2-sulfamoylethyl)acetamide | δ 9.06-8.91 (m, 1H), 8.61-8.51 (m, 1H), 8.48-8.41 (m, 1H), 8.36-8.24 (m, 1H), 8.21-8.14 (m, 1H), 7.97-7.83 (m, 1H), 7.02-6.91 (m, 2H), 6.09-5.99 (m, 1H), 3.68-3.56 (m, 2H), 3.24 (s, 3H), 3.22-3.14 (m, 2H) | 0.81 M 486.8 | 14 | 22 |
| B34 | 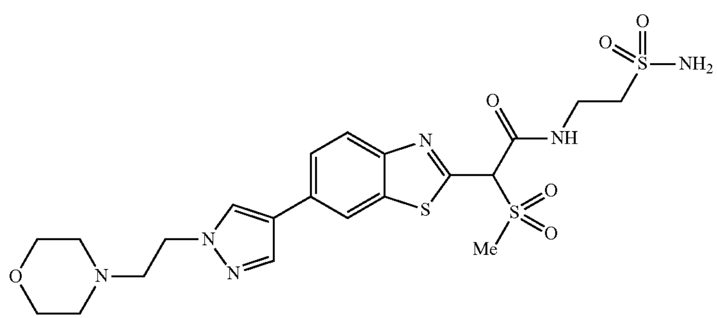 | 2-(methylsulfonyl)-2-(6-(1-(2-(4-morpholinyl)ethyl)-1H-pyrazol-4-yl)-1,3-benzothiazol-2-yl)-N-(2-sulfamoylethyl)acetamide | δ 8.98 (s, 1H), 8.38 (d, J = 5.5 Hz, 2H), 8.13 (br. s., 1H), 8.09 (d, J = 8.5 Hz, 1H), 7.81 (d, J = 8.5 Hz, 1H), 6.96 (s, 2H), 6.01 (s, 1H), 4.59 (br. s., 2H), 4.04 (q, J = 1.2 Hz, 2H), 3.67 (br. s., 6H), 3.61 (dd, J = 12.7, 6.3 Hz, 2H), 3.24 (s, 3H), 3.22-3.17 (m, 2H) | 0.55 M 556.9 | <10 | 313 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B35 | 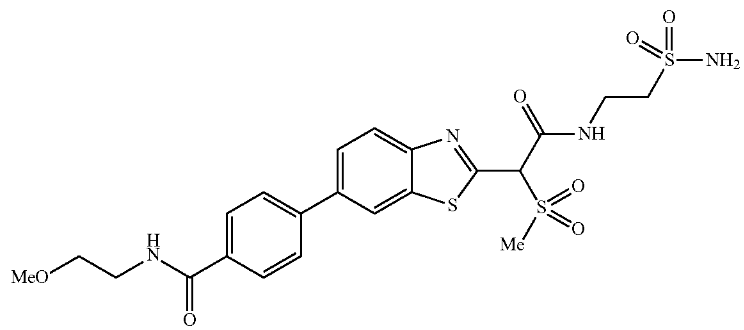 [SMILES: COCCNC(=O)c1ccc(-c2ccc3nc(C(C(=O)NCCS(N)(=O)=O)S(C)(=O)=O)sc3c2)cc1] | N-(2-methoxyethyl)-4-(2-{1-(methylsulfonyl)-2-oxo-2-[(2-sulfamoylethyl)amino]ethyl}-1,3-benzothiazol-6-yl)benzamide | ¹H NMR (500 MHz, METHANOL-d₄) δ 8.49-8.29 (m, 1H), 8.23-8.08 (m, 1H), 8.01-7.70 (m, 5H), 3.92-3.70 (m, 2H), 3.60 (s, 3H), 3.40 (m, 6H), 3.22 (s, 3H) | 0.70 M 554.9 | <10 | 43 |
| B36 | 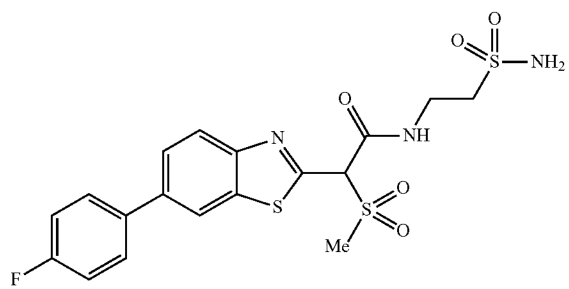 [SMILES: CS(=O)(=O)C(C(=O)NCCS(N)(=O)=O)c1nc2ccc(-c3ccc(F)cc3)cc2s1] | 2-(6-(4-fluorophenyl)-1,3-benzothiazol-2-yl)-2-(methylsulfonyl)-N-(2-sulfamoylethyl)acetamide | δ 9.13-8.87 (m, 1H), 8.54-8.41 (m, 1H), 8.23-8.07 (m, 1H), 7.93-7.73 (m, 3H), 7.42-7.26 (m, 2H), 7.12-6.81 (m, 2H), 3.65-3.53 (m, 2H), 3.27 (s, 3H), 3.22-3.13 (m, 2H) | 0.89 M 471.9 | <10 | <10 |
| B37 | 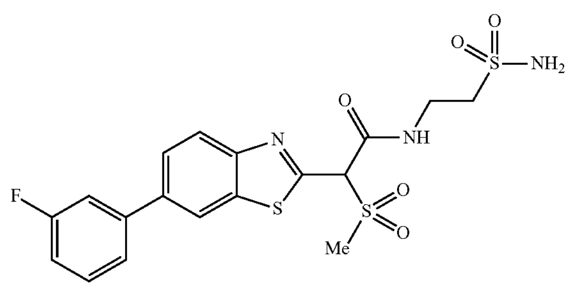 [SMILES: CS(=O)(=O)C(C(=O)NCCS(N)(=O)=O)c1nc2ccc(-c3cccc(F)c3)cc2s1] | 2-(6-(3-fluorophenyl)-1,3-benzothiazol-2-yl)-2-(methylsulfonyl)-N-(2-sulfamoylethyl)acetamide | δ 9.21-8.85 (m, 1H), 8.67-8.47 (m, 1H), 8.26-8.11 (m, 1H), 8.00-7.88 (m, 1H), 7.71-7.60 (m, 2H), 7.59-7.50 (m, 2H), 7.35-7.18 (m, 1H), 6.95 (s, 2H), 3.66-3.52 (m, 2H), 3.24 (s, 3H), 3.22-3.12 (m, 2H) | 0.88 M 471.9 | <10 | <10 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B38 | 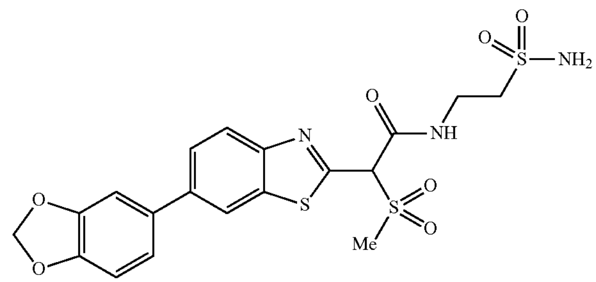 [SMILES: CS(=O)(=O)C(C(=O)NCCS(N)(=O)=O)c1nc2ccc(-c3ccc4c(c3)OCO4)cc2s1] | 2-(6-(1,3-benzodioxol-5-yl)-1,3-benzothiazol-2-yl)-2-(methylsulfonyl)-N-(2-sulfamoylethyl)acetamide | δ 9.13-8.91 (m, 1H), 8.40 (s, 1H), 8.17-8.06 (m, 1H), 7.95 (s, 1H), 7.87-7.75 (m, 1H), 7.35 (s, 1H), 7.28-7.20 (m, 1H), 7.09-7.01 (m, 1H), 6.95 (s, 2H), 6.08 (s, 2H), 6.01 (s, 1H), 3.66-3.53 (m, 2H), 3.23 (s, 3H), 3.18 (m, 2H) | 1.43 N 498.1 | <10 | <10 |
| B39 | 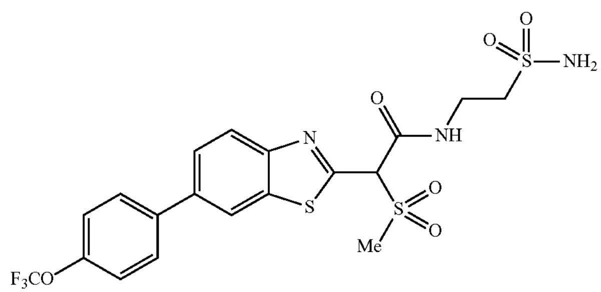 [SMILES: CS(=O)(=O)C(C(=O)NCCS(N)(=O)=O)c1nc2ccc(-c3ccc(OC(F)(F)F)cc3)cc2s1] | 2-(methylsulfonyl)-N-(2-sulfamoylethyl)-2-(6-(4-(trifluoromethoxy)phenyl)-1,3-benzothiazol-2-yl)acetamide | ¹H NMR (500 MHz, METHANOL-d₄) δ 8.32 (br. s., 1H), 8.20-8.08 (m, 1H), 7.91-7.31 (m, 8H), 5.49 (s, 1H), 3.90-3.74 (m, 2H), 3.33-3.36 (m, 2H), 3.22 (s, 3H) | 0.98 M 537.8 | <10 | <10 |
| B40 | 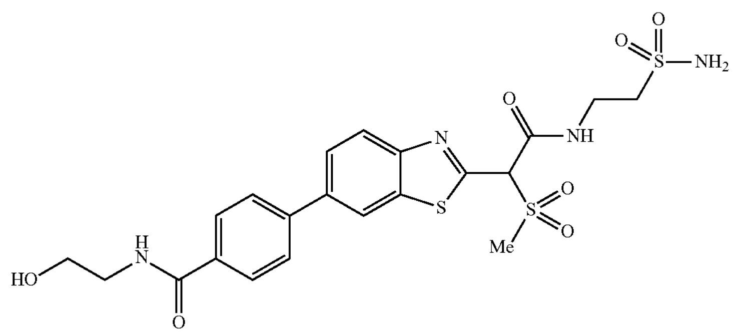 [SMILES: CS(=O)(=O)C(C(=O)NCCS(N)(=O)=O)c1nc2ccc(-c3ccc(C(=O)NCCO)cc3)cc2s1] | N-(2-hydroxyethyl)-4-(2-(1-(methylsulfonyl)-2-oxo-2-((2-sulfamoylethyl)amino)ethyl)-1,3-benzothiazol-6-yl)benzamide | δ 9.05-8.94 (m, 1H), 8.62-8.55 (m, 1H), 8.54-8.42 (m, 1H), 8.24-8.12 (m, 1H), 7.98 (s, 3H), 7.88 (s, 3H), 6.95 (s, 2H), 6.04 (s, 1H), 3.69-3.57 (m, 2H), 3.56-3.48 (m, 2H), 3.42-3.34 (m, 2H), 3.24 (s, 3H), 3.22-3.14 (m, 2H) | 0.63 M 540.8 | <10 | 19 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B41 | 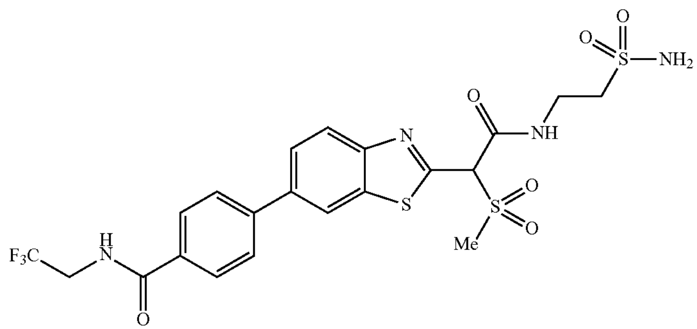 [SMILES: CS(=O)(=O)C(C(=O)NCCS(N)(=O)=O)c1nc2ccc(-c3ccc(C(=O)NCC(F)(F)F)cc3)cc2s1] | 4-(2-(1-(methylsulfonyl)-2-oxo-2-((2-sulfamoylethyl)amino)ethyl)-1,3-benzothiazol-6-yl)-N-(2,2,2-trifluoroethyl)benzamide | ¹H NMR (400 MHz, DMSO-d₆) δ 9.51-9.10 (m, 1H), 9.05-8.93 (m, 1H), 8.64-8.52 (m, 1H), 8.29-8.13 (m, 1H), 8.03 (d, J = 8.6 Hz, 2H), 7.92 (d, J = 8.6 Hz, 2H), 7.92 (d, J = 8.6 Hz, 3H), 6.95 (s, 2H), 6.04 (s, 1H), 4.33-4.05 (m, 2H), 3.70-3.53 (m, 2H), 3.24 (s, 3H), 3.22-3.15 (m, 2H) | 0.83 M 578.7 | <10 | 17 |
| B42 | 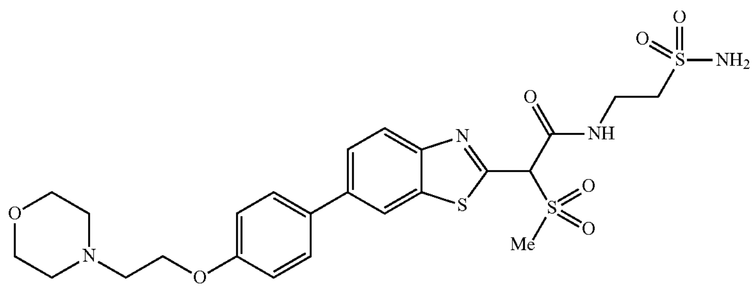 [SMILES: CS(=O)(=O)C(C(=O)NCCS(N)(=O)=O)c1nc2ccc(-c3ccc(OCCN4CCOCC4)cc3)cc2s1] | 2-(methylsulfonyl)-2-(6-(4-(2-(1-piperidinyl)ethoxy)phenyl)-1,3-benzothiazol-2-yl)-N-(2-sulfamoylethyl)acetamide | δ 9.05-8.92 (m, 1H), 8.48-8.38 (m, 1H), 8.15-8.02 (m, 1H), 7.87-7.80 (m, 1H), 7.78-7.71 (m, 2H), 7.19-7.09 (m, 2H), 6.99-6.88 (m, 2H), 6.11-5.94 (m, 1H), 4.46-4.34 (m, 2H), 3.65-3.57 (m, 2H), 3.57-3.47 (m, 4H), 3.22 (s, 3H), 3.21-3.13 (m, 2H), 3.08-2.96 (m, 2H), 2.68-2.59 (m, 1H), 2.39-2.31 (m, 1H), 1.92-1.79 (m, 2H), 1.76-1.62 (m, 3H), 1.47-1.31 (m, 1H) | 0.66 M 580.8 | <10 | 10 |
| B43 | 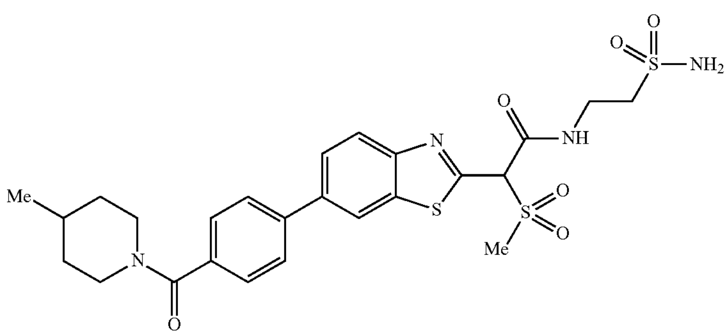 | 2-(6-{4-[(4-methyl-1-piperidinyl)carbonyl]phenyl}-1,3-benzothiazol-2-yl)-2-(methylsulfonyl)-N-(2-sulfamoylethyl)acetamide | δ 9.10-8.82 (m, 1H), 8.77-8.43 (m, 1H), 8.23-8.11 (m, 1H), 7.98-7.87 (m, 1H), 7.86-7.75 (m, 2H), 7.59-7.40 (m, 3H), 7.04-6.86 (m, 2H), 6.19-5.96 (m, 1H), 4.64-4.37 (m, 2H), 3.69-3.55 (m, 2H), 3.23 (s, 3H), 3.21-3.13 (m, 2H), 3.11-2.91 (m, 1H), 2.87-2.69 (m, 1H), 1.78-1.52 (m, 3H), 1.18-1.03 (m, 2H), 0.98-0.86 (m, 3H). | 0.83 M 578.7 | <10 | <10 |

| Ex # | Structure | Name | ¹H NMR (500 MHz, DMSO-d₆, unless indicated otherwise) | LC/MS RT (min) Method M+H | EL IC$_{50}$ (nM) | HL IC$_{50}$ (nM) |
|---|---|---|---|---|---|---|
| B44 | 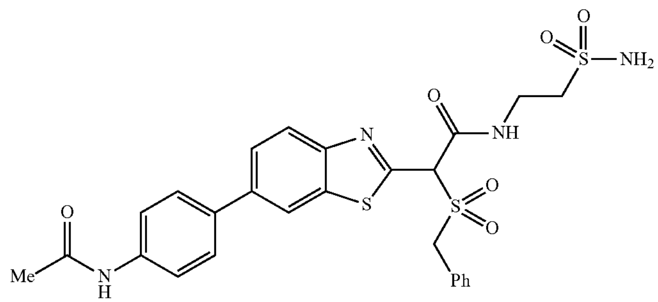 [SMILES: CC(=O)Nc1ccc(-c2ccc3nc(C(C(=O)NCCS(N)(=O)=O)S(=O)(=O)Cc4ccccc4)sc3c2)cc1] | 2-(6-(4-acetamidophenyl)-1,3-benzothiazol-2-yl)-2-(benzylsulfonyl)-N-(2-sulfamoylethyl)acetamide | δ 10.07 (s, 1H), 9.22-8.82 (m, 1H), 8.44 (d, J = 1.7 Hz, 1H), 8.15 (d, J = 8.5 Hz, 1H), 7.95 (s, 1H), 7.90-7.83 (m, 1H), 7.72 (s, 2H), 7.66 (s, 2H), 7.39 (s, 3H), 7.36-7.17 (m, 2H), 6.95 (s, 2H), 6.08 (s, 1H), 4.74 (d, J = 14.0 Hz, 1H), 4.67-4.48 (m, 1H), 3.60 (br. s., 2H), 3.20 (s, 2H), 2.50 (s, 3H) | 1.46 N 587.1 | <10 | 148 |
| B45 | 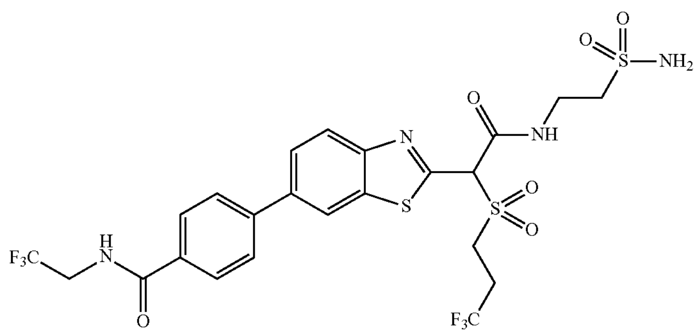 [SMILES: NS(=O)(=O)CCNC(=O)C(c1nc2ccc(-c3ccc(C(=O)NCC(F)(F)F)cc3)cc2s1)S(=O)(=O)CCC(F)(F)F] | 4-(2-(2-oxo-2-((2-sulfamoylethyl)amino)-1-((3,3,3-trifluoropropyl)sulfonyl)ethyl)-1,3-benzothiazol-6-yl)-N-(2,2,2-trifluoroethyl)benzamide | δ 9.23-9.06 (m, 1H), 8.99-8.85 (m, 1H), 8.69-8.51 (m, 1H), 8.19-8.13 (m, 1H), 8.08-7.75 (m, 5H), 7.76-7.38 (m, 1H), 7.17-6.80 (m, 2H), 6.50-6.08 (m, 1H), 4.25-4.00 (m, 2H), 3.84-3.51 (m, 4H), 3.23-3.14 (m, 2H), 2.96-2.78 (m, 2H) | 0.83 M 660.8 | <10 | 38 |
| B46 | 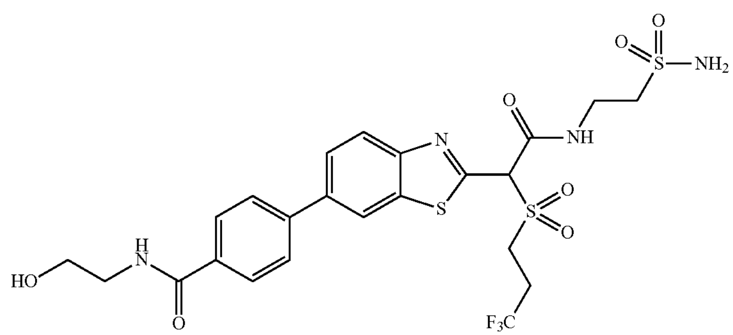 [SMILES: NS(=O)(=O)CCNC(=O)C(c1nc2ccc(-c3ccc(C(=O)NCCO)cc3)cc2s1)S(=O)(=O)CCC(F)(F)F] | N-(2-hydroxyethyl)-4-(2-(2-oxo-2-((2-sulfamoylethyl)amino)-1-((3,3,3-trifluoropropyl)sulfonyl)ethyl)-1,3-benzothiazol-6-yl)benzamide | δ 9.03-8.87 (m, 1H), 8.66-8.55 (m, 1H), 8.55-8.41 (m, 1H), 8.23-8.10 (m, 1H), 8.05-7.91 (m, 3H), 7.92-7.83 (m, 2H), 7.83-7.72 (m, 2H), 6.95 (s, 2H), 6.26 (s, 1H), 4.83-4.58 (m, 1H), 3.88-3.58 (m, 4H), 3.58-3.45 (m, 2H), 3.42-3.32 (m, 2H), 3.26-3.09 (m, 2H), 2.93-2.68 (m, 2H) | 0.77 M 622.8 | <10 | 520 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B47 | 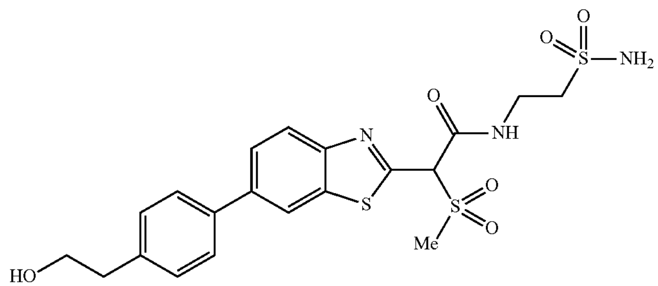 [SMILES: CS(=O)(=O)C(C(=O)NCCS(N)(=O)=O)c1nc2ccc(-c3ccc(CCO)cc3)cc2s1] | 2-(6-(4-(2-hydroxyethyl)phenyl)-1,3-benzothiazol-2-yl)-N-(2-(methylsulfonyl)-2-sulfamoylethyl)acetamide | δ 9.05-8.86 (m, 1H), 8.53-8.41 (m, 1H), 8.24-8.08 (m, 1H), 7.95-7.82 (m, 1H), 7.73-7.64 (m, 2H), 7.44-7.33 (m, 2H), 6.95 (s, 2H), 6.10-5.96 (m, 1H), 4.83-4.61 (m, 1H), 3.79-3.46 (m, 4H), 3.24 (s, 3H), 3.22-3.13 (m, 2H), 2.89-2.74 (m, 2H) | 0.72 M 497.8 | <10 | 35 |
| B48 | 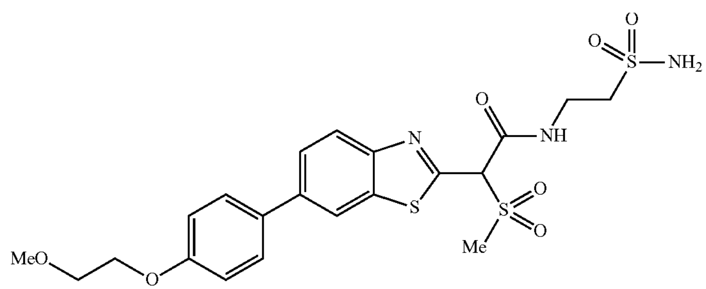 [SMILES: COCCOc1ccc(-c2ccc3nc(C(C(=O)NCCS(N)(=O)=O)S(C)(=O)=O)sc3c2)cc1] | 2-(6-(4-(2-methoxyethoxy)phenyl)-1,3-benzothiazol-2-yl)-N-(2-(methylsulfonyl)-2-sulfamoylethyl)acetamide | δ 9.08-8.85 (m, 1H), 8.41 (s, 1H), 8.17-8.08 (m, 1H), 7.88-7.79 (m, 1H), 7.70 (d, J = 8.0 Hz, 2H), 7.08 (d, J = 8.3 Hz, 2H), 6.95 (s, 2H), 6.01 (s, 1H), 4.16 (br. s., 2H), 3.69 (br. s., 2H), 3.59 (br. s., 2H), 3.31 (s, 3H), 3.23 (s, 3H), 3.19 (br. s., 2H) | 1.55 N 528.1 | <10 | 11 |
| B49 | 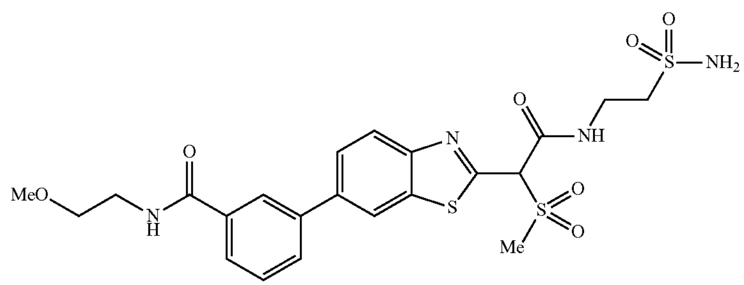 [SMILES: COCCNC(=O)c1cccc(-c2ccc3nc(C(C(=O)NCCS(N)(=O)=O)S(C)(=O)=O)sc3c2)c1] | N-(2-methoxyethyl)-3-(2-(1-(methylsulfonyl)-2-oxo-2-((2-sulfamoylethyl)amino)ethyl)-1,3-benzothiazol-6-yl)benzamide | δ 9.06-8.93 (m, 1H), 8.73-8.65 (m, 1H), 8.55 (br. s., 1H), 8.24 (br. s., 1H), 8.21-8.16 (m, 1H), 7.95 (br. s., 4H), 7.67-7.56 (m, 1H), 6.95 (br. s., 2H), 6.04 (br. s., 1H), 3.67-3.57 (m, 2H), 3.48 (d, J = 1.7 Hz, 4H), 3.28 (br. s., 3H), 3.24 (br. s., 3H), 3.19 (br. s., 2H) | 1.29 N 555.1 | <10 | 152 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B50 | 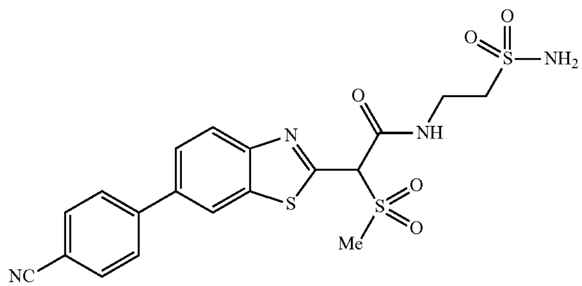 [SMILES: CS(=O)(=O)C(C(=O)NCCS(N)(=O)=O)c1nc2ccc(-c3ccc(C#N)cc3)cc2s1] | 2-(6-(4-cyanophenyl)-1,3-benzothiazol-2-yl)-2-(methylsulfonyl)-N-(2-Sulfamoylethyl)acetamide | δ 9.05-8.88 (m, 1H), 8.60 (br. s., 1H), 8.29-8.13 (m, 1H), 8.05-7.90 (m, 6H), 6.95 (br. s., 2H), 6.05 (br. s., 1H), 3.61 (d, J = 5.5 Hz, 2H), 3.24 (br. s., 3H), 3.19 (br. s., 2H) | 1.48 N 479.1 | <10 | 14 |
| B51 | 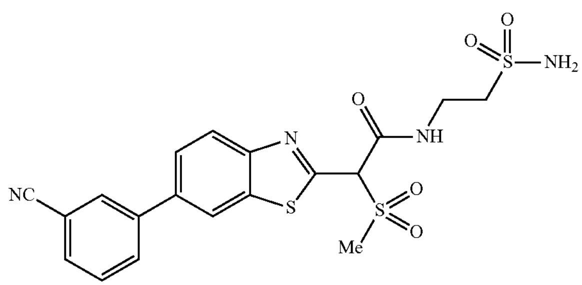 [SMILES: CS(=O)(=O)C(C(=O)NCCS(N)(=O)=O)c1nc2ccc(-c3cccc(C#N)c3)cc2s1] | 2-(6-(3-cyanophenyl)-1,3-benzothiazol-2-yl)-2-(methylsulfonyl)-N-(2-sulfamoylethyl)acetamide | δ 9.03-8.91 (m, 1H), 8.59 (br. s., 1H), 8.27 (br. s., 1H), 8.22-8.16 (m, 1H), 8.16-8.05 (m, 1H), 7.95 (br. s., 2H), 7.91-7.83 (m, 1H), 7.78-7.67 (m, 1H), 6.95 (br. s., 2H), 6.05 (br. s., 1H), 3.61 (d, J = 5.2 Hz, 2H), 3.24 (br. s., 3H), 3.19 (br. s., 2H) | 1.51 N 479.1 | <10 | <10 |
| B52 | 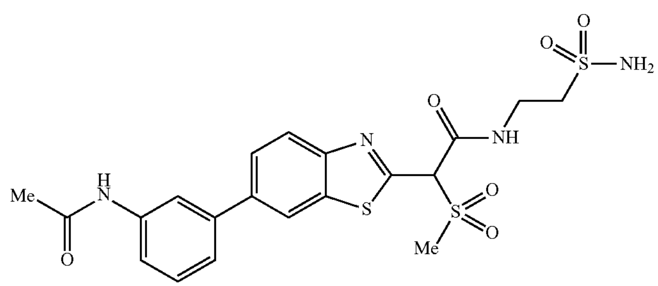 [SMILES: CC(=O)Nc1cccc(-c2ccc3nc(C(C(=O)NCCS(N)(=O)=O)S(C)(=O)=O)sc3c2)c1] | 2-(6-(3-acetamidophenyl)-1,3-benzothiazol-2-yl)-2-(methylsulfonyl)-N-(2-sulfamoylethyl)acetamide | δ 10.06 (br. s., 1H), 9.10-8.81 (m, 1H), 8.40 (br. s., 1H), 8.23-8.11 (m, 1H), 7.97 (d, J = 16.8 Hz, 2H), 7.83-7.72 (m, 1H), 7.65-7.52 (m, 1H), 7.41 (br. s., 2H), 6.95 (br. s., 2H), 6.03 (br. s., 1H), 3.68-3.53 (m, 2H), 3.24 (br. s., 3H), 3.19 (br. s., 2H), 2.08 (br. s., 3H) | 1.28 N 511.1 | <10 | 66 |

-continued

| Ex # | Structure | Name | $^1$H NMR (500 MHz, DMSO-$d_6$, unless indicated otherwise) | LC/MS RT (min) Method M+H | EL IC$_{50}$ (nM) | HL IC$_{50}$ (nM) |
|---|---|---|---|---|---|---|
| B53 | 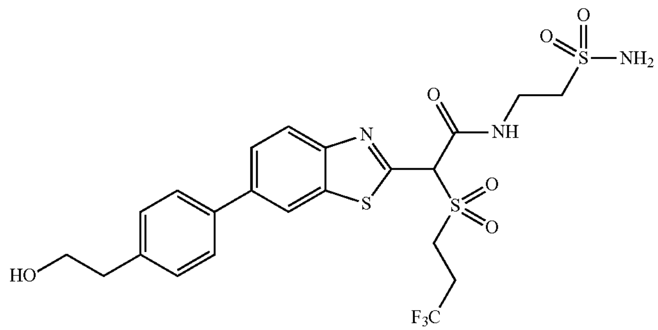 [SMILES: NS(=O)(=O)CCNC(=O)C(c1nc2ccc(-c3ccc(CCO)cc3)cc2s1)S(=O)(=O)CCC(F)(F)F] | 2-(6-(4-(2-hydroxyethyl)phenyl)-1,3-benzothiazol-2-yl)-N-(2-sulfamoylethyl)-2-((3,3,3-trifluoropropyl)sulfonyl)acetamide | δ 8.94 (br. s., 1H), 8.46 (br. s., 1H), 8.13 (d, J = 8.3 Hz, 1H), 7.86 (d, J = 8.3 Hz, 1H), 7.67 (d, J = 6.9 Hz, 2H), 7.35 (d, J = 7.2 Hz, 2H), 6.95 (br. s., 2H), 6.25 (br. s., 1H), 4.65 (br. s., 1H), 3.65 (br. s., 6H), 3.18 (br. s., 2H), 2.93-2.69 (m, 4H) | 1.63 N 580.1 | <10 | 152 |
| B54 | 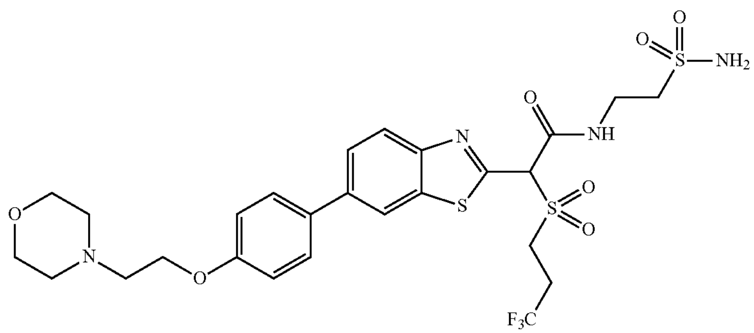 [SMILES: NS(=O)(=O)CCNC(=O)C(c1nc2ccc(-c3ccc(OCCN4CCOCC4)cc3)cc2s1)S(=O)(=O)CCC(F)(F)F] | 2-(6-(4-(2-(1-piperidinyl)ethoxy)phenyl)-1,3-benzothiazol-2-yl)-N-(2-sulfamoylethyl)-2-((3,3,3-trifluoropropyl)sulfonyl)acetamide | δ 9.57-9.28 (m, 1H), 9.09-8.95 (m, 1H), 8.45 (br. s., 1H), 8.29-8.08 (m, 1H), 7.76 (d, J = 8.0 Hz, 3H), 7.15 (d, J = 8.3 Hz, 2H), 6.98 (br. s., 2H), 6.26 (br. s., 1H), 4.41 (br. s., 2H), 3.53 (br. s., 8H), 3.18 (br. s., 2H), 3.10-2.96 (m, 2H), 2.89 (br. s., 2H), 1.83 (br. s., 2H), 1.70 (d, J = 11.3 Hz, 3H), 1.52-1.32 (m, 1H) | 1.48 N 663.2 | <10 | 23 |
| B55 | 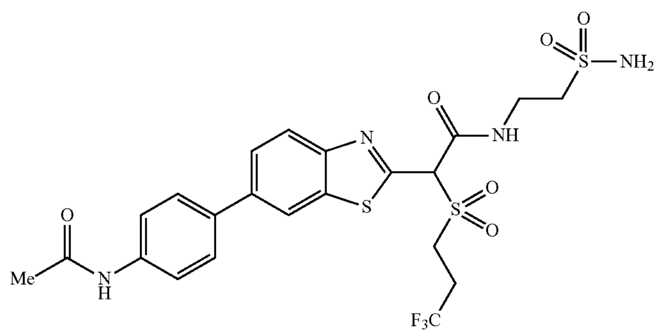 [SMILES: CC(=O)Nc1ccc(-c2ccc3nc(C(C(=O)NCCS(N)(=O)=O)S(=O)(=O)CCC(F)(F)F)sc3c2)cc1] | 2-(6-(4-acetamidophenyl)-1,3-benzothiazol-2-yl)-N-(2-sulfamoylethyl)-2-((3,3,3-trifluoropropyl)sulfonyl)acetamide | δ 10.09 (br. s., 1H), 8.98 (br. s., 1H), 8.46 (br. s., 1H), 8.12 (d, J = 7.7 Hz, 1H), 7.85 (d, J = 8.0 Hz, 1H), 7.76-7.59 (m, 4H), 6.98 (br. s., 2H), 6.25 (br. s., 1H), 3.85-3.46 (m, 4H), 3.18 (br. s., 2H), 2.85 (d, J = 9.4 Hz, 2H), 2.07 (br. s., 3H) | 1.45 N 593.2 | <10 | 55 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B56 | 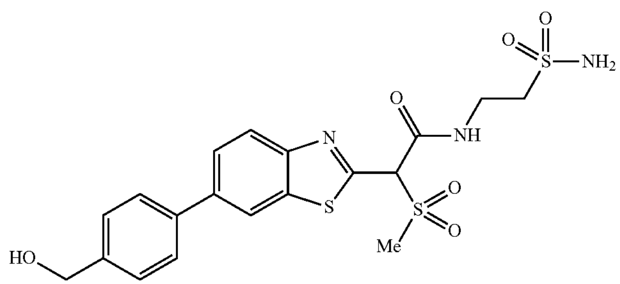 [SMILES: CS(=O)(=O)C(C(=O)NCCS(N)(=O)=O)c1nc2ccc(-c3ccc(CO)cc3)cc2s1] | 2-(6-(4-(hydroxymethyl)phenyl)-1,3-benzothiazol-2-yl)-2-(methylsulfonyl)-N-(2-sulfamoylethyl)acetamide | δ 9.01 (t, J = 5.6 Hz, 1H), 8.48 (d, J = 1.4 Hz, 1H), 8.14 (d, J = 8.5 Hz, 1H), 7.87 (dd, J = 8.8, 1.7 Hz, 1H), 7.73 (d, J = 8.3 Hz, 2H), 7.45 (d, J = 8.3 Hz, 2H), 6.97 (s, 2H), 6.12-5.92 (m, 1H), 4.65-4.50 (m, 2H), 3.60 (q, J = 6.8 Hz, 2H), 3.27-3.21 (m, 3H), 3.22-3.13 (m, 2H) | 1.22 N 484.1 | <10 | 122 |
| B57 | 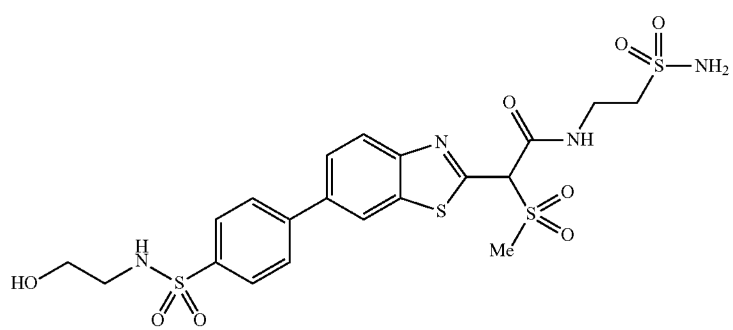 [SMILES: CS(=O)(=O)C(C(=O)NCCS(N)(=O)=O)c1nc2ccc(-c3ccc(S(=O)(=O)NCCO)cc3)cc2s1] | 2-(6-(4-((2-hydroxyethyl)sulfamoyl)phenyl)-1,3-benzothiazol-2-yl)-2-(methylsulfonyl)-N-(2-sulfamoylethyl)acetamide | δ 9.08-8.93 (m, 1H), 8.59 (d, J = 1.7 Hz, 1H), 8.20 (d, J = 8.5 Hz, 1H), 8.04-7.87 (m, 5H), 7.71 (s, 1H), 6.97 (s, 2H), 6.05 (s, 1H), 4.72 (s, 1H), 3.60 (d, J = 6.1 Hz, 2H), 3.39 (d, J = 5.8 Hz, 2H), 3.24 (s, 3H), 3.19 (d, J = 1.9 Hz, 2H), 2.83 (d, J = 6.1 Hz, 2H) | 1.15 N 577.1 | <10 | 144 |
| B58 | 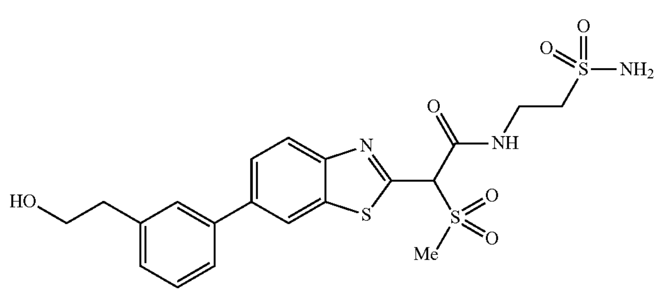 [SMILES: CS(=O)(=O)C(C(=O)NCCS(N)(=O)=O)c1nc2ccc(-c3cccc(CCO)c3)cc2s1] | 2-(6-(3-(2-hydroxyethyl)phenyl)-1,3-benzothiazol-2-yl)-2-(methylsulfonyl)-N-(2-sulfamoylethyl)acetamide | δ 9.10-8.91 (m, 1H), 8.47 (d, J = 1.7 Hz, 1H), 8.13 (s, 1H), 7.95 (s, 1H), 7.92-7.80 (m, 1H), 7.64-7.55 (m, 2H), 7.46-7.36 (m, 1H), 7.32-7.21 (m, 1H), 6.97 (s, 2H), 6.03 (s, 1H), 4.69 (s, 1H), 3.67 (d, J = 5.2 Hz, 2H), 3.63-3.54 (m, 2H), 3.24 (s, 3H), 3.21-3.13 (m, 2H), 2.82 (s, 2H) | 1.38 N 498.1 | <10 | 36 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B59 | 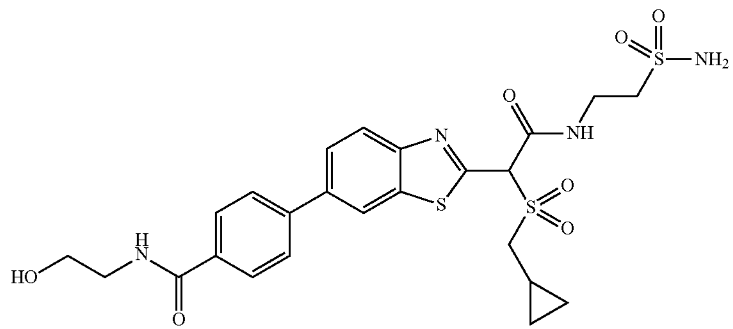 [SMILES: NS(=O)(=O)CCNC(=O)C(c1nc2ccc(-c3ccc(C(=O)NCCO)cc3)cc2s1)S(=O)(=O)CC1CC1] | 4-(2-(1-((cyclopropylmethyl)sulfonyl)-2-oxo-2-((2-sulfamoylethyl)amino)ethyl)-1,3-benzothiazol-6-yl)-N-(2-hydroxyethyl)benzamide | δ 9.16-8.89 (m, 1H), 8.56 (br. s., 2H), 8.23-8.10 (m, 1H), 8.05-7.62 (m, 6H), 6.97 (br. s., 1H), 6.94-6.84 (m, 1H), 6.06 (br. s., 1H), 4.75 (br. s., 1H), 3.60 (br. s., 2H), 3.53 (d, J = 4.4 Hz, 2H), 3.45-3.37 (m, 2H), 3.28 (br. s., 2H), 3.18 (br. s., 2H), 1.16-0.89 (m, 1H), 0.63 (br. s., 1H), 0.40 (br. s., 2H), 0.31-0.03 (m, 1H) | 1.26 N 581.1 | <10 | 102 |
| B60 | 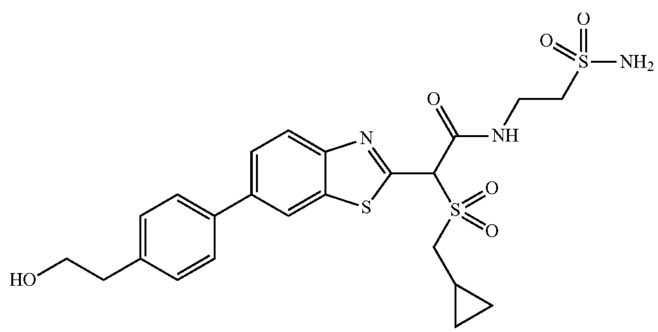 [SMILES: NS(=O)(=O)CCNC(=O)C(c1nc2ccc(-c3ccc(CCO)cc3)cc2s1)S(=O)(=O)CC1CC1] | 2-((cyclopropylmethyl)sulfonyl)-2-(6-(4-(2-hydroxyethyl)phenyl)-1,3-benzothiazol-2-yl)-N-(2-sulfamoylethyl)acetamide | δ 9.16-8.97 (m, 1H), 8.54-8.38 (m, 1H), 8.17-8.06 (m, 1H), 7.95 (br. s., 1H), 7.90-7.79 (m, 1H), 7.70-7.54 (m, 2H), 7.35 (br. s., 2H), 6.96 (br. s., 2H), 6.16-5.99 (m, 1H), 4.79-4.62 (m, 1H), 3.63 (m, 1H), 3.27 (br. s., 2H), 3.18 (br. s., 2H), 2.77 (br. s., 2H), 1.15-0.88 (m, 1H), 0.71-0.56 (m, 1H), 0.40 (br. s., 2H), 0.29-0.08 (m, 1H) | 1.53 N 538.1 | <10 | 61 |
| B61 | 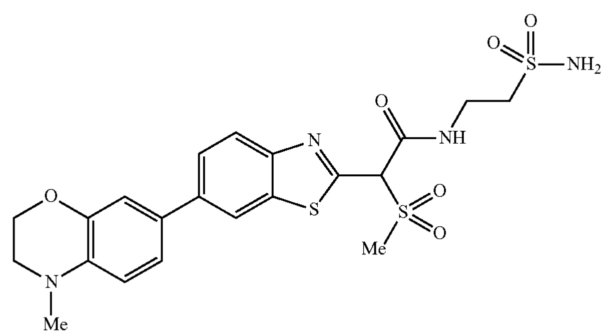 [SMILES: CN1CCOc2cc(-c3ccc4nc(C(C(=O)NCCS(N)(=O)=O)S(C)(=O)=O)sc4c3)ccc21] | 2-(6-(4-methyl-3,4-dihydro-2H-1,4-benzoxazin-7-yl)-1,3-benzothiazol-2-yl)-2-(methylsulfonyl)-N-(2-sulfamoylethyl)acetamide | δ 9.16-8.96 (m, 1H), 8.40-8.31 (m, 1H), 8.13-7.99 (m, 1H), 7.84-7.70 (m, 1H), 7.28-7.20 (m, 1H), 7.14-7.07 (m, 1H), 7.02-6.92 (m, 2H), 6.86-6.74 (m, 1H), 6.19-5.90 (m, 1H), 4.43-4.21 (m, 2H), 3.62-3.53 (m, 2H), 3.31-3.25 (m, 2H), 3.20-3.14 (m, 2H), 2.89 (s, 3H) | 1.63 N 525.1 | <10 | 50 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B62 | 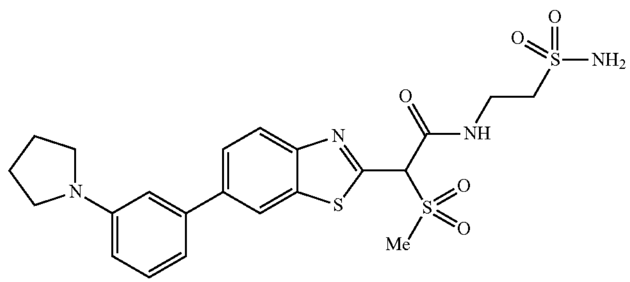 [SMILES: CS(=O)(=O)C(C(=O)NCCS(N)(=O)=O)c1nc2ccc(-c3cccc(N4CCCC4)c3)cc2s1] | 2-(methylsulfonyl)-2-(6-(3-(1-pyrrolidinyl)phenyl)-1,3-benzothiazol-2-yl)-N-(2-sulfamoylethyl)acetamide | δ 9.00 (t, J = 5.6 Hz, 1H), 8.45 (s, 1H), 8.13 (s, 1H), 7.84 (d, J = 8.5 Hz, 1H), 7.27 (t, J = 7.8 Hz, 1H), 7.05-6.90 (m, 3H), 6.83 (s, 1H), 6.58 (d, J = 8.0 Hz, 1H), 6.02 (s, 1H), 3.60 (q, J = 6.6 Hz, 2H), 3.31 (t, J = 6.1 Hz, 4H), 3.23 (s, 3H), 3.18 (t, J = 7.2 Hz, 2H), 1.98 (br. s, 4H) | 1.92 N 523.1 | 1.2 | 1 |
| B63 | 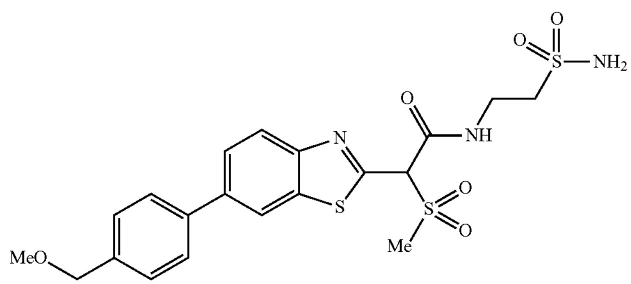 [SMILES: COCc1ccc(-c2ccc3nc(C(C(=O)NCCS(N)(=O)=O)S(C)(=O)=O)sc3c2)cc1] | 2-(6-(4-(methoxymethyl)phenyl)-1,3-benzothiazol-2-yl)-2-(methylsulfonyl)-N-(2-sulfamoylethyl)acetamide | δ 9.01 (t, J = 5.6 Hz, 1H), 8.49 (s, 1H), 8.15 (d, J = 8.5 Hz, 1H), 7.88 (s, 1H), 7.76 (d, J = 7.7 Hz, 2H), 7.45 (d, J = 7.7 Hz, 2H), 6.97 (s, 2H), 6.03 (s, 1H), 4.56-4.43 (m, 2H), 3.60 (q, J = 6.6 Hz, 2H), 3.32 (s, 3H), 3.24 (s, 3H), 3.19 (t, J = 7.2 Hz, 2H) | 1.48 N 498.1 | 0.5 | 2.6 |
| B64 | 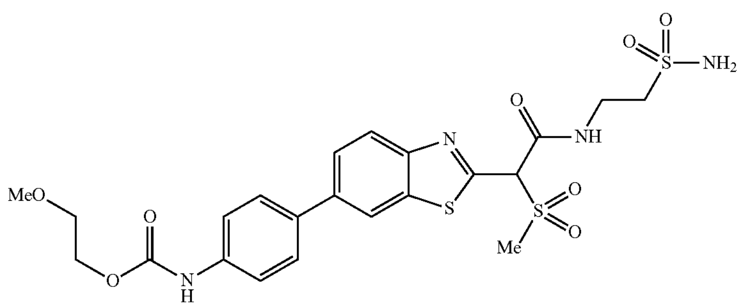 [SMILES: COCCOC(=O)Nc1ccc(-c2ccc3nc(C(C(=O)NCCS(N)(=O)=O)S(C)(=O)=O)sc3c2)cc1] | 2-methoxyethyl(4-(2-(1-(methylsulfonyl)-2-oxo-2-((2-sulfamoylethyl)amino)ethyl)-1,3-benzothiazol-6-yl)phenyl)carbamate | δ 9.92 (br. s., 1H), 9.00 (s, 1H), 8.43 (s, 1H), 8.11 (d, J = 8.5 Hz, 1H), 7.84 (d, J = 8.5 Hz, 1H), 7.71 (d, J = 8.3 Hz, 2H), 7.60 (d, J = 8.3 Hz, 2H), 6.97 (s, 2H), 6.01 (s, 1H), 4.37-4.16 (m, 2H), 3.70-3.52 (m, 4H), 3.29 (s, 3H), 3.23 (s, 3H), 3.18 (t, J = 7.2 Hz, 2H) | 1.32 N 571.1 | 0.5 | 1.9 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B65 | 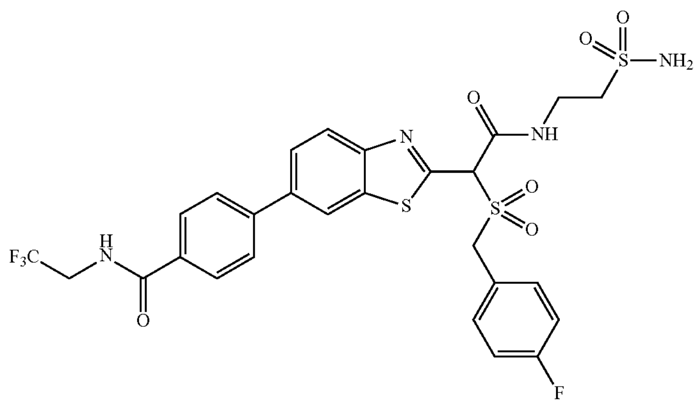 [SMILES: NS(=O)(=O)CCNC(=O)C(c1nc2ccc(-c3ccc(C(=O)NCC(F)(F)F)cc3)cc2s1)S(=O)(=O)Cc1ccc(F)cc1] | 4-(2-(1-((4-fluorobenzyl)sulfonyl)-2-oxo-2-((2-sulfamoylethyl)amino)ethyl)-1,3-benzothiazol-6-yl)-N-(2,2,2-trifluoroethyl)benzamide | δ 9.35-9.13 (m, 1H), 9.05 (br. s., 1H), 8.60 (s, 1H), 8.26-8.16 (m, 1H), 8.09-7.89 (m, 4H), 7.88-7.71 (m, 2H), 7.46 (t, J = 6.2 Hz, 1H), 7.39 (br. s., 1H), 7.24 (t, J = 8.3 Hz, 1H), 7.17-7.07 (m, 1H), 7.06-6.90 (m, 2H), 6.08 (s, 1H), 4.75 (br. s., 1H), 4.67-4.52 (m, 1H), 4.12 (d, J = 7.2 Hz, 2H), 3.70-3.53 (m, 2H), 3.27-3.11 (m, 2H) | 1.73 N 673.1 | <10 | 61 |
| B66 | 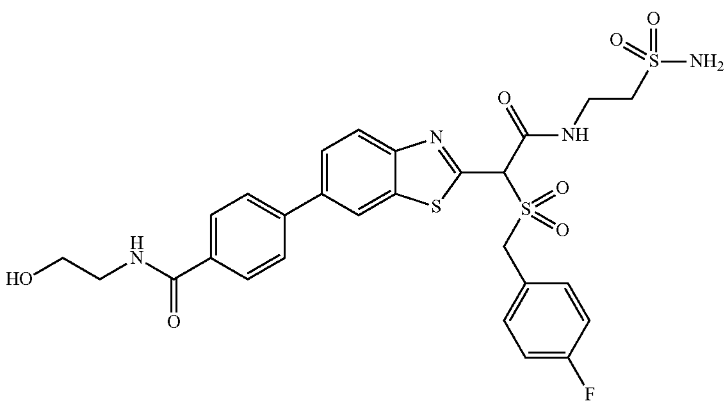 [SMILES: NS(=O)(=O)CCNC(=O)C(c1nc2ccc(-c3ccc(C(=O)NCCO)cc3)cc2s1)S(=O)(=O)Cc1ccc(F)cc1] | 4-(2-(1-((4-fluorobenzyl)sulfonyl)-2-oxo-2-((2-sulfamoylethyl)amino)ethyl)-1,3-benzothiazol-6-yl)-N-(2-hydroxyethyl)benzamide | δ 8.62-8.45 (m, 2H), 8.28-8.12 (m, 1H), 8.05-7.85 (m, 5H), 7.84-7.67 (m, 2H), 7.56-7.44 (m, 1H), 7.38 (br. s., 1H), 7.24 (t, J = 8.3 Hz, 1H), 7.18-7.05 (m, 1H), 7.04-6.89 (m, 2H), 6.07 (s, 1H), 4.75 (br. s., 2H), 4.65 (br. s., 1H), 3.60 (d, J = 6.1 Hz, 2H), 3.53 (t, J = 5.4 Hz, 2H), 3.36 (d, J = 5.8 Hz, 2H), 3.19 (t, J = 7.2 Hz, 2H) | 1.87 N 555.1 | <10 | 103 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B67 | 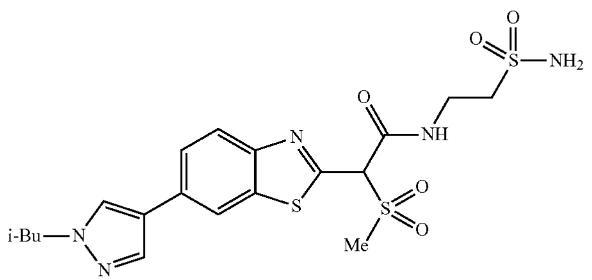 | 2-[6-(1-isobutyl-1H-pyrazol-4-yl)-1,3-benzothiazol-2-yl]-2-(methylsulfonyl)-N-(2-sulfamoylethyl)acetamide | δ 9.03-8.96 (m, 1H), 8.36 (d, J = 1.7 Hz, 1H), 8.29 (s, 1H), 8.05 (d, J = 8.5 Hz, 1H), 8.00 (s, 1H), 7.80 (dd, J = 8.5, 1.7 Hz, 1H), 6.98 (s, 2H), 5.99 (s, 1H), 3.96 (d, J = 7.2 Hz, 2H), 3.60 (dd, J = 13.2, 6.9 Hz, 4H), 3.23 (s, 3H), 3.21-3.15 (m, 2H), 0.92-0.86 (m, 6H) | 0.81 M 499.8 | <10 | 41 |
| B68 | 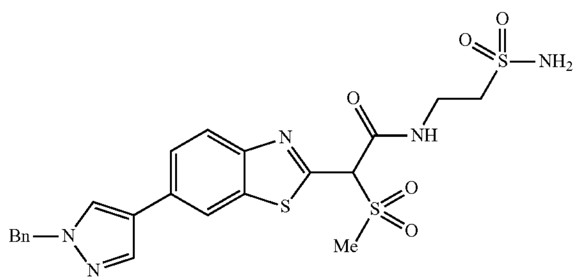 [SMILES: CS(=O)(=O)C(C(=O)NCCS(N)(=O)=O)c1nc2ccc(-c3cnn(Cc4ccccc4)c3)cc2s1] | 2-[6-(1-benzyl-1H-pyrazol-4-yl)-1,3-benzothiazol-2-yl]-2-(methylsulfonyl)-N-(2-sulfamoylethyl)acetamide | δ 8.39 (d, J = 13.8 Hz, 1H), 8.21 (s, 1H), 8.08-8.00 (m, 1H), 7.88 (s, 1H), 7.82 (br. s., 1H), 7.36 (t, J = 7.2 Hz, 3H), 7.34-7.26 (m, 2H), 6.95 (s, 1H), 6.86 (s, 1H), 5.38 (s, 1H), 5.33 (s, 1H), 3.65-3.55 (m, 3H), 3.25-3.13 (m, 5H) | 0.82 M 533.8 | <10 | <10 |
| B69 | 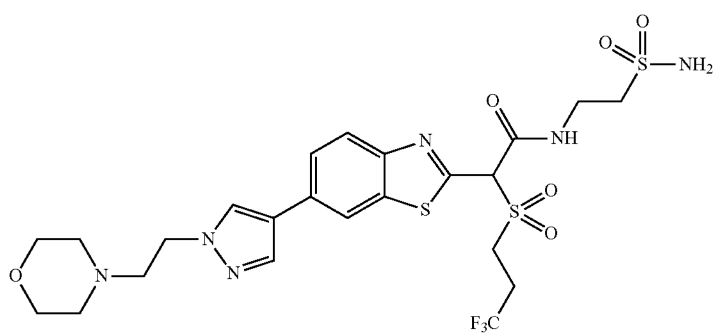 [SMILES: NS(=O)(=O)CCNC(=O)C(c1nc2ccc(-c3cnn(CCN4CCOCC4)c3)cc2s1)S(=O)(=O)CCC(F)(F)F] | 2-(6-(1-(2-(4-morpholinyl)ethyl)-1H-pyrazol-4-yl)-1,3-benzothiazol-2-yl)-N-((3,3,3-trifluoropropyl)sulfonyl)acetamide | ¹H NMR (500 MHz, ACETONITRILE-d₃) δ 8.25 (d, J = 1.4 Hz, 1H), 8.10 (t, J = 4.1 Hz, 1H), 8.03-7.97 (m, 1H), 7.96-7.88 (m, 1H), 7.79 (dd, J = 8.5, 1.9 Hz, 1H), 7.66-7.57 (m, 1H), 5.58-5.45 (m, 2H), 4.69-4.58 (m, 2H), 3.91 (br. s., 3H), 3.87-3.69 (m, 2H), 3.65-3.43 (m, 3H), 3.37-3.29 (m, 2H), 3.23 (br. s., 2H), 2.84-2.66 (m, 2H) | 0.69 M 638.9 | <10 | 612 |

-continued

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B70 | 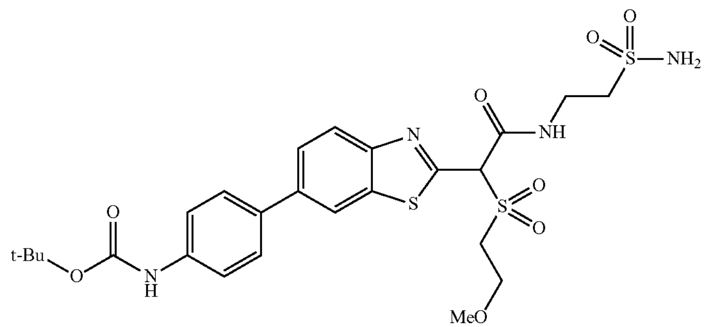 [SMILES: COCCS(=O)(=O)C(C(=O)NCCS(N)(=O)=O)c1nc2ccc(-c3ccc(NC(=O)OC(C)(C)C)cc3)cc2s1] | tert-butyl (4-(2-(1-((2-methoxyethyl)sulfonyl)-2-oxo-2-((2-sulfamoylethyl)amino)ethyl)-1,3-benzothiazol-6-yl)phenyl)carbamate | δ 9.49 (s, 1H), 8.95 (t, J = 5.5 Hz, 1H), 8.43 (s, 1H), 8.12 (d, J = 8.5 Hz, 1H), 7.84 (d, J = 8.8 Hz, 1H), 7.69 (d, J = 8.5 Hz, 1H), 7.63-7.52 (m, 2H), 6.96 (s, 2H), 6.02 (s, 1H), 3.81-3.73 (m, 1H), 3.70-3.65 (m, 2H), 3.60 (q, J = 6.8 Hz, 2H), 3.28 (s, 3H), 3.23-3.15 (m, 2H), 2.90 (s, 1H), 2.74 (s, 1H), 1.54-1.48 (m, 9H) | 1.81 N 613.3 | <10 | <10 |
| B71 | 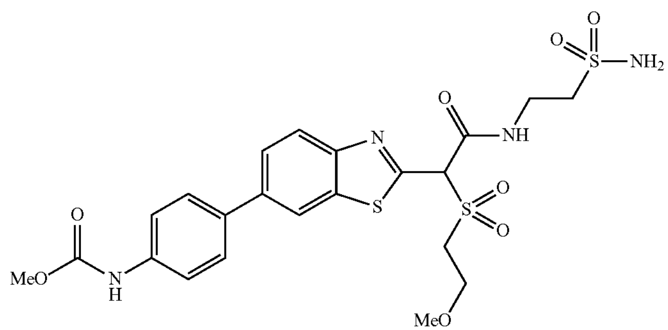 [SMILES: COCCS(=O)(=O)C(C(=O)NCCS(N)(=O)=O)c1nc2ccc(-c3ccc(NC(=O)OC)cc3)cc2s1] | methyl (4-(2-(1-((2-methoxyethyl)sulfonyl)-2-oxo-2-((2-sulfamoylethyl)amino)ethyl)-1,3-benzothiazol-6-yl)phenyl)carbamate | δ 9.80 (s, 1H), 8.95 (s, 1H), 8.44 (s, 1H), 8.12 (d, J = 8.5 Hz, 1H), 7.93-7.80 (m, 1H), 7.72 (d, J = 8.5 Hz, 2H), 7.60 (d, J = 8.5 Hz, 2H), 6.96 (s, 2H), 6.02 (s, 1H), 3.83-3.73 (m, 2H), 3.73-3.65 (m, 5H), 3.60 (q, J = 6.6 Hz, 2H), 3.28 (s, 3H), 3.24-3.16 (m, 2H) | 1.34 N 571.1 | <10 | <10 |
| B72 | 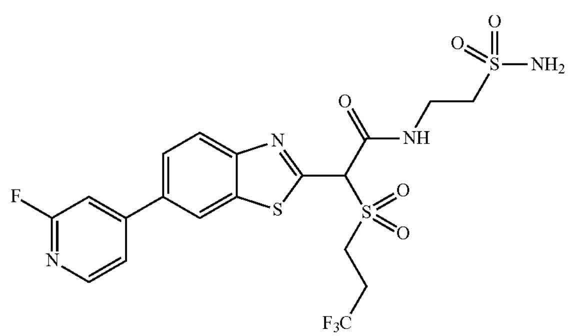 [SMILES: NS(=O)(=O)CCNC(=O)C(c1nc2ccc(-c3ccnc(F)c3)cc2s1)S(=O)(=O)CCC(F)(F)F] | 2-(6-(2-fluoro-4-pyridinyl)-1,3-benzothiazol-2-yl)-N-(2-sulfamoylethyl)-2-(3,3,3-trifluoropropyl)sulfonyl)acetamide | δ 8.97 (t, J = 5.6 Hz, 1H), 8.75 (d, J = 1.7 Hz, 1H), 8.36 (d, J = 5.2 Hz, 1H), 8.22 (d, J = 8.8 Hz, 1H), 8.07 (dd, J = 8.7, 1.8 Hz, 1H), 7.92 (br. s., 1H), 7.81 (d, J = 5.5 Hz, 1H), 7.64 (m, 1H), 6.96 (s, 2H), 6.29 (s, 1H), 3.82-3.59 (m, 5H), 3.22-3.16 (m, 3H) | 1.55 N 555.1 | <10 | 68 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B73 | 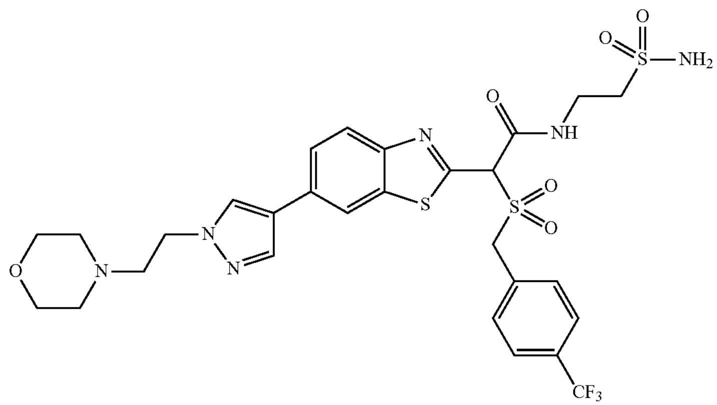 [SMILES: NS(=O)(=O)CCNC(=O)C(c1nc2ccc(-c3cnn(CCN4CCOCC4)c3)cc2s1)S(=O)(=O)Cc1ccc(C(F)(F)F)cc1] | 2-(6-(1-(2-(4-morpholinyl)ethyl)-1H-pyrazol-4-yl)-1,3-benzothiazol-2-yl)-N-(2-sulfamoylethyl)-2-((4-(trifluoromethyl)benzyl)sulfonyl)acetamide | $^1$H NMR (400 MHz, DMSO-$d_6$) δ 9.02 (s, 1H), 8.38 (s, 1H), 8.11 (d, J = 8.6 Hz, 1H), 7.96 (s, 1H), 7.82 (d, J = 9.0 Hz, 1H), 7.76 (d, J = 8.6 Hz, 2H), 7.64 (d, J = 8.1 Hz, 2H), 7.59 (s, 2H), 6.96 (s, 2H), 6.09 (s, 1H), 4.89 (d, J = 2.2 Hz, 2H), 3.79-3.56 (m, 12H), 3.25-3.15 (m, 6H) | 0.76 M 700.7 | <10 | 15860 |
| B74 | 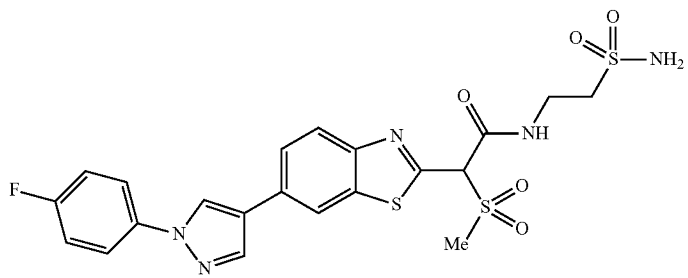 [SMILES: CS(=O)(=O)C(C(=O)NCCS(N)(=O)=O)c1nc2ccc(-c3cnn(-c4ccc(F)cc4)c3)cc2s1] | 2-(6-(1-(4-fluorophenyl)-1H-pyrazol-4-yl)-1,3-benzothiazol-2-yl)-2-(methylsulfonyl)-N-(2-sulfamoylethyl)acetamide | $^1$H NMR (400 MHz, DMSO-$d_6$) δ 9.05 (s, 1H), 8.93 (s, 1H), 8.43 (s, 1H), 8.27 (s, 1H), 8.06 (d, J = 8.6 Hz, 1H), 7.87 (dt, J = 8.8, 2.4 Hz, 2H), 7.34 (t, J = 8.8 Hz, 2H), 6.91 (s, 1H), 5.95 (s, 1H), 5.69 (s, 1H), 3.58-3.47 (m, 2H), 3.17 (s, 3H), 3.15-3.07 (m, 3H) | 0.91 M 537.7 | <10 | <10 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B75 | 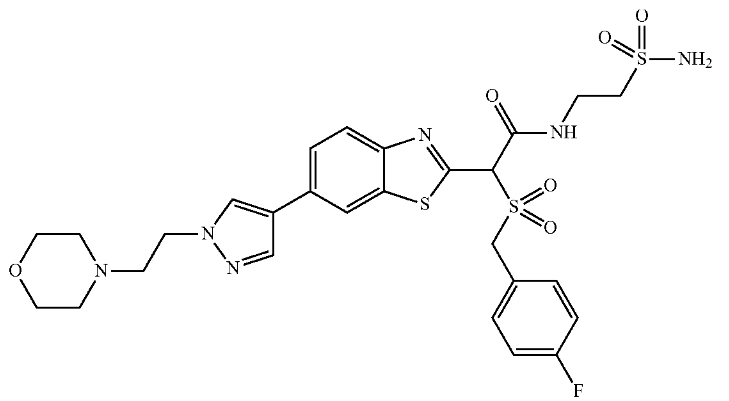 [SMILES: NS(=O)(=O)CCNC(=O)C(c1nc2ccc(-c3cnn(CCN4CCOCC4)c3)cc2s1)S(=O)(=O)Cc1ccc(F)cc1] | 2-((4-fluorobenzyl)sulfonyl)-2-(6-(1-(2-(4-morpholinyl)ethyl)-1H-pyrazol-4-yl)-1,3-benzothiazol-2-yl)-N-(2-sulfamoylethyl)acetamide | ¹H NMR (400 MHz, DMSO-d₆) δ 8.93 (t, J = 5.7 Hz, 1H), 8.36-8.27 (m, 1H), 8.17 (br. s., 1H), 8.03 (d, J = 8.6 Hz, 1H), 7.98-7.85 (m, 1H), 7.74 (dd, J = 8.6, 1.8 Hz, 1H), 7.50 (s, 1H), 7.38 (dd, J = 8.9, 5.4 Hz, 2H), 7.16 (t, J = 8.9 Hz, 1H), 7.02 (br. s., 1H), 6.88 (s, 2H), 5.96 (s, 1H), 4.71-4.62 (m, 2H), 4.49 (br. s., 3H), 3.52 (dd, J = 13.1, 6.7 Hz, 7H), 3.12 (dd, J = 8.8, 6.6 Hz, 5H) | 0.70 M 650.8 | <10 | 25000 |
| B76 | 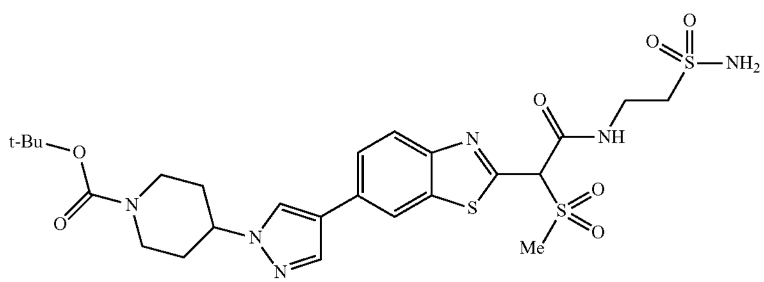 [SMILES: CC(C)(C)OC(=O)N1CCC(n2cc(-c3ccc4nc(C(C(=O)NCCS(N)(=O)=O)S(C)(=O)=O)sc4c3)cn2)CC1] | tert-butyl 4-(4-(2-(1-(methylsulfonyl)-2-oxo-2-((2-sulfamoylethyl)amino)ethyl)-1,3-benzothiazol-6-yl)-1H-pyrazol-1-yl)-1-piperidinecarboxylate | ¹H NMR (400 MHz, DMSO-d₆) δ 8.97 (s, 1H), 8.43-8.33 (m, 2H), 8.09-7.98 (m, 2H), 7.81 (dd, J = 8.6, 1.8 Hz, 1H), 6.95 (s, 2H), 5.99 (s, 1H), 4.40 (s, 1H), 4.06 (d, J = 12.8 Hz, 3H), 3.68-3.52 (m, 5H), 3.22-3.14 (m, 6H), 2.14-1.99 (m, 2H), 1.90-1.75 (m, 2H), 1.44 (s, 9H) | 0.88 M 626.7 | <10 | 21 |
| B77 | 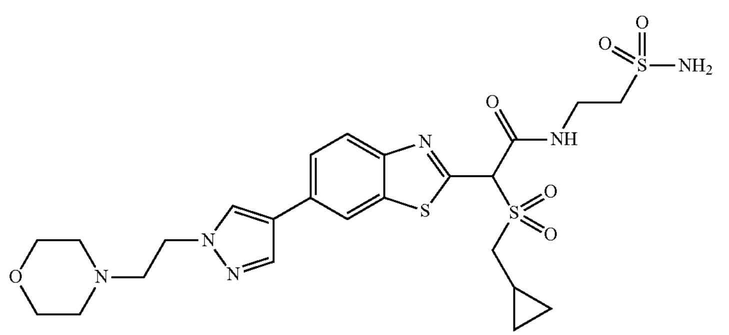 [SMILES: NS(=O)(=O)CCNC(=O)C(c1nc2ccc(-c3cnn(CCN4CCOCC4)c3)cc2s1)S(=O)(=O)CC1CC1] | 2-[(cyclopropylmethyl)sulfonyl]-2-(6-{1-[2-(4-morpholinyl)ethyl]-1H-pyrazol-4-yl}-1,3-benzothiazol-2-yl)-N-(2-sulfamoylethyl)acetamide | ¹H NMR (400 MHz, ACETONITRILE-d₃) δ 8.22 (d, J = 1.3 Hz, 1H), 8.14-8.02 (m, 1H), 7.98 (d, J = 5.3 Hz, 1H), 7.91-7.84 (m, 1H), 7.76 (dd, J = 8.6, 1.8 Hz, 1H), 7.61-7.52 (m, 1H), 5.82 (s, 1H), 5.53 (br. s., 2H), 4.63 (dt, J = 8.3, 6.1 Hz, 2H), 3.92 (br. s., 4H), 3.85-3.72 (m, 2H), 3.64 (q, J = 6.2 Hz, 2H), 3.38-3.25 (m, 4H), 3.22-3.10 (m, 2H), 1.28-0.99 (m, 1H), 0.75-0.69 (m, 1H), 0.57-0.43 (m, 2H), 0.31 (d, J = 4.6 Hz, 1H) | 0.64 M 596.8 | <10 | 2261 |

-continued

| Ex # | Structure | Name | 1H NMR (500 MHz, DMSO-d6, unless indicated otherwise) | LC/MS RT (min) Method M + H | EL IC50 (nM) | HL IC50 (nM) |
|---|---|---|---|---|---|---|
| B78 | 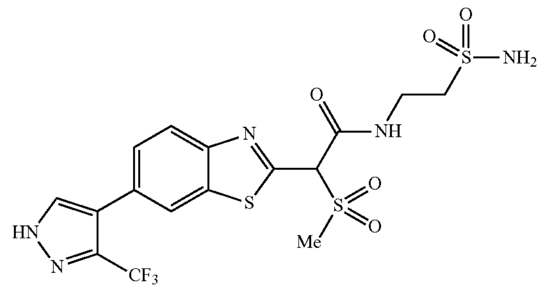 [SMILES: CS(=O)(=O)C(C(=O)NCCS(N)(=O)=O)c1nc2ccc(-c3c[nH]nc3C(F)(F)F)cc2s1] | 2-(methylsulfonyl)-N-(2-sulfamoylethyl)-2-(6-(3-(trifluoromethyl)-1H-pyrazol-4-yl)-1,3-benzothiazol-2-yl)acetamide | 1H NMR (400 MHz, DMSO-d6) δ 13.85 (br. s., 1H), 9.06-8.93 (m, 1H), 8.29 (s, 1H), 8.21 (d, J = 1.5 Hz, 1H), 8.14 (d, J = 8.4 Hz, 1H), 7.60 (dd, J = 8.7, 1.7 Hz, 1H), 6.95 (s, 2H), 6.52 (s, 1H), 6.04 (s, 1H), 3.67-3.54 (m, 2H), 3.25 (s, 3H), 3.22-3.15 (m, 2H) | 0.72 M 511.7 | <10 | 68 |
| B79 | 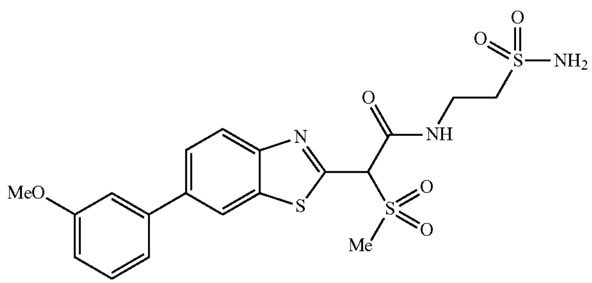 [SMILES: COc1cccc(-c2ccc3nc(C(C(=O)NCCS(N)(=O)=O)S(C)(=O)=O)sc3c2)c1] | 2-(6-(3-methoxyphenyl)-1,3-benzothiazol-2-yl)-2-(methylsulfonyl)-N-(2-sulfamoylethyl)acetamide | δ 9.10-8.84 (m, 1H), 8.49 (br. s., 1H), 8.20-8.09 (m, 1H), 7.95 (br. s., 1H), 7.91-7.84 (m, 1H), 7.47-7.38 (m, 1H), 7.29 (br. s., 2H), 7.06-6.95 (m, 2H), 6.95 (br. s., 2H), 6.03 (br. s., 1H), 3.85 (br. s., 3H), 3.66-3.56 (m, 2H), 3.23 (br. s., 3H), 3.19 (br. s., 2H) | 1.63 N 484.9 | <10 | <10 |
| B80 | 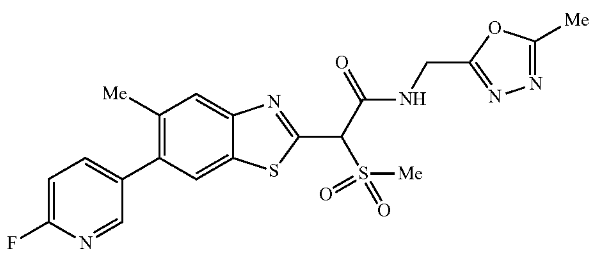 [SMILES: Cc1nnc(CNC(=O)C(c2nc3cc(C)c(-c4ccc(F)nc4)cc3s2)S(C)(=O)=O)o1] | 2-[6-(6-fluoro-3-pyridinyl)-5-methyl-1,3-benzothiazol-2-yl]-N-[(5-methyl-1,3,4-oxadiazol-2-yl)methyl]-2-(methylsulfonyl)acetamide | δ 9.51 (t, J = 5.50 Hz, 1H), 8.30 (s, 1H), 8.08 (s, 2H), 7.32 (dd, J = 2.20, 8.25 Hz, 1H), 6.08 (s, 1H), 4.68 (d, J = 5.78 Hz, 2H), 3.26 (s, 3H), 2.47 (s, 3H), 2.37 (s, 3H). | 1.6 O 476.1 | <10 | <10 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B81 | 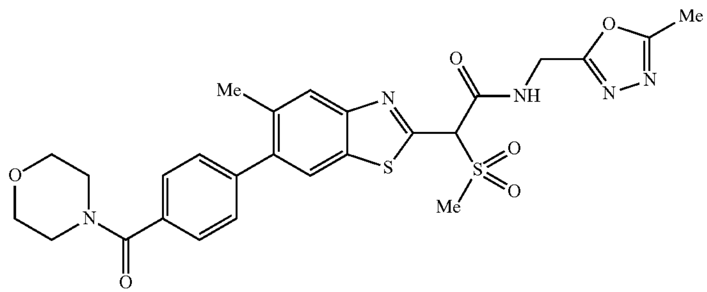 [SMILES: Cc1nnc(CNC(=O)C(c2nc3cc(C)c(-c4ccc(C(=O)N5CCOCC5)cc4)cc3s2)S(C)(=O)=O)o1] | 2-{5-methyl-6-[4-(4-morpholinylcarbonyl)phenyl]-1,3-benzothiazol-2-yl}-N-[(5-methyl-1,3,4-oxadiazol-2-yl)methyl]-2-(methylsulfonyl)acetamide | δ 9.51 (t, J = 5.64 Hz, 1H), 8.04 (d, J = 11.83 Hz, 2H), 7.45-7.52 (m, 3H), 6.07 (s, 1H), 4.68 (d, J = 5.78 Hz, 2H), 3.64 (br. s., 4H), 3.26 (s, 3H), 2.90 (s, 1H), 2.74 (s, 1H), 2.47 (s, 3H), 2.38 (s, 3H) | 1.60 O 570.1 | 14 | 196 |
| B82 | 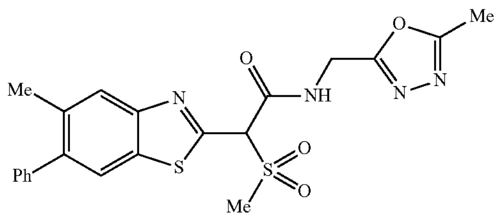 [SMILES: Cc1nnc(CNC(=O)C(c2nc3cc(C)c(-c4ccccc4)cc3s2)S(C)(=O)=O)o1] | N-((5-methyl-1,3,4-oxadiazol-2-yl)methyl)-2-(5-methyl-6-phenyl-1,3-benzothiazol-2-yl)-2-(methylsulfonyl)acetamide | ¹H NMR (500 MHz, METHANOL-d₄) δ 7.98 (d, J = 13.48 Hz, 1H), 7.84 (d, J = 8.80 Hz, 1H), 7.43-7.48 (m, 2H), 7.36-7.40 (m, 3H), 5.01 (s, 1H), 4.74 (d, J = 4.13 Hz, 2H), 3.23 (s, 3H), 2.50-2.54 (m, 3H), 2.35-2.41 (m, 3H) | 3.36 B 457.1 | 85 | 177 |
| B83 | 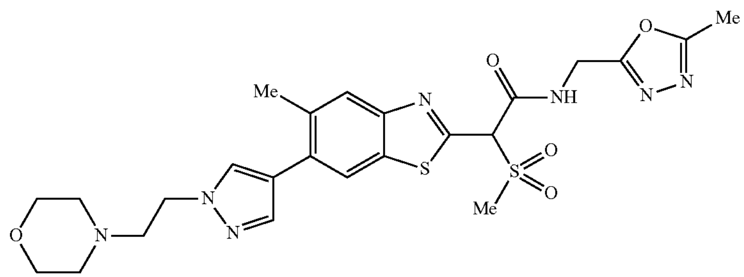 [SMILES: Cc1nnc(CNC(=O)C(c2nc3cc(C)c(-c4cnn(CCN5CCOCC5)c4)cc3s2)S(C)(=O)=O)o1] | 2-(5-methyl-6-(1-(2-(4-morpholinyl)ethyl)-1H-pyrazol-4-yl)-1,3-benzothiazol-2-yl)-N-((5-methyl-1,3,4-oxadiazol-2-yl)methyl)-2-(methylsulfonyl)acetamide | δ 8.15-8.20 (m, 2H), 8.01 (s, 1H), 7.89 (br. s., 1H), 6.05 (s, 1H), 4.67 (d, J = 6.05 Hz, 2H), 4.58 (br. s., 2H), 3.87-4.09 (m, 2H), 3.68 (d, J = 17.61 Hz, 6H), 3.25 (s, 3H), 2.90 (s, 1H), 2.74 (s, 1H), 2.54 (s, 3H), 2.47 (s, 3H) | 0.61 O 560.9 | 77 | 229 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B84 | 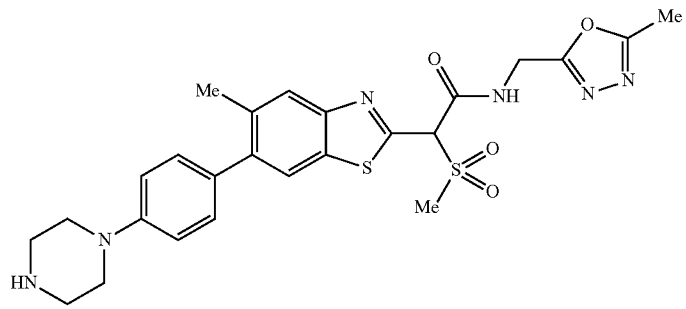 [SMILES: Cc1nnc(CNC(=O)C(c2nc3cc(C)c(-c4ccc(N5CCNCC5)cc4)cc3s2)S(C)(=O)=O)o1] | N-((5-methyl-1,3,4-oxadiazol-2-yl)methyl)-2-(5-methyl-6-(4-(piperazin-1-yl)phenyl)-1,3-benzothiazol-2-yl)-2-(methylsulfonyl)acetamide | δ 7.29 (d, J = 8.25 Hz, 1H), 7.05 (d, J = 8.53 Hz, 1H), 5.19 (s, 1H), 4.61 (br. s., 2H), 3.17 (s, 3H), 3.04-3.14 (m, 6H), 2.90 (s, 1H), 2.74 (s, 1H), 2.48 (s, 3H), 2.38 (s, 3H) | 0.66 O 541.1 | 34 | 350 |
| B85 | 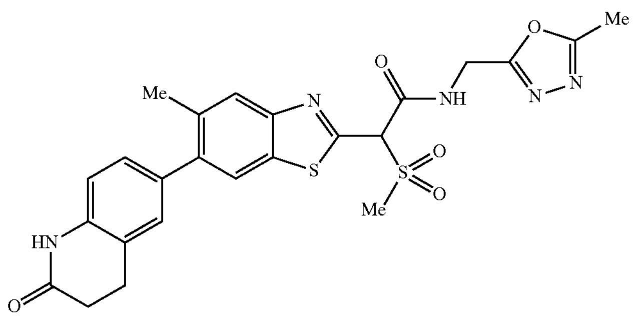 [SMILES: Cc1nnc(CNC(=O)C(c2nc3cc(C)c(-c4ccc5c(c4)CCC(=O)N5)cc3s2)S(C)(=O)=O)o1] | N-((5-methyl-1,3,4-oxadiazol-2-yl)methyl)-2-(5-methyl-6-(2-oxo-1,2,3,4-tetrahydro-6-quinolinyl)-1,3-benzothiazol-2-yl)-2-(methylsulfonyl)acetamide | δ 7.96 (d, J = 4.68 Hz, 1H), 7.11-7.21 (m, 1H), 6.06 (s, 1H), 4.60-4.70 (m, 2H), 3.45 (m, 1H), 3.26 (s, 3H), 3.18 (m, 1H), 2.92-2.99 (m, 2H), 2.47 (s, 3H) | 1.31 O 526.1 | 11 | 124 |
| B86 | 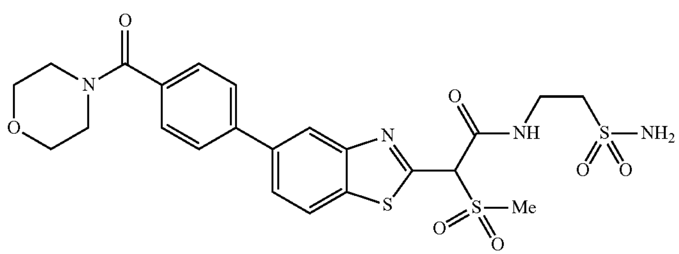 [SMILES: CS(=O)(=O)C(C(=O)NCCS(N)(=O)=O)c1nc2cc(-c3ccc(C(=O)N4CCOCC4)cc3)ccc2s1] | 2-(methylsulfonyl)-2-(5-(4-(4-morpholinylcarbonyl)phenyl)-1,3-benzothiazol-2-yl)-N-(2-sulfamoylethyl)acetamide | δ 9.00 (br. s., 1H), 8.42 (s, 1H), 8.28 (d, J = 8.3 Hz, 1H), 7.89 (d, J = 6.9 Hz, 3H), 7.56 (d, J = 7.2 Hz, 2H), 6.96 (br. s., 2H), 6.07 (s, 1H), 3.92 (s, 2H), 3.62 (d, J = 6.1 Hz, 9H), 3.27 (s, 3H), 3.21 (br. s., 2H) | 1.28 O 567.1 | <10 | 494 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B87 | 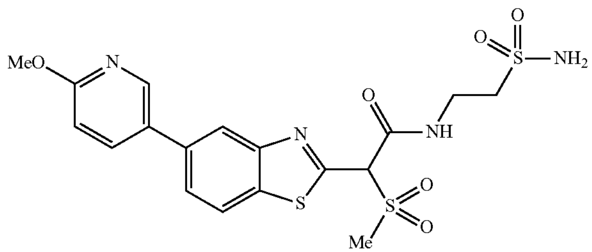 [SMILES: COc1ccc(-c2ccc3sc(C(C(=O)NCCS(N)(=O)=O)S(C)(=O)=O)nc3c2)cn1] | 2-(5-(6-methoxy-3-pyridinyl)-1,3-benzothiazol-2-yl)-2-(methylsulfonyl)-N-(2-sulfamoylethyl)acetamide | δ 9.03 (t, J = 5.6 Hz, 1H), 8.64 (d, J = 2.5 Hz, 1H), 8.39 (d, J = 0.8 Hz, 1H), 8.26 (d, J = 8.5 Hz, 1H), 8.17 (dd, J = 8.5, 2.5 Hz, 1H), 7.85 (dd, J = 8.5, 1.4 Hz, 1H), 7.01-6.93 (m, 3H), 6.06 (s, 1H), 3.97-3.87 (m, 3H), 3.61 (q, J = 6.7 Hz, 2H), 3.26 (s, 3H), 3.23-3.17 (m, 2H) | 1.2 O 485 | 0.5 | 2.6 |
| B88 | 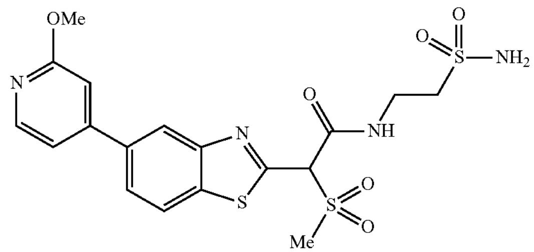 [SMILES: COc1cc(-c2ccc3sc(C(C(=O)NCCS(N)(=O)=O)S(C)(=O)=O)nc3c2)ccn1] | 2-(5-(2-methoxy-4-pyridinyl)-1,3-benzothiazol-2-yl)-2-(methylsulfonyl)-N-(2-sulfamoylethyl)acetamide | δ 9.02 (t, J = 5.8 Hz, 1H), 8.52 (s, 1H), 8.35-8.25 (m, 2H), 8.00-7.90 (m, 2H), 7.48 (d, J = 5.2 Hz, 1H), 6.99 (s, 2H), 6.07 (s, 1H), 3.93 (s, 3H), 3.62 (q, J = 6.8 Hz, 2H), 3.26 (s, 3H), 3.23-3.18 (m, 2H) | 1.1 O 485.1 | 0.5 | 2.2 |
| B89 | 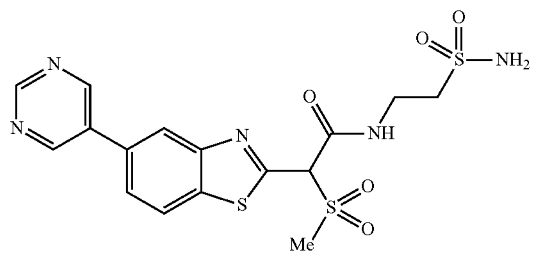 [SMILES: CS(=O)(=O)C(C(=O)NCCS(N)(=O)=O)c1nc2cc(-c3cncnc3)ccc2s1] | 2-(methylsulfonyl)-2-(5-(5-pyrimidinyl)-1,3-benzothiazol-2-yl)-N-(2-sulfamoylethyl)acetamide | δ 9.30 (s, 1H), 9.24 (s, 1H), 9.02 (t, J = 5.5 Hz, 1H), 8.59 (s, 1H), 8.35 (d, J = 8.5 Hz, 1H), 7.99 (d, J = 8.3 Hz, 1H), 6.99 (s, 2H), 6.08 (s, 1H), 3.62 (q, J = 6.5 Hz, 2H), 3.27 (s, 3H), 3.21 (t, J = 7.2 Hz, 2H) | 1.0 O 456.0 | 4.4 | 70 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B90 | 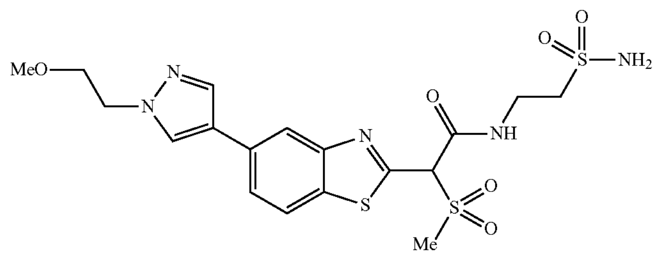 [SMILES: COCCn1cc(-c2ccc3sc(C(C(=O)NCCS(N)(=O)=O)S(C)(=O)=O)nc3c2)cn1] | 2-(5-(1-(2-methoxyethyl)-1H-pyrazol-4-yl)-1,3-benzothiazol-2-yl)-2-(methylsulfonyl)-N-(2-sulfamoylethyl)acetamide | $^1$H NMR (400 MHz, DMSO-$d_6$) δ 8.13 (s, 1H), 8.09 (s, 1H), 7.93 (d, J = 8.4 Hz, 1H), 7.86 (s, 1H), 7.59 (m, 1H), 4.15 (m, 2H), 3.61-3.54 (m, 4H), 3.21 (m, 2H), 3.12 (s, 3H), 3.09-3.06 (s, 3H) | 1.4 B 502.0 | <10 | 100 |
| B91 | 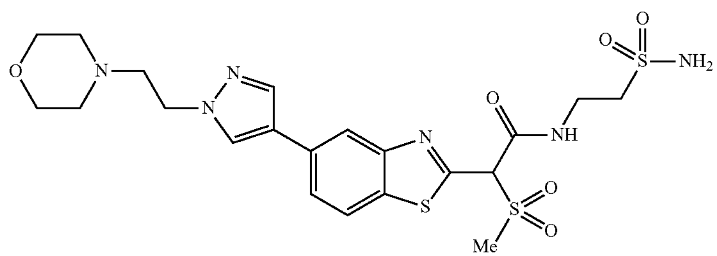 [SMILES: CS(=O)(=O)C(C(=O)NCCS(N)(=O)=O)c1nc2cc(-c3cnn(CCN4CCOCC4)c3)ccc2s1] | 2-(methylsulfonyl)-2-(5-(1-(2-(4-morpholinyl)ethyl)-1H-pyrazol-4-yl)-1,3-benzothiazol-2-yl)-N-(2-sulfamoylethyl)acetamide | $^1$H NMR (400 MHz, METHANOL-$d_4$) δ 8.24 (d, J = 1.3 Hz, 1H), 8.21 (s, 1H), 8.05 (d, J = 0.7 Hz, 1H), 8.03-7.99 (m, 1H), 7.71 (dd, J = 8.5, 1.7 Hz, 1H), 4.15-3.88 (m, 4H), 3.87-3.66 (m, 8H), 3.35 (m, 4H), 3.23 (s, 3H) | 1.14 B 557.0 | <10 | 1800 |
| B92 | 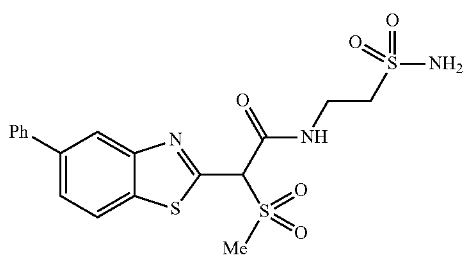 [SMILES: CS(=O)(=O)C(C(=O)NCCS(N)(=O)=O)c1nc2cc(-c3ccccc3)ccc2s1] | 2-(methylsulfonyl)-2-(5-phenyl-1,3-benzothiazol-2-yl)-N-(2-sulfamoylethyl)acetamide | $^1$H NMR (400 MHz, DMSO-$d_6$) δ 8.95 (t, J = 5.6 Hz, 1H), 8.29 (s, 1H), 8.18 (d, J = 8.4 Hz, 1H), 7.80-7.70 (m, 3H), 7.45 (t, J = 7.5 Hz, 2H), 7.36 (d, J = 7.5 Hz, 1H), 6.92 (s, 2H), 5.98 (s, 1H), 3.53 (q, J = 6.5 Hz, 2H), 3.12 (t, J = 7.0 Hz, 2H). | 1.71 B 454.0 | <10 | <10 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B93 | 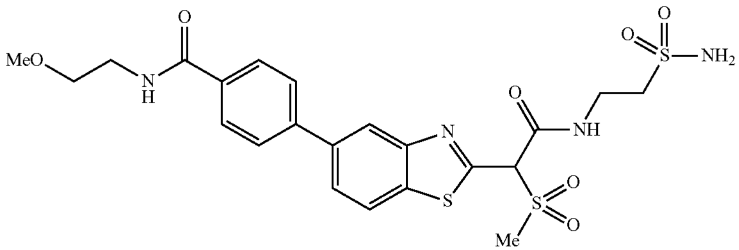 [SMILES: COCCNC(=O)c1ccc(-c2ccc3sc(C(C(=O)NCCS(N)(=O)=O)S(C)(=O)=O)nc3c2)cc1] | N-(2-methoxyethyl)-4-(2-(1-(methylsulfonyl)-2-oxo-2-((2-sulfamoylethyl)amino)ethyl)-1,3-benzothiazol-5-yl)benzamide | δ 8.63 (t, J = 5.1 Hz, 1H), 8.46 (s, 1H), 8.29 (d, J = 8.5 Hz, 1H), 8.02-7.90 (m, 5H), 6.99 (s, 2H), 6.07 (s, 1H), 3.62 (q, J = 6.8 Hz, 2H), 3.52-3.45 (m, 4H), 3.30 (s, 3H), 3.27 (s, 3H), 3.20 (t, J = 7.3 Hz, 2H). | 1.17 N 555.2 | 0.5 | 7.1 |
| B94 | 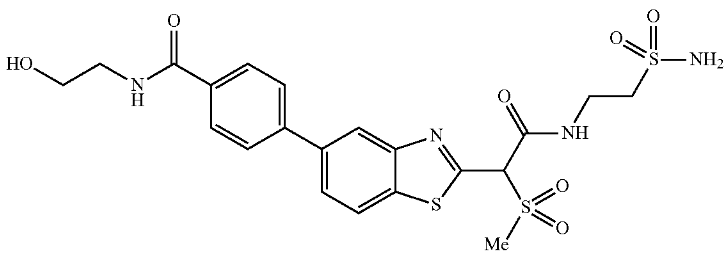 [SMILES: CS(=O)(=O)C(C(=O)NCCS(N)(=O)=O)c1nc2cc(-c3ccc(C(=O)NCCO)cc3)ccc2s1] | N-(2-hydroxyethyl)-4-(2-(1-(methylsulfonyl)-2-oxo-2-((2-sulfamoylethyl)amino)ethyl)-1,3-benzothiazol-5-yl)benzamide | δ 9.02 (t, J = 5.8 Hz, 1H), 8.54 (t, J = 5.6 Hz, 1H), 8.46 (d, J = 1.1 Hz, 1H), 8.29 (d, J = 8.3 Hz, 1H), 8.04-7.86 (m, 6H), 6.99 (s, 2H), 6.07 (s, 1H), 4.78 (t, J = 5.6 Hz, 1H), 3.62 (d, J = 6.3 Hz, 2H), 3.55 (q, J = 5.9 Hz, 2H), 3.37 (d, J = 6.1 Hz, 2H), 3.24-3.16 (m, 2H) | 1.71 O 541.1 | <10 | 123 |
| B95 | 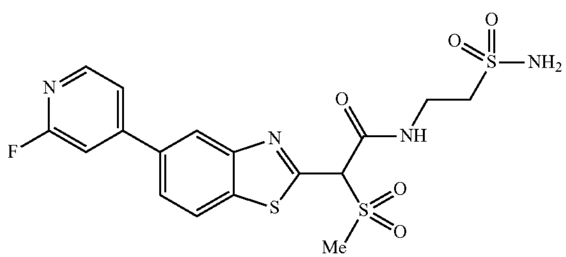 [SMILES: CS(=O)(=O)C(C(=O)NCCS(N)(=O)=O)c1nc2cc(-c3ccnc(F)c3)ccc2s1] | 2-[5-(2-fluoro-4-pyridinyl)-1,3-benzothiazol-2-yl]-2-(methylsulfonyl)-N-(2-sulfamoylethyl)acetamide | δ 9.02 (br. s., 1H), 8.64 (br. s., 1H), 8.36 (br. s., 2H), 8.09-7.94 (m, 1H), 7.88 (br. s., 1H), 7.73 (br. s., 1H), 6.99 (br. s., 2H), 6.09 (br. s., 1H), 3.62 (br. s., 2H), 3.27 (br. s., 3H), 3.20 (br. s., 2H) | 1.35 N 473.1 | <10 | 70 |

| Ex # | Structure | Name | 1H NMR (500 MHz, DMSO-d6, unless indicated otherwise) | LC/MS RT (min) Method M + H | EL IC50 (nM) | HL IC50 (nM) |
|---|---|---|---|---|---|---|
| B96 | 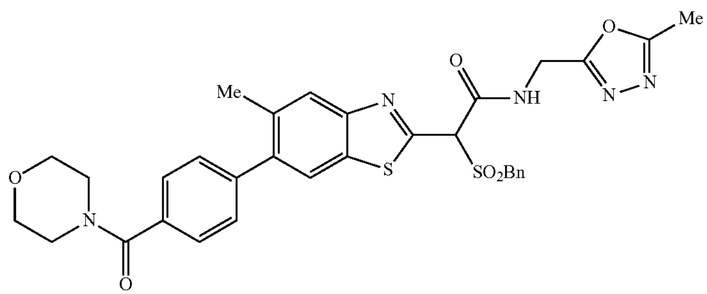 | 2-(benzylsulfonyl)-2-(5-methyl-6-(4-(4-morpholinylcarbonyl)phenyl)-1,3-benzothiazol-2-yl)-N-((5-methyl-1,3,4-oxadiazol-2-yl)methyl)acetamide | δ 8.30-7.84 (m, 2H), 7.69-7.09 (m, 9H), 5.09-4.26 (m, 4H), 3.98-3.46 (m, 7H), 2.99-2.65 (m, 3H), 2.49-2.20 (m, 5H). | 1.55 Q 646.2 | 27 | 251 |
| B97 | 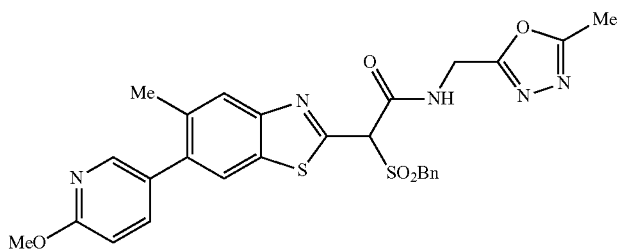 | 2-(benzylsulfonyl)-2-(6-(6-methoxy-3-pyridinyl)-5-methyl-1,3-benzothiazol-2-yl)-N-((5-methyl-1,3,4-oxadiazol-2-yl)methyl)acetamide | 1H NMR (400 MHz, CHLOROFORM-d) δ 8.35-6.59 (m, 10H), 4.64-4.26 (m, 3H), 4.09-3.85 (m, 3H), 3.74-3.01 (m, 2H), 2.67-2.49 (m, 3H), 2.45-2.13 (m, 3H) | 3.79 L 564.1 | 24 | 57 |
| B100 | 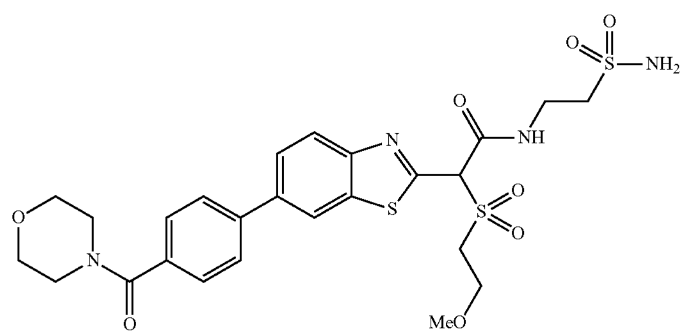 [SMILES: COCCS(=O)(=O)C(C(=O)NCCS(N)(=O)=O)c1nc2ccc(-c3ccc(C(=O)N4CCOCC4)cc3)cc2s1] | 2-((2-methoxyethyl)sulfonyl)-2-(6-(4-(4-morpholinyl-carbonyl)phenyl)-1,3-benzothiazol-2-yl)-N-(2-sulfamoylethyl)acetamide | δ 8.60-8.49 (m, 1H), 8.23-8.14 (m, 1H), 7.84 (m, 4H), 7.62-7.43 (m, 3H), 6.95 (s, 2H), 3.81-3.53 (m, 14H), 3.27 (s, 3H), 3.24-3.13 (m, 2H) | 0.74 M 610.9 | <10 | 1236 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B101 | 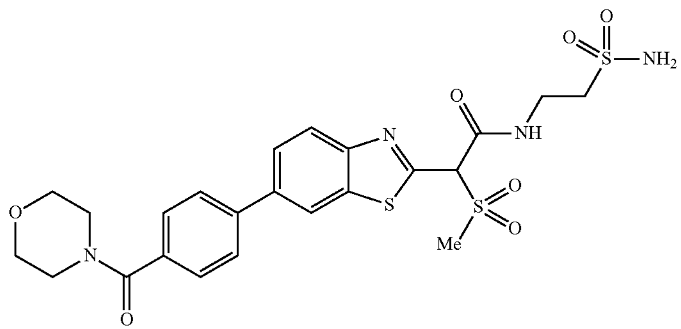 [SMILES: CS(=O)(=O)C(C(=O)NCCS(N)(=O)=O)c1nc2ccc(-c3ccc(C(=O)N4CCOCC4)cc3)cc2s1] | 2-(methylsulfonyl)-2-(6-(4-(4-morpholinylcarbonyl)phenyl)-1,3-benzothiazol-2-yl)-N-(2-sulfamoylethyl)acetamide | ¹H NMR (400 MHz, DMSO-d₆) 8.97 (s, 1H), 8.53 (s, 1H), 8.17 (d, J = 8.6 Hz, 1H), 7.91 (d, J = 8.4 Hz, 1H), 7.85 (d, J = 7.9 Hz, 2H), 7.55 (d, J = 7.9 Hz, 2H), 6.94 (s, 2H), 6.04 (s, 1H), 3.61 (d, J = 5.5 Hz, 5H), 3.52 (br. s., 2H), 3.19 (t, J = 7.2 Hz, 2H) | 0.77 M 567.2 | <10 | 63 |
| B102 | 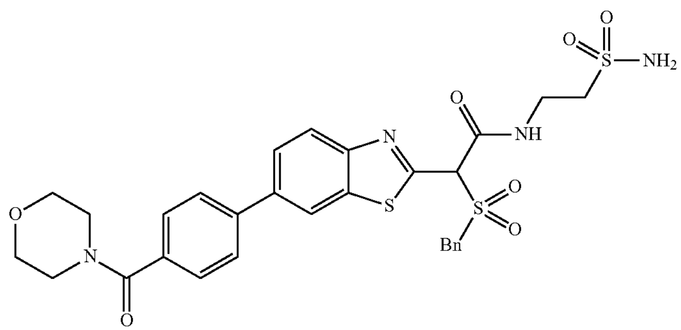 | 2-(benzylsulfonyl)-2-(6-(4-(4-morpholinylcarbonyl)phenyl)-1,3-benzothiazol-2-yl)-N-(2-sulfamoylethyl)acetamide | δ 9.03 (s, 1H), 8.54 (d, J = 1.7 Hz, 1H), 8.23 (br. s., 1H), 7.97-7.83 (m, 2H), 7.76 (br. s., 2H), 7.60-7.47 (m, 2H), 7.40 (m, 3H), 7.37-7.14 (m, 2H), 7.04-6.87 (m, 2H), 4.89-4.69 (m, 1H), 4.67-4.52 (m, 1H), 3.77-3.52 (m, 10H), 3.20 (t, J = 7.6 Hz, 2H) | 0.83 M 642.8 | 18 | 5288 |
| B103 | 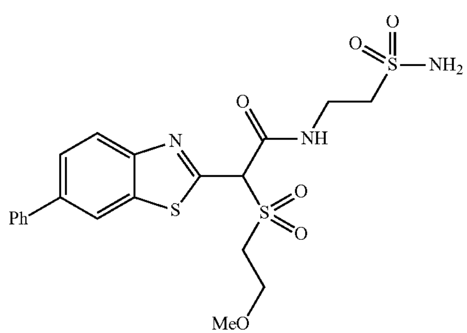 [SMILES: COCCS(=O)(=O)C(C(=O)NCCS(N)(=O)=O)c1nc2ccc(-c3ccccc3)cc2s1] | 2-((2-methoxyethyl)sulfonyl)-2-(6-phenyl-1,3-benzothiazol-2-yl)-N-(2-sulfamoylethyl)acetamide | ¹H NMR (500 MHz, CHLOROFORM-d) δ 7.78 (s, 1H), 7.60 (dd, J = 17.5, 8.1 Hz, 3H), 7.52-7.43 (m, 2H), 7.40 (d, J = 7.4 Hz, 2H), 4.03-3.89 (m, 2H), 3.83 (t, J = 5.6 Hz, 2H), 3.49 (m, 3H), 3.41 (t, J = 5.6 Hz, 2H), 3.26 (m, 2H). | 0.92 M 497.8 | <10 | <10 |

| Ex # | Structure | Name | $^1$H NMR (500 MHz, DMSO-d$_6$, unless indicated otherwise) | LC/MS RT (min) Method M + H | EL IC$_{50}$ (nM) | HL IC$_{50}$ (nM) |
|---|---|---|---|---|---|---|
| B104 | 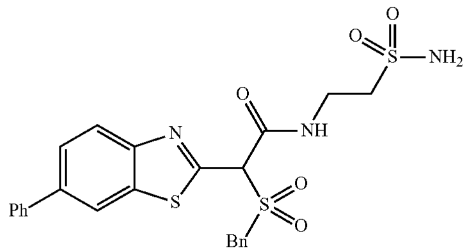 | 2-(benzylsulfonyl)-2-(6-phenyl-1,3-benzothiazol-2-yl)-N-(2-sulfamoylethyl)acetamide | $^1$H NMR (500 MHz, METHANOL-d$_4$) δ 7.97-7.13 (m, 13H), 4.54 (br. s., 2H), 3.90-3.68 (m, 2H), 3.29-3.31 (m., 2H) | 1.0 M 529.8 | <10 | <10 |
| B105 | 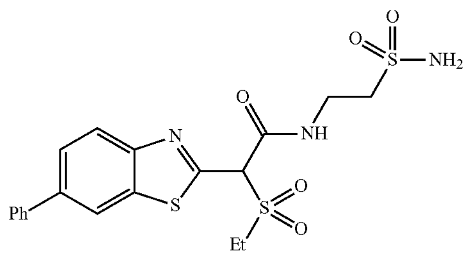 [SMILES: CCS(=O)(=O)C(C(=O)NCCS(N)(=O)=O)c1nc2ccc(-c3ccccc3)cc2s1] | 2-(ethylsulfonyl)-2-(6-phenyl-1,3-benzothiazol-2-yl)-N-(2-sulfamoylethyl)acetamide | δ 9.09-8.93 (m, 1H), 8.47 (d, J = 1.1 Hz, 1H), 8.14 (d, J = 8.8 Hz, 1H), 7.87 (d, J = 1.9 Hz, 1H), 7.76 (d, J = 7.7 Hz, 2H), 7.60-7.37 (m, 3H), 6.95 (s, 2H), 6.07 (s, 1H), 3.60 (d, J = 6.3 Hz, 2H), 3.36-3.38 (m, 2H), 3.20 (d, J = 6.3 Hz, 2H), 1.27 (t, J = 7.4 Hz, 3H) | 1.61 M 468.1 | <10 | <10 |
| B106 | 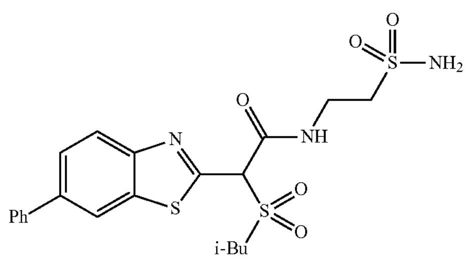 | 2-(isobutylsulfonyl)-2-(6-phenyl-1,3-benzothiazol-2-yl)-N-(2-sulfamoylethyl)acetamide | δ 9.15-8.93 (m, 1H), 8.58-8.40 (m, 1H), 8.22-8.07 (m, 1H), 7.91-7.82 (m, 1H), 7.76 (s, 2H), 7.51 (s, 2H), 7.47-7.34 (m, 1H), 6.95 (s, 2H), 6.02 (s, 1H), 3.75-3.54 (m, 2H), 3.29-3.12 (m, 4H), 2.32-2.19 (m, 1H), 1.03 (d, J = 6.9 Hz, 6H) | 1.93 N 496.1 | <10 | <10 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B107 | 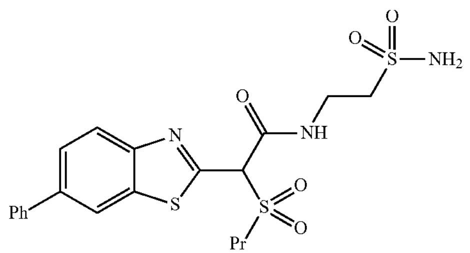 | 2-(6-phenyl-1,3-benzothiazol-2-yl)-2-(propylsulfonyl)-N-(2-sulfamoylethyl)acetamide | $^1$H NMR (500 MHz, METHANOL-$d_4$) δ 8.40-8.25 (m, 1H), 8.18-8.07 (m, 1H), 8.00-7.92 (m, 1H), 7.88-7.80 (m, 1H), 7.75-7.69 (m, 1H), 7.70-7.59 (m, 1H), 7.53-7.30 (m, 3H), 3.91-3.73 (m, 2H), 3.35 (br. s., 4H), 1.99-1.72 (m, 2H), 1.05 (d, J = 12.1 Hz, 3H) | 0.96 M 481.8 | <10 | <10 |
| B108 | 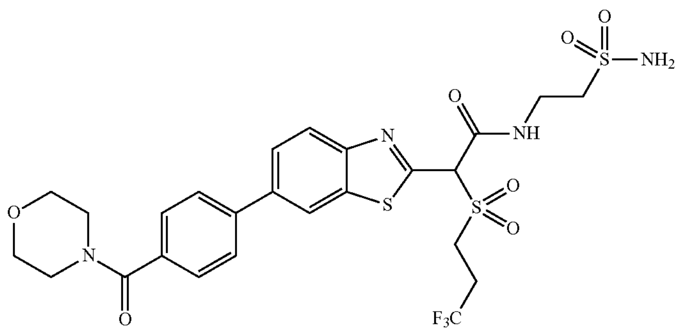 | 2-(6-(4-(4-morpholinylcarbonyl)phenyl)-1,3-benzothiazol-2-yl)-2-((3,3,3-trifluoropropyl)sulfonyl)-N-(2-sulfamoylethyl)acetamide | δ 9.25-8.84 (m, 1H), 8.71-8.50 (m, 1H), 8.34-8.10 (m, 1H), 7.97-7.89 (m, 1H), 7.89-7.83 (m, 2H), 7.81-7.69 (m, 1H), 7.63-7.38 (m, 2H), 7.09-6.85 (m, 2H), 6.41-6.11 (m, 1H), 3.88-3.45 (m, 12H), 3.25-3.11 (m, 2H), 2.94-2.72 (m, 2H) | 0.84 M 648.8 | <10 | 23 |
| B109 | 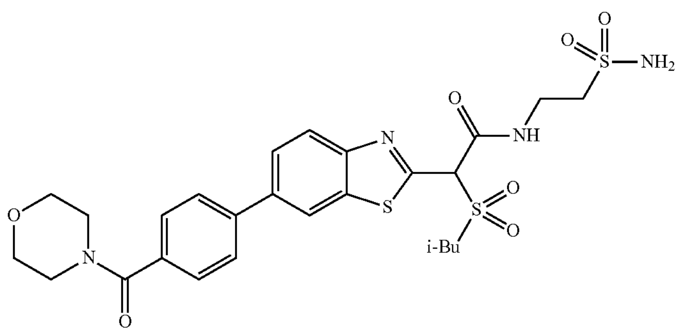 | 2-(isobutylsulfonyl)-2-(6-(4-(4-morpholinylcarbonyl)phenyl)-1,3-benzothiazol-2-yl)-N-(2-sulfamoylethyl)acetamide | δ 9.08-8.94 (m, 1H), 8.59-8.51 (m, 1H), 8.24-8.13 (m, 1H), 7.95-7.88 (m, 1H), 7.88-7.80 (m, 2H), 7.63-7.48 (m, 2H), 7.02-6.88 (m, 2H), 6.15-5.99 (m, 1H), 3.76-3.50 (m, 8H), 3.28-3.13 (m, 4H), 2.30-2.18 (m, 1H), 1.09-0.98 (m, 6H) | 0.82 M 608.8 | <10 | 191 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B110 | 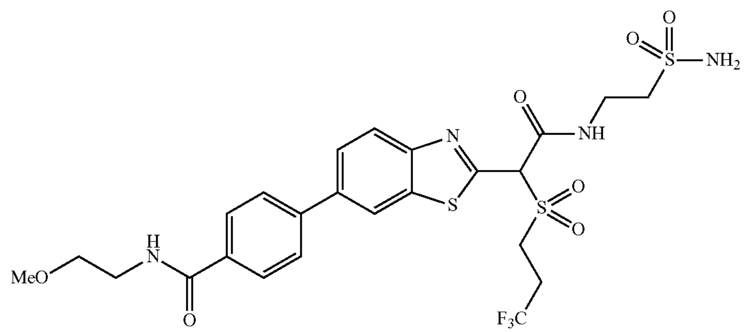 [SMILES: COCCNC(=O)c1ccc(-c2ccc3nc(C(C(=O)NCCS(N)(=O)=O)S(=O)(=O)CCC(F)(F)F)sc3c2)cc1] | N-(2-methoxyethyl)-4-(2-(2-oxo-2-((2-sulfamoyl-ethyl)amino)-1-((3,3,3-trifluoropropyl)sulfonyl)eth-yl)-1,3-benzothiazol-6-yl)benzamide | ¹H NMR (400 MHz, DMSO-d₆) δ 9.05-8.88 (m, 1H), 8.63-8.56 (m, 2H), 8.20-8.13 (m, 1H), 8.03-7.97 (m, 2H), 7.97-7.92 (m, 1H), 7.90-7.85 (m, 2H), 7.84-7.72 (m, 1H), 7.04-6.92 (m, 2H), 6.32-6.24 (m, 1H), 3.84-3.56 (m, 4H), 3.52-3.40 (m, 4H), 3.29-3.27 (m, 3H), 3.22-3.12 (m, 2H), 2.92-2.77 (m, 2H) | 0.85 M 636.9 | <10 | 180 |
| B111 | 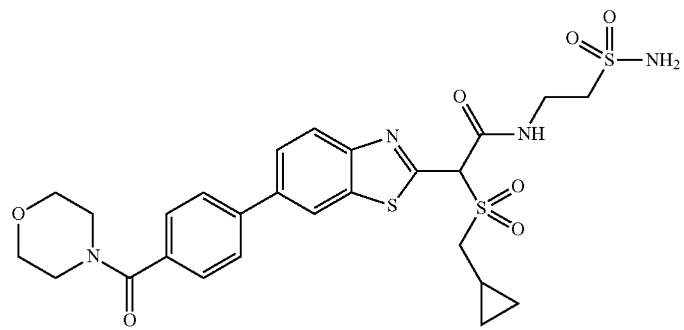 [SMILES: NS(=O)(=O)CCNC(=O)C(c1nc2ccc(-c3ccc(C(=O)N4CCOCC4)cc3)cc2s1)S(=O)(=O)CC1CC1] | 2-((cyclopropylmethyl)sul-fonyl)-2-(6-(4-(4-morpholinylcarbonyl)phen-yl)-1,3-benzothiazol-2-yl)-N-(2-sulfamoylethyl)a-cetamide | δ 9.14-8.92 (m, 1H), 8.52 (br. s., 1H), 8.30-8.10 (m, 1H), 8.01-7.81 (m, 4H), 7.80-7.66 (m, 1H), 7.55 (d, J = 7.7 Hz, 2H), 6.94 (br. s., 2H), 3.59-3.62 (m, 10H), 3.28 (br.s., 2H), 3.19 (br.s., 2H), 1.21-0.93 (m, 1H), 0.63 (d, J = 7.2 Hz, 1H), 0.55-0.34 (m, 2H), 0.31-0.20 (m, 1H) | 1.64 N 607.1 | <10 | 1460 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B112 | 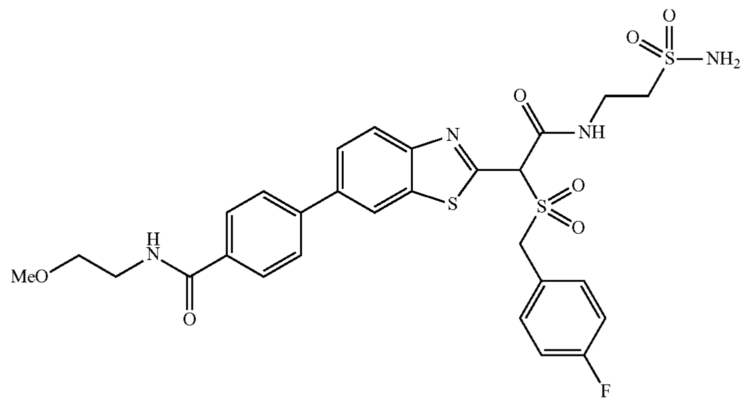 [SMILES: COCCNC(=O)c1ccc(-c2ccc3nc(C(C(=O)NCCS(N)(=O)=O)S(=O)(=O)Cc4ccc(F)cc4)sc3c2)cc1] | 4-(2-(1-((4-fluorobenzyl)sulfonyl)-2-oxo-2-((2-sulfamoylethyl)amino)ethyl)-1,3-benzothiazol-6-yl)-N-(2-methoxyethyl)benzamide | δ 9.09-8.96 (m, 1H), 8.66-8.49 (m, 1H), 8.27-8.12 (m, 1H), 7.95 (d, J = 5.2 Hz, 3H), 7.89 (br. s., 3H), 7.53-7.43 (m, 1H), 7.42-7.33 (m, 1H), 7.28-7.19 (m, 1H), 7.17-7.05 (m, 1H), 6.95 (br. s., 2H), 6.14-6.04 (m, 1H), 4.83-4.71 (m, 1H), 4.68-4.53 (m, 1H), 3.71-3.58 (m, 2H), 3.47 (br. s., 4H), 3.28 (br. s., 3H), 3.24-3.12 (m, 2H) | 1.58 N 649.1 | <10 | 8333 |
| B113 | 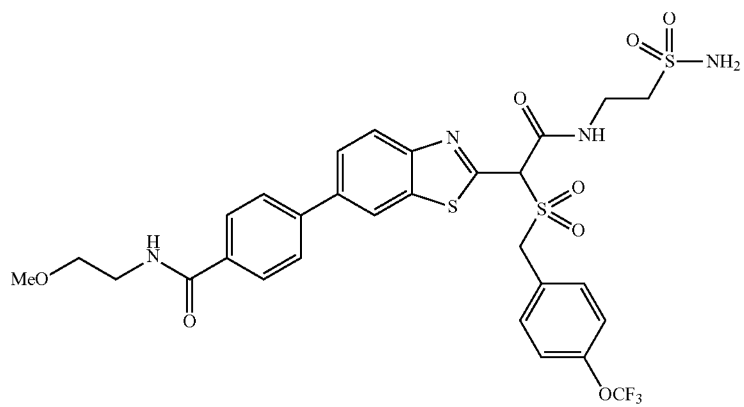 | N-(2-methoxyethyl)-4-(2-(2-oxo-2-((2-sulfamoylethyl)amino)-1-((4-(trifluoromethoxy)benzyl)sulfonyl)ethyl)-1,3-benzothiazol-6-yl)benzamide | δ 9.05 (t, J = 5.6 Hz, 1H), 8.77-8.46 (m, 2H), 8.29-8.10 (m, 1H), 8.07-7.84 (m, 4H), 7.87-7.65 (m, 2H), 7.59-7.36 (m, 3H), 7.32-7.20 (m, 1H), 7.10-6.87 (m, 2H), 6.11 (s, 1H), 4.89-4.74 (m, 1H), 4.75-4.58 (m, 1H), 3.72-3.54 (m, 2H), 3.54-3.41 (m, 5H), 3.28 (d, J = 2.5 Hz, 3H), 3.25-3.11 (m, 2H) | 1.69 N 715.1 | 0.7 | 48.2 |

-continued

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B114 | 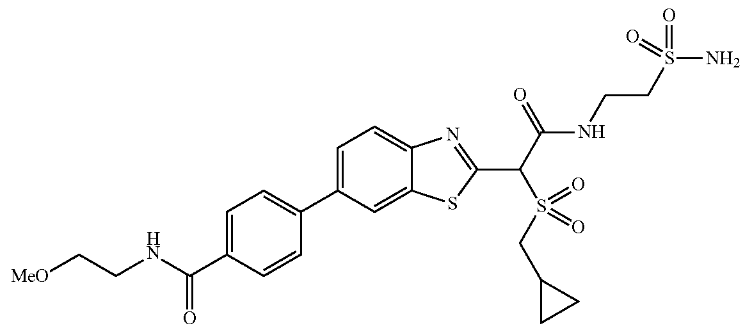 [SMILES: COCCNC(=O)c1ccc(-c2ccc3nc(C(C(=O)NCCS(N)(=O)=O)S(=O)(=O)CC4CC4)sc3c2)cc1] | 4-(2-(1-((cyclopropylmethyl)sulfonyl)-2-oxo-2-((2-sulfamoylethyl)amino)ethyl)-1,3-benzothiazol-6-yl)-N-(2-methoxyethyl)benzamide | δ 8.82 (t, J = 5.5 Hz, 1H), 8.50-8.21 (m, 2H), 7.84-7.60 (m, 7H), 6.85-6.62 (m, 3H), 3.37 (q, J = 6.9 Hz, 2H), 3.29-3.17 (m, 5H), 3.08 (s, 3H), 3.00-2.87 (m, 3H), 0.47-0.31 (m, 2H), 0.34-0.10 (m, 3H) | 1.35 N 593.12 | 0.8 | 119 |
| B115 | 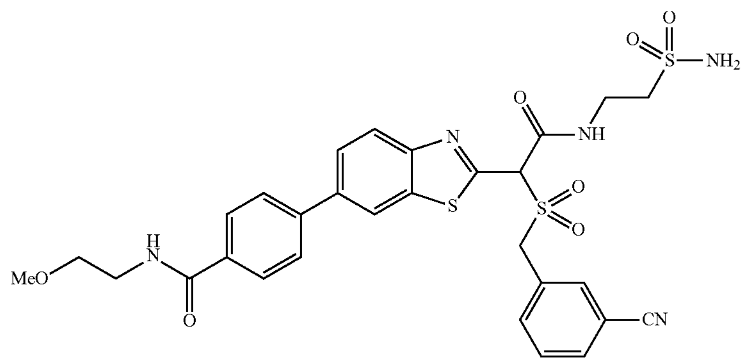 [SMILES: COCCNC(=O)c1ccc(-c2ccc3nc(C(C(=O)NCCS(N)(=O)=O)S(=O)(=O)Cc4cccc(C#N)c4)sc3c2)cc1] | 2-((3-cyanobenzyl)sulfonyl)-2-(6-phenyl-1,3-benzothiazol-2-yl)-N-(2-sulfamoylethyl)acetamide | δ 9.05 (t, J = 5.5 Hz, 1H), 8.48 (m, 1H), 8.20 (d, J = 8.5 Hz, 1H), 8.07-7.35 (m, 10H), 7.08-6.90 (m, 2H), 4.86 (s, 1H), 4.79-4.59 (m, 1H), 3.60 (d, J = 6.1 Hz, 2H), 3.52-3.42 (m, 4H), 3.28 (s, 3H), 3.19 (t, J = 7.0 Hz, 2H) | 1.41 N 656.1 | 1.2 | 107 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B116 | 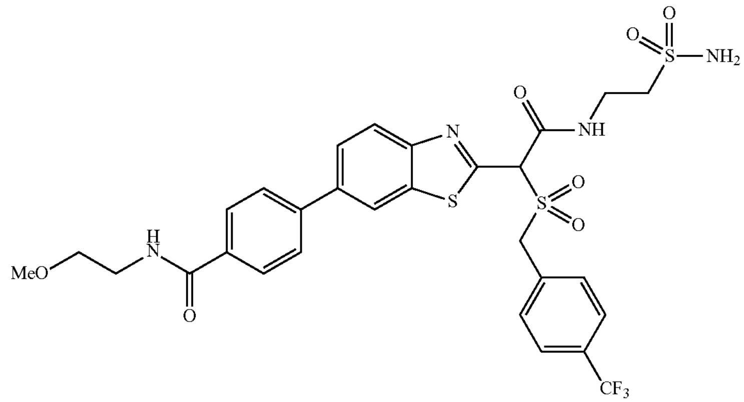 [SMILES: COCCNC(=O)c1ccc(-c2ccc3nc(C(C(=O)NCCS(N)(=O)=O)S(=O)(=O)Cc4ccc(C(F)(F)F)cc4)sc3c2)cc1] | N-(2-methoxyethyl)-4-(2-(2-oxo-2-((2-sulfamoylethyl)amino)-1-((4-(trifluoromethyl)benzyl)sulfonyl)ethyl)amino)-1,3-benzothiazol-6-yl)benzamide | δ 9.06 (t, J = 5.2 Hz, 1H), 8.69-8.49 (m, 1H), 8.25-8.13 (m, 1H), 8.05-7.86 (m, 5H), 7.82-7.70 (m, 3H), 7.70-7.50 (m, 4H), 7.05-6.91 (m, 2H), 6.12 (s, 1H), 4.89 (d, J = 3.0 Hz, 1H), 4.81-4.68 (m, 1H), 3.61 (d, J = 6.3 Hz, 2H), 3.52-3.42 (m, 4H), 3.28 (s, 3H), 3.26-3.12 (m, 2H) | 1.64 N 699.2 | <10 | 182 |
| B117 | 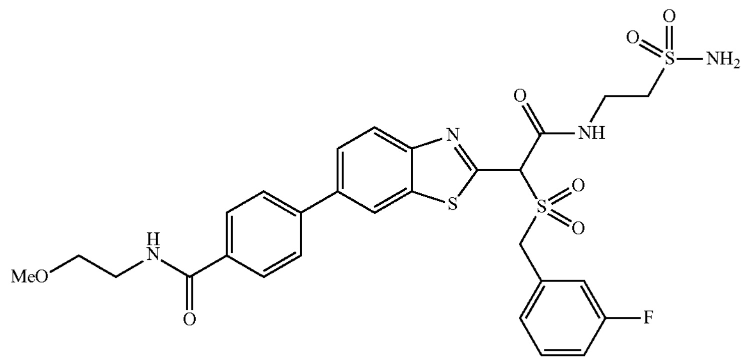 [SMILES: COCCNC(=O)c1ccc(-c2ccc3nc(C(C(=O)NCCS(N)(=O)=O)S(=O)(=O)Cc4cccc(F)c4)sc3c2)cc1] | 4-(2-(1-((3-fluorobenzyl)sulfonyl)-2-oxo-2-((2-sulfamoylethyl)amino)ethyl)-1,3-benzothiazol-6-yl)-N-(2-methoxyethyl)benzamide | δ 9.06 (br. s., 1H), 8.68-8.55 (m, 2H), 8.26-8.15 (m, 1H), 8.04-7.86 (m, 4H), 7.85-7.72 (m, 2H), 7.45 (d, J = 7.2 Hz, 1H), 7.37-7.17 (m, 3H), 7.04-6.91 (m, 2H), 6.10 (s, 1H), 4.79 (d, J = 3.9 Hz, 1H), 4.71-4.55 (m, 1H), 3.60 (d, J = 6.1 Hz, 2H), 3.51-3.41 (m, 4H), 3.28 (s, 3H), 3.25-3.08 (m, 2H) | 1.50 N 649.1 | <10 | 176 |

| Ex # | Structure | Name | $^1$H NMR (500 MHz, DMSO-d$_6$, unless indicated otherwise) | LC/MS RT (min) Method M + H | EL IC$_{50}$ (nM) | HL IC$_{50}$ (nM) |
|---|---|---|---|---|---|---|
| B118 | 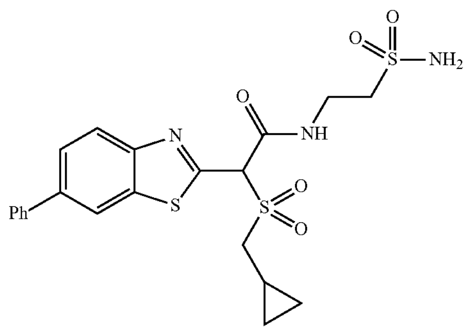 [SMILES: NS(=O)(=O)CCNC(=O)C(c1nc2ccc(-c3ccccc3)cc2s1)S(=O)(=O)CC1CC1] | 2-((cyclopropylmethyl)sulfonyl)-2-(6-phenyl-1,3-benzothiazol-2-yl)-N-(2-sulfamoylethyl)acetamide | δ 9.04 (br. s., 1H), 8.47 (s, 1H), 8.14 (d, J = 8.8 Hz, 1H), 7.86 (d, J = 8.5 Hz, 1H), 7.76 (d, J = 7.4 Hz, 1H), 7.68 (br. s., 1H), 7.58-7.35 (m, 3H), 7.03-6.81 (m, 2H), 6.05 (s, 1H), 3.59 (br. s., 2H), 3.39 (d, J = 6.9 Hz, 1H), 3.30-3.22 (m, 1H), 3.22-3.13 (m, 2H), 1.10 (br. s., 1H), 0.62 (d, J = 7.7 Hz, 1H), 0.53-0.36 (m, 2H), 0.26 (br. s., 1H) | 1.78 N 494.09 | <10 | 10 |
| B119 | 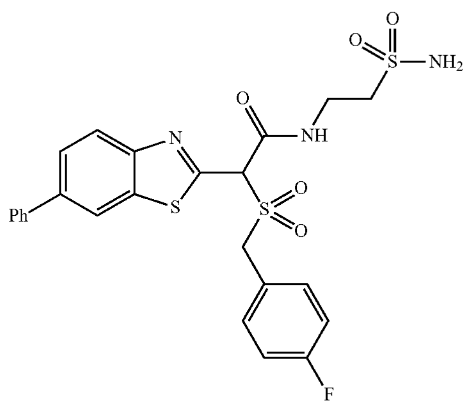 [SMILES: NS(=O)(=O)CCNC(=O)C(c1nc2ccc(-c3ccccc3)cc2s1)S(=O)(=O)Cc1ccc(F)cc1] | 2-((4-fluorobenzyl)sulfonyl)-2-(6-phenyl-1,3-benzothiazol-2-yl)-N-(2-sulfamoylethyl)acetamide | δ 9.04 (br. s., 1H), 8.49 (s, 1H), 8.18 (d, J = 8.5 Hz, 1H), 7.88 (d, J = 8.3 Hz, 1H), 7.77 (d, J = 7.2 Hz, 1H), 7.68 (br. s., 1H), 7.59-7.32 (m, 5H), 7.24 (t, J = 8.3 Hz, 1H), 7.10 (br. s., 1H), 7.05-6.88 (m, 2H), 6.06 (s, 1H), 4.75 (d, J = 5.8 Hz, 1H), 4.69-4.50 (m, 1H), 3.60 (d, J = 6.1 Hz, 2H), 3.26-3.09 (m, 2H) | 1.96 N 548.1 | <10 | 11 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B120 | 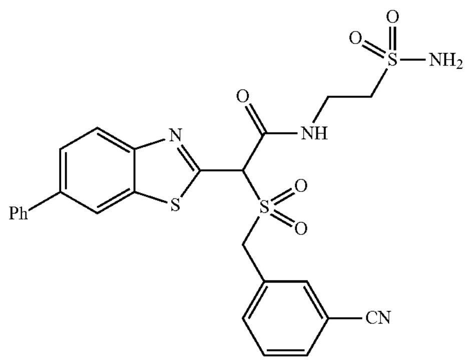 [SMILES: N#Cc1cccc(CS(=O)(=O)C(C(=O)NCCS(N)(=O)=O)c2nc3ccc(-c4ccccc4)cc3s2)c1] | 2-((3-cyanobenzyl)sulfonyl)-2-(6-phenyl-1,3-benzothiazol-2-yl)-N-(2-sulfamoylethyl)acetamide | δ 9.04 (br. s., 1H), 8.49 (s, 1H), 8.23-8.06 (m, 1H), 7.98-7.58 (m, 7H), 7.56-7.31 (m, 3H), 7.12-6.86 (m, 2H), 6.10 (s, 1H), 4.86 (br. s., 1H), 4.77-4.57 (m, 1H), 3.61 (br. s., 2H), 3.19 (t, J = 6.2 Hz, 2H) | 1.87 N 555.1 | <10 | 15 |
| B121 | 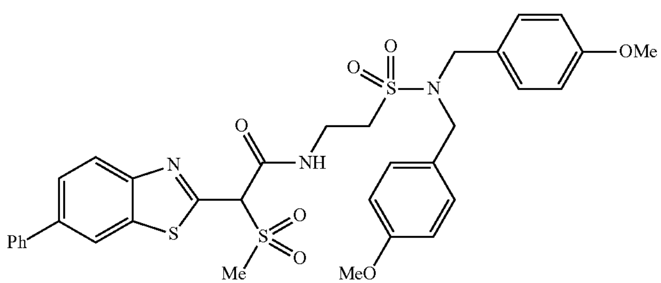 [SMILES: COc1ccc(CN(Cc2ccc(OC)cc2)S(=O)(=O)CCNC(=O)C(c2nc3ccc(-c4ccccc4)cc3s2)S(C)(=O)=O)cc1] | N-(2-(bis(4-methoxybenzyl)sulfamoyl)ethyl)-2-(methylsulfonyl)-2-(6-phenyl-1,3-benzothiazol-2-yl)acetamide | δ 9.04 (t, J = 5.8 Hz, 1H), 8.48 (d, J = 1.4 Hz, 1H), 8.16 (s, 1H), 7.94-7.84 (m, 1H), 7.77 (d, J = 7.4 Hz, 2H), 7.53 (t, J = 7.7 Hz, 2H), 7.46-7.39 (m, 1H), 7.13 (d, J = 8.5 Hz, 4H), 6.88-6.80 (m, 4H), 6.07 (s, 1H), 4.19 (s, 4H), 3.71 (s, 6H), 3.67-3.60 (m, 2H), 3.58 (s, 3H), 3.26 (s, 3H) | 1.15 M 694.0 | 80 | 11 |
| B122 | 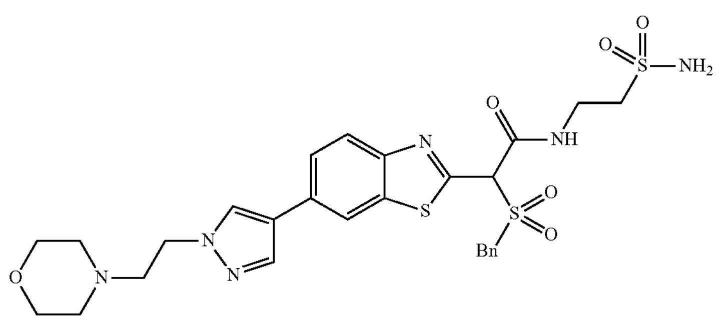 | 2-(benzylsulfonyl)-2-(6-{1-[2-(4-morpholinyl)ethyl]-1H-pyrazol-4-yl}-1,3-benzothiazol-2-yl)-N-(2-sulfamoylethyl)acetamide | δ 9.02 (s, 1H), 8.44-8.34 (m, 1H), 8.12 (d, J = 8.5 Hz, 1H), 7.96 (s, 1H), 7.82 (dd, J = 8.5, 1.7 Hz, 1H), 7.40 (m, 3H), 7.33 (s, 2H), 6.96 (s, 2H), 6.07 (s, 1H), 5.76 (s, 1H), 4.85-4.67 (m, 2H), 4.66-4.41 (m, 2H), 3.61 (dd, J = 13.1, 7.0 Hz, 8H), 3.23-3.01 (m, 6H) | 0.69 M 632.9 | 44 | 631 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B123 | 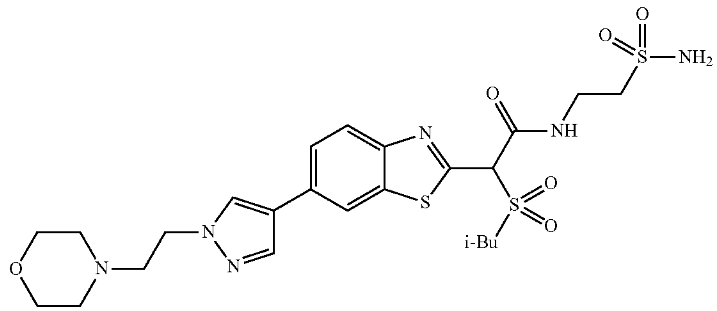 [SMILES: NS(=O)(=O)CCNC(=O)C(c1nc2ccc(-c3cnn(CCN4CCOCC4)c3)cc2s1)S(=O)(=O)Cc1ccccc1] | 2-(isobutylsulfonyl)-2-(6-{1-[2-(4-morpholinyl)ethyl]-1H-pyrazol-4-yl}-1,3-benzothiazol-2-yl)-N-(2-sulfamoylethyl)acetamide | δ 8.99 (t, J = 5.8 Hz, 1H), 8.42-8.32 (m, 2H), 8.11 (br. s., 1H), 8.08 (d, J = 8.5 Hz, 1H), 7.80 (dd, J = 8.4, 1.5 Hz, 1H), 6.96 (s, 2H), 6.00 (s, 1H), 4.58 (br. s., 2H), 4.00 (br. s., 2H), 3.67 (br. s., 4H), 3.64-3.57 (m, 3H), 3.28-3.21 (m, 2H), 3.21-3.15 (m, 3H), 2.28-2.19 (m, 1H), 1.07-0.96 (m, 6H) | 0.67 M 599.0 | 18 | 400 |
| B124 | 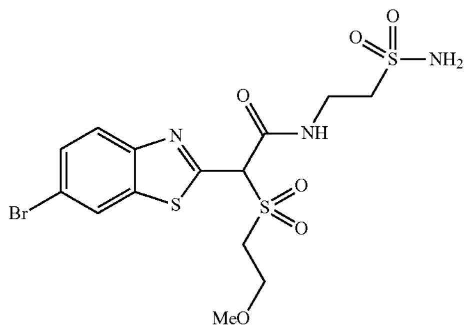 | 2-(6-bromo-1,3-benzothiazol-2-yl)-2-((2-methoxyethyl)sulfonyl)-N-(2-sulfamoylethyl)acetamide | δ 8.86 (t, J = 5.5 Hz, 1H), 8.40 (d, J = 1.9 Hz, 1H), 7.95 (d, J = 8.8 Hz, 1H), 7.65 (dd, J = 8.8, 1.9 Hz, 1H), 6.88 (s, 2H), 5.94 (s, 1H), 3.72-3.62 (m, 3H), 3.62-3.54 (m, 2H), 3.54-3.48 (m, 2H), 3.19 (s, 3H), 3.14-3.07 (m, 2H) | 0.83 M 499.7 | 26 | 830 |
| B125 | 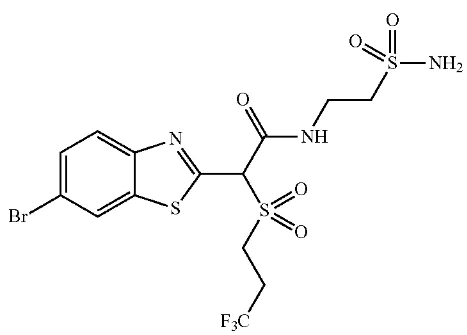 | 2-(6-bromo-1,3-benzothiazol-2-yl)-N-(2-sulfamoylethyl)-2-((3,3,3-trifluoropropyl)sulfonyl)acetamide | δ 8.94 (s, 1H), 8.50 (d, J = 1.9 Hz, 1H), 8.03 (d, J = 8.8 Hz, 1H), 7.76-7.69 (m, 1H), 6.95 (s, 2H), 6.24 (s, 1H), 3.72 (dd, J = 16.6, 8.1 Hz, 2H), 3.61 (dt, J = 12.6, 6.5 Hz, 3H), 3.21-3.14 (m, 2H), 2.85 (dd, J = 10.6, 7.8 Hz, 2H) | 0.95 M 537.5 | 99 | 300 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B126 | 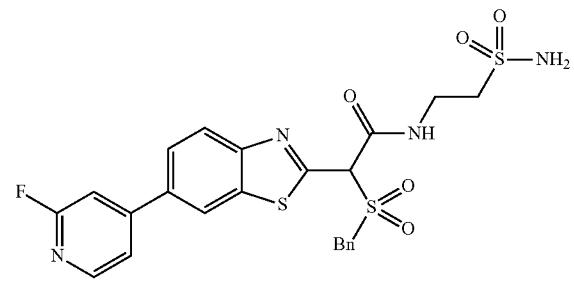 | 2-(benzylsulfonyl)-2-(6-(2-fluoro-4-pyridinyl)-1,3-benzothiazol-2-yl)-N-(2-sulfamoylethyl)acetamide | ¹H NMR (500 MHz, ACETONITRILE-d₃) δ 8.41-8.22 (m, 1H), 8.05 (dd, J = 3.7, 1.8 Hz, 1H), 8.00-7.90 (m, 1H), 7.89-7.76 (m, 1H), 7.75-7.61 (m, 1H), 7.61-7.51 (m, 1H), 7.51-7.43 (m, 1H), 7.43-7.38 (m, 2H), 7.35-7.29 (m, 2H), 7.27 (t, J = 7.7 Hz, 1H), 5.58-5.42 (m, 2H), 4.55 (s, 1H), 4.49 (s, 1H), 3.84-3.74 (m, 1H), 3.71 (d, J = 6.1 Hz, 1H), 3.41-3.17 (m, 2H) | 0.90 M 548.8 | <10 | 51 |
| B127 | 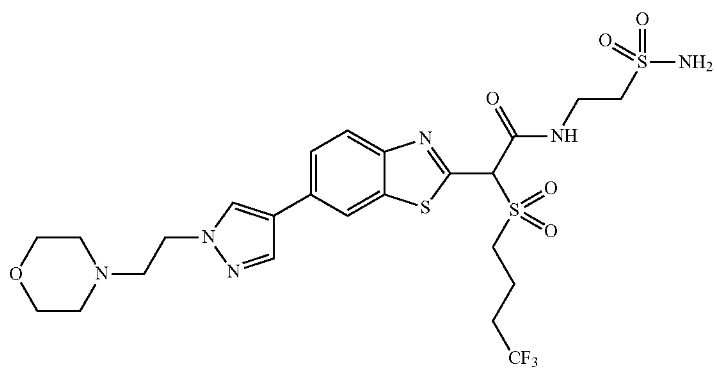 [SMILES: NS(=O)(=O)CCNC(=O)C(c1nc2ccc(-c3cnn(CCN4CCOCC4)c3)cc2s1)S(=O)(=O)CCCC(F)(F)F] | 2-(6-(1-(2-(4-morpholinyl)ethyl)-1H-pyrazol-4-yl)-1,3-benzothiazol-2-yl)-N-(2-sulfamoylethyl)-2-((4,4,4-trifluorobutyl)sulfonyl)acetamide | δ 9.01 (t, J = 5.8 Hz, 1H), 8.43-8.33 (m, 2H), 8.12 (br. s., 1H), 8.07 (d, J = 8.5 Hz, 1H), 7.81 (dd, J = 8.7, 1.8 Hz, 1H), 7.01-6.90 (m, 2H), 6.10 (s, 1H), 3.71-3.57 (m, 6H), 3.56-3.46 (m, 6H), 3.19 (dq, J = 9.4, 7.1 Hz, 5H), 2.00-1.90 (m, 3H) | 0.71 M 652.8 | <10 | 933 |
| B128 | 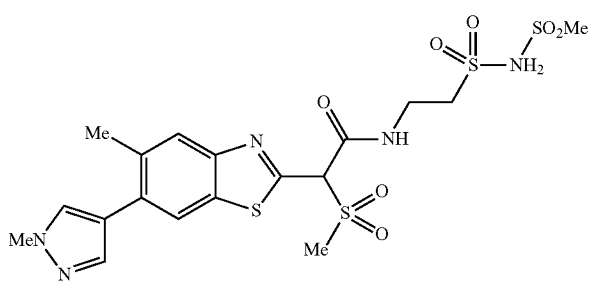 [SMILES: Cc1cc2nc(C(C(=O)NCCS(=O)(=O)NS(C)(=O)=O)S(C)(=O)=O)sc2cc1-c1cnn(C)c1] | 2-(5-methyl-6-(1-methyl-1H-pyrazol-4-yl)-1,3-benzothiazol-2-yl)-N-(2-(methylsulfonyl)ethyl)-2-((methylsulfonyl)sulfamoyl)ethyl)acetamide | ¹H NMR (500 MHz, METHANOL-d₄) d 7.99 (s, 1H), 7.96 (s, 1H), 7.90 (s, 1H), 7.76 (d, J = 0.55 Hz, 1H), 5.49 (s, 1H), 3.95-4.01 (m, 3H), 3.80 (d, J = 2.48 Hz, 1H), 3.57 (d, J = 7.15 Hz, 1H), 3.19-3.25 (m, 3H), 3.16 (s, 2H), 2.44-2.57 (m, 3H) | 0.64 M 571.9 | 28 | 290 |

-continued

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B129 | 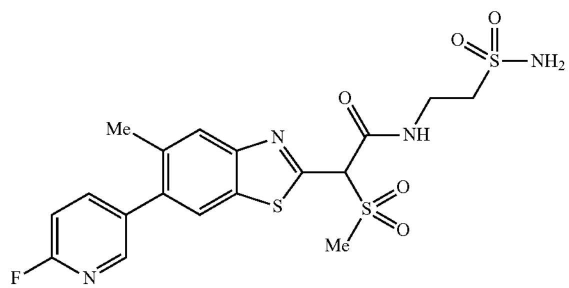 | 2-(6-(6-fluoro-3-pyridinyl)-5-methyl-1,3-benzothiazol-2-yl)-2-methyl-N-(2-sulfamoyl-ethyl)acetamide | ¹H NMR (500 MHz, METHANOL-d₄) δ 8.31 (d, J = 2.48 Hz, 1H), 8.06-8.11 (m, 2H), 8.03 (s, 1H), 7.26 (dd, J = 2.61, 8.39 Hz, 1H), 4.62-4.62 (m, 1H), 3.78-3.83 (m, 2H), 3.37 (dt, J = 2.89, 6.81 Hz, 3H), 3.29 (s, 3H), 3.16-3.22 (m, 1H), 2.46 (s, 3H) | 0.80 M 486.7 | <10 | <10 |
| B130 | 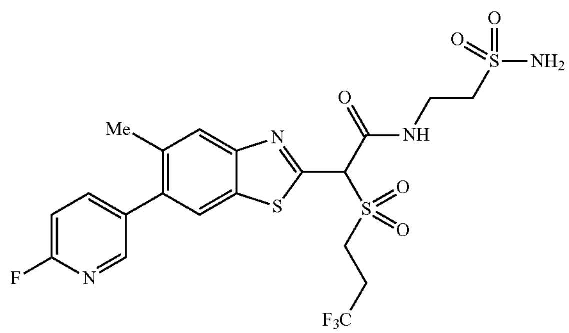 [SMILES: Cc1cc2nc(C(C(=O)NCCS(N)(=O)=O)S(=O)(=O)CCC(F)(F)F)sc2cc1-c1ccc(F)nc1] | 2-(6-(6-fluoro-3-pyridinyl)-5-methyl-1,3-benzothiazol-2-yl)-2-(3,3,3-trifluoropropyl-sulfonyl)-N-(2-sulfamoylethyl)acetamide | ¹H NMR (500 MHz, Acetone) δ 8.19-8.29 (m, 1H), 7.96-8.06 (m, 2H), 7.65-7.75 (m, 1H), 7.14-7.23 (m, 1H), 6.28 (d, J = 3.58 Hz, 2H), 3.77-3.91 (m, 3H), 3.49-3.57 (m, 1H), 3.31-3.40 (m, 2H), 2.76 (td, J = 11.24, 16.30 Hz, 2H), 2.31-2.42 (m, 3H) | 1.87 B 569.1 | <10 | 13 |
| B131 | 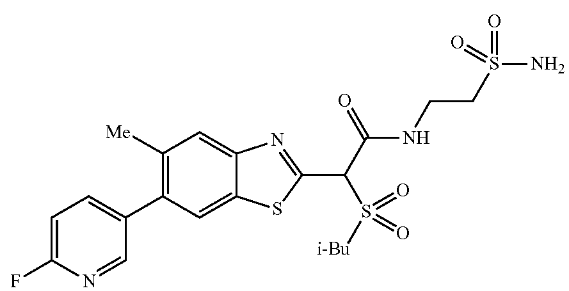 | 2-(6-(6-fluoro-3-pyridinyl)-5-methyl-1,3-benzothiazol-2-yl)-2-(isobutylsulfonyl)-N-(2-sulfamoylethyl)acetamide | ¹H NMR (500 MHz, Acetone) δ 8.20-8.30 (m, 1H), 7.96-8.09 (m, 2H), 7.63-7.78 (m, 1H), 7.15-7.27 (m, 1H), 6.20-6.32 (m, 1H), 3.49-3.94 (m, 2H), 3.31-3.40 (m, 2H), 3.15-3.29 (m, 2H), 2.31-2.43 (m, 3H), 2.27 (td, J = 6.33, 12.65 Hz, 1H), 1.04-1.12 (m, 6H) | 0.93 M 528.9 | <10 | 12 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B132 | 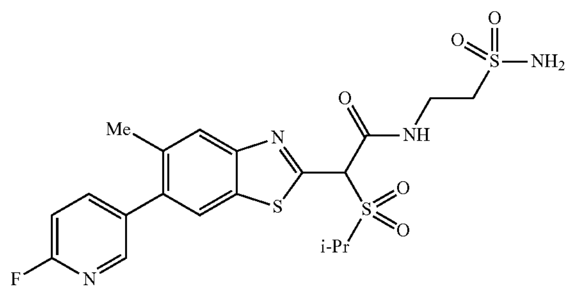 [SMILES: Cc1cc2nc(C(C(=O)NCCS(N)(=O)=O)S(=O)(=O)C(C)C)sc2cc1-c1ccc(F)nc1] | 2-(6-(6-fluoro-3-pyridinyl)-5-methyl-1,3-benzothiazol-2-yl)-2-(isopropyl)sulfonyl)-N-(2-sulfamoylethyl)acetamide | ¹H NMR (500 MHz, Acetone) δ 8.20-8.30 (m, 1H), 7.96-8.03 (m, 1H), 7.51-7.65 (m, 2H), 7.14-7.25 (m, 1H), 6.27 (d, J = 6.60 Hz, 1H), 3.80-3.91 (m, 1H), 3.45-3.59 (m, 1H), 3.34 (td, J = 6.36, 19.46 Hz, 2H), 2.30-2.42 (m, 3H), 1.83-1.93 (m, 1H), 1.27-1.47 (m, 6H) | 0.90 M 515.1 | <10 | 411 |
| B133 | 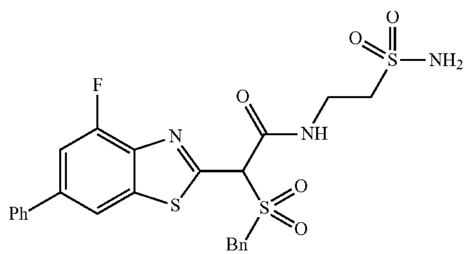 [SMILES: NS(=O)(=O)CCNC(=O)C(c1nc2c(F)cc(-c3ccccc3)cc2s1)S(=O)(=O)Cc1ccccc1] | 2-(benzylsulfonyl)-2-(4-fluoro-6-phenyl-1,3-benzothiazol-2-yl)-N-(2-sulfamoylethyl)acetamide | ¹H NMR (400 MHz, Acetone) δ 8.27 (d, J = 1.54 Hz, 1H), 7.78-7.84 (m, 1H), 7.72 (d, J = 8.14 Hz, 1H), 7.67 (dd, J = 1.65, 11.99 Hz, 1H), 7.47-7.58 (m, 4H), 7.38-7.47 (m, 3H), 7.21-7.33 (m, 1H), 4.80 (d, J = 5.72 Hz, 1H), 3.75-3.91 (m, 1H), 3.29-3.41 (m, 2H), 2.92 (br. s., 3H) | 0.95 M 548.0 | <10 | 22 |
| B134 | 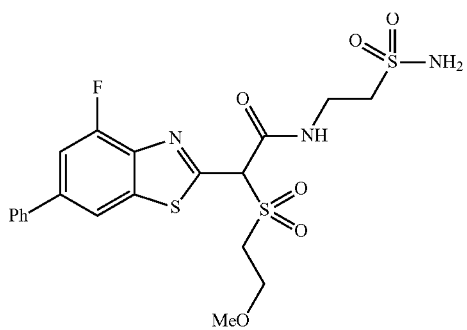 | 2-(4-fluoro-6-phenyl-1,3-benzothiazol-2-yl)-2-((2-methoxyethyl)sulfonyl)-N-(2-sulfamoylethyl)acetamide | ¹H NMR (400 MHz, Acetone) δ 8.26 (d, J = 1.54 Hz, 1H), 7.79-7.83 (m, 2H), 7.66 (dd, J = 1.65, 11.99 Hz, 1H), 7.51-7.56 (m, 2H), 7.42-7.48 (m, 1H), 6.29 (d, J = 3.74 Hz, 1H), 3.82-3.97 (m, 5H), 3.71-3.78 (m, 2H), 3.42 (s, 3H), 3.37-3.41 (m, 2H) | 0.86 M 516.0 | <10 | 18 |

| Ex # | Structure | Name | $^1$H NMR (500 MHz, DMSO-$d_6$, unless indicated otherwise) | LC/MS RT (min) Method M+H | EL IC$_{50}$ (nM) | HL IC$_{50}$ (nM) |
|---|---|---|---|---|---|---|
| B135 | 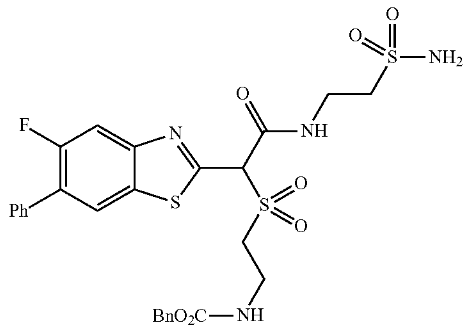 | benzyl (2-((1-(5-fluoro-6-phenyl-1,3-benzothiazol-2-yl)-2-oxo-2-((2-sulfamoyl-ethyl)amino)ethyl)sulfonyl)ethyl)carbamate | $^1$H NMR (500 MHz, METHANOL-$d_4$) δ 8.13 (dd, J = 13.3, 7.3 Hz, 1H), 7.92-7.76 (m, 1H), 7.65-7.57 (m, 2H), 7.54-7.37 (m, 5H), 7.37-7.27 (m, 4H), 5.12-5.04 (m, 2H), 3.84-3.73 (m, 2H), 3.65 (s, 3H), 3.58-3.51 (m, 1H), 3.45 (t, J = 1.7 Hz, 1H), 3.20-3.15 (m, 1H) | 0.95 M 634.4 | <10 | 56 |
| B136 | 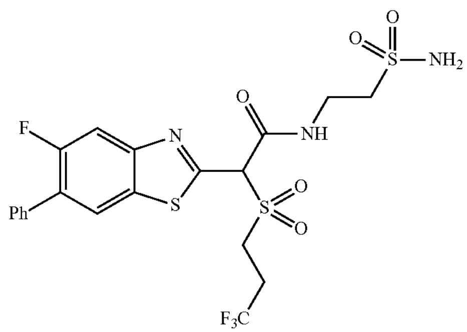 [SMILES: NS(=O)(=O)CCNC(=O)C(c1nc2cc(F)c(-c3ccccc3)cc2s1)S(=O)(=O)CCC(F)(F)F] | 2-(5-fluoro-6-phenyl-1,3-benzothiazol-2-yl)-N-(2-sulfamoylethyl)-2-[(3,3,3-trifluoropropyl)sulfonyl]acetamide | $^1$H NMR (400 MHz, Chloroform-d containing Methanol-$d_4$) δ 8.00 (br. s., 1H), 7.85-7.64 (m, 4H), 7.55 (d, J = 8.1 Hz, 2H), 3.96-3.85 (m, 5H), 3.84-3.73 (m, 5H), 3.72-3.64 (m, 3H), 3.61 (t, J = 8.1 Hz, 3H), 3.58-3.49 (m, 2H), 3.41-3.35 (m, 4H), 3.35-3.25 (m, 2H). | 2.12 Q 554.0 | <10 | 11 |
| B137 | 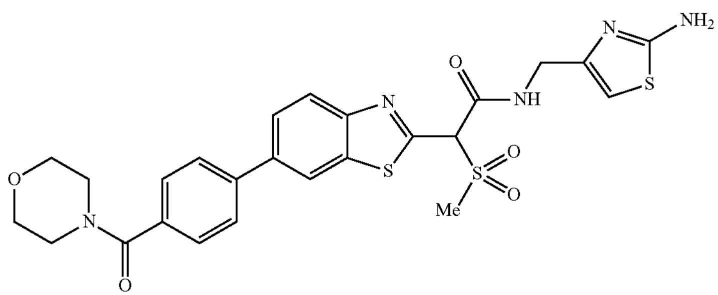 [SMILES: CS(=O)(=O)C(C(=O)NCc1csc(N)n1)c1nc2ccc(-c3ccc(C(=O)N4CCOCC4)cc3)cc2s1] | N-((2-amino-1,3-thiazol-4-yl)methyl)-2-(methylsulfonyl)-2-(6-(4-(4-morpholinylcarbonyl)phenyl)-1,3-benzothiazol-2-yl)acetamide | δ 9.22 (t, J = 5.4 Hz, 1H), 8.55 (d, J = 1.7 Hz, 1H), 8.19 (d, J = 8.5 Hz, 1H), 7.97 (s, 1H), 7.93 (dd, J = 8.7, 1.8 Hz, 2H), 7.86 (d, J = 8.3 Hz, 2H), 7.57 (d, J = 8.3 Hz, 2H), 6.52 (s, 1H), 6.09 (s, 1H), 4.36-4.21 (m, 2H), 3.26 (s, 3H) | 1.25 N 572 | <10 | 17480 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B138 | 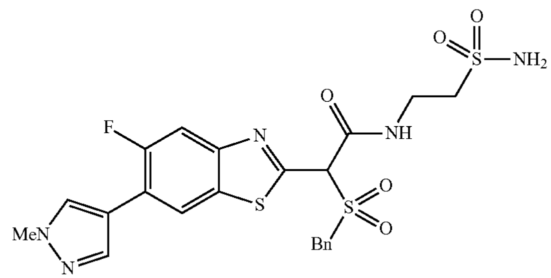 [SMILES: Cn1cc(-c2cc3sc(C(C(=O)NCCS(N)(=O)=O)S(=O)(=O)Cc4ccccc4)nc3cc2F)cn1] | 2-(benzylsulfonyl)-2-(5-fluoro-6-(1-methyl-1H-pyrazol-4-yl)-1,3-benzothiazol-2-yl)-N-(2-sulfamoylethyl)acetamide | ¹H NMR (400 MHz, METHANOL-d₄) δ 8.48-7.71 (m, 3H), 7.55-6.94 (m, 6H), 4.98-4.41 (m, 2H), 4.08-3.88 (m, 3H), 3.84-3.58 (m, 2H), 3.48-3.16 (m, 2H) | 1.79 Q 552.0 | <10 | 142 |
| B139 | 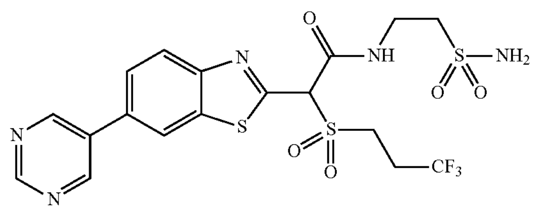 [SMILES: NS(=O)(=O)CCNC(=O)C(c1nc2ccc(-c3cncnc3)cc2s1)S(=O)(=O)CCC(F)(F)F] | 2-(6-(5-Pyrimidinyl)-1,3-benzothiazol-2-yl)-2-sulfamoylethyl)-N-(2-((3,3,3-trifluoropropyl)sulfonyl)acetamide | δ 9.31-9.23 (m, 1H), 9.22-9.15 (m, 1H), 9.04-8.94 (m, 1H), 8.72-8.64 (m, 1H), 8.27-8.21 (m, 1H), 8.08-8.00 (m, 1H), 7.04-6.93 (m, 2H), 6.34-6.25 (m, 1H), 3.83-3.59 (m, 4H), 3.25-3.16 (m, 3H), 2.89-2.82 (m, 2H). | 1.4 Q 538 | 16 | 2090 |
| B140 | 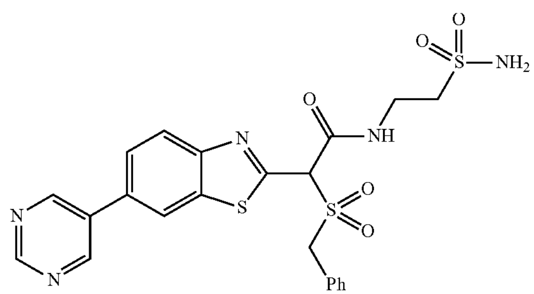 [SMILES: NS(=O)(=O)CCNC(=O)C(c1nc2ccc(-c3cncnc3)cc2s1)S(=O)(=O)Cc1ccccc1] | 2-(benzylsulfonyl)-2-(6-(5-pyrimidinyl)-1,3-benzothiazol-2-yl)-N-(2-sulfamoylethyl)acetamide | ¹H NMR (400 MHz, DMSO-d₆) δ 9.27 (s, 2H), 9.21-9.14 (m, 2H), 8.72-8.66 (m, 1H), 8.28 (d, J = 8.6 Hz, 2H), 7.41 (s, 5H), 7.08-6.97 (m, 2H), 6.14 (s, 1H), 4.84-4.68 (m, 2H), 3.65-3.56 (m, 2H), 3.28-3.04 (m, 2H) | 1.7 Q 532 | 13.7 | 8789 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B141 | 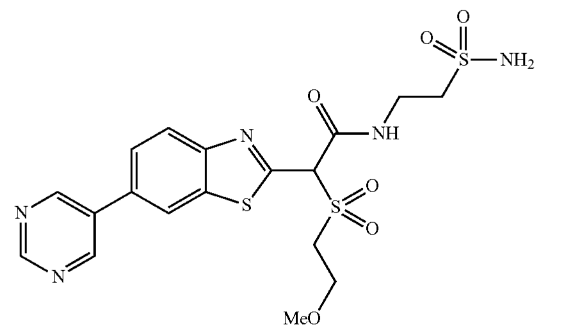 [SMILES: COCCS(=O)(=O)C(C(=O)NCCS(N)(=O)=O)c1nc2ccc(-c3cncnc3)cc2s1] | 2-((2-methoxyethyl)sulfonyl)-2-(6-(5-pyrimidinyl)-1,3-benzothiazol-2-yl)-N-(2-sulfamoylethyl)acetamide | ¹H NMR (400 MHz, DMSO-d₆) δ 9.34-9.15 (m, 4H), 9.00 (t, J = 5.5 Hz, 1H), 8.68 (d, J = 1.5 Hz, 1H), 8.25 (d, J = 8.4 Hz, 1H), 8.09-8.01 (m, 1H), 6.99 (s, 3H), 6.07 (s, 1H), 3.90-3.47 (m, 4H), 3.28 (s, 3H), 3.22-3.16 (m, 2H) | 1.4 Q 500 | 14.7 | 2211 |
| B142 | 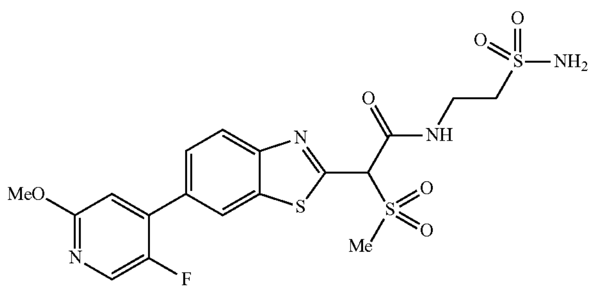 [SMILES: COc1cc(-c2ccc3nc(C(C(=O)NCCS(N)(=O)=O)S(C)(=O)=O)sc3c2)c(F)cn1] | 2-(6-(5-fluoro-2-methoxy-4-pyridinyl)-1,3-benzothiazol-2-yl)-2-(methylsulfonyl)-N-(2-sulfamoylethyl)acetamide | ¹H NMR (400 MHz, DMSO-d₆) δ 9.02 (t, J = 5.5 Hz, 1H), 8.51 (s, 1H), 8.35-8.29 (m, 1H), 8.26-8.19 (m, 1H), 7.90-7.80 (m, 1H), 7.17-7.09 (m, 1H), 7.05-6.94 (m, 2H), 6.13-5.96 (m, 1H), 3.91 (s, 3H), 3.65-3.57 (m, 2H), 3.25 (s, 3H), 3.22-3.16 (m, 2H) | 1.8 Q 503 | >10 | 77 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B143 | 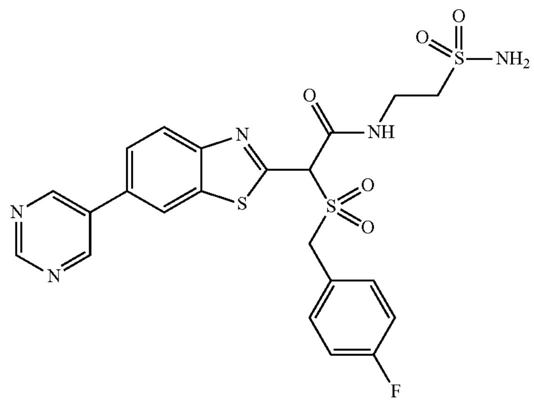 [SMILES: NS(=O)(=O)CCNC(=O)C(c1nc2ccc(-c3cncnc3)cc2s1)S(=O)(=O)Cc1ccc(F)cc1] | 2-((4-fluorobenzyl)sulfonyl)-2-(6-(5-pyrimidinyl)-1,3-benzothiazol-2-yl)-N-(2-sulfamoylethyl)acetamide | ¹H NMR (400 MHz, DMSO-d₆) δ 9.30-9.23 (m, 2H), 9.22-9.14 (m, 2H), 8.69 (d, J = 1.8 Hz, 1H), 8.28 (d, J = 8.4 Hz, 1H), 7.53-7.44 (m, 1H), 7.31-7.22 (m, 2H), 6.99 (s, 2H), 6.11 (s, 1H), 4.92-4.32 (m, 2H), 3.71-3.54 (m, 2H), 3.29-3.07 (m, 4H) | 0.9 M 550 | 18 | 4735 |
| B144 | 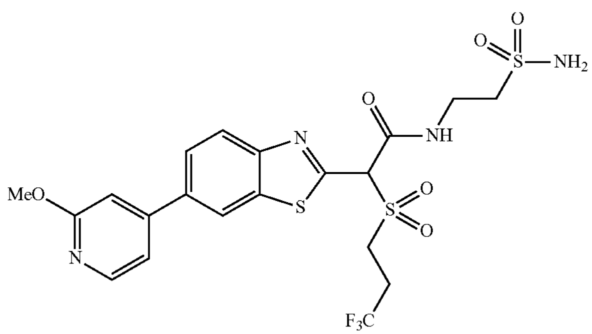 [SMILES: COc1cc(-c2ccc3nc(C(C(=O)NCCS(N)(=O)=O)S(=O)(=O)CCC(F)(F)F)sc3c2)ccn1] | 2-(6-(2-methoxy-4-pyridinyl)-1,3-benzothiazol-2-yl)-N-(2-sulfamoylethyl)-2-((3,3,3-trifluoropropyl)sulfonyl)acetamide | δ 8.97 (s, 1H), 8.67 (s, 1H), 8.29 (d, J = 5.5 Hz, 1H), 8.20 (d, J = 8.5 Hz, 1H), 8.00 (d, J = 8.5 Hz, 1H), 7.44-7.39 (m, 1H), 7.23 (s, 1H), 6.97 (s, 3H), 6.29 (s, 1H), 3.92 (s, 3H), 3.68-3.60 (m, 2H), 3.23-3.17 (m, 2H), 2.89-2.82 (m, 2H) | 1.5 O 567 | <10 | 33 |

| Ex # | Structure | Name | $^1$H NMR (500 MHz, DMSO-$d_6$, unless indicated otherwise) | LC/MS RT (min) Method M+H | EL IC$_{50}$ (nM) | HL IC$_{50}$ (nM) |
|---|---|---|---|---|---|---|
| B145 | 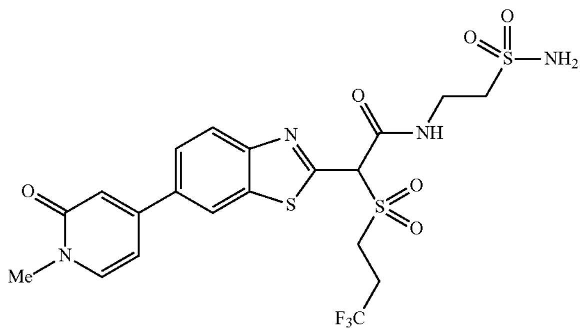 [SMILES: Cn1ccc(-c2ccc3nc(C(C(=O)NCCS(N)(=O)=O)S(=O)(=O)CCC(F)(F)F)sc3c2)cc1=O] | 2-(6-(1-methyl-2-oxo-1,2-dihydro-4-pyridinyl)-1,3-benzothiazol-2-yl)-N-(2-sulfamoylethyl)-2-((3,3,3-trifluoropropyl)sulfonyl)acetamide | δ 8.96 (t, J = 5.6 Hz, 1H), 8.61 (d, J = 1.4 Hz, 1H), 8.16 (d, J = 8.5 Hz, 1H), 7.96-7.90 (m, 1H), 7.86-7.81 (m, 1H), 7.02-6.91 (m, 2H), 6.85-6.77 (m, 1H), 6.71-6.64 (m, 1H), 6.34-6.25 (m, 1H), 3.66-3.57 (m, 2H), 3.49 (s, 3H), 3.46 (s, 2H), 3.24-3.15 (m, 2H), 2.90-2.81 (m, 2H) | 1.3 O 567 | <10 | 362 |
| B146 | 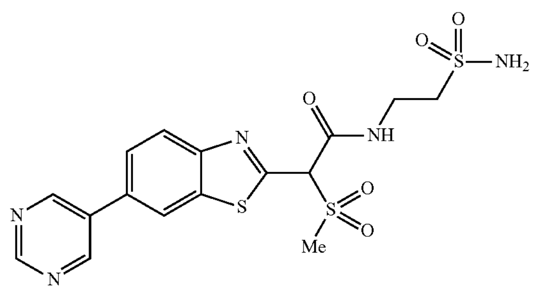 [SMILES: CS(=O)(=O)C(C(=O)NCCS(N)(=O)=O)c1nc2ccc(-c3cncnc3)cc2s1] | 2-(methylsulfonyl)-2-(6-(5-pyrimidinyl)-1,3-benzothiazol-2-yl)-N-(2-sulfamoylethyl)acetamide | $^1$H NMR (400 MHz, DMSO-$d_6$) δ 9.33-9.21 (m, 1H), 9.07-8.96 (m, 1H), 8.68 (d, J = 1.5 Hz, 1H), 8.33-8.19 (m, 1H), 8.03 (dd, J = 8.6, 1.8 Hz, 1H), 6.97 (s, 2H), 6.07 (s, 1H), 3.65-3.58 (m, 2H), 3.57-3.46 (m, 2H), 3.25 (s, 3H), 3.20 (dd, J = 8.0, 6.5 Hz, 2H) | 0.7 M 456.1 | <10 | 916 |
| B147 | 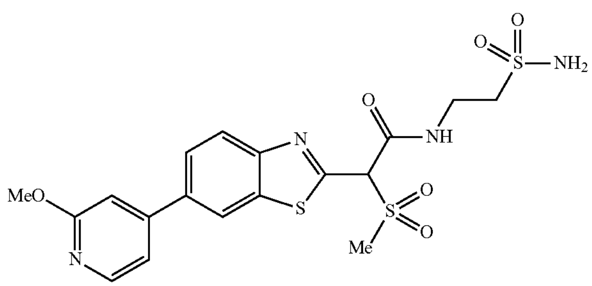 | 2-(6-(2-methoxy-4-pyridinyl)-1,3-benzothiazol-2-yl)-2-(methylsulfonyl)-N-(2-sulfamoylethyl)acetamide | $^1$H NMR (400 MHz, DMSO-$d_6$) δ 8.97 (t, J = 5.8 Hz, 1H), 8.60 (d, J = 1.5 Hz, 1H), 8.27-8.18 (m, 1H), 8.16-8.08 (m, 1H), 7.96-7.89 (m, 1H), 7.40-7.32 (m, 1H), 7.20-7.15 (m, 1H), 6.95-6.88 (m, 2H), 6.06-5.96 (m, 1H), 3.86 (s, 3H), 3.61-3.44 (m, 2H), 3.23-3.17 (m, 3H), 3.15-3.10 (m, 2H) | 0.9 M 485 | <10 | <10 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B148 | 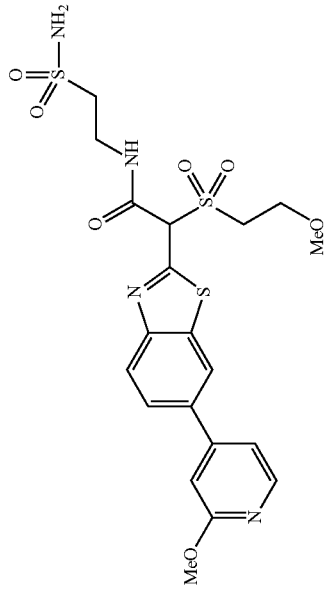 | 2-((2-methoxyethyl)sulfonyl)-2-(6-(2-methoxy-4-pyridinyl)-1,3-benzothiazol-2-yl)-N-(2-sulfamoylethyl)acetamide | ¹H NMR (400 MHz, DMSO-d₆) δ 8.99 (t, J = 5.6 Hz, 1H), 8.66 (d, J = 1.5 Hz, 1H), 8.32-8.26 (m, 1H), 8.22-8.16 (m, 1H), 8.02-7.96 (m, 1H), 7.48-7.41 (m, 1H), 7.25-7.20 (m, 1H), 7.02-6.93 (m, 2H), 6.06 (s, 1H), 3.95-3.92 (m, 3H), 3.71-3.44 (m, 6H), 3.28 (s, 3H), 3.21-3.16 (m, 2H) | 1.4 Q 529 | <10 | 13 |
| B149 | 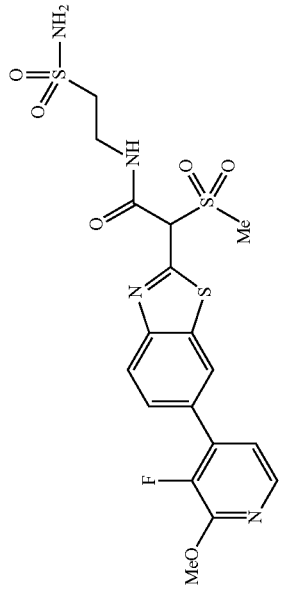 | 2-(6-(3-fluoro-2-methoxy-4-pyridinyl)-1,3-benzothiazol-2-yl)-2-(methylsulfonyl)-N-(2-sulfamoylethyl)acetamide | ¹H NMR (400 MHz, DMSO-d₆) d 9.00 (t, J = 5.7 Hz, 1H), 8.50 (s, 1H), 8.22 (d, J = 8.6 Hz, 1H), 8.09 (d, J = 5.3 Hz, 1H), 7.82 (dt, J = 8.5, 1.7 Hz, 1H), 7.26 (t, J = 5.2 Hz, 1H), 6.96 (s, 2H), 6.07 (s, 1H), 4.08-3.90 (m, 3H), 3.62 (d, J = 6.4 Hz, 2H), 3.25 (s, 3H), 3.22-3.16 (m, 2H) | 1.0 O 503.1 | <10 | 64 |
| B150 | 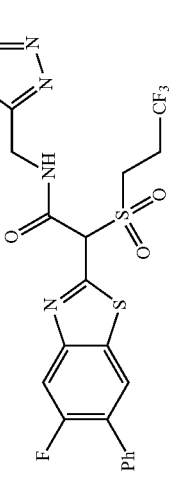 | 2-(5-Fluoro-6-phenyl-1,3-benzothiazol-2-yl)-N-((5-methyl-1,3,4-oxadiazol-2-yl)methyl)-2-((3,3,3-trifluoropropyl)sulfonyl)acetamide | ¹H NMR (400 MHz, METHANOL-d₄) δ 8.33-7.23 7H), 4.77-4.68 (m, 2H), 4.25-3.50 (m, 2H), 3.13-2.66 (m, 2H), 2.60-2.32 (m, 3H) | 2.18 Q 543.0 | <10 | 84 |

| Ex # | Structure | Name | $^1$H NMR (500 MHz, DMSO-d$_6$, unless indicated otherwise) | LC/MS RT (min) Method M + H | EL IC$_{50}$ (nM) | HL IC$_{50}$ (nM) |
|---|---|---|---|---|---|---|
| B151 | 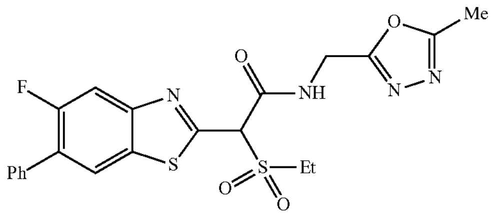 [SMILES: CCS(=O)(=O)C(C(=O)NCc1nnc(C)o1)c1nc2cc(F)c(-c3ccccc3)cc2s1] | 2-(ethylsulfonyl)-2-(5-fluoro-6-phenyl-1,3-benzothiazol-2-yl)-N-((5-methyl-1,3,4-oxadiazol-2-yl)methyl)acetamide | $^1$H NMR (400 MHz, METHANOL-d$_4$) δ 8.36-6.98 (m, 7H), 4.80-4.53 (m, 2H), 3.65-3.32 (m, 2H), 2.51 (m, 3H), 1.63-1.12 (m, 3H) | 2.01 Q 475.0 | <10 | 47 |
| B152 | 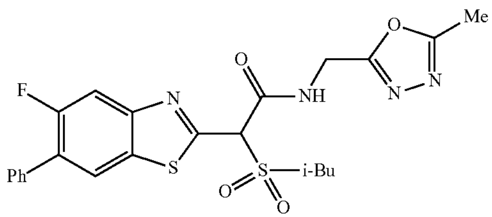 | 2-(5-fluoro-6-phenyl-1,3-benzothiazol-2-yl)-2-(isobutylsulfonyl)-N-((5-methyl-1,3,4-oxadiazol-2-yl)methyl)acetamide | $^1$H NMR (400 MHz, METHANOL-d$_4$) δ 8.22-7.28 (m, 7H), 4.81-4.55 (m, 2H), 3.68-3.26 (m, 2H), 2.68-2.43 (m, 3H), 2.39-2.08 (m, 1H), 1.28-0.76 (m, 6H) | 2.25 Q 503.1 | <10 | 39 |
| B153 | 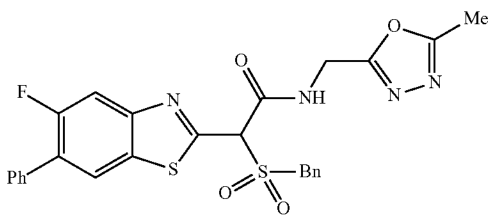 [SMILES: Cc1nnc(CNC(=O)C(c2nc3cc(F)c(-c4ccccc4)cc3s2)S(=O)(=O)Cc2ccccc2)o1] | 2-(benzylsulfonyl)-2-(5-fluoro-6-phenyl-1,3-benzothiazol-2-yl)-N-((5-methyl-1,3,4-oxadiazol-2-yl)methyl)acetamide | $^1$H NMR (400 MHz, METHANOL-d$_4$) δ 8.47-7.57 (m, 2H), 7.56-7.31 (m, 8H), 7.27-6.95 (m, 2H), 4.80-4.41 (m, 4H), 2.75-2.20 (m, 3H) | 2.17 Q 537.1 | <10 | 39 |
| B154 | 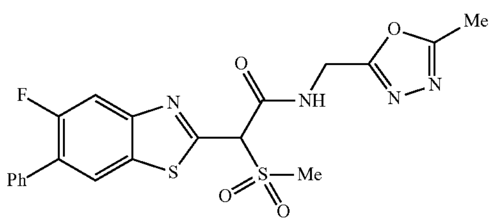 [SMILES: Cc1nnc(CNC(=O)C(c2nc3cc(F)c(-c4ccccc4)cc3s2)S(C)(=O)=O)o1] | 2-(5-fluoro-6-phenyl-1,3-benzothiazol-2-yl)-N-((5-methyl-1,3,4-oxadiazol-2-yl)methyl]-2-(methylsulfonyl)acetamide | $^1$H NMR (400 MHz, METHANOL-d$_4$) δ 8.27-7.08 (m, 7H), 4.82-4.51 (m, 2H), 3.27-3.07 (m, 3H), 2.64-2.29 (m, 3H) | 1.93 Q 461.0 | <10 | 11 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B155 | 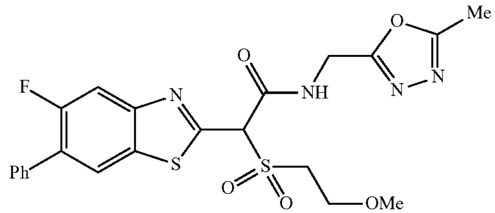 [SMILES: COCCS(=O)(=O)C(C(=O)NCc1nnc(C)o1)c1nc2cc(F)c(-c3ccccc3)cc2s1] | 2-(5-fluoro-6-phenyl-1,3-benzothiazol-2-yl)-2-[(2-methoxyethyl)sulfonyl]-N-[(5-methyl-1,3,4-oxadiazol-2-yl)methyl]acetamide | ¹H NMR (400 MHz, METHANOL-d₄) δ 8.43-6.86 (m, 7H), 4.73 (m, 2H), 4.10-3.51 (m, 4H), 3.39-3.19 (m, 3H), 2.69-2.07 (m, 3H) | 1.99 Q 505.0 | <10 | <10 |
| B156 | 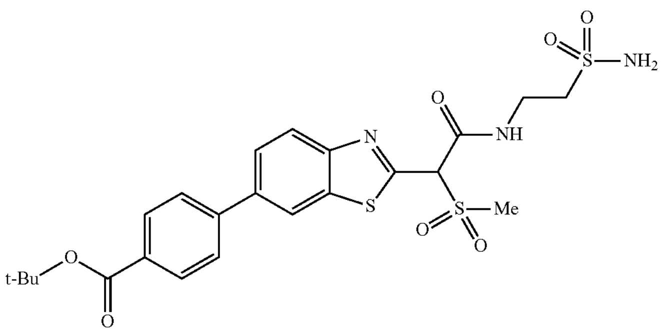 [SMILES: CC(C)(C)OC(=O)c1ccc(-c2ccc3nc(C(C(=O)NCCS(N)(=O)=O)S(C)(=O)=O)sc3c2)cc1] | tert-butyl 4-(2-(1-(methylsulfonyl)-2-oxo-2-(2-sulfamoylethylamino)ethyl)benzo[d]thiazol-6-yl)benzoate | ¹H NMR (400 MHz, DMSO-d₆) δ 9.02 (br. s., 1H), 8.59 (br. s., 1H), 8.30-8.16 (m, 1H), 8.12-7.75 (m, 5H), 6.99 (br. s., 2H), 6.06 (br. s., 1H), 3.62 (br. s., 2H), 3.32-3.11 (m, 5H), 1.59 (br. s., 9H). | 2.0 Q 554.1 | <10 | <10 |
| B158 | 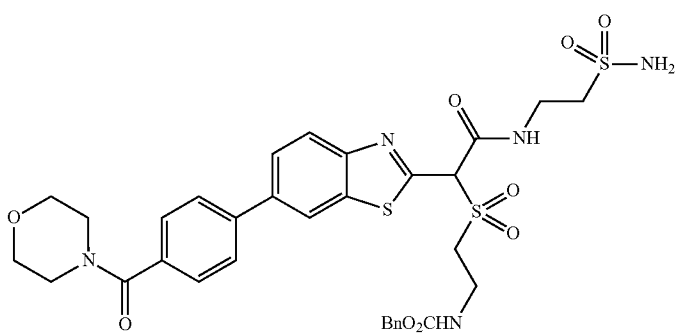 | benzyl (2-((1-(6-(4-(4-morpholinylcarbonyl)phenyl)-1,3-benzothiazol-2-yl)-2-oxo-2-((2-sulfamoyl)ethyl)amino)ethyl)sulfonyl)ethyl)carbamate | ¹H NMR (400 MHz, DMF) δ 9.15-9.05 (m, 1H), 8.63-8.57 (m, 1H), 8.34-8.23 (m, 1H), 8.22-8.15 (m, 1H), 8.00-7.96 (m, 2H), 7.94 (d, J = 8.3 Hz, 2H), 7.89-7.82 (m, 1H), 7.63 (d, J = 8.5 Hz, 3H), 7.43-7.35 (m, 5H), 7.03 (s, 3H), 6.38-5.76 (m, 1H), 5.12 (s, 2H), 3.48-3.31 (m, 2H) | 0.86 M 730.2 | <10 | 31 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B159 | 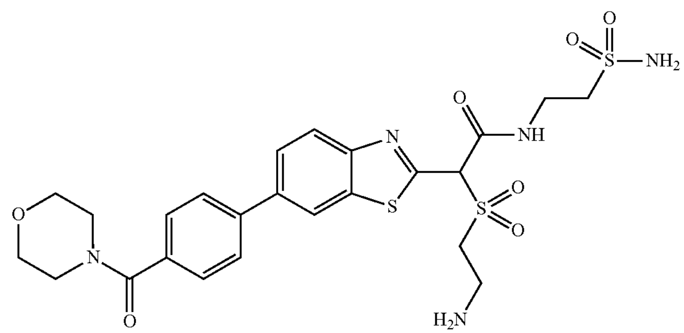 | 2-((2-aminoethyl)sulfonyl)-2-(6-phenyl-1,3-benzothiazol-2-yl)-N-(2-sulfamoylethyl)acetamide | ¹H NMR (400 MHz, DMSO-d₆) δ 9.15-8.99 (m, 1H), 8.52 (d, J = 1.3 Hz, 1H), 8.17 (d, J = 8.4 Hz, 1H), 7.96 (br. s., 2H), 7.91 (dd, J = 8.6, 2.0 Hz, 2H), 7.82-7.75 (m, 3H), 7.59-7.48 (m, 3H), 7.44 (d, J = 7.3 Hz, 1H), 7.25 (s, 3H), 7.12 (s, 3H), 7.01-6.89 (m, 5H), 6.31-6.21 (m, 1H), 3.92-3.67 (m, 2H), 3.63 (br. s., 3H), 3.27 (d, J = 5.5 Hz, 2H), 3.20 (t, J = 7.0 Hz, 2H) | 0.93 M 596.2 | <10 | 22 |
| B160 | 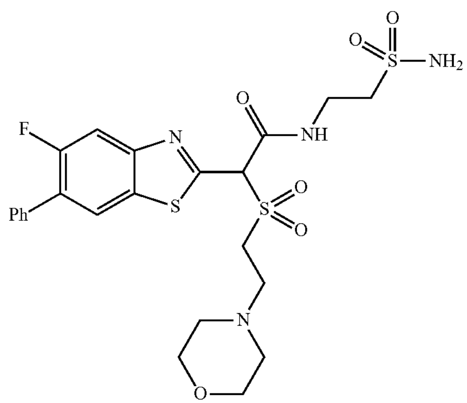 [SMILES: NS(=O)(=O)CCNC(=O)C(c1nc2cc(F)c(-c3ccccc3)cc2s1)S(=O)(=O)CCN1CCOCC1] | 2-(5-fluoro-6-phenyl-1,3-benzothiazol-2-yl)-2-((2-(4-morpholinyl)ethyl)sulfonyl)-N-(2-sulfamoylethyl)acetamide | ¹H NMR (500 MHz, Acetone) δ 7.69-7.60 (m, 3H), 7.52 (t, J = 7.6 Hz, 3H), 7.47-7.40 (m, 2H), 3.90 (br. s., 7H), 3.66-3.55 (m, 3H), 3.40 (br. s., 3H), 3.31 (d, J = 12.7 Hz, 3H) | 0.73 O 571.1 | <10 | 20 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B161 | 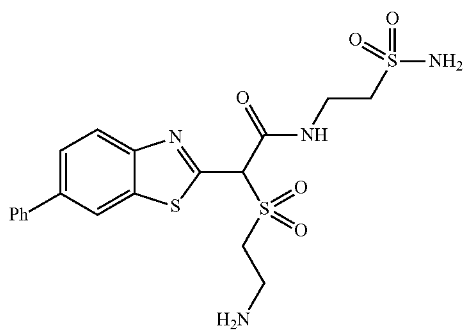 [SMILES: NCCS(=O)(=O)C(C(=O)NCCS(N)(=O)=O)c1nc2ccc(-c3ccccc3)cc2s1] | 2-((2-aminoethyl)sulfonyl)-2-(6-phenyl-1,3-benzothiazol-2-yl)-N-(2-sulfamoylethyl)acetamide | ¹H NMR (400 MHz, DMSO-d₆) δ 9.15-8.99 (m, 1H), 8.52 (d, J = 1.3 Hz, 1H), 8.17 (d, J = 8.4 Hz, 1H), 7.96 (br. s., 2H), 7.91 (dd, J = 8.6, 2.0 Hz, 2H), 7.82-7.75 (m, 3H), 7.59-7.48 (m, 3H), 7.44 (d, J = 7.3 Hz, 1H), 7.25 (s, 3H), 7.12 (s, 3H), 7.01-6.89 (m, 5H), 6.31-6.21 (m, 1H), 3.92-3.67 (m, 2H), 3.63 (br. s., 3H), 3.27 (d, J = 5.5 Hz, 2H), 3.20 (t, J = 7.0 Hz, 2H) | 0.88 M 483.1 | <10 | 22 |
| B163 | 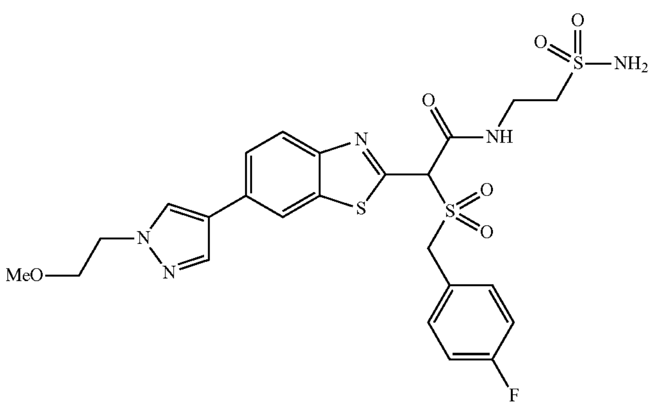 [SMILES: COCCn1cc(-c2ccc3nc(C(C(=O)NCCS(N)(=O)=O)S(=O)(=O)Cc4ccc(F)cc4)sc3c2)cn1] | 2-((4-fluorobenzyl)sulfonyl)-2-(6-(1-(2-methoxyethyl)-1H-pyrazol-4-yl)-1,3-benzothiazol-2-yl)-N-(2-sulfamoylethyl)acetamide | ¹H NMR (400 MHz, DMSO-d₆) δ 9.00 (s, 1H), 8.37 (d, J = 1.1 Hz, 1H), 8.28 (s, 1H), 8.08 (d, J = 8.8 Hz, 1H), 8.01 (d, J = 0.7 Hz, 1H), 7.85-7.77 (m, 2H), 7.46 (dd, J = 8.9, 5.6 Hz, 1H), 7.24 (t, J = 8.8 Hz, 1H), 6.95 (s, 2H), 6.03 (s, 1H), 4.75 (d, J = 3.7 Hz, 1H), 4.34-4.24 (m, 2H), 3.77-3.69 (m, 3H), 3.60 (d, J = 5.5 Hz, 4H), 3.26 (s, 1H), 3.23-3.15 (m, 2H) | 0.83 M 596.8 | 28 | 2554 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B164 | 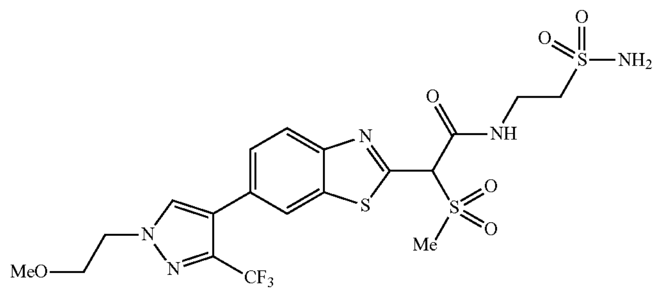 [SMILES: COCCn1cc(-c2ccc3nc(C(C(=O)NCCS(N)(=O)=O)S(C)(=O)=O)sc3c2)c(C(F)(F)F)n1] | 2-(6-(1-(2-methoxyethyl)-3-(trifluoromethyl)-1H-pyrazol-4-yl)-1,3-benzothiazol-2-yl)-2-(methylsulfonyl)-N-(2-sulfamoylethyl)acetamide | δ 9.00 (br. s., 1H), 8.27 (br. s., 1H), 8.21 (br. s., 1H), 8.15 (d, J = 8.5 Hz, 1H), 7.97 (br. s., 1H), 7.59 (d, J = 8.5 Hz, 1H), 6.96 (br. s., 1H), 6.05 (br. s., 1H), 4.43 (br. s., 1H), 3.79 (br. s., 1H), 3.66-3.57 (m, 1H), 3.29 (br. s., 3H), 3.25 (br. s., 3H), 3.20 (t, J = 6.5 Hz, 1H), 2.91 (s, 2H), 2.75 (s, 2H) | 1.52 N 572.1 | <10 | 199 |
| B165 | 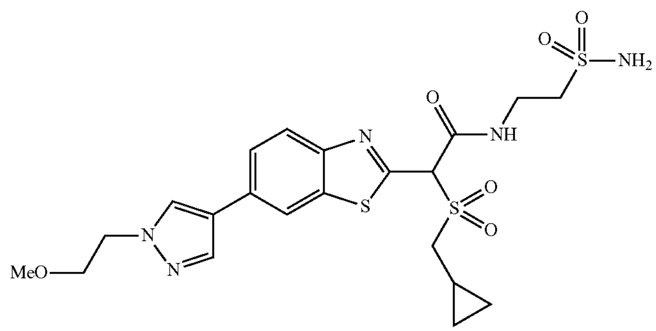 [SMILES: COCCn1cc(-c2ccc3nc(C(C(=O)NCCS(N)(=O)=O)S(=O)(=O)CC4CC4)sc3c2)cn1] | 2-((cyclopropylmethyl)sulfonyl)-2-(6-(1-(2-methoxyethyl)-1H-pyrazol-4-yl)-1,3-benzothiazol-2-yl)-N-(2-sulfamoylethyl)acetamide | δ 9.13-8.93 (m, 1H), 8.39-8.32 (m, 1H), 8.29-8.23 (m, 1H), 8.08-7.97 (m, 2H), 7.82-7.73 (m, 1H), 6.96 (s, 2H), 6.16-5.94 (m, 1H), 4.34-4.25 (m, 2H), 3.82-3.68 (m, 2H), 3.63-3.55 (m, 2H), 3.44-3.37 (m, 4H), 3.25 (s, 4H), 3.21-3.13 (m, 2H), 1.17-1.02 (m, 1H), 0.70-0.58 (m, 2H), 0.52-0.34 (m, 2H) | 1.31 N 542.1 | 37 | 317 |
| B167 | 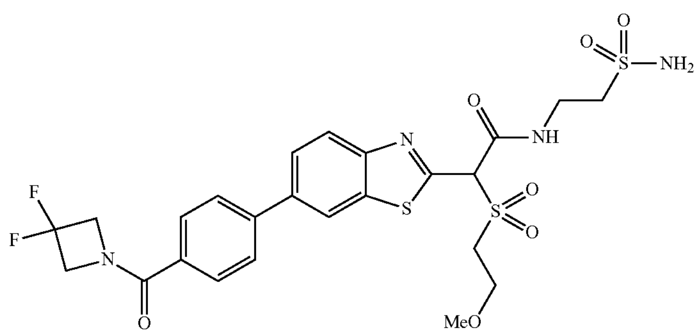 [SMILES: COCCS(=O)(=O)C(C(=O)NCCS(N)(=O)=O)c1nc2ccc(-c3ccc(C(=O)N4CC(F)(F)C4)cc3)cc2s1] | 2-(6-(4-((3,3-difluoro-1-azetidinyl)carbonyl)phenyl)-1,3-benzothiazol-2-yl)-2-((2-methoxyethyl)sulfonyl)-N-(2-sulfamoylethyl)acetamide | δ 8.96 (t, J = 4.8 Hz, 1H), 8.58 (s, 1H), 8.19 (d, J = 8.5 Hz, 1H), 7.99-7.92 (m, 1H), 7.91-7.87 (m, 2H), 7.86-7.79 (m, 3H), 6.96 (s, 2H), 6.06 (s, 1H), 3.82-3.74 (m, 2H), 3.72-3.67 (m, 2H), 3.65-3.56 (m, 2H), 3.29 (s, 3H), 3.23-3.17 (m, 2H) | 1.4 O 617.1 | <10 | 79 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B168 | 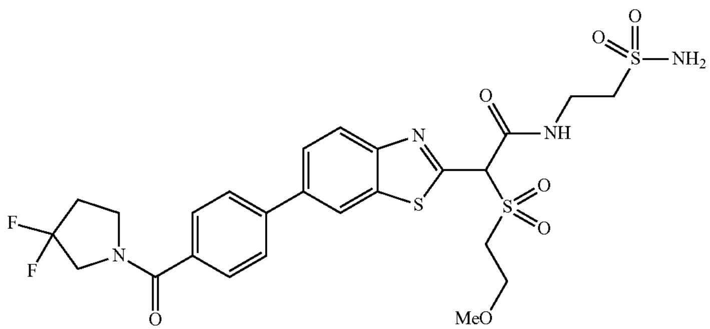 [SMILES: COCCS(=O)(=O)C(C(=O)NCCS(N)(=O)=O)c1nc2ccc(-c3ccc(C(=O)N4CCC(F)(F)C4)cc3)cc2s1] | 2-(6-(4-((3,3-difluoro-1-pyrrolidinyl)carbonyl)phenyl)-1,3-benzothiazol-2-yl)-2-((2-methoxyethyl)sulfonyl)-N-(2-sulfamoylethyl)acetamide | ¹H NMR (400 MHz, DMSO-d₆) δ 9.09-8.87 (m, 1H), 8.57 (s, 1H), 8.19 (d, J = 8.8 Hz, 1H), 7.99-7.85 (m, 4H), 7.82-7.63 (m, 3H), 6.96 (s, 2H), 3.94 (d, J = 19.3 Hz, 2H), 3.82-3.74 (m, 4H), 3.72-3.66 (m, 2H), 3.61 (d, J = 6.3 Hz, 2H), 3.29 (s, 3H), 3.24-3.17 (m, 3H) | 1.5 O 631.1 | <10 | 60 |
| B169 | 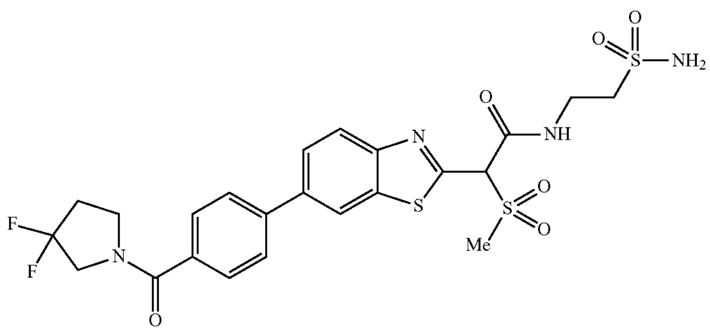 [SMILES: CS(=O)(=O)C(C(=O)NCCS(N)(=O)=O)c1nc2ccc(-c3ccc(C(=O)N4CCC(F)(F)C4)cc3)cc2s1] | 2-(6-(4-((3,3-difluoro-1-pyrrolidinyl)carbonyl)phenyl)-1,3-benzothiazol-2-yl)-2-(methylsulfonyl)-N-(2-sulfamoylethyl)acetamide | δ 9.00 (t, J = 5.4 Hz, 1H), 8.57 (s, 1H), 8.19 (d, J = 8.5 Hz, 1H), 7.97-7.91 (m, 1H), 7.90-7.84 (m, 2H), 7.75-7.69 (m, 2H), 6.96 (s, 2H), 6.06 (s, 1H), 4.07-3.85 (m, 3H), 3.77 (t, J = 7.2 Hz, 2H), 3.62 (q, J = 6.4 Hz, 2H), 3.26 (s, 3H), 3.21 (t, J = 7.0 Hz, 2H) | 1.4 O 587.1 | <10 | 91 |
| B170 | 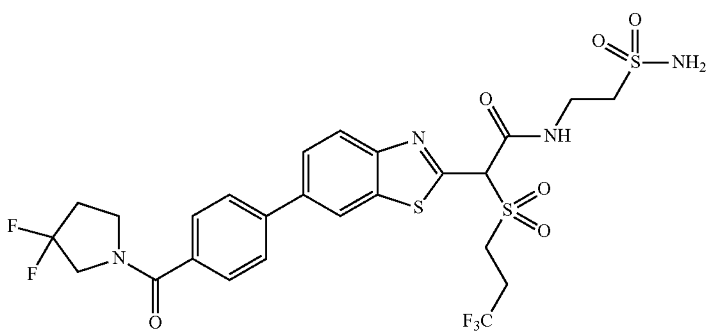 | 2-(6-(4-((3,3-difluoro-1-pyrrolidinyl)carbonyl)phenyl)-1,3-benzothiazol-2-yl)-2-((3,3,3-trifluoropropyl)sulfonyl)-N-(2-sulfamoylethyl)acetamide | δ 8.97 (t, J = 5.5 Hz, 1H), 8.59 (s, 1H), 8.19 (d, J = 8.3 Hz, 1H), 7.99-7.91 (m, 1H), 7.88 (d, J = 7.7 Hz, 2H), 7.74-7.69 (m, 2H), 6.97 (s, 2H), 6.28 (s, 1H), 4.03-3.90 (m, 3H), 3.80-3.73 (m, 5H), 3.68-3.59 (m, 2H), 3.21 (t, J = 7.2 Hz, 2H), 2.90-2.82 (m, 2H) | 1.7 O 669.1 | <10 | 32 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B171 | 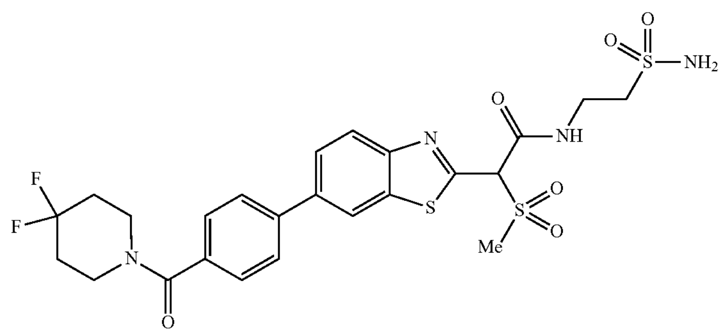 [SMILES: CS(=O)(=O)C(C(=O)NCCS(N)(=O)=O)c1nc2ccc(-c3ccc(C(=O)N4CCC(F)(F)CC4)cc3)cc2s1] | 2-(6-(4-((4,4-difluoro-1-piperidinyl)carbonyl)phenyl)-1,3-benzothiazol-2-yl)-2-(methylsulfonyl)-N-(2-sulfamoylethyl)acetamide | ¹H NMR (400 MHz, DMSO-d₆) δ 9.01 (t, J =5.8 Hz, 1H), 8.56 (d, J = 1.5 Hz, 1H), 8.18 (d, J = 8.6 Hz, 1H), 7.93 (dd, J = 8.6, 1.8 Hz, 1H), 7.86 (d, J = 8.4 Hz, 2H), 7.60 (d, J = 8.4 Hz, 2H), 6.97 (s, 2H), 6.05 (s, 1H), 3.62 (dd, J = 13.1, 6.9 Hz, 6H), 3.25 (s, 3H), 3.20 (t, J = 7.2 Hz, 2H), 2.09 (s, 4H) | 1.0 M 601.2 | <10 | 19 |
| B175 | 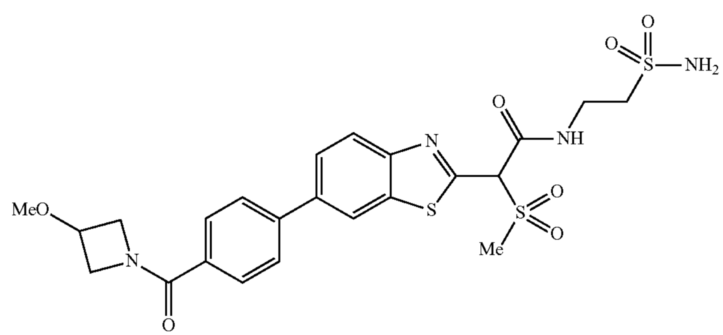 [SMILES: COC1CN(C(=O)c2ccc(-c3ccc4nc(C(C(=O)NCCS(N)(=O)=O)S(C)(=O)=O)sc4c3)cc2)C1] | 2-(6-(4-((3-methoxy-1-azetidinyl)carbonyl)phenyl)-1,3-benzothiazol-2-yl)-2-(methylsulfonyl)-N-(2-sulfamoylethyl)acetamide | δ 9.03 (br. s., 1H), 8.57 (br. s., 1H), 8.19 (d, J = 8.5 Hz, 1H), 7.96-7.90 (m, 1H), 7.90-7.84 (m, 2H), 7.81-7.76 (m, 2H), 6.99 (br. s., 2H), 6.06 (br. s., 1H), 4.52 (br. s., 1H), 4.28 (br. s., 3H), 3.90 (d, J = 16.0 Hz, 1H), 3.62 (br. s., 2H), 3.25 (br. s., 4H), 3.20 (br. s., 2H) | 1.2 O 567.1 | <10 | 118 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B176 | 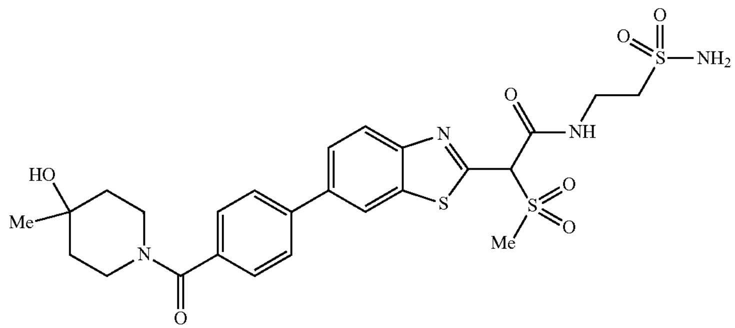 [SMILES: CC1(O)CCN(C(=O)c2ccc(-c3ccc4nc(C(C(=O)NCCS(N)(=O)=O)S(C)(=O)=O)sc4c3)cc2)CC1] | 2-(6-(4-((4-hydroxy-4-methyl-1-piperidinyl)carbonyl)phenyl)-1,3-benzothiazol-2-yl)-2-(methylsulfonyl)-N-(2-sulfamoylethyl)acetamide | δ 9.03 (br. s., 1H), 8.55 (br. s., 1H), 8.18 (d, J = 8.0 Hz, 1H), 8.01-7.89 (m, 2H), 7.86-7.80 (m, 2H), 7.52 (d, J = 7.4 Hz, 2H), 6.99 (br. s., 2H), 6.06 (br. s., 1H), 4.11 (br. s., 1H), 3.92 (br. s., 1H), 3.68-3.31 (m, 4H), 3.30-3.10 (m, 5H), 1.70-1.34 (m, 4H), 1.18 (br. s., 3H) | 1.1 O 595.2 | <10 | 92 |
| B177 | 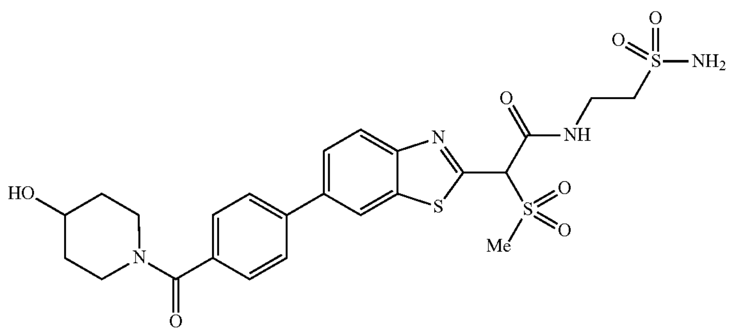 [SMILES: CS(=O)(=O)C(C(=O)NCCS(N)(=O)=O)c1nc2ccc(-c3ccc(C(=O)N4CCC(O)CC4)cc3)cc2s1] | 2-(6-(4-((4-hydroxy-1-piperidinyl)phenyl)carbonyl)-1,3-benzothiazol-2-yl)-2-(methylsulfonyl)-N-(2-sulfamoylethyl)acetamide | δ 9.00 (br. s., 1H), 8.55 (br. s., 1H), 8.18 (d, J = 8.5 Hz, 1H), 8.00-7.87 (m, 2H), 7.87-7.79 (m, 2H), 7.57-7.49 (m, 2H), 6.96 (br. s., 2H), 6.05 (br. s., 1H), 4.81 (br. s., 1H), 4.05 (br. s., 1H), 3.92 (br. s., 1H), 3.77 (br. s., 1H), 3.62 (br. s., 2H), 3.29-3.15 (m, 6H), 2.91 (br. s., 2H), 2.75 (br. s., 2H) | 1.0 O 581.0 | <10 | 495 |
| B178 | 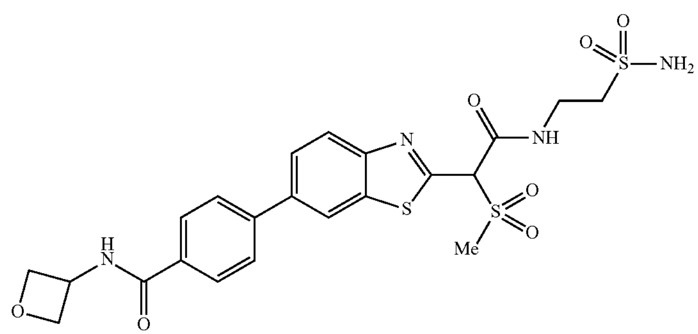 [SMILES: CS(=O)(=O)C(C(=O)NCCS(N)(=O)=O)c1nc2ccc(-c3ccc(C(=O)NC4COC4)cc3)cc2s1] | 4-(2-(1-(methylsulfonyl)-2-oxo-2-((2-sulfamoylethyl)amino)ethyl)-1,3-benzothiazol-6-yl)-N-3-oxetanylbenzamide | ¹H NMR (400 MHz, DMSO-d₆) δ 8.99 (t, J = 5.7 Hz, 1H), 8.60 (d, J = 1.5 Hz, 1H), 8.19 (d, J = 8.6 Hz, 1H), 8.07-8.01 (m, 2H), 7.98-7.93 (m, 3H), 6.96 (s, 3H), 6.05 (s, 1H), 4.70-4.53 (m, 1H), 4.43 (br. s., 2H), 3.69-3.58 (m, 4H), 3.25 (s, 3H), 3.21 (d, J = 8.1 Hz, 2H) | 1.2 Q 553.0 | <10 | 91 |

-continued

| Ex # | Structure | Name | $^1$H NMR (500 MHz, DMSO-d$_6$, unless indicated otherwise) | LC/MS RT (min) Method M + H | EL IC$_{50}$ (nM) | HL IC$_{50}$ (nM) |
|---|---|---|---|---|---|---|
| B179 | 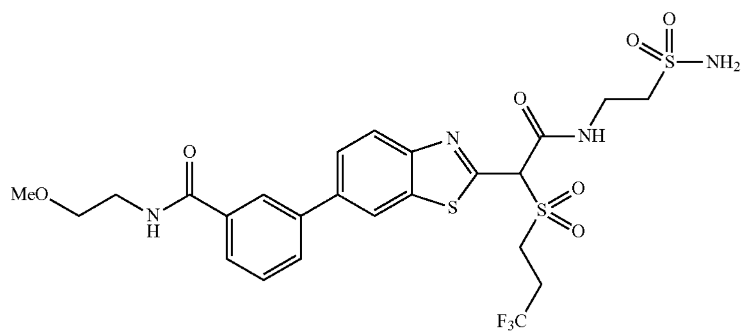 [SMILES: COCCNC(=O)c1cccc(-c2ccc3nc(C(C(=O)NCCS(N)(=O)=O)S(=O)(=O)CCC(F)(F)F)sc3c2)c1] | N-(2-Methoxyethyl)-3-(2-(2-oxo-2-((2-sulfamoylethyl)amino)-1-((3,3,3-trifluoropropyl)sulfonyl)ethyl)benzo[d]thiazol-6-yl)benzamide | δ 8.58 (s, 1H), 8.14 (d, J = 8.5 Hz, 2H), 7.86 (d, J = 8.8 Hz, 2H), 4.88-4.48 (m, 4H), 3.81-3.52 (m, 4H), 3.18 (s, 2H), 2.89 (m, 2H) | 1.5 O 637.1 | 24 | 170 |
| B181 | 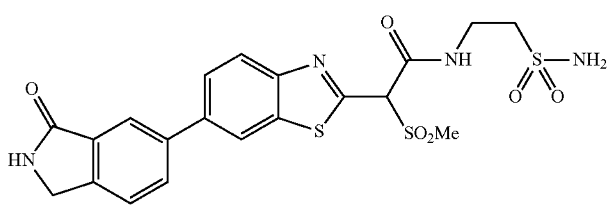 [SMILES: CS(=O)(=O)C(C(=O)NCCS(N)(=O)=O)c1nc2ccc(-c3ccc4c(c3)C(=O)NC4)cc2s1] | 2-(methylsulfonyl)-2-(6-(3-oxo-2,3-dihydro-1H-isoindol-5-yl)-1,3-benzothiazol-2-yl)-N-(2-sulfamoylethyl)acetamide | δ 9.03 (br. s., 1H), 8.62-8.52 (m, 1H), 8.21-8.12 (m, 1H), 8.03-7.99 (m, 2H), 7.98-7.92 (m, 1H), 7.76-7.71 (m, 1H), 6.99 (br. s., 2H), 6.06 (br. s., 1H), 4.46 (br. s., 2H), 3.62 (br. s., 2H), 3.26 (br. s., 3H), 3.21 (br. s., 2H) | 1.0 O 509.1 | <10 | 145 |
| B182 | 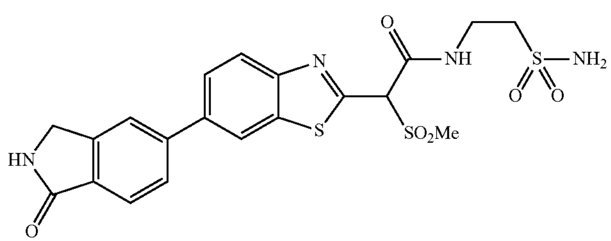 [SMILES: CS(=O)(=O)C(C(=O)NCCS(N)(=O)=O)c1nc2ccc(-c3ccc4c(c3)CNC4=O)cc2s1] | 2-(methylsulfonyl)-2-(6-(1-oxo-2,3-dihydro-1H-isoindol-5-yl)-1,3-benzothiazol-2-yl)-N-(2-sulfamoylethyl)acetamide | δ 9.03 (br. s., 1H), 8.59-8.56 (m, 1H), 8.23-8.18 (m, 1H), 7.97 (br. s., 3H), 7.83-7.78 (m, 1H), 6.99 (br. s., 2H), 6.06 (br. s., 1H), 4.48 (br. s., 2H), 3.62 (br. s., 2H), 3.26 (br. s., 3H), 3.23-3.17 (m, 2H) | 1.4 O 509 | <10 | 36 |
| B183 | 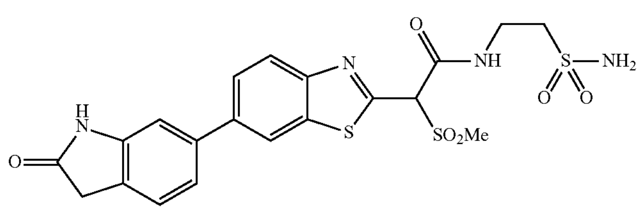 [SMILES: CS(=O)(=O)C(C(=O)NCCS(N)(=O)=O)c1nc2ccc(-c3ccc4c(c3)NC(=O)C4)cc2s1] | 2-(methylsulfonyl)-2-(6-(2-oxo-2,3-dihydro-1H-indol-6-yl)-1,3-benzothiazol-2-yl)-N-(2-sulfamoylethyl)acetamide | δ 9.04 (t, J = 5.6 Hz, 1H), 8.45 (s, 1H), 8.21-8.12 (m, 1H), 7.96 (s, 2H), 7.82 (d, J = 8.5 Hz, 1H), 7.39-7.30 (m, 2H), 6.99 (s, 2H), 6.05 (s, 1H), 3.65-3.58 (m, 2H), 3.57-3.53 (m, 2H), 3.25 (s, 3H), 3.22-3.16 (m, 2H) | 1.2 O 509 | <10 | 139 |

| Ex # | Structure | Name | $^1$H NMR (500 MHz, DMSO-$d_6$, unless indicated otherwise) | LC/MS RT (min) Method M+H | EL IC$_{50}$ (nM) | HL IC$_{50}$ (nM) |
|---|---|---|---|---|---|---|
| B184 | 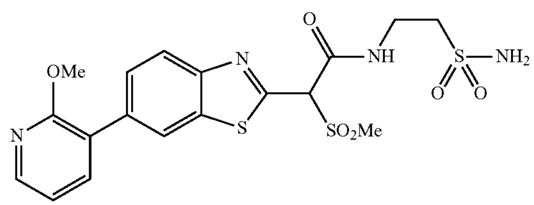 [SMILES: COc1ncccc1-c1ccc2nc(C(C(=O)NCCS(N)(=O)=O)S(C)(=O)=O)sc2c1] | 2-(6-(2-methoxy-3-pyridinyl)-1,3-benzothiazol-2-yl)-2-(methylsulfonyl)-N-(2-sulfamoylethyl)acetamide | δ 9.02 (br. s., 1H), 8.35 (br. s., 1H), 8.27-8.22 (m, 1H), 8.18-8.09 (m, 1H), 7.99-7.93 (m, 1H), 7.88-7.81 (m, 1H), 7.80-7.69 (m, 1H), 7.20-7.12 (m, 1H), 7.04-6.93 (m, 2H), 6.11-5.94 (m, 1H), 3.91 (br. s., 3H), 3.31-3.13 (m, 5H) | 1.5 O 485 | <10 | 65 |
| B185 | 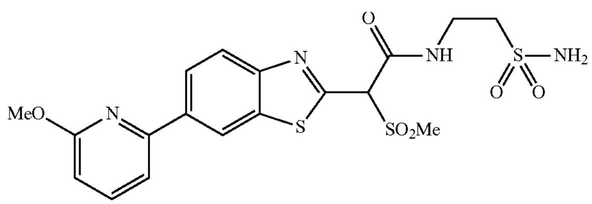 [SMILES: COc1cccc(-c2ccc3nc(C(C(=O)NCCS(N)(=O)=O)S(C)(=O)=O)sc3c2)n1] | 2-(6-(6-methoxy-2-pyridinyl)-1,3-benzothiazol-2-yl)-2-(methylsulfonyl)-N-(2-sulfamoylethyl)acetamide | δ 9.02-8.98 (m, 1H), 8.95-8.89 (m, 1H), 8.37-8.27 (m, 1H), 8.23-8.14 (m, 1H), 8.01-7.95 (m, 1H), 7.90-7.82 (m, 1H), 7.74-7.68 (m, 1H), 6.96 (br. s., 2H), 6.09-6.02 (m, 1H), 4.02 (br. s., 3H), 3.68-3.57 (m, 2H), 3.29-3.24 (m, 3H), 3.23-3.18 (m, 2H) | 1.6 O 485 | <10 | |
| B186 | 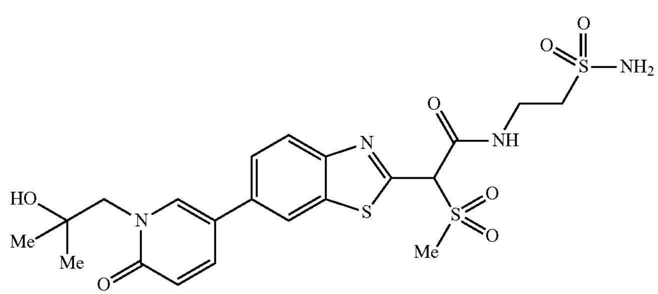 [SMILES: CC(C)(O)Cn1cc(-c2ccc3nc(C(C(=O)NCCS(N)(=O)=O)S(C)(=O)=O)sc3c2)ccc1=O] | 2-(6-(1-(2-hydroxy-2-methylpropyl)-6-oxo-1,6-dihydro-3-pyridinyl)-1,3-benzothiazol-2-yl)-2-(methylsulfonyl)-N-(2-sulfamoylethyl)acetamide | δ 9.01 (t, J = 5.6 Hz, 1H), 8.35 (s, 1H), 8.20-8.06 (m, 2H), 8.02-7.88 (m, 2H), 7.75 (d, J = 8.5 Hz, 1H), 7.03-6.89 (m, 2H), 6.57 (d, J = 9.4 Hz, 1H), 4.88 (s, 1H), 4.03 (s, 2H), 3.61 (q, J = 6.6 Hz, 2H), 3.24 (s, 3H), 3.20 (t, J = 7.2 Hz, 2H), 1.13 (s, 6H) | 1.0 O 543.1 | 1.1 | 10000 |
| B188 | 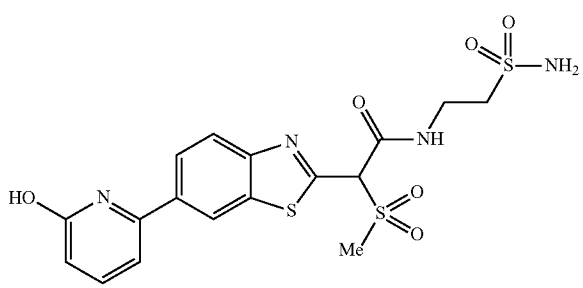 | 2-(methylsulfonyl)-2-(6-(6-oxo-1,6-dihydro-2-pyridinyl)-1,3-benzothiazol-2-yl)-N-(2-sulfamoylethyl)acetamide | δ 9.03 (br. s., 1H), 8.57 (br. s., 1H), 8.19 (d, J = 8.5 Hz, 1H), 7.96-7.90 (m, 1H), 7.90-7.84 (m, 2H), 7.81-7.76 (m, 2H), 6.99 (br. s., 2H), 6.06 (br. s., 1H), 4.52 (br. s., 1H), 4.28 (s, 3H), 3.90 (d, J = 16.0 Hz, 1H), 3.62 (br. s., 2H), 3.25 (br. s., 4H), 3.20 (br. s., 2H) | 1.2 Q 471.1 | <10 | 398 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B189 | 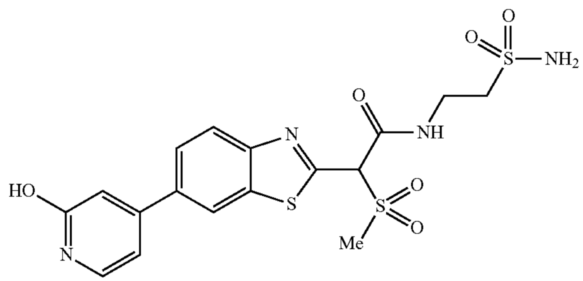 | 2-(methylsulfonyl)-2-(6-(2-oxo-1,2-dihydro-4-pyridinyl)-1,3-benzothiazol-2-yl)-N-(2-sulfamoylethyl)acetamide | δ 11.66 (br. s., 1H), 9.00 (t, J = 5.4 Hz, 1H), 8.57 (s, 1H), 8.16 (d, J = 8.8 Hz, 1H), 7.89 (dd, J = 8.5, 1.7 Hz, 1H), 7.51 (d, J = 6.9 Hz, 1H), 6.96 (s, 2H), 6.71 (s, 1H), 6.65-6.54 (m, 1H), 6.06 (s, 1H), 3.68-3.56 (m, 2H), 3.27-3.23 (m, 3H), 3.20 (t, J = 7.2 Hz, 2H) | 0.9 O 471.0 | <10 | 13 |
| B190 | 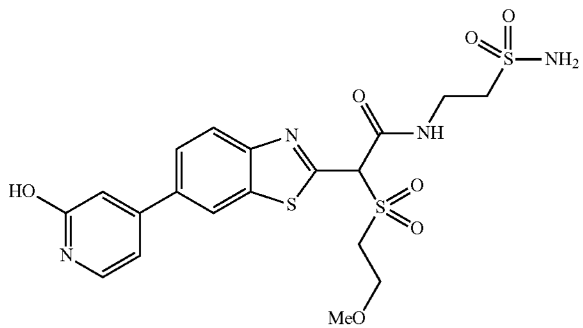 [SMILES: COCCS(=O)(=O)C(C(=O)NCCS(N)(=O)=O)c1nc2ccc(-c3ccnc(O)c3)cc2s1] | 2-((2-methoxyethyl)sulfonyl)-2-(6-(2-oxo-1,2-dihydro-4-pyridinyl)-1,3-benzothiazol-2-yl)-N-(2-sulfamoylethyl)acetamide | δ 11.66 (br. s., 1H), 8.96 (t, J = 5.5 Hz, 1H), 8.57 (s, 1H), 8.16 (d, J = 8.5 Hz, 1H), 7.89 (dd, J = 8.5, 1.4 Hz, 1H), 7.54-7.47 (m, 1H), 6.99-6.90 (m, 3H), 6.74-6.68 (m, 1H), 6.67-6.58 (m, 2H), 6.15-6.00 (m, 1H), 3.71-3.66 (m, 2H), 3.64-3.57 (m, 2H), 3.28 (s, 3H), 3.22-3.16 (m, 2H) | 0.9 O 515.1 | <10 | 272 |
| B191 | 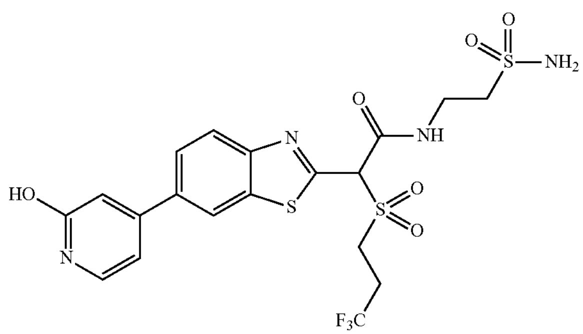 [SMILES: NS(=O)(=O)CCNC(=O)C(c1nc2ccc(-c3ccnc(O)c3)cc2s1)S(=O)(=O)CCC(F)(F)F] | 2-(6-(2-oxo-1,2-dihydro-4-pyridinyl)-1,3-benzothiazol-2-yl)-N-(2-sulfamoylethyl)-2-((3,3,3-trifluoropropyl)sulfonyl)acetamide | δ 11.78-11.27 (m, 1H), 8.96 (s, 1H), 8.69-8.43 (m, 1H), 8.20-8.13 (m, 1H), 8.00-7.86 (m, 2H), 7.56-7.49 (m, 1H), 6.97 (s, 3H), 6.71 (s, 1H), 6.66-6.58 (m, 2H), 6.28 (s, 1H), 3.66-3.59 (m, 2H), 3.20 (s, 2H), 2.90-2.82 (m, 2H) | 1.3 O 553.1 | <10 | 445 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B192 | 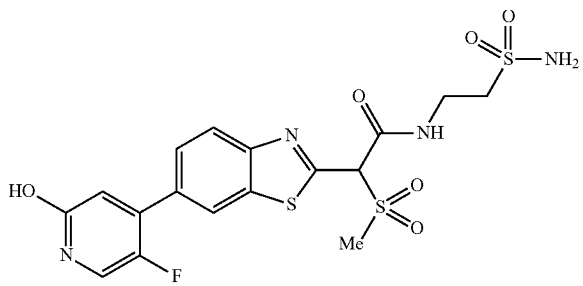 [SMILES: CS(=O)(=O)C(C(=O)NCCS(N)(=O)=O)c1nc2ccc(-c3cc(O)ncc3F)cc2s1] | 2-(6-(5-fluoro-2-oxo-1,2-dihydro-4-pyridinyl)-1,3-benzothiazol-2-yl)-N-(2-(methylsulfonyl)ethyl)-2-sulfamoylethyl)acetamide | ¹H NMR (400 MHz, DMSO-d₆) δ 9.02 (t, J = 5.5 Hz, 1H), 8.51 (s, 1H), 8.35-8.29 (m, 1H), 8.26-8.19 (m, 1H), 7.90-7.80 (m, 1H), 7.17-7.09 (m, 1H), 7.05-6.94 (m, 2H), 6.13-5.96 (m, 1H), 3.65-3.57 (m, 2H), 3.25 (s, 3H), 3.22-3.16 (m, 2H). | 0.7 M 489.0 | <10 | 20600 |
| B193 | 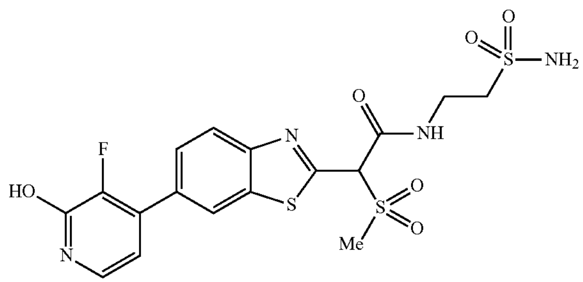 [SMILES: CS(=O)(=O)C(C(=O)NCCS(N)(=O)=O)c1nc2ccc(-c3ccnc(O)c3F)cc2s1] | 2-[6-(3-fluoro-2-hydroxy-4-pyridinyl)-1,2-benzothiazol-2-yl]-2-(methylsulfonyl)-N-(2-sulfamoylethyl)acetamide | δ 12.25 (br. s., 1H), 9.02 (t, J = 5.5 Hz, 1H), 8.46 (s, 1H), 8.21 (d, J = 8.5 Hz, 1H), 7.78 (d, J = 8.5 Hz, 1H), 7.37 (d, J = 6.6 Hz, 1H), 6.98 (s, 2H), 6.40 (t, J = 6.3 Hz, 1H), 6.07 (s, 1H), 3.61 (q, J = 6.6 Hz, 2H), 3.25 (s, 2H), 3.20 (t, J = 7.0 Hz, 2H) | 0.93 O 489.0 | 0.5 | 238 |
| B194 | 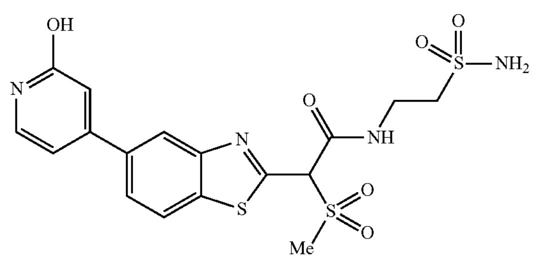 [SMILES: CS(=O)(=O)C(C(=O)NCCS(N)(=O)=O)c1nc2cc(-c3ccnc(O)c3)ccc2s1] | 2-(methylsulfonyl)-2-(5-(2-oxo-1,2-dihydro-4-pyridinyl)-1,3-benzothiazol-2-yl)-N-(2-sulfamoylethyl)acetamide | δ 11.68 (br. s., 1H), 9.02 (t, J = 5.5 Hz, 1H), 8.41 (s, 1H), 8.28 (d, J = 8.5 Hz, 1H), 7.86 (d, J = 8.5 Hz, 1H), 7.50 (d, J = 6.9 Hz, 1H), 6.99 (s, 2H), 6.82-6.71 (m, 1H), 6.69-6.63 (m, 1H), 6.07 (s, 1H), 3.61 (q, J = 6.4 Hz, 2H), 3.26 (s, 3H), 3.20 (t, J = 7.2 Hz, 2H) | 0.94 O 471.0 | 2 | 95 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B195 | 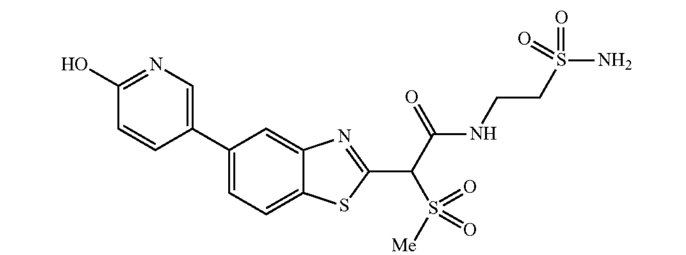 [SMILES: CS(=O)(=O)C(C(=O)NCCS(N)(=O)=O)c1nc2cc(-c3ccc(O)nc3)ccc2s1] | 2-(methylsulfonyl)-2-(5-(6-oxo-1,6-dihydro-3-pyridinyl)-1,3-benzothiazol-2-yl)acetamide | δ 11.94 (br. s., 1H), 9.01 (t, J = 5.5 Hz, 1H), 8.39-8.23 (m, 1H), 8.22-8.17 (m, 1H), 8.02-7.95 (m, 2H), 7.93-7.84 (m, 1H), 7.79-7.68 (m, 1H), 6.99 (s, 2H), 6.52-6.40 (m, 1H), 3.61 (q, J = 6.4 Hz, 2H), 3.25 (s, 3H), 3.20 (t, J = 7.0 Hz, 2H) | 0.95 O 471.0 | 1 | 105 |
| B198 | 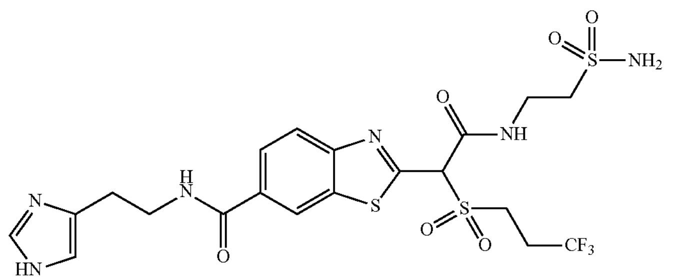 [SMILES: NS(=O)(=O)CCNC(=O)C(c1nc2ccc(C(=O)NCCc3c[nH]cn3)cc2s1)S(=O)(=O)CCC(F)(F)F] | N-(2-(1H-imidazol-4-yl)ethyl)-2-(2-oxo-2-((2-sulfamoylethyl)amino)-1-((3,3,3-trifluoropropyl)sulfonyl)ethyl)-1,3-benzothiazole-6-carboxamide | δ 9.00-8.70 (m, 1H), 8.56-8.26 (m, 2H), 8.19-7.87 (m, 3H), 7.70 (d, J = 8.5 Hz, 1H), 7.29-7.15 (m, 1H), 6.88 (s, 2H), 3.62 (d, J = 6.3 Hz, 8H), 2.92-2.82 (m, 4H) | 1.1 O 597.0 | 148 | 3933 |
| B199 | 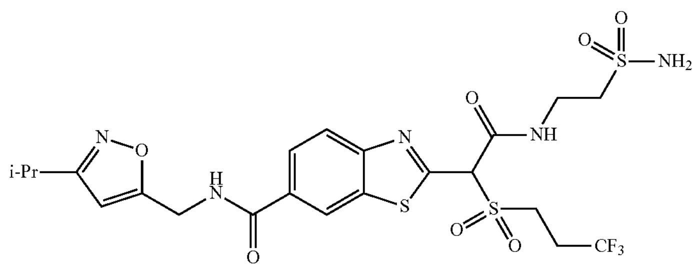 [SMILES: CC(C)c1cc(CNC(=O)c2ccc3nc(C(C(=O)NCCS(N)(=O)=O)S(=O)(=O)CCC(F)(F)F)sc3c2)on1] | N-((3-isopropyl-5-isoxazolyl)methyl)-2-(2-oxo-2-((2-sulfamoylethyl)amino)-1-((3,3,3-trifluoropropyl)sulfonyl)ethyl)-1,3-benzothiazole-6-carboxamide | 1H NMR (400 MHz, METHANOL-d₄) δ 8.22 (d, J = 1.3 Hz, 1H), 7.92 (dd, J = 8.5, 1.7 Hz, 1H), 7.66 (d, J = 7.7 Hz, 1H), 6.31-6.26 (m, 1H), 4.71-4.65 (m, 2H), 3.93-3.56 (m, 4H), 3.31 (m, 2H), 3.18-2.93 (m, 1H), 2.89-2.60 (m, 2H), 1.35-1.16 (m, 6H) | 1.74 O 626.1 | 166 | 3671 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B200 | 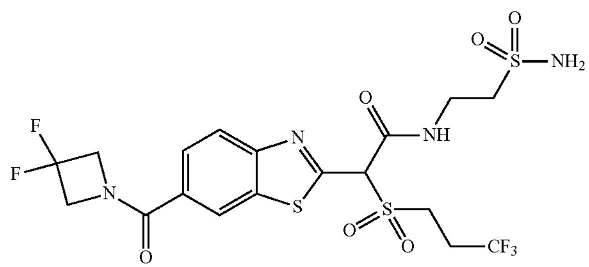 [SMILES: NS(=O)(=O)CCNC(=O)C(c1nc2ccc(C(=O)N3CC(F)(F)C3)cc2s1)S(=O)(=O)CCC(F)(F)F] | 2-(6-((3,3-difluoro-1-azetidinyl)carbonyl)-1,3-benzothiazol-2-yl)-N-(2-sulfamoylethyl)-2-((3,3,3-trifluoropropyl)sulfonyl)acetamide | δ 8.58 (s, 1H), 8.14 (d, J = 8.5 Hz, 2H), 7.86 (d, J = 8.8 Hz, 2H), 4.88-4.48 (m, 4H), 3.81-3.52 (m, 4H), 3.18 (s, 2H), 2.89 (m, 2H) | 1.43 O 579.1 | 26 | 10,000 |
| B201 | 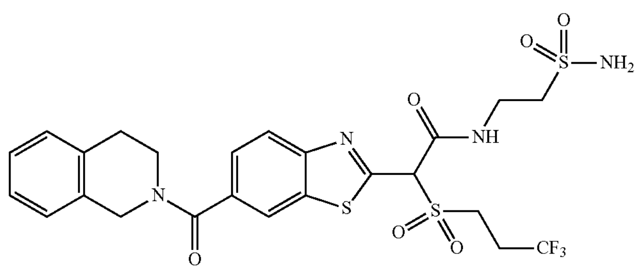 [SMILES: NS(=O)(=O)CCNC(=O)C(c1nc2ccc(C(=O)N3CCc4ccccc4C3)cc2s1)S(=O)(=O)CCC(F)(F)F] | 2-(6-(3,4-dihydro-2(1H)-isoquinolinylcarbonyl)-1,3-benzothiazol-2-yl)-N-(2-sulfamoylethyl)-2-((3,3,3-trifluoropropyl)sulfonyl)acetamide | δ 8.33 (m, 1H), 8.15 (d, J = 8.5 Hz, 1H), 7.86 (m, 1H), 7.19 (m, 3H), 6.96 (m, 1H), 4.85-4.54 (m, 2H), 3.93-3.52 (m, 6H), 3.22-3.14 (m, 2H), 2.92-2.83 (m, 4H) | 1.43 O 619.0 | 23 | 311 |
| B204 | 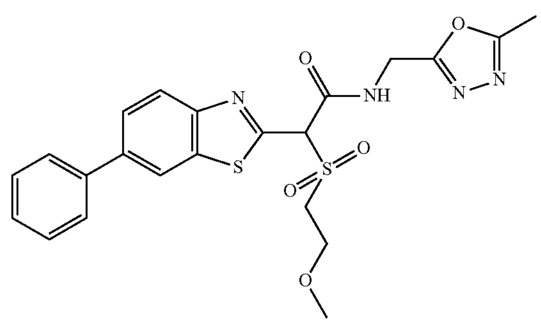 [SMILES: COCCS(=O)(=O)C(C(=O)NCc1nnc(C)o1)c1nc2ccc(-c3ccccc3)cc2s1] | 2-(2-methoxyethanesulfonyl)-N-[(5-methyl-1,3,4-oxadiazol-2-yl)methyl]-2-(6-phenyl-1,3-benzothiazol-2-yl)acetamide | δ 9.54 (br. s., 1H), 8.51 (br. s., 1H), 8.17 (d, J = 8.5 Hz, 1H), 7.89 (d, J = 8.3 Hz, 1H), 7.78 (m, 2H), 7.53 (t, J = 7.0 Hz, 2H), 7.44 (d, J = 6.9 Hz, 1H), 6.10 (br. s., 1H), 4.68 (m, 2H), 3.82-3.68 (m, 4H), 3.28 (br. s., 3H), 2.47 (br. s., 3H) | 1.8 N 486.9 | 23.7 | 17.5 |

| Ex # | Structure | Name | ¹H NMR (500 MHz, DMSO-d₆, unless indicated otherwise) | LC/MS RT (min) Method M+H | EL IC₅₀ (nM) | HL IC₅₀ (nM) |
|---|---|---|---|---|---|---|
| B205 | 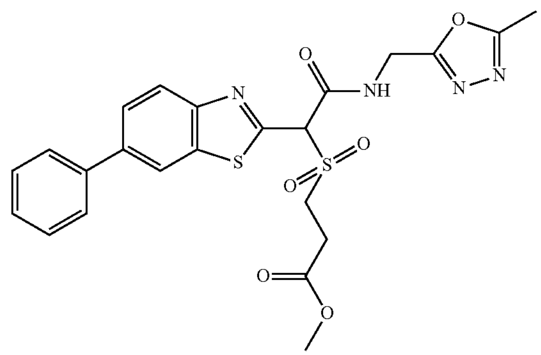 [SMILES: COC(=O)CCS(=O)(=O)C(C(=O)NCc1nnc(C)o1)c1nc2ccc(-c3ccccc3)cc2s1] | methyl 3-{[(5-methyl-1,3,4-oxadiazol-2-yl)methyl]carbamoyl}(6-phenyl-1,3-benzothiazol-2-yl)methanesulfonyl)propanoate | δ 9.56 (m, 1H), 8.52 (br. s., 1H), 8.24-8.10 (m, 1H), 7.98-7.64 (m, 3H), 7.58-7.35 (m, 3H), 6.21 (br. s., 1H), 4.78-4.62 (m, 2H), 3.84-3.65 (m, 2H), 3.63 (br. s., 3H), 2.90-2.75 (m, 2H), 2.47 (m, 3H) | 1.7 N 515.3 | 205.0 | 100.6 |
| B207 | 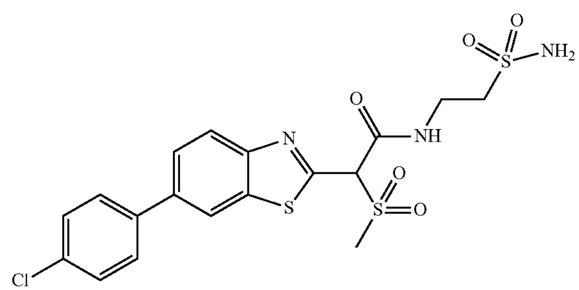 [SMILES: CS(=O)(=O)C(C(=O)NCCS(N)(=O)=O)c1nc2ccc(-c3ccc(Cl)cc3)cc2s1] | 2-[6-(4-chlorophenyl)-1,3-benzothiazol-2-yl]-2-methanesulfonyl-N-(2-sulfamoylethyl)acetamide | δ 9.01 (t, J = 5.6 Hz, 1H), 8.51 (d, J = 1.5 Hz, 1H), 8.16 (d, J = 8.5 Hz, 1H), 7.88 (dd, J = 8.5, 1.8 Hz, 1H), 7.84-7.75 (m, 2H), 7.64-7.51 (m, 2H), 6.97 (s, 2H), 6.05 (s, 1H), 3.67-3.55 (m, 2H), 3.24 (s, 3H), 3.22-3.14 (m, 2H) | 2.56 R 488.1 | 1.4 | 2.8 |
| B208 | 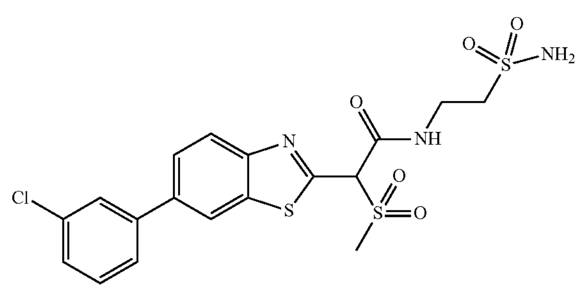 [SMILES: CS(=O)(=O)C(C(=O)NCCS(N)(=O)=O)c1nc2ccc(-c3cccc(Cl)c3)cc2s1] | 2-[6-(3-chlorophenyl)-1,3-benzothiazol-2-yl]-2-methanesulfonyl-N-(2-sulfamoylethyl)acetamide | δ 9.01 (t, J = 5.5 Hz, 1H), 8.55 (s, 1H), 8.17 (d, J = 8.5 Hz, 1H), 8.00-7.88 (m, 1H), 7.85 (s, 1H), 7.76 (d, J = 7.9 Hz, 1H), 7.55 (t, J = 7.9 Hz, 1H), 7.48 (d, J = 8.2 Hz, 1H), 6.97 (s, 2H), 6.05 (s, 1H), 3.61 (q, J = 6.6 Hz, 2H), 3.25 (s, 3H), 3.20 (t, J = 7.3 Hz, 2H) | 2.5 R 488.1 | 0.8 | 0.8 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B209 | 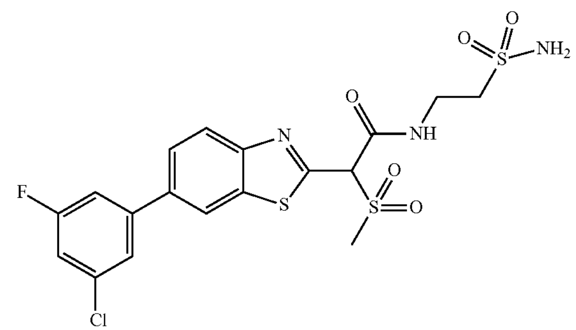 [SMILES: CS(=O)(=O)C(C(=O)NCCS(N)(=O)=O)c1nc2ccc(-c3cc(F)cc(Cl)c3)cc2s1] | 2-[6-(3-chloro-5-fluorophenyl)-1,3-benzothiazol-2-yl]-2-methanesulfonyl-N-(2-sulfamoylethyl)acetamide | δ 9.02 (t, J = 5.5 Hz, 1H), 8.61 (s, 1H), 8.17 (d, J = 8.5 Hz, 1H), 8.01-7.92 (m, 1H), 7.75 (s, 1H), 7.49 (d, J = 8.2 Hz, 2H), 6.97 (s, 2H), 6.06 (s, 1H), 3.66-3.57 (m, 2H), 3.25 (s, 3H), 3.23-3.17 (m, 2H) | 2.6 R 506.1 | 8.0 | 13.9 |
| B210 | 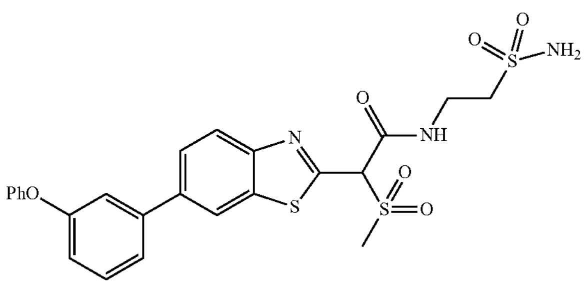 [SMILES: CS(=O)(=O)C(C(=O)NCCS(N)(=O)=O)c1nc2ccc(-c3cccc(Oc4ccccc4)c3)cc2s1] | 2-methanesulfonyl-2-[6-(3-phenoxyphenyl)-1,3-benzothiazol-2-yl]-N-(2-sulfamoylethyl)acetamide | δ 9.01 (s, 1H), 8.50 (s, 1H), 8.14 (d, J = 8.5 Hz, 1H), 7.86 (d, J = 7.0 Hz, 1H), 7.61-7.46 (m, 3H), 7.46-7.38 (m, 3H), 7.23-7.13 (m, 2H), 7.10 (d, J = 7.6 Hz, 2H), 7.03 (d, J = 7.6 Hz, 1H), 6.97 (s, 2H), 6.04 (s, 1H), 3.61 (d, J = 6.7 Hz, 2H), 3.24 (s, 3H), 3.22-3.13 (m, 2H) | 2.83 R 541.1 | 0.6 | 1.9 |
| B211 | 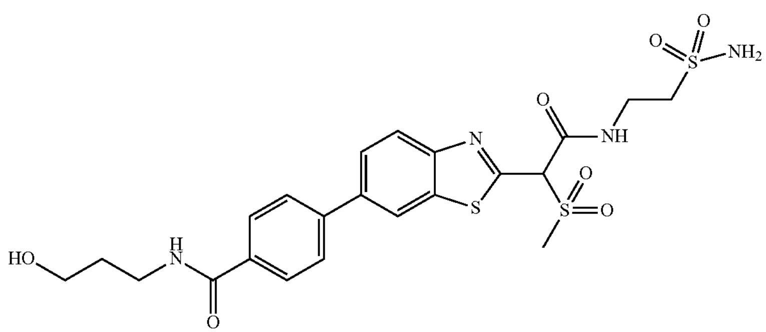 [SMILES: CS(=O)(=O)C(C(=O)NCCS(N)(=O)=O)c1nc2ccc(-c3ccc(C(=O)NCCCO)cc3)cc2s1] | N-(3-hydroxypropyl)-4-(2-{[methanesulfonyl][(2-sulfamoylethyl)carbamoyl]methyl}-1,3-benzothiazol-6-yl)benzamide | δ 9.07-8.97 (m, 1H), 8.57 (d, J = 1.8 Hz, 1H), 8.53 (t, J = 5.6 Hz, 1H), 8.18 (d, J = 8.5 Hz, 1H), 8.01-7.92 (m, 4H), 7.88 (d, J = 8.5 Hz, 2H), 6.97 (s, 2H), 6.05 (s, 1H), 4.50 (t, J = 5.2 Hz, 1H), 3.62 (q, J = 6.7 Hz, 2H), 3.53-3.43 (m, 2H), 3.39-3.35 (m, 2H), 3.25 (s, 3H), 3.22-3.17 (m, 2H), 1.71 (t, J = 6.9 Hz, 2H) | 1.53 R 554.1 | 0.7 | 57.0 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B212 | 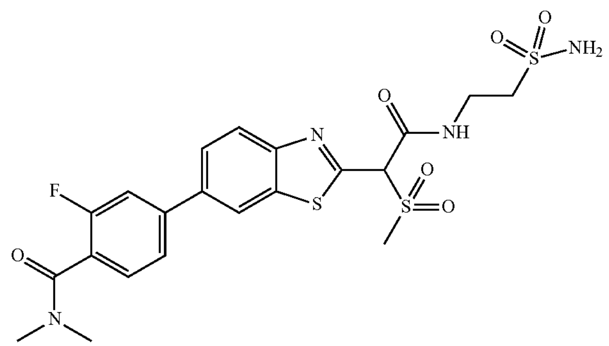 [SMILES: CN(C)C(=O)c1ccc(-c2ccc3nc(C(C(=O)NCCS(N)(=O)=O)S(C)(=O)=O)sc3c2)cc1F] | 2-fluoro-4-(2-{[methanesulfonyl][(2-sulfamoylethyl)carbamoyl]methyl}-1,3-benzothiazol-6-yl)-N,N-dimethylbenzamide | δ 9.03 (t, J = 5.5 Hz, 1H), 8.60 (d, J = 1.8 Hz, 1H), 8.18 (d, J = 8.5 Hz, 1H), 8.01-7.90 (m, 1H), 7.79-7.66 (m, 2H), 7.53 (t, J = 7.6 Hz, 1H), 6.97 (s, 2H), 6.06 (s, 1H), 3.66-3.55 (m, 2H), 3.25 (s, 3H), 3.20 (t, J = 7.5 Hz, 2H), 3.07-3.00 (m, 3H), 2.91 (s, 3H) | 1.86 R 542.1 | 1.2 | 87.9 |
| B213 | 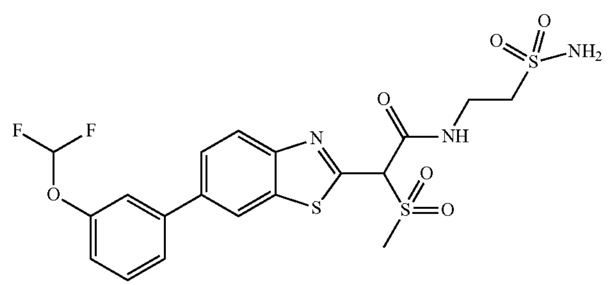 [SMILES: CS(=O)(=O)C(C(=O)NCCS(N)(=O)=O)c1nc2ccc(-c3cccc(OC(F)F)c3)cc2s1] | 2-{6-[3-(difluoromethoxy)phenyl]-1,3-benzothiazol-2-yl}-2-methanesulfonyl-N-(2-sulfamoylethyl)acetamide | δ 9.01 (t, J = 5.8 Hz, 1H), 8.55 (s, 1H), 8.18 (d, J = 8.5 Hz, 1H), 7.92 (d, J = 8.5 Hz, 1H), 7.67 (d, J = 7.9 Hz, 1H), 7.62-7.48 (m, 2H), 7.23 (d, J = 5.5 Hz, 1H), 6.97 (s, 2H), 6.05 (s, 1H), 3.66-3.56 (m, 2H), 3.25 (s, 3H), 3.20 (t, J = 7.0 Hz, 2H) | 2.40 R 519.0 | 2.8 | 3.0 |
| B214 | 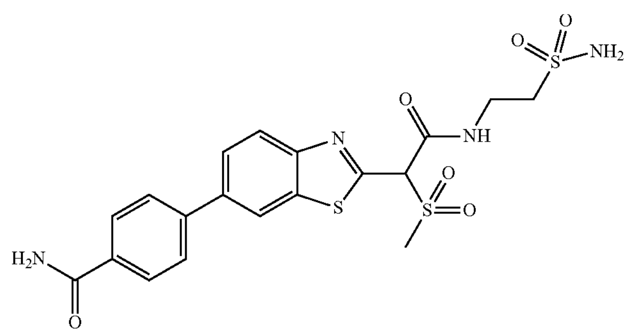 [SMILES: CS(=O)(=O)C(C(=O)NCCS(N)(=O)=O)c1nc2ccc(-c3ccc(C(N)=O)cc3)cc2s1] | 4-(2-{[methanesulfonyl][(2-sulfamoylethyl)carbamoyl]methyl}-1,3-benzothiazol-6-yl)benzamide | δ 9.01 (t, J = 5.8 Hz, 1H), 8.57 (d, J = 1.5 Hz, 1H), 8.18 (d, J = 8.5 Hz, 1H), 8.06 (br. s., 1H), 8.04-7.99 (m, 2H), 7.99-7.92 (m, 2H), 7.87 (d, J = 8.2 Hz, 2H), 7.42 (br. s., 1H), 6.97 (s, 2H), 6.05 (s, 1H), 3.66-3.57 (m, 2H), 3.25 (s, 3H), 3.22-3.16 (m, 2H) | 1.5 R 497.1 | 1.6 | 159.9 |

| Ex # | Structure | Name | ¹H NMR (500 MHz, DMSO-d₆, unless indicated otherwise) | LC/MS RT (min) Method M+H | EL IC$_{50}$ (nM) | HL IC$_{50}$ (nM) |
|---|---|---|---|---|---|---|
| B215 | 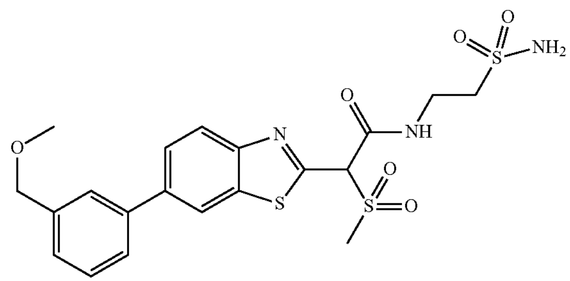 [SMILES: COCc1cccc(-c2ccc3nc(C(C(=O)NCCS(N)(=O)=O)S(C)(=O)=O)sc3c2)c1] | 2-methanesulfonyl-2-{6-[3-(methoxymethyl)phenyl]-1,3-benzothiazol-2-yl}-N-(2-sulfamoylethyl)acetamide | δ 9.01 (t, J = 5.8 Hz, 1H), 8.50 (d, J = 1.5 Hz, 1H), 8.16 (d, J = 8.5 Hz, 1H), 7.96 (s, 1H), 7.88 (dd, J = 8.5, 1.8 Hz, 1H), 7.75-7.67 (m, 2H), 7.67-7.59 (m, 1H), 7.59-7.53 (m, 1H), 7.50 (t, J = 7.6 Hz, 1H), 7.37 (d, J = 7.6 Hz, 1H), 6.97 (s, 2H), 6.04 (s, 1H), 4.52 (s, 2H), 3.61 (q, J = 6.7 Hz, 2H), 3.35 (br. s., 3H), 3.25 (br. s., 3H) 3.20 (t, J = 7.3 Hz, 2H) | 2.2 R 498.2 | 4.4 | 3.6 |
| B216 | 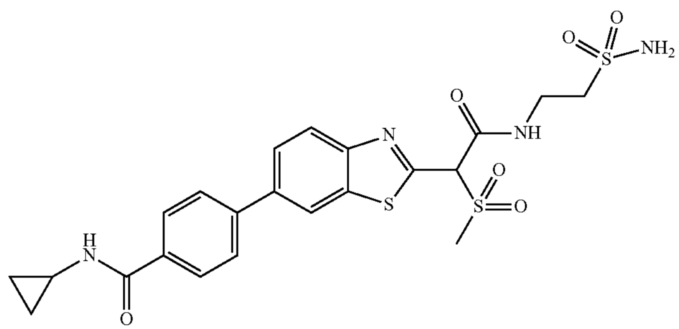 [SMILES: CS(=O)(=O)C(C(=O)NCCS(N)(=O)=O)c1nc2ccc(-c3ccc(C(=O)NC4CC4)cc3)cc2s1] | N-cyclopropyl-4-(2-{methanesulfonyl[(2-sulfamoylethyl)carbamoyl]methyl}-1,3-benzothiazol-6-yl)benzamide | δ 9.02 (d, J = 5.8 Hz, 1H), 8.57 (d, J = 1.5 Hz, 1H), 8.52 (d, J = 4.0 Hz, 1H), 8.18 (d, J = 8.5 Hz, 1H), 8.01-7.89 (m, 3H), 7.89-7.77 (m, 2H), 6.97 (s, 2H), 6.05 (s, 1H), 3.61 (q, J = 6.7 Hz, 2H), 3.25 (s, 3H), 3.23-3.15 (m, 2H), 2.89-2.85 (m, 1H), 0.76-0.68 (m, 2H), 0.64-0.58 (m, 2H) | 1.8 R 537.2 | 2.1 | 154.9 |
| B217 | 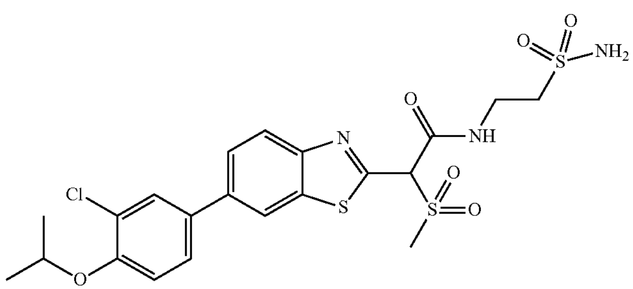 [SMILES: CC(C)Oc1ccc(-c2ccc3nc(C(C(=O)NCCS(N)(=O)=O)S(C)(=O)=O)sc3c2)cc1Cl] | 2-{6-[3-chloro-4-(propan-2-yloxy)phenyl]-1,3-benzothiazol-2-yl}-2-methanesulfonyl-N-(2-sulfamoylethyl)acetamide | δ 9.00 (t, J = 5.8 Hz, 1H), 8.48 (d, J = 1.5 Hz, 1H), 8.12 (d, J = 8.9 Hz, 1H), 7.86-7.82 (m, 1H), 7.70 (dd, J = 8.5, 2.4 Hz, 1H), 7.30 (d, J = 8.9 Hz, 1H), 6.97 (s, 2H), 6.03 (s, 1H), 4.76 (dt, J = 12.1, 6.2 Hz, 1H), 3.61 (q, J = 6.7 Hz, 2H), 3.24 (s, 3H), 3.20 (t, J = 7.5 Hz, 2H), 1.37-1.30 (m, 6H) | 2.8 R 546.1 | 2.3 | 3.6 |

| Ex # | Structure | Name | ¹H NMR (500 MHz, DMSO-d₆, unless indicated otherwise) | LC/MS RT (min) Method M+H | EL IC$_{50}$ (nM) | HL IC$_{50}$ (nM) |
|---|---|---|---|---|---|---|
| B218 | 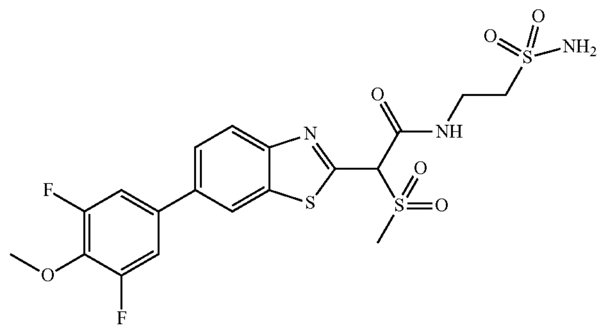 [SMILES: COc1c(F)cc(-c2ccc3nc(C(C(=O)NCCS(N)(=O)=O)S(C)(=O)=O)sc3c2)cc1F] | 2-[6-(3,5-difluoro-4-methoxyphenyl)-1,3-benzothiazol-2-yl]-2-methanesulfonyl-N-(2-sulfamoylethyl)acetamide | δ 9.01 (t, J = 5.6 Hz, 1H), 8.60 (s, 1H), 8.17 (d, J = 8.5 Hz, 1H), 8.02-7.89 (m, 3H), 7.57 (d, J = 8.5 Hz, 2H), 6.97 (s, 2H), 6.05 (s, 1H), 5.31 (t, J = 5.6 Hz, 1H), 4.55 (d, J = 5.2 Hz, 2H), 3.61 (q, J = 6.6 Hz, 2H), 3.24 (s, 3H), 3.20 (t, J = 7.3 Hz, 2H) | 1.84 R 519.0 | 1.7 | 5.2 |
| B219 | 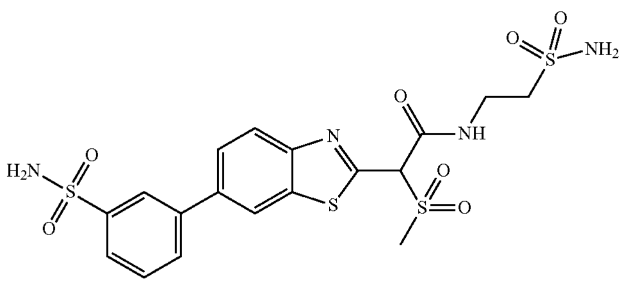 [SMILES: CS(=O)(=O)C(C(=O)NCCS(N)(=O)=O)c1nc2ccc(-c3cccc(S(N)(=O)=O)c3)cc2s1] | 2-methanesulfonyl-N-(2-sulfamoylethyl)-2-[6-(3-sulfamoylphenyl)-1,3-benzothiazol-2-yl]acetamide | δ 9.01 (t, J = 5.5 Hz, 1H), 8.56 (d, J = 1.5 Hz, 1H), 8.26-8.17 (m, 2H), 8.01 (d, J = 7.6 Hz, 1H), 7.96 (s, 2H), 7.91 (dd, J = 8.5, 1.8 Hz, 1H), 7.87 (d, J = 7.9 Hz, 1H), 7.72 (t, J = 7.8 Hz, 1H), 7.45 (s, 2H), 6.97 (s, 2H), 6.06 (s, 1H), 3.62 (q, J = 6.9 Hz, 2H), 3.26 (s, 3H), 3.23-3.15 (m, 2H) | 1.62 R 532.0 | 2.2 | 141.8 |
| B220 | 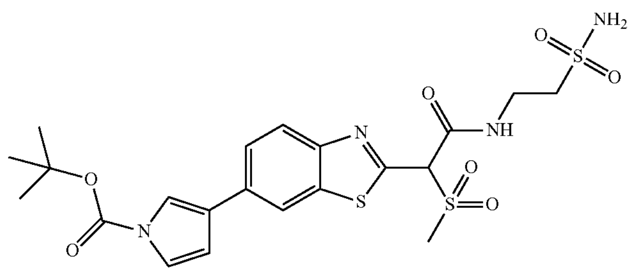 [SMILES: CC(C)(C)OC(=O)n1ccc(-c2ccc3nc(C(C(=O)NCCS(N)(=O)=O)S(C)(=O)=O)sc3c2)c1] | tert-butyl 3-(2-{[methanesulfonyl][(2-sulfamoylethyl)carbamoyl]methyl}-1,3-benzothiazol-6-yl)-1H-pyrrole-1-carboxylate | δ 9.00 (br. s., 1H), 8.48 (br. s., 1H), 8.05 (d, J = 8.3 Hz, 1H), 7.90 (d, J = 8.5 Hz, 1H), 7.85 (br. s., 1H), 7.38 (br. s., 1H), 6.98 (br. s., 2H), 6.86 (br. s., 1H), 6.01 (br. s., 1H), 3.68-3.54 (m, 2H), 3.24 (br. s., 3H), 3.19 (br. s., 2H), 1.61 (br. s., 9H) | 1.8 N 543.2 | 51.4 | 2.8 |

| Ex # | Structure | Name | 1H NMR (500 MHz, DMSO-d6, unless indicated otherwise) | LC/MS RT (min) Method M + H | EL IC50 (nM) | HL IC50 (nM) |
|---|---|---|---|---|---|---|
| B221 | 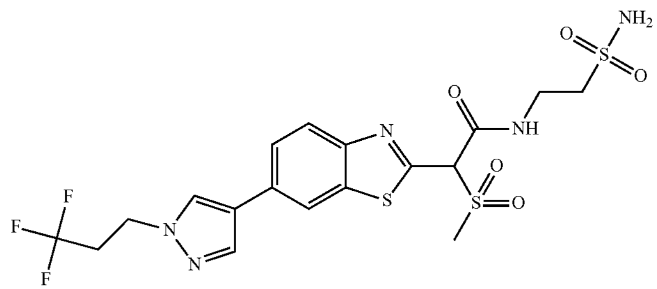 [SMILES: CS(=O)(=O)C(C(=O)NCCS(N)(=O)=O)c1nc2ccc(-c3cnn(CCC(F)(F)F)c3)cc2s1] | 2-methanesulfonyl-N-(2-sulfamoylethyl)-2-{6-[1-(3,3,3-trifluoropropyl)-1H-pyrazol-4-yl]-1,3-benzothiazol-2-yl}acetamide | δ 8.98 (t, J = 5.6 Hz, 1H), 8.43-8.31 (m, 2H), 8.12-8.00 (m, 2H), 7.79 (dd, J = 8.5, 1.7 Hz, 1H), 6.96 (s, 2H), 6.00 (s, 1H), 4.44 (t, J = 6.9 Hz, 2H), 3.61 (q, J = 6.6 Hz, 2H), 3.27-3.22 (m, 3H), 3.22-3.14 (m, 2H), 3.02-2.87 (m, 2H) | 1.4 N 540.1 | 78.1 | 308.1 |
| B222 | 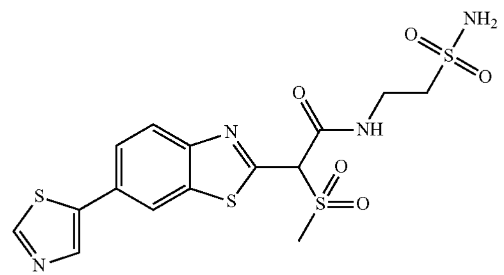 [SMILES: CS(=O)(=O)C(C(=O)NCCS(N)(=O)=O)c1nc2ccc(-c3cncs3)cc2s1] | 2-methanesulfonyl-N-(2-sulfamoylethyl)-2-{6-(1,3-thiazol-5-yl)-1,3-benzothiazol-2-yl]acetamide | δ 9.15 (s, 1H), 9.01 (s, 1H), 8.55 (d, J = 1.7 Hz, 1H), 8.44 (s, 1H), 8.15 (d, J = 8.8 Hz, 1H), 7.92 (dd, J = 8.5, 1.7 Hz, 1H), 6.96 (s, 2H), 6.05 (s, 1H), 3.66-3.56 (m, 2H), 3.25 (s, 3H), 3.23-3.14 (m, 2H) | 1.1 N 461 | 12.3 | 31.6 |
| B223 | 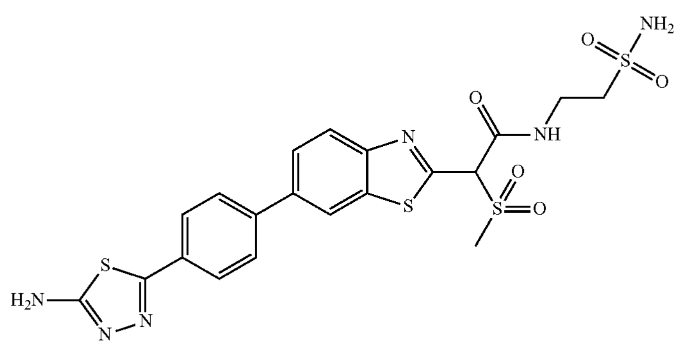 [SMILES: CS(=O)(=O)C(C(=O)NCCS(N)(=O)=O)c1nc2ccc(-c3ccc(-c4nnc(N)s4)cc3)cc2s1] | 2-{6-[4-(5-amino-1,3,4-thiadiazol-2-yl)phenyl]-1,3-benzothiazol-2-yl}-2-methanesulfonyl-N-(2-sulfamoylethyl)acetamide | δ 9.02 (t, J = 5.8 Hz, 1H), 8.58 (s, 1H), 8.19 (d, J = 8.5 Hz, 1H), 8.00-7.92 (m, 3H), 7.48 (br. s., 2H), 6.97 (s, 2H), 6.06 (s, 1H), 3.92 (s, 1H), 3.67-3.60 (m, 2H), 3.26 (s, 3H), 3.24-3.14 (m, 2H) | 1.2 N 553.1 | 1.2 | 7.7 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B224 | 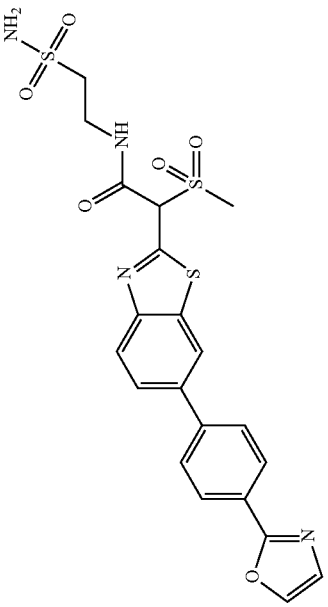 | 2-methanesulfonyl-2-{6-[4-(1,3-oxazol-2-yl)phenyl]-1,3-benzothiazol-2-yl}-N-(2-sulfamoylethyl)acetamide | δ 9.01 (br. s., 1H), 8.60 (s, 1H), 8.40 (d, J = 9.4 Hz, 1H), 8.29 (d, J = 6.3 Hz, 1H), 8.22-8.01 (m, 4H), 7.97 (d, J = 7.2 Hz, 2H), 7.45 (d, J = 6.1 Hz, 1H), 7.02 (s, 1H), 6.97 (s, 1H), 3.62 (d, J = 6.1 Hz, 2H), 3.46 (s, 2H), 3.21 (d, J = 6.9 Hz, 3H) | 1.5 N 521.1 | 8.4 | 10.0 |
| B225 | 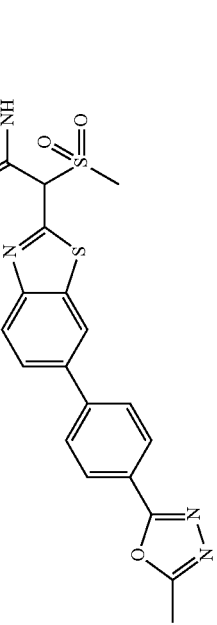 | 2-methanesulfonyl-2-{6-[4-(5-methyl-1,3,4-oxadiazol-2-yl)phenyl]-1,3-benzothiazol-2-yl}-N-(2-sulfamoylethyl)acetamide | δ 9.03 (s, 1H), 8.63 (s, 1H), 8.21 (d, J = 8.5 Hz, 1H), 8.15-8.09 (m, J = 8.3 Hz, 2H), 8.07-8.01 (m, J = 9.6 Hz, 2H), 7.98 (d, J = 9.6 Hz, 1H), 6.97 (s, 2H), 6.07 (s, 1H), 3.63 (q, J = 6.6 Hz, 2H), 3.26 (s, 3H), 3.21 (t, J = 7.0 Hz, 2H), 2.63 (s, 3H) | 1.3 N 536.2 | 4.9 | 15.4 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B226 | 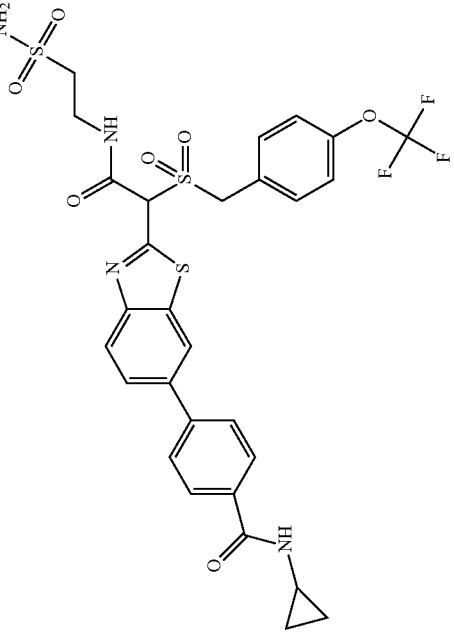 | N-cyclopropyl-4-(2-{[(2-sulfamoylethyl)carbamoyl][4-(trifluoromethoxy)phenyl]methyl}-1,3-benzothiazol-6-yl)benzamide | δ 9.05 (br. s., 1H), 8.50 (d, J = 18.7 Hz, 1H), 8.26-8.10 (m, 1H), 8.01-7.90 (m, 2H), 7.90-7.82 (m, 1H), 7.78 (d, J = 11.0 Hz, 1H), 7.55 (d, J = 7.7 Hz, 1H), 7.52-7.44 (m, 1H), 7.40 (d, J = 7.7 Hz, 1H), 7.27 (br. s., 1H), 6.97 (br. s., 2H), 4.89-4.78 (m, 1H), 4.76-4.59 (m, 1H), 3.63 (d, J = 5.5 Hz, 2H), 3.27-3.13 (m, 2H), 2.91 (br. s., 1H), 0.73 (br. s., 2H), 0.62 (br. s., 2H) | 1.6 N 697.1 | 0.5 | 74.0 |
| B227 | 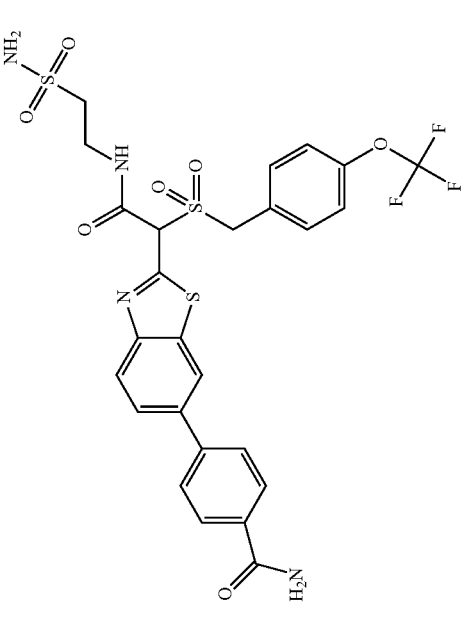 | 4-(2-{[(2-sulfamoylethyl)carbamoyl][4-(trifluoromethoxy)phenyl]methyl}-1,3-benzothiazol-6-yl)benzamide | δ 9.05 (br. s., 1H), 8.09-8.00 (m, 2H), 8.00-7.93 (m, 2H), 7.88 (d, J = 7.7 Hz, 1H), 7.77 (br. s., 2H), 7.56 (d, J = 8.0 Hz, 1H), 7.49 (d, J = 7.7 Hz, 1H), 7.40 (d, J = 8.5 Hz, 2H), 6.97 (br. s., 2H), 4.83 (d, J = 5.8 Hz, 1H), 4.75-4.57 (m, 1H), 3.63 (d, J = 6.1 Hz, 2H), 3.22 (t, J = 6.9 Hz, 2H) | 1.5 N 657.2 | 0.5 | 80.8 |

| Ex # | Structure | Name | $^1$H NMR (500 MHz, DMSO-$d_6$, unless indicated otherwise) | LC/MS RT (min) Method M+H | EL IC$_{50}$ (nM) | HL IC$_{50}$ (nM) |
|---|---|---|---|---|---|---|
| B228 | 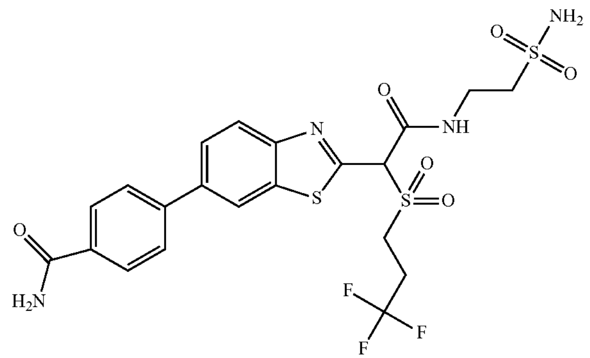 [SMILES: NC(=O)c1ccc(-c2ccc3nc(C(C(=O)NCCS(N)(=O)=O)S(=O)(=O)CCC(F)(F)F)sc3c2)cc1] | 4-(2-{[(2-sulfamoylethyl)carbamoyl](3,3,3-trifluoropropanesulfonyl)methyl}-1,3-benzothiazol-6-yl)benzamide | δ 8.98 (br. s., 1H), 8.60 (s, 1H), 8.19 (d, J = 8.5 Hz, 1H), 8.10-8.01 (m, 2H), 8.01-7.93 (m, 2H), 7.88 (d, J = 8.0 Hz, 2H), 7.80 (d, J = 6.6 Hz, 1H), 7.42 (br. s., 1H), 6.97 (s, 2H), 6.29 (s, 1H), 3.86-3.67 (m, 2H), 3.67-3.57 (m, 2H), 3.21 (t, J = 7.0 Hz, 2H), 2.87 (d, J = 9.1 Hz, 2H) | 1.3 N 579.15 | 9.2 | 249.6 |
| B229 | 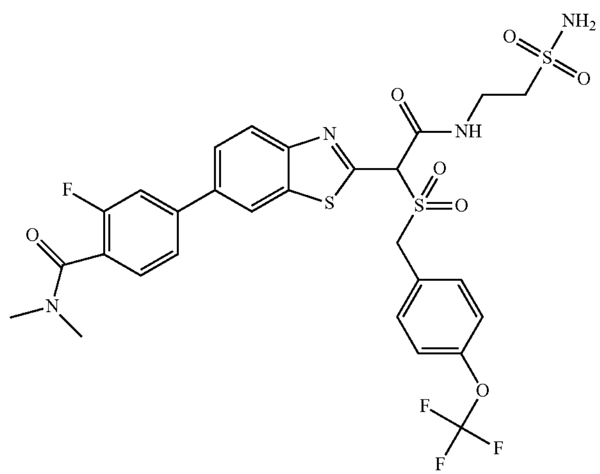 [SMILES: CN(C)C(=O)c1ccc(-c2ccc3nc(C(C(=O)NCCS(N)(=O)=O)S(=O)(=O)Cc4ccc(OC(F)(F)F)cc4)sc3c2)cc1F] | 2-fluoro-N,N-dimethyl-4-(2-{[(2-sulfamoylethyl)carbamoyl][4-(trifluoromethoxy)phenyl]methanesulfonyl]methyl}-1,3-benzothiazol-6-yl)benzamide | δ 8.26-8.12 (m, 1H), 8.01-7.95 (m, 1H), 7.94-7.79 (m, 1H), 7.78-7.69 (m, 1H), 7.68-7.58 (m, 1H), 7.58-7.51 (m, 1H), 7.48 (br. s., 1H), 7.40 (d, J = 7.7 Hz, 1H), 7.28 (d, J = 9.1 Hz, 1H), 7.22 (br. s., 1H), 7.11 (br. s., 1H), 7.01 (br. s., 1H), 6.97 (br. s., 1H), 4.92-4.76 (m, 1H), 4.75-4.60 (m, 1H), 3.63 (d, J = 5.5 Hz, 2H), 3.26-3.17 (m, 2H), 3.05 (br. s., 3H), 2.95-2.88 (m, 3H) | 1.67 N 703.1 | 29.2 | 242.3 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B230 | 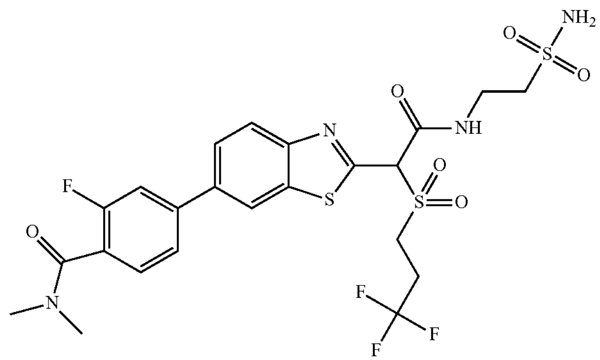 [SMILES: CN(C)C(=O)c1ccc(-c2ccc3nc(C(C(=O)NCCS(N)(=O)=O)S(=O)(=O)CCC(F)(F)F)sc3c2)cc1F] | 2-fluoro-N,N-dimethyl-4-(2-{[(2-sulfamoylethyl)carbamoyl](3,3,3-trifluoropropanesulfonyl)methyl}-1,3-benzothiazol-6-yl)benzamide | δ 9.00 (br. s., 1H), 8.62 (s, 1H), 8.19 (d, J = 8.3 Hz, 1H), 8.02-7.93 (m, 1H), 7.78-7.70 (m, 1H), 7.65 (br. s., 1H), 7.57-7.43 (m, 1H), 6.97 (br. s., 2H), 6.29 (s, 1H), 3.86-3.69 (m, 2H), 3.68-3.56 (m, 2H), 3.21 (t, J = 7.6 Hz, 2H), 3.05 (br. s., 3H), 2.92 (d, J = 6.6 Hz, 4H), 2.89-2.81 (m, 1H) | 1.4 N 625.1 | 4.6 | 37.4 |
| B231 | 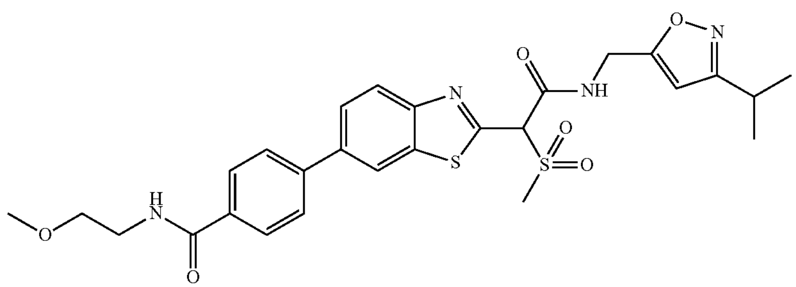 [SMILES: COCCNC(=O)c1ccc(-c2ccc3nc(C(C(=O)NCc4cc(C(C)C)no4)S(C)(=O)=O)sc3c2)cc1] | 4-{2-[methanesulfonyl({[3-(propan-2-yl)-1,2-oxazol-5-yl]methyl}carbamoyl)methyl]-1,3-benzothiazol-6-yl}-N-(2-methoxyethyl)benzamide | δ 9.40 (t, J = 5.8 Hz, 1H), 8.56 (t, J = 5.2 Hz, 1H), 8.53 (d, J = 1.7 Hz, 1H), 8.14 (d, J = 8.5 Hz, 1H), 7.98-7.92 (m, 2H), 7.92-7.88 (m, 1H), 7.86-7.78 (m, 1H), 7.92-7.88 (m, 1H), 6.30 (s, 1H), 6.02 (s, 1H), Hz, 2H), 6.30 (s, 1H), 6.02 (s, 1H), 4.61-4.41 (m, 2H), 3.51-3.39 (m, 4H), 3.25-3.23 (m, 3H), 3.20 (s, 3H), 2.92 (quin, J = 6.9 Hz, 1H), 1.15 (s, 3H), 1.13 (s, 3H) | 1.50 N 573.2 | 290.9 | 18.5 |
| B232 | 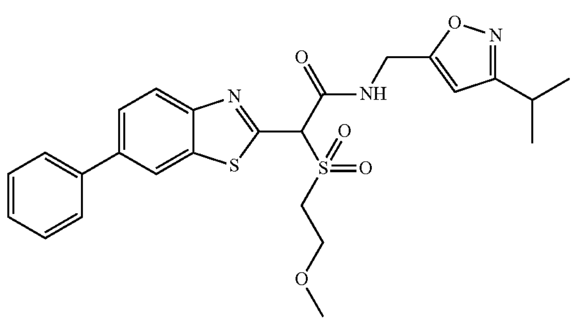 [SMILES: COCCS(=O)(=O)C(C(=O)NCc1cc(C(C)C)no1)c1nc2ccc(-c3ccccc3)cc2s1] | 2-(2-methoxyethanesulfonyl)-2-(6-phenyl-1,3-benzothiazol-2-yl)-N-{[3-(propan-2-yl)-1,2-oxazol-5-yl]methyl}acetamide | δ 9.43 (s, 1H), 8.50 (d, J = 1.7 Hz, 1H), 8.17 (d, J = 8.8 Hz, 1H), 7.89 (dd, J = 8.5, 1.9 Hz, 1H), 7.82-7.74 (m, 2H), 7.53 (t, J = 7.7 Hz, 2H), 7.44 (d, J = 7.4 Hz, 1H), 6.34 (s, 1H), 6.08 (s, 1H), 4.56 (dd, J = 5.5, 3.3 Hz, 2H), 3.83-3.72 (m, 2H), 3.72-3.64 (m, 2H), 3.28 (s, 3H), 3.02-2.92 (m, 1H), 1.23-1.17 (m, 6H) | 2.09 N 514.25 | 45.9 | 0.8 |

| Ex # | Structure | Name | $^1$H NMR (500 MHz, DMSO-$d_6$, unless indicated otherwise) | LC/MS RT (min) Method M+H | EL IC$_{50}$ (nM) | HL IC$_{50}$ (nM) |
|---|---|---|---|---|---|---|
| B233 | 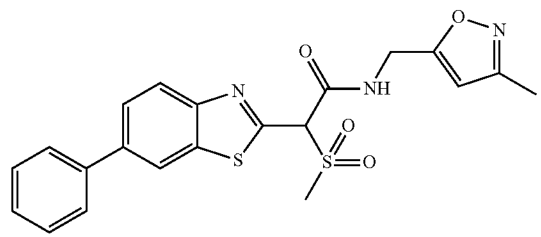 [SMILES: Cc1cc(CNC(=O)C(c2nc3ccc(-c4ccccc4)cc3s2)S(C)(=O)=O)on1] | 2-methanesulfonyl-N-[(3-methyl-1,2-oxazol-5-yl)methyl]-2-(6-phenyl)-1,3-benzothiazol-2-yl)acetamide | δ 9.44 (s, 1H), 8.50 (d, J = 1.4 Hz, 1H), 8.18 (d, J = 8.5 Hz, 1H), 7.89 (dd, J = 8.5, 1.9 Hz, 1H), 7.81-7.75 (m, 2H), 7.53 (t, J = 7.7 Hz, 2H), 7.44 (d, J = 7.2 Hz, 1H), 6.26 (s, 1H), 6.06 (s, 1H), 4.57 (dd, J = 8.0, 5.8 Hz, 2H), 3.25 (s, 3H), 2.21 (s, 3H) | 1.79 N 442.1 | 31.6 | 3.6 |
| B234 | 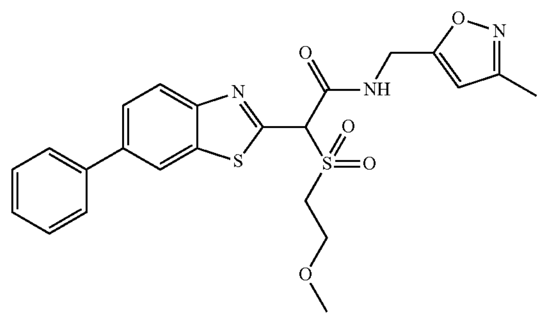 [SMILES: COCCS(=O)(=O)C(C(=O)NCc1cc(C)no1)c1nc2ccc(-c3ccccc3)cc2s1] | 2-(2-methoxyethane-sulfonyl)-N-[(3-methyl-1,2-oxazol-5-yl)methyl]-2-(6-phenyl)-1,3-benzothiazol-2-yl)acetamide | δ 9.47 (s, 1H), 8.50 (d, J = 1.7 Hz, 1H), 8.17 (d, J = 8.5 Hz, 1H), 7.89 (dd, J = 8.7, 1.8 Hz, 1H), 7.83-7.74 (m, 2H), 7.53 (t, J = 7.7 Hz, 2H), 7.44 (d, J = 7.4 Hz, 1H), 6.26 (s, 1H), 6.09 (s, 1H), 4.64-4.45 (m, 2H), 3.85-3.70 (m, 2H), 3.70-3.62 (m, 2H), 3.27 (s, 3H), 2.21 (s, 3H) | 1.89 N 486.15 | 4.9 | 0.5 |
| B235 | 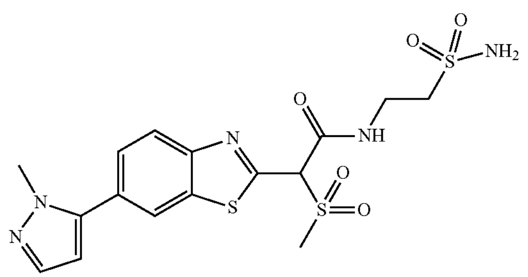 [SMILES: Cn1nccc1-c1ccc2nc(C(C(=O)NCCS(N)(=O)=O)S(C)(=O)=O)sc2c1] | 2-methanesulfonyl-2-[6-(1-methyl-1H-pyrazol-5-yl)-1,3-benzothiazol-2-yl]-N-(2-sulfamoylethyl)acetamide | δ 9.00 (t, J = 5.6 Hz, 1H), 8.44-8.34 (m, 1H), 8.19 (d, J = 8.5 Hz, 1H), 7.77-7.67 (m, 1H), 7.52 (d, J = 1.7 Hz, 1H), 6.96 (s, 2H), 6.51 (d, J = 1.9 Hz, 1H), 6.06 (s, 1H), 3.91 (s, 3H), 3.65-3.57 (m, 2H), 3.25 (s, 3H), 3.22-3.16 (m, 2H) | 0.64 M 457.7 | 5.1 | 3051.0 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B236 | 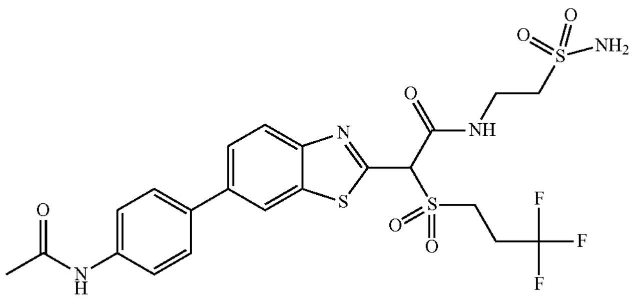 [SMILES: CC(=O)Nc1ccc(-c2ccc3nc(C(C(=O)NCCS(N)(=O)=O)S(=O)(=O)CCC(F)(F)F)sc3c2)cc1] | 2-[6-(4-acetamidophenyl)-1,3-benzothiazol-2-yl]-N-(2-sulfamoylethyl)-2-(3,3,3-trifluoropropanesulfonyl)acetamide | δ 10.25-9.93 (m, 1H), 9.09-8.88 (m, 1H), 8.53-8.41 (m, 1H), 8.21-8.08 (m, 1H), 7.97-7.83 (m, 1H), 7.71 (s, 4H), 6.95 (s, 2H), 6.39-6.13 (m, 1H), 3.84-3.48 (m, 4H), 3.25-3.11 (m, 2H), 2.95-2.76 (m, 2H), 2.08 (s, 3H) | 1.42 N 593.1 | 0.8 | 55.3 |
| B237 | 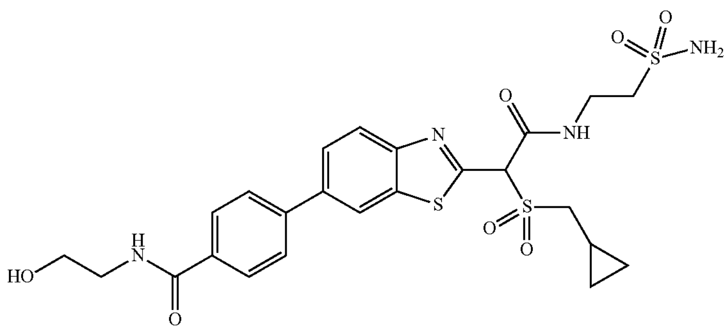 [SMILES: NS(=O)(=O)CCNC(=O)C(c1nc2ccc(-c3ccc(C(=O)NCCO)cc3)cc2s1)S(=O)(=O)CC1CC1] | 4-(2-{cyclopropylmethanesulfonyl[(2-sulfamoylethyl)carbamoyl]methyl}-1,3-benzothiazol-6-yl)-N-(2-hydroxyethyl)benzamide | δ 9.21-8.89 (m, 1H), 8.55 (d, J = 1.4 Hz, 2H), 8.15 (d, J = 8.8 Hz, 1H), 8.04-7.66 (m, 5H), 6.94 (s, 2H), 6.05 (s, 1H), 4.91-4.65 (m, 1H), 3.53 (d, J = 5.5 Hz, 4H), 3.35 (d, J = 5.8 Hz, 3H), 3.18 (br. s., 3H), 1.14-0.97 (m, 1H), 0.61 (s, 3H), 0.43-0.14 (m, 1H) | 0.69 O 476.7 | 3.7 | 499.2 |
| B238 | 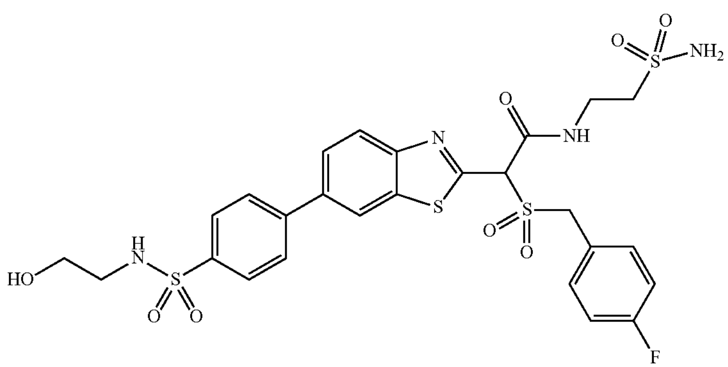 [SMILES: NS(=O)(=O)CCNC(=O)C(c1nc2ccc(-c3ccc(S(=O)(=O)NCCO)cc3)cc2s1)S(=O)(=O)Cc1ccc(F)cc1] | 2-[(4-fluorophenyl)methanesulfonyl]-2-(6-{4-[(2-hydroxyethyl)sulfamoyl]phenyl}-1,3-benzothiazol-2-yl)-N-(2-sulfamoylethyl)acetamide | δ 8.29-8.12 (m, 1H), 8.04-7.83 (m, 6H), 7.73-7.64 (m, 1H), 7.46 (br. s., 1H), 7.38 (br. s., 1H), 7.24 (t, J = 8.3 Hz, 1H), 7.09 (br. s., 1H), 7.04-6.91 (m, 2H), 6.08 (s, 1H), 4.73 (d, J=15.1 Hz, 2H), 4.68-4.54 (m, 1H), 3.59 (br. s., 2H), 3.39 (br. s., 2H), 3.23-3.10 (m, 2H), 2.83 (br. s., 2H) | 1.42 N 671.1 | 9.8 | 233.8 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B239 | 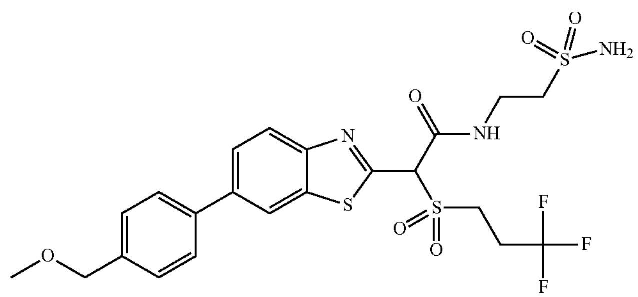 [SMILES: COCc1ccc(-c2ccc3nc(C(C(=O)NCCS(N)(=O)=O)S(=O)(=O)CCC(F)(F)F)sc3c2)cc1] | 2-{6-[4-(methoxymethyl)phenyl]-1,3-benzothiazol-2-yl}-N-(2-sulfamoylethyl)-2-(3,3,3-trifluoropropanesulfonyl)acetamide | δ 8.83 (s, 1H), 8.58 (s, 1H), 8.47 (d, J = 1.4 Hz, 1H), 8.03 (d, J = 8.5 Hz, 1H), 8.00-7.93 (m, 2H), 7.92-7.80 (m, 3H), 4.51-4.13 (m, 2H), 4.05-3.84 (m, 2H), 3.64 (s, 2H), 3.53-3.41 (m, 4H), 3.33-3.21 (m, 3H) | 1.79 N 580.1 | 9.4 | 7.3 |
| B240 | 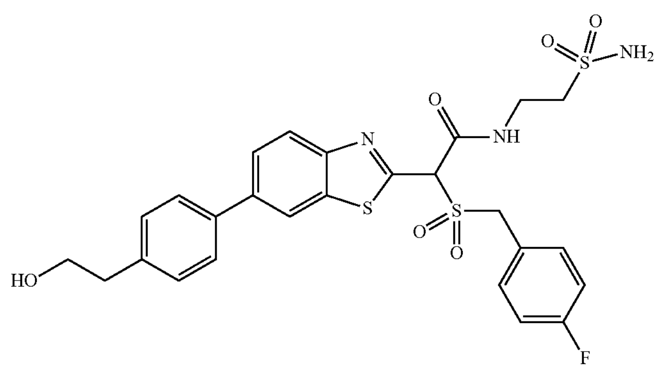 [SMILES: NS(=O)(=O)CCNC(=O)C(c1nc2ccc(-c3ccc(CCO)cc3)cc2s1)S(=O)(=O)Cc1ccc(F)cc1] | 2-[(4-fluorophenyl)methanesulfonyl]-2-{6-[4-(2-hydroxyethyl)phenyl]-1,3-benzothiazol-2-yl}-N-(2-sulfamoylethyl)acetamide | δ 8.24-7.97 (m, 1H), 7.88-7.57 (m, 3H), 7.52-7.10 (m, 5H), 6.97 (br. s., 2H), 4.85-4.52 (m, 3H), 3.72-3.53 (m, 4H), 3.25-3.08 (m, 2H), 2.87-2.68 (m, 2H) | 1.55 N 592.1 | 25.7 | 76.6 |
| B241 | 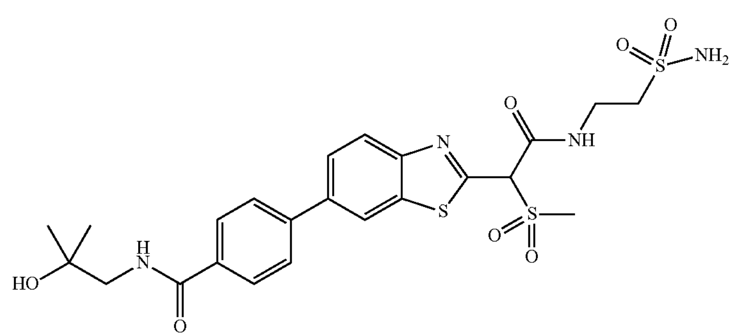 [SMILES: CC(C)(O)CNC(=O)c1ccc(-c2ccc3nc(C(C(=O)NCCS(N)(=O)=O)S(C)(=O)=O)sc3c2)cc1] | N-(2-hydroxy-2-methylpropyl)-4-(2-{(methanesulfonyl)[(2-sulfamoylethyl)carbamoyl]methyl}-1,3-benzothiazol-6-yl)benzamide | δ 9.13-8.90 (m, 1H), 8.62-8.49 (m, 1H), 8.44-8.31 (m, 1H), 8.25-8.15 (m, 1H), 8.07-7.84 (m, 4H), 7.24-6.93 (m, 2H), 6.15-5.95 (m, 1H), 4.75-4.52 (m, 1H), 3.65-3.54 (m, 2H), 3.32-3.13 (m, 8H), 1.12 (br. s., 6H) | 1.11 N 569.1 | 6.4 | 607.0 |

| Ex # | Structure | Name | $^1$H NMR (500 MHz, DMSO-d$_6$, unless indicated otherwise) | LC/MS RT (min) Method M + H | EL IC$_{50}$ (nM) | HL IC$_{50}$ (nM) |
|---|---|---|---|---|---|---|
| B242 | 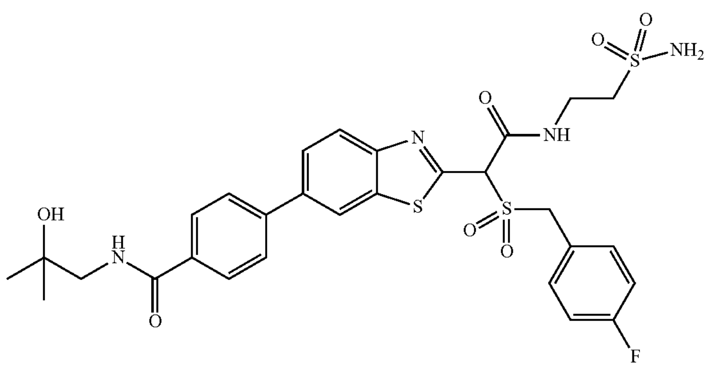 [SMILES: CC(C)(O)CNC(=O)c1ccc(-c2ccc3nc(C(C(=O)NCCS(N)(=O)=O)S(=O)(=O)Cc4ccc(F)cc4)sc3c2)cc1] | 4-{2-[(4-fluorophenyl)methanesulfonyl][(2-sulfamoylethyl)carbamoyl]methyl]-1,3-benzothiazol-6-yl}-N-(2-hydroxy-2-methylpropyl)benzamide | δ 8.44-8.12 (m, 2H), 8.06-7.76 (m, 5H), 7.46 (br. s., 2H), 7.26-6.95 (m, 5H), 6.08 (s, 1H), 4.75 (d, J = 5.5 Hz, 1H), 4.57 (br. s., 1H), 3.60 (d, J = 6.1 Hz, 2H), 3.29 (br. s., 2H), 3.20 (d, J = 6.9 Hz, 2H), 1.13 (br. s., 6H) | 1.42 N 663.1 | 2.7 | 109.3 |
| B243 | 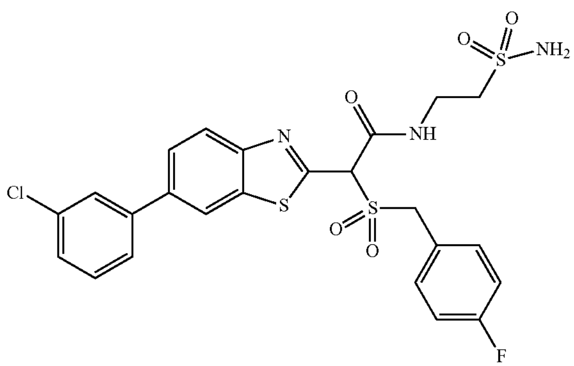 [SMILES: NS(=O)(=O)CCNC(=O)C(c1nc2ccc(-c3cccc(Cl)c3)cc2s1)S(=O)(=O)Cc1ccc(F)cc1] | 2-[6-(3-chlorophenyl)-1,3-benzothiazol-2-yl]-2-[(4-fluorophenyl)methanesulfonyl]-N-(2-sulfamoylethyl)acetamide | δ 8.25-8.03 (m, 1H), 7.98-7.65 (m, 4H), 7.59-7.09 (m, 6H), 6.95 (s, 2H), 6.07 (s, 1H), 4.75 (d, J = 5.2 Hz, 2H), 3.60 (d, J = 6.1 Hz, 2H), 3.19 (t, J = 6.9 Hz, 2H) | 2.05 N 582.0 | 4.8 | 2.4 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B244 | 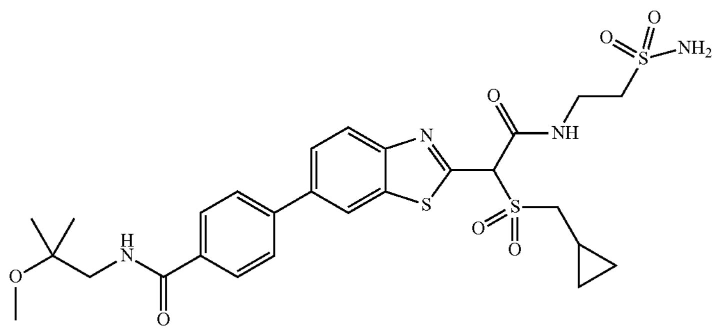 [SMILES: COC(C)(C)CNC(=O)c1ccc(-c2ccc3nc(C(C(=O)NCCS(N)(=O)=O)S(=O)(=O)CC4CC4)sc3c2)cc1] | 4-(2-{cyclopropylmethane-sulfonyl[(2-sulfamoyl-ethyl)carbamoyl]methyl}-1,3-benzothiazol-6-yl)-N-(2-methoxy-2-methyl-propyl)benzamide | δ 9.02-8.80 (m, 1H), 8.49-8.37 (m, 1H), 8.25-8.12 (m, 1H), 8.07-7.98 (m, 1H), 7.93-7.72 (m, 4H), 7.70-7.57 (m, 1H), 6.89-6.70 (m, 2H), 6.06-5.85 (m, 1H), 3.88-3.64 (m, 1H), 3.58-3.42 (m, 2H), 3.33-3.21 (m, 3H), 3.17-3.11 (m, 6H), 3.09-2.99 (m, 5H), 0.98-0.93 (m, 1H), 0.58-0.35 (m, 2H), 0.36-0.11 (m, 2H) | 1.43 N 623.2 | 0.9 | 12.0 |
| B245 | 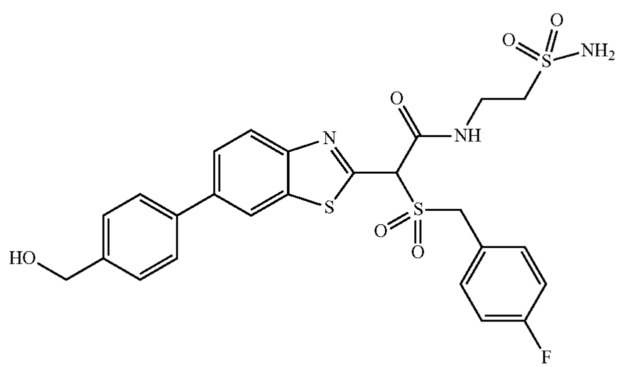 [SMILES: NS(=O)(=O)CCNC(=O)C(c1nc2ccc(-c3ccc(CO)cc3)cc2s1)S(=O)(=O)Cc1ccc(F)cc1] | 2-[(4-fluorophenyl)meth-anesulfonyl]-2-{6-[4-(hydroxymethyl)phenyl]-1,3-benzothiazol-2-yl}-N-(2-sulfamoylethyl)a-cetamide | δ 9.02 (s, 1H), 8.48 (d, J = 1.7 Hz, 1H), 8.17 (d, J = 8.5 Hz, 1H), 7.88 (dd, J = 8.5, 1.9 Hz, 1H), 7.74 (d, J = 8.3 Hz, 2H), 7.64 (br. s., 1H), 7.50-7.32 (m, 4H), 7.23 (t, J = 8.8 Hz, 1H), 7.16-7.07 (m, 1H), 6.95 (s, 2H), 5.42-5.10 (m, 1H), 4.75 (d, J = 6.9 Hz, 1H), 4.67-4.50 (m, 3H), 3.79-3.57 (m, 2H), 3.25-3.12 (m, 2H) | 1.49 N 578.1 | 2.1 | 130.4 |

| Ex # | Structure | Name | 1H NMR (500 MHz, DMSO-d6, unless indicated otherwise) | LC/MS RT (min) Method M + H | EL IC50 (nM) | HL IC50 (nM) |
|---|---|---|---|---|---|---|
| B246 | 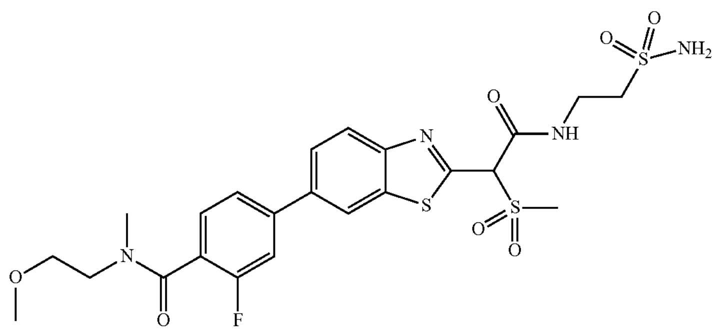 [SMILES: COCCN(C)C(=O)c1ccc(-c2ccc3nc(C(C(=O)NCCS(N)(=O)=O)S(C)(=O)=O)sc3c2)cc1F] | 2-fluoro-4-(2-{methanesulfonyl[(2-sulfamoylethyl)carbamoyl]methyl}-1,3-benzothiazol-6-yl)-N-(2-methoxyethyl)-N-methylbenzamide | δ 9.09-8.95 (m, 1H), 8.47-8.39 (m, 1H), 8.24-8.17 (m, 1H), 7.81-7.75 (m, 1H), 7.73-7.65 (m, 1H), 7.51-7.31 (m, 2H), 7.05-6.91 (m, 2H), 6.29-5.98 (m, 1H), 3.74-3.58 (m, 4H), 3.52-3.42 (m, 2H), 3.29-3.24 (m, 5H), 3.23-3.12 (m, 3H), 3.09-2.96 (m, 3H) | 1.17 N 587.1 | 2.8 | 94.4 |
| B247 | 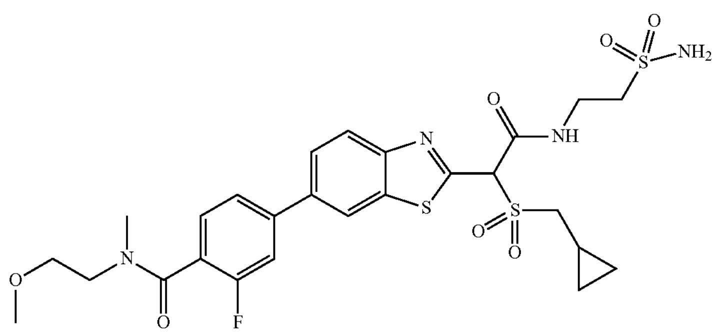 | 4-(2-{cyclopropylmethanesulfonyl[(2-sulfamoylethyl)carbamoyl]methyl}-1,3-benzothiazol-6-yl)-2-fluoro-N-(2-methoxyethyl)-N-methylbenzamide | δ 9.16-8.89 (m, 1H), 8.62-8.29 (m, 1H), 8.23-7.53 (m, 4H), 7.46-7.19 (m, 2H), 7.05-6.81 (m, 2H), 6.15-5.99 (m, 1H), 3.81-3.53 (m, 4H), 3.52-3.37 (m, 3H), 3.28-3.11 (m, 6H), 3.00 (br. s., 3H), 1.21-1.00 (m, 1H), 0.75-0.45 (m, 2H), 0.45-0.08 (m, 2H) | 1.39 N 627.1 | 6.1 | 127.3 |
| B248 | 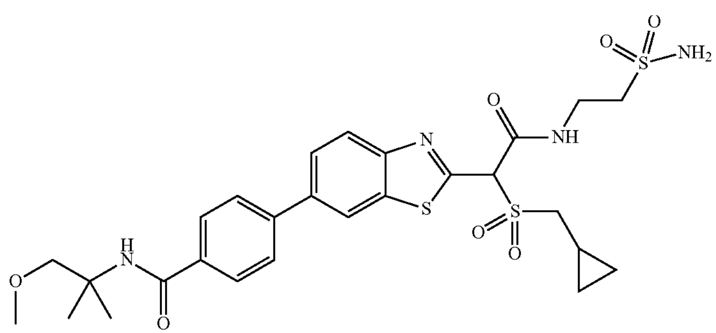 [SMILES: COCC(C)(C)NC(=O)c1ccc(-c2ccc3nc(C(C(=O)NCCS(N)(=O)=O)S(=O)(=O)CC4CC4)sc3c2)cc1] | 4-(2-{cyclopropylmethanesulfonyl[(2-sulfamoylethyl)carbamoyl]methyl}-1,3-benzothiazol-6-yl)-N-(1-methoxy-2-methylpropan-2-yl)benzamide | δ 9.12-8.91 (m, 1H), 8.54 (d, J = 1.7 Hz, 1H), 8.16 (d, J = 8.8 Hz, 1H), 8.01-7.90 (m, 3H), 7.83 (d, J = 8.5 Hz, 1H), 7.76-7.63 (m, 1H), 7.00-6.89 (m, 2H), 6.05 (s, 1H), 3.90 (s, 1H), 3.72-3.57 (m, 3H), 3.57-3.51 (m, 1H), 3.45-3.31 (m, 4H), 3.32-3.27 (m, 3H), 3.27-3.12 (m, 4H), 1.10 (s, 1H), 0.70-0.49 (m, 2H), 0.40 (dd, J = 4.8, 1.5 Hz, 2H) | 1.65 N 623.17 | 7.5 | 17.6 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B249 | 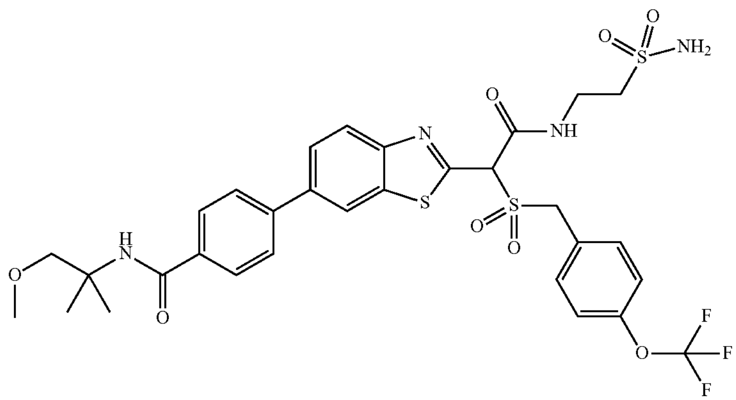 [SMILES: COCC(C)(C)NC(=O)c1ccc(-c2ccc3nc(C(C(=O)NCCS(N)(=O)=O)S(=O)(=O)Cc4ccc(OC(F)(F)F)cc4)sc3c2)cc1] | N-(1-methoxy-2-methyl-propan-2-yl)-4-(2-{[(2-sulfamoylethyl)carbamoyl][4-(trifluoromethoxy)phenyl]methanesulfonyl}-1,3-benzothiazol-6-yl)benzamide | δ 8.64-8.51 (m, 1H), 8.24-8.11 (m, 1H), 7.99-7.82 (m, 3H), 7.73 (s, 2H), 7.53 (s, 1H), 7.51-7.45 (m, 1H), 7.43-7.36 (m, 1H), 7.32-7.21 (m, 1H), 6.98 (s, 2H), 6.11 (s, 1H), 4.87-4.76 (m, 1H), 4.75-4.57 (m, 1H), 3.68-3.58 (m, 2H), 3.54 (d, J = 4.4 Hz, 2H), 3.29 (d, J = 2.8 Hz, 3H), 3.24-3.13 (m, 2H), 1.35 (d, J = 4.4 Hz, 6H) | 1.98 N 743.2 | 8.3 | 29.4 |
| B250 | 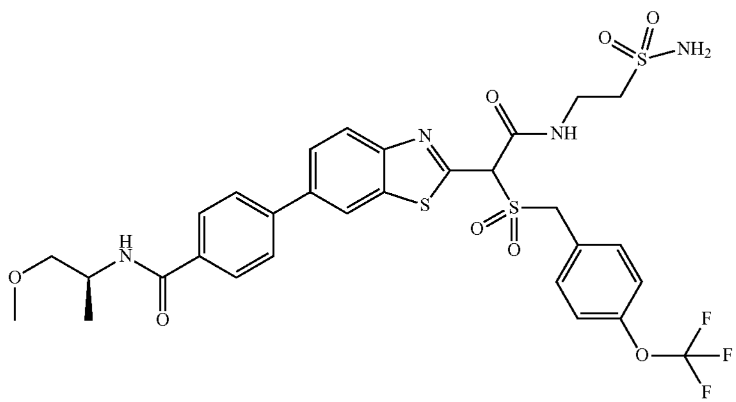 [SMILES: COC[C@H](C)NC(=O)c1ccc(-c2ccc3nc(C(C(=O)NCCS(N)(=O)=O)S(=O)(=O)Cc4ccc(OC(F)(F)F)cc4)sc3c2)cc1] | N-[(2S)-1-methoxypropan-2-yl]-4-(2-{[(2-sulfamoyl-ethyl)carbamoyl][4-(trifluoromethoxy)phenyl]methanesulfonyl}-1,3-benzothiazol-6-yl)benzamide | δ 9.19-8.98 (m, 1H), 8.40-8.12 (m, 2H), 8.05-7.85 (m, 4H), 7.83-7.67 (m, 2H), 7.63-7.35 (m, 3H), 7.34-7.17 (m, 1H), 7.06-6.88 (m, 2H), 6.31-5.97 (m, 1H), 5.05-4.76 (m, 1H), 4.74-4.57 (m, 1H), 4.35-4.17 (m, 1H), 3.71-3.57 (m, 2H), 3.51-3.40 (m, 2H), 3.28 (d, J = 2.5 Hz, 3H), 3.24-3.09 (m, 2H), 1.29-1.10 (m, 3H) | 1.73 N 729.1 | 5.3 | 38.4 |

| Ex # | Structure | Name | 1H NMR (500 MHz, DMSO-d6, unless indicated otherwise) | LC/MS RT (min) Method M + H | EL IC50 (nM) | HL IC50 (nM) |
|---|---|---|---|---|---|---|
| B251 | 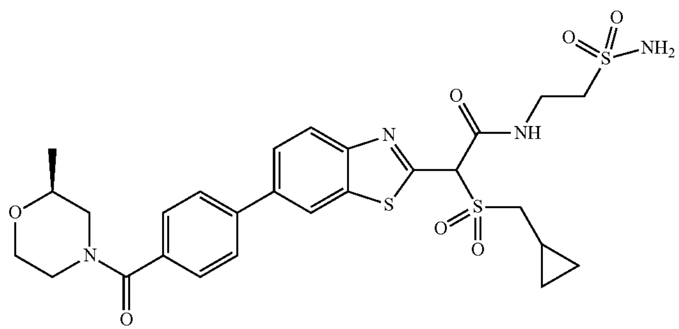 [SMILES: C[C@H]1CN(C(=O)c2ccc(-c3ccc4nc(C(C(=O)NCCS(N)(=O)=O)S(=O)(=O)CC5CC5)sc4c3)cc2)CCO1] | 2-cyclopropylmethane-sulfonyl-2-(6-{4-[(2S)-2-methylmorpholine-4-carbonyl]phenyl}-1,3-benzothiazol-2-yl)-N-(2-sulfamoylethyl)acetamide | δ 9.05 (s, 1H), 8.53 (d, J = 1.7 Hz, 1H), 8.15 (d, J = 8.5 Hz, 1H), 7.90 (d, J = 1.7 Hz, 1H), 7.84 (d, J = 8.0 Hz, 1H), 7.79-7.63 (m, 1H), 7.52 (d, J = 8.3 Hz, 2H), 6.97 (s, 2H), 6.06 (s, 1H), 3.88-3.77 (m, 1H), 3.90 (s, 1H), 3.73-3.50 (m, 4H), 3.48-3.37 (m, 4H), 3.28 (d, J = 7.4 Hz, 2H), 3.19 (d, J = 7.4 Hz, 2H), 1.27 (d, J = 6.6 Hz, 3H), 1.14-0.96 (m, 1H), 0.62 (d, J = 8.0 Hz, 2H), 0.44-0.15 (m, 2H) | 1.46 N 621.1 | 2.6 | 362.7 |
| B252 | 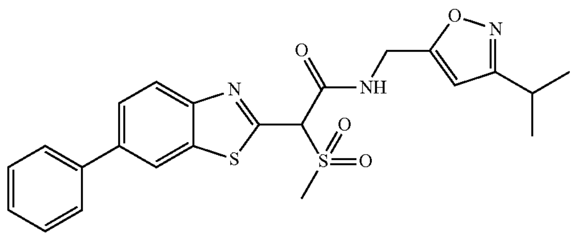 [SMILES: CC(C)c1cc(CNC(=O)C(c2nc3ccc(-c4ccccc4)cc3s2)S(C)(=O)=O)on1] | 2-methanesulfonyl-2-(6-phenyl-1,3-benzothiazol-2-yl)-N-{[3-(propan-2-yl)-1,2-oxazol-5-yl]methyl}acetamide | δ 9.44 (t, J = 5.8 Hz, 1H), 8.51 (d, J = 1.4 Hz, 1H), 8.17 (d, J = 8.5 Hz, 1H), 7.90 (dd, J = 8.5, 1.9 Hz, 1H), 7.81-7.75 (m, 2H), 7.59-7.50 (m, 2H), 7.47-7.38 (m, 1H), 6.35 (s, 1H), 6.06 (s, 1H), 4.58 (dd, J = 8.3, 5.8 Hz, 2H), 3.26 (s, 3H), 3.04-2.93 (m, 1H), 1.27-1.12 (m, 6H) | 1.6 N 697.1 | 21.5 | 1.4 |
| B253 | 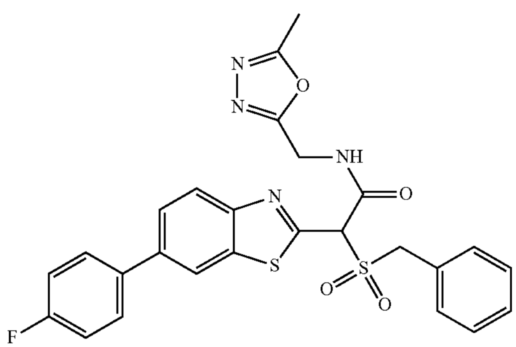 [SMILES: Cc1nnc(CNC(=O)C(c2nc3ccc(-c4ccc(F)cc4)cc3s2)S(=O)(=O)Cc2ccccc2)o1] | 2-[6-(4-fluorophenyl)-1,3-benzothiazol-2-yl]-N-{(5-methyl-1,3,4-oxadiazol-2-yl)methyl)-2-phenyl-methanesulfonylacetamide | δ 7.58-10.10 (m, 5H), 5.84-7.52 (m, 9H), 4.79 (m, 1H), 4.64-4.72 (m, 2H), 4.60 (m, 1H), 2.48 ppm (m, 3H) | 3.85 R 537.2 | 42.2 | 9.4 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B254 | 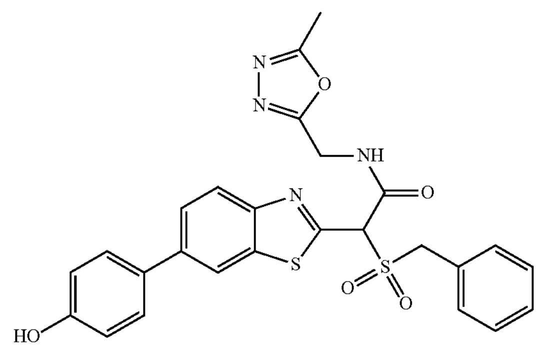 [SMILES: Cc1nnc(CNC(=O)C(c2nc3ccc(-c4ccc(O)cc4)cc3s2)S(=O)(=O)Cc2ccccc2)o1] | 2-[6-(4-hydroxyphenyl)-1,3-benzothiazol-2-yl]-N-[(5-methyl-1,3,4-oxadiazol-2-yl)methyl]-2-phenylmethanesulfonyl-acetamide | δ 7.38-10.00 (m, 11H), 6.00-7.35 (m, 4H), 4.19-5.01 (m, 4H), 2.48 ppm (m, 3H) | 2.36 R 535.3 | 293.6 | 259.3 |
| B255 | 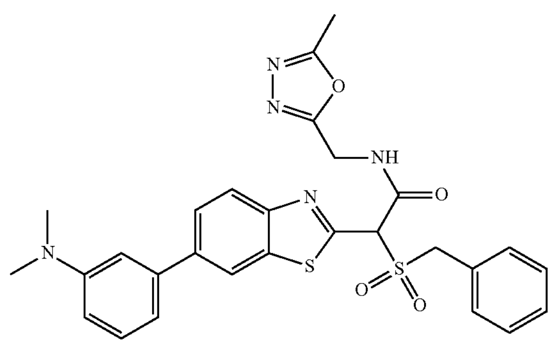 [SMILES: Cc1nnc(CNC(=O)C(c2nc3ccc(-c4cccc(N(C)C)c4)cc3s2)S(=O)(=O)Cc2ccccc2)o1] | 2-{6-[3-(dimethylamino)phenyl]-1,3-benzothiazol-2-yl}-N-[(5-methyl-1,3,4-oxadiazol-2-yl)methyl]-2-phenylmethanesulfonyl-acetamide | δ 7.36-14.64 (m, 7H), 5.69-7.31 (m, 7H), 4.23-5.14 (m, 4H), 3.00 (s, 3H), 2.97 (s, 3H), 2.49 ppm (m, 3H) | 3.04 R 562.3 | 225.2 | 43.5 |
| B256 | 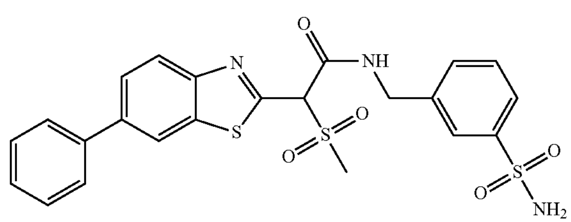 [SMILES: CS(=O)(=O)C(C(=O)NCc1cccc(S(N)(=O)=O)c1)c1nc2ccc(-c3ccccc3)cc2s1] | 2-methanesulfonyl-2-(6-phenyl-1,3-benzothiazol-2-yl)-N-[(3-sulfamoylphenyl)methyl]acetamide | δ 9.27 (t, J = 5.9 Hz, 1H), 8.39 (d, J = 1.7 Hz, 1H), 8.07 (d, J = 8.5 Hz, 1H), 7.78 (dd, J = 8.7, 1.8 Hz, 1H), 7.72-7.59 (m, 4H), 7.51-7.38 (m, 4H), 7.37-7.28 (m, 1H), 7.25 (s, 2H), 5.95 (s, 1H), 4.44 (dd, J = 10.0, 5.9 Hz, 2H), 3.14 (br. s, 3H) | 1.71 N 516.1 | 189.7 | 14.7 |

| Ex # | Structure | Name | 1H NMR (500 MHz, DMSO-d6, unless indicated otherwise) | LC/MS RT (min) Method M + H | EL IC50 (nM) | HL IC50 (nM) |
|---|---|---|---|---|---|---|
| B257 | 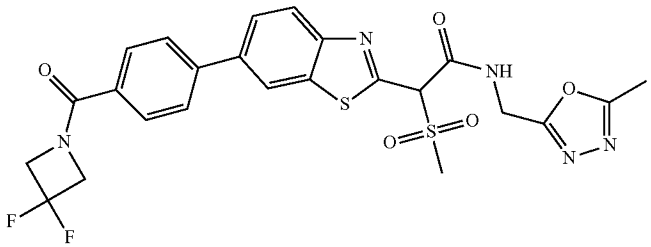 [SMILES: Cc1nnc(CNC(=O)C(c2nc3ccc(-c4ccc(C(=O)N5CC(F)(F)C5)cc4)cc3s2)S(C)(=O)=O)o1] | 2-{6-[4-(3,3-difluoro azetidine-1-carbonyl)phenyl]-1,3-benzothiazol-2-yl}-2-methanesulfonyl-N-[(5-methyl-1,3,4-oxadiazol-2-yl)methyl]acetamide | δ 9.54 (t, J = 5.6 Hz, 1H), 8.59 (d, J = 1.7 Hz, 1H), 8.20 (d, J = 8.5 Hz, 1H), 7.99-7.92 (m, 1H), 7.91-7.87 (m, 2H), 7.87-7.82 (m, 2H), 6.11 (s, 1H), 4.84 (br. s., 2H), 4.69 (d, J = 6.1 Hz, 2H), 4.64-4.46 (m, 2H), 3.29 (s, 3H), 2.50-2.46 (m, 3H) | 1.41 N 562.2 | 32.0 | 53.3 |
| B258 | 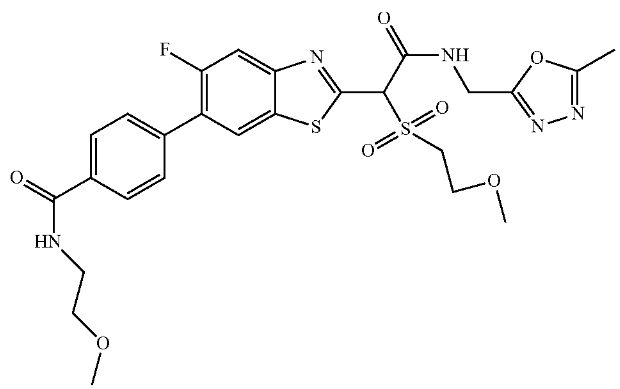 [SMILES: COCCNC(=O)c1ccc(-c2cc3sc(C(C(=O)NCc4nnc(C)o4)S(=O)(=O)CCOC)nc3cc2F)cc1] | 4-[5-fluoro-2-[(2-methoxyethanesulfonyl)({[(5-methyl-1,3,4-oxadiazol-2-yl)methyl]carbamoyl})methyl]-1,3-benzothiazol-6-yl]-N-(2-methoxyethyl)benzamide | δ 9.52 (t, J = 5.5 Hz, 1H), 8.69-8.54 (m, 1H), 8.43 (d, J = 7.2 Hz, 1H), 8.11 (d, J = 11.0 Hz, 1H), 8.04-7.90 (m, 2H), 7.72 (d, J = 8.0 Hz, 2H), 6.12 (s, 1H), 4.71-4.63 (m, 2H), 3.89-3.62 (m, 2H), 3.53-3.42 (m, 2H), 3.29 (m, 3H), 2.50-2.42 (m, 3H) | 1.36 N 606.2 | 57.2 | 888.7 |
| B259 | 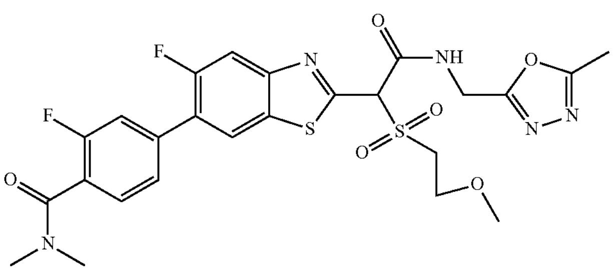 [SMILES: COCCS(=O)(=O)C(C(=O)NCc1nnc(C)o1)c1nc2cc(F)c(-c3ccc(C(=O)N(C)C)c(F)c3)cc2s1] | 2-fluoro-4-{5-fluoro-2-[(2-methoxyethanesulfonyl)({[(5-methyl-1,3,4-oxadiazol-2-yl)methyl]carbamoyl})methyl]-1,3-benzothiazol-6-yl}-N,N-dimethylbenzamide | δ 9.53 (br. s., 1H), 8.46 (d, J = 7.2 Hz, 1H), 8.13 (d, J = 11.3 Hz, 1H), 7.81-7.68 (m, 1H), 7.63-7.46 (m, 2H), 6.13 (s, 1H), 4.71-4.64 (m, 4H), 3.29 (s, 3H), 3.82-3.65 (m, 4H), 3.29 (s, 3H), 3.05 (m, 3H), 2.92 (m, 3H), 2.48 (d, J = 31.6 Hz, 3H) | 1.38 N 594.2 | 121.3 | 207.7 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B260 | 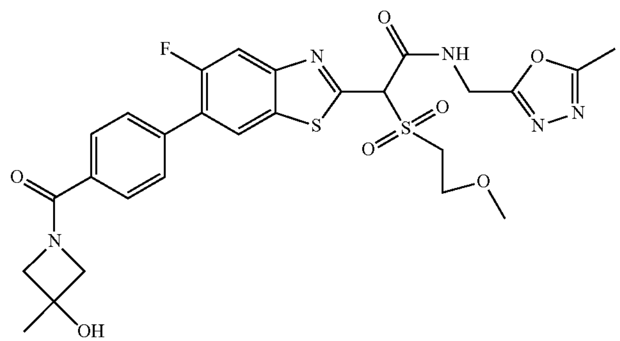 [SMILES: COCCS(=O)(=O)C(C(=O)NCc1nnc(C)o1)c1nc2cc(F)c(-c3ccc(C(=O)N4CC(C)(O)C4)cc3)cc2s1] | 2-{5-fluoro-6-[4-(3-hydroxy-3-methyl-azetidine-1-carbonyl)phenyl]-1,3-benzothiazol-2-yl}-2-(2-methoxyethane-sulfonyl)-N-[(5-methyl-1,3,4-oxadiazol-2-yl)methyl]acetamide | δ 9.56-9.49 (m, 1H), 8.43 (d, J = 7.7 Hz, 1H), 8.12 (d, J = 11.3 Hz, 1H), 7.82-7.62 (m, 5H), 6.13 (s, 1H), 4.71-4.65 (m, 2H), 4.25-4.13 (m, 2H), 3.99-3.89 (m, 3H), 3.82-3.66 (m, 4H), 3.16-3.14 (m, 2H), 3.29 (s, 3H), 2.50-2.43 (m, 3H) | 1.21 N 618.2 | 67.0 | 1345.0 |
| B261 | 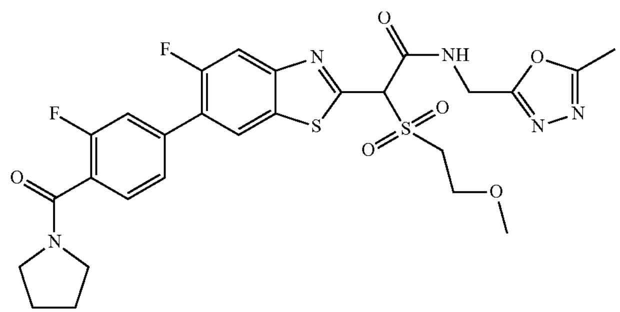 [SMILES: COCCS(=O)(=O)C(C(=O)NCc1nnc(C)o1)c1nc2cc(F)c(-c3ccc(C(=O)N4CCCC4)c(F)c3)cc2s1] | 2-{5-fluoro-6-[3-fluoro-4-(pyrrolidine-1-carbonyl)phenyl]-1,3-benzothiazol-2-yl}-2-(2-methoxyethanesulfonyl)-N-[(5-methyl-1,3,4-oxadiazol-2-yl)methyl]acetamide | δ 9.54 (t, J = 5.0 Hz, 1H), 8.47 (m, 1H), 8.14 (m, 1H), 7.66-7.45 (m, 3H), 6.13 (s, 1H), 4.68 (m, 2H), 3.85-3.59 (m, 2H), 3.57-3.48 (m, 4H), 3.32-3.23 (m, 4H), 3.29 (s, 3H), 2.50-2.45 (m, 3H), 2.04-1.79 (m, 2H) | 1.49 N 620.2 | 101.4 | 764.6 |
| B262 | 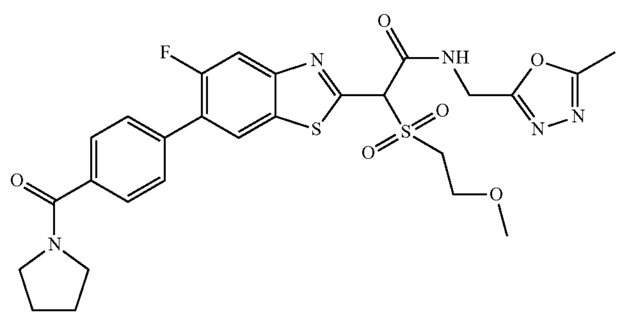 [SMILES: COCCS(=O)(=O)C(C(=O)NCc1nnc(C)o1)c1nc2cc(F)c(-c3ccc(C(=O)N4CCCC4)cc3)cc2s1] | 2-{5-fluoro-6-[4-(pyrrolidine-1-carbonyl)phenyl]-1,3-benzothiazol-2-yl}-2-(2-methoxyethanesulfonyl)-N-[(5-methyl-1,3,4-oxadiazol-2-yl)methyl]acetamide | δ 9.61-9.45 (m, 1H), 8.42 (d, J = 7.4 Hz, 1H), 8.11 (d, J = 11.3 Hz, 1H), 7.69 (m, 4H), 6.13 (s, 1H), 4.85-4.50 (m, 2H), 3.86-3.63 (m, 4H), 3.58-3.43 (m, 4H), 3.29 (s, 3H), 2.50-2.45 (m, 3H), 1.96-1.76 (m, 2H) | 1.42 N 602.15 | 101.5 | 373.7 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
| --- | --- | --- | --- | --- | --- | --- |
| B263 | 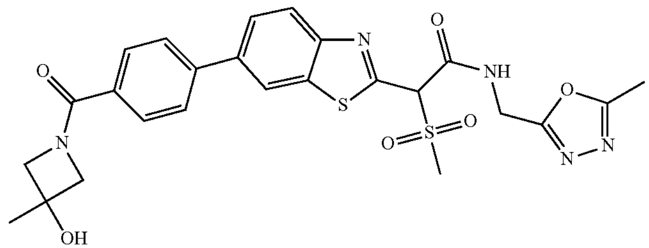 | 2-{6-[4-(3-hydroxy-3-methylazetidine-1-carbonyl)phenyl]-1,3-benzothiazol-2-yl}-2-methanesulfonyl-N-[(5-methyl-1,3,4-oxadiazol-2-yl)methyl]acetamide | δ 9.54 (t, J = 5.6 Hz, 1H), 8.62-8.51 (m, 1H), 8.25-8.15 (m, 1H), 7.99-7.91 (m, 1H), 7.86 (d, J = 8.5 Hz, 2H), 7.77 (m, 2H), 6.11 (s, 1H), 4.69 (d, J = 6.1 Hz, 2H), 4.25-4.13 (m, 2H), 3.98-3.92 (m, 2H), 3.32-3.26 (m, 3H), 2.47 (s, 3H), 1.42 (s, 3H) | 1.17 N 556.2 | 77.0 | 10000.0 |
| B264 | 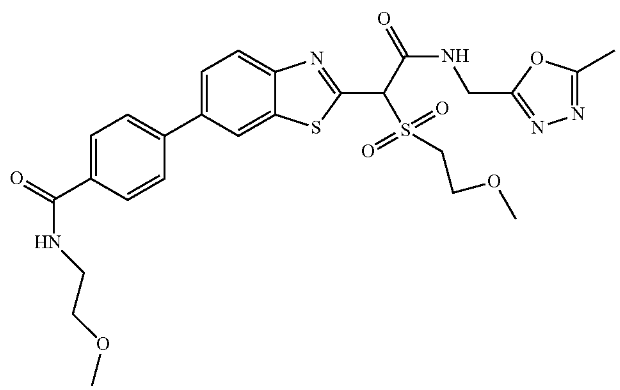 [SMILES: COCCNC(=O)c1ccc(-c2ccc3nc(C(C(=O)NCc4nnc(C)o4)S(=O)(=O)CCOC)sc3c2)cc1] | 4-{2-[(2-methoxyethanesulfonyl)({[(5-methyl-1,3,4-oxadiazol-2-yl]methyl]carbamoyl]methyl]-1,3-benzothiazol-6-yl}-N-(2-methoxyethyl)benzamide | δ 9.52 (t, J = 5.2 Hz, 1H), 8.64-8.54 (m, 2H), 8.19 (d, J = 8.5 Hz, 1H), 8.06-7.93 (m, 4H), 7.92-7.84 (m, 2H), 6.11 (s, 1H), 4.68 (t, J = 5.1 Hz, 2H), 3.82-3.69 (m, 3H), 3.54-3.43 (m, 4H), 3.30 (s, 3H), 3.29 (s, 3H), 2.50-2.45 (m, 3H) | 1.34 N 588.1 | 93.0 | 184.5 |
| B265 | 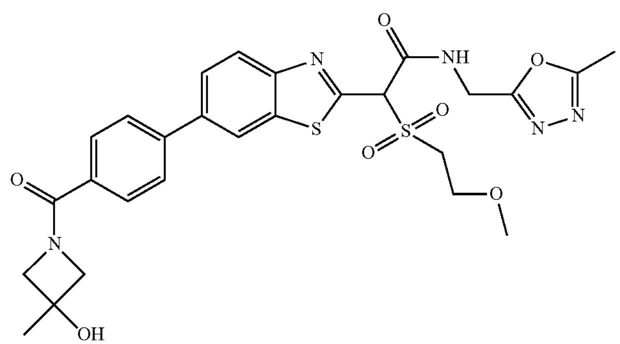 [SMILES: COCCS(=O)(=O)C(C(=O)NCc1nnc(C)o1)c1nc2ccc(-c3ccc(C(=O)N4CC(C)(O)C4)cc3)cc2s1] | 2-{6-[4-(3-hydroxy-3-methylazetidine-1-carbonyl)phenyl]-1,3-benzothiazol-2-yl}-2-(2-methoxyethanesulfonyl)-N-[(5-methyl-1,3,4-oxadiazol-2-yl)methyl]acetamide | δ 9.52 (t, J = 5.4 Hz, 1H), 8.57 (s, 1H), 8.19 (d, J = 8.5 Hz, 1H), 8.00-7.90 (m, 2H), 7.89-7.83 (m, 1H), 7.81-7.73 (m, 2H), 6.11 (s, 1H), 4.71-4.61 (m, 2H), 4.20 (m, 2H), 3.84-3.74 (m, 2H), 3.74-3.61 (m, 4H), 3.28 (s, 3H), 2.47 (s, 3H), 1.42 (br. s., 3H) | 1.19 N 600.2 | 59.0 | 634.0 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B266 | 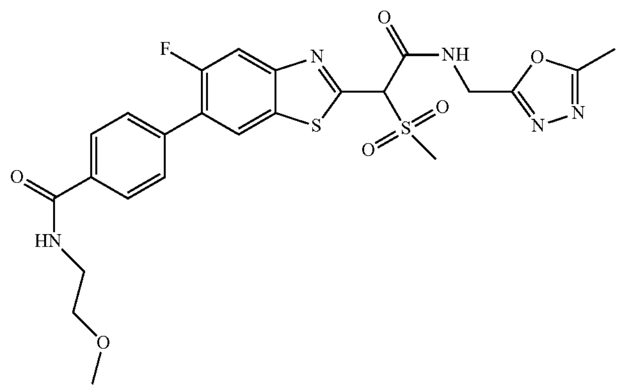 [SMILES: COCCNC(=O)c1ccc(-c2cc3sc(C(C(=O)NCc4nnc(C)o4)S(C)(=O)=O)nc3cc2F)cc1] | 4-{5-fluoro-2-[methanesulfonyl({[(5-methyl-1,3,4-oxadiazol-2-yl)methyl]carbamoyl})methyl]-1,3-benzothiazol-6-yl}-N-(2-methoxyethyl)benzamide | δ 9.55 (t, J = 5.6 Hz, 1H), 8.63 (t, J = 5.2 Hz, 1H), 8.53-8.32 (m, 1H), 8.21-8.07 (m, 1H), 8.06-7.91 (m, 2H), 7.80-7.62 (m, 2H), 6.12 (s, 1H), 4.69 (d, J = 5.8 Hz, 2H), 3.59-3.42 (m, 4H), 3.31-3.26 (m, 3H), 2.50-2.42 (m, 3H) | 1.22 N 562.15 | 39.1 | 947.5 |
| B267 | 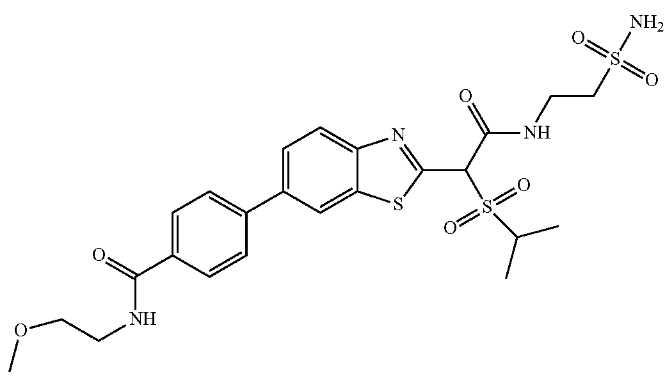 [SMILES: COCCNC(=O)c1ccc(-c2ccc3nc(C(C(=O)NCCS(N)(=O)=O)S(=O)(=O)C(C)C)sc3c2)cc1] | N-(2-methoxyethyl)-4-{2-[(propane-2-sulfonyl)](2-sulfamoyl)carbamoyl]methyl]-1,3-benzothiazol-6-yl}benzamide | δ 14.20-5.53 (m, 12H), 3.80-3.39 (m, 9H), 3.33 (m, 3H), 3.24-3.12 (m, 2H), 1.48-1.21 (m, 6H) | 1.29 N 583.20 | 44.5 | 289.0 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B268 | 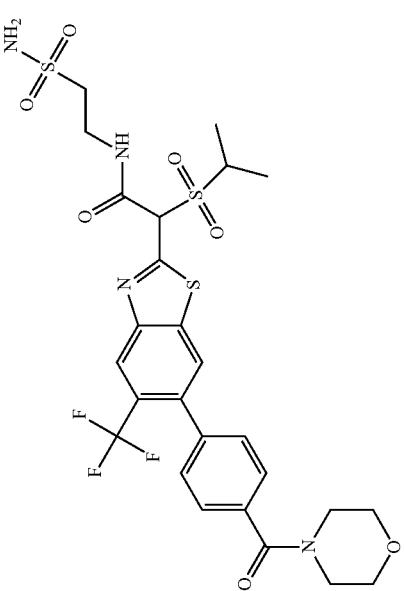 | 2-{6-[4-(morpholine-4-carbonyl)phenyl]-5-(trifluoromethyl)-1,3-benzothiazol-2-yl}-2-(propane-2-sulfonyl)-N-(2-sulfamoylethyl)acetamide | δ 14.35-5.91 (m, 9H), 3.88-3.49 (m, 11H), 3.30-2.98 (m, 2H), 1.60-1.03 (m, 6H) | 1.41 N 663.20 | 9.2 | 405.8 |
| B269 | 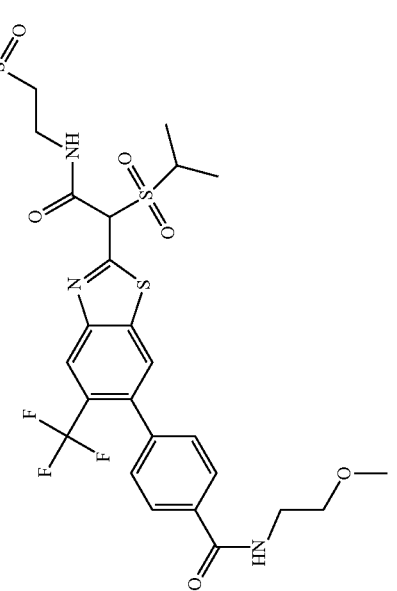 | N-(2-methoxyethyl)-4-{2-[(propane-2-sulfonyl)](2-sulfamoylethyl)carbamoyl]methyl]-5-(trifluoromethyl)-1,3-benzothiazol-6-yl}benzamide | δ 14.33-5.35 (m, 10H), 3.85-3.45 (m, 9H), 3.30 (s, 3H), 3.25-3.17 (m, 2H), 1.49-1.16 (m, 6H) | 1.45 N 651.15 | 10.0 | 312.1 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B270 | 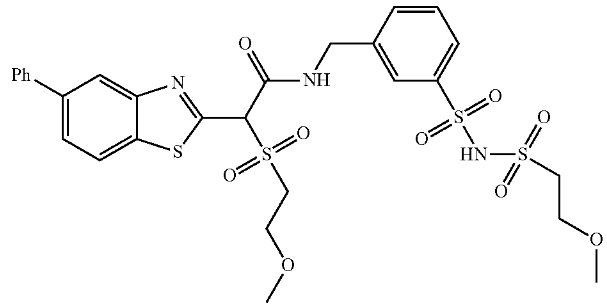 [SMILES: COCCS(=O)(=O)NS(=O)(=O)c1cccc(CNC(=O)C(c2nc3cc(-c4ccccc4)ccc3s2)S(=O)(=O)CCOC)c1] | N-({3-[(2-methoxyethane-sulfonamido)sulfonyl]phen-yl}methyl)-2-(2-methoxyethanesulfonyl)-2-(5-phenyl-1,3-benzothiazol-2-yl)a-cetamide | δ 9.35 (t, J = 5.6 Hz, 1H), 8.38 (s, 1H), 8.26 (d, J = 8.5 Hz, 1H), 8.02-7.77 (m, 4H), 7.73-7.60 (m, 2H), 7.57-7.49 (m, 2H), 7.47-7.34 (m, 3H), 6.07 (s, 1H), 4.71-4.38 (m, 2H), 3.89-3.59 (m, 6H), 3.27 (s, 3H), 3.24-3.16 (m, 5H) | 1.55 N 682.05 | 204.6 | 211.9 |
| B271 | 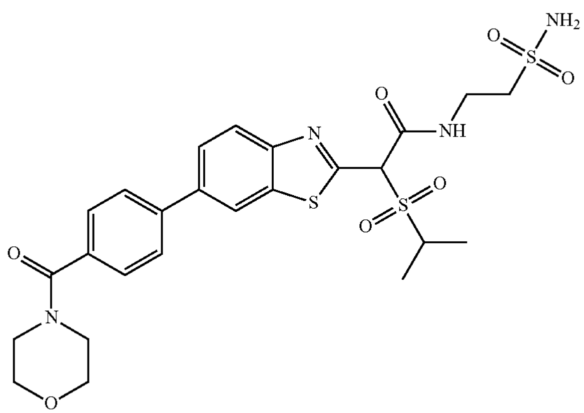 [SMILES: CC(C)S(=O)(=O)C(C(=O)NCCS(N)(=O)=O)c1nc2ccc(-c3ccc(C(=O)N4CCOCC4)cc3)cc2s1] | 2-{6-[4-(morpholine-4-carbonyl)phenyl]-1,3-benzothiazol-2-yl}-2-(propane-2-sulfonyl)-N-(2-sulfamoylethyl)acetamide | δ 14.71-7.66 (m, 6H), 7.69-5.91 (m, 5H), 3.81-3.50 (m, 5H), 3.27-3.00 (m, 2H), 1.65-1.11 (m, 6H) | 1.55 N 682.05 | 7.5 | 1004.0 |
| B272 | 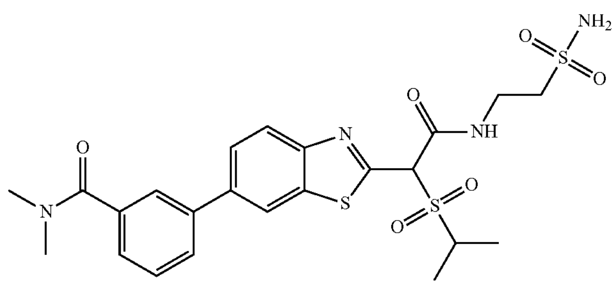 [SMILES: CC(C)S(=O)(=O)C(C(=O)NCCS(N)(=O)=O)c1nc2ccc(-c3cccc(C(=O)N(C)C)c3)cc2s1] | N,N-dimethyl-3-{2-[(propane-2-sulfonyl)][(2-sul-famoylethyl)carbamoyl]meth-yl]-1,3-benzothiazol-6-yl}benzamide | δ 14.21-7.64 (m, 6H), 7.63-5.94 (m, 5H), 3.82-3.50 (m, 3H), 3.30-3.15 (m, 2H), 3.04 (br. s., 3H), 2.98 (br. s., 3H), 1.56-1.19 (m, 6H) | 1.35 N 553.15 | 35.3 | 611.6 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B273 | 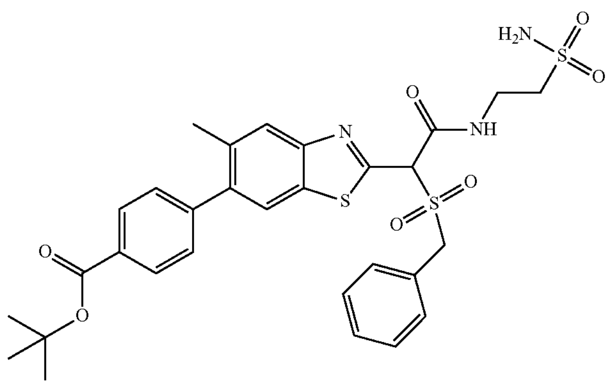 [SMILES: Cc1cc2nc(C(C(=O)NCCS(N)(=O)=O)S(=O)(=O)Cc3ccccc3)sc2cc1-c1ccc(C(=O)OC(C)(C)C)cc1] | tert-butyl 4-(5-methyl-2-{phenylmethanesulfonyl[(2-sulfamoylethyl)carbamoyl]methyl}-1,3-benzothiazol-6-yl)benzoate | δ 9.02 (t, J = 5.64 Hz, 1H), 8.08 (s, 1H), 7.99-8.04 (m, 2H), 7.94 (d, J = 7.15 Hz, 2H), 7.54 (d, J = 7.98 Hz, 2H), 7.48 (d, J = 7.70 Hz, 2H), 7.25 (br. s., 2H), 6.08 (s, 1H), 4.68-4.78 (m, 2H), 4.65 (br. s., 1H), 3.60 (q, J = 6.69 Hz, 2H), 3.19 (t, J = 7.29 Hz, 2H), 2.36 (s, 3H), 1.58 (s, 9H) | 2.25 B 644.1 | 1.4 | 3.0 |
| B274 | 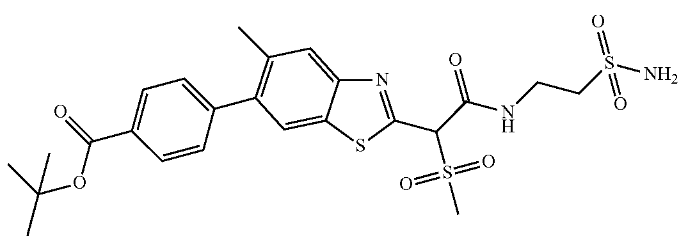 [SMILES: Cc1cc2nc(C(C(=O)NCCS(N)(=O)=O)S(C)(=O)=O)sc2cc1-c1ccc(C(=O)OC(C)(C)C)cc1] | tert-butyl 4-(2-{methanesulfonyl[(2-sulfamoylethyl)carbamoyl]methyl}-5-methyl-1,3-benzothiazol-6-yl)benzoate | δ 8.98 (t, J = 5.64 Hz, 1H), 8.04 (s, 1H), 8.01 (d, J = 4.40 Hz, 2H), 7.99 (s, 1H), 7.53 (d, J = 7.98 Hz, 2H), 6.02 (s, 1H), 3.60 (q, J = 6.88 Hz, 2H), 3.22 (s, 3H), 3.18 (t, J = 7.15 Hz, 2H), 1.58 (s, 9H) | 0.96 M 568 | 1.7 | 5.1 |
| B275 | 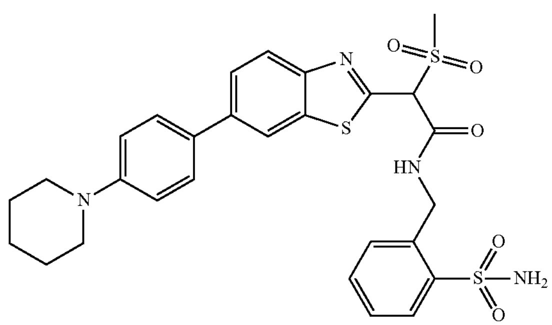 [SMILES: CS(=O)(=O)C(C(=O)NCc1ccccc1S(N)(=O)=O)c1nc2ccc(-c3ccc(N4CCCCC4)cc3)cc2s1] | 2-methanesulfonyl-2-{6-[4-(piperidin-1-yl)phenyl]-1,3-benzothiazol-2-yl}-N-[(2-sulfamoylphenyl)methyl]acetamide | δ 7.94-8.69 (m, 4H), 7.61-7.89 (m, 4H), 7.47-7.60 (m, 1H), 7.11-7.44 (m, 3H), 5.93 (s, 1H), 5.02 (d, J = 5.23 Hz, 1H), 4.83 (d, J = 5.23 Hz, 1H), 2.89 (s, 3H), 2.72-2.76 (m, 4H), 1.70 (d, J = 19.53 Hz, 4H), 1.60 (br. s., 2H) | 2.02 B 599.2 | 173.3 | 218.5 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B276 | 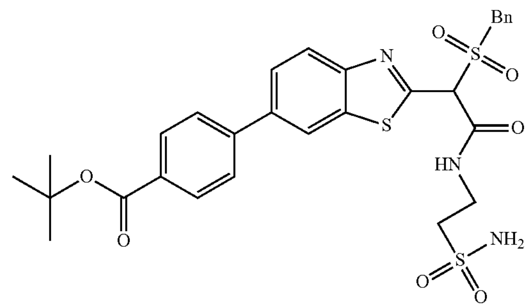 [SMILES: CC(C)(C)OC(=O)c1ccc(-c2ccc3nc(C(C(=O)NCCS(N)(=O)=O)S(=O)(=O)Cc4ccccc4)sc3c2)cc1] | tert-butyl 4-(2-{[phenylmethanesulfonyl][(2-sulfamoylethyl)carbamoyl]methyl}-1,3-benzothiazol-6-yl)benzoate | δ 8.58 (s, 1H), 8.22 (d, J = 8.53 Hz, 1H), 8.02 (d, J = 7.43 Hz, 2H), 7.95-7.99 (m, 2H), 7.90-7.94 (m, 2H), 7.78-7.85 (m, 2H), 7.32-7.36 (m, 2H), 7.27 (d, J = 7.43 Hz, 2H), 6.11 (s, 1H), 4.74 (q, J = 13.30 Hz, 2H), 4.54-4.65 (m, 1H), 3.58-3.64 (m, 3H), 3.09-3.23 (m, 4H), 1.58 (s, 9H) | 2.16 B 630.1 | 1.1 | 0.8 |
| B277 | 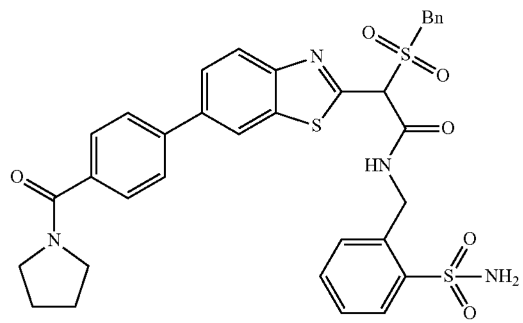 [SMILES: NS(=O)(=O)c1ccccc1CNC(=O)C(c1nc2ccc(-c3ccc(C(=O)N4CCCC4)cc3)cc2s1)S(=O)(=O)Cc1ccccc1] | 2-phenylmethanesulfonyl-2-{6-[4-(pyrrolidine-1-carbonyl)phenyl]-1,3-benzothiazol-2-yl}-N-[(3-sulfamoylphenyl)methyl]acetamide | δ 9.42 (br. s., 1H), 8.22 (d, J = 8.80 Hz, 1H), 7.95 (s, 2H), 7.84 (d, J = 7.70 Hz, 1H), 7.72 (br. s., 1H), 7.66 (d, J = 7.43 Hz, 1H), 7.61 (d, J = 7.43 Hz, 2H), 7.55 (br. s., 1H), 7.39 (s, 3H), 7.30-7.36 (m, 2H), 6.12 (s, 1H), 4.67-4.79 (m, 1H), 4.53 (d, J = 3.85 Hz, 1H), 4.34-4.65 (m, 2H), 3.41-3.53 (m, 4H), 1.80-1.93 (m, 4H) | 0.88 M 689 | 191.2 | 84.9 |
| B278 | 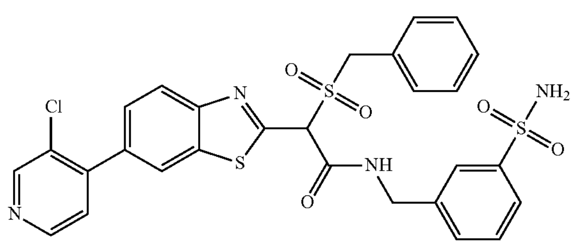 [SMILES: NS(=O)(=O)c1cccc(CNC(=O)C(c2nc3ccc(-c4ccncc4Cl)cc3s2)S(=O)(=O)Cc2ccccc2)c1] | 2-[6-(3-chloropyridin-4-yl)-1,3-benzothiazol-2-yl]-2-phenylmethanesulfonyl-N-[(3-sulfamoylphenyl)methyl]acetamide | δ 9.41 (t, J = 5.91 Hz, 1H), 8.63-8.68 (m, 1H), 8.26 (d, J = 8.25 Hz, 1H), 7.70-7.76 (m, 2H), 7.59 (d, J = 4.95 Hz, 1H), 7.53-7.57 (m, 2H), 7.37-7.42 (m, 5H), 7.33 (m, 3H), 6.15 (s, 1H), 4.66-4.83 (m, 1H), 4.50-4.57 (m, 1H) | 0.86 M 627.1 | 157.8 | 355.1 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B279 | 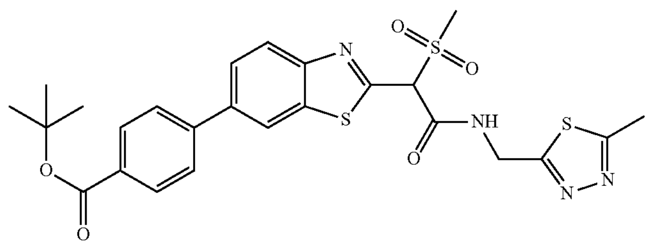 [SMILES: Cc1nnc(CNC(=O)C(c2nc3ccc(-c4ccc(C(=O)OC(C)(C)C)cc4)cc3s2)S(C)(=O)=O)s1] | tert-butyl 4-{2-[methanesulfonyl({[(5-methyl-1,3,4-thiadiazol-2-yl)methyl]carbamoyl}methyl]-1,3-benzothiazol-6-yl}benzoate | δ 9.65 (t, J = 5.78 Hz, 1H), 8.58 (d, J = 1.65 Hz, 1H), 8.19 (d, J = 8.53 Hz, 1H), 8.02 (d, J = 8.25 Hz, 2H), 7.93 (dd, J = 1.79, 8.67 Hz, 1H), 7.90 (d, J = 8.25 Hz, 2H), 6.08 (s, 1H), 4.81 (d, J = 6.05 Hz, 2H), 3.25 (s, 3H), 2.68 (s, 3H), 1.57 (br. s., 9H) | 2.13 B 559.1 | 15.6 | 2.8 |
| B280 | 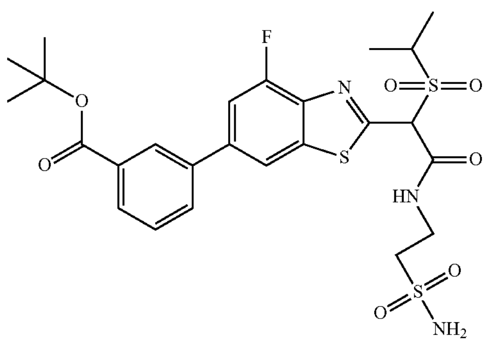 [SMILES: CC(C)S(=O)(=O)C(C(=O)NCCS(N)(=O)=O)c1nc2c(F)cc(-c3cccc(C(=O)OC(C)(C)C)c3)cc2s1] | tert-butyl 3-{4-fluoro-2-[(propane-2-sulfonyl)][(2-sulfamoylethyl)carbamoyl]methyl]-1,3-benzothiazol-6-yl}benzoate | δ 9.09 (t, J = 5.78 Hz, 1H), 8.23 (s, 1H), 8.03 (d, J = 7.70 Hz, 1H), 7.90-8.00 (m, 2H), 7.80 (d, J = 12.10 Hz, 1H), 7.65 (t, J = 7.84 Hz, 1H), 6.97 (s, 2H), 6.25 (s, 1H), 3.55-3.63 (m, 2H), 3.47-3.55 (m, 1H), 3.12-3.25 (m, 2H), 2.89 (s, 3H), 2.73 (s, 3H) | 1.01 M 600.1 | 4.8 | 2.9 |
| B281 | 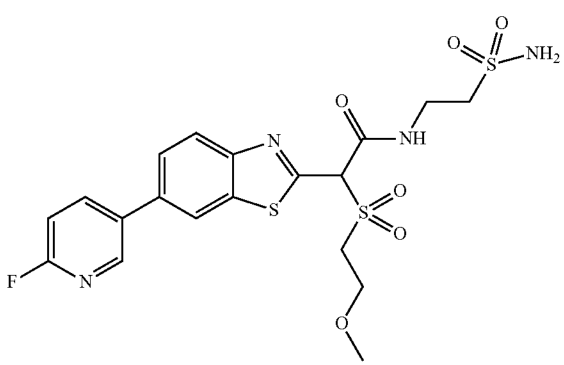 [SMILES: COCCS(=O)(=O)C(C(=O)NCCS(N)(=O)=O)c1nc2ccc(-c3ccc(F)nc3)cc2s1] | 2-[6-(6-fluoropyridin-3-yl)-1,3-benzothiazol-2-yl]-2-(2-methoxyethanesulfonyl)-N-(2-sulfamoylethyl)acetamide | δ 8.96 (t, J = 5.8 Hz, 1H), 8.67 (d, J = 2.5 Hz, 1H), 8.57 (dd, J = 1.7 Hz, 1H), 8.40 (dd, J = 8.2, 2.6 Hz, 1H), 8.20 (d, J = 8.5 Hz, 1H), 8.00-7.89 (m, 2H), 7.36 (dd, J = 8.7, 2.6 Hz, 1H), 6.97 (s, 2H), 3.84-3.73 (m, 2H), 3.72-3.66 (m, 2H), 3.64-3.58 (m, 2H), 3.29 (s, 3H), 3.22-3.17 (m, 2H) | 1.25 N 517.2 | 17.9 | 109.7 |

-continued

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B282 | 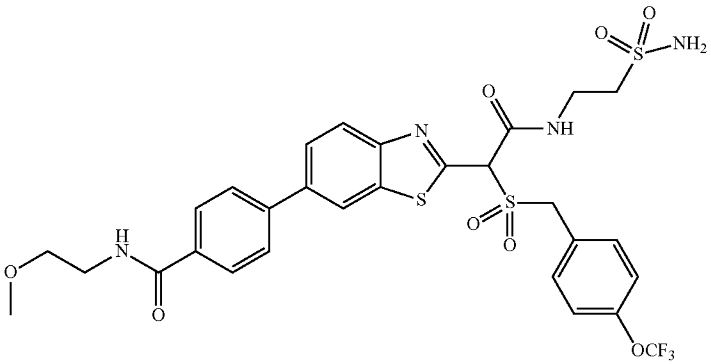 [SMILES: COCCNC(=O)c1ccc(-c2ccc3nc(C(C(=O)NCCS(N)(=O)=O)S(=O)(=O)Cc4ccc(OC(F)(F)F)cc4)sc3c2)cc1] | N-(2-methoxyethyl)-4-(2-{[(2-sulfamoylethyl)carbamoyl][4-(trifluoromethoxyphenyl]methanesulfonylmethyl}-1,3-benzothiazol-6-yl)benzamide | δ 9.05 (t, J = 5.6 Hz, 1H), 8.77-8.46 (m, 2H), 8.29-8.10 (m, 1H), 8.07-7.84 (m, 4H), 7.87-7.65 (m, 2H), 7.59-7.36 (m, 3H), 7.32-7.20 (m, 1H), 7.10-6.87 (m, 2H), 6.11 (s, 1H), 4.89-4.74 (m, 1H), 4.75-4.58 (m, 1H), 3.72-3.54 (m, 2H), 3.54-3.41 (m, 5H), 3.28 (d, J = 2.5 Hz, 3H), 3.25-3.11 (m, 2H) | 1.69 N 715.1 | 2.6 | 306.1 |
| B283 | 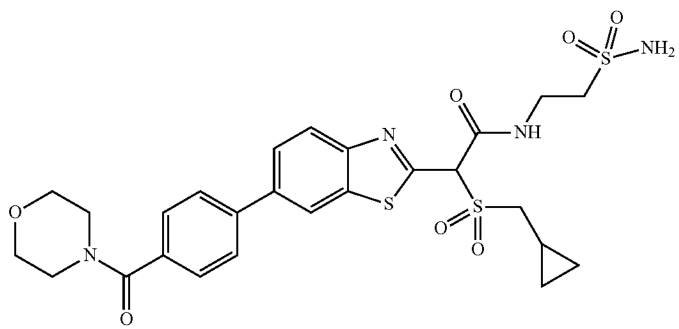 [SMILES: NS(=O)(=O)CCNC(=O)C(c1nc2ccc(-c3ccc(C(=O)N4CCOCC4)cc3)cc2s1)S(=O)(=O)CC1CC1] | 2-cyclopropylmethanesulfonyl-2-{6-[4-(morpholine-4-carbonyl)phenyl]-1,3-benzothiazol-2-yl}-N-(2-sulfamoylethyl)acetamide | δ 9.14-8.92 (m, 1H), 8.52 (br. s., 1H), 8.30-8.10 (m, 1H), 8.01-7.81 (m, 4H), 7.80-7.66 (m, 1H), 7.55 (d, J = 7.7 Hz, 2H), 6.94 (br. s., 2H), 3.59-3.62 (m, 10H), 3.28 (br. s., 2H), 3.19 (br. s., 2H), 1.21-0.93 (m, 1H), 0.63 (d, J = 7.2 Hz, 1H), 0.55-0.34 (m, 2H), 0.31-0.20 (m, 1H) | 1.64 N 607.1 | 53.8 | 364.6 |
| B284 | 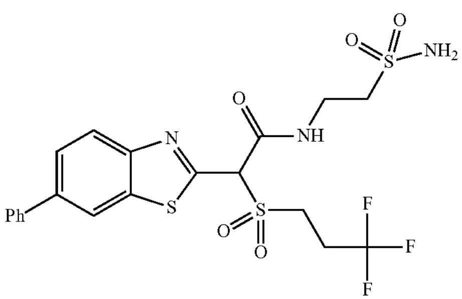 [SMILES: NS(=O)(=O)CCNC(=O)C(c1nc2ccc(-c3ccccc3)cc2s1)S(=O)(=O)CCC(F)(F)F] | 2-(6-phenyl-1,3-benzothiazol-2-yl)-N-(2-sulfamoylethyl)-2-(3,3,3-trifluoropropanesulfonyl)acetamide | δ 8.50 (s, 1H), 8.15 (d, J = 8.3 Hz, 1H), 7.88 (d, J = 8.5 Hz, 1H), 7.77 (d, J = 7.4 Hz, 2H), 7.74-7.63 (m, 1H), 7.57-7.46 (m, 2H), 7.42 (d, J = 7.2 Hz, 1H), 6.98 (br. s., 2H), 6.27 (s, 1H), 3.84-3.51 (m, 4H), 3.18 (t, J = 7.0 Hz, 2H), 2.85 (d, J = 9.4 Hz, 2H) | 1.87 N 536.1 | 6.8 | 2.6 |

| Ex # | Structure | Name | $^1$H NMR (500 MHz, DMSO-d$_6$, unless indicated otherwise) | LC/MS RT (min) Method M + H | EL IC$_{50}$ (nM) | HL IC$_{50}$ (nM) |
|---|---|---|---|---|---|---|
| B285 | 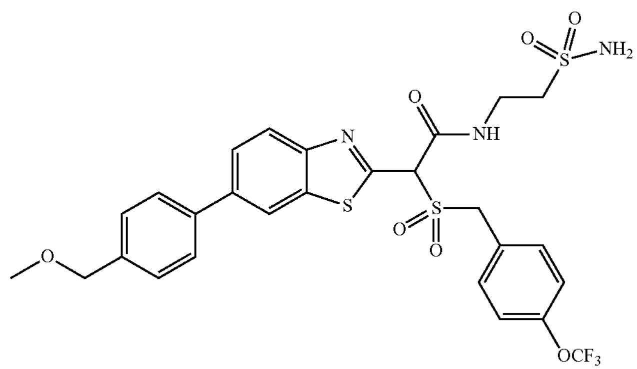 [SMILES: COCc1ccc(-c2ccc3nc(C(C(=O)NCCS(N)(=O)=O)S(=O)(=O)Cc4ccc(OC(F)(F)F)cc4)sc3c2)cc1] | 2-{6-[4-(methoxymethyl)phenyl]-1,3-benzothiazol-2-yl}-N-(2-sulfamoylethyl)-2-[[4-(trifluoromethoxy)phenyl]methanesulfonyl]-acetamide | δ 8.49 (br. s., 1H), 8.22-8.05 (m, 1H), 7.89 (d, J = 8.8 Hz, 1H), 7.76 (d, J = 6.9 Hz, 1H), 7.65 (br. s., 1H), 7.54 (d, J = 7.7 Hz, 1H), 7.51-7.36 (m, 4H), 7.27 (d, J = 10.5 Hz, 1H), 6.97 (br. s., 2H), 4.81 (br. s., 1H), 4.72-4.59 (m, 1H), 4.46 (d, J = 13.2 Hz, 2H), 3.60 (br. s., 2H), 3.19 (br. s., 2H) | 2.0 N 658.1 | 5.4 | 126.4 |
| B286 | 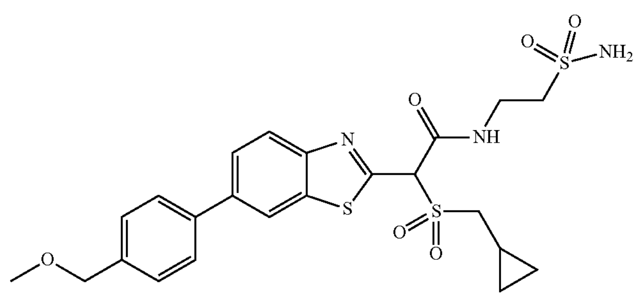 [SMILES: COCc1ccc(-c2ccc3nc(C(C(=O)NCCS(N)(=O)=O)S(=O)(=O)CC4CC4)sc3c2)cc1] | 2-cyclopropylmethanesulfonyl-2-{6-[4-(methoxymethyl)phenyl]-1,3-benzothiazol-2-yl}-N-(2-sulfamoylethyl)acetamide | δ 9.04 (br. s., 1H), 8.48 (br. s., 1H), 8.13 (d, J = 8.5 Hz, 1H), 7.86 (d, J = 8.5 Hz, 1H), 7.75 (d, J = 7.2 Hz, 1H), 7.67 (br. s., 1H), 7.55-7.34 (m, 2H), 6.97 (br. s., 2H), 4.75-4.32 (m, 2H), 3.59 (br. s., 2H), 3.39 (d, J = 6.1 Hz, 1H), 3.29-3.04 (m, 3H), 1.09 (br. s., 1H), 0.62 (d, J = 6.9 Hz, 2H), 0.40 (br. s., 2H) | 1.71 N 538.1 | 3.9 | 55.5 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B287 | 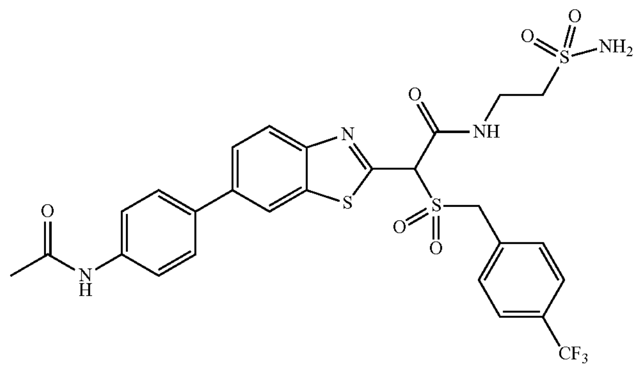 [SMILES: CC(=O)Nc1ccc(-c2ccc3nc(C(C(=O)NCCS(N)(=O)=O)S(=O)(=O)Cc4ccc(C(F)(F)F)cc4)sc3c2)cc1] | 2-[6-(4-acetamidophenyl)-1,3-benzothiazol-2-yl]-N-(2-sulfamoylethyl)-2-{[4-(trifluoromethyl)phenyl]methanesulfonyl}acetamide | δ 7.95 (s, 1H),7.91-7.80 (m, 1H), 7.83-7.50 (m, 10H), 6.95 (s, 2H), 5.02-4.63 (m, 2H), 3.69-3.50 (m, 2H), 3.24-3.06 (m, 2H), 2.07 (d, J = 6.9 Hz, 3H) | 1.65 N 655.1 | 7.0 | 90.0 |
| B288 | 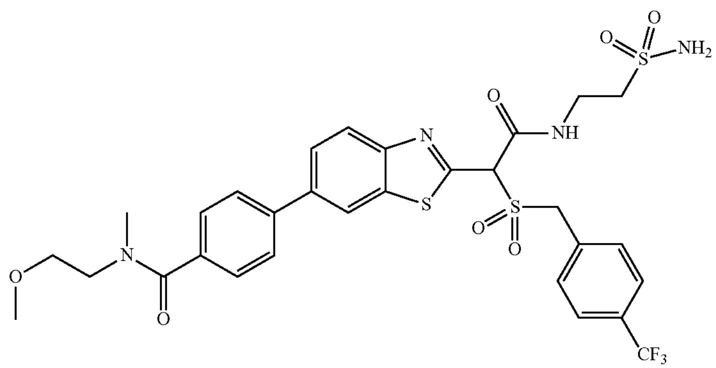 | N-(2-methoxyethyl)-N-methyl-4-(2-{[(2-sulfamoylethyl)carbamoyl][4-(trifluoromethyl)phenyl]methanesulfonyl}methyl)-1,3-benzothiazol-6-yl)benzamide | δ 8.33-7.38 (m, 11H), 7.07-6.88 (m, 2H), 6.19-6.05 (m, 1H), 4.98-4.84 (m, 1H), 4.81-4.62 (m, 1H), 3.77-3.52 (m, 4H), 3.55-3.39 (m, 3H), 3.27-3.10 (m, 4H), 3.00 (br. s., 3H) | 1.73 N 713.14 | 0.8 | 123.5 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B289 | 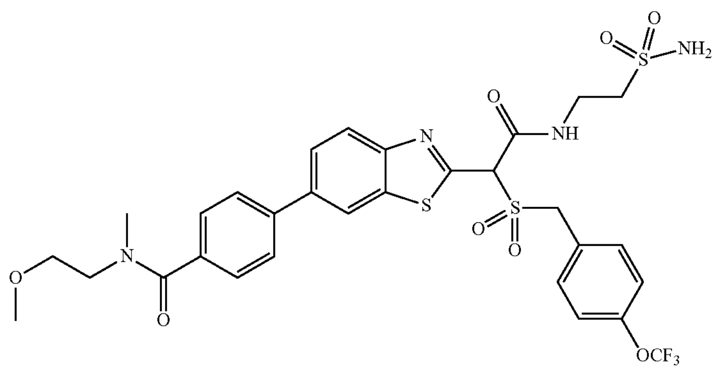 [SMILES: COCCN(C)C(=O)c1ccc(-c2ccc3nc(C(C(=O)NCCS(N)(=O)=O)S(=O)(=O)Cc4ccc(C(F)(F)F)cc4)sc3c2)cc1] | N-(2-methoxyethyl)-N-methyl-4-(2-{[(2-sulfamoylethyl)carbamoyl][4-(trifluoromethoxy)phenyl]methanesulfonyl}-1,3-benzothiazol-6-yl)benzamide | δ 8.65-8.43 (m, 1H), 8.26-8.04 (m, 1H), 8.01-7.63 (m, 4H), 7.59-7.16 (m, 6H), 7.03-6.84 (m, 2H), 6.27-6.03 (m, 1H), 4.98-4.74 (m, 1H), 4.77-4.55 (m, 1H), 3.73-3.52 (m, 4H), 3.52-3.39 (m, 3H), 3.23-3.10 (m, 4H), 3.00 (br. s., 3H) | 1.78 N 729.13 | 3.1 | 21.7 |
| B290 | 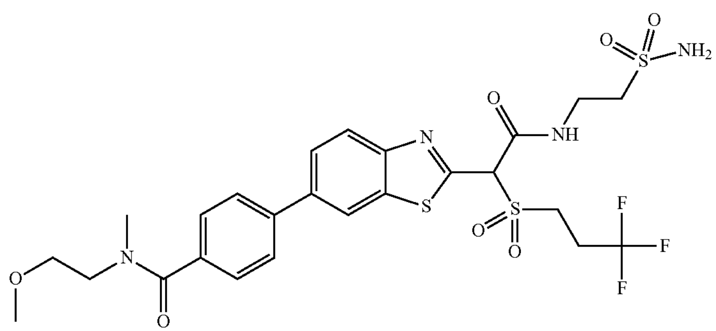 [SMILES: COCCN(C)C(=O)c1ccc(-c2ccc3nc(C(C(=O)NCCS(N)(=O)=O)S(=O)(=O)CCC(F)(F)F)sc3c2)cc1] | N-(2-methoxyethyl)-N-methyl-4-(2-{[(2-sulfamoylethyl)carbamoyl](3,3,3-trifluoropropanesulfonyl)methyl}-1,3-benzothiazol-6-yl)benzamide | δ 9.04-8.90 (m, 1H), 8.69-8.47 (m, 1H), 8.32-8.11 (m, 1H), 8.03-7.66 (m, 4H), 7.61-7.43 (m, 2H), 6.95 (s, 2H), 6.49-6.12 (m, 1H), 4.00-3.51 (m, 5H), 3.57-3.38 (m, 2H), 3.27-3.10 (m, 4H), 3.00 (br. s., 3H), 2.92-2.80 (m, 2H) | 1.51 N 651.1 | 12.1 | 114.5 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B291 | 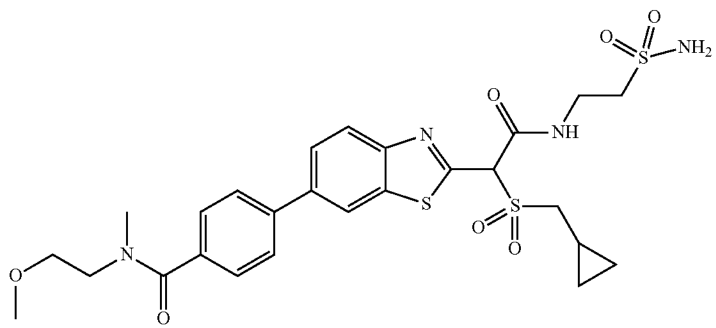 [SMILES: COCCN(C)C(=O)c1ccc(-c2ccc3nc(C(C(=O)NCCS(N)(=O)=O)S(=O)(=O)CC4CC4)sc3c2)cc1] | 4-(2-{cyclopropylmethanesulfonyl[(2-sulfamoylethyl)carbamoyl]methyl}-1,3-benzothiazol-6-yl)-N-(2-methoxyethyl)-N-methylbenzamide | δ 9.17-8.93 (m, 1H), 8.62-8.44 (m, 1H), 8.23-8.08 (m, 1H), 7.94-7.68 (m, 3H), 7.61-7.41 (m, 2H), 7.06-6.86 (m, 2H), 6.11-6.01 (m, 1H), 3.74-3.54 (m, 4H), 3.50-3.40 (m, 4H), 3.25-3.14 (m, 5H), 3.00 (br. s., 3H), 1.23-1.04 (m, 1H), 0.72-0.46 (m, 2H), 0.42-0.18 (m, 2H) | 1.34 N 609.2 | 0.7 | 35.2 |
| B292 | 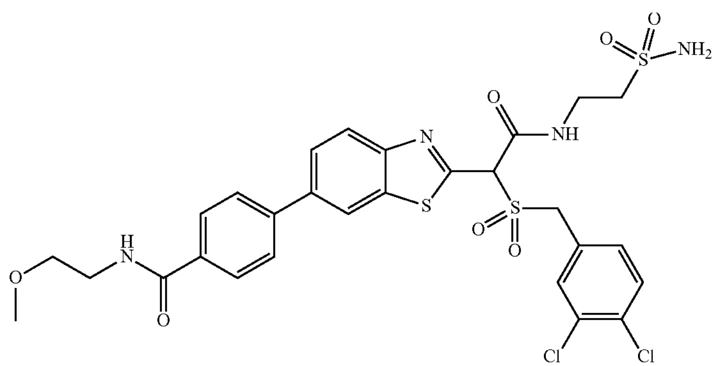 [SMILES: COCCNC(=O)c1ccc(-c2ccc3nc(C(C(=O)NCCS(N)(=O)=O)S(=O)(=O)Cc4ccc(Cl)c(Cl)c4)sc3c2)cc1] | 4-{2-[(3,4-dichlorophenyl)methanesulfonyl](2-sulfamoylethyl)carbamoyl]methyl]-1,3-benzothiazol-6-yl}-N-(2-methoxyethyl)benzamide | δ 9.15-8.99 (m, 1H), 8.57 (d, J = 1.4 Hz, 1H), 8.18 (d, J = 8.5 Hz, 1H), 8.05-7.74 (m, 4H), 7.71-7.50 (m, 2H), 7.47-7.31 (m, 1H), 6.97 (s, 2H), 6.08 (s, 1H), 4.80 (s, 1H), 4.72-4.59 (m, 1H), 3.72-3.56 (m, 2H), 3.53-3.41 (m, 4H), 3.28 (d, J = 2.2 Hz, 3H), 3.19 (s, 2H) | 1.61 N 699.1 | 20.2 | 112.0 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B293 | 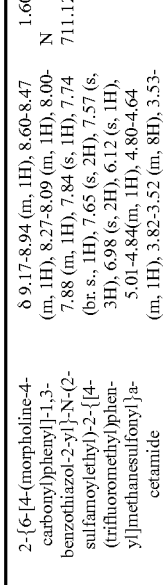 | 2-{6-[4-(morpholine-4-carbonyl)phenyl]-1,3-benzothiazol-2-yl}-N-(2-sulfamoylethyl)-2-{[4-(trifluoromethyl)phenyl]methanesulfonyl}acetamide | δ 9.17-8.94 (m, 1H), 8.60-8.47 (m, 1H), 8.27-8.09 (m, 1H), 8.00-7.88 (m, 1H), 7.84 (s, 1H), 7.74 (br. s., 1H), 7.65 (s, 2H), 7.57 (s, 3H), 6.98 (s, 2H), 6.12 (s, 1H), 5.01-4.84(m, 1H), 4.80-4.64 (m, 1H), 3.82-3.52 (m, 8H), 3.53-3.37 (m, 2H), 3.26-3.10 (m, 2H) | 1.60 N 711.12 | 145.6 | 328.5 |
| B294 | 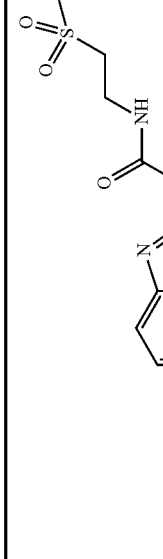 | 2-{6-[4-(morpholine-4-carbonyl)phenyl]-1,3-benzothiazol-2-yl}-N-(2-sulfamoylethyl)-2-{[4-(trifluoromethoxy)phenyl]methanesulfonyl}acetamide | δ 9.14-8.99 (m, 1H), 8.61-8.45 (m, 1H), 8.25-8.17 (m, 1H), 8.15-8.08 (m, 1H), 7.85 (d, J = 8.3 Hz, 3H), 7.55 (t, J = 8.0 Hz, 3H), 7.40 (s, 1H), 7.35-7.20 (m, 1H), 6.97 (s, 2H), 6.12 (s, 1H), 4.88-4.76 (m, 1H), 4.74-4.58 (m, 1H), 3.81-3.51 (m, 8H), 3.46-3.36 (m, 2H), 3.30-3.13 (m, 2H) | 1.65 N 725.10 | 74.8 | 180.7 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B295 | 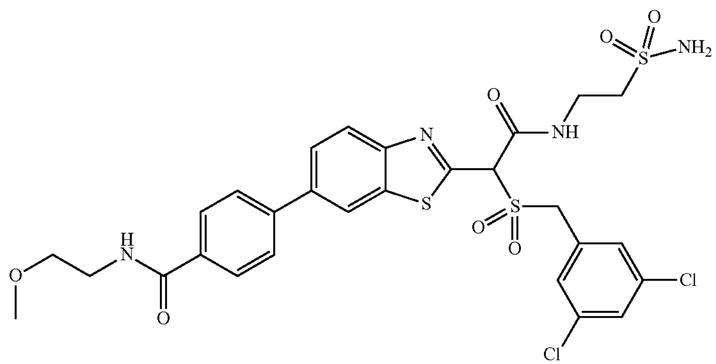 [SMILES: COCCNC(=O)c1ccc(-c2ccc3nc(C(C(=O)NCCS(N)(=O)=O)S(=O)(=O)Cc4cc(Cl)cc(Cl)c4)sc3c2)cc1] | 4-{2-[(3,5-dichlorophenyl)methanesulfonyl][(2-sulfamoylethyl)carbamoyl]methyl]-1,3-benzothiazol-6-yl}-N-(2-methoxyethyl)benzamide | δ 9.15-8.93 (m, 1H), 8.68-8.53 (m, 2H), 8.28-8.16 (m, 1H), 8.07-7.76 (m, 7H), 7.55-7.37 (m, 3H), 7.06-6.91 (m, 2H), 6.23-6.06 (m, 1H), 4.91-4.76 (m, 1H), 4.75-4.57 (m, 1H), 3.75-3.56 (m, 2H), 3.53-3.41 (m, 4H), 3.28 (d, J = 1.9 Hz, 3H), 3.25-3.12 (m, 2H) | 1.64 N 699.06 | 20.9 | 140.4 |
| B296 | 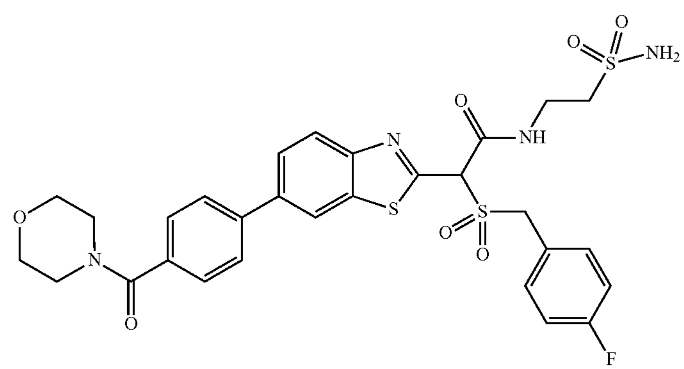 [SMILES: NS(=O)(=O)CCNC(=O)C(c1nc2ccc(-c3ccc(C(=O)N4CCOCC4)cc3)cc2s1)S(=O)(=O)Cc1ccc(F)cc1] | 2-[(4-fluorophenyl)methanesulfonyl]-2-{6-[4-(morpholine-4-carbonyl)phenyl]-1,3-benzothiazol-2-yl}-N-(2-sulfamoylethyl)acetamide | δ 9.15-8.99 (m, 1H), 8.62-8.48 (m, 1H), 8.28-8.13 (m, 1H), 7.85 (d, J = 8.3 Hz, 5H), 7.56 (d, J = 8.3 Hz, 4H), 7.29-7.06 (m, 3H), 6.97 (s, 2H), 6.07 (s, 1H), 4.86-4.71 (m, 1H), 4.71-4.53 (m, 1H), 3.60 (d, J = 6.3 Hz, 10H), 3.27-3.10 (m, 2H) | 1.51 N 661.1 | 2.9 | 266.7 |

| Ex # | Structure | Name | $^1$H NMR (500 MHz, DMSO-$d_6$, unless indicated otherwise) | LC/MS RT (min) Method M+H | EI IC$_{50}$ (nM) | HL IC$_{50}$ (nM) |
|---|---|---|---|---|---|---|
| B297 | 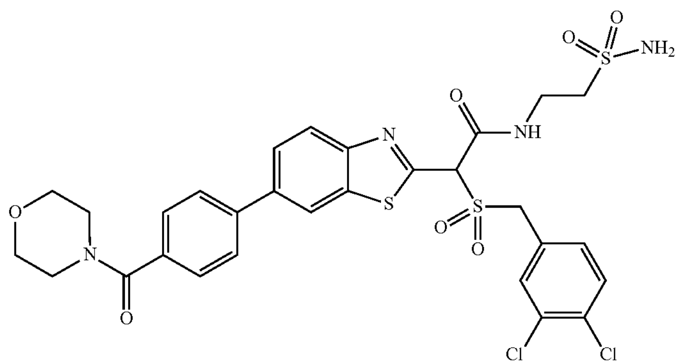 [SMILES: NS(=O)(=O)CCNC(=O)C(c1nc2ccc(-c3ccc(C(=O)N4CCOCC4)cc3)cc2s1)S(=O)(=O)Cc1ccc(Cl)c(Cl)c1] | 2-[(3,4-dichlorophenyl)methanesulfonyl]-2-{6-[4-(morpholine-4-carbonyl)phenyl]-1,3-benzothiazol-2-yl}-N-(2-sulfamoylethyl)acetamide | δ 9.19-9.84 (m, 1H), 8.66-8.45 (m, 1H), 8.28-8.09 (m, 1H), 8.00-7.46 (m, 8H), 7.48-7.27 (m, 1H), 6.97 (s, 2H), 4.80 (s, 1H), 4.72-4.56 (m, 10H), 3.61 (dd, J = 13.2, 6.6 Hz, 10H), 3.19 (s, 2H) | 1.68 N 711.08 | 5.3 | 555.7 |
| B298 | 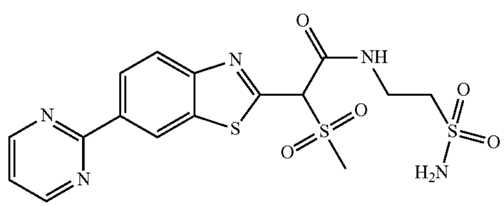 [SMILES: CS(=O)(=O)C(C(=O)NCCS(N)(=O)=O)c1nc2ccc(-c3ncccn3)cc2s1] | 2-methanesulfonyl-2-[6-(pyrimidin-2-yl)-1,3-benzothiazol-2-yl]-N-(2-sulfamoylethyl)acetamide | δ 9.35-8.93 (m, 4H), 8.88-8.22 (m, 2H), 8.19-7.82 (m, 2H), 7.08-6.77 (m, 2H), 6.08 (br. s., 1H), 3.83-3.49 (m, 2H), 3.26 (br. s., 4H) | 1.00 O 534.0 | 41.5 | 865.7 |
| B299 | 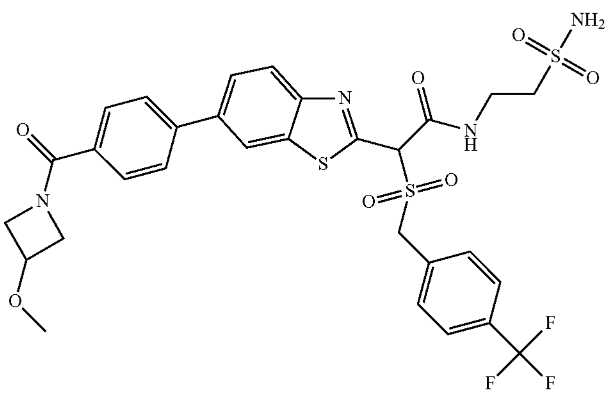 [SMILES: COC1CN(C(=O)c2ccc(-c3ccc4nc(C(C(=O)NCCS(N)(=O)=O)S(=O)(=O)Cc5ccc(C(F)(F)F)cc5)sc4c3)cc2)C1] | 2-{6-[4-(3-methoxyazetidine-1-carbonyl)phenyl]-1,3-benzothiazol-2-yl}-N-(2-sulfamoylethyl)-2-[[4-(trifluoromethyl)phenyl]methanesulfonyl]acetamide | $^1$H NMR (400 MHz, DMSO-$d_6$) δ 9.17-8.53 (m, 1H), 8.27-8.10 (m, 1H), 7.85 (s, 3H), 7.76 (d, J = 9.5 Hz, 4H), 7.67-7.58 (m, 2H), 6.96 (m, 1H), 4.93-4.70 (m, 2H), 4.51 (br. s., 1H), 4.33-4.11 (m, 3H), 3.88 (br. s., 1H), 3.62 (d, J = 6.2 Hz, 2H), 3.29 (s, 2H), 3.25 (d, J = 1.8 Hz, 3H), 3.21 (s, 1H | 1.90 B 711.0 | 5.6 | 74.2 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B300 | 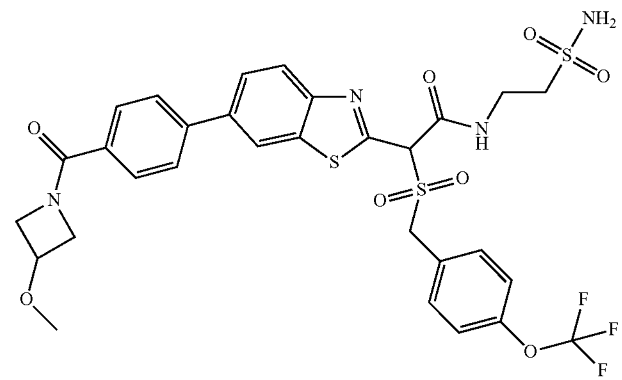 [SMILES: COC1CN(C(=O)c2ccc(-c3ccc4nc(C(C(=O)NCCS(N)(=O)=O)S(=O)(=O)Cc5ccc(OC(F)(F)F)cc5)sc4c3)cc2)C1] | 2-{6-[4-(3-methoxy-azetidine-1-carbonyl)phenyl]-1,3-benzothiazol-2-yl}-N-(2-sulfamoyl-ethyl)-2-{[4-(trifluoromethoxy)phenyl]methanesulfonyl}acetamide | δ 9.15-8.52 (m, 1H), 8.32-8.10 (m, 1H), 7.99-7.66 (m, 6H), 7.59-7.37 (m, 3H), 7.28 (dd, J = 18.7, 6.9 Hz, 1H), 7.03-6.90 (m, 2H), 4.97-4.60 (m, 2H), 4.57-4.43 (m, 1H), 4.31-4.17 (m, 3H), 3.94-3.83 (m, 1H), 3.70-3.56 (m, 2H), 3.28-3.16 (m, 5H) | 1.73 O 727.1 | 5.5 | 85.1 |
| B301 | 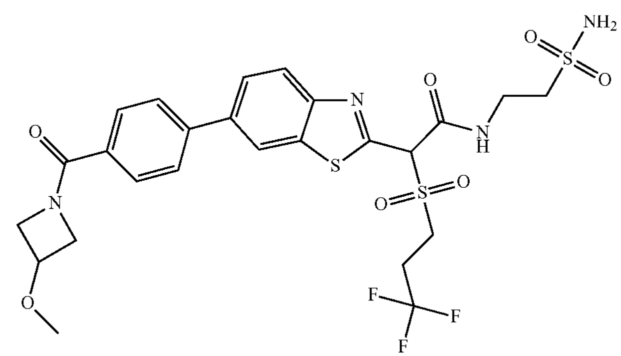 [SMILES: COC1CN(C(=O)c2ccc(-c3ccc4nc(C(C(=O)NCCS(N)(=O)=O)S(=O)(=O)CCC(F)(F)F)sc4c3)cc2)C1] | 2-{6-[4-(3-methoxy-azetidine-1-carbonyl)phenyl]-1,3-benzothiazol-2-yl}-N-(2-sulfamoyl-ethyl)-2-(3,3,3-trifluoropropanesulfonyl)acetamide | δ 9.00-8.95 (m, 1H), 8.64-8.50 (m, 1H), 8.19 (d, J = 8.5 Hz, 1H), 7.99-7.91 (m, 2H), 7.90-7.84 (m, 2H), 7.82-7.71 (m, 3H), 7.00-6.89 (m, 2H), 6.28 (s, 1H), 4.56-4.45 (m, 1H), 4.33-4.14 (m, 3H), 3.95-3.84 (m, 1H), 3.84-3.51 (m, 4H), 3.25 (s, 3H), 3.23-3.18 (m, 1H), 2.90-2.82 (m, 1H) | 1.54 O 649.1 | 7.8 | 112.9 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B302 | 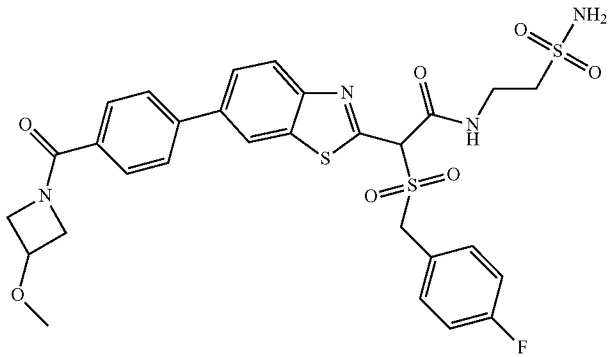 [SMILES: COC1CN(C(=O)c2ccc(-c3ccc4nc(C(C(=O)NCCS(N)(=O)=O)S(=O)(=O)Cc5ccc(F)cc5)sc4c3)cc2)C1] | 2-[(4-fluorophenyl)methanesulfonyl]-2-{6-[4-(3-methoxyazetidine-1-carbonyl)phenyl]-1,3-benzothiazol-2-yl}-N-(2-sulfamoylethyl)acetamide | δ 9.22-8.54 (m, 1H), 8.34-8.16 (m, 1H), 7.87 (d, J = 8.0 Hz, 2H), 7.83-7.71 (m, 3H), 7.48 (d, J = 2.5 Hz, 2H), 7.25 (s, 2H), 6.96 (s, 2H), 6.09 (s, 1H), 4.81-4.56 (m, 2H), 4.54-4.45 (m, 1H), 4.34-4.17 (m, 3H), 3.94-3.84 (m, 2H), 3.71-3.56 (m, 2H), 3.26-3.15 (m, 5H) | 1.55 O 661.1 | 7.2 | 52.0 |
| B303 | 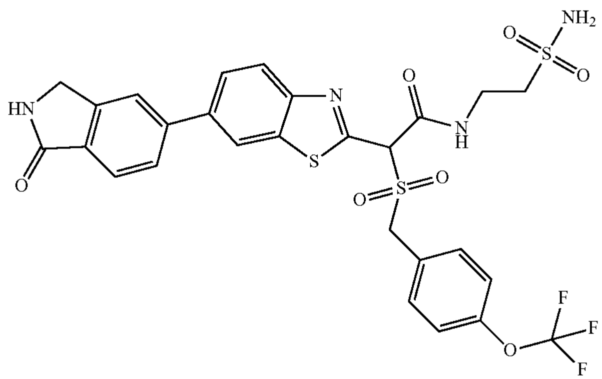 [SMILES: NS(=O)(=O)CCNC(=O)C(c1nc2ccc(-c3ccc4c(c3)CNC4=O)cc2s1)S(=O)(=O)Cc1ccc(OC(F)(F)F)cc1] | 2-[6-(1-oxo-2,3-dihydro-1H-isoindol-5-yl)-1,3-benzothiazol-2-yl]-N-(2-sulfamoylethyl)-2-[[4-(trifluoromethoxy)phenyl]methanesulfonyl]acetamide | δ 9.05 (t, J = 5.5 Hz, 1H), 8.65-8.56 (m, 2H), 8.29-8.10 (m, 2H), 8.00-7.94 (m, 3H), 7.93-7.85 (m, 2H), 7.83-7.73 (m, 3H), 7.59-7.53 (m, 2H), 7.51-7.46 (m, 1H), 7.43-7.36 (m, 2H), 7.35-7.24 (m, 2H), 6.97 (s, 4H), 6.18-6.09 (m, 1H), 4.95-4.78 (m, 2H), 4.76-4.62 (m, 2H), 4.52-4.41 (m, 3H), 3.74-3.55 (m, 4H), 3.27-3.14 (m, 4H), 2.63-2.55 (m, 2H) | 1.56 O 669.1 | 2.5 | 51.2 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B304 | 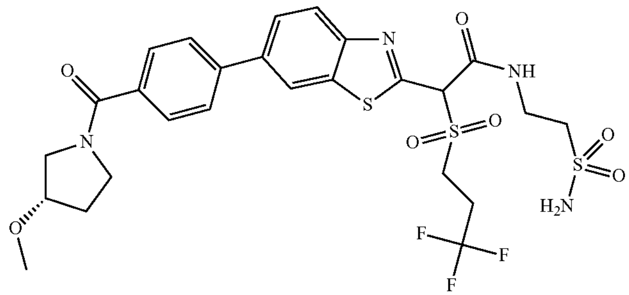 [SMILES: CO[C@H]1CCN(C(=O)c2ccc(-c3ccc4nc(C(C(=O)NCCS(N)(=O)=O)S(=O)(=O)CCC(F)(F)F)sc4c3)cc2)C1] | 2-(6-{4-[(3S)-3-methoxypyrrolidine-1-carbonyl]phenyl}-1,3-benzothiazol-2-yl)-N-(2-sulfamoylethyl)-2-(3,3,3-trifluoropropanesulfonyl)acetamide | δ 9.34 (br. s., 1H), 9.06-8.89 (m, 1H), 8.70 (s, 1H), 8.61-8.55 (m, 1H), 8.42-8.35 (m, 1H), 8.27-8.16 (m, 2H), 8.09-8.03 (m, 1H), 7.99-7.89 (m, 4H), 7.88-7.83 (m, 2H), 7.81-7.75 (m, 1H), 7.74-7.60 (m, 4H), 7.03-7.01 (m, 1H), 6.97 (br. s., 2H), 6.33-6.25 (m, 1H), 4.10-3.91 (m, 2H), 3.86-3.40 (m, 1H), 3.30 (br. s., 4H), 3.20 (br. s., 4H), 2.57 (br. s., 8H), 2.02 (br. s., 4H). | 1.50 O 663.1 | 0.7 | 16.6 |
| B305 | 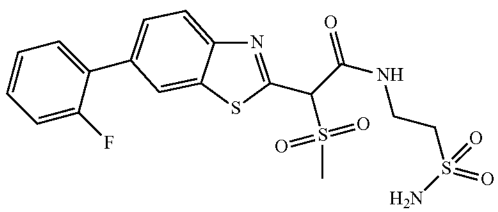 [SMILES: CS(=O)(=O)C(C(=O)NCCS(N)(=O)=O)c1nc2ccc(-c3ccccc3F)cc2s1] | 2-[6-(2-fluorophenyl)-1,3-benzothiazol-2-yl]-2-methanesulfonyl-N-(2-sulfamoylethyl)acetamide | δ 9.07-8.95 (m, 1H), 8.38 (s, 1H), 8.23-8.15 (m, 1H), 7.81-7.72 (m, 1H), 7.66-7.61 (m, 1H), 7.45-7.33 (m, 3H), 6.97 (s, 2H), 6.16-6.02 (m, 1H), 3.65-3.58 (m, 2H), 3.29-3.24 (m, 3H), 3.21 (t, J = 7.0 Hz, 2H). | 1.52 O 471.9 | 3.0 | 1.0 |
| B306 | 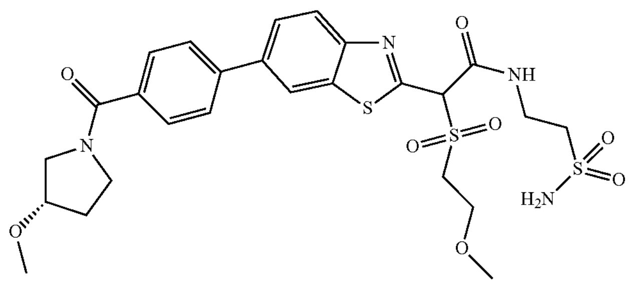 [SMILES: COCCS(=O)(=O)C(C(=O)NCCS(N)(=O)=O)c1nc2ccc(-c3ccc(C(=O)N4CC[C@H](OC)C4)cc3)cc2s1] | 2-(2-methoxyethanesulfonyl)-2-(6-{4-[(3S)-3-methoxypyrrolidine-1-carbonyl]phenyl}-1,3-benzothiazol-2-yl)-N-(2-sulfamoylethyl)acetamide | δ 8.98 (br. s., 1H), 8.56 (s, 1H), 8.18 (d, J = 8.3 Hz, 1H), 8.01-7.90 (m, 2H), 7.88-7.83 (m, 2H), 7.81-7.73 (m, 1H), 7.70-7.61 (m, 3H), 7.22 (s, 1H), 7.12 (s, 1H), 7.02 (s, 1H), 6.99-6.91 (m, 3H), 6.10-6.04 (m, 1H), 4.10-3.95 (m, 2H), 3.92 (s, 1H), 3.39 (br. s., 32H), 3.25-3.17 (m, 6H), 2.05-1.84 (m, 4H) | 1.20 N 625.1 | 3.8 | 149.3 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B307 | 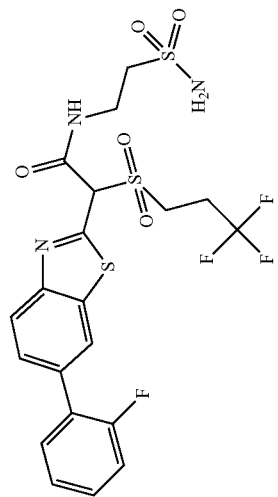 | 2-[6-(2-fluorophenyl)-1,3-benzothiazol-2-yl]-N-(2-sulfamoylethyl)-2-(3,3,3-trifluoropropanesulfonyl)acetamide | δ 9.11-8.97(m, 1H), 8.33 (m, 2H), 7.63-7.45 (m, 2H), 6.97 (m, 2H), 3.71-3.53 (m, 2H), 3.26-3.13 (m, 2H), 2.91 (s, 3H) | 1.5 N 540.1 | 3.0 | 1.5 |
| B308 | 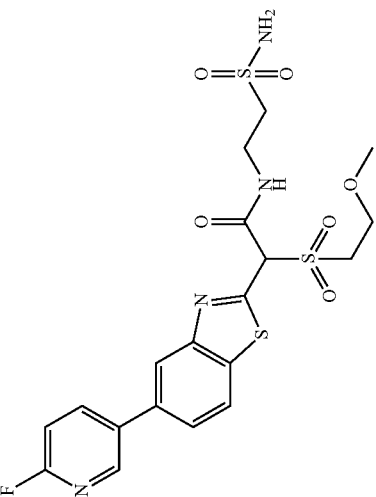 | 2-[5-(6-fluoropyridin-3-yl)-1,3-benzothiazol-2-yl]-2-(2-methoxyethanesulfonyl)-N-(2-sulfamoylethyl)acetamide | δ 8.96 (t, J = 5.8 Hz, 1H), 8.71 (d, J = 2.5 Hz, 1H), 8.51-8.39 (m, 2H), 8.30 (d, J = 8.3 Hz, 1H), 7.90 (dd, J = 8.5, 1.9 Hz, 1H), 7.34 (dd, J = 8.5, 2.5 Hz, 1H), 6.96 (s, 2H), 6.07 (s, 1H), 3.83-3.67 (m, 4H), 3.64-3.58 (m, 2H), 3.29 (s, 3H), 3.20 (td, J = 7.1, 2.3 Hz, 2H). | 1.32 N 517 | 1.3 | 194.0 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B309 | 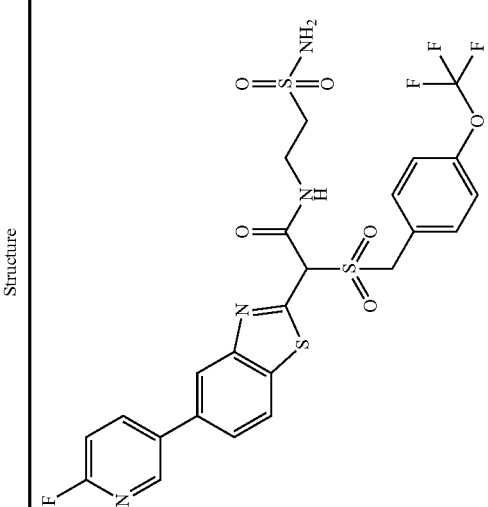 | 2-[5-(6-fluoropyridin-3-yl)-1,3-benzothiazol-2-yl]-N-(2-sulfamoylethyl)-2-{[4-(trifluoromethoxy)phenyl]methanesulfonyl}acetamide | δ 9.07 (t, J = 5.8 Hz, 1H), 8.72 (d, J = 2.5 Hz, 1H), 8.54 (br. s., 1H), 8.50 (d, J = 1.4 Hz, 1H), 8.46 (td, J = 8.3, 2.8 Hz, 1H), 8.31 (d, J = 8.3 Hz, 2H), 8.21-8.03 (m, 1H), 7.97-7.81 (m, 3H), 7.57 (d, J = 8.8 Hz, 3H), 7.51-7.21 (m, 7H), 6.99 (s, 4H), 6.14 (s, 1H), 4.90-4.78 (m, 2H), 4.75-4.62 (m, 2H), 3.72-3.55 (m, 4H), 3.28-3.14 (m, 4H). | 1.91 O 633 | 0.5 | 67.0 |
| B310 | 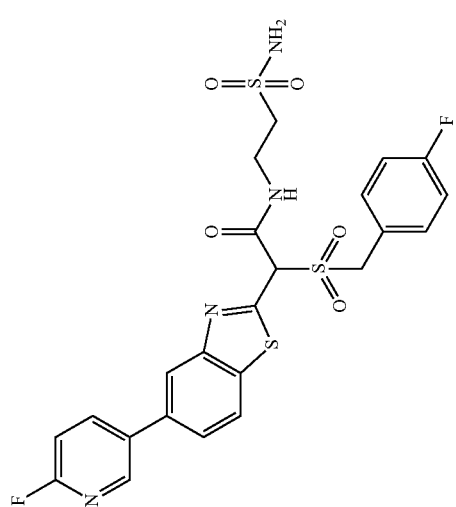 | 2-[(4-fluorophenyl)methanesulfonyl]-2-[5-(6-fluoropyridin-3-yl)-1,3-benzothiazol-2-yl]-N-(2-sulfamoylethyl)acetamide | δ 9.06 (t, J = 5.6 Hz, 1H), 8.72 (d, J = 2.2 Hz, 1H), 8.51 (d, J = 1.4 Hz, 1H), 8.46 (td, J = 8.1, 2.8 Hz, 1H), 8.32 (d, J = 8.5 Hz, 1H), 7.91 (dd, J = 8.3, 1.7 Hz, 1H), 7.48 (dd, J = 8.5, 5.5 Hz, 2H), 7.43-7.32 (m, 2H), 7.25 (t, J = 8.9 Hz, 1H), 7.17-7.06 (m, 1H), 6.99 (s, 2H), 6.10 (s, 1H), 4.83-4.73 (m, 2H), 4.70-4.56 (m, 1H), 3.65-3.55 (m, 2H), 3.26-3.14 (m, 2H) | 1.67 N 567 | 1.0 | 51.4 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B311 | 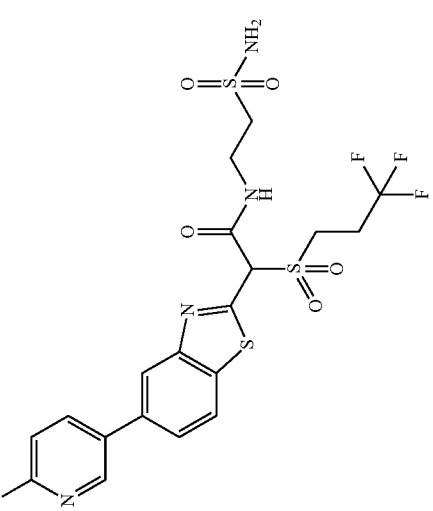 | 2-[5-(6-fluoropyridin-3-yl)-1,3-benzothiazol-2-yl]-N-(2-sulfamoylethyl)-2-(3,3,3-trifluoropropanesulfonyl)acetamide | δ 9.00 (t, J = 5.6 Hz, 1H), 8.71 (d, J = 2.2 Hz, 1H), 8.49-8.43 (m, 2H), 8.33 (d, J = 8.3 Hz, 1H), 7.92 (dd, J = 8.4, 1.5 Hz, 1H), 7.35 (dd, J = 8.4, 2.6 Hz, 1H), 6.99 (s, 1H), 6.30 (s, 1H), 3.86-3.69 (m, 1H), 3.63 (dd, J = 12.0, 6.2 Hz, 3H), 3.25-3.16(m, 2H), 2.89-2.81 (m, 1H) | 1.65 N 555 | 3.1 | 24.2 |
| B312 | 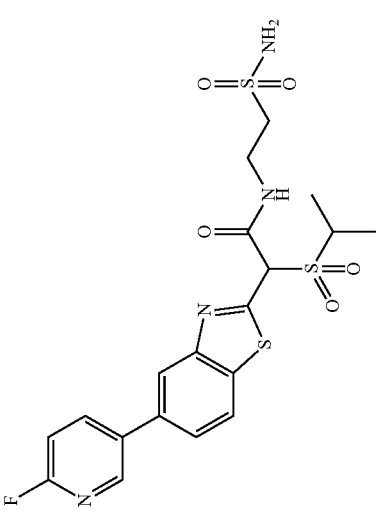 | 2-[5-(6-fluoropyridin-3-yl)-1,3-benzothiazol-2-yl]-2-(propane-2-sulfonyl)-N-(2-sulfamoylethyl)acetamide | δ 9.08 (t, J = 5.6 Hz, 1H), 8.71 (d, J = 2.5 Hz, 1H), 8.49-8.40 (m, 2H), 8.30 (d, J = 8.3 Hz, 2H), 7.90 (dd, J = 8.4, 1.8 Hz, 1H), 7.35 (dd, J = 8.5, 2.8 Hz, 1H), 6.98 (s, 2H), 6.22 (s, 1H), 3.71-3.51 (m, 3H), 3.28-3.13 (m, 2H), 1.39 (d, J = 6.9 Hz, 3H), 1.28 (d, J = 6.9 Hz, 3H) | 1.45 N 501 | 6.2 | 152.7 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B313 | 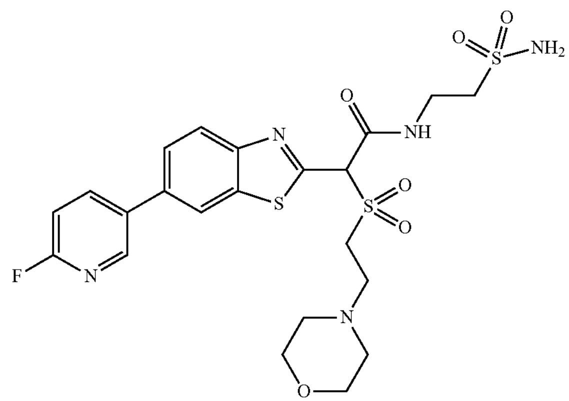 [SMILES: NS(=O)(=O)CCNC(=O)C(c1nc2ccc(-c3ccc(F)nc3)cc2s1)S(=O)(=O)CCN1CCOCC1] | 2-[6-(6-fluoropyridin-3-yl)-1,3-benzothiazol-2-yl]-2-[2-(morpholin-4-yl)ethanesulfonyl]-N-(2-sulfamoylethyl)acetamide | δ 8.64 (br. s., 1H), 8.41-8.35 (m, 1H), 7.88 (d, J = 7.4 Hz, 1H), 7.33 (dd, J = 8.5, 2.2 Hz, 1H), 6.95 (s, 2H), 3.68-3.49 (m, 8H), 3.19 (t, J = 6.9 Hz, 3H), 2.78 (br. s., 2H), 2.40 (br. s., 4H) | 1.93 B 572.1 | 10.8 | 106.5 |
| B314 | 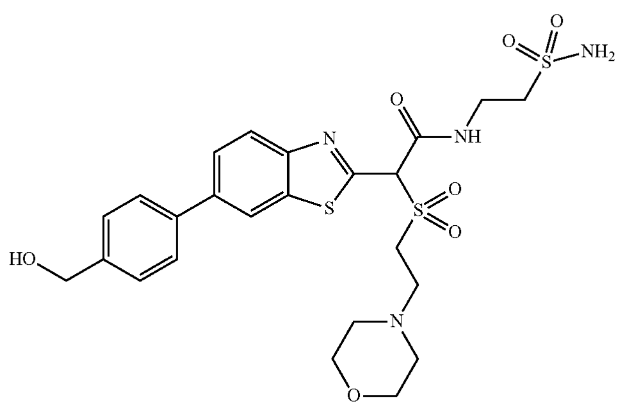 [SMILES: NS(=O)(=O)CCNC(=O)C(c1nc2ccc(-c3ccc(CO)cc3)cc2s1)S(=O)(=O)CCN1CCOCC1] | 2-[6-[4-(hydroxymethyl)phenyl]-1,3-benzothiazol-2-yl]-2-[2-(morpholin-4-yl)ethanesulfonyl]-N-(2-sulfamoylethyl)acetamide | δ 7.70 (br. s., 2H), 7.43 (d, J = 7.2 Hz, 2H), 6.94 (br. s., 2H), 5.21 (br. s., 1H), 4.55 (d, J = 5.5 Hz, 2H), 3.68-3.41 (m, 8H), 3.19 (t, J = 6.9 Hz, 2H), 2.75 (br. s., 2H), 2.38 (br. s., 4H) | 1.41 B 583.1 | 16.1 | 35.1 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B315 | 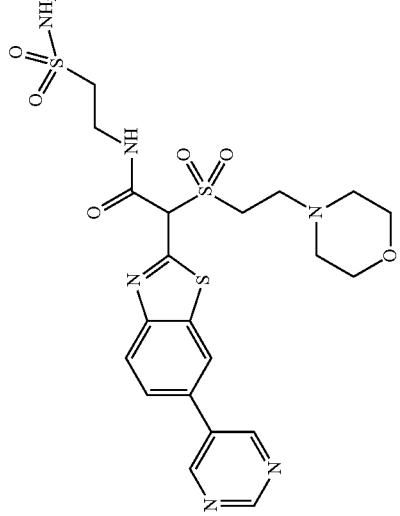 | 2-[2-(morpholin-4-yl)ethanesulfonyl]-2-[6-(pyrimidin-5-yl)-1,3-benzothiazol-2-yl]-N-(2-sulfamoylethyl)acetamide | δ 9.23 (br. s., 2H), 8.63 (br. s., 1H), 8.19 (br. s., 1H), 8.07-7.91 (m, 2H), 7.04-6.90 (m, 2H), 3.90-3.31 (m, 16H) | 1.24 B 555.1 | 55.6 | 10000.0 |
| B316 | 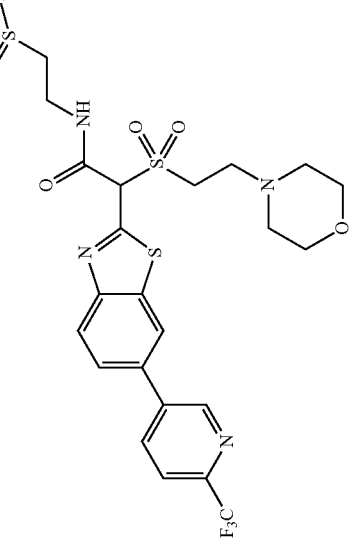 | 2-[2-(morpholin-4-yl)ethanesulfonyl]-N-(2-sulfamoylethyl)-2-{6-[6-(trifluoromethyl)pyridin-3-yl]-1,3-benzothiazol-2-yl}acetamide | δ 9.20 (br. s., 1H), 8.66 (br. s., 1H), 8.47 (d, J = 5.8 Hz, 1H), 8.22 (br. s., 1H), 8.06 (d, J = 8.0 Hz, 2H), 7.01-6.97 (m, 2H), 3.70-3.31 (m, 12H), 3.22 (br. s., 4H) | 1.63 B 622.1 | 145.4 | 399.1 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B317 | 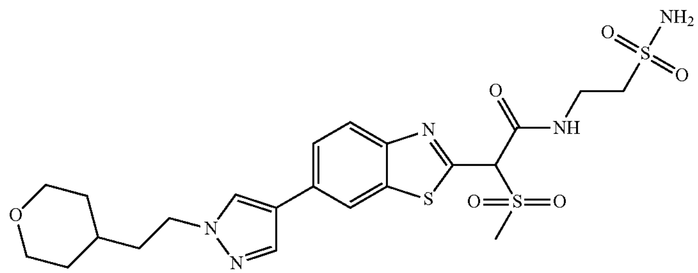 [SMILES: CS(=O)(=O)C(C(=O)NCCS(N)(=O)=O)c1nc2ccc(-c3cnn(CCC4CCOCC4)c3)cc2s1] | 2-methanesulfonyl-2-(6-{1-[2-(oxan-4-yl)ethyl]-1H-pyrazol-4-yl}-1,3-benzothiazol-2-yl)-N-(2-sulfamoylethyl)acetamide | $^1$H NMR (400 MHz, METHANOL-d4) δ 8.23 (d, J = 1.3 Hz, 1H), 8.14 (s, 1H), 8.07-8.01 (m, 1H), 7.96-7.89 (m, 1H), 7.77 (dd, J = 8.6, 1.8 Hz, 1H), 4.27-4.23 (m, 2H), 3.91 (dd, J = 10.9, 3.9 Hz, 3H), 3.81-3.74 (m, 1H), 3.42-3.36 (m, 2H), 3.35-3.32 (m, 3H), 3.20 (s, 3H), 1.86 (q, J = 6.8 Hz, 3H), 1.67 (d, J = 12.5 Hz, 2H), 1.39-1.27 (m, 2H) | 0.68 M 556.1 | 13.0 | 391.3 |
| B318 | 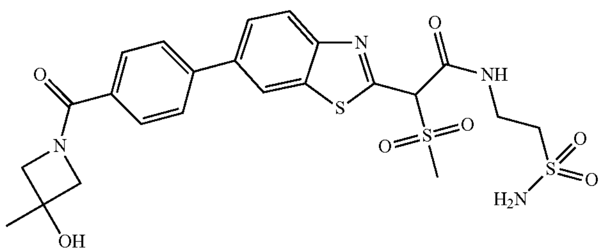 [SMILES: CC1(O)CN(C(=O)c2ccc(-c3ccc4nc(C(C(=O)NCCS(N)(=O)=O)S(C)(=O)=O)sc4c3)cc2)C1] | 2-{6-[4-(3-hydroxy-3-methylazetidine-1-carbonyl)phenyl]-1,3-benzothiazol-2-yl}-2-methanesulfonyl-N-(2-sulfamoylethyl)acetamide | δ 9.00 (br. s., 1H), 8.56 (br. s., 1H), 8.19 (d, J = 8.5 Hz, 1H), 8.01-7.91 (m, 1H), 7.89-7.81 (m, 2H), 7.80-7.71 (m, 2H), 7.01-6.89 (m, 2H), 6.12-5.98 (m, 1H), 5.85-5.63 (m, 1H), 4.31-4.13 (m, 2H), 4.00-3.87 (m, 3H), 3.67-3.55 (m, 3H), 3.29-3.16 (m, 4H), 1.50-1.40 (m, 3H) | 1.06 O 567.0 | 1.8 | 910.9 |
| B319 | 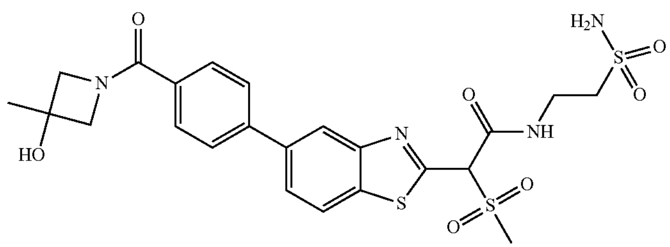 [SMILES: CC1(O)CN(C(=O)c2ccc(-c3ccc4sc(C(C(=O)NCCS(N)(=O)=O)S(C)(=O)=O)nc4c3)cc2)C1] | 2-{5-[4-(3-hydroxy-3-methylazetidine-1-carbonyl)phenyl]-1,3-benzothiazol-2-yl}-2-methanesulfonyl-N-(2-sulfamoylethyl)acetamide | δ 9.03 (br. s., 1H), 8.53-8.36 (m, 1H), 8.29 (m, 3H), 7.77 (d, J = 6.6 Hz, 2H), 6.99 (br. s., 2H), 6.06 (br. s., 2H), 4.29-4.11 (m, 2H), 4.01-3.84 (m, 3H), 3.66-3.57 (m, 2H), 3.26 (br. s., 3H), 3.20 (br. s., 2H), 1.42 (br. s., 3H) | 1.14 O 567.1 | 4.8 | 1001.0 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B320 | 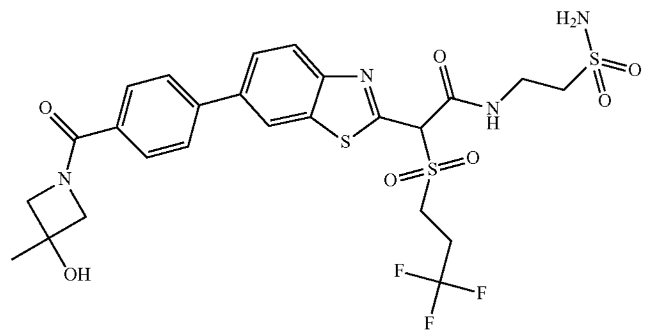 [SMILES: CC1(O)CN(C(=O)c2ccc(-c3ccc4nc(C(C(=O)NCCS(N)(=O)=O)S(=O)(=O)CCC(F)(F)F)sc4c3)cc2)C1] | 2-{6-[4-(3-hydroxy-3-methylazetidine-1-carbonyl)phenyl]-1,3-benzothiazol-2-yl}-N-(2-sulfamoylethyl)-2-(3,3,3-trifluoropropanesulfonyl)acetamide | δ 8.98 (br. s., 1H), 8.70-8.49 (m, 1H), 8.22-8.13 (m, 1H), 7.94 (d, J = 8.3 Hz, 1H), 7.86 (d, J = 7.7 Hz, 1H), 7.81-7.67 (m, 3H), 6.99 (br. s., 2H), 6.56-6.05 (m, 1H), 5.89-5.50 (m, 1H), 4.20 (d, J = 18.7 Hz, 2H), 3.94 (br. s., 2H), 3.83-3.53 (m, 4H), 3.20 (br. s., 2H), 2.97-2.81 (m, 2H), 1.42 (br. s., 3H) | 1.41 O 649.2 | 1.9 | 1264.0 |
| B321 | 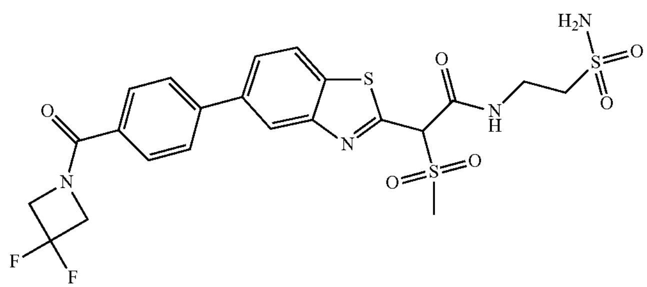 [SMILES: CS(=O)(=O)C(C(=O)NCCS(N)(=O)=O)c1nc2cc(-c3ccc(C(=O)N4CC(F)(F)C4)cc3)ccc2s1] | 2-{5-[4-(3,3-difluoroazetidine-1-carbonyl)phenyl]-1,3-benzothiazol-2-yl]-2-methanesulfonyl-N-(2-sulfamoylethyl)acetamide | δ 9.03 (br. s., 1H), 8.45 (br. s., 1H), 8.37-8.25 (m, 1H), 8.02-7.88 (m, 3H), 7.84 (d, J = 7.7 Hz, 2H), 6.99 (br. s., 2H), 6.07 (br. s., 1H), 4.87 (br. s., 2H), 4.65-4.38 (m, 2H), 3.62 (br. s., 2H), 3.27 (br. s., 3H), 3.20 (br. s., 2H) | 1.41 O 573.1 | 0.6 | 175.0 |

| Ex # | Structure | Name | $^1$H NMR (500 MHz, DMSO-d$_6$, unless indicated otherwise) | LC/MS RT (min) Method M + H | EL IC$_{50}$ (nM) | HL IC$_{50}$ (nM) |
|---|---|---|---|---|---|---|
| B322 | 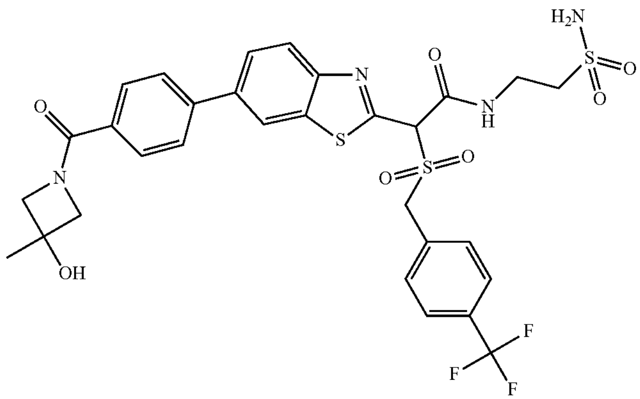 [SMILES: CC1(O)CN(C(=O)c2ccc(-c3ccc4nc(C(C(=O)NCCS(N)(=O)=O)S(=O)(=O)Cc5ccc(C(F)(F)F)cc5)sc4c3)cc2)C1] | 2-{6-[4-(3-hydroxy-3-methylazetidine-1-carbonyl)phenyl]-1,3-benzothiazol-2-yl}-N-(2-sulfamoylethyl)-2-{[4-(trifluoromethyl)phenyl]methanesulfonyl}acetamide | δ 9.11-8.54 (m, 1H), 8.30-8.10 (m, 1H), 8.04-7.89 (m, 1H), 7.88-7.84 (m, 1H), 7.76 (d, J = 8.3 Hz, 4H), 7.68-7.56 (m, 3H), 7.15-6.65 (m, 2H), 5.82-5.48 (m, 1H), 5.03-4.45 (m, 2H), 4.31-4.13 (m, 2H), 4.03-3.82 (m, 3H), 3.67-3.53 (m, 2H), 3.26-3.13 (m, 2H), 1.42 (d, J = 3.3 Hz, 3H) | 1.51 O 711.1 | 2.4 | 37.4 |
| B323 | 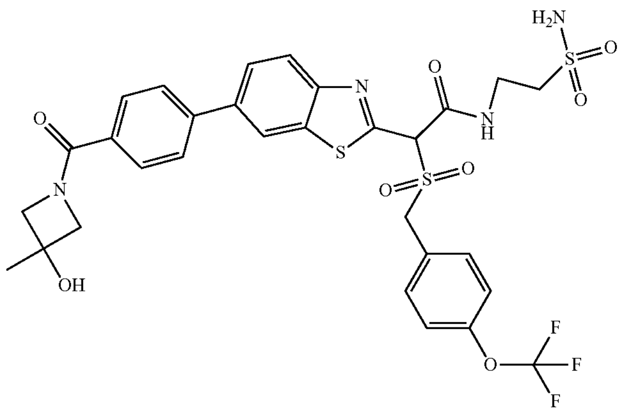 [SMILES: CC1(O)CN(C(=O)c2ccc(-c3ccc4nc(C(C(=O)NCCS(N)(=O)=O)S(=O)(=O)Cc5ccc(OC(F)(F)F)cc5)sc4c3)cc2)C1] | 2-{6-[4-(3-hydroxy-3-methylazetidine-1-carbonyl)phenyl]-1,3-benzothiazol-2-yl}-N-{2-sulfamoylethyl)-2-{[4-(trifluoromethoxy)phenyl]methanesulfonyl}acetamide | δ 9.19-8.51 (m, 1H), 8.21 (d, J = 8.5 Hz, 1H), 7.86 (s, 2H), 7.82-7.69 (m, 4H), 7.55 (s, 3H), 7.32-7.22 (m, 1H), 6.97 (s, 2H), 5.69 (d, J = 5.5 Hz, 1H), 5.05-4.53 (m, 2H), 4.33-4.09 (m, 2H), 4.02-3.83 (m, 3H), 3.69-3.51 (m, 2H), 3.22 (t, J = 7.2 Hz, 2H), 1.42 (d, J = 3.3 Hz, 3H) | 1.59 O 727.1 | 2.6 | 81.7 |

| Ex # | Structure | Name | 1H NMR (500 MHz, DMSO-d6, unless indicated otherwise) | LC/MS RT (min) Method M + H | EL IC50 (nM) | HL IC50 (nM) |
|---|---|---|---|---|---|---|
| B324 | 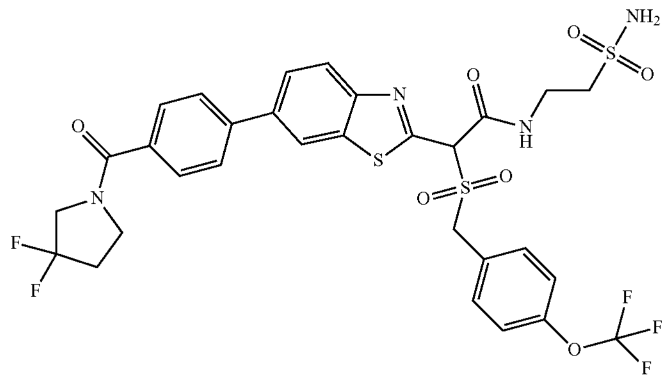 [SMILES: NS(=O)(=O)CCNC(=O)C(c1nc2ccc(-c3ccc(C(=O)N4CCC(F)(F)C4)cc3)cc2s1)S(=O)(=O)Cc1ccc(OC(F)(F)F)cc1] | 2-{6-[4-(3,3-difluoro pyrrolidine-1-carbonyl)phen-yl]-1,3-benzothiazol-2-yl}-N-(2-sulfamoyl-ethyl)-2-{[4-(trifluoro-methoxy)phen-yl]methanesulfonyl}a-cetamide | δ 9.17-8.47 (m, 1H), 8.27-8.09 (m, 1H), 8.00-7.93 (m, 1H), 7.90-7.86 (m, 1H), 7.73 (br. s., 3H), 7.59-7.46 (m, 2H), 7.44-7.37 (m, 1H), 7.33-7.24 (m, 1H), 7.03-6.92 (m, 2H), 4.89-4.78 (m, 1H), 4.73-4.61 (m, 1H), 4.03-3.91 (m, 2H), 3.77 (q, J = 6.8 Hz, 2H), 3.69-3.59 (m, 2H), 3.28-3.15 (m, 2H), 2.52 (br. s., 2H) | 1.92 O 747.1 | 9.1 | 58.1 |
| B325 | 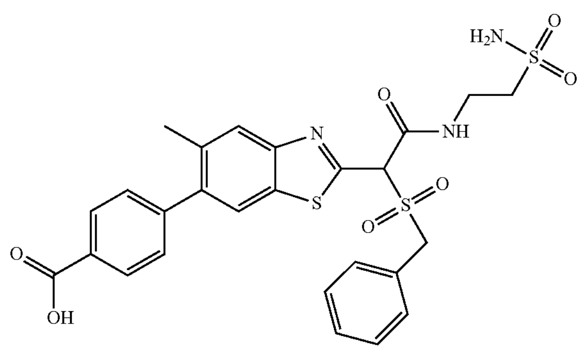 [SMILES: Cc1cc2nc(C(C(=O)NCCS(N)(=O)=O)S(=O)(=O)Cc3ccccc3)sc2cc1-c1ccc(C(=O)O)cc1] | 4-(5-methyl-2-{phen-ylmethanesulfonyl[(2-sulfa-moylethyl)carbamoyl]meth-yl}-1,3-benzothiazol-6-yl)benzoic acid | δ 8.03-8.07 (m, 2H), 8.00 (d, J = 8.25 Hz, 1H), 7.55 (d, J = 7.98 Hz, 1H), 7.48 (d, J = 6.88 Hz, 1H), 7.40 (s, 3H), 7.30 (d, J = 19.26 Hz, 2H), 6.95 (s, 2H), 6.08 (s, 1H), 4.68-4.79 (m, 1H), 4.62 (br. s., 1H), 3.60 (q, J = 6.69 Hz, 2H), 3.07-3.21 (m, 2H), 2.24-2.40 (m, 3H) | 1.85 B 588 | 1.2 | 104.0 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B326 | 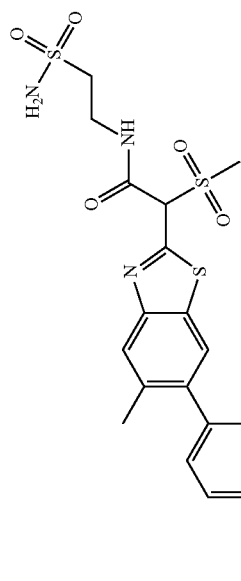 | 4-(2-{methanesulfonyl[(2-sulfamoylethyl)carbamoyl]methyl}-5-methyl-1,3-benzothiazol-6-yl)benzoic acid | δ 8.04 (d, J = 7.70 Hz, 4H), 7.54 (d, J = 7.98 Hz, 2H), 6.95 (s, 2H), 6.02 (s, 1H), 3.60 (q, J = 6.60 Hz, 2H), 3.23 (s, 3H), 3.14-3.19 (m, 2H), 2.36 (s, 3H) | 1.56 B 512 | 1.6 | 201.4 |
| B327 | 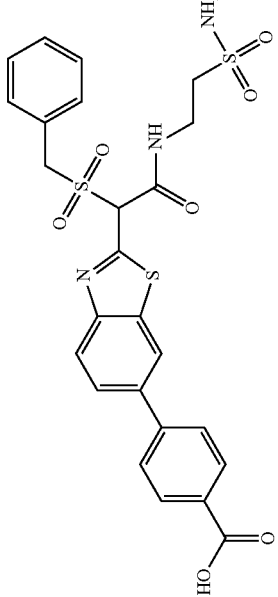 | 4-(2-[phenylmethanesulfonyl][(2-sulfamoylethyl)carbamoyl]methyl]-1,3-benzothiazol-6-yl)benzoic acid | δ 8.59 (s, 1H), 8.22 (d, J = 8.53 Hz, 1H), 8.07 (d, J = 7.70 Hz, 2H), 8.02 (d, J = 7.70 Hz, 1H), 7.95 (br. s., 1H), 7.91 (d, J = 7.98 Hz, 2H), 7.79-7.84 (m, 1H), 7.32-7.36 (m, 1H), 7.27 (d, J = 5.50 Hz, 1H), 6.96 (m, 1H), 6.95 (s, 2H), 6.11 (s, 1H), 4.69-4.80 (m, 1H), 4.55-4.66 (m, 1H), 3.61 (d, J = 6.05 Hz, 2H), 3.20 (t, J = 6.88 Hz, 2H) | 1.45 B 572 | 3.0 | 1797.0 |
| B328 | 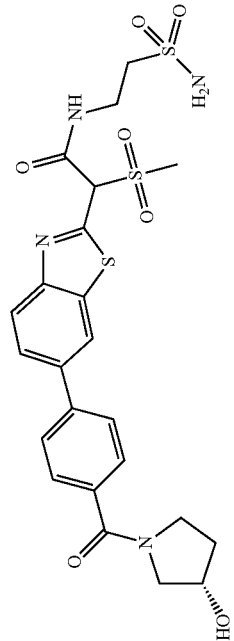 | 2-(6-{4-[(3S)-3-hydroxypyrrolidine-1-carbonyl]phenyl}-1,3-benzothiazol-2-yl)-2-methanesulfonyl-N-(2-sulfamoylethyl)acetamide | δ 9.02 (br. s., 1H), 8.56 (br. s., 1H), 8.19 (d, J = 8.0 Hz, 1H), 7.97-7.90 (m, 1H), 7.88-7.81 (m, 2H), 7.73-7.63 (m, 2H), 6.99 (br. s., 2H), 6.05 (br. s., 1H), 4.40-4.20 (m, 1H), 3.92 (br. s., 2H), 3.71-3.58 (m, 4H), 3.28-3.24 (m, 3H), 3.23-3.14 (m, 2H), 2.05-1.74 (m, 2H) | 1.06 O 567.1 | 4.0 | 2624.0 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B329 | 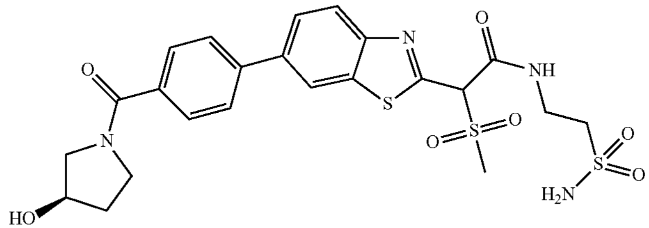 [SMILES: CS(=O)(=O)C(C(=O)NCCS(N)(=O)=O)c1nc2ccc(-c3ccc(C(=O)N4CC[C@@H](O)C4)cc3)cc2s1] | 2-(6-{4-[(3R)-3-hydroxy-pyrrolidine-1-carbonyl]phenyl}-1,3-benzothiazol-2-yl)-2-methanesulfonyl-N-(2-sulfamoylethyl)acetamide | δ 9.03 (br. s., 1H), 8.56 (br. s., 1H), 8.19 (d, J = 9.1 Hz, 1H), 7.96-7.91 (m, 1H), 7.88-7.81 (m, 2H), 7.67 (br. s, 2H), 6.99 (br. s., 2H), 6.05 (br. s., 1H), 4.43-4.16 (m, 1H), 3.92 (br. s., 2H), 3.61 (br. s., 4H), 3.25 (br. s., 3H), 3.20 (br. s., 2H), 2.03-1.75 (m, 2H) | 1.06 O 567.1 | 1.8 | 261.6 |
| B330 | 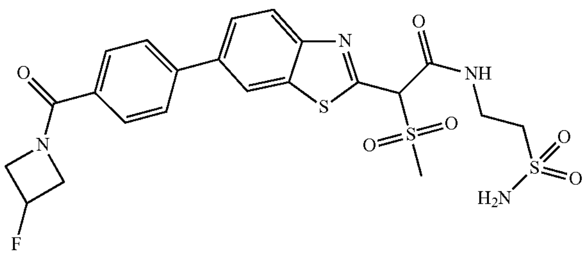 [SMILES: CS(=O)(=O)C(C(=O)NCCS(N)(=O)=O)c1nc2ccc(-c3ccc(C(=O)N4CC(F)C4)cc3)cc2s1] | 2-{6-[4-(3-fluoroazetidine-1-carbonyl)phenyl]-1,3-benzothiazol-2-yl}-2-methanesulfonyl-N-(2-sulfamoylethyl)acetamide | δ 9.02 (br. s., 1H), 8.58 (br. s., 1H), 8.19 (d, J = 8.5 Hz, 1H), 7.99-7.91 (m, 2H), 7.90-7.85 (m, 2H), 7.83-7.78 (m, 2H), 6.99 (br. s., 2H), 6.06 (br. s., 1H), 5.56-5.38 (m, 1H), 4.59-4.38 (m, 2H), 4.21-4.03 (m, 1H), 3.65-3.56 (m, 2H), 3.25 (br. s., 3H), 3.20 (br. s., 2H) | 1.23 O 555.1 | 0.7 | 46.7 |
| B331 | 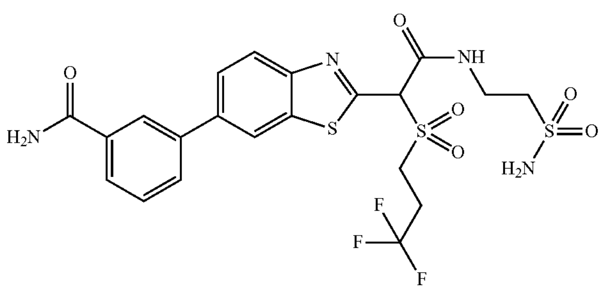 [SMILES: NC(=O)c1cccc(-c2ccc3nc(C(C(=O)NCCS(N)(=O)=O)S(=O)(=O)CCC(F)(F)F)sc3c2)c1] | 3-(2-{[(2-sulfamoylethyl)carbamoyl](3,3,3-trifluoropropanesulfonyl)methyl}-1,3-benzothiazol-6-yl)benzamide | δ 8.98 (s, 1H), 8.58 (d, J = 1.7 Hz, 1H), 8.29 (s, 1H), 8.20 (d, J = 8.8 Hz, 1H), 8.14 (br. s., 1H), 8.01-7.86 (m, 3H), 7.61 (m, 1H), 7.47 (br. s., 1H), 3.64 (m, 4H), 2.86 (m, 2H) | 1.36 N 579.1 | 72.5 | 214.2 |

| Ex # | Structure | Name | 1H NMR (500 MHz, DMSO-d6, unless indicated otherwise) | LC/MS RT (min) Method M + H | EL IC50 (nM) | HL IC50 (nM) |
|---|---|---|---|---|---|---|
| B332 | 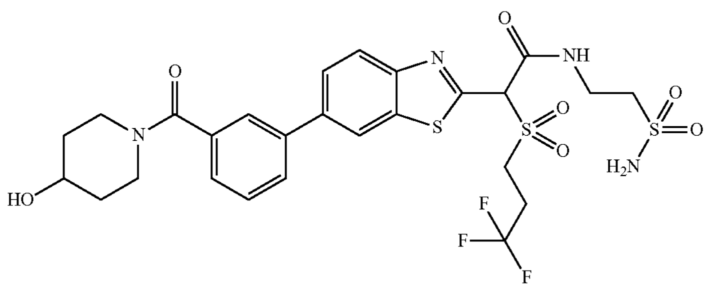 [SMILES: NS(=O)(=O)CCNC(=O)C(c1nc2ccc(-c3cccc(C(=O)N4CCC(O)CC4)c3)cc2s1)S(=O)(=O)CCC(F)(F)F] | 2-{6-[3-(4-hydroxy-piperidine-1-carbonyl)phenyl]-1,3-benzothiazol-2-yl}-N-(2-sulfamoyl-ethyl)-2-(3,3,3-trifluoropropanesulfonyl)acetamide | δ 8.99 (m, 1H), 8.57 (m, 1H), 8.17 (m, 1H), 7.98-7.84 (m, 2H), 7.75 (m, 1H), 7.59 (d, J = 6.1 Hz, 1H), 7.41 (m, 1H), 4.05 (m, 1H), 3.85-3.53 (m, 8H), 3.21 (br. s., 4H), 1.91-1.66 (m, 2H), 1.54-1.28 (m, 2H) | 1.37 N 663.1 | 1.5 | 136.5 |
| B333 | 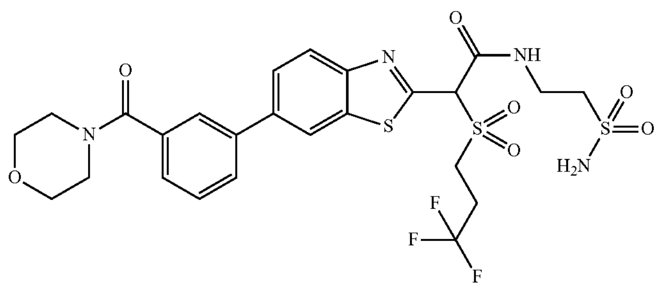 [SMILES: NS(=O)(=O)CCNC(=O)C(c1nc2ccc(-c3cccc(C(=O)N4CCOCC4)c3)cc2s1)S(=O)(=O)CCC(F)(F)F] | 2-{6-[3-(morpholine-4-carbonyl)phenyl]-1,3-benzothiazol-2-yl}-N-(2-sulfamoylethyl)-2-(3,3,3-trifluoropropanesulfonyl)acetamide | δ 9.05-8.92 (m, 1H), 8.57 (d, J = 1.7 Hz, 1H), 8.18 (d, J = 8.8 Hz, 1H), 7.96-7.84 (m, 3H), 7.79 (m, 2H), 7.61 (m, 1H), 7.46 (d, J = 7.7 Hz, 1H), 3.84-3.48 (m, 12H), 3.25-3.14 (m, 2H), 2.96-2.81 (m, 2H) | 1.48 N 649.8 | 9.8 | 119.3 |
| B334 | 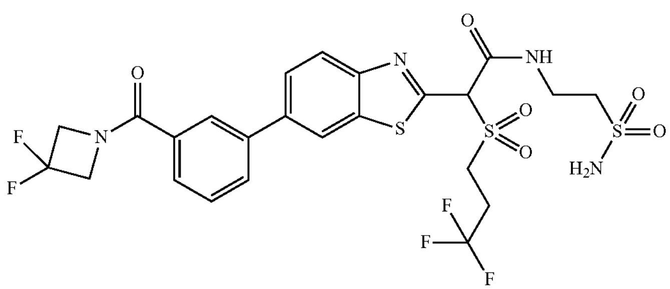 [SMILES: NS(=O)(=O)CCNC(=O)C(c1nc2ccc(-c3cccc(C(=O)N4CC(F)(F)C4)c3)cc2s1)S(=O)(=O)CCC(F)(F)F] | 2-{6-[3-(3,3-difluoroazetidine-1-carbonyl)phenyl]-1,3-benzothiazol-2-yl}-N-(2-sulfamoylethyl)-2-(3,3,3-trifluoropropanesulfonyl)acetamide | δ 8.99 (m, 1H), 8.59 (d, J = 1.7 Hz, 1H), 8.18 (d, J = 8.5 Hz, 1H), 8.03-7.91 (m, 4H), 7.76-7.57 (m, 3H), 4.97-4.81 (m, 2H), 4.62-4.42 (m, 2H), 3.87-3.54 (m, 5H), 2.95-2.81 (m, 2H) | 1.66 N 655.1 | 14.2 | 60.4 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B335 | 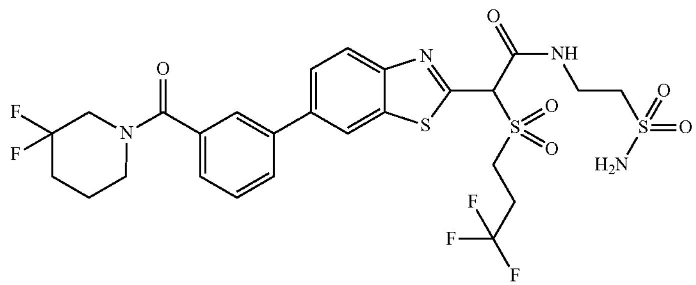 [SMILES: NS(=O)(=O)CCNC(=O)C(c1nc2ccc(-c3cccc(C(=O)N4CCCC(F)(F)C4)c3)cc2s1)S(=O)(=O)CCC(F)(F)F] | 2-{6-[3-(3,3-difluoropiperidine-1-carbonyl)phenyl]-1,3-benzothiazol-2-yl}-N-(2-sulfamoylethyl)-2-(3,3,3-trifluoropropanesulfonyl)acetamide | δ 8.98 (m, 1H), 8.57 (s, 1H), 8.18 (d, J = 8.5 Hz, 1H), 7.96-7.86 (m, 2H), 7.63 (m, 1H), 7.43 (d, J = 7.7 Hz, 1H), 3.87-3.53 (m, 8H), 3.20 (m, 2H), 2.96-2.81 (m, 2H), 2.25-2.06 (m, 2H), 1.85-1.64 (m, 2H) | 1.7 N 683.2 | 5.5 | 14.7 |
| B336 | 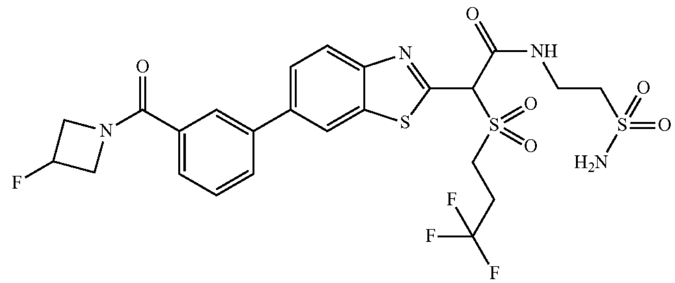 [SMILES: NS(=O)(=O)CCNC(=O)C(c1nc2ccc(-c3cccc(C(=O)N4CC(F)C4)c3)cc2s1)S(=O)(=O)CCC(F)(F)F] | 2-{6-[3-(3-fluoroazetidine-1-carbonyl)phenyl]-1,3-benzothiazol-2-yl}-N-(2-sulfamoylethyl)-2-(3,3,3-trifluoropropanesulfonyl)acetamide | δ 8.97 (s, 1H), 8.58 (s, 1H), 8.18 (d, J = 8.5 Hz, 1H), 7.97 (m, 5H), 7.71-7.59(m, 2H), 4.71-4.33 (m, 4H), 4.24-4.00 (m, 1H), 3.89-3.49 (m, 4H), 2.90 (m, 4H) | 1.54 N 637 | 8.2 | 22.6 |
| B337 | 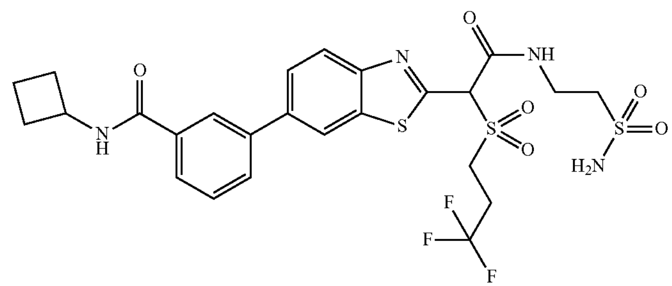 [SMILES: NS(=O)(=O)CCNC(=O)C(c1nc2ccc(-c3cccc(C(=O)NC4CCC4)c3)cc2s1)S(=O)(=O)CCC(F)(F)F] | N-cyclobutyl-3-(2-{[(2-sulfamoylethyl)carbamoyl](3,3,3-trifluoropropanesulfonyl)methyl}-1,3-benzothiazol-6-yl)benzamide | δ 8.98 (s, 1H), 8.75 (d, J = 7.4 Hz, 1H), 8.58 (s, 1H), 8.26-8.16 (m, 2H), 7.97 (m, 4H), 7.67-7.49 (m, 1H), 4.56-4.40 (m, 1H), 3.90-3.53 (m, 5H), 3.27-3.14 (m, 2H), 2.93-2.79 (m, 2H), 2.34-2.19 (m, 2H), 2.18-2.06 (m, 2H), 1.83-1.62 (m, 2H) | 1.71 N 633.1 | 6.8 | 28.4 |

| Ex # | Structure | Name | ¹H NMR (500 MHz, DMSO-d₆, unless indicated otherwise) | LC/MS RT (min) Method M+H | EL IC$_{50}$ (nM) | HL IC$_{50}$ (nM) |
|---|---|---|---|---|---|---|
| B338 | 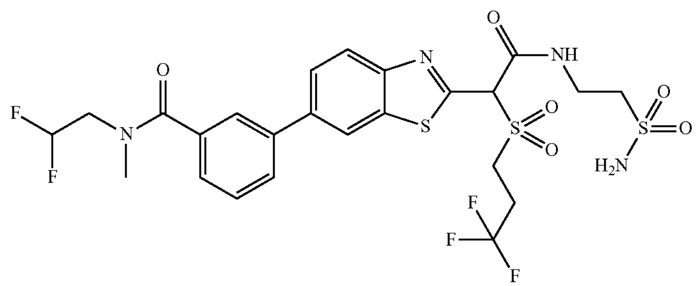 [SMILES: CN(CC(F)F)C(=O)c1cccc(-c2ccc3nc(C(C(=O)NCCS(N)(=O)=O)S(=O)(=O)CCC(F)(F)F)sc3c2)c1] | N-(2,2-difluoroethyl)-N-methyl-3-(2-{[(2-sulfamoylethyl)carbamoyl](3,3,3-trifluoropropanesulfonyl)methyl}-1,3-benzothiazol-6-yl)benzamide | δ 8.57 (s, 1H), 8.18 (d, J = 8.5 Hz, 1H), 7.98-7.86 (m, 2H), 7.80 (br. s., 1H), 7.62 (s, 1H), 7.51-7.35 (m, 1H), 3.92 (m, 3H), 3.85-3.57 (m, 4H), 3.24-3.16 (m, 1H), 3.07 (s., 3H), 2.90 (m, 2H) | 1.66 N 657.1 | 26.9 | 99.7 |
| B339 | 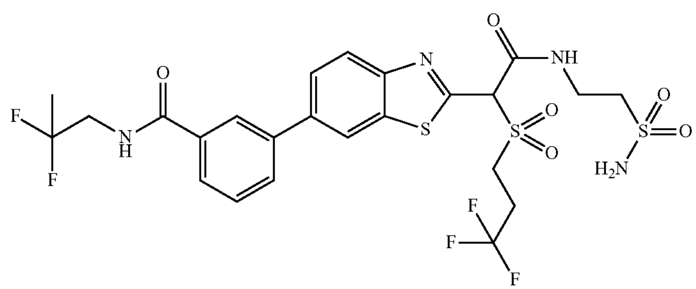 [SMILES: CC(F)(F)CNC(=O)c1cccc(-c2ccc3nc(C(C(=O)NCCS(N)(=O)=O)S(=O)(=O)CCC(F)(F)F)sc3c2)c1] | N-(2,2-difluoropropyl)-3-(2-{[(2-sulfamoylethyl)carbamoyl](3,3,3-trifluoropropanesulfonyl)methyl}-1,3-benzothiazol-6-yl)benzamide | δ 9.07-8.92 (m, 2H), 8.20 (m, 2H), 8.01-7.84 (m, 3H), 7.71-7.46 (m, 2H), 3.86-3.54 (m, 6H), 3.26-3.14 (m, 2H), 1.74-1.56 (m, 3H) | 1.68 N 657.1 | 9.7 | 49.2 |
| B340 | 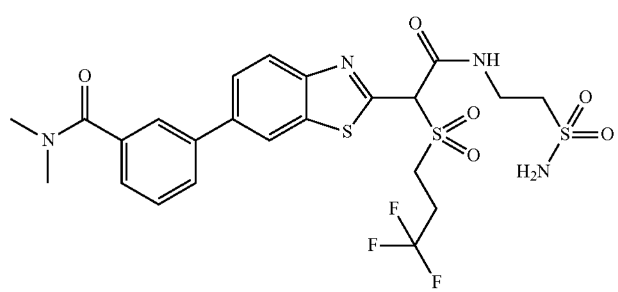 [SMILES: CN(C)C(=O)c1cccc(-c2ccc3nc(C(C(=O)NCCS(N)(=O)=O)S(=O)(=O)CCC(F)(F)F)sc3c2)c1] | N,N-dimethyl-3-(2-{[(2-sulfamoylethyl)carbamoyl](3,3,3-trifluoropropanesulfonyl)methyl}-1,3-benzothiazol-6-yl)benzamide | δ 9.01-8.92 (m, 1H), 8.57 (s, 1H), 8.17 (d, J = 8.5 Hz, 1H), 7.99-7.91 (m, 2H), 7.89-7.81 (m, 2H), 7.81-7.72 (m, 2H), 7.64-7.55 (m, 1H), 3.83-3.57 (m, 6H), 3.20 (m, 2H), 3.04 (s, 3H), 2.98 (s, 3H) | 1.54 N 607.1 | 14.6 | 79.5 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B341 | 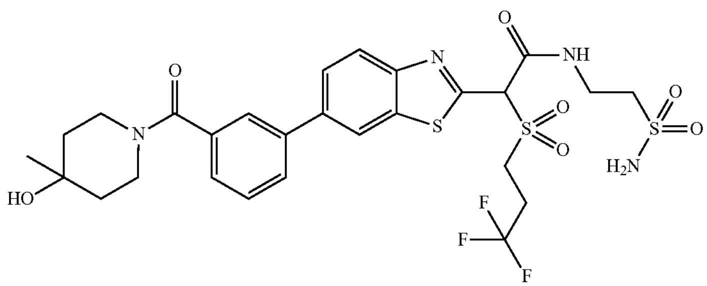 [SMILES: CC1(O)CCN(C(=O)c2cccc(-c3ccc4nc(C(C(=O)NCCS(N)(=O)=O)S(=O)(=O)CCC(F)(F)F)sc4c3)c2)CC1] | 2-{6-[3-(4-hydroxy-4-methylpiperidine-1-carbonyl)phenyl]-1,3-benzothiazol-2-yl}-N-(2-sulfamoylethyl)-2-(3,3,3-trifluoropropanesulfonyl)acetamide | δ 8.57 (s, 1H), 8.17 (s, 1H), 8.06-7.99 (m, 2H), 7.92-7.83 (m, 2H), 7.75 (m, 2H), 7.64 (m, 2H), 3.64 (m, 10H), 2.87 (m, 2H), 1.56-1.45 (m, 4H), 1.18 (s, 3H) | 1.48 N 677.1 | 6.0 | 111.8 |
| B342 | 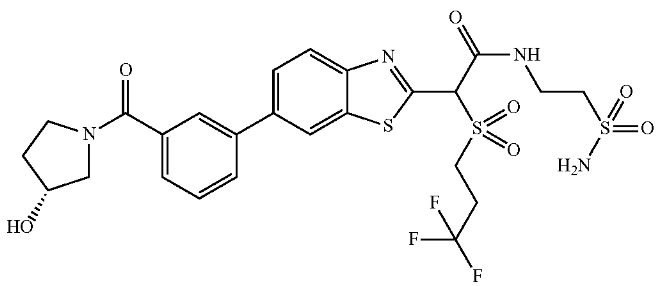 [SMILES: NS(=O)(=O)CCNC(=O)C(c1nc2ccc(-c3cccc(C(=O)N4CC[C@@H](O)C4)c3)cc2s1)S(=O)(=O)CCC(F)(F)F] | 2-(6-{3-[(3R)-3-hydroxypyrrolidine-1-carbonyl]phenyl}-1,3-benzothiazol-2-yl)-N-(2-sulfamoylethyl)-2-(3,3,3-trifluoropropanesulfonyl)acetamide | δ 8.98 (m, 1H), 8.58 (s, 1H), 8.17 (d, J = 8.5 Hz, 1H), 7.95-7.91 (m, 1H), 7.87 (m, 2H), 7.82-7.73 (m, 1H), 7.63-7.52 (m, 2H), 4.39-4.23 (m, 1H), 3.64 (m, 8H), 3.20 (s, 2H), 2.90-2.80 (m, 2H), 2.03-1.74 (m, 2H) | 1.37 N 649.1 | 9.5 | 153.7 |
| B343 | 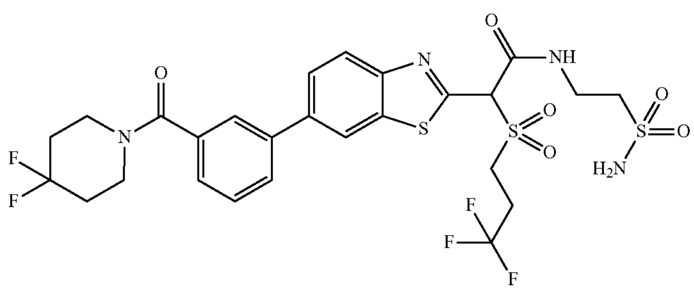 [SMILES: NS(=O)(=O)CCNC(=O)C(c1nc2ccc(-c3cccc(C(=O)N4CCC(F)(F)CC4)c3)cc2s1)S(=O)(=O)CCC(F)(F)F] | 2-{6-[3-(4,4-difluoropiperidine-1-carbonyl)phenyl]-1,3-benzothiazol-2-yl}-N-(2-sulfamoylethyl)-2-(3,3,3-trifluoropropanesulfonyl)acetamide | δ 8.98 (s, 1H), 8.57 (s, 1H), 8.19 (d, J = 8.5 Hz, 1H), 7.85 (m, 5H), 7.66-7.55 (m, 1H), 7.50 (s, 1H), 3.90-3.43 (m, 8H), 3.25-3.16 (m, 2H), 2.91-2.81 (m, 2H), 2.17-2.00 (m, 4H) | 1.76 N 683.1 | 13.5 | 38.1 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B344 | 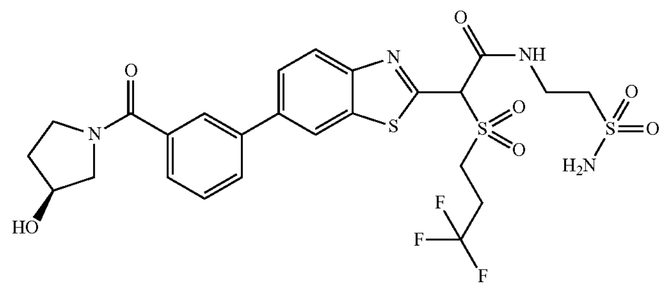 [SMILES: NS(=O)(=O)CCNC(=O)C(c1nc2ccc(-c3cccc(C(=O)N4CC[C@H](O)C4)c3)cc2s1)S(=O)(=O)CCC(F)(F)F] | 2-(6-{3-[(3S)-3-hydroxy-pyrrolidine-1-carbonyl]phenyl}-1,3-benzothiazol-2-yl)-N-(2-sulfamoylethyl)-2-(3,3,3-trifluoropropanesulfonyl)acetamide | δ 8.97 (m, 1H), 8.58 (s, 1H), 8.18 (d, J = 8.5 Hz, 1H), 7.99-7.91 (m, 1H), 7.88 (m, 2H), 7.78 (m, 2H), 7.57-7.49 (m, 2H), 4.26 (m, 1H), 3.64 (m, 9H), 3.21 (m, 2H), 2.90-2.81 (m, 2H), 2.02-1.79 (m, 2H) | 1.38 O 649.1 | 13.1 | 22.2 |
| B345 | 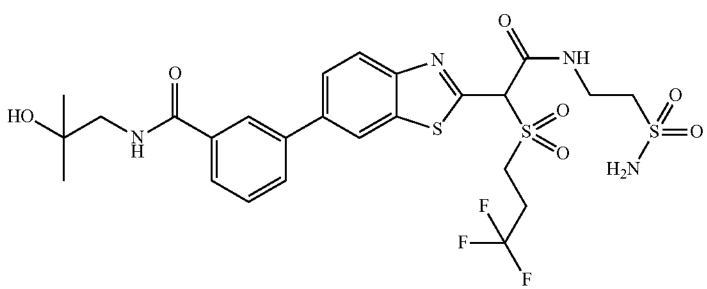 [SMILES: CC(C)(O)CNC(=O)c1cccc(-c2ccc3nc(C(C(=O)NCCS(N)(=O)=O)S(=O)(=O)CCC(F)(F)F)sc3c2)c1] | N-(2-hydroxy-2-methylpropyl)-3-(2-{[(2-sulfamoyl)ethyl)carbamoyl](3,3,3-trifluoropropanesulfonyl)methyl}-1,3-benzothiazol-6-yl)benzamide | δ 9.00 (s, 1H), 8.59 (s, 1H), 8.49-8.41 (m, 1H), 8.26 (s, 1H), 8.20 (d, J = 8.8 Hz, 1H), 8.01-7.89 (m, 4H), 7.66-7.56 (m, 1H), 3.64 (m, 5H), 3.21 (m, 2H), 2.90-2.81 (m, 2H), 1.15 (m, 6H) | 1.46 N 651.1 | 1.0 | 213.0 |
| B346 | 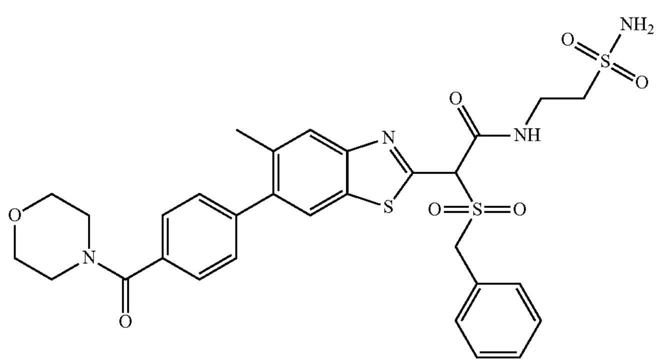 [SMILES: Cc1cc2nc(C(C(=O)NCCS(N)(=O)=O)S(=O)(=O)Cc3ccccc3)sc2cc1-c1ccc(C(=O)N2CCOCC2)cc1] | 2-{5-methyl-6-[4-(morpholine-4-carbonyl)phenyl]-1,3-benzothiazol-2-yl}-2-phenylmethanesulfonyl-N-(2-sulfamoylethyl)acetamide | ¹H NMR (400 MHz, Acetone) δ 7.86 (d, J = 6.60 Hz, 1H), 7.75-7.81 (m, 1H), 7.53-7.59 (m, 3H), 7.45-7.51 (m, 4H), 7.33-7.43 (m, 3H), 4.64 (s, 2H), 3.75-3.83 (m, 1H), 3.58-3.72 (m, 11H), 2.38 (s, 3H) | 0.69 M 656.7 | 5.3 | 400.4 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B347 | 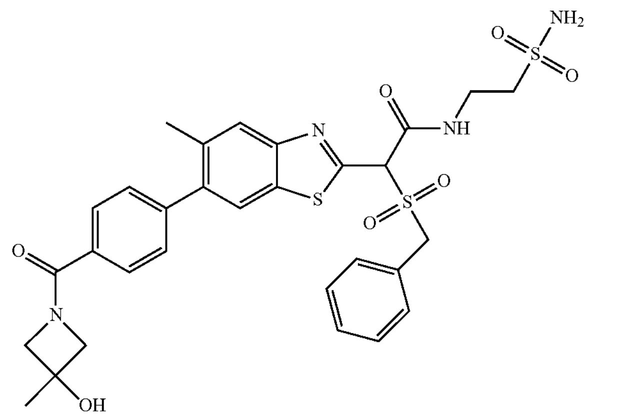 [SMILES: Cc1cc2nc(C(C(=O)NCCS(N)(=O)=O)S(=O)(=O)Cc3ccccc3)sc2cc1-c1ccc(C(=O)N2CC(C)(O)C2)cc1] | 2-{6-[4-(3-hydroxy-3-methylazetidine-1-carbonyl)phenyl]-5-methyl-1,3-benzothiazol-2-yl}-2-phenylmethanesulfonyl-N-(2-sulfamoylethyl)acetamide | δ 9.01 (t, J = 5.78 Hz, 1H), 8.02-8.09 (m, 1H), 7.74 (d, J = 8.25 Hz, 1H), 7.70 (d, J = 8.25 Hz, 1H), 7.49 (d, J = 7.98 Hz, 1H), 7.39-7.45 (m, 4H), 7.25-7.37 (m, 2H), 6.90-6.99 (m, 2H), 4.67-4.80 (m, 1H), 4.50-4.64 (m, 1H), 4.12-4.25 (m, 2H), 3.89-3.97 (m, 2H), 3.55-3.65 (m, 2H), 3.19 (t, J = 7.43 Hz, 2H), 2.23-2.40 (m, 3H), 1.41 (d, J = 3.03 Hz, 3H) | 1.74 B 657 | 3.4 | 579.6 |
| B348 | 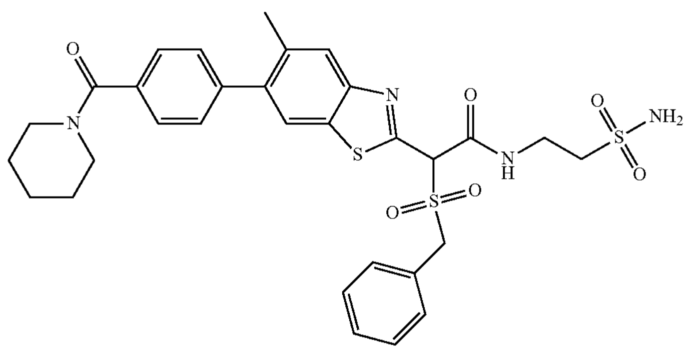 [SMILES: Cc1cc2nc(C(C(=O)NCCS(N)(=O)=O)S(=O)(=O)Cc3ccccc3)sc2cc1-c1ccc(C(=O)N2CCCCC2)cc1] | 2-{5-methyl-6-[4-(piperidine-1-carbonyl)phenyl]-1,3-benzothiazol-2-yl}-2-phenylmethanesulfonyl-N-(2-sulfamoylethyl)acetamide | δ 8.01-8.10 (m, 1H), 7.62-7.75 (m, 1H), 7.47 (s, 3H), 7.39-7.45 (m, 4H), 7.22-7.36 (m, 2H), 6.90-7.00 (m, 2H), 4.67-4.79 (m, 1H), 4.50-4.65 (m, 1H), 3.65-3.87 (m, 8H), 3.51-3.64 (m, 4H), 3.06-3.23 (m, 2H), 2.23-2.42 (m, 3H) | 1.96 B 655.1 | 1.0 | 37.1 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B349 | 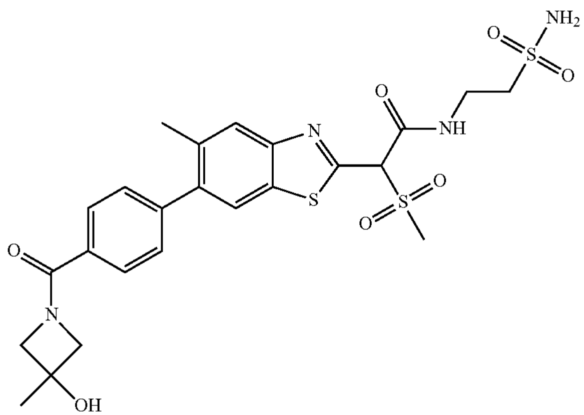 [SMILES: Cc1cc2nc(C(C(=O)NCCS(N)(=O)=O)S(C)(=O)=O)sc2cc1-c1ccc(C(=O)N2CC(C)(O)C2)cc1] | 2-{6-[4-(3-hydroxy-3-methylazetidine-1-carbonyl)phenyl]-5-methyl-1,3-benzothiazol-2-yl}-2-methanesulfonyl-N-(2-sulfamoylethyl)acetamide | δ 8.03 (d, J = 9.63 Hz, 1H), 7.95 (s, 1H), 7.73 (d, J = 7.98 Hz, 2H), 7.47 (s, 2H), 6.95 (s, 2H), 6.02 (s, 1H), 5.69 (br. s., 1H), 4.19 (d, J = 11.83 Hz, 2H), 3.93 (d, J = 5.23 Hz, 2H), 3.55-3.64 (m, 2H), 3.23 (s, 3H), 3.16-3.20 (m, 2H), 2.34-2.38 (m, 3H), 1.41 (s, 3H) | 1.44 B 581.1 | 2.3 | 347.2 |
| B350 | 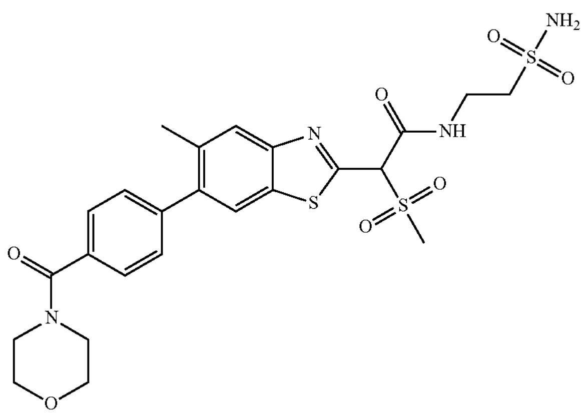 [SMILES: Cc1cc2nc(C(C(=O)NCCS(N)(=O)=O)S(C)(=O)=O)sc2cc1-c1ccc(C(=O)N2CCOCC2)cc1] | 2-methanesulfonyl-2-{5-methyl-6-[4-(morpholine-4-carbonyl)phenyl]-1,3-benzothiazol-2-yl}-N-(2-sulfamoylethyl)acetamide | δ 8.03 (s, 1H), 8.01 (s, 1H), 7.95 (s, 2H), 7.50-7.53 (m, 2H), 7.46-7.50 (m, 2H), 6.95 (s, 1H), 6.02 (s, 1H), 3.60 (td, J = 6.81, 13.34 Hz, 10H), 3.22 (s, 3H), 3.18 (t, J = 7.15 Hz, 2H), 2.37 (s, 3H) | 1.48 B 581.1 | 3.2 | 90.5 |

| Ex # | Structure | Name | $^1$H NMR (500 MHz, DMSO-$d_6$, unless indicated otherwise) | LC/MS RT (min) Method M + H | EL IC$_{50}$ (nM) | HL IC$_{50}$ (nM) |
|---|---|---|---|---|---|---|
| B351 | 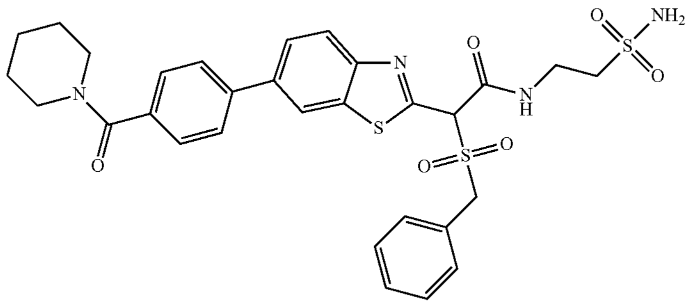 [SMILES: NS(=O)(=O)CCNC(=O)C(c1nc2ccc(-c3ccc(C(=O)N4CCCCC4)cc3)cc2s1)S(=O)(=O)Cc1ccccc1] | 2-phenylmethanesulfonyl-2-[6-[4-(piperidine-1-carbonyl)phenyl]-1,3-benzothiazol-2-yl]-N-(2-sulfamoylethyl)acetamide | δ 8.54 (s, 1H), 8.20 (d, J = 8.25 Hz, 1H), 7.95 (s, 1H), 7.92 (d, J = 8.53 Hz, 1H), 7.84 (d, J = 7.70 Hz, 2H), 7.51 (d, J = 7.70 Hz, 2H), 7.46 (d, J = 7.70 Hz, 1H), 7.33-7.36 (m, 1H), 6.95 (br. s., 2H), 6.10 (s, 1H), 4.69-4.81 (m, 1H), 4.54-4.65 (m, 1H), 3.61 (d, J = 6.05 Hz, 4H), 3.17-3.23 (m, 2H), 3.11 (br. s., 2H), 1.63 (br. s., 2H), 1.52 (br. s., 5H) | 1.63 B 641.2 | 6.2 | 14.9 |
| B352 | 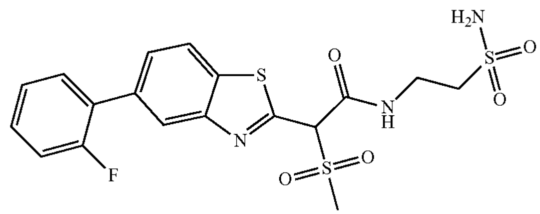 [SMILES: CS(=O)(=O)C(C(=O)NCCS(N)(=O)=O)c1nc2cc(-c3ccccc3F)ccc2s1] | 2-[5-(2-fluorophenyl)-1,3-benzothiazol-2-yl]-2-methanesulfonyl-N-(2-sulfamoylethyl)acetamide | δ 9.02 (br. s., 1H), 8.33-8.21 (m, 2H), 7.75-7.62 (m, 2H), 7.48 (br. s., 1H), 7.43-7.32 (m, 2H), 7.07-6.71 (m, 2H), 6.12-5.82 (m, 1H), 3.61 (br. s., 2H), 3.26 (br. s., 3H), 3.20 (br. s., 2H) | 1.57 O 472.1 | 0.8 | 13.7 |
| B353 | 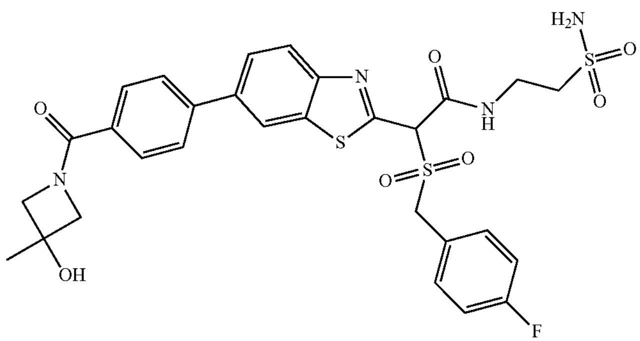 [SMILES: CC1(O)CN(C(=O)c2ccc(-c3ccc4nc(C(C(=O)NCCS(N)(=O)=O)S(=O)(=O)Cc5ccc(F)cc5)sc4c3)cc2)C1] | 2-[(4-fluorophenyl)methanesulfonyl]-2-{6-[4-(3-hydroxy-3-methylazetidine-1-carbonyl)phenyl]-1,3-benzothiazol-2-yl}-N-(2-sulfamoylethyl)acetamide | δ 9.16-8.54 (m, 1H), 8.32-8.12 (m, 1H), 7.99-7.84 (m, 2H), 7.81-7.70 (m, 3H), 7.51-7.35 (m, 2H), 6.96 (s, 4H), 6.09 (s, 1H), 5.70 (d, J = 5.5 Hz, 1H), 5.07-4.48 (m, 2H), 4.35-4.12 (m, 2H), 4.01-3.88 (m, 3H), 3.70-3.52 (m, 2H), 3.26-3.11 (m, 2H), 1.42 (d, J = 3.0 Hz, 3H) | 1.43 N 661.1 | 2.0 | 18.5 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B354 | 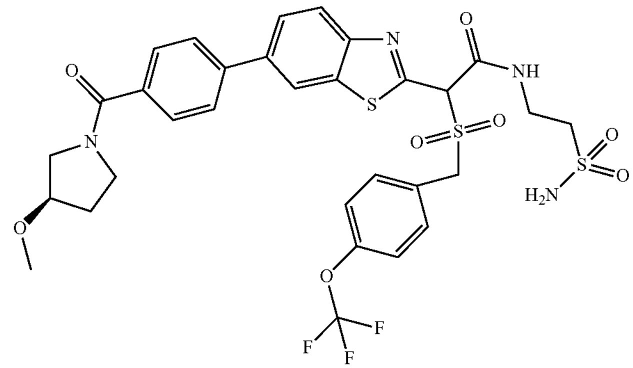 [SMILES: CO[C@@H]1CCN(C(=O)c2ccc(-c3ccc4nc(C(C(=O)NCCS(N)(=O)=O)S(=O)(=O)Cc5ccc(OC(F)(F)F)cc5)sc4c3)cc2)C1] | 2-(6-{4-[(3R)-3-methoxypyrrolidine-1-carbonyl]phenyl}-1,3-benzothiazol-2-yl)-N-(2-sulfamoylethyl)-2-{[4-(trifluoromethoxy)phenyl]methanesulfonyl}acetamide | δ 9.05 (t, J = 5.5 Hz, 1H), 8.56 (s, 1H), 8.21 (s, 1H), 8.16-8.10 (m, 1H), 8.01-7.90 (m, 2H), 7.88-7.83 (m, 2H), 7.78-7.60 (m, 6H), 7.56 (d, J = 8.3 Hz, 2H), 7.52-7.46 (m, 2H), 7.43-7.38 (m, 2H), 7.33-7.24 (m, 1H), 7.02-6.94 (m, 4H), 6.13 (s, 1H), 4.89-4.77 (m, 2H), 4.73-4.60 (m, 2H), 4.09-3.94 (m, 2H), 3.92 (s, 1H), 3.73-3.47 (m, 10H), 3.30 (s, 3H), 3.26-3.16 (m, 6H), 2.10-1.90 (m, 4H) | 1.73 O 741.1 | 3.8 | 552.8 |
| B355 | 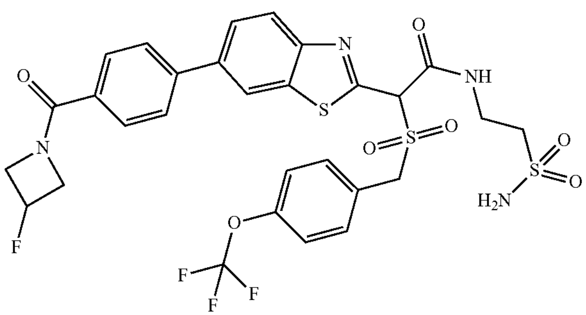 [SMILES: NS(=O)(=O)CCNC(=O)C(c1nc2ccc(-c3ccc(C(=O)N4CC(F)C4)cc3)cc2s1)S(=O)(=O)Cc1ccc(OC(F)(F)F)cc1] | 2-[6-[4-(3-fluoroazetidine-1-carbonyl)phenyl]-1,3-benzothiazol-2-yl]-N-(2-sulfamoylethyl)-2-{[4-(trifluoromethoxy)phenyl]}acetamide | δ 9.05 (t, J = 5.6 Hz, 1H), 8.58 (s, 1H), 8.30-8.19 (m, 1H), 8.17-8.12 (m, 1H), 7.99-7.93 (m, 2H), 7.92-7.85 (m, 3H), 7.84-7.69 (m, 7H), 7.59-7.54 (m, 2H), 7.51-7.45 (m, 2H), 7.43-7.37 (m, 2H), 7.32-7.22 (m, 2H), 7.03-6.94 (m, 4H), 6.14 (s, 1H), 5.66-5.30 (m, 2H), 4.91-4.78 (m, 2H), 4.75-4.60 (m, 3H), 4.48 (br. s., 4H), 4.13 (d, J = 11.3 Hz, 2H), 3.74-3.55 (m, 4H), 3.27-3.12 (m, 4H) | 1.74 O 715.1 | 6.6 | 235.2 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B356 | 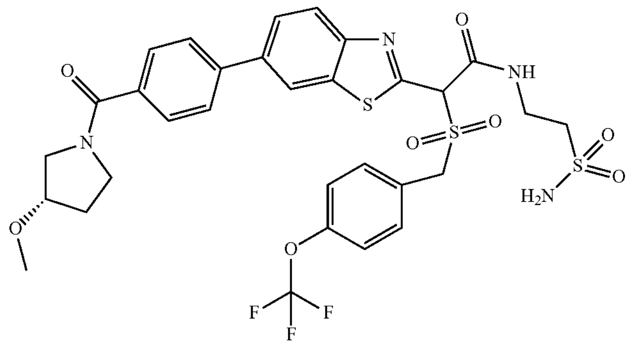 [SMILES: CO[C@H]1CCN(C(=O)c2ccc(-c3ccc4nc(C(C(=O)NCCS(N)(=O)=O)S(=O)(=O)Cc5ccc(OC(F)(F)F)cc5)sc4c3)cc2)C1] | 2-(6-{4-[(3S)-3-methoxy-pyrrolidine-1-carbonyl]phenyl}-1,3-benzothiazol-2-yl)-N-(2-sulfamoylethyl)-2-{[4-(trifluoromethoxy)phenyl]methanesulfonyl}acetamide | δ 14.04 and 11.48 (br. s., 1H), 9.05 (br. s., 1H), 8.56 (s, 1H), 8.24-8.19 (m, 1H), 8.17-8.11 (m, 1H), 7.98-7.60 (m, 1H), 7.58-7.53 (m, 2H), 7.49 (d, J = 7.7 Hz, 2H), 7.41 (d, J = 8.0 Hz, 2H), 7.35-7.24 (m, 2H), 7.04-6.93 (m, 3H), 6.13 (s, 1H), 4.88-4.78 (m, 2H), 4.74-4.60 (m, 2H), 4.11-3.94 (m, 16H), 3.35-3.28 (m, 3H), 3.25-3.20 (m, 3H), 2.02 (br. s., 4H) | 1.74 O 741.1 | 2.7 | 26.7 |
| B357 | 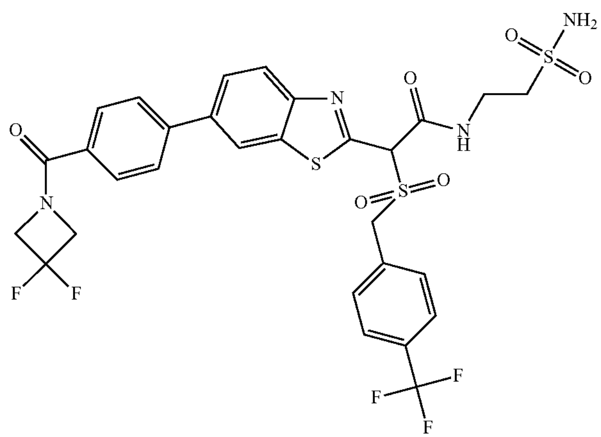 [SMILES: NS(=O)(=O)CCNC(=O)C(c1nc2ccc(-c3ccc(C(=O)N4CC(F)(F)C4)cc3)cc2s1)S(=O)(=O)Cc1ccc(C(F)(F)F)cc1] | 2-{6-[4-(3,3-difluoroazetidine-1-carbonyl)phenyl]-1,3-benzothiazol-2-yl}-N-(2-sulfamoylethyl)-2-{[4-(trifluoromethyl)phenyl]methanesulfonyl}acetamide | δ 14.05 and 11.44 and 6.14 (s, 1H), 9.07-9.02 and 8.66-8.55 (m, 1H), 8.27-8.14 (m, 1H), 7.99-7.93 (m, 1H), 7.92-7.83 (m, 2H), 7.83-7.74 (m, 3H), 7.68-7.63 (m, 1H), 7.61-7.58(m, 1H), 7.01-6.94 (m, 2H), 4.98-4.45 (m, 6H), 3.75-3.59 (m, 2H), 3.26-3.15 (m, 2H) | 1.83 O 717.1 | 15.0 | 93.2 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B358 | 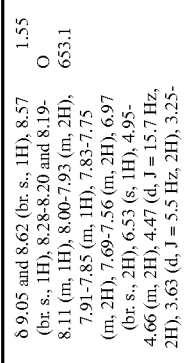 | 2-[6-(1-oxo-2,3-dihydro-1H-isoindol-5-yl)-1,3-benzothiazol-2-yl]-N-(2-sulfamoylethyl)-2-{[4-(trifluoromethyl)phenyl]methanesulfonyl}-acetamide | δ 9.05 and 8.62 (br. s., 1H), 8.57 (br. s., 1H), 8.28-8.20 and 8.19-8.11 (m, 1H), 8.00-7.93 (m, 2H), 7.91-7.85 (m, 1H), 7.83-7.75 (m, 2H), 7.69-7.56 (m, 2H), 6.97 (br. s., 2H), 6.53 (s, 1H), 4.95-4.66 (m, 2H), 4.47 (d, J = 15.7 Hz, 2H), 3.63 (d, J = 5.5 Hz, 2H), 3.25-3.11 (m, 2H) | 1.55 O 653.1 | 3.7 | 67.6 |
| B359 | 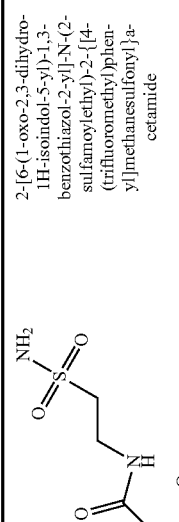 | 2-{6-[4-(3,3-difluoroazetidine-1-carbonyl)phenyl]-1,3-benzothiazol-2-yl}-N-(2-sulfamoylethyl)-2-{[3-(trifluoromethyl)phenyl]methanesulfonyl}-acetamide | δ 14.05 and 11.55 (br. s., 1H), 9.08 (br. s., 1H), 8.59 (s, 1H), 8.20 (d, J = 8.8 Hz, 2H), 8.00-7.94 (m, 2H), 7.93-7.88 (m, 2H), 7.88-7.73 (m, 10H), 7.70-7.53 (m, 4H), 7.06-6.87 (m, 6H), 6.15 (s, 1H), 5.12-4.34 (m, 12H), 3.63 (br. s., 4H), 3.27-3.13 (m, 4H) | 1.83 O 717.1 | 4.7 | 47.0 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B360 | 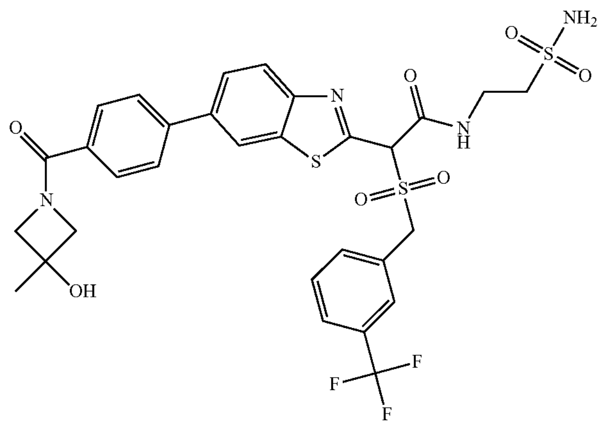 [SMILES: CC1(O)CN(C(=O)c2ccc(-c3ccc4nc(C(C(=O)NCCS(N)(=O)=O)S(=O)(=O)Cc5cccc(C(F)(F)F)c5)sc4c3)cc2)C1] | 2-{6-[4-(3-hydroxy-3-methylazetidine-1-carbonyl)phenyl]-1,3-benzothiazol-2-yl}-N-(2-sulfamoylethyl)-2-{[3-(trifluoromethyl)phenyl]methanesulfonyl}acetamide | δ 14.03 and 11.54 (br. s., 1H), 9.06 (br. s., 1H), 8.57 (s, 1H), 8.30-8.13 (m, 2H), 7.99-7.85 (m, 4H), 7.83-7.71 (m, 10H), 7.70-7.51 (m, 4H), 7.07-6.92 (m, 6H), 6.14 (s, 1H), 5.70 (d, J = 3.9 Hz, 2H), 5.01-4.69 (m, 4H), 4.34-4.06 (m, 4H), 3.99-3.89 (m, 4H), 3.63 (br. s., 4H), 3.27-3.15 (m, 4H), 1.42 (br. s., 6H) | 1.55 O 711.1 | 6.2 | 471.4 |
| B361 | 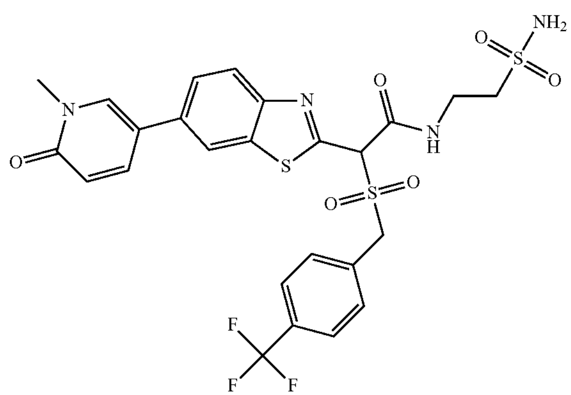 [SMILES: Cn1cc(-c2ccc3nc(C(C(=O)NCCS(N)(=O)=O)S(=O)(=O)Cc4ccc(C(F)(F)F)cc4)sc3c2)ccc1=O] | 2-[6-(1-methyl-6-oxo-1,6-dihydropyridin-3-yl)-1,3-benzothiazol-2-yl]-N-(2-sulfamoylethyl)-2-{[4-(trifluoromethyl)phenyl]methanesulfonyl}acetamide | δ 14.03 and 11.41 (br. s., 1H), 9.54-8.69 (m, 1H), 8.47-8.33 (m, 1H), 8.33-8.25 (m, 1H), 8.19-8.09 (m, 2H), 8.00-7.92 (m, 2H), 7.86-7.80 (m, 2H), 7.78-7.74 (m, 2H), 7.70-7.51 (m, 5H), 7.26-7.18 and 7.13-7.09 (m, 1H), 6.97 (s, 4H), 6.62-6.44 (m, 2H), 6.12 (s, 1H), 4.97-4.85 (m, 2H), 4.82-4.61 (m, 2H), 3.92 (s, 1H), 3.70-3.59 (m, 4H), 3.53 (s, 2H), 3.26-3.13 (m, 4H), 2.52 (br. s., 6H) | 1.41 O 629.1 | 121.1 | 1231.0 |

| Ex # | Structure | Name | $^1$H NMR (500 MHz, DMSO-d$_6$, unless indicated otherwise) | LC/MS RT (min) Method M + H | EL IC$_{50}$ (nM) | HL IC$_{50}$ (nM) |
|---|---|---|---|---|---|---|
| B362 | 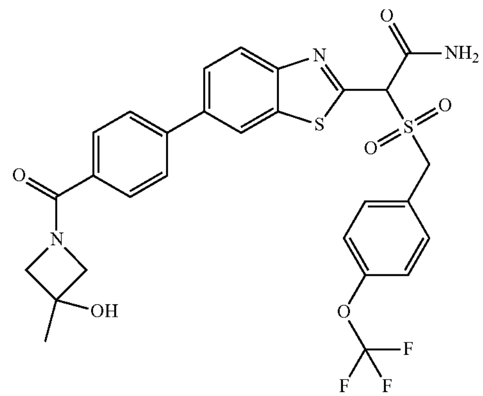 [SMILES: CC1(O)CN(C(=O)c2ccc(-c3ccc4nc(C(C(N)=O)S(=O)(=O)Cc5ccc(OC(F)(F)F)cc5)sc4c3)cc2)C1] | 2-{6-[4-(3-hydroxy-3-methylazetidine-1-carbonyl)phenyl]-1,3-benzothiazol-2-yl}-2-{[4-(trifluoromethoxy)phenyl]methanesulfonyl}acetamide | δ 8.75-8.11 (m, 2H), 8.06-7.92 (m, 1H), 7.90-7.85 (m, 1H), 7.80-7.71 (m, 3H), 7.56-7.43 (m, 2H), 7.42-7.24 (m, 2H), 6.05 (s, 1H), 5.84-5.49 (m, 1H), 4.99-4.55 (m, 2H), 4.36-4.10 (m, 2H), 3.94 (br. s., 2H), 1.61-1.39 (m, 3H) | 1.53 O 620.1 | 157.9 | 30.3 |
| B363 | 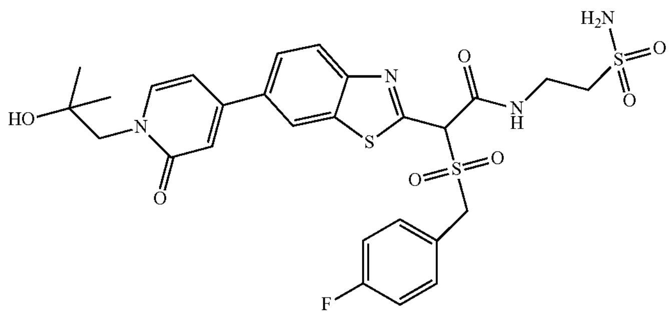 [SMILES: CC(C)(O)Cn1ccc(-c2ccc3nc(C(C(=O)NCCS(N)(=O)=O)S(=O)(=O)Cc4ccc(F)cc4)sc3c2)cc1=O] | 2-[(4-fluorophenyl)methanesulfonyl]-2-{6-[1-(2-hydroxy-2-methylpropyl)-2-oxo-1,2-dihydropyridin-4-yl]-1,3-benzothiazol-2-yl}-N-(2-sulfamoylethyl)acetamide | δ 9.11-8.53 (m, 1H), 8.20 (d, J = 8.5 Hz, 1H), 8.03-7.85 (m, 1H), 7.81-7.66 (m, 2H), 7.53-7.44 (m, 1H), 7.42-7.31 (m, 1H), 7.28-7.06 (m, 2H), 7.03-6.92 (m, 1H), 6.75-6.67 (m, 1H), 6.10 (s, 1H), 5.02-4.83 (m, 1H), 4.81-4.55 (m, 2H), 3.96 (d, J = 12.9 Hz, 2H), 3.92 (s, 1H), 3.71-3.52 (m, 2H), 3.27-3.06 (m, 2H), 1.13 (d, J = 8.3 Hz, 7H) | 1.36 O 637.1 | 11.6 | 10000.0 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B364 | 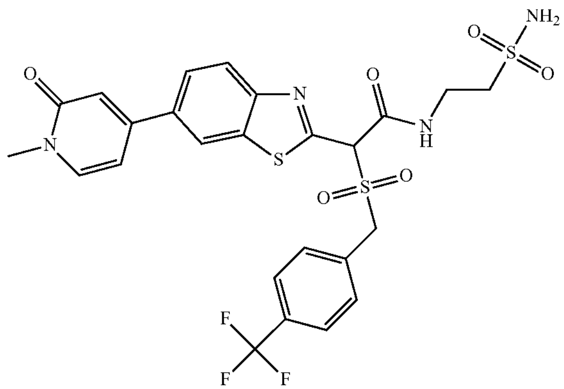 [SMILES: Cn1ccc(-c2ccc3nc(C(C(=O)NCCS(N)(=O)=O)S(=O)(=O)Cc4ccc(C(F)(F)F)cc4)sc3c2)cc1=O] | 2-[6-(1-methyl-2-oxo-1,2-dihydropyridin-4-yl)-1,3-benzothiazol-2-yl]-N-(2-sulfamoylethyl)-2-{[4-(trifluoromethyl)phenyl]methanesulfonyl}acetamide | δ 9.05 and 8.59 (s., 1H), 8.23-8.10 (m, 1H), 8.00-7.82 (m, 2H), 7.82-7.73 (m, 2H), 7.68-7.63 (m, 1H), 7.61-7.57 (m, 1H), 6.97 (br. s., 2H), 6.83-6.76 and 6.63-6.55 (m, 1H), 6.72-6.66 (m, 1H), 5.10-4.53 (m, 2H), 3.82-3.58 (m, 2H), 3.54-3.43 (m, 3H), 3.26-3.15 (m, 2H) | 1.5 O 629.1 | 28.3 | 10000.0 |
| B365 | 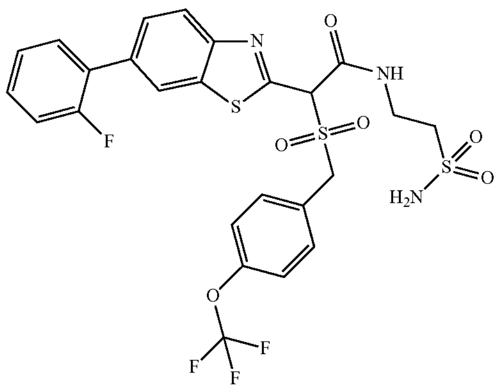 [SMILES: NS(=O)(=O)CCNC(=O)C(c1nc2ccc(-c3ccccc3F)cc2s1)S(=O)(=O)Cc1ccc(OC(F)(F)F)cc1] | 2-[6-(2-fluorophenyl)-1,3-benzothiazol-2-yl]-2-{[4-(trifluoromethoxy)phenyl]methanesulfonyl}-N-(2-sulfamoylethyl)acetamide | δ 14.06 and 11.47 (br. s., 1H), 9.04 (br. s., 1H), 8.49-8.31 (m, 1H), 8.21 (d, J = 8.5 Hz, 1H), 8.07-7.72 (m, 4H), 7.69-7.60 (m, 1H), 7.58-7.23 (m, 16H), 7.05-6.88 (m, 4H), 6.14 (s, 1H), 4.97-4.77 (m, 2H), 4.76-4.59 (m, 2H), 3.63 (d, J = 6.1 Hz, 4H), 3.28-3.16 (m, 4H) | 2.02 O 632.1 | 17.2 | 2.1 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B366 | 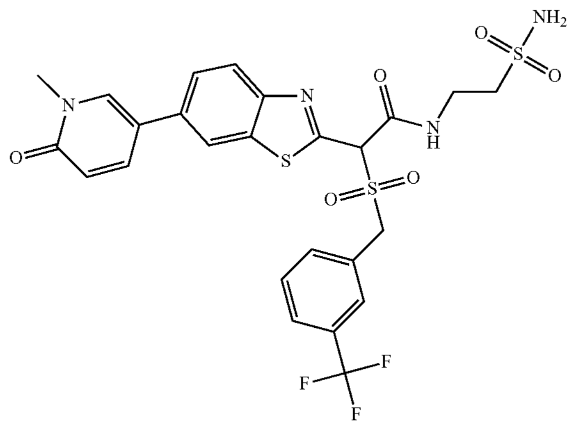 [SMILES: Cn1cc(-c2ccc3nc(C(C(=O)NCCS(N)(=O)=O)S(=O)(=O)Cc4cccc(C(F)(F)F)c4)sc3c2)ccc1=O] | 2-{6-(1-methyl-6-oxo-1,6-dihydropyridin-3-yl)-1,3-benzothiazol-2-yl]-N-(2-sulfamoylethyl)-2-{[3-(trifluoromethyl)phenyl]methanesulfonyl}acetamide | δ 14.31-8.88 (m, 1H), 8.47-8.26 (m, 1H), 8.19-8.07 (d, 1H), 8.00-7.93 (m, 1H), 7.89-7.49 (m, 6H), 6.97 (br. s., 2H), 6.63-6.43 (m, 1H), 6.11 (s, 1H), 5.06-4.66 (m, 2H), 3.68-3.59 (m, 2H), 3.54 (d, J = 16.5 Hz, 3H), 3.21 (t, J = 6.9 Hz, 2H) | 1.50 O 629.1 | 4.4 | 219.1 |
| B367 | 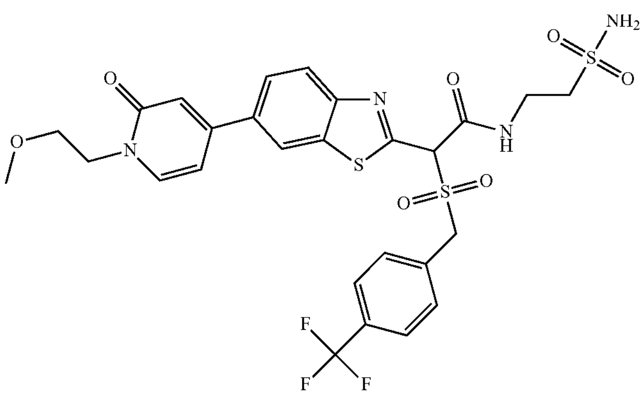 [SMILES: COCCn1ccc(-c2ccc3nc(C(C(=O)NCCS(N)(=O)=O)S(=O)(=O)Cc4ccc(C(F)(F)F)cc4)sc3c2)cc1=O] | 2-{6-[1-(2-methoxyethyl)-2-oxo-1,2-dihydropyridin-4-yl]-1,3-benzothiazol-2-yl}-N-(2-sulfamoylethyl)-2-{[4-(trifluoromethyl)phenyl]methanesulfonyl}acetamide | δ 14.40-11.02 (m, 1H), 9.04 (t, J = 5.6 Hz, 1H), 8.59 (d, J = 1.7 Hz, 1H), 8.23-8.10 (m, 2H), 7.95-7.91 (m, 1H), 7.75 (d, J = 7.2 Hz, 4H), 7.71-7.69 (m, 1H), 7.67-7.63 (m, 2H), 7.59 (s, 3H), 7.04-6.94 (m, 5H), 6.82-6.73 (m, 1H), 6.72-6.63 (m, 2H), 6.63-6.53 (m, 1H), 6.14 (s, 1H), 5.02-4.83 (m, 2H), 4.81-4.68 (m, 2H), 4.18-4.06 (m, 4H), 3.92 (s, 1H), 3.70-3.56 (m, 9H), 3.28 (s, 3H), 3.24-3.16 (m, 4H) | 1.57 O 673.1 | 13.5 | 2208.0 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B368 | 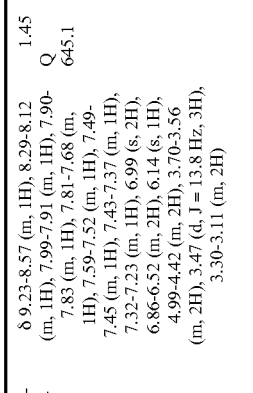 | 2-[6-(1-methyl-2-oxo-1,2-dihydropyridin-4-yl)-1,3-benzothiazol-2-yl]-N-(2-sulfamoylethyl)-2-{[4-(trifluoromethoxy)phenyl]methanesulfonyl}-acetamide | δ 9.23-8.57 (m, 1H), 8.29-8.12 (m, 1H), 7.99-7.91 (m, 1H), 7.90-7.83 (m, 1H), 7.81-7.68 (m, 1H), 7.59-7.52 (m, 1H), 7.49-7.45 (m, 1H), 7.43-7.37 (m, 1H), 7.32-7.23 (m, 1H), 6.99 (s, 2H), 6.86-6.52 (m, 2H), 6.14 (s, 1H), 4.99-4.42 (m, 2H), 3.70-3.56 (m, 2H), 3.47 (d, J = 13.8 Hz, 3H), 3.30-3.11 (m, 2H) | 1.45 Q 645.1 | 15.8 | 1597.0 |
| B369 | 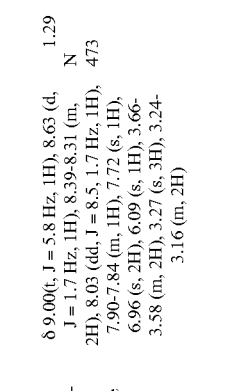 | 2-[5-(2-fluoropyridin-4-yl)-1,3-benzothiazol-2-yl]-2-methanesulfonyl-N-(2-sulfamoylethyl)acetamide | δ 9.00(t, J = 5.8 Hz, 1H), 8.63 (d, J = 1.7 Hz, 1H), 8.39-8.31 (m, 2H), 8.03 (dd, J = 8.5, 1.7 Hz, 1H), 7.90-7.84 (m, 1H), 7.72 (s, 1H), 6.96 (s, 2H), 6.09 (s, 1H), 3.66-3.58 (m, 2H), 3.27 (s, 3H), 3.24-3.16 (m, 2H) | 1.29 N 473 | 1.5 | 414.5 |

-continued

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B370 | 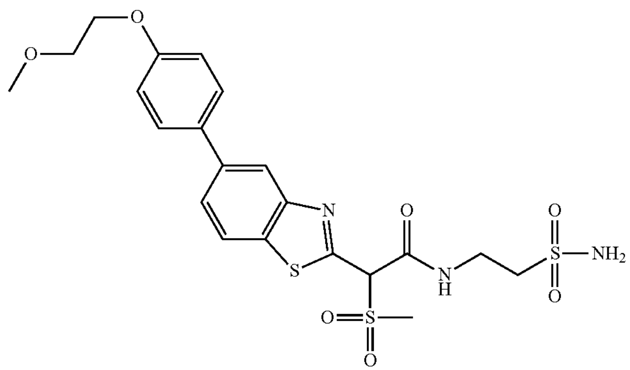 [SMILES: COCCOc1ccc(-c2ccc3sc(C(C(=O)NCCS(N)(=O)=O)S(C)(=O)=O)nc3c2)cc1] | 2-methanesulfonyl-2-{5-[4-(2-methoxyethoxy)phenyl]-1,3-benzothiazol-2-yl}-N-(2-sulfamoylethyl)acetamide | δ 9.02 (br. s., 1H), 8.38-8.13 (m, 2H), 7.87-7.64 (m, 3H), 7.15-6.89 (m, 4H), 6.04 (br. s., 1H), 4.17 (br. s., 2H), 3.70 (d, J = 2.5 Hz, 2H), 3.61 (d, J = 5.2 Hz, 2H), 3.34 (br. s., 3H), 3.26 (br. s., 3H), 3.20 (br. s., 2H) | 1.47 N 528 | 1.8 | 15.5 |
| B371 | 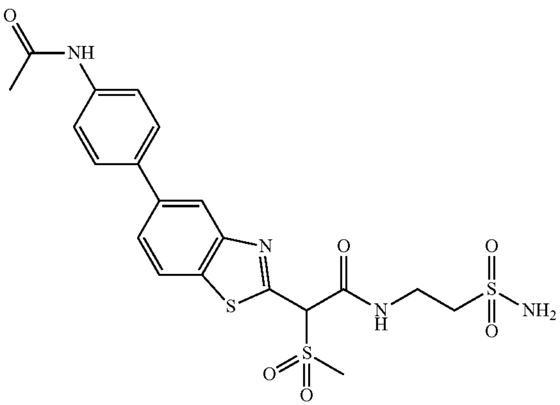 [SMILES: CC(=O)Nc1ccc(-c2ccc3sc(C(C(=O)NCCS(N)(=O)=O)S(C)(=O)=O)nc3c2)cc1] | 2-[5-(4-acetamidophenyl)-1,3-benzothiazol-2-yl]-2-methanesulfonyl-N-(2-sulfamoylethyl)acetamide | δ 9.01 (br. s., 1H), 8.33 (br. s., 1H), 8.22 (d, J = 8.3 Hz, 1H), 7.87-7.66 (m, 6H), 6.98 (br. s., 3H), 6.04 (br. s., 1H), 3.61 (br. s., 2H), 3.25 (br. m., 5H), 2.08 (br. s., 3H) | 1.17 N 511 | 3.0 | 96.3 |

| Ex # | Structure | Name | ¹H NMR (500 MHz, DMSO-d₆, unless indicated otherwise) | LC/MS RT (min) Method M+H | EL IC₅₀ (nM) | HL IC₅₀ (nM) |
|---|---|---|---|---|---|---|
| B372 | 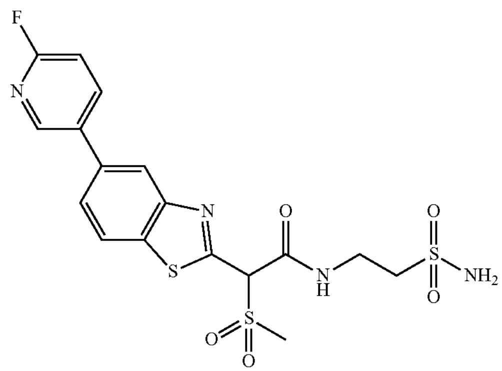 [SMILES: CS(=O)(=O)C(C(=O)NCCS(N)(=O)=O)c1nc2cc(-c3ccc(F)nc3)ccc2s1] | 2-[5-(6-fluoropyridin-3-yl)-1,3-benzothiazol-2-yl]-2-methanesulfonyl-N-(2-sulfamoylethyl)acetamide | δ 9.00 (t, J = 5.8 Hz, 1H), 8.70 (d, J = 2.5 Hz, 1H), 8.47 (d, J = 1.4 Hz, 1H), 8.44 (td, J = 8.2, 2.6 Hz, 1H), 8.30 (d, J = 8.3 Hz, 1H), 7.97 (s, 1H), 7.90 (dd, J = 8.4, 1.8 Hz, 1H), 7.34 (dd, J = 8.7, 2.9 Hz, 1H), 6.96 (s, 2H), 6.07 (s, 1H), 3.62 (q, J = 6.9 Hz, 2H), 3.26 (s, 3H), 3.23-3.18 (m, 2H) | 1.25 N 473 | 2.5 | 124.2 |
| B373 | 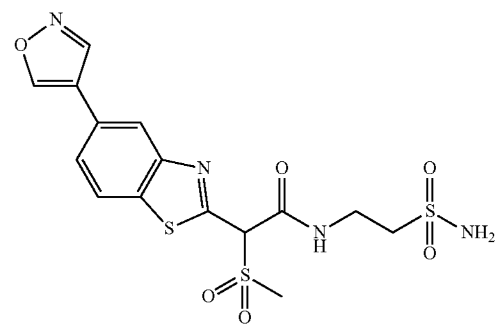 [SMILES: CS(=O)(=O)C(C(=O)NCCS(N)(=O)=O)c1nc2cc(-c3cnoc3)ccc2s1] | 2-methanesulfonyl-2-[5-(1,2-oxazol-4-yl)-1,3-benzothiazol-2-yl]-N-(2-sulfamoylethyl)acetamide | δ 9.60 (s, 1H), 9.33 (s, 1H), 8.98 (t, J = 5.6 Hz, 1H), 8.51 (d, J = 1.1 Hz, 1H), 8.25 (d, J = 8.5 Hz, 1H), 7.88 (dd, J = 8.4, 1.5 Hz, 1H), 6.96 (s, 2H), 6.06 (s, 1H), 3.61 (q, J = 6.8 Hz, 2H), 3.25 (s, 3H), 3.20 (dd, J = 8.8, 6.6 Hz, 2H) | 1.09 N 445 | 3.3 | 45.7 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B374 | 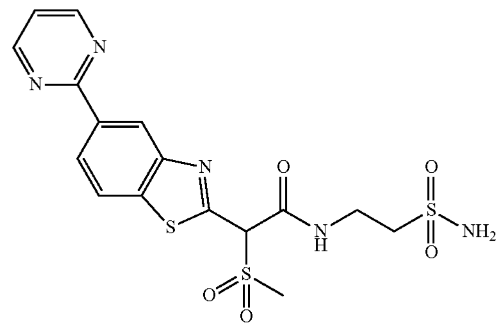 [SMILES: CS(=O)(=O)C(C(=O)NCCS(N)(=O)=O)c1nc2cc(-c3ncccn3)ccc2s1] | 2-methanesulfonyl-2-[5-(pyrimidin-2-yl)-1,3-benzothiazol-2-yl]-N-(2-sulfamoylethyl)acetamide | δ 9.30 (s, 2H), 9.24 (s, 1H), 9.01 (t, J = 5.8 Hz, 1H), 8.59 (d, J = 1.7 Hz, 1H), 8.35 (d, J = 8.5 Hz, 1H), 7.99 (dd, J = 8.5, 1.7 Hz, 1H), 7.21 (s, 1H), 7.11 (s, 1H), 7.01 (s, 1H), 6.96 (s, 2H), 6.08 (s, 1H), 3.62 (q, J = 6.8 Hz, 2H), 3.26 (s, 3H), 3.23-3.17 (m, 2H) | 0.98 N 456 | 0.8 | 23.7 |
| B375 | 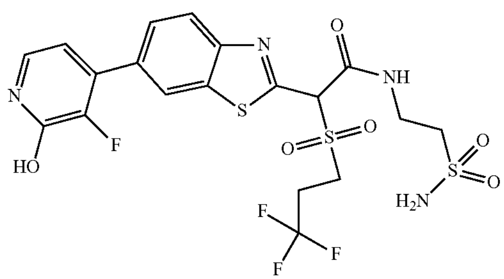 [SMILES: NS(=O)(=O)CCNC(=O)C(c1nc2ccc(-c3ccnc(O)c3F)cc2s1)S(=O)(=O)CCC(F)(F)F] | 2-[6-(3-fluoro-2-hydroxy-pyridin-4-yl)-1,3-benzothiazol-2-yl]-N-(2-sulfamoylethyl)-2-(3,3,3-trifluoropropanesulfonyl)acetamide | δ 12.30-12.07 (m, 1H), 8.98 (br. s., 1H), 8.52-8.44 (m, 1H), 8.27-8.19 (m, 1H), 7.83-7.76 (m, 1H), 7.43-7.33 (m, 1H), 7.01 (br. s., 1H), 6.97 (s, 2H), 6.31 (s, 1H), 3.85-3.53 (m, 4H), 3.23-3.17 (m, 2H), 2.90-2.83 (m, 2H) | 1.10 N 571.0 | 14.0 | 786.9 |
| B376 | 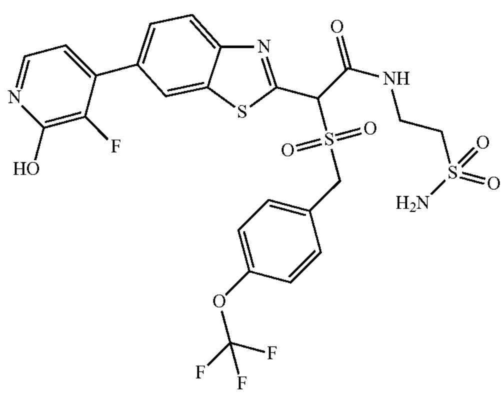 [SMILES: NS(=O)(=O)CCNC(=O)C(c1nc2ccc(-c3ccnc(O)c3F)cc2s1)S(=O)(=O)Cc1ccc(OC(F)(F)F)cc1] | 2-[6-(3-fluoro-2-hydroxy-pyridin-4-yl)-1,3-benzothiazol-2-yl]-N-(2-sulfamoylethyl)-2-{[4-(trifluoromethoxy)phenyl]methanesulfonyl}-acetamide | 8 14.84-10.51 (m, 1H), 9.13-8.19 (m, 2H), 7.97 (s, 2H), 7.67-7.52 (m, 1H), 7.50-7.45 (m, 1H), 7.43-7.19 (m, 3H), 6.97 (br. s., 2H), 6.44-6.27 (m, 1H), 6.15 (s, 1H), 5.05-4.62 (m, 2H), 3.63 (d, J = 5.8 Hz, 2H), 3.28-3.15 (m, 2H) | 1.40 O 633.5 | 7.1 | 4695.0 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B377 | 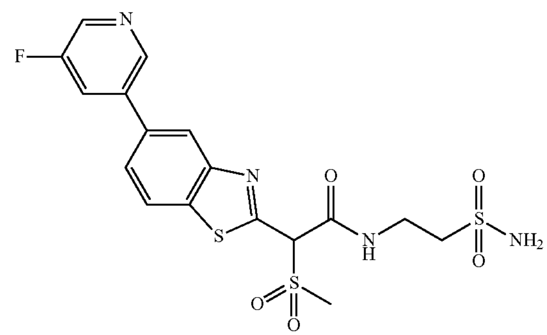 [SMILES: CS(=O)(=O)C(C(=O)NCCS(N)(=O)=O)c1nc2cc(-c3cncc(F)c3)ccc2s1] | 2-[5-(5-fluoropyridin-3-yl)-1,3-benzothiazol-2-yl]-2-methanesulfonyl-N-(2-sulfamoylethyl)acetamide | δ 9.00 (t, J = 5.6 Hz, 1H), 8.96 (s, 1H), 8.64 (d, J = 1.7 Hz, 1H), 8.56 (s, 1H), 8.33 (d, J = 8.5 Hz, 1H), 8.25 (d, J = 10.2 Hz, 1H), 7.97 (d, J = 8.3 Hz, 1H), 6.96 (s, 2H), 6.08 (s, 1H), 3.62 (q, J = 6.8 Hz, 2H), 3.27 (s, 3H), 3.24-3.17 (m, 2H) | 1.17 N 495 | 2.9 | 82.1 |
| B378 | 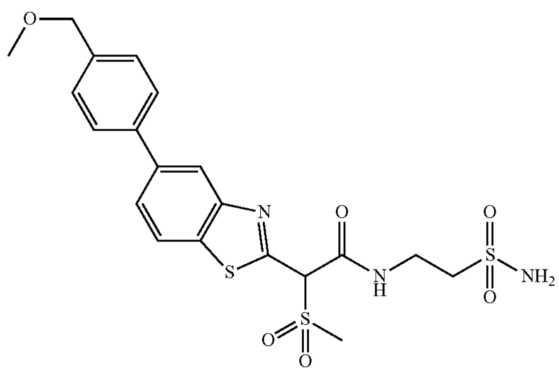 [SMILES: COCc1ccc(-c2ccc3sc(C(C(=O)NCCS(N)(=O)=O)S(C)(=O)=O)nc3c2)cc1] | 2-methanesulfonyl-2-{5-[4-(methoxymethyl)phenyl]-1,3-benzothiazol-2-yl}-N-(2-sulfamoylethyl)acetamide | δ 9.00 (t, J = 5.6 Hz, 1H), 8.37 (s, 1H), 8.25 (d, J = 8.5 Hz, 1H), 7.86 (d, J = 8.5 Hz, 1H), 7.80 (d, J = 8.0 Hz, 2H), 7.46 (d, J = 8.0 Hz, 2H), 6.96 (s, 2H), 6.06 (s, 1H), 4.49 (s, 2H), 3.62 (q, J = 6.6 Hz, 2H), 3.35 (s, 3H), 3.27 (s, 3H), 3.21 (t, J = 7.0 Hz, 2H) | 1.52 N 498 | 0.7 | 6.7 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B379 | 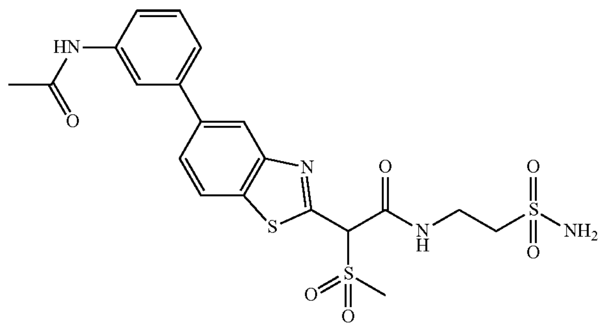 [SMILES: CC(=O)Nc1cccc(-c2ccc3sc(C(C(=O)NCCS(N)(=O)=O)S(C)(=O)=O)nc3c2)c1] | 2-[5-(3-acetamidophenyl)-1,3-benzothiazol-2-yl]-2-methanesulfonyl-N-(2-sulfamoylethyl)acetamide | δ 10.07 (br. s., 1H), 8.99 (t, J = 5.2 Hz, 1H), 8.34-8.20 (m, 2H), 8.03 (br. s., 1H), 7.78 (d, J = 8.0 Hz, 1H), 7.61 (d, J = 7.2 Hz, 1H), 7.51-7.37 (m, 2H), 6.96 (s, 2H), 6.07 (s, 1H), 3.62 (d, J = 6.1 Hz, 2H), 3.27 (s, 3H), 3.24-3.18 (m, 2H), 2.10 (s, 3H) | 1.26 N 511 | 0.5 | 83.7 |
| B380 | 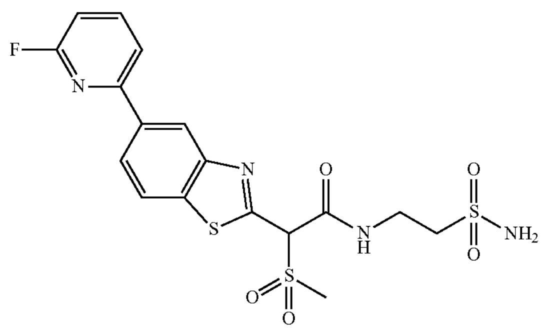 [SMILES: CS(=O)(=O)C(C(=O)NCCS(N)(=O)=O)c1nc2cc(-c3cccc(F)n3)ccc2s1] | 2-[5-(6-fluoropyridin-2-yl)-1,3-benzothiazol-2-yl]-2-methanesulfonyl-N-(2-sulfamoylethyl)acetamide | δ 8.99 (t, J = 5.2 Hz, 1H), 8.77 (s, 1H), 8.34-8.28 (m, 1H), 8.27-8.21 (m, 1H), 8.14 (br. s., 2H), 7.20 (d, J = 2.5 Hz, 1H), 6.96 (s, 2H), 6.08 (s, 1H), 3.62 (q, J = 6.6 Hz, 2H), 3.27 (s, 3H), 3.21 (t, J = 7.0 Hz, 2H) | 1.4 O 473 | 2.0 | 18.5 |
| B381 | 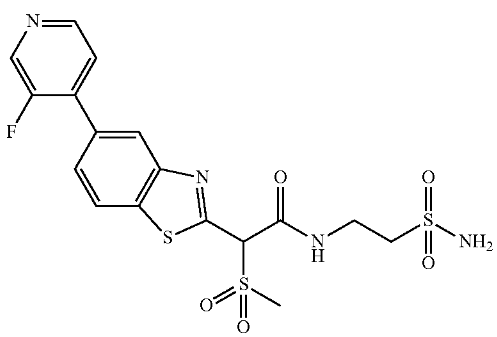 [SMILES: CS(=O)(=O)C(C(=O)NCCS(N)(=O)=O)c1nc2cc(-c3ccncc3F)ccc2s1] | 2-[5-(3-fluoropyridin-4-yl)-1,3-benzothiazol-2-yl]-2-methanesulfonyl-N-(2-sulfamoylethyl)acetamide | δ 9.01 (t, J = 5.0 Hz, 1H), 8.73 (s, 1H), 8.57 (d, J = 4.7 Hz, 1H), 8.41 (s, 1H), 8.36 (d, J = 8.3 Hz, 1H), 7.97 (s, 1H), 7.85-7.76 (m, 2H), 6.96 (s, 2H), 6.09 (s, 1H), 3.66-3.59 (m, 2H), 3.27 (s, 3H), 3.21 (t, J = 7.0 Hz, 2H) | 1.15 N 473 | 1.1 | 40.2 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B382 | 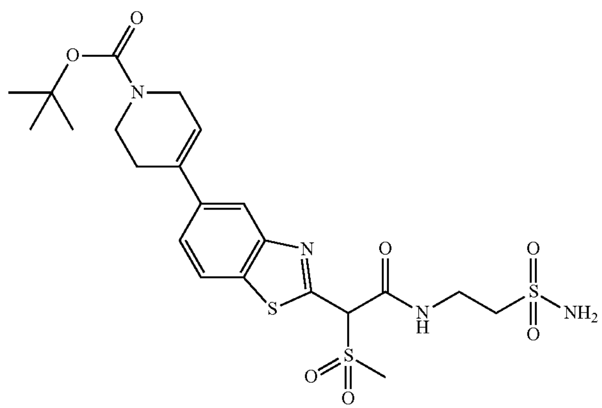 [SMILES: CC(C)(C)OC(=O)N1CC=C(c2ccc3sc(C(C(=O)NCCS(N)(=O)=O)S(C)(=O)=O)nc3c2)CC1] | tert-butyl 4-(2-{methanesulfonyl[(2-sulfamoylethyl)carbamoyl]methyl}-1,3-benzothiazol-5-yl)-1,2,3,6-tetrahydropyridine-1-carboxylate | δ 9.02 (t, J = 5.4 Hz, 1H), 8.20-8.12 (m, 1H), 8.12 (d, J = 8.5 Hz, 1H), 7.71 (d, J = 8.5 Hz, 1H), 7.00 (s, 2H), 6.07 (s, 1H), 5.38 (t, J = 4.8 Hz, 1H), 4.10 (br. s., 1H), 3.70-3.60 (m, 4H), 3.29 (s, 3H), 3.24 (t, J = 6.9 Hz, 3H), 2.12-1.93 (m, 3H), 1.50 (s, 9H) | 1.71 N 559 | 3.1 | 36.5 |
| B383 | 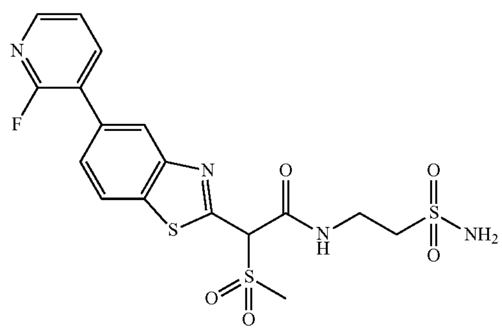 [SMILES: CS(=O)(=O)C(C(=O)NCCS(N)(=O)=O)c1nc2cc(-c3cccnc3F)ccc2s1] | 2-[5-(2-fluoropyridin-3-yl)-1,3-benzothiazol-2-yl]-2-methanesulfonyl-N-(2-sulfamoylethyl)acetamide | δ 9.00 (br. s., 1H), 8.36-8.29 (m, 3H), 8.26 (t, J = 8.9 Hz, 1H), 7.77 (d, J = 8.3 Hz, 1H), 7.54 (t, J = 5.8 Hz, 1H), 6.96 (s, 2H), 6.08 (s, 1H), 3.62 (q, J = 6.3 Hz, 2H), 3.27 (s, 3H), 3.21 (t, J = 7.0 Hz, 2H) | 1.25 N 473 | 0.7 | 13.0 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B384 | 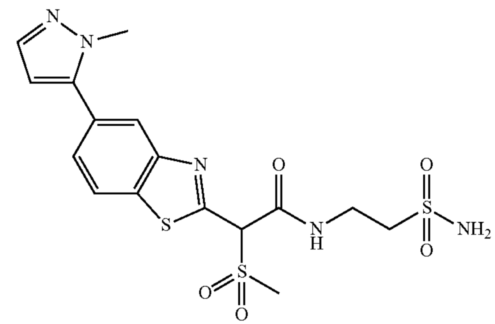 [SMILES: Cn1nccc1-c1ccc2sc(C(C(=O)NCCS(N)(=O)=O)S(C)(=O)=O)nc2c1] | 2-methanesulfonyl-2-[5-(1-methyl-1H-pyrazol-5-yl)-1,3-benzothiazol-2-yl]-N-(2-sulfamoylethyl)acetamide | δ 9.00 (br. s., 1H), 8.30 (d, J = 8.0 Hz, 1H), 8.25 (s, 1H), 7.68 (d, J = 8.3 Hz, 1H), 7.52 (s, 1H), 6.96 (br. s.., 2H), 6.53 (s, 1H), 6.06 (s, 1H), 3.93 (s, 3H), 3.62 (d, J = 6.3 Hz, 2H), 3.26 (s, 3H), 3.20 (t, J = 6.9 Hz, 2H) | 1.02 N 458 | 8.2 | 827.6 |
| B385 | 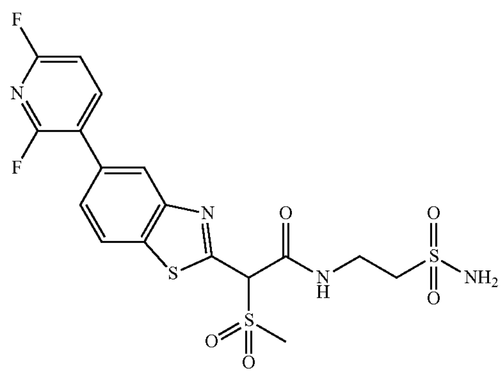 [SMILES: CS(=O)(=O)C(C(=O)NCCS(N)(=O)=O)c1nc2cc(-c3ccc(F)nc3F)ccc2s1] | 2-[5-(2,6-difluoropyridin-3-yl)-1,3-benzothiazol-2-yl]-2-methanesulfonyl-N-(2-sulfamoylethyl)acetamide | δ 9.00 (t, J = 5.6 Hz, 1H), 8.53-8.40 (m, 1H), 8.37-8.27 (m, 2H), 7.76 (d, J = 8.3 Hz, 1H), 7.37 (dd, J = 8.3, 2.5 Hz, 1H), 6.96 (s, 2H), 6.08 (s, 1H), 3.62 (q, J = 6.7 Hz, 2H), 3.26 (s, 3H), 3.23-3.16 (m, 2H) | 1.38 N 491 | 3.5 | 20.5 |

| Ex # | Structure | Name | ¹H NMR (500 MHz, DMSO-d₆, unless indicated otherwise) | LC/MS RT (min) Method M + H | EL IC₅₀ (nM) | HL IC₅₀ (nM) |
|---|---|---|---|---|---|---|
| B386 | 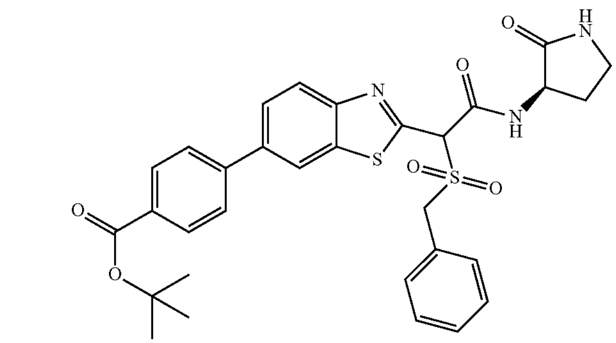 [SMILES: CC(C)(C)OC(=O)c1ccc(-c2ccc3nc(C(C(=O)N[C@@H]4CCNC4=O)S(=O)(=O)Cc4ccccc4)sc3c2)cc1] | tert-butyl 4-[2-[({[(3R)-2-oxopyrrolidin-3-yl]carbamoyl}(phenyl-methanesulfonyl)methyl)-1,3-benzothiazol-6-yl]benzoate | ¹H NMR (400 MHz, DMSO-d₆) δ 9.18 (dd, J = 11.2, 7.7 Hz, 1H), 8.58 (d, J = 5.7 Hz, 1H), 8.22 (dd, J = 8.5, 5.4 Hz, 1H), 8.07-7.68 (m, 4H), 7.46-7.38 (m, 3H), 7.34-7.15 (m, 1H), 6.14 (d, J = 6.4 Hz, 1H), 4.87-4.58 (m, 3H), 4.44-4.22 (m, 1H), 3.25-3.15 (m, 3H), 1.63-1.52 (m, 10H) | 2.25 M 606.1 | 17.1 | 14.3 |
| B388 | 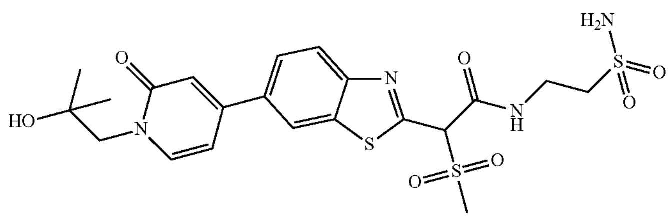 [SMILES: CC(C)(O)Cn1ccc(-c2ccc3nc(C(C(=O)NCCS(N)(=O)=O)S(C)(=O)=O)sc3c2)cc1=O] | 2-{6-[1-(2-hydroxy-2-methylpropyl)-2-oxo-1,2-dihydropyridin-4-yl]-1,3-benzothiazol-2-yl}-2-methanesulfonyl-N-(2-sulfamoylethyl)acetamide | δ 9.03 (br. s., 1H), 8.62 (br. s., 1H), 8.17 (d, J = 8.5 Hz, 1H), 7.94 (d, J = 8.3 Hz, 1H), 7.82-7.72 (m, 1H), 6.99 (br. s., 2H), 6.82 (br. s., 1H), 6.69 (d, J = 3.6 Hz, 1H), 6.06 (br. s., 1H), 4.87 (br. s., 1H), 3.96 (br. s., 2H), 3.62 (br. s., 2H), 3.25 (br. s., 3H), 3.20 (br. s., 2H), 1.13 (br. s., 6H). | 1.02 O 541.0 | 5.3 | 4444.0 |
| B389 | 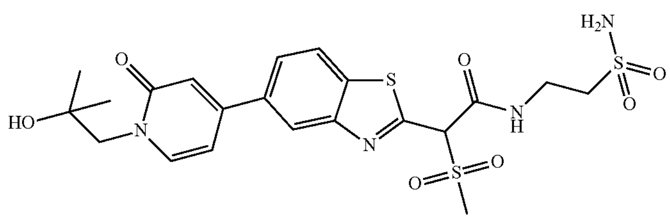 [SMILES: CC(C)(O)Cn1ccc(-c2ccc3sc(C(C(=O)NCCS(N)(=O)=O)S(C)(=O)=O)nc3c2)cc1=O] | 2-{5-[1-(2-hydroxy-2-methylpropyl)-2-oxo-1,2-dihydropyridin-4-yl]-1,3-benzothiazol-2-yl}-2-methanesulfonyl-N-(2-sulfamoylethyl)acetamide | δ 9.02 (br. s., 1H), 8.46 (br. s., 1H), 8.29 (d, J = 8.0 Hz, 1H), 8.02-7.69 (m, 2H), 6.98 (br. s., 2H), 6.85 (br. s., 1H), 6.75 (d, J = 4.7 Hz, 1H), 6.07 (br. s., 1H), 4.88 (br. s., 1H), 4.00-3.89 (m, 3H), 3.61 (br. s., 2H), 3.26 (br. s., 3H), 3.19 (d, J = 9.6 Hz, 2H), 1.13 (br. s., 6H) | 1.03 O 543.1 | 2.0 | 6304.0 |

| Ex # | Structure | Name | ¹H NMR (500 MHz, DMSO-d₆, unless indicated otherwise) | LC/MS RT (min) Method M + H | EL IC$_{50}$ (nM) | HL IC$_{50}$ (nM) |
|---|---|---|---|---|---|---|
| B390 | 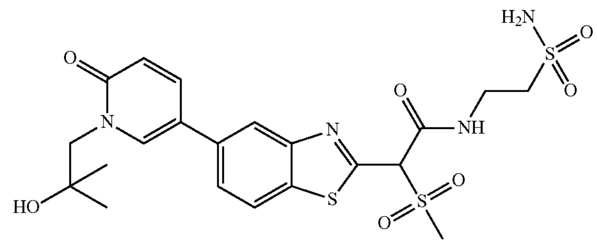 [SMILES: CC(C)(O)Cn1cc(-c2ccc3sc(C(C(=O)NCCS(N)(=O)=O)S(C)(=O)=O)nc3c2)ccc1=O] | 2-{5-[1-(2-hydroxy-2-methylpropyl)-6-oxo-1,6-dihydropyridin-3-yl]-1,3-benzothiazol-2-yl}-2-methanesulfonyl-N-(2-sulfamoylethyl)acetamide | δ 9.00 (br. s., 1H), 8.30-8.26 (m, 1H), 8.22 (d, J = 8.8 Hz, 1H), 8.17-8.13 (m, 1H), 8.01-7.95 (m, 1H), 7.75-7.68 (m, 1H), 6.99 (br. s., 2H), 6.55 (d, J = 9.1 Hz, 1H), 6.04 (br. s., 1H), 4.03 (br. s., 2H), 3.60 (br. s., 2H), 3.25 (br. s., 3H), 3.19 (br. s., 2H), 1.13 (br. s., 6H) | 1.07 O 543.1 | 3.5 | 10000.0 |
| B393 | 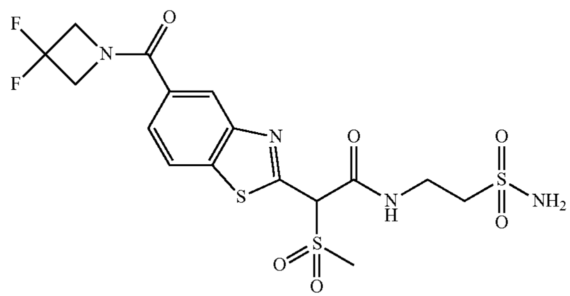 [SMILES: CS(=O)(=O)C(C(=O)NCCS(N)(=O)=O)c1nc2cc(C(=O)N3CC(F)(F)C3)ccc2s1] | 2-[5-(3,3-difluoroazetidine-1-carbonyl)-1,3-benzothiazol-2-yl]-2-methanesulfonyl-N-(2-sulfamoylethyl)acetamide | δ 9.02 (br. s., 1H), 8.38 (s, 1H), 8.29 (d, J = 8.5 Hz, 1H), 7.97 (br. s., 1H), 7.83 (dd, J = 8.3 Hz, 1H), 6.96 (br. s., 2H), 6.08 (s, 1H), 5.00-4.75 (m, 2H), 4.69-4.44 (m, 2H), 3.62 (d, J = 5.8 Hz, 2H), 3.26 (s, 3H), 3.20 (t, J = 6.6 Hz, 2H) | 0.98 N 497 | 50.3 | 5747.0 |
| B394 | 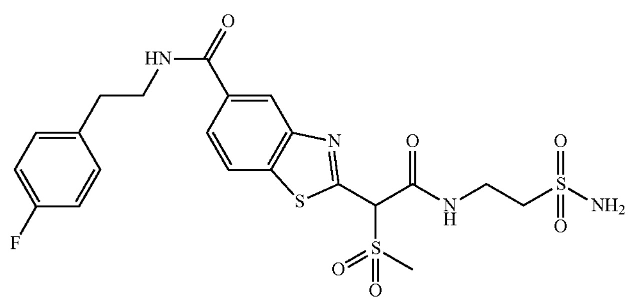 [SMILES: CS(=O)(=O)C(C(=O)NCCS(N)(=O)=O)c1nc2cc(C(=O)NCCc3ccc(F)cc3)ccc2s1] | N-[2-(4-fluorophenyl)ethyl]-2-{methanesulfonyl[(2-sulfamoylethyl)carbamoyl]methyl}-1,3-benzothiazole-5-carboxamide | δ 9.04 (t, J = 5.8 Hz, 1H), 8.38 (d, J = 1.4 Hz, 1H), 8.30 (d, J = 8.5 Hz, 1H), 7.83 (dd, J = 8.4, 1.5 Hz, 1H), 6.99 (s, 2H), 6.08 (s, 1H), 4.89 (br. s., 2H), 4.55 (br. s., 2H), 3.65-3.56 (m, 2H), 3.26 (s, 3H), 3.20 (dd, J = 7.7, 6.1 Hz, 2H) | 1.25 N 543 | 37.4 | 1595.0 |

Reference 1

2-(6-Phenyl-1,3-benzothiazol-2-yl)-N-(2-sulfamoyl-ethyl)-4-pentenamide

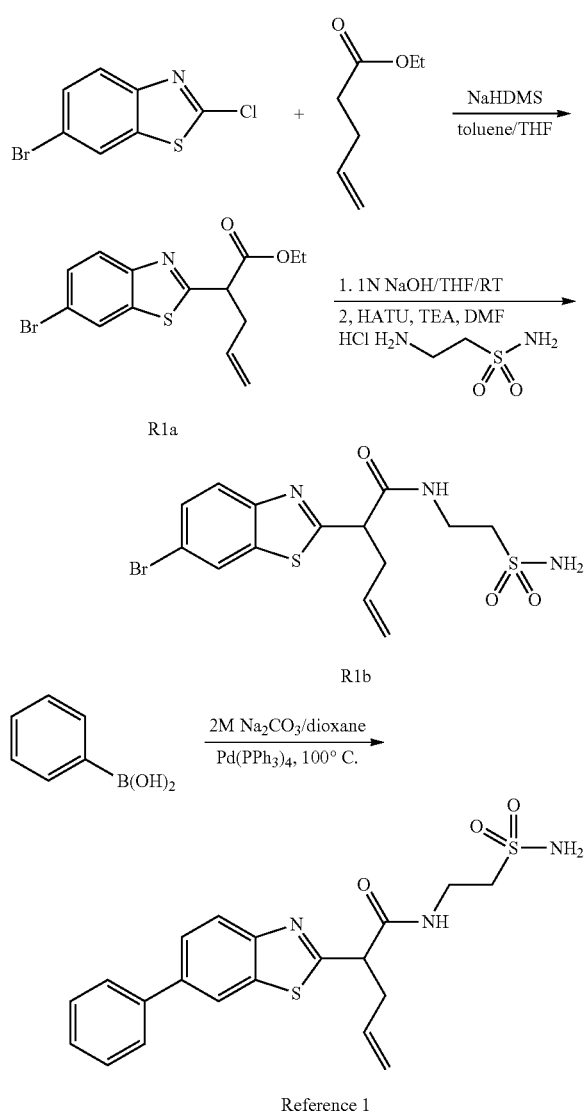

Compound R1a. Ethyl 2-(6-bromobenzo[d]thiazol-2-yl)pent-4-enoate

Compound R1a (2.4 g, 35% yield) was prepared from ethyl 6-bromo-2-chlorobenzo[d]thiazole as described in the general procedure given for Compound B196b. HPLC: RT=1.15 (LCMS Method M). MS (ES): m/z=341.7 [M+H]$^+$. $^1$H NMR (500 MHz, CHLOROFORM-d) δ 8.01 (d, J=1.9 Hz, 1H), 7.94-7.79 (m, 1H), 7.58 (dd, J=8.5, 1.9 Hz, 1H), 5.80 (ddt, J=17.1, 10.2, 6.9 Hz, 1H), 5.15 (dq, J=17.1, 1.5 Hz, 1H), 5.08 (dd, J=10.2, 1.4 Hz, 1H), 4.34-4.18 (m, 3H), 3.03-2.90 (m, 1H), 2.90-2.73 (m, 1H), 1.35-1.22 (m, 3H).

Compound R1b. Ethyl 2-(6-phenylbenzo[d]thiazol-2-yl)pent-4-enoate

Compound R1b (120 mg, 29%) was prepared from Compound R1a as described in the general procedure given for Compound A1a. HPLC: RT=0.86 (LCMS Method M). MS (ES): m/z=419.7 [M+H]$^+$. $^1$H NMR (500 MHz, DMSO-d$_6$) δ 8.70-8.54 (m, 1H), 8.36 (d, J=1.9 Hz, 1H), 7.89 (d, J=8.8 Hz, 1H), 7.68-7.59 (m, 1H), 6.89 (s, 2H), 5.82-5.66 (m, 1H), 5.08 (dd, J=17.1, 1.7 Hz, 1H), 5.04-4.94 (m, 1H), 4.18 (dd, J=8.0, 7.2 Hz, 1H), 3.55-3.37 (m, 2H), 3.16-3.04 (m, 2H), 2.76 (d, J=1.1 Hz, 1H), 2.66 (d, J=7.2 Hz, 1H).

Reference 1

Reference 1 (14 mg, 46%) was prepared from Compound R1b as described in the general procedure given for Compound B2a. HPLC: RT=0.93 (LCMS Method M). MS (ES): m/z=416.0 [M+H]$^+$. $^1$H NMR (500 MHz, DMSO-d$_6$) δ 8.63 (t, J=5.8 Hz, 1H), 8.38 (d, J=1.4 Hz, 1H), 8.03 (d, J=8.5 Hz, 1H), 7.80 (dd, J=8.4, 1.8 Hz, 1H), 7.78-7.70 (m, 2H), 7.56-7.46 (m, 2H), 7.44-7.33 (m, 1H), 6.91 (s, 2H), 5.87-5.70 (m, 1H), 5.12 (dd, J=17.2, 1.8 Hz, 1H), 5.07-4.97 (m, 1H), 4.28-4.16 (m, 1H), 3.49 (td, J=13.9, 7.4 Hz, 2H), 3.18 (d, J=5.0 Hz, 1H), 3.13 (t, J=7.3 Hz, 2H), 2.87-2.76 (m, 1H), 2.77-2.65 (m, 1H).

Reference 2

N-((3-isopropylisoxazol-5-yl)methyl)-2-methyl-2-(6-phenylbenzo[d]thiazol-2-yl)propanamide

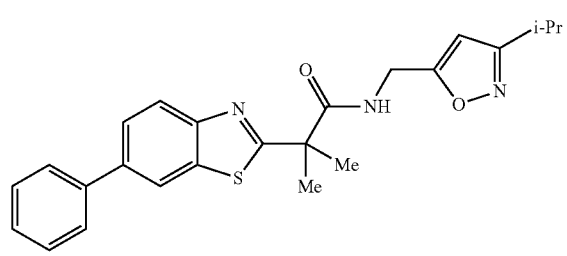 [SMILES: CC(C)c1cc(CNC(=O)C(C)(C)c2nc3ccc(-c4ccccc4)cc3s2)on1]

Reference 2 was prepared as described in the general procedure given for Reference 1. HPLC: RT=2.16 (LCMS Method B). MS (ES): m/z=420.1 [M+H]$^+$. $^1$H NMR (400 MHz, CHLOROFORM-d) δ 8.11-8.05 (m, 2H), 7.90 (m, 1H), 7.75 (dd, J=8.5, 1.8 Hz, 1H), 7.68-7.62 (m, 2H), 7.52-7.46 (m, 2H), 7.44-7.37 (m, 1H), 5.93 (s, 1H), 4.55 (dd, J=5.9, 0.6 Hz, 2H), 3.07-2.95 (m, 1H), 1.84 (s, 6H), 1.24 (s, 3H), 1.22 (s, 3H).

Reference 3

N-((3-isopropylisoxazol-5-yl)methyl)-2-methyl-2-(6-phenylbenzo[d]thiazol-2-yl)propanamide

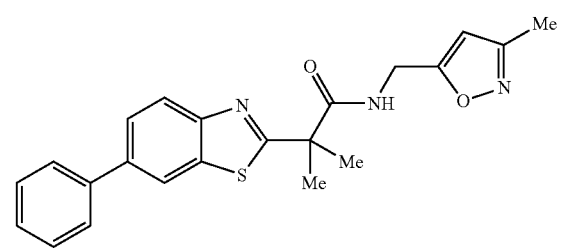 [SMILES: Cc1cc(CNC(=O)C(C)(C)c2nc3ccc(-c4ccccc4)cc3s2)on1]

Reference 3 was prepared as described in the general procedure given for Reference 1. HPLC: RT=1.97 (LCMS Method B). MS (ES): m/z=393.1 [M+H]⁺. ¹H NMR (400 MHz, CHLOROFORM-d) δ 8.12-8.06 (m, 2H), 7.77 (dd, J=8.5, 1.8 Hz, 1H), 7.67-7.62 (m, 2H), 7.53-7.46 (m, 2H), 7.44-7.38 (m, 1H), 4.70 (d, J=6.0 Hz, 2H), 2.55 (s, 3H), 1.86 (s, 6H).

What is claimed is:

1. A compound of Formula (I):

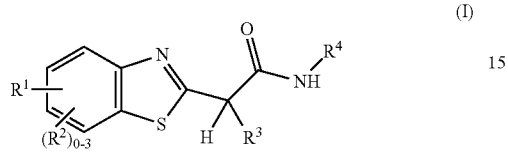

(I)

or a stereoisomer, a tautomer, or a pharmaceutically acceptable salt thereof, wherein:

$R^1$ is independently selected from: halogen, CN, $CO_2(C_{1-4}$ alkyl), —CO—$R^j$, —CONH—$(CH_2)_m$—$R^j$,

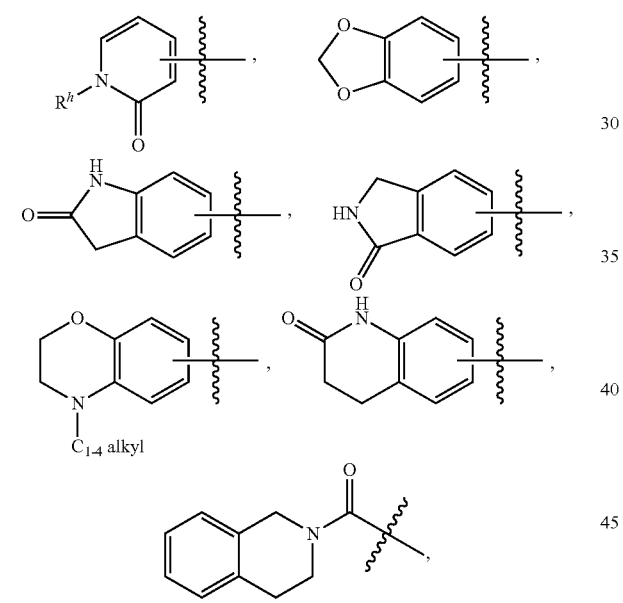

phenyl substituted with 0-3 $R^a$, and a 5- to 6-membered heteroaryl comprising: carbon atoms and 1-4 heteroatoms selected from N, $NR^c$, O, and $S(O)_p$; wherein said heteroaryl is substituted with 0-3 $R^a$;

$R^2$ is, independently at each occurrence, selected from: halogen, OH, $C_{1-4}$ alkyl, $C_{1-4}$ alkoxy, $C_{1-4}$ haloalkyl, $C_{1-4}$ haloalkoxy, CN, $NH_2$, $NO_2$, $NH(C_{1-4}$ alkyl), $N(C_{1-4}$ alkyl)$_2$, $CO_2H$, $CO_2(C_{1-4}$ alkyl), and $CONH_2$;

$R^3$ is independently selected from: —$SO_2R^5$ and —NH-$COR^6$;

$R^4$ independently selected from

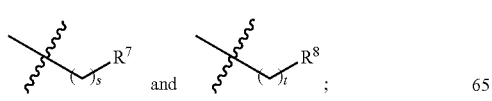

$R^5$ is independently selected from: $C_{1-6}$ alkyl substituted with 0-1 $R^9$, $C_{2-6}$ alkenyl, $C_{1-6}$ haloalkyl, $C_{1-6}$ alkoxy, —$(CH_2)_m$—$(O)_n$—$(C_{3-6}$ carbocycle substituted with 0-3 $R^b$), and —$(CH_2)_m$—$(O)_n$-(5- to 6-membered heterocycle comprising: carbon atoms and 1-4 heteroatoms selected from N, $NR^c$, O, and $S(O)_p$; wherein said heterocycle is substituted with 0-2 $R^b$);

$R^6$ is independently selected from: $C_{1-6}$alkyl, $C_{2-6}$ alkenyl, $C_{1-6}$ alkoxy, $C_{1-4}$ haloalkyl, —$(CH_2)_m$—$(C_{3-6}$ carbocycle substituted with 0-3 $R^b$), —$(CH_2)_m$-(pyridyl substituted with 0-2 $R^b$), —$NH(C_{1-4}$ alkyl), —$NHCH_2CO_2(C_{1-4}$ alkyl), —NH(4-halo-Ph), —NHBn, and

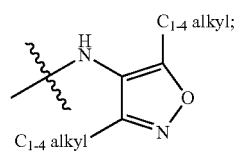

$R^7$ is independently selected from: $CONH_2$, $CONH(C_{1-4}$ alkyl), $CON(C_{1-4}$ alkyl)$_2$, $SO_2NHSO_2(C_{1-4}$ alkyl), $SO_2NH(CH_2)_{2-4}CO_2(C_{1-4}$ alkyl), $NHSO_2NH_2$, $NHSO_2$ ($C_{1-4}$ alkyl), $N(C_{1-4}$ alkyl)$SO_2NH_2$, $N(CO_2C_{1-4}$ alkyl) $SO_2(C_{1-4}$ alkyl), $SO_2R^{10}$, and

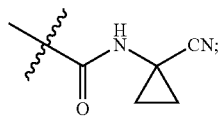 [SMILES: *C(=O)NC1(C#N)CC1]

$R^8$ is independently selected from

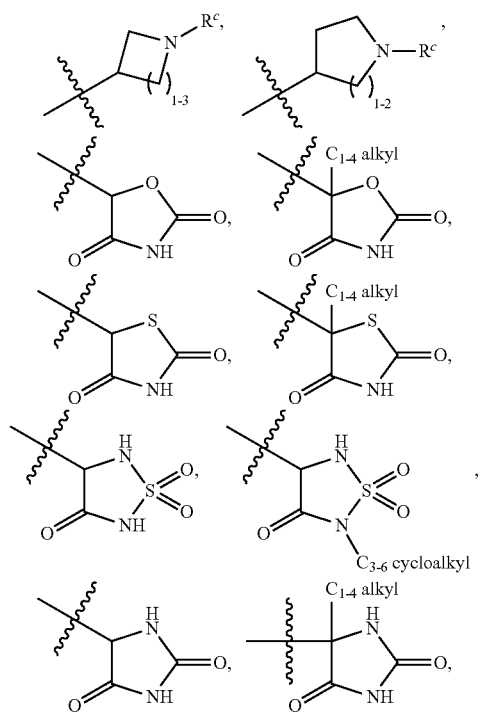

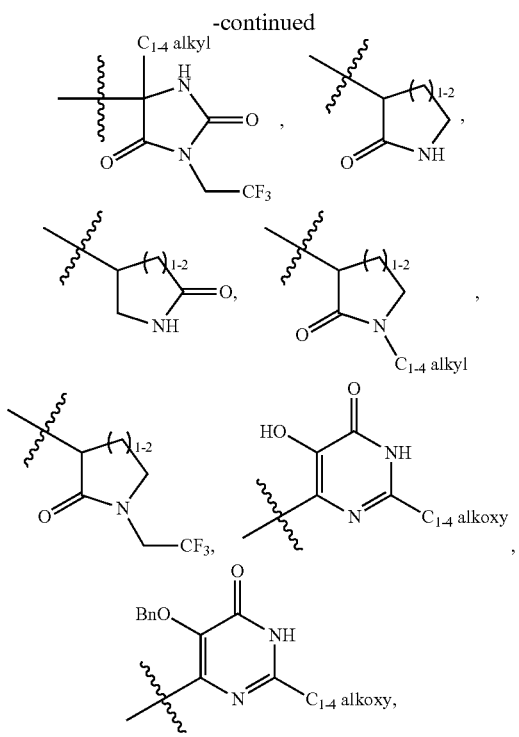

phenyl and a 5- to 6-membered heteroaryl comprising: carbon atoms and 1-4 heteroatoms selected from N, $NR^c$, O, and $S(O)_p$; wherein said phenyl and heteroaryl are is substituted with 0-2 $R^{11}$;

$R^9$ is independently selected from: halogen, $C_{1-4}$ alkoxy, $C_{1-4}$ haloalkyl, $C_{1-4}$ haloalkoxy, $NH_2$, $CO_2H$, $CO_2(C_{1-4}$ alkyl), $SO_3H$, $CONHR^d$, $NHCONHR^d$, $NHCO_2R^d$,

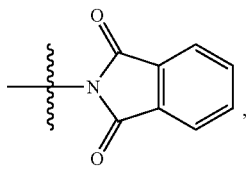 [SMILES: *N1C(=O)c2ccccc2C1=O]

and 5- to 6-membered heterocycle comprising: carbon atoms and 1-4 heteroatoms selected from N, $NR^g$, O, and $S(O)_p$;

$R^{10}$ is independently selected from: OH, $C_{1-6}$ alkyl, $C_{2-6}$ alkenyl, $NH_2$, $NH(C_{1-6}$ alkyl substituted with 0-1 $CO_2$ $(C_{1-4}$ alkyl)), $NH(C_{2-6}$ alkyl), $NH(C_{1-4}$ haloalkyl), NHPh, phenyl substituted with 0-2 halogens, and

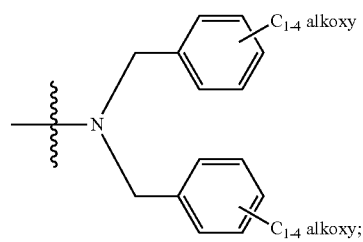

$R^{11}$ is, independently at each occurrence, selected from: halogen, $C_{1-4}$ alkyl, $C_{1-4}$ haloalkyl, $NH_2$, and phenyl;

$R^a$ is, independently at each occurrence, selected from: halogen, $C_{1-6}$ alkyl substituted with 0-1 $R^f$, $C_{1-4}$ alkoxy substituted with 0-1 $R^f$, $C_{1-6}$ haloalkyl, $C_{1-6}$ haloalkoxy, OH, CN, $NO_2$, $CO_2H$, $CO_2(C_{1-4}$ alkyl), $NR^gR^h$, $CONR^gR^h$, $CONR^gR^j$, $NHCOR^i$, $NHCO_2R^i$, $SO_2NR^gR^h$, $-(O)_n-(CH_2)_t-R^j$, and $-CO-R^j$;

$R^b$ is, independently at each occurrence, selected from: halogen, $C_{1-4}$ alkyl, $C_{1-4}$ alkoxy, $C_{1-4}$ haloalkyl, $C_{1-4}$ haloalkoxy, OH, CN, $NH_2$, $NO_2$, $NH(C_{1-4}$ alkyl), $N(C_{1-4}$ alkyl)$_2$, $CO_2H$, $CO_2(C_{1-4}$ alkyl), $SO_2(C_{1-4}$ alkyl), $CONH_2$, and $CONH(C_{1-4}$ alkyl);

$R^c$ is, independently at each occurrence, selected from: H, $C_{1-6}$ alkyl substituted with 0-1 $R^e$, $CO(C_{1-4}$ alkyl), $CO_2$ $(C_{1-4}$ alkyl), COBn, $CO_2Bn$, $-(CH_2)_t$-piperidinyl, $-(CH_2)_t$-morpholinyl, $-(CH_2)_t$-piperazinyl, pyrimidinyl, $-(CH_2)_t-(C_{3-6}$ carbocycle substituted with 0-2 $R^e$), and

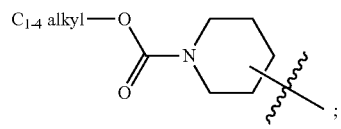

$R^d$ is, independently at each occurrence, selected from: $C_{1-6}$ alkyl and $-(CH_2)_t$-(phenyl substituted with 0-2 $R^e$);

$R^e$ is, independently at each occurrence, selected from: halogen, $C_{1-4}$ alkyl, $C_{1-4}$ alkoxy, $C_{1-4}$ haloalkyl, and $C_{1-4}$ haloalkoxy;

$R^f$ is, independently at each occurrence, selected from: OH, halogen, $C_{1-4}$ alkyl, $C_{1-4}$ alkoxy, $C_{1-4}$ haloalkyl, and $C_{1-4}$ haloalkoxy;

$R^g$ is, independently at each occurrence, selected from: H and $C_{1-4}$ alkyl;

$R^h$ is, independently at each occurrence, selected from: H, $C_{1-6}$ haloalkyl and $C_{1-6}$ alkyl substituted with 0-1 $R^f$;

$R^i$ is, independently at each occurrence, selected from: $C_{1-4}$ haloalkyl and $C_{1-4}$ alkyl substituted with 0-1 $R^f$;

$R^j$ is, independently at each occurrence: $C_{3-6}$ carbocycle or a 4- to 6-membered heterocycle comprising: carbon atoms and 1-4 heteroatoms selected from N, $NR^g$, O, and $S(O)_p$; wherein said carbocycle and heterocycle are substituted with 0-2 $R^f$;

m and t are, independently at each occurrence, selected from 0, 1, and 3;

n is, independently at each occurrence, selected from 0 and 1;

p is, independently at each occurrence, selected from 0, 1, and 2; and s is, independently at each occurrence, selected from 1, 2, and 3.

2. A compound according to claim 1, wherein the compound is of Formula (Ia) or (Ib):

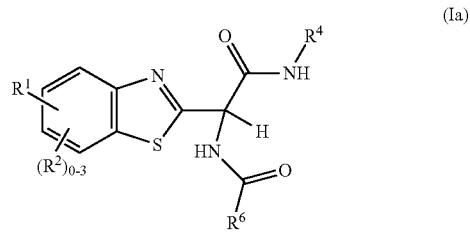

-continued

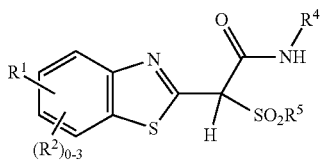
(Ib)

or a stereoisomer, a tautomer, or a pharmaceutically acceptable salt thereof, wherein:

m and t are, independently at each occurrence, selected from 0, 1, and 2; and s is, independently at each occurrence, selected from 1 and 2.

3. A compound according to claim 1, wherein the compound is of Formula (IIa) or (IIb):

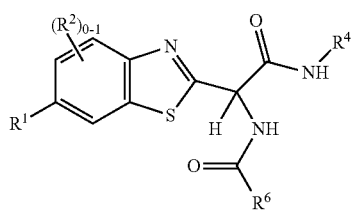
(IIa)

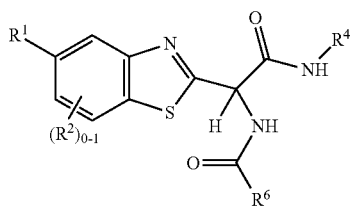
(IIb)

or a stereoisomer, a tautomer, or a pharmaceutically acceptable salt thereof, wherein:

$R^2$ is independently selected from: halogen and $C_{1-4}$ alkyl.

4. A compound according to claim 3, wherein:

$R^1$ is independently selected from: 4-halo-Ph, 6-halo-pyrid-3-yl, and

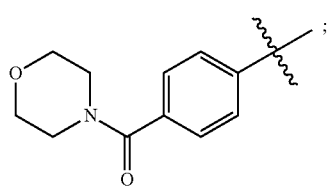 [SMILES: *c1ccc(C(=O)N2CCOCC2)cc1]

$R^4$ is

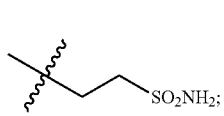

and $R^6$ is independently selected from $C_{1-4}$ alkyl, —$CHF_2$, NHBn, 4-$CF_3$-Ph, and pyrid-3-yl.

5. A compound according to claim 1, wherein the compound is of Formula (IIIa) or (IIIb):

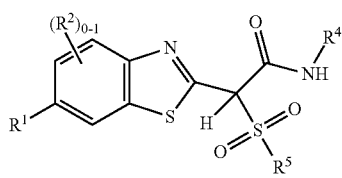
(IIIa)

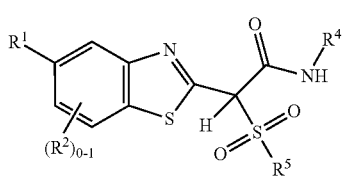
(IIIb)

or a stereoisomer, a tautomer, or a pharmaceutically acceptable salt thereof, wherein:

$R^2$ is independently selected from: halogen, $C_{1-4}$ alkyl and $C_{1-4}$ haloalkyl.

6. A compound according to claim 5, wherein:

$R^1$ is independently selected from:

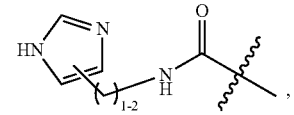

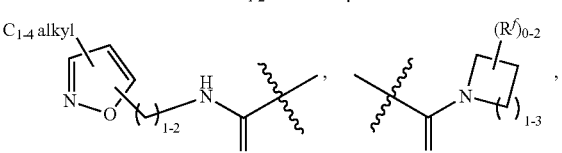

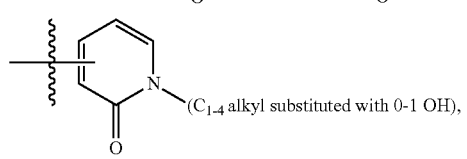

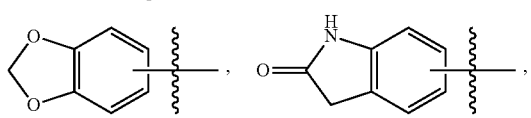

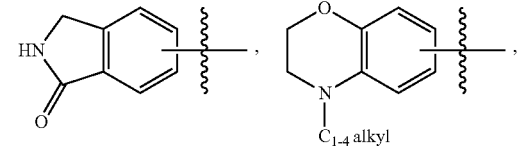

phenyl substituted with 0-2 $R^a$, and a heteroaryl substituted with 0-2 $R^a$ and selected from: isoxazolyl, pyrazolyl, 1-$R^c$-pyrazolyl, pyridyl, and pyrimidinyl;

$R^4$ is independently selected from

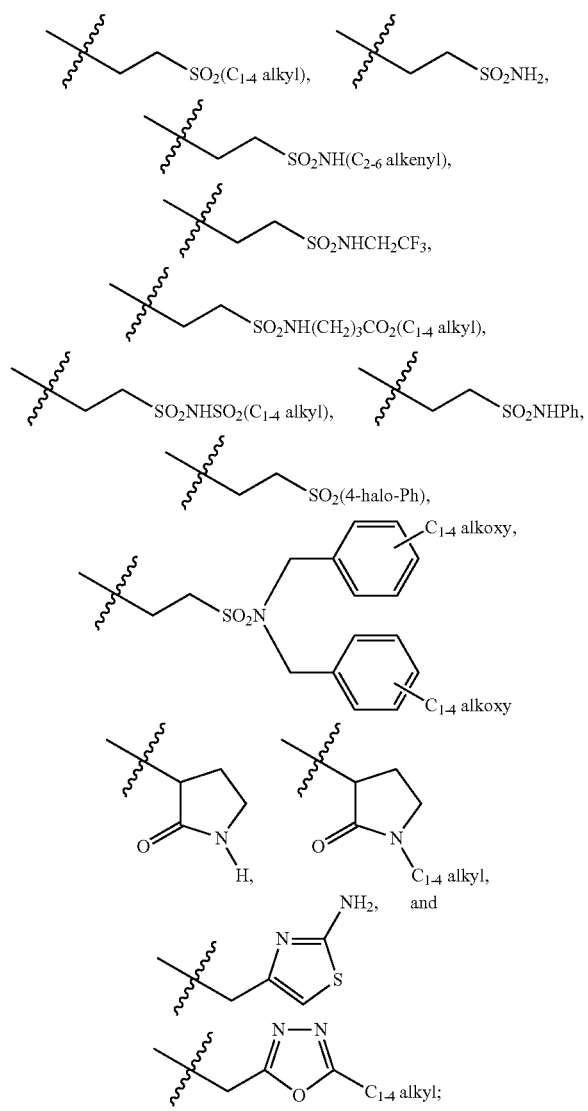

$R^5$ is independently selected from: $C_{1-4}$ alkyl substituted with 0-1 $R^9$, $C_{2-4}$ alkenyl, $-(CH_2)_{0-1}-C_{3-6}$ cycloalkyl, $-(CH_2)_{0-1}-$(phenyl substituted with 0-1 $R^b$) and

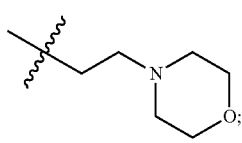 [SMILES: *CCN1CCOCC1]

$R^9$ is independently selected from: $C_{1-4}$ alkoxy, $C_{1-4}$ haloalkyl, $NH_2$, and $NHCO_2Bn$;

$R^a$ is, independently at each occurrence, selected from: OH, halogen, CN, $C_{1-4}$ alkyl substituted with 0-1 OH, $C_{1-4}$ alkoxy, $-O(CH_2)_{1-2}O(C_{1-4}$ alkyl), $C_{1-4}$ haloalkyl, $C_{1-4}$ haloalkoxy, $NH_2$, $CO_2H$, $CO_2(C_{1-4}$ alkyl), $CONH_2$, $CONH(C_{1-4}$ alkyl), $CONH(CH_2)_{2-3}OH$, $CONH(CH_2)_{1-3}O(C_{1-4}$ alkyl), $CON(C_{1-4}$ alkyl)$(CH_2)_{1-3}O(C_{1-4}$ alkyl), $CONH(C_{1-4}$ haloalkyl), $NHCO(C_{1-4}$ alkyl), $NHCO(C_{1-4}$ haloalkyl), $NHCO_2(C_{1-4}$ alkyl), $SO_2N(C_{1-4}$ alkyl)$_2$, $SO_2NH(CH_2)_{2-3}OH$, pyrazolyl, $-(CH_2)_{0-2}$-morpholinyl, $-CO$-morpholinyl, piperazinyl,

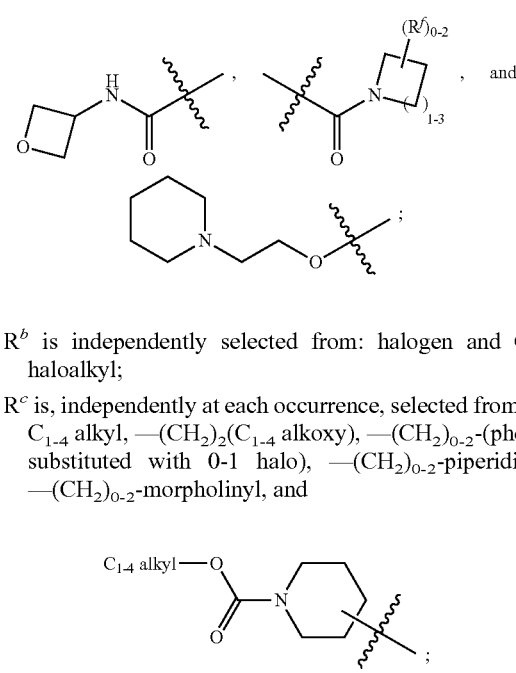

$R^b$ is independently selected from: halogen and $C_{1-4}$ haloalkyl;

$R^c$ is, independently at each occurrence, selected from: H, $C_{1-4}$ alkyl, $-(CH_2)_2(C_{1-4}$ alkoxy), $-(CH_2)_{0-2}$-(phenyl substituted with 0-1 halo), $-(CH_2)_{0-2}$-piperidinyl, $-(CH_2)_{0-2}$-morpholinyl, and

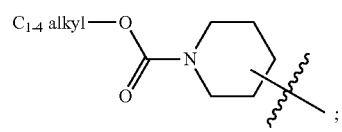

and $R^f$ is, independently at each occurrence, selected from: OH, halogen, $C_{1-4}$ alkyl, $C_{1-4}$ haloalkyl, $C_{1-4}$ alkoxy, and $C_{1-4}$ haloalkoxy.

7. A compound according to claim 6, wherein:

$R^1$ is independently selected from: Ph, 3-halo-Ph, 4-halo-Ph, 3-$C_{1-4}$ alkoxy-Ph, 4-$CH_2OH$-Ph, 3-CN-Ph, 4-CN-Ph, 4-$CO_2H$-Ph, 4-$CO_2(C_{1-4}$ alkyl)-Ph, 3-NHCO($C_{1-4}$ alkyl)-Ph, 4-NHCO($C_{1-4}$ alkyl)-Ph, 4-(pyrazol-1-yl)-Ph, 2-$C_{1-4}$ alkoxy-pyridyl, pyrimidinyl and

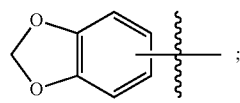

$R^4$ is independently selected from:

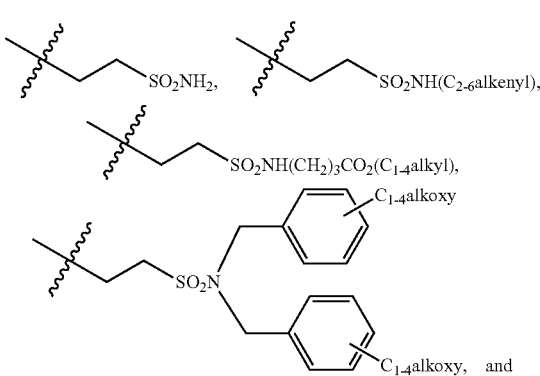

-continued

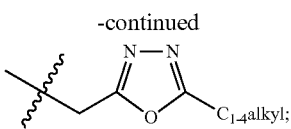

$R^5$ is independently selected from: $C_{1-4}$ alkyl substituted with 0-1 $R^9$, and $C_{2-4}$ alkenyl, Bn, and 4-halo-Bn; and $R^9$ is independently selected from: $C_{1-4}$ alkoxy, $C_{1-4}$ haloalkyl, $NH_2$, and $NHCO_2Bn$.

8. A compound according, to claim 7, wherein:

$R^1$ is independently selected from: Ph, 3-halo-Ph, 4-halo-Ph, 3-$C_{1-4}$ alkoxy-Ph, 4-$CH_2OH$-Ph, 3-CN-Ph, 4-CN-Ph, 4-$CO_2H$-Ph, 4-$CO_2(C_{1-4}$ alkyl)-Ph, 3-NHCO($C_{1-4}$ alkyl)-Ph, 4-NHCO($C_{1-4}$ alkyl)-Ph, 4-(pyrazol-1-yl)-Ph, pyrimidinyl and

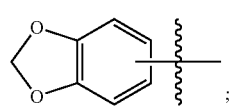

$R^4$ is

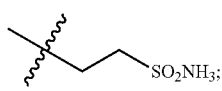

$R^5$ is independently selected from: $C_{1-4}$ alkyl substituted with 0-1 $R^9$, and $C_{2-4}$ alkenyl, Bn, and 4-halo-Bn; and $R^9$ is independently selected from: $C_{1-4}$ alkoxy, $C_{1-4}$ haloalkyl, $NH_2$, and $NHCO_2Bn$.

9. A compound according to claim 8, wherein:

$R^1$ is independently selected from: Ph, 3-F-Ph, 4-F-Ph, 3-OMe-Ph, 4-$CH_2OH$-Ph, 3-CN-Ph, 4-CN-Ph, 4-$CO_2H$-Ph, 4-$CO_2Me$-Ph, 3-NHCOMe-Ph, 4-NHCOMe-Ph, 4-(pyrazol-1-yl)-Ph, pyrimidin-5-yl, and

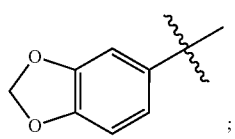 [SMILES: *c1ccc2c(c1)OCO2]

and $R^5$ is independently selected from: Me, Et, Pr, i-Bu,

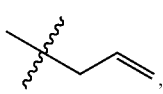 [SMILES: *CC=C]

Bn, 4-F-Bn, —$(CH_2)_2OMe$, —$(CH_2)_2CF_3$, —$(CH_2)_2NH_2$, and —$(CH_2)_2NHCO_2Bn$.

10. A compound according to claim 7, wherein:
$R^1$ is Ph;
$R^4$ is independently selected from:

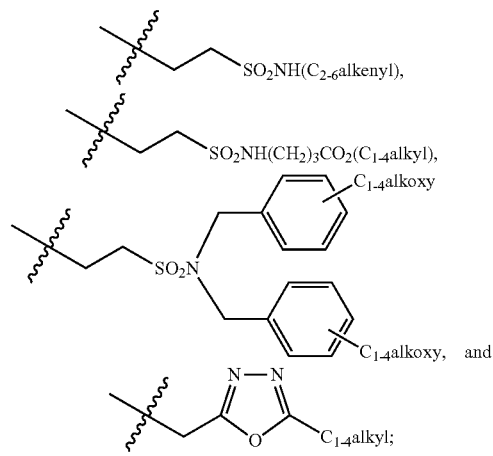

$R^5$ is independently selected from: $C_{1-4}$ alkyl, $C_{2-4}$ alkenyl, —$(CH_2)_2O(C_{1-4}$ alkyl), and —$(CH_2)_2NHCO_2Bn$.

11. A compound according to claim 10, wherein:
$R^4$ is independently selected from:

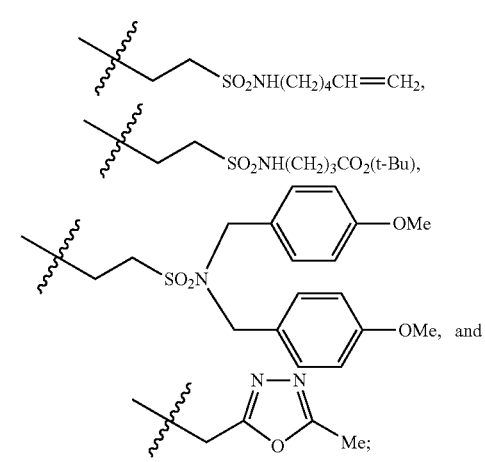

$R^5$ is independently selected from: Me,

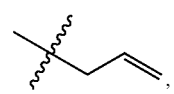 [SMILES: *CC=C]

—$(CH_2)_2OMe$, and —$(CH_2)_2NHCO_2Bn$.

12. A compound according to claim 6, wherein:
$R^1$ is independently selected from:

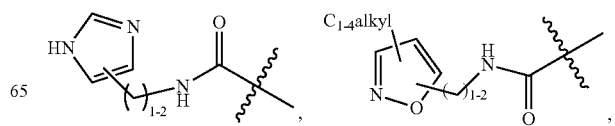

-continued

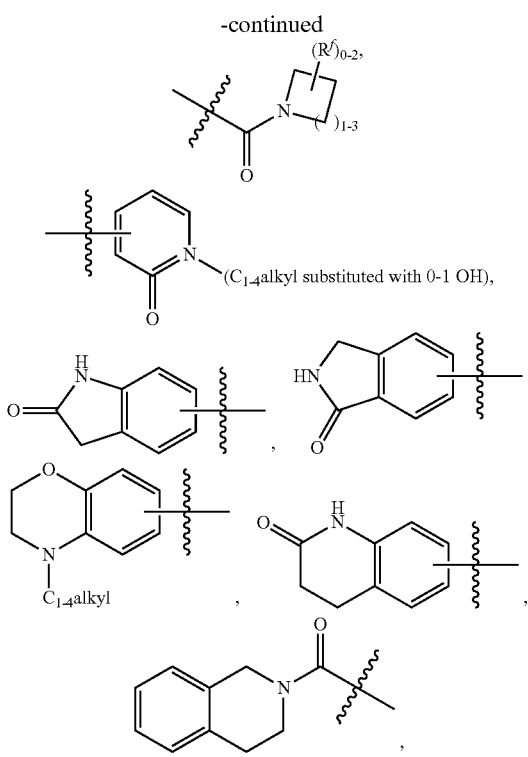

phenyl substituted with 0-2 $R^a$, and a heteroaryl substituted with 0-2 $R^a$ and selected from: isoxazolyl, pyrazolyl, 1-$R^c$-pyrazolyl, pyridyl, and pyrimidinyl;

$R^4$ is independently selected from:

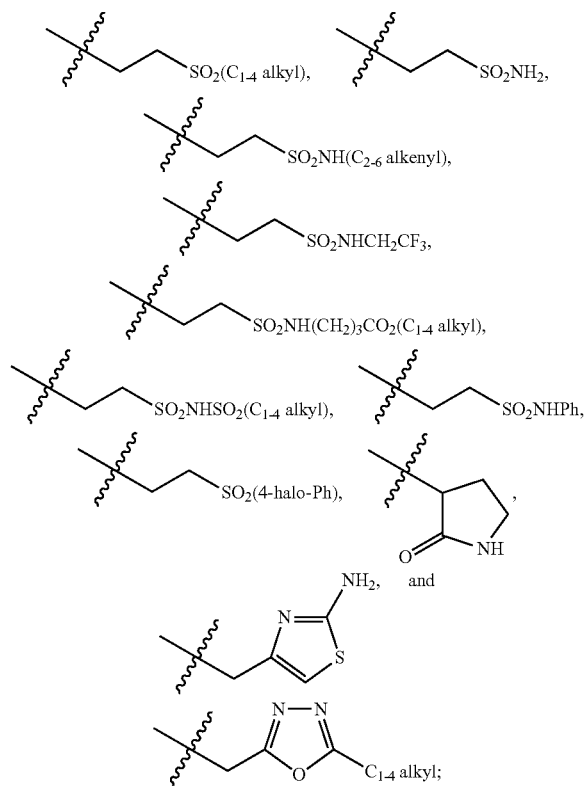

$R^5$ is independently selected from: $C_{1-4}$ alkyl substituted with 0-1 $R^9$, —$(CH_2)_{0-1}$—$C_{3-6}$ cycloalkyl, benzyl substituted with 0-1 $R^b$, and

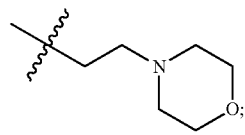

$R^9$ is independently selected from: $C_{1-4}$ alkoxy, $C_{1-4}$ haloalkyl, $NH_2$, and $NHCO_2Bn$;

$R^a$ is, independently at each occurrence, selected from: OH, halogen, $C_{1-4}$ alkyl substituted with 0-1 OH, $C_{1-4}$ alkoxy, —$O(CH_2)_2O(C_{1-4}$ alkyl), $C_{1-4}$ haloalkyl, $C_{1-4}$ haloalkoxy, $NH_2$, $CONH_2$, $CONH(C_{1-4}$ alkyl), $CONH(CH_2)_{2-3}OH$, $CONH(CH_2)_{1-3}O(C_{1-4}$ alkyl), $CON(C_{1-4}$ alkyl)$(CH_2)_{1-3}O(C_{1-4}$ alkyl), $CONH(C_{1-4}$ haloalkyl), $NHCO_2(C_{1-4}$ alkyl), $SO_2N(C_{1-4}$ alkyl)$_2$, $SO_2NH(CH_2)_{2-3}OH$, —$(CH_2)_{0-2}$-morpholinyl, —CO-morpholinyl, piperazinyl,

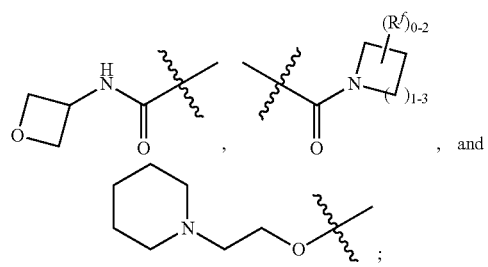

$R^b$ is independently selected from: CN, halogen and $C_{1-4}$ haloalkyl;

$R^c$ is, independently at each occurrence, selected from: H, $C_{1-4}$ alkyl substituted with 0-1 $C_{1-4}$ alkoxy, —$(CH_2)_{0-2}$-(phenyl substituted with 0-1 halo), —$(CH_2)_{0-2}$-piperidinyl, —$(CH_2)_{0-2}$-morpholinyl, and

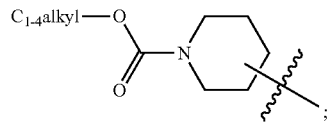

and $R^f$ is, independently at each occurrence, selected from: OH, CN, halogen, $C_{1-4}$ alkyl, and $C_{1-4}$ alkoxy.

13. A compound according to claim 12, wherein:
$R^1$ is independently selected from: 3-$(CH_2)_2OH$-Ph, 4-$(CH_2)_2OH$-Ph, 4-$O(CH_2)_2O(C_{1-4}$ alkyl)-Ph, 4-$C_{1-4}$ haloalkoxy-Ph, 4-$NH_2$-Ph, 4-$CONH_2$-Ph, 4-CONH $(C_{1-4}$ alkyl)-Ph, 4-$CONH(CH_2)_2OH$-Ph, 3-CONH $(CH_2)_2O(C_{1-4}$ alkyl)-Ph, 4-$CONH(CH_2)_2O(C_{1-4}$ alkyl)-Ph, 4-$CONH(C_{1-4}$, haloalkyl)-Ph, 3-$CON(C_{1-4}$ alkyl) $(CH_2)_2O(C_{1-4}$ alkyl)-Ph, 4-$NHCO_2(C_{1-4}$ alkyl)-Ph, 4-$SO_2N(C_{1-4}$ alkyl)$_2$-Ph, 4-$SO_2NH(CH_2)_2OH$-Ph, 1H-3-$C_{1-4}$ haloalkyl-pyrazol-4-yl, 1-$C_{1-4}$ alkyl-pyrazol-4-yl, 1-Bn-pyrazol-4-yl, 3-$C_{1-4}$ alkyl-pyrid-4-yl, 6-OH-pyrid-2-yl, 6-OH-pyrid-3-yl, 2-OH-pyrid-4-yl, 6-$C_{1-4}$ alkoxy-pyrid-2-yl, 2-$C_{1-4}$ alkoxy-pyrid-3-yl, 6-$C_{1-4}$ alkoxy-pyrid-3-yl, 2-$C_{1-4}$ alkoxy-pyrid-4-yl, 6-halo-pyrid-3-yl, 2-halo-pyrid-4-yl, 6-C$_{1-4}$ haloalkyl-pyrid-3-yl, 5-C$_{1-4}$ alkyl-6-halo-pyrid-3-yl, 3-halo-6-C$_{1-4}$ alkoxy-pyrid-4-yl, pyrimidin-5-yl,
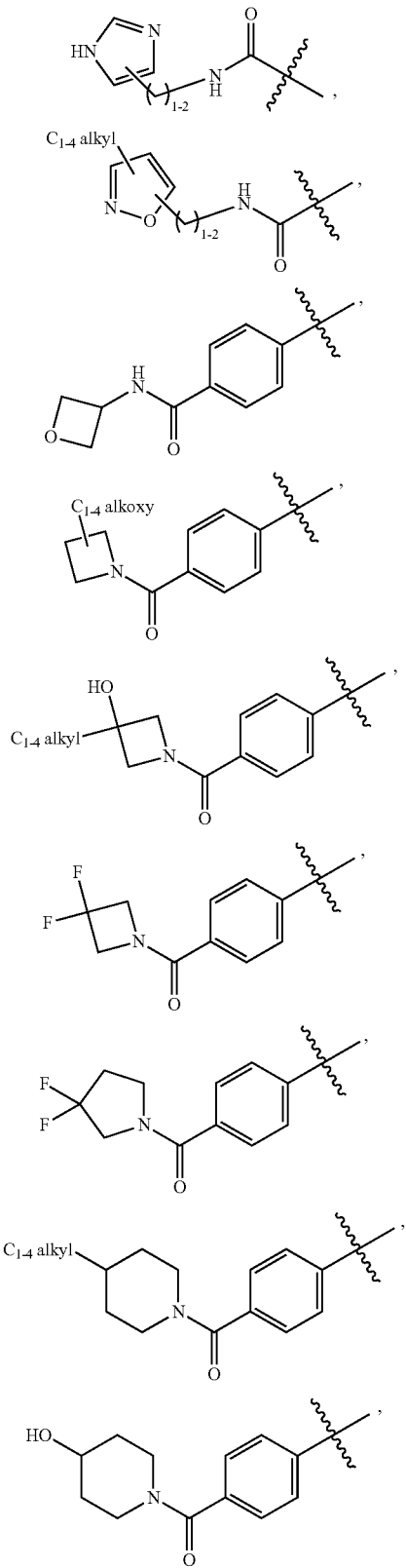
-continued
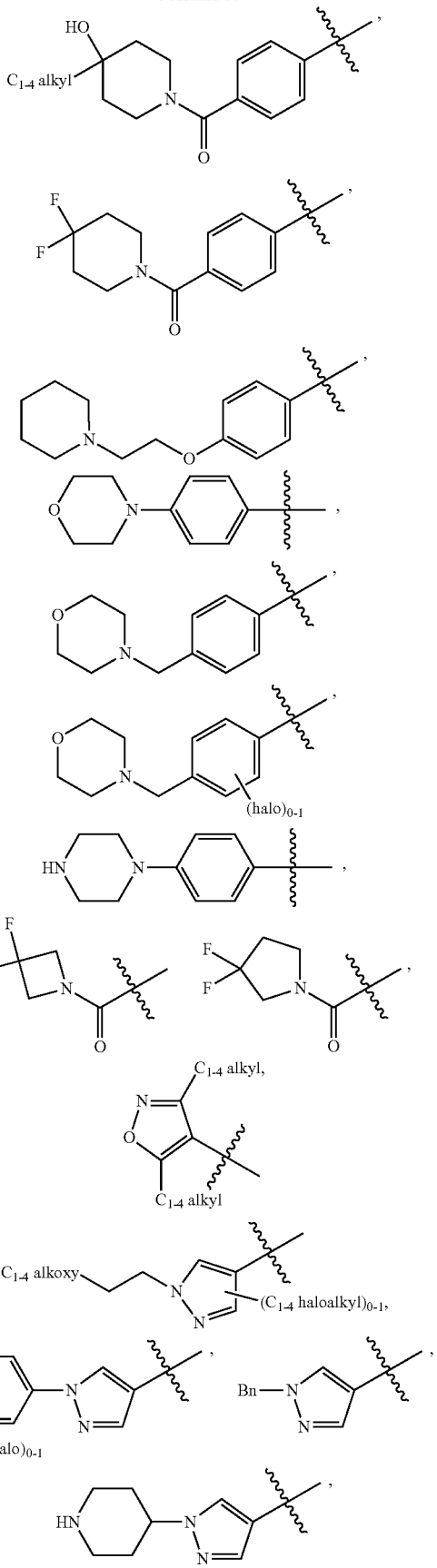

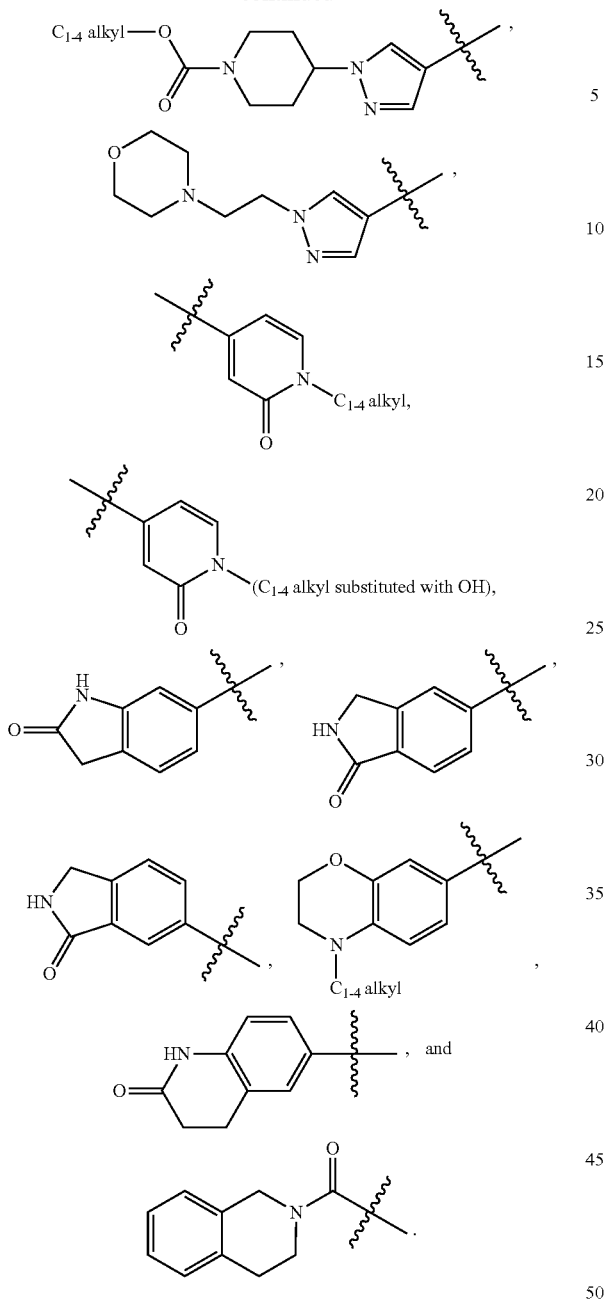

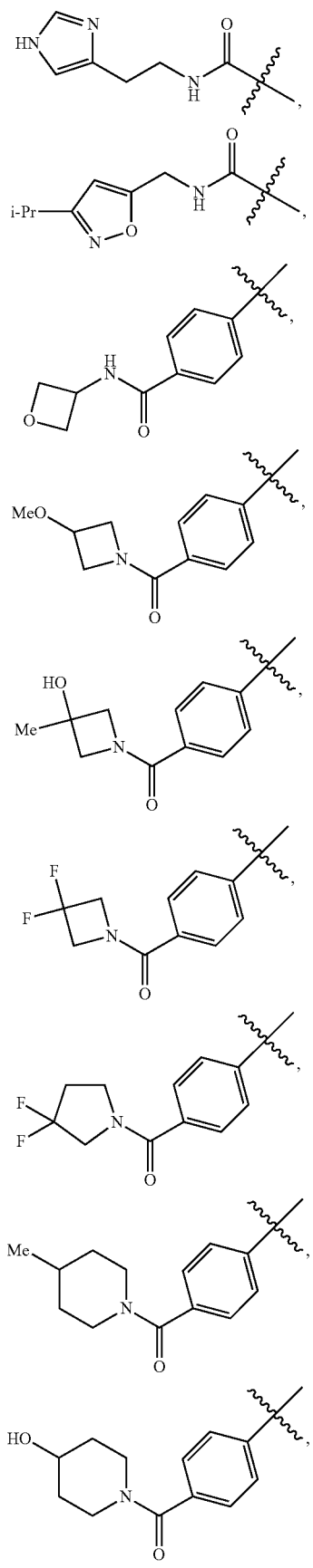

14. A compound according to claim 13, wherein:

$R^1$ is independently selected from: 3-$(CH_2)_2$OH-Ph, 4-$(CH_2)_2$OH-Ph, 4-O$(CH_2)_2$OMe-Ph, 4-OCF$_3$-Ph, 4-NH$_2$-Ph, 4-CONH$_2$-Ph, 4-CONH(t-Bu)-Ph, 4-CONH$(CH_2)_2$OH-Ph, 3-CONH$(CH_2)_2$OMe-Ph, 4-CONH$(CH_2)_2$OMe-Ph, 4-CON(Me)$(CH_2)_2$OMe-Ph, 4-CONHCH$_2$CF$_3$-Ph, 4-NHCO$_2$Me-Ph, 4-NHCO$_2$(t-Bu)-Ph, 4-SO$_2$N(Me)$_2$-Ph, 4-SO$_2$NH$(CH_2)_2$OH-Ph, 1H-3-CF$_3$-pyrazol-4-yl, 1-Me-pyrazol-4-yl, 1-(i-Bu)-pyrazol-4-yl, 1-Bn-pyrazol-4-yl, 3-Me-pyrid-4-yl, 6-OH-pyrid-2-yl, 6-OH-pyrid-3-yl, 2-OH-pyrid-4-yl, 6-OMe-pyrid-2-yl, 2-OMe-pyrid-3-yl, 6-OMe-pyrid-3-yl, 2-OMe-pyrid-4-yl, 6-F-pyrid-3-yl, 2-F-pyrid-4-yl, 2-Cl-pyrid-4-yl, 6-CF$_3$-pyrid-3-yl, 5-Me-6-F-pyrid-3-yl, 3-F-6-OMe-pyrid-4-yl, pyrimidin-5-yl, 407
-continued
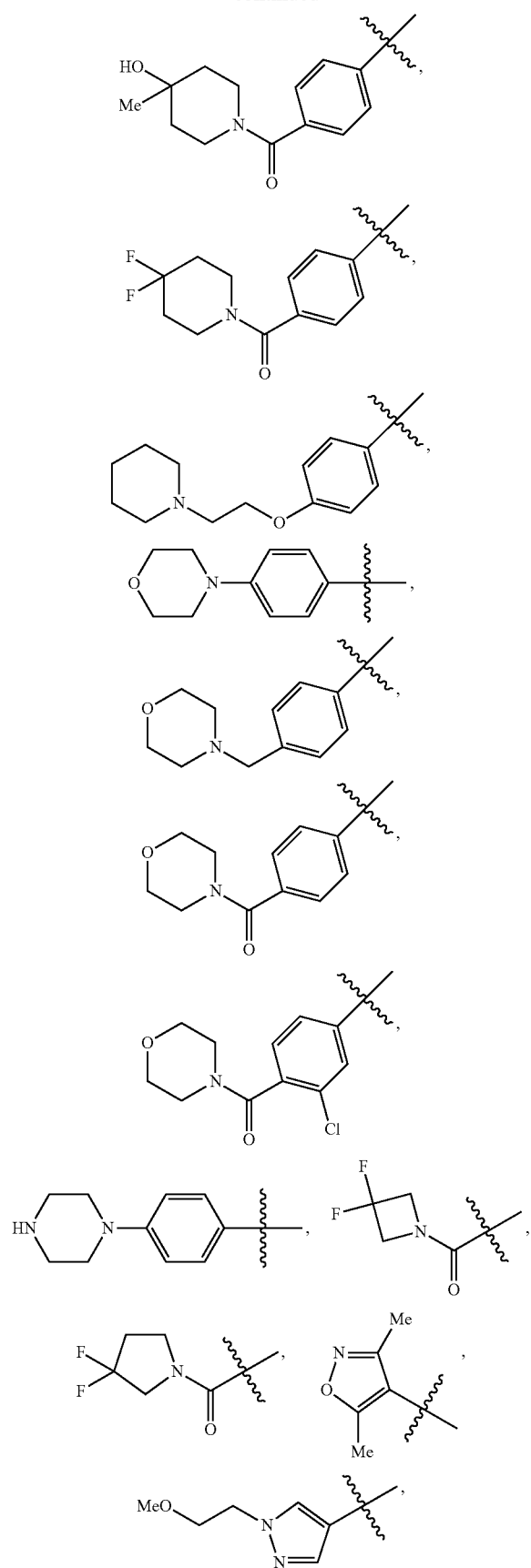
408
-continued
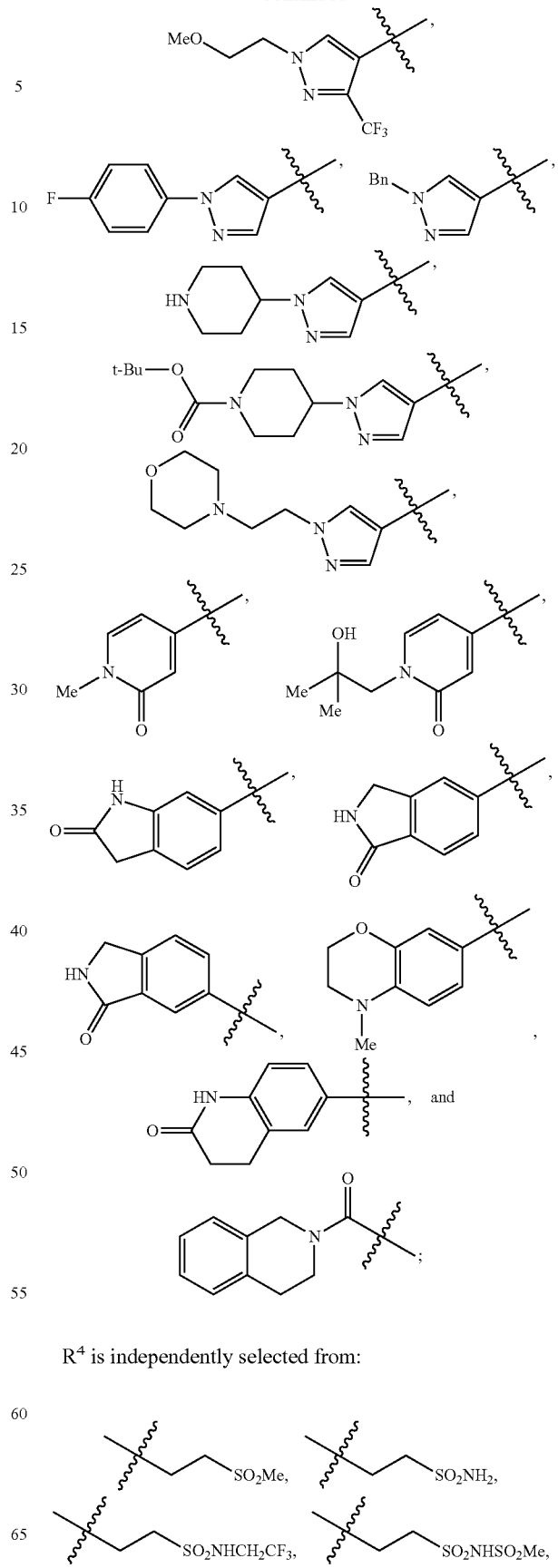
R⁴ is independently selected from:

-continued

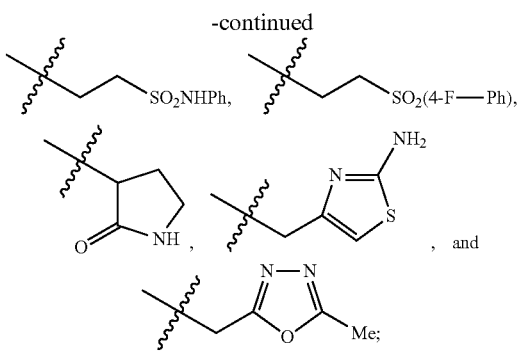

and

R⁵ is independently selected from: Me, Pr, i-Pr, i-Bu, —(CH₂)₂OMe, —(CH₂)₂CF₃, —(CH₂)₃CF₃, —(CH₂)₂NH₂, cyclopropylmethyl, Bn, 4-F-Bn, 4-CF₃-Bn, —(CH₂)₂NHCO₂Bn, and

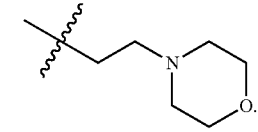 [SMILES: *CCN1CCOCC1]

15. A compound as defined in claim 1, selected from the exemplified examples of the Specification, or a stereoisomer, a tautomer, or a pharmaceutically acceptable salt thereof.

16. A pharmaceutical composition, comprising: a pharmaceutically acceptable carrier and a compound of claim 1, or a stereoisomer, a tautomer, or a pharmaceutically acceptable salt thereof.

* * * * *